US006410585B1

United States Patent
Larsen et al.

(10) Patent No.: US 6,410,585 B1
(45) Date of Patent: Jun. 25, 2002

(54) INHIBITORS OF PROTEIN TYROSINE PHOSPHATASE

(76) Inventors: Scott D. Larsen, 56 Naples Ct., Kalamazoo, MI (US) 49009; Paul D. May, 7890 N. 32nd St., Richland, MI (US) 49083; John E. Bleasdale, 3230 Lites End Ct., Portage, MI (US) 49024; Charlotta Liljebris, Torpkäller.33, S-74192 Knivsta (SE); Heinrich Josef Schostarez, 3236 Lost Pine Way, Portage, MI (US) 49024; Tjeerd Barf, Vikingagatan 32, S-753 34 Uppsala; Marianne Nilsson, PL 2654 Ubby, SE-762 94 Rimbo, both of (SE)

( * ) Notice: Subject to any disclaimer, the term of this patent is extended or adjusted under 35 U.S.C. 154(b) by 0 days.

(21) Appl. No.: 09/265,410

(22) Filed: Mar. 10, 1999

Related U.S. Application Data

(63) Continuation-in-part of application No. 09/138,642, filed on Aug. 24, 1998.
(60) Provisional application No. 60/057,730, filed on Aug. 28, 1997.

(51) Int. Cl.$^7$ ..................... C07C 235/00; C07C 237/22; A61K 31/165
(52) U.S. Cl. ........................ 514/424; 514/533; 514/538; 514/562; 548/546; 558/30; 560/37; 560/42; 562/442; 562/451
(58) Field of Search ............................. 548/546; 558/30; 560/42, 37; 562/442, 451; 514/424, 533, 538, 563

(56) References Cited

FOREIGN PATENT DOCUMENTS

| EP | 0832875 A | 4/1998 |
|---|---|---|
| EP | 0930299 A | 7/1999 |
| WO | 96/23813 | 8/1996 |
| WO | 96/30332 | 10/1996 |
| WO | WO9638415 A | 12/1996 |
| WO | 96/40109 | 12/1996 |
| WO | 96/40113 | 12/1996 |
| WO | WO9911606 | 3/1999 |

OTHER PUBLICATIONS

XP002142376, Burke et al., Tetrahedron, vol. 54, No. 34 (1998) pp. 9981–9994.
XP002142377, DesMarais et al., Arch. Biochem. Biophys., vol. 354, No. 2 (1998) pp. 225–231.
XP002142378, Kole et al., Indian J. Biochem. Biophys., vol. 34, Nos. 1–2 (1997) pp. 50–55.
XP002142379, Akamatsu et al., Bioorg. Med. Chem., vol. 5, No. 1 (1997) pp. 157–163.
XP002142380, Kole et al., J. Biol. Chem., vol. 271, No. 24 (1996) pp. 14302–14307.
XP002142381, Akamatsu et al., Pept. Chem. vol. 33 (1996) pp. 369–372.
XP002142382, Kole et al., Biochem. Biophys. Res. Commun. vol. 209, No. 3 (1995) pp. 817–822.
XP002142383, Liotta et al., J. Biol. Chem., vol. 269, No. 37 (1994) pp. 22996–23001.
XP002142384, Burke et al., Bioorg. Med. Chem. Lett., vol. 9, No. 3 (1999) pp. 347–352.
XP002087254, Charifson et al., Biochem., US, Amer. Chem. Soc., vol. 36 (1997) pp. 6283–6293.
XP000609794, Taylor et al., Ann. Rev. Cell Bio., vol. 8 (1992) pp. 429–462.

*Primary Examiner*—Robert Gerstl
(74) *Attorney, Agent, or Firm*—Fish & Richardson P.C.

(57) ABSTRACT

The present invention comprises small molecular weight, non-peptidic inhibitors of formulae I–VII of Protein Tyrosine Phosphatase 1 (PTP1) which are useful for the treatment and/or prevention of Non-Insulin Dependent Diabetes Mellitus (NIDDM).

10 Claims, No Drawings

INHIBITORS OF PROTEIN TYROSINE PHOSPHATASE

CROSS-REFERENCE TO RELATED APPLICATIONS

This application is a continuation-in-part of U.S. application Ser. No. 09/138,642 filed Aug. 24, 1998 which claims the benefit of provisional application U.S. Ser. No. 60/057,730, filed Aug. 28, 1997, under 35 USC 119(e)(i). The entire contents of both of these applications are hereby incorporated by reference.

FIELD OF THE INVENTION

The present invention comprises small molecular weight, non-peptidic inhibitors of Protein Tyrosine Phosphatase 1 (PTP1) which are useful for the treatment and/or prevention of Non-Insulin Dependent Diabetes Mellitus (NIDDM).

BACKGROUND OF THE INVENTION

The mechanism of insulin action depends critically upon the phosphorylation of tyrosine residues in several proteins in the insulin signaling cascade. Enzymes that dephosphorylate these proteins, protein tyrosine phosphatases (PTPs), are important negative regulators of insulin action. Therefore, the use of specific PTP inhibitors may therapeutically enhance insulin action.

The insulin resistance that is central to noninsulin-dependent diabetes mellitus (NIDDM) appears to involve a defect in an early process in insulin signal transduction rather than a structural defect in the insulin receptor itself. (J. M. Olefsky, W. T. Garvey, R. R. Henry, D. Brillon, S. Matthai and G. R. Freidenberg, G. R. (1988).) Cellular mechanisms of insulin resistance in non-insulin-dependent (Type II) diabetes. (Am. J. Med. 85: Suppl. 5A, 86–105.) A drug that improved insulin sensitivity would have several advantages over traditional therapy of NIDDM using sulfonylureas, which do not alleviate insulin resistance but instead compensate by increasing insulin secretion.

The binding of insulin to the α-subunits of the insulin receptor permits the β-subunits to catalyze phosphorylation of target proteins on tyrosine residues. There are 22 tyrosine residues in each insulin receptor β-subunit itself and autophosphorylation of at least 6 of these tyrosines, in 3 distinct domains, is known to be involved in insulin action. (C. R. Kahn (1994) Insulin action, diabetogenes, and the cause of type II diabetes. Diabetes 43: 1066–1084.) Autophosphorylation of $Tyr^{960}$ in the juxtamembrane domain is important for receptor internalization and for the interaction of the receptor with downstream signaling molecules such as insulin receptor substrate 1 (IRS-1).) (T. J. O'Neill, A. Craparo and T. A. Gustafson (1994) Characterization of an interaction between insulin receptor substrate 1 and the insulin receptor by using the two-hybrid system. Mol. Cell Biol. 14: 6433–6442.) Autophosphorylation of tyrosine residues 1146, 1150 and 1151 in the regulatory domain permits continued tyrosine kinase activity of β-subunits, even after insulin has dissociated from the α-subunits, and activates the kinase toward other protein substrates. (R. Herrera and O. M. Rosen (1986) Autophosphorylation of the insulin receptor in vitro: designation of phosphorylation sites and correlation with receptor kinase activation. J. Biol. Chem. 261: 11980–11985.) Deletion of autophosphorylation sites at $Tyr^{1316}$ and $Tyr^{1322}$ in the C-terminal domain attenuates the metabolic actions of insulin, but augments its mitogenic actions. (H. Maegawa, D. McClain, G. Freidenberg, J. Olefsky, M. Napier, T. Lipari, T. Dull, J. Lee, and A. Ullrich (1988) Properties of a human insulin receptor with a COOH-terminal truncation. II. Truncated receptors have normal kinase activity but are defective in signaling metabolic effects. J. Biol. Chem. 263: 8912–8917.) (Y. Takata, N. J. G. Webster, and J. M. Olefsky (1991) Mutation of the two carboxyl-terminal tyrosines results in an insulin receptor with normal metabolic signaling but enhanced mitogenic signaling properties. J. Biol. Chem. 266: 9135–9139.) Dephosphorylation of these autophosphorylated sites occurs rapidly in vivo, suggesting that a protein tyrosine phosphatase (PTPase) is involved in terminating insulin action. A compound that inhibited this PTPase, therefore, should potentiate insulin action. Indeed, vanadate potentiates insulin action, at least in part, by such a mechanism (Y. Schechter (1990). Insulin-mimetic effects of vanadate. Possible implications for future treatment of diabetes. Diabetes 39: 1–5.) The PTPase(s) that act on the insulin receptor, however, has not been identified definitively.

It has been estimated that the human genome encodes as many as 500 PTP enzymes (T. Hunter (1995) Protein kinases and phosphatases: The Yin and Yang of protein phosphorylation and signaling. Cell 80: 225–236), but less than 100 have been identified and have been grouped into 4 sub-families (E. A. Fauman and M. A. Saper (1996) Structure and function of the protein tyrosine phosphatases. Trends Biochem. Sci. 21: 413–417.) Members of the tyrosine-specific PTP sub-family are further divided into the receptor PTPases (such as CD45 and LAR) which typically have a large variable extracellular domain, a single transmembrane spanning region, and two intracellular phosphatase catalytic domains and the non-receptor PTPases. This latter group includes PTP that resemble PTP1. (D. A. Pot and J. E. Dixon (1992) A thousand and two protein tyrosine phosphatases. Biochim. Biophys. Acta 1136:35–43.) There is data to support the proposition that the insulin receptor PTPase may be PTP1-like. For instance, an insulin-dependent association of PTP1 with insulin receptors has been described. (D. Bandyopadhyay, A. Kursari, K. A. Kenner, F. Liu, J. Chernoff, T. A. Gustafson, J. Kusari (1997) Protein-tyrosine phosphatase 1B complexes with the insulin receptor in vivo and is tyrosine-phosphorylated in the presence of insulin. J. Biol. Chem. 272: 1639–1645; and L. Seely, et al. (1996) Protein tyrosine phosphatase 1B interacts with the activated insulin receptor. Diabetes 45: 1379.) Furthermore, PTP1 dephosphorylates purified insulin receptors sequentially in the order observed in vivo (i.e., $Tyr^{1150}=Tyr^{1151}>Tyr^{1146}$), (C. Ramachandran, R. Aebersold, N. Tonks and D. A. Pot (1992) Sequential dephosphorylation of a multiply phosphorylated insulin receptor peptide by protein tyrosine phosphatases. Biochemistry 31: 4232–4238) and insulin acutely increases PTP1 mRNA in hepatoma cells. (N. Hashimoto and B. J. Goldstein (1992) Differential regulation of mRNAs encoding three protein-tyrosine phosphatases by insulin and activation of protein kinase C. Biochem. Biophys. Res. Commun. 188: 1305–1311.) Insulin resistance induced in Rat 1 fibroblasts by high glucose (27 mM) is preceded by an approximate doubling of cytosolic PTP1 activity that is blocked by the insulin-sensitizer, pioglitazone. (H. Maegawa, R. Ide, M. Hasegawa, S. Ugi, K. Egawa, M. Iwanishi, R. Kikkawa, Y. Shigeta, and A. Kashiwagi (1995)

Thiazolidinedione derivatives ameliorate high glucose-induced insulin resistance via the normalization of protein tyrosine phosphatase activities. J. Biol. Chem. 270: 7724–7730.) Thus, a specific inhibitor of PTP1 could be used to potentiate insulin action. While there are no known small molecules that specifically inhibit PTP1, it was found that osmotic loading of hepatoma cells with neutralizing antibodies against PTP1b (the human homologue of rat PTP1) resulted in increased autophosphorylation of insulin receptors and phosphorylation of IRS-1 in response to insulin. (F. Ahmad, P.-M. Li, J. Meyerovitch, and B. J. Goldstein (1995) Osmotic loading of neutralizing antibodies demonstrates a role for PTPase 1B in negative regulation of the insulin signaling pathway. Diabetes 44: Suppl. 1 104A.) See also B. J. Goldstein (1993) Regulation of insulin receptor signaling by protein-tyrosine dephosphorylation. Receptor 3: 1–15.)

INFORMATION DISCLOSURE

International Publication No. WO 96/30332, "O-Malonyltyrosyl Compounds, O-Malonyltyrosyl Compound-Containing Peptides, and Uses thereof," published Oct. 3, 1996, disclose non-phosphorus containing O-malonyltyrosyl compounds, derivatives thereof, uses of the O-malonyltyrosyl compounds in the synthesis of peptides, and O-malonyltyrosyl compound-containing peptides. The O-malonyltyrosyl compounds and O-malonyltyrosyl compound-containing peptides are disclosed as being useful as inhibitors of protein-tyrosine phosphatase; however, no specific non-peptidic compounds or data is disclosed.

International Publication No. WO 96/23813, "Peptides and Compounds that Bind to SH2 Domains," published Aug. 8, 1996, discloses tyrosine-containing peptides and compounds which bind to the SH2 domain or domains of various proteins, as well as methods for identifying such peptides and compounds. These peptides and compounds have application as agonists and antagonists of SH2 domain containing proteins, and as diagnostic or therapeutic agents for the diagnosis or treatment of disease conditions.

International Publication No. WO 96/40113, "Phosphatase Inhibitors," published Dec. 19, 1996, discloses heterocyclic nitrogen containing compounds, such as nitropyridine or nitrothiazole, capable of inhibiting protein tyrosine phosphatase activity. Such molecules are disclosed as being useful to modulate or regulate signal transduction by inhibiting protein tyrosine phosphatase activity and to treat various disease states including diabetes mellitus.

International Publication No. WO 96/40109, "Methods of Inhibiting Phosphatase Activity and Treatment of Disorders Associated Therewith Using Napthopyrones and Derivatives Thereof," published Dec. 19, 1996, discloses the use of naphthopyrone compounds to inhibit protein tyrosine phosphatase activity. Such compounds are disclosed as being useful to modulate or regulate signal transduction by inhibiting protein tyrosine phosphatase activity and to treat various disease states including diabetes mellitus.

The compounds of the present invention have surprising activity in that they are small molecular weight and non-peptidic compounds.

SUMMARY OF THE INVENTION

One aspect of the invention provides a compound of formula I or II

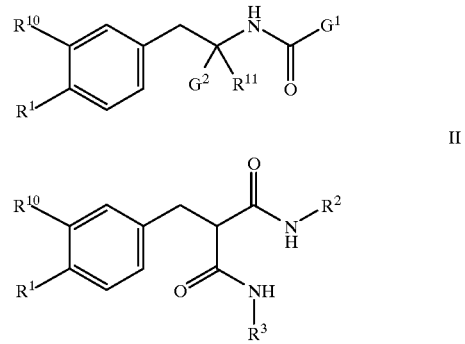

wherein $G^1$ is
   a) —$R^2$, or
   b) —$NR^8R^4$;
wherein $G^2$ is
   a) $CONR^{99}R^3$,
   b) H,
   c) $CH_2OH$, or
   d) $CH=CHR^3$;
wherein $R^{99}$ is H or $C_1$–$C_6$ alkyl;
wherein $R^1$ is
   a) —$OSO_3H$,
   b) —$OCH(CO_2R^5)_2$,
   c) —$OCH_2(CO_2R^5)$,
   d) —$OCH(CO_2R^5)CH_2CO_2R^5$,
   e) —$OC(CO_2R^5)=CHCO_2R^5$,
   f) —$CH_2CH(CO_2R^5)_2$,
   g) —$CH=C(CO_2R^5)_2$,
   h) —$OCH_2CONHOH$,
   i) —$N(CH_2CO_2R^5)_2$, or
   j) —$OCHF(CO_2R^5)$;
wherein $R^2$ is
   a) —$C_1$–$C_{10}$ alkyl optionally substituted with one or two —$CO_2R^5$ bonded to the same or different carbon atoms or with one —CO—$NH_2$,
   b) —$C_3$–$C_8$ cycloalkyl optionally substituted with one —$CO_2R^5$,
   c) —$C_0$–$C_6$ alkyl-phenyl optionally substituted with one or two —$CO_2R^5$ bonded to the same or different carbon atoms or with —$CH_2CH(CO_2R^5)_2$,
   d) —$CH(R^7)NHXR^6$, or
   e)

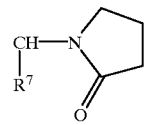

wherein $R^3$ is
   a) —$C_1$–$C_{12}$ alkyl, optionally substituted with one to three —O—$C_1$–$C_4$ alkyl, —S—$C_1$–$C_4$ alkyl, —O—$G^3$, —S—$G^3$, or —OH, and optionally interrupted with one to three —O—, —S—, or —N—, b) —$C_1$–$C_4$alkyl —$C_3$–$C_6$ cycloalkyl,
c) —$C_2$–$C_{12}$ alkenyl,
d) —$C_3$–$C_{12}$ alkynyl,
e) —$C_0$–$C_{10}$ alkyl($G^3$)$_n$ wherein alkyl is optionally interrupted with one to three —O—, —S—, or —N—, or
f) —CH(CONH$_2$)$C_1$–$C_{12}$ alkyl;
wherein $R^4$ is
a) —H,
b) —$C_1$–$C_{18}$ alkyl or alkenyl, or
c) —$C_0$–$C_6$-alkyl-$G^3$;
wherein $R^5$ is
a) —H,
b) —$C_1$–$C_{10}$ alkyl, or
c) —$C_1$–$C_5$ alkyl-phenyl;
wherein $R^6$ is
a) $C_1$–$C_{10}$ alkyl,
b) $C_0$–$C_6$ alkyl-$G^3$,
c) $C_1$–$C_6$ alkyl CONH$_2$,
d) $C_1$–$C_6$ alkyl NHCO$_2$R$^5$,
e) $C_1$–$C_6$ alkyl-OR$^5$,
f) $C_1$–$C_6$ alkyl-NHSO$_2$Me,
g) $C_1$–$C_6$ alkyl-O—$G^3$,
h) $C_1$–$C_6$ alkyl-S—$G^3$, or
i) —$C_1$–$C_6$ alkyl-CO$_2$R$^5$;
wherein $R^7$ is
a) —H,
b) —$C_1$–$C_6$ alkyl-$G^3$,
c) —$C_1$–$C_6$ alkyl-CO$_2$R$^5$,
d) $C_1$–$C_6$ alkyl CONH$_2$,
e) $C_1$–$C_6$ alkyl NHCO$_2$R$^5$,
f) $C_1$–$C_{10}$ alkyl,
g) $C_1$–$C_{10}$ cycloalkyl,
h) —$C_1$–$C_6$ alkyl-SR$^5$, or
i) —$C_1$–$C_6$ alkyl-S(=O)R$^5$;
wherein $R^8$ is
a) $C_0$–$C_6$ alkyl-$G^3$,
b) CH(R$^7$)CO$_2$R$^5$,
c) CH(R$^7$)CH$_2$CO$_2$R$^5$, or
d) CH(R$^7$)CONHCH$_2$CO$_2$R$^5$;
wherein $G^3$ is
a) phenyl substituted by zero (0) to three (3) R$^9$,
b) naphthyl substituted by zero (0) to three (3) R$^9$, or
c) het$_1$ substituted by zero (0) to three (3) R$^9$;
wherein het$_1$ is a 5- or 6-membered saturated or unsaturated ring containing from one (1) to four (4) heteroatoms selected from the group consisting of nitrogen, oxygen and sulfur; and including any bicyclic group in which any of the above heterocyclic rings is fused to a benzene ring, $C_3$–$C_8$ cycloalkyl, or another heterocycle; and optionally, the nitrogen and sulfur heteroatoms may be in oxidized form if chemically feasible;
wherein $R^9$ may be any of the following:
a) $C_1$–$C_8$ alkyl substituted by zero (0) to three (3) halo,
b) $C_2$–$C_8$ alkenyl,
c) OH,
d) O—$C_1$–$C_5$ alkyl,
e) O—$C_0$–$C_5$ alkyl-phenyl,
e) —(CH$_2$)$_n$—O—$C_1$–$C_5$ alkyl substituted by zero (0) to three (3) hydroxy,
f) —(CH$_2$)$_n$—O—$C_2$–$C_7$ alkenyl substituted by zero (0) to three (3) hydroxy,
g) halo,
h) NH$_2$,
i) amino-$C_1$–$C_5$ alkyl,
j) mono- or di-$C_1$–$C_5$ alkylamino,
k) —C(O)—$C_1$–$C_5$ alkyl,
l) —CHO,
m) —C(O)—$C_0$–$C_5$ alkyl-phenyl,
n) —COOR$^5$,
o) —CON(R$^5$)$_2$,
p) —$C_3$–$C_7$ cycloalkyl,
q) —NO$_2$,
r) —CN,
s) —SO$_3$H,
t) —SO$_2$N(R$_5$)$_2$,
u) —O[(CH$_2$)$_2$—O]$_n$—CH$_3$,
v) —[CH$_2$—O]$_n$—$C_1$–$C_3$ alkyl,
w) —NR$^5$(CO)—NR$^5$,
x) —CF$_3$,
y) —NR$^5$(CO)$C_1$–$C_5$ alkyl,
z) —N(R$^5$)—SO$_2$—R$^5$,
a1) —O—C(O)—R$^5$,
b1) —S(O)—R$^5$,
c1) —SR$^5$, or
d1) —SO$_2$—R$^5$;
wherein $R^{10}$ is
a) —H,
b) CO$_2$R$^5$,
c) CONHOH,
d) 5-tetrazolyl,
e) F, or
f) OCH$_2$CO$_2$R$^5$;
wherein $R^{11}$ is
a) H, or
b) methyl;
wherein X is —CO— or —SO$_2$— or —CO$_2$—;
wherein n is zero, one, two or three;
or a pharmaceutically acceptable salt thereof;
provided that when R$^{10}$ is H, R$^1$ is other than —OCH$_2$(CO$_2$R$^5$).

The present invention particularly provides the compounds of formula III or IV:

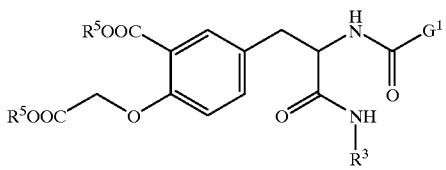

-continued

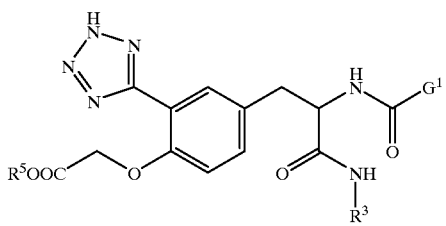

IV wherein $G^1$ is
a) —CH(CH$_2$phenyl)NHCO$_2$t-Bu,
b) —CH(CH$_2$phenyl)NHCOC$_1$-C$_3$ alkyl-G$^3$,
c) —CH(CH$_2$phenyl)NHCOC$_1$-C$_3$ alkyl-CO$_2$R$^5$, or
d)

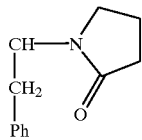

wherein $R^3$ is
a) —C$_5$-C$_6$ alkyl, or
b) —C$_3$-C$_6$ alkyl-phenyl;
wherein $R^5$ is —H;
wherein the configuration of the chiral center(s) is (S).

Another aspect of the invention provides compounds of formula V:

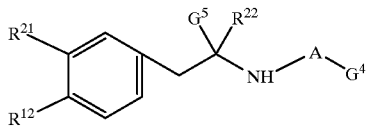

V wherein A is —C(O)— or —SO$_2$—;
wherein $G^4$ is
a) —R$^{13}$, or
b) —NR$^{19}$R$^{15}$;
wherein $G^5$ is
a) CONR$^{99}$R$^{14}$,
b) H,
c) CH$_2$OH, or
d) CH=CHR$^{14}$;
wherein $R^{99}$ is H or C$_1$-C$_6$ alkyl;
wherein $R^{12}$ is
a) —OSO$_3$H,
b) —OCH(CO$_2$R$^{16}$)$_2$,
c) —OCH$_2$(CO$_2$R$^{16}$),
d) —OCH(CO$_2$R$^{16}$)CH$_2$CO$_2$R$^{16}$,
e) —OC(CO$_2$R$^{16}$)=CHCO$_2$R$^{16}$,
f) —CH$_2$CH(CO$_2$R$^{16}$)$_2$,
g) —CH=C(CO$_2$R$^{16}$)$_2$,
h) —OCH$_2$CONHOH,
i) —N(CH$_2$CO$_2$R$^{16}$)$_2$, or
j) —OCHF(CO$_2$R$^{16}$);

wherein $R^{13}$ is
a) —C$_1$-C$_{10}$ alkoxy,
b) —C$_0$-C$_{10}$ alkyl-(G$^6$)$_n$, wherein alkyl is optionally substituted with one to three —O—C$_1$-C$_4$ alkyl, halo, or trifluoromethyl, and optionally interrupted with one to three —O—, —S—, or —N—,
c) —C$_2$-C$_{10}$ alkenyl-(G$^6$)$_n$,
d) —C$_1$-C$_{10}$ alkyl-O—(G$^6$)$_n$,
e) —C$_1$-C$_6$ alkyl-C$_3$-C$_{10}$ cycloalkyl optionally substituted with one to three R$^{20}$, or
f) —C$_0$-C$_{10}$ alkylcarbonyl-(G$^6$)$_n$ wherein alkyl is optionally interrupted with one to three —O—, —S—, or —N—;
wherein $R^{14}$ is
a) —C$_1$-C$_{12}$ alkyl, optionally substituted with one to three —O—C$_1$-C$_4$ alkyl, —S—C$_1$-C$_4$ alkyl, —O—G$^6$, —S—G$^6$, or —OH, and optionally interrupted with one to three —O—, —S—, or —N—,
b) —C$_1$-C$_4$ alkyl-C$_3$-C$_6$ cycloalkyl,
c) —C$_2$-C$_{12}$ alkenyl,
d) —C$_3$-C$_{12}$ alkynyl,
e) —C$_0$-C$_{10}$ alkyl(G$^6$)$_n$ wherein alkyl is optionally interrupted with one to three —O—, —S—, or —N—,
f) —CH(CONH$_2$)C$_1$-C$_{12}$ alkyl,
g) —C$_0$-C$_6$ alkyl-NR$^{23}$R$^{24}$, wherein alkyl is substituted with zero to three OH,
h) —NR$^{24}$—CO—R$^{26}$, or
i) —O—C$_1$-C$_{10}$ alkyl(G$^6$)$_n$, wherein alkyl is optionally interrupted with one to three —O—, —S—, or —N—;
wherein $R^{15}$ is
a) —H,
b) —C$_1$-C$_{18}$ alkyl or alkenyl, or
c) —C$_0$-C$_6$-alkyl-G$^6$;
wherein $R^{16}$ is
a) —H,
b) —C$_1$-C$_{10}$ alkyl, or
c) —C$_1$-C$_5$ alkyl-phenyl;
wherein $R^{17}$ is
a) —C$_1$-C$_{10}$ alkyl,
b) —C$_0$-C$_6$ alkyl-G$^6$,
c) —C$_1$-C$_6$ alkyl CONH$_2$,
d) —C$_1$-C$_6$ alkyl NHCO$_2$R$^{16}$,
e) —C$_1$-C$_6$ alkyl-OR$^{16}$,
f) —C$_1$-C$_6$ alkyl-NHSO$_2$Me,
g) —C$_1$-C$_6$ alkyl-O—G$^6$,
h) —C$_1$-C$_6$ alkyl-S—G$^6$, or
i) —C$_1$-C$_6$ alkyl-CO$_2$R$^{16}$;
wherein $R^{18}$ is
a) —H,
b) —C$_1$-C$_6$ alkyl-G$^6$,
c) —C$_1$-C$_6$ alkyl-CO$_2$R$^{16}$,
d) —C$_1$-C$_6$ alkyl CONH$_2$,
e) —C$_1$-C$_6$ alkyl NHCO$_2$R$^{16}$,
f) —C$_1$-C$_{10}$ alkyl,
g) —C$_1$-C$_{10}$ cycloalkyl,
h) —C$_1$-C$_6$ alkyl-SR$^{16}$, or
i) —C$_1$-C$_6$ alkyl-S(=O)R$^{16}$;

wherein $R^{19}$ is
- a) $C_0$–$C_6$ alkyl-$G^6$,
- b) $CH(R^{18})CO_2R^{16}$,
- c) $CH(R^{18})CH_2CO_2R^{16}$, or
- d) $CH(R^{18})CONHCH_2CO_2R^{16}$;

wherein $G^6$ is
- a) phenyl substituted by zero (0) to four (4) $R^{20}$,
- b) naphthyl substituted by zero (0) to three (3) $R^{20}$, or
- c) $het_1$ substituted by zero (0) to three (3) $R^{20}$;

wherein $het_1$ is a 5- or 6-membered saturated or unsaturated ring containing from one (1) to four (4) heteroatoms selected from the group consisting of nitrogen, oxygen and sulfur; and including any bicyclic group in which any of the above heterocyclic rings is fused to a benzene ring, $C_3$–$C_8$ cycloalkyl, or another heterocycle; and optionally, the nitrogen and sulfur heteroatoms may be in oxidized form if chemically feasible;

wherein $R^{20}$ may be any of the following:
- a) $C_1$–$C_8$ alkyl substituted by zero (0) to three (3) halo,
- b) $C_2$–$C_8$ alkenyl,
- c) OH,
- d) O—$C_1$–$C_5$ alkyl,
- e) O—$C_0$–$C_5$ alkyl-phenyl,
- e) —$(CH_2)_n$—O—$C_1$–$C_5$ alkyl substituted by zero (0) to three (3) hydroxy,
- f) —$(CH_2)_n$—O—$C_2$–$C_7$ alkenyl substituted by zero (0) to three (3) hydroxy,
- g) halo,
- h) $NH_2$,
- i) amino-$C_1$–$C_5$ alkyl,
- j) mono- or di-$C_1$–$C_5$ alkylamino,
- k) —C(O)—$C_1$–$C_5$ alkyl,
- l) —CHO,
- m) —C(O)—$C_0$–$C_5$ alkyl-phenyl,
- n) —$COOR^{16}$,
- o) —$CON(R^{16})_2$,
- p) —$C_3$–$C_7$ cycloalkyl,
- q) —$NO_2$,
- r) —CN,
- s) —$SO_3H$,
- t) —$SO_2N(R^{16})_2$,
- u) —$O[(CH_2)_2$—$O]_n$—$CH_3$,
- v) —$[CH_2$—$O]_n$—$C_1$–$C_3$ alkyl,
- w) —$NR^{16}(CO)$—$NR^{16}$,
- x) —$CF_3$,
- y) —$NR^{16}(CO)C_1$–$C_5$ alkyl,
- z) —$N(R^{16})$—$SO_2$—$R^{16}$,
- a1) —O—C(O)—$R^{16}$,
- b1) —S(O)—$R^{16}$,
- c1) —$SR^{16}$,
- d1) —$SO_2$—$R^{16}$,
- e1) phenyl, or
- f1) oxo;

wherein $R^{21}$ is
- a) —H,
- b) —$CO_2R^{16}$,
- c) —CONHOH,
- d) $het_2$ substituted by zero to three $R^{20}$, where in $het_2$ is a 5- or 6-membered saturated or unsaturated ring containing from one (1) to four (4) heteroatoms selected from the group consisting of nitrogen, oxygen and sulfur,
- e) F,
- f) $OCH_2CO_2R^{16}$, or
- g)

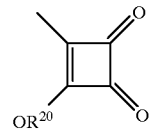

wherein $R^{22}$ is
- a) H, or
- b) methyl;

wherein $R^{23}$ and $R^{24}$ are
- a) H,
- b) $C_1$–$C_6$ alkyl, or
- c) $C_0$–$C_6$ alkyl-phenyl;

wherein $R^{25}$ is
- a) H, or
- b) $C_1$–$C_4$ alkyl;

wherein $R^{26}$ is
- a) $C_0$–$C_6$ alkyl-phenyl, wherein alkyl is optionally substituted with one OH and phenyl is substituted with one to three OH or phenyl, or
- b) $C_0$–$C_6$ alkyl-$NR^{25}$—CO-phenyl, wherein alkyl is optionally substituted with one OH and phenyl is substituted with zero to three OH or phenyl;

wherein X is —CO— or —$SO_2$— or —$CO_2$—;
wherein n is zero, one, two or three;
or a pharmaceutically acceptable salt thereof; provided that when $R^{21}$ is H, $R^{12}$ is other than —$OCH_2(CO_2R^{16})$; and that when (i) A is —$SO_2$; and/or (ii) $R^{14}$ is —$C_0$–$C_6$ alkyl-$NR^{23}R^{24}$, wherein alkyl is substituted with zero to three OH; and/or (iii) $R^{14}$ is —$NR^{24}$—CO—$R^{26}$; and/or (iv) $R^{14}$ is —O—$C_1$–$C_{10}$ alkyl $(G^6)_n$, wherein alkyl is optionally interrupted with one to three —O—, —S—, or —N—; and/or (v) $R^{21}$ is $het_2$ other than 5-tetrazolyl; then $R^{13}$ may also be
- g) —$C_1$–$C_{10}$ alkyl optionally substituted with (i) one or two —$CO_2R^{16}$ bonded to the same or different carbon atoms or (ii) one —CO—$NH_2$,
- h) —$C_0$–$C_6$ alkyl-$C_3$–$C_8$ cycloalkyl optionally substituted with one —$CO_2R^{16}$,
- i) —$C_0$–$C_6$ alkyl-phenyl optionally substituted with (i) one or two —$CO_2R^{16}$ bonded to the same or different carbon atoms or (ii) —$CH_2CH(CO_2R^{16})_2$,
- j) —$CH(R^{18})NHXR^{17}$, or
- k)

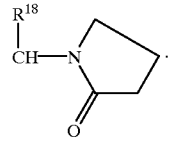

Another aspect of the invention provides compounds of formulae VI and VIII:

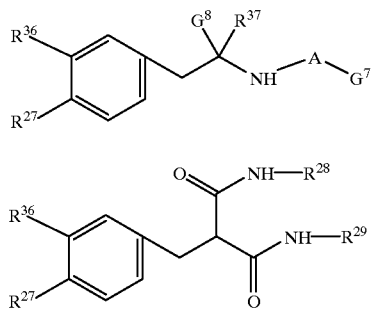

VI

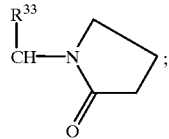

VIII wherein A is —C(O)— or —SO$_2$—;

wherein G$^7$ is
 a) —R$^{28}$ or
 b) —NR$^{34}$R$^{30}$;

wherein G$^8$ is
 a) CONR$^{99}$R$^{29}$,
 b) H,
 c) CH$_2$OH, or
 d) CH=CHR$^{29}$;

wherein R$^{99}$ is H or C$_1$–C$_6$ alkyl;

wherein R$^{27}$ is
 a) —OSO$_3$H,
 b) —OCH(CO$_2$R$^{31}$)$_2$,
 c) —OCH$_2$(CO$_2$R$^{31}$),
 d) —OCH(CO$_2$R$^{31}$)CH$_2$CO$_2$R$^{31}$,
 e) —OC(CO$_2$R$^{31}$)=CHCO$_2$R$^{31}$,
 f) —CH$_2$CH(CO$_2$R$^{31}$)$_2$,
 g) —CH=C(CO$_2$R$^{31}$)$_2$,
 h) —OCH$_2$CONHOH,
 i) —N(CH$_2$CO$_2$R$^{31}$)$_2$, or
 j) —OCHF(CO$_2$R$^{31}$);

wherein R$^{28}$ is
 a) —C$_1$–C$_{10}$ alkoxy,
 c) —C$_0$–C$_6$ alkyl-(G$^9$)$_n$, wherein alkyl is optionally substituted with one to three —O—C$_1$–C$_4$ alkyl, halo, or trifluoromethyl, and optionally interrupted with one to three —O—, —S—, or —N—,
 c) —C$_2$–C$_{10}$ alkenyl-(G$^9$)$_n$,
 d) —C$_1$–C$_{10}$ alkyl-O—(G$^9$)$_n$,
 e) —C$_1$–C$_6$ alkyl-C$_3$–C$_{10}$ cycloalkyl optionally substituted with one to three R$^{35}$,
 f) —C$_0$–C$_{10}$ alkylcarbonyl-(G$^9$)$_n$, wherein alkyl is optionally optionally interrupted with one to three —O—, —S—, or —N—,
 g) —C$_1$–C$_{10}$ alkyl optionally substituted with one or two —CO$_2$R$^{31}$ bonded to the same or different carbon atoms or with one —CO—NH$_2$,
 h) —C$_3$–C$_8$ cycloalkyl optionally substituted with one —CO$_2$R$^{31}$,
 i) —C$_0$–C$_6$ alkyl-phenyl optionally substituted with one or two —CO$_2$R$^{31}$ bonded to the same or different carbon atoms or with —CH$_2$CH(CO$_2$R$^{31}$)$_2$,
 j) —CH(R$^{33}$)NHXR$^{32}$, or
 k)

![structure k]

wherein R$^{29}$ is
 a) —C$_1$–C$_{12}$ alkyl, optionally substituted with one to three —O—C$_1$–C$_4$ alkyl, —S—C$_1$–C$_4$ alkyl, —O—G$^9$, —S—G$^9$, or —OH, and optionally interrupted with one to three —O—, —S—, or —N—,
 b) —C$_1$–C$_4$ alkyl-C$_3$–C$_6$ cycloalkyl,
 c) —C$_2$–C$_{12}$ alkenyl,
 d) —C$_3$–C$_{12}$ alkynyl,
 e) —C$_0$–C$_{10}$ alkyl(G$^9$)$_n$ wherein alkyl is optionally interrupted with one to three —O—, —S—, or —N—,
 f) —CH(CONH$_2$)C$_1$–C$_{12}$ alkyl,
 g) —C$_0$–C$_6$ alkyl-NR$^{38}$R$^{39}$, wherein alkyl is substituted with zero to three OH,
 h) —NR$^{39}$—CO—R$^{41}$, or
 i) —O—C$_1$–C$_{10}$ alkyl(G$^9$)$_n$, wherein alkyl is optionally interrupted with one to three —O—, —S—, or —N—;

wherein R$^{30}$ is
 a) —H,
 b) —C$_1$–C$_{18}$ alkyl or alkenyl, or
 c) —C$_0$–C$_6$-alkyl-G$^9$;

wherein R$^{31}$ is
 a) —H,
 b) —C$_1$–C$_{10}$ alkyl, or
 c) —C$_1$–C$_5$ alkyl-phenyl;

wherein R$^{32}$ is
 a) —C$_1$–C$_{10}$ alkyl,
 b) —C$_0$–C$_6$ alkyl-G$^9$,
 c) —C$_1$–C$_6$ alkyl CONH$_2$,
 d) —C$_1$–C$_6$ alkyl NHCO$_2$R$^{31}$,
 e) —C$_1$–C$_6$ alkyl-OR$^{31}$,
 f) —C$_1$–C$_6$ alkyl-NHSO$_2$Me,
 g) —C$_1$–C$_6$ alkyl-O—G$^9$,
 h) —C$_1$–C$_6$ alkyl-S—G$^9$, or
 i) —C$_1$–C$_6$ alkyl-CO$_2$R$^{31}$;

wherein R$^{33}$ is
 a) —H,
 b) —C$_1$–C$_6$ alkyl-G$^9$,
 c) —C$_1$–C$_6$ alkyl-CO$_2$R$^{31}$,
 d) —C$_1$–C$_6$ alkyl CONH$_2$,
 e) —C$_1$–C$_6$ alkyl NHCO$_2$R$^{31}$,
 f) —C$_1$–C$_{10}$ alkyl,
 g) —C$_1$–C$_{10}$ cycloalkyl,
 h) —C$_1$–C$_6$ alkyl-SR$^{31}$, or
 i) —C$_1$–C$_6$ alkyl-S(=O)R$^{31}$;

wherein R$^{34}$ is
 a) C$_0$–C$_6$ alkyl-G$^9$,
 b) CH(R$^{33}$)CO$_2$R$^{31}$, c) $CH(R^{33})CH_2CO_2R^{31}$, or d) $CH(R^{33})CONHCH_2CO_2R^{31}$;

wherein $G^9$ is a) phenyl substituted by zero (0) to four (4) $R^{35}$, b) naphthyl substituted by zero (0) to three (3) $R^{35}$, or c) $het_1$ substituted by zero (0) to three (3) $R^{35}$;

wherein $het_1$ is a 5- or 6-membered saturated or unsaturated ring containing from one (1) to four (4) heteroatoms selected from the group consisting of nitrogen, oxygen and sulfur; and including any bicyclic group in which any of the above heterocyclic rings is fused to a benzene ring, $C_3$–$C_8$ cycloalkyl, or another heterocycle; and optionally, the nitrogen and sulfur heteroatoms may be in oxidized form if chemically feasible;

wherein $R^{35}$ may be any of the following:

a) $C_1$–$C_8$ alkyl substituted by zero (0) to three (3) halo, b) $C_2$–$C_8$ alkenyl, c) OH, d) O—$C_1$–$C_5$ alkyl, e) O—$C_0$–$C_5$ alkyl-phenyl, f) —$(CH_2)_n$—O—$C_1$–$C_5$ alkyl substituted by zero (0) to three (3) hydroxy, g) —$(CH_2)_n$—O—$C_2$–$C_7$ alkenyl substituted by zero (0) to three (3) hydroxy, h) halo, i) $NH_2$, j) amino-$C_1$–$C_5$ alkyl, k) mono- or di-$C_1$–$C_5$ alkylamino, l) —C(O)—$C_1$–$C_5$ alkyl, m) —CHO, n) —C(O)—$C_0$–$C_5$ alkyl-phenyl, o) —$COOR^{31}$, p) —$CON(R^{31})_2$, q) —$C_3$–$C_7$ cycloalkyl, r) —$NO_2$, s) —CN, t) —$SO_3H$, u) —$SO_2N(R^{31})_2$, v) —$O[(CH_2)_2$—$O]_n$—$CH_3$, w) —$[CH_2$—$O]_n$—$C_1$–$C_3$ alkyl, x) —$NR^{31}(CO)$—$NR^{31}$, y) —$CF_3$, z) —$NR^{31}(CO)C_1$–$C_5$ alkyl, a1) —$N(R^{31})$—$SO_2$—$R^{31}$, b1) —O—C(O)—$R^{31}$, c1) —S(O)—$R^{31}$, d1) —$SR^{31}$, e1) —$SO_2$—$R^{31}$, f1) phenyl, or g1) oxo;

wherein $R^{36}$ is a) —H, b) —$CO_2R^{31}$, c) —CONHOH, d) $het_2$ substituted by zero to three $R^{35}$, where in $het_2$ is a 5- or 6-membered saturated or unsaturated ring containing from one (1) to four (4) heteroatoms selected from the group consisting of nitrogen, oxygen and sulfur, e) F, f) $OCH_2CO_2R^{31}$, or g) 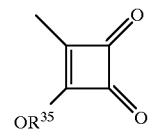

wherein $R^{37}$ is a) H, or b) methyl;

wherein $R^{38}$ and $R^{39}$ are a) H, b) $C_1$–$C_6$ alkyl, or c) $C_0$–$C_6$ alkyl-phenyl;

wherein $R^{40}$ is a) H, or b) $C_1$–$C_4$ alkyl;

wherein $R^{41}$ is a) $C_0$–$C_6$ alkyl-phenyl, wherein alkyl is optionally substituted with one OH and phenyl is substituted with one to three OH or phenyl, or b) $C_0$–$C_6$ alkyl-$NR^{40}$—CO-phenyl, wherein alkyl is optionally substituted with one OH and phenyl is substituted with zero to three OH or phenyl;

wherein X is —CO— or —$SO_2$— or —$CO_2$—;

wherein n is zero, one, two or three;

or a pharmaceutically acceptable salt thereof;

provided that when $R^{36}$ is H, $R^{27}$ is other than —$OCH_2(CO_2R^{31})$.

Another aspect of the invention provides compounds of formula VII:

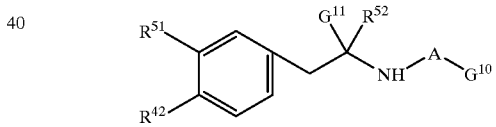

VII wherein A is —C(O)— or —$SO_2$—;

wherein $G^{10}$ is —$R^{43}$;

wherein $G^{11}$ is a) $CONR^{99}R^{44}$, b) H, c) $CH_2OH$, or d) $CH$=$CHR^{44}$;

wherein $R^{99}$ is H or $C_1$–$C_6$ alkyl;

wherein $R^{42}$ is a) —$OSO_3H$, b) —$OCH(CO_2R^{46})_2$, c) —$OCH_2(CO_2R^{46})$, d) —$OCH(CO_2R^{46})CH_2CO_2R^{46}$, e) —$OC(CO_2R^{46})$=$CHCO_2R^{46}$, f) —$CH_2CH(CO_2R^{46})_2$, g) —CH=$C(CO_2R^{46})_2$, h) —$OCH_2CONHOH$, i) —$N(CH_2CO_2R^{46})_2$, or j) —$OCHF(CO_2R^{46})$;

wherein $R^{43}$ is
- a) —$C_1$–$C_{10}$ alkoxy,
- b) —$C_0$–$C_6$ alkyl-$(G^{12})_n$, wherein alkyl is optionally substituted with one to three —O—$C_1$–$C_4$ alkyl, halo, or trifluoromethyl, and optionally interrupted with one to three —O—, —S—, or —N—, with the proviso that when $G^{12}$ is phenyl, the phenyl group must be substituted by one (1) to four (4) $R^{50}$ groups, provided that —$COOR^{46}$ is not a substituent,
- c) —$C_2$–$C_{10}$ alkenyl-$(G^{12})_n$,
- d) —$C_1$–$C_{10}$ alkyl-O—$(G^{12})_n$,
- e) —$C_1$–$C_6$ alkyl-$C_3$–$C_{10}$ cycloalkyl optionally substituted with one to three $R^{50}$, or
- f) —$C_0$–$C_{10}$ alkylcarbonyl-$(G^{12})_n$ wherein alkyl is optionally interrupted with one to three —O—, —S—, or —N—;

wherein $R^{44}$ is
- a) —$C_1$–$C_{12}$ alkyl, optionally substituted with one to three —O—$C_1$–$C_4$ alkyl, —S—$C_1$–$C_4$ alkyl, —O—$G^{12}$, —S—$G^{12}$, or —OH, and optionally interrupted with one to three —O—, —S—, or —N—,
- b) —$C_1$–$C_4$ alkyl-$C_3$–$C_6$ cycloalkyl,
- c) —$C_2$–$C_{12}$ alkenyl,
- d) —$C_3$–$C_{12}$ alkynyl,
- e) —$C_0$–$C_{10}$ alkyl$(G^{12})_n$ wherein alkyl is optionally interrupted with one to three —O—, —S—, or —N—,
- f) —$CH(CONH_2)C_1$–$C_{12}$ alkyl,
- g) —$C_0$–$C_6$ alkyl-$NR^{53}R^{54}$, wherein alkyl is substituted with zero to three OH,
- h) —$NR^{54}$—CO—$R^{56}$, or
- i) —O—$C_1$–$C_{10}$ alkyl$(G^{12})_n$, wherein alkyl is optionally interrupted with one to three —O—, —S—, or —N—;

wherein $R^{46}$ is
- a) —H,
- b) —$C_1$–$C_{10}$ alkyl, or
- c) —$C_1$–$C_5$ alkyl-phenyl;

wherein $R^{47}$ is
- a) —$C_1$–$C_{10}$ alkyl,
- b) —$C_0$–$C_6$ alkyl-$G^{12}$,
- c) —$C_1$–$C_6$ alkyl-$CONH_2$,
- d) —$C_1$–$C_6$ alkyl $NHCO_2R^{46}$,
- e) —$C_1$–$C_6$ alkyl-$OR^{46}$,
- f) —$C_1$–$C_6$ alkyl-$NHSO_2Me$,
- g) —$C_1$–$C_6$ alkyl-O—$G^{12}$,
- h) —$C_1$–$C_6$ alkyl-S—$G^{12}$, or
- i) —$C_1$–$C_6$ alkyl-$CO_2R^{46}$;

wherein $R^{48}$ is
- a) —H,
- b) —$C_1$–$C_6$ alkyl-$G^{12}$,
- c) —$C_1$–$C_6$ alkyl-$CO_2R^{46}$,
- d) —$C_1$–$C_6$ alkyl $CONH_2$,
- e) —$C_1$–$C_6$ alkyl $NHCO_2R^{46}$,
- f) —$C_1$–$C_{10}$ alkyl,
- g) —$C_1$–$C_{10}$ cycloalkyl,
- h) —$C_1$–$C_6$ alkyl-$SR^{46}$, or
- i) —$C_1$–$C_6$ alkyl-$S(=O)R^{46}$;

wherein $G^{12}$ is
- a) phenyl substituted by zero (0) to four (4) $R^{50}$,
- b) naphthyl substituted by zero (0) to three (3) $R^{50}$, or
- c) $het_1$ substituted by zero (0) to three (3) $R^{50}$;

wherein $het_1$ is a 5- or 6-membered saturated or unsaturated ring containing from one (1) to four (4) heteroatoms selected from the group consisting of nitrogen, oxygen and sulfur; and including any bicyclic group in which any of the above heterocyclic rings is fused to a benzene ring, $C_3$–$C_8$ cycloalkyl, or another heterocycle; and optionally, the nitrogen and sulfur heteroatoms may be in oxidized form if chemically feasible;

wherein $R^{50}$ may be any of the following:
- a) $C_1$–$C_8$ alkyl substituted by zero (0) to three (3) halo,
- b) $C_2$–$C_8$ alkenyl,
- c) OH,
- d) O—$C_1$–$C_5$ alkyl,
- e) O—$C_0$–$C_5$ alkyl-phenyl,
- f) —$(CH_2)_n$—O—$C_1$–$C_5$ alkyl substituted by zero (0) to three (3) hydroxy,
- g) —$(CH_2)_n$—O—$C_2$–$C_7$ alkenyl substituted by zero (0) to three (3) hydroxy,
- h) halo,
- i) $NH_2$,
- j) amino-$C_1$–$C_5$ alkyl,
- k) mono- or di-$C_1$–$C_5$ alkylamino,
- l) —C(O)—$C_1$–$C_5$ alkyl,
- m) —CHO,
- n) —C(O)—$C_0$–$C_5$ alkyl-phenyl,
- o) —$COOR^{46}$,
- p) —$CON(R^{46})_2$,
- q) —$C_3$–$C_7$ cycloalkyl,
- r) —$NO_2$,
- s) —CN,
- t) —$SO_3H$,
- u) —$SO_2N(R^{46})_2$,
- v) —$O[(CH_2)_2$—$O]_n$—$CH_3$,
- w) —$[CH_2$—$O]_n$—$C_1$–$C_3$ alkyl,
- x) —$NR^{46}(CO)$—$NR^{46}$,
- y) —$CF_3$,
- z) —$NR^{46}(CO)C_1$–$C_5$ alkyl,
- a1) —$N(R^{46})$—$SO_2$—$R^{46}$,
- b1) —O—C(O)—$R^{46}$,
- c1) —S(O)—$R^{46}$,
- d1) —$SR^{46}$,
- e1) —$SO_2$—$R^{46}$,
- f1) phenyl, or
- g1) oxo;

wherein $R^{51}$ is
- a) —H,
- b) —$CO_2R^{46}$,
- c) —CONHOH,
- d) $het_2$ substituted by zero to three $R^{50}$, where in $het_2$ is a 5- or 6-membered saturated or unsaturated ring containing from one (1) to four (4) heteroatoms selected from the group consisting of nitrogen, oxygen and sulfur,
- e) F,
- f) $OCH_2CO_2R^{46}$, or g)

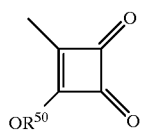

wherein $R^{52}$ is
  a) H, or
  b) methyl;
wherein $R^{53}$ and $R^{54}$ are
  a) H,
  b) $C_1$–$C_6$ alkyl, or
  c) $C_0$–$C_6$ alkyl-phenyl;
wherein $R^{55}$ is
  a) H, or
  b) $C_1$–$C_4$ alkyl;
wherein $R^{56}$ is
  a) $C_0$–$C_6$ alkyl-phenyl, wherein alkyl is optionally substituted with one OH and phenyl is substituted with one to three OH or phenyl, or
  b) $C_0$–$C_6$ alkyl-$NR^{55}$—CO-phenyl, wherein alkyl is optionally substituted with one OH and phenyl is substituted with zero to three OH or phenyl;
wherein X is —CO— or —$SO_2$— or —$CO_2$—;
wherein n is zero, one, two or three;
or a pharmaceutically acceptable salt thereof;
provided that when $R^{51}$ is H, $R^{42}$ is other than —$OCH_2$($CO_2R^{46}$); and that when (i) A is —$SO_2$—; and/or (ii) $R^{44}$ is —$C_0$–$C_6$ alkyl-$NR^{53}R^{54}$, wherein alkyl is substituted with zero to three OH; and/or (iii) $R^{44}$ is —$NR^{54}$—CO—$R^{56}$; and/or (iv) $R^{44}$ is —O—$C_1$–$C_{10}$ alkyl ($G^{12}$)$_n$, wherein alkyl is optionally interrupted with one to three —O—, —S—, or —N—; and/or (v) $R^{51}$ is $het_2$ other than 5-tetrazolyl; and/or (vi) $R^{99}$ is $C_1$–$C_6$ alkyl; then
(1) $R^{43}$ may also be
  g) —$C_1$–$C_{10}$ alkyl optionally substituted with (i) one or two —$CO_2R^{46}$ bonded to the same or different carbon atoms or (ii) one —CO—$NH_2$,
  h) —$C_0$–$C_6$ alkyl-$C_3$–$C_8$ cycloalkyl optionally substituted with one —$CO_2R^{46}$,
  i) —$C_0$–$C_6$ alkyl-phenyl optionally substituted with (i) one or two —$CO_2R^{46}$ bonded to the same or different carbon atoms or (ii) —$CH_2CH(CO_2R^{46})_2$,
  j) —CH($R^{48}$)$NHXR^{47}$, or
  k)

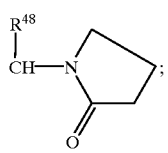

and
(2) $G^{10}$ may also be
  b) —$NR^{49}R^{45}$;
wherein $R^{45}$ is
  a) —H,
  b) —$C_1$–$C_{18}$ alkyl or alkenyl, or
  c) —$C_0$–$C_6$-alkyl-$G^{12}$; and wherein $R^{49}$ is
  a) $C_0$–$C_6$ alkyl-$G^{12}$,
  b) CH($R^{48}$)$CO_2R^{46}$,
  c) CH($R^{48}$)$CH_2CO_2R^{46}$, or
  d) CH($R^{48}$)$CONHCH_2CO_2R^{46}$.

Another aspect of this invention provides a pharmaceutical composition, comprising the compounds of formulae I–VIII and a pharmaceutically acceptable carrier.

Another aspect of this invention provides a method for treating a patient by administering an effective amount of a compound of formulae I–VIII.

Another aspect of this invention provides a method of inhibiting protein tyrosine phosphatases, comprising contacting a cell with the compounds of formulae I–VIII.

Another aspect of this invention provides the compounds of formulae I–VIII above excluding the compounds disclosed in U.S. Ser. No. 09/138,642 and PCT/US98/17327, which are hereby incorporated by reference.

The compounds of the present invention are named according to the IUPAC or CAS nomenclature system.

The carbon atoms content of various hydrocarbon-containing moieties is indicated by a prefix designating the minimum and maximum number of carbon atoms in the moiety, i.e., the prefix $C_i$–$C_j$ indicates a moiety of the integer "i" to the integer "j" carbon atoms, inclusive. Thus, for example, $C_1$–$C_3$ alkyl refers to alkyl of one to three carbon atoms, inclusive, or methyl, ethyl, propyl, and isopropyl, straight and branched forms thereof.

Also, the carbon atom content of various hydrocarbon-containing moieties of the present invention may be indicated by a subscripted integer representing the number of carbon and hydrogen atoms in the moiety, e.g., "$C_nH_{2n}$" indicates a moiety of the integer "n" carbon atoms, inclusive, and the integer "2n" hydrogen atoms, inclusive. Thus, for example, "$C_nH_{2n}$" wherein n is one to three carbon atoms, inclusive, and two to six hydrogen atoms, inclusive, or methyl, ethyl, propyl and isopropyl, and all isomeric, straight and branched forms thereof.

Examples of alkyl of one to nine carbon atoms, inclusive, are methyl, ethyl, propyl, butyl, pentyl, hexyl, heptyl, octyl, and nonyl, and all isomeric forms thereof and straight and branched forms thereof.

Examples of alkenyl of one to five carbon atoms, inclusive, are ethenyl, propenyl, butenyl, pentenyl, all isomeric forms thereof, and straight and branched forms thereof.

By "halo" is meant the typical halogen atoms, such as fluorine, chlorine, bromine, and iodine.

The present invention encompasses all possible combinations of configurations at each of the possible chiral centers. The preferred configuration for the chiral center depicted in formulae I–VIII is (S), and the preferred configuration for the chiral center present in $R^2$ (d and e) is (S).

The compounds of formulae I–VIII of the present invention are prepared as described in the Charts, Preparations and Examples below, or are prepared by methods analogous thereto, which are readily known and available to one of ordinary skill in the art of organic synthesis.

CHART A

Commercially available tyrosine benzyl ester A-1 is acylated with monomethyl succinate under standard amide coupling conditions employing 1-(3-dimethylaminopropyl)-3-ethylcarbodiimide hydrochloride (EDC) as the coupling reagent (Tet. Lett. 1993, 34:7685) to afford A-2. Alkylation of the phenol is effected with diethylchloromalonate in acetone with potassium carbonate as catalyst, conditions analogous to those previously described for alkylation of phenols (J. Am. Chem. Soc. 1951, 73:872). Standard hydrogenolysis of the benzyl ester A-3 affords A-4, which is then acylated with various amines ($R^3NH_2$) under the influence of EDC. The target acids A-5 are obtained by saponification.

CHART B

Commercially available Cbz-tyrosine (B-1) is coupled with n-pentylamine under standard EDC conditions, affording amide B-2. Alkylation of the phenol as described in Chart A gives ether B-3, which is then hydrogenolytically deprotected to obtain amine B-4, isolated as the corresponding HCl salt. Acylation of the free amine with various carboxylic acids $R^2COOH$ is accomplished with EDC. Final saponification with dilute lithium hydroxide followed by acidification gives the sparingly soluble malonic acids B-5.

CHART C

Amine hydrochloride B-4 (from Chart B) is acylated with various isocyanates in the presence of triethylamine in methylene chloride to afford the corresponding urethanes. Saponification of the esters then provides the acids C-1.

CHART D

Amine B-4 (from Chart B) is converted to the corresponding isocyanate D-1 by reaction with diphosgene and Proton Sponge at 0 C (J. Org. Chem. 1996, 61:3883). Addition of N-benzylglycine ethyl ester followed by saponification then affords the desired urethane triacid D-2.

CHART E

Commercially available Boc-(L)-tyrosine E-1 is coupled with n-pentylamine, as described for Chart B, to give E-2. The Boc group is removed with HCl in acetic acid, and the resulting amine E-3 is coupled with a mono succinate ester as described for Chart A. The resulting phenol amides E-4 and E-5 are added directly to a dialkyl acetylenedicarboxylate in the presence of triethylamine (Aust. J. Chem. 1995, 48:677). Fumarate ester E-6 is hydrogenated with 10% palladium on carbon to give the saturated triacid E-8. Alternatively, fumarate ester E-7 is saponified to give the unsaturated triacid E-9.

CHART F

Amine hydrochloride E-3 (from Chart E) is reacted with succinic anhydride in the presence of triethylamine to afford the acid F-1. Sulfation of the phenol is effected with sulfur trioxide/pyridine complex in DMF (Int. J. Pep. Prot. Res. 1990, 35:566) and purification is accomplished with reverse phase HPLC to give F-2.

CHART G

Previously described E-2 (from Chart E) is treated with trifluoromethanesulfonic anhydride in the presence of pyridine to afford triflate G-1. Palladium-catalyzed cross-coupling of G-1 with tributyl(vinyl)tin affords G-2. G-2 is then ozonized followed by reduction with dimethyl sulfide to give G-3. This aldehyde is then condensed with dibenzylmalonate in the presence of piperidine acetate to afford G-4. Deprotection of the Boc group with saturated HCl/HOAc affords G-5 which is subsequently reacted with succinic anhydride to afford G-6. Hydrogenation of G-6 with $H_2$ and 10% Pd/C gives final triacid G-7.

CHART H

Direct saponification of dibenzylester G-6 (from Chart G) affords the unsaturated triacid H-1.

CHART I

Alkylation of phenol E-4 (from Chart E) is accomplished by a carbenoid insertion reaction with di-t-butyl diazomalonate (Synthesis 1974, 347) catalyzed by rhodium acetate (J. Med. Chem. 1995, 38:4270), affording malonate ether I-1. Removal of the t-butyl esters is accomplished with trifluroacetic acid in methylene chloride, and the benzyl ester is removed by hydrogenolysis, affording the desired triacid I-3.

CHART J

Amide E-2 (from Chart E) is alkylated on the phenolic hydroxyl with dibenzyl bromomalonate as described for Chart A (potassium carbonate/acetone) to give J-3. The Boc group is removed with HCl in acetic acid, affording the amine hydrochloride J-4. The free amine is added to various cyclic anhydrides in the presence of triethylamine, giving acids J-5. Hydrogenolysis of the benzyl esters then affords the desired triacids J-6.

CHART K

Chart K describes an alternative synthesis of A-5 (from Chart A) (now K-6 in Chart K) wherein benzyl esters are used as the protecting group for the malonate carboxyls instead of ethyl esters. Tyrosine t-butyl ester K-1 is acylated with monobenzyl succinate under the influence of EDC to afford amide K-2. Alkylation with dibenzyl bromomalonate under the conditions described in Chart A affords ether K-3. The t-butyl ester is removed with TFA in methylene chloride, giving carboxylic acid K-4, which is coupled with various amines using EDC as the coupling reagent. Final deprotection of K-5 is accomplished by hydrogenolysis to give K-6.

CHART L

Chart L describes an extension of Chart J wherein amine J-4 (from chart J) is coupled (EDC) with a protected amino acid to afford L-2. The Boc group is removed with HCl in acetic acid to give amine L-3. Addition to succinic anhydride followed by hydrogenolysis of the benzyl esters L-4 then provides the desired tetracids L-5.

CHART M

Cbz-tyrosine M-1 is coupled (EDC) with norleucine amide to provide M-2. Alkylation of the phenol with diethyl chloromalonate as described for Chart A gives ether M-3. The Cbz group is removed by hydrogenation, and the resulting free amine M-4 is acylated with succinic anhydride. Carboxylic acid M-5 is then saponified to give the target triacid M-6.

CHART N

Commercially available N-1 is condensed with dibenzylmalonate in the presence of piperidine acetate to afford N-2. N-2 is coupled to previously described J-4 (from Chart J) to afford N-3. Hydrogenation of N-3 leads to final tetraacid N-4.

CHART O

Direct hydrogenation of benzyl ester L-2 (from Chart L) gives the Boc-protected triacid O-1.

CHART P

Acylation of amine L-3 (from Chart L) with hexanoyl chloride gives amide P-1. Hydrogenation then removes the benzyl esters, providing triacid P-2.

CHART Q

Commercially available Q-1 is N-protected as the Boc derivative by reaction with Boc$_2$O, and the resulting compound is converted to amylamide Q-2 by coupling (EDC) with amylamine. Palladium catalyzed carbonylation with carbon monoxide and methanol affords methyl ester Q-3. Alkylation of the phenolic oxygen with methylbromoacetate yields ether Q-4, which is N-deblocked with trifluoroacetic acid in methylene chloride and then acylated with succinic anhydride, leading to amide Q-5. Saponification under standard conditions then produced the desired triacid Q-6.

CHART R

Q-4 is deblocked with HCl/dioxane before coupling with 3-phenylpropanoic acid in the presence of EDC and saponified to afford R-4. Alternatively, Q-4 may be deblocked as before, followed by coupling with Boc-L-Phe to afford R-1. R-1 may be saponified directly to R-2, or the Boc group can be removed with HCl/dioxane, and the resulting amine can be coupled with an acid chloride or carboxylic acid to afford R-3 after saponification.

CHART S

S-1 is alkylated with diethylchloromalonate to afford S-2. Removal of the Boc group with HCl/dioxane followed by coupling with Boc-L-p-benzoyl-Phe gives S-3. Removal of the Boc group again followed by addition of succinic anhydride and saponification provides triacid S-4.

CHART T

Iodotyrosine Q-2 is converted to nitrile T-1 by the action of zinc cyanide and Pd catalyst. Alkylation with methyl bromoacetate affords ether T-2, which is coupled with Boc-L-Phe after deblocking of the amine group with HCl. The nitrile is converted to the corresponding tetrazole T-4 with TMS-azide and catalytic dibutyltin oxide. Final saponification affords the acid T-5.

CHART U

Q-2 is carbonylated with carbon monoxide and palladium catalyst to afford esters U-1 and Q-3. The phenols are alkylated with methyl or benzyl bromoacetate to afford U-2 and U-3. The Boc group is removed with TFA, followed by coupling with Boc-L-Phe, affording amides U-4 and U-5. Catalytic hydrogenation removes the benzyl esters, providing U-6 and U-7. Coupling of the free carboxylic acids with hydroxylamine generates the hydroxamic acids U-8 and U-9, and the methyl esters are saponified with lithium hydroxide to provide acids U-10 and U-11.

CHART V

Ester V-1 is reduced with DIBAL to afford aldehyde V-2, which is subsequently converted by a Wittig reaction to olefin V-3. The phenol is alkylated with dibenzyl bromomalonate to afford ether V-4. Deprotection of the amine with TFA, followed by acylation of the free amine with monobenzylsuccinate affords amide V-5. Saponification of the esters (LiOH) then provides the triacid V-6.

CHART W

Commercially available acid W-1 is amidated with n-pentylamine (EDC), and the resulting amide W-2 is catalytically hydrogenated to aniline W-3. The aniline is bis(alkylated) with methyl bromoacetate to afford W-4. Removal of the Boc group (TFA) followed by acylation of the amine with Boc-L-Phe affords W-5. Final saponification (LiOH) then provides the diacid W-6.

CHART X

Commercially available meta-iodotyrosine is esterified with benzyl alcohol before coupling with Boc-L-Phe, affording X-2. The iodine is carboxylated with CO under palladium catalysis, providing ester X-3, which is alkylated with methyl bromoacetate. The resulting ether X-4 is hydrogenated to remove the benzyl ester protecting group, and the resulting acid X-5 is reduced with sodium borohydride via the corresponding acyl imidazole to alcohol X-6. Final saponification of the esters affords the diacid X-7.

CHART Y

Commercially available methyl tyrosine Y-1 is protected as the N-Boc derivative under standard conditions before conversion of the carboxylic acid to amide Y-3. This amide is alkylated with dibenzyl bromomalonate to afford ether Y-4. Boc cleavage with HCl is followed by acylation of the free amine with succinic anhydride, providing acid Y-5. Final saponification with LiOH affords triacid Y-6.

CHART Z

Meta fluorotyrosine Z-1 is converted to triacid Z-6 exactly as described in Chart Y.

CHART AA

4-Hydroxybenzaldehyde AA-1 is alkylated with diethyl chloromalonate to afford ether AA-2. Mono ethyl malonate AA-3 is coupled with amylamine under standard conditions (DEPC) to afford amide AA-4. Hydrolysis of the ester with aq NaOH provides acid AA-5. Coupling of AA-5 with beta-alanine ethyl ester provides malondiamide AA-6, which is condensed with aldehyde AA-2 under Knoevenagel conditions. The resulting methylidene malondiamide AA-7 (a mixture of olefin isomers) is saturated by catalytic hydrogenation, and the ester AA-8 is saponified to triacid AA-9 with aq NaOH.

CHART BB

Amine B-4 (from Chart B) is acylated with the appropriate protected amino acid under the influence of EDC and triethylamine. The resulting amides BB-1 is directly saponified to give BB-3. Alternatively, where $R^6$ is t-butylcarboxy (Boc), the Boc group is removed with HCl/acetic acid, and the resulting free amine acylated with succinic anhydride. Final saponification then affords the triacids BB-2.

CHART CC

Diol CC-1 (reference given in Example 142) is bis(alkylated) with ethyl bromoacetate, and the resulting bis(ether) CC-2 is hydrogenated to remove the benzyl ester. The carboxylic acid CC-3 is coupled with amylamine under standard conditions (DEPC) before cleavage of the Boc group with TFA. Free amine CC-5 is then coupled with Boc-L-Phe (DEPC), and the resulting amide CC-6 is saponified to the diacid CC-7.

CHART DD

Diester Q-4 (Chart Q) is reacted with TFA to cleave the Boc group, and the free amine DD-1 is coupled (DEPC) with the appropriate amino acid (see Example 143) to afford amide DD-2. Saponification provides diacid DD-3.

CHART EE

Q-2 (Chart Q) is carbonylated with CO under palladium catalysis to afford ester EE-1. The phenol is alkylated with ethyl bromofluoroacetate/potassium carbonate to afford ether EE-2. Boc deprotection and amide coupling of the free amine with Boc-L-Phe under standard conditions affords diester EE-3, which is saponified to provide the diacid EE-4.

CHART FF

Acid X-5 (Chart X) is coupled with 4-phenylbutylamine under standard amide coupling conditions to provide FF-1. Saponification of the esters affords diacid FF-2.

Preferred methods of preparation are depicted in Charts A, B, BB, Q and R.

The present invention provides for compounds of formulae I–VIII or pharmacologically acceptable salts and/or hydrates thereof. Pharmacologically acceptable salts refers to those salts which would be readily apparent to a manufacturing pharmaceutical chemist to be equivalent to the parent compound in properties such as formulation, stability, patient acceptance and bioavailability. Examples of salts of the compounds of formula I–VII include lithium, sodium and potassium.

Where $R^5$, $R^{16}$, $R^{31}$ and $R^{46}$ are other than H, the compounds would not be expected to have intrinsic activity, but would be expected to possess activity in vivo following hydrolysis by non-specific esterases to the corresponding carboxylic acids.

The compounds of the present invention are useful for treating patients, such as human patients, with noninsulin-dependent diabetes mellitus (NIDDM) and conditions resulting from NIDDM, such as obesity. For this indication, these compounds may be administered by oral, intranasal, transdermal, subcutaneous and parenteral (including intramuscular and intravenous) routes in doses of 0.1 mg to 1000 mg/kg of body weight per day.

Those skilled in the art would know how to formulate the compounds of this invention into appropriate pharmaceutical dosage forms. Examples of the dosage forms include oral formulations, such as tablets or capsules, or parenteral formulations, such as sterile solutions.

When the compounds in this invention are administered orally, an effective amount is from about 0.1 mg to 100 mg per kg of body weight per day. Either solid or fluid dosage forms can be prepared for oral administration. Solid compositions, such as compressed tablets, are prepared by mixing the compounds of this invention with conventional pharmaceutical carriers such as talc, magnesium stearate, dicalcium phosphate, magnesium aluminum silicate, calcium sulfate, starch, lactose, acacia, methyl cellulose, or functionally similar pharmaceutical diluents and carriers. Capsules are prepared by mixing the compounds of this invention with an inert pharmaceutical diluent and placing the mixture into an appropriately sized hard gelatin capsule. Soft gelatin capsules are prepared by machine encapsulation of a slurry of the compounds of this invention with an acceptable inert oil such as vegetable oil or light liquid petrolatum.

Syrups are prepared by dissolving the compounds of this invention in an aqueous vehicle and adding sugar, aromatic flavoring agents and preservatives. Elixirs are prepared using a hydroalcoholic vehicle such as ethanol, suitable sweeteners such as sugar or saccharin and an aromatic flavoring agent. Suspensions are prepared with an aqueous vehicle and a suspending agent such as acacia, tragacanth, or methyl cellulose.

When the compounds of this invention are administered parenterally, they can be given by injection or by intravenous infusion. An effective amount is from about 0.1 mg to 100 mg per kg of body weight per day. Parenteral solutions are prepared by dissolving the compounds of this invention in aqueous vehicle and filter sterilizing the solution before placing in a suitable sealable vial or ampule. Parenteral suspensions are prepared in substantially the same way except a sterile suspension vehicle is used and the compounds of this invention are sterilized with ethylene oxide or suitable gas before it is suspended in the vehicle.

The exact route of administration, dose, or frequency of administration would be readily determined by those skilled in the art and is dependant on the age, weight, general physical condition, or other clinical symptoms specific to the patient to be treated.

The utility of representative compounds of the present invention has been demonstrated in the biological assays described below:

PTP1 Assays: A construct, which consisted of a C-terminal truncation of rat PTP1 (amino acid residues 1–322) (cloned from a rat brain library) with an N-terminal glutathione S-transferase (GST) tag and an adjacent thrombin cleavage site, was inserted into vector plasmid pGEX-2T and transformed into *E. coli* strain TG-1 under the control of a lac promoter (K. L. Guan and J. E. Dixon (1991) Eukaryotic proteins expressed in *Escherichia coli*: an improved thrombin cleavage and purification procedure of fusion proteins with glutathione S-transferase. Analyt. Biochem. 192: 262–267). The GST-fusion protein was purified on a glutathione agarose affinity column, the GST tag was cleaved with thrombin, and the active enzyme was recovered for use in an assay to identify PTP inhibitors.

The equivalent construct of human PTP1B (amino acid residues 1–321) (cloned from a human placental library), without the GST tag and thrombin cleavage site, was inserted into a pMB replicon and transformed into *E. coli* BL21(DE3), a strain containing a chromosomal copy of the gene for T7 RNA polymerase under control of a lacUV5 promoter. Expression of PTP1B was induced with isopropyl thiogalactose and the soluble protein was purified by ion exchange, hydrophobic interaction and gel exclusion chromatography for use in the assay to identify PTP inhibitors.

PTP1 activity is measured using either p-nitrophenol phosphate (pNPP) or a triphosphopeptide (that matches residues 1142 through 1153 of the β-subunit and the insulin receptor) as substrate in a 96-well microtiter plate format. An assay pH of 7.2 is used for standard assays (measured $_{405}$=9800 at pH 7.2).

Human PTP1B, which is highly homologous to rat PTP1, was assayed exactly as described above for PTP1. The PTP inhibitors described here also inhibit PTP1B with similar or identical potencies.

Standard assays are conducted at room temperature in a total volume of 0.2 ml that contains Hepes buffer (50 mM, pH 7.2), NaCl (50 mM), EDTA (1 mM), DTT (1 mM), bovine serum albumin (1 mg/ml), pNPP (1 mM) and PTP1 (35 ng/ml). Compounds (2 μl of 10 mM solutions) are pipetted into wells of microtiter plates followed by 198 μl of premixed reaction mix (with PTP1 and pNPP added immediately before use). The rate of change in $A_{405}$ is recorded for 60 min. Two wells on each plate contain DMSO controls and two wells contain sodium orthovanadate (1 mM) which inhibits PTP1-catalyzed hydrolysis of pNPP completely. Data are expressed as percent inhibition relative to the average of the DMSO controls measured on the same microtiter plate.

When triphosphopeptide 142–1153 is used as substrate, the rate of release of inorganic phosphate is measured using a Malachite Green/phosphomolybdate reaction (A. A. Baykov, O. A. Evtushenko, and S. M. Avaeva (1988) A Malachite Green procedure for orthophosphate determination and its use in alkaline phosphatase-based enzyme immunoassay. Anal. Biochem. 171: 266–270.) in a microtiter plate format. Standard assays are conducted at room temperature in a total volume of 50 µl that contains Hepes buffer (50 mM, pH 7.2), NaCl (50 mM), EDTA (1 mM), DTT (1 mM), bovine serum albumin (1 mg/ml), triphosphopeptide 142–1153 (200 µM) and PTP1 (87 ng/ml). Reactions are terminated with the addition of 0.15 ml of Malachite Green/ammonium molybdate reagent [10 ml Malachite Green (0.44 g in 6N $H_2SO_4$), 2.5 ml ammonium molybdate (7.5% w/v), 0.2 ml Tween 20 (11% w/v)] that is diluted with 8 parts of water immediately before use, and after 1 h absorbance at 650 nm is measured. The phosphate assay is calibrated using either $KH_2PO_4$ or pNPP (after ashing with $Mg(NO_3)_2$) which gives essentially identical standard curves. The phosphate assay is useful in the range of 1 to 10 mmol $P_i$.

The % inhibition of pNPP-hydrolysis by compounds of the present invention are listed in Tables 1 through 3 below.

The following compounds within the scope of formulae I–IV of the present invention are preferred:

(S)-5-[[[[1-[[4-(Dicarboxymethoxy)phenyl]methyl]-2-oxo-2-(pentylamino)ethyl]amino]carbonyl]amino]-1,3-benzenedicarboxylic acid;

(S)-N-[[[1-[[4-(Dicarboxymethoxy)phenyl]methyl]-2-oxo-2-(pentylamino)ethyl]amino]carbonyl]-L-glutamic acid;

N-[(1,1-Dimethylethoxy)carbonyl]-L-α-aspartyl-O-(dicarboxymethyl)-N-pentyl-L-tyrosinamide;

N-(3-Carboxy-1-oxopropyl)-L-α-aspartyl-O-(dicarboxymethyl)-N-pentyl-L-tyrosinamide;

N-(3-Carboxy-1-oxopropyl)-L-α-glutamyl-O-(dicarboxymethyl)-N-pentyl-L-tyrosinamide;

N-(3-Carboxy-1-oxopropyl)-O-(dicarboxymethyl)-L-tyrosyl-L-norleucinamide;

N-(1-Oxohexyl)-L-α-aspartyl-O-(dicarboxymethyl)-N-pentyl-L-tyrosinamide;

N-[(Phenylmethoxy)carbonyl]-L-α-aspartyl-O-(dicarboxymethyl)-N-pentyl-L-tyrosinamide;

N-[(1,1-Dimethylethoxy)carbonyl]-D-α-aspartyl-O-(dicarboxymethyl)-N-pentyl-L-tyrosinamide;

4-Benzoyl-N-(3-carboxy-1-oxopropy)-L-phenylalanyl-O-(dicarboxymethyl)-N-pentyl-L-tyrosinamide; and (S)-2-(Carboxymethoxy)-5-[2-[(3-carboxy-1-oxopropyl)amino]-3-oxo-3-(pentylamino)propyl]benzoic acid; and pharmaceutically acceptable salts thereof.

The following compounds of the present invention are more preferred:

2-{4-[(2S)-2-({(2S)-2-[(3-carboxypropanoyl)amino]-3-phenylpropanoyl}amino)-3-oxo-3-(pentylamino)propyl]phenoxy}malonic acid;

5-[(2S)-2-({(2S)-2-[(tert-butoxycarbonyl)amino]-3-phenylpropanoyl}amino)-3-oxo-3-(pentylamino)propyl]-2-(carboxymethoxy)benzoic acid;

2-{4-[(2S)-2-{[(dibenzylamino)carbonyl]amino}-3-oxo-3-(pentylamino)propyl]phenoxy}malonic acid;

2-(carboxymethoxy)-5-[(2S)-2-{[(dibenzylamino)carbonyl]amino}-3-oxo-3-(pentylamino)propyl]benzoic acid;

2-(carboxymethoxy)-5-[(2S)-2-({(2S)-2-[(3-carboxypropanoyl)amino]-3-phenylpropanoyl}amino)-3-oxo-3-(pentylamino)propyl]benzoic acid;

2-(carboxymethoxy)-5-{(2S)-3-oxo-3-(pentylamino)-2-[((2S)-3-phenyl-2-{[2-(5-sulfanyl-1H-1,2,3,4-tetraazol-1-yl)acetyl]amino}propanoyl)amino]propyl}benzoic acid;

2-(carboxymethoxy)-5-{(2S)-3-oxo-3-(pentylamino)-2-[((2S)-3-phenyl-2-{[2-(1H-1,2,3-triazol-5-ylsulfanyl)acetyl]amino}propanoyl)amino]propyl}benzoic acid;

2-[4-[(2S)-2-({(2S)-2-[(tert-butoxycarbonyl)amino]-3-phenylpropanoyl}amino)-3-oxo-3-(pentylamino)propyl]-2-(2H-1,2,3,4-tetraazol-5-yl)phenoxy]acetic acid;

2-(carboxymethoxy)-5-[(2S)-3-oxo-3-(pentylamino)-2-({(2S)-3-phenyl-2-[(2-phenylacetyl)amino]propanoyl}amino)propyl]benzoic acid;

2-(carboxymethoxy)-5-[(2S)-3-oxo-3-(pentylamino)-2-({(2S)-3-phenyl-2-[(4-phenylbutanoyl)amino]propanoyl}amino)propyl]benzoic acid;

2-(carboxymethoxy)-5-[(2S)-2-({(2S)-2-[(3-methoxypropanoyl)amino]-3-phenylpropanoyl}amino)-3-oxo-3-(pentylamino)propyl]benzoic acid;

2-(carboxymethoxy)-5-((2S)-3-oxo-3-(pentylamino)-2-{[(2S)-3-phenyl-2-({2-[4-(trifluoromethyl)phenyl]acetyl}amino)propanoyl]amino}propyl)benzoic acid;

2-(carboxymethoxy)-5-[(2S)-2-[((2S)-2-{[2-(4-methoxyphenyl)acetyl]amino}-3-phenylpropanoyl)amino]-3-oxo-3-(pentylamino)propyl]benzoic acid;

2-(carboxymethoxy)-5-[(2S)-3-oxo-3-(pentylamino)-2-({(2S)-3-phenyl-2-[(3-phenylpropanoyl)amino]propanoyl}amino)propyl]benzoic acid;

2-(carboxymethoxy)-5-[(2S)-3-oxo-2-{[(2R)-2-(2-oxo-1-pyrrolidinyl)-3-phenylpropanoyl]amino}-3-(pentylamino)propyl]benzoic acid; and 5-{(2S)-2-({(2S)-2-[(tert-butoxycarbonyl)amino]-3-phenylpropanoyl}amino)-3-oxo-3-[(4-phenylbutyl)amino]propyl}-2-(carboxymethoxy)benzoic acid; and pharmaceutically acceptable salts thereof.

Also preferred are:

2-(carboxymethoxy)-5-[(2S)-3-oxo-3-(pentylamino)-2-({(2S)-2-[(phenoxycarbonyl)amino]-3-phenylpropanoyl}amino)propyl]benzoic acid;

5-((2R)-2-({(2S)-2-[(tert-butoxycarbonyl)amino]-3-phenylpropanoyl}amino)-3-oxo-3-{[3-(2-oxo-1-pyrrolidinyl)propyl]amino}propyl)-2-(carboxymethoxy)benzoic acid;

5-{(2S)-2-({(2S)-2-[(tert-butoxycarbonyl)amino]-3-phenylpropanoyl}amino)-3-oxo-3-[(3-pyridinylmethyl)amino]propyl}-2-(carboxymethoxy)benzoic acid;

5-{(2S)-2-({(2S)-2-[(tert-butoxycarbonyl)amino]-3-phenylpropanoyl}amino)-3-oxo-3-[(3-isopropoxypropyl)amino]-3-oxopropyl}-2-(carboxymethoxy)benzoic acid;

5-{(2S)-2-({(2S)-2-[(tert-butoxycarbonyl)amino]-3-phenylpropanoyl}amino)-3-[(3-hydroxypropyl)amino]-3-oxopropyl}-2-(carboxymethoxy)benzoic acid;

2-(carboxymethoxy)-5-[(2R)-2-{[2-(2-methoxyphenyl)acetyl]amino}-3-oxo-3-(pentylamino)propyl]benzoic acid;

Methyl-2-[4-{(2S)-benzoylamino)-3-oxo-3-[(4-phenylbutyl)amino]propyl}-2-(2H-1,2,3,4-tetrazol-5-yl)phenoxy]acetate;

2-[4-{(2S)-2-benzoylamino-3-oxo-3-[(4-phenylbutyl)amino]propyl}-2-(2H-1,2,3,4-tetrazol-5-yl)phenoxy] acetic acid;

2-[4-{(2S)-3-furoylamino)-3-oxo-3-[(4-phenylbutyl)amino]propyl}-2-(2H-1,2,3,4-tetrazol-5-yl)phenoxy] acetic acid;

5-{(2S)-2-({(2S)-2-[(tert-butoxycarbonyl)amino]-3-phenylpropanoyl}amino)-3-oxo-3-[(3-phenylpropoxy)amino]propyl}-2-(carboxymethoxy)benzoic acid;

5-{(2S)-2-({(2S)-2-[(tert-butoxycarbonyl)amino]-3-phenylpropanoyl}amino)-3-oxo-3-[(3-phenylbutyl)amino]propyl}-2-(carboxymethoxy)benzoic acid;

5-{(2S)-2-({(2S)-2-[(tert-butoxycarbonyl)amino]-3-phenylpropanoyl}amino)-3-oxo-3-[(2-hydroxyethyl)amino]-3-oxopropyl}-2-(carboxymethoxy)benzoic acid;

5-{(2S)-2-({(2S)-2-[(tert-butoxycarbonyl)amino]-3-phenylpropanoyl}amino)-3-oxo-3-[(3-phenylbutyl)amino]propyl}-2-(carboxymethoxy)benzoic acid;

5-[(2S)-2-({(2S)-2-[(tert-butoxycarbonyl)amino]-3-phenylpropanoyl}amino)-3-hydroxypropy]-2-(carboxymethoxy)benzoic acid;

2-(carboxymethoxy)-5-[(2S)-2-{[(5,6-dichloro-3-pyridinyl)carbonyl]amino}-3-oxo-3-(pentylamino) propyl]benzoic acid;

5-{(2S)-2-benzoylamino)-3-oxo-3-[(4-phenylbutyl)amino]propyl}-2-(carboxymethoxy)benzoic acid;

2-(carboxymethoxy)-5-{(2S)-2-[(4-chlorobenzoyl)amino]-3-oxo-3-[(4-phenylbutyl)amino]propyl}benzoic acid;

2-(carboxymethoxy)-5-{(2S)-3-oxo-3-[(4-phenylbutyl)amino]-2-[(3-pyridinylcarbonyl)amino]propyl}benzoic acid;

2-(carboxymethoxy)-5-{(2S)-2-(3-furoylamino)-3-oxo-3-[(4-phenylbutyl)amino]propyl}benzoic acid;

5-((2S)-2-(benzoylamino)-3-{[4-(4-chlorophenyl)butyl]amino}-3-oxopropyl)-2-(carboxymethoxy)benzoic acid;

2-(carboxymethoxy)-5-((2S)-2-[(4-chlorobenzoyl)amino]-3-{[4-(4-chlorophenyl)butyl]amino}-3-oxopropyl)benzoic acid;

2-(carboxymethoxy)-5-[(2S)-3-{[4-(4-chlorophenyl)butyl]amino}-2-(3-furoylamino)-3-oxopropyl]benzoic acid;

2-(carboxymethoxy)-5-((2S)-2-{[(6-chloro-3-pyridinyl)carbonyl]amino}-3-{[4-(4-methoxyphenyl)butyl]amino}-3-oxopropyl)benzoic acid;

2-(carboxymethoxy)-5-((2S)-3-{[4-(4-chlorophenyl)butyl]amino}-2-{[(2,4-diflurophenyl)sulfonyl]amino}-3-oxopropyl)benzoic acid; and 2-(carboxymethoxy)-5-[(2S)-3-{[4-(4-chlorophenyl)butyl]amino}-3-oxo-2-({[(E)-2-phenylethenyl]sulfonyl}amino)propyl]benzoic acid;

and pharmaceutically acceptable salts thereof.

The following compounds within the scope of formula V of the present invention are preferred:

2-(carboxymethoxy)-5-[(2S)-3-oxo-3-(pentylamino)-2-({(2S)-2-[(phenoxycarbonyl)amino]-3-phenylpropanoyl}amino)propyl]benzoic acid;

5-((2R)-2-({(2S)-2-[(tert-butoxycarbonyl)amino]-3-phenylpropanoyl}amino)-3-oxo-3-{[3-(2-oxo-1-pyrrolidinyl)propyl]amino}propyl)-2-(carboxymethoxy)benzoic acid;

5-{(2S)-2-({(2S)-2-[(tert-butoxycarbonyl)amino]-3-phenylpropanoyl}amino)-3-oxo-3-[(3-pyridinylmethyl)amino]propyl}-2-(carboxymethoxy)benzoic acid;

5-{(2S)-2-({(2S)-2-[(tert-butoxycarbonyl)amino]-3-phenylpropanoyl}amino)-3-[(3-isopropoxypropyl)amino]-3-oxopropyl}-2-(carboxymethoxy)benzoic acid;

5-{(2S)-2-({(2S)-2-[(tert-butoxycarbonyl)amino]-3-phenylpropanoyl}amino)-3-[(3-hydroxypropyl)amino]-3-oxopropyl}-2-(carboxymethoxy)benzoic acid;

2-(carboxymethoxy)-5-[(2R)-2-{[2-(2-methoxyphenyl)acetyl]amino}-3-oxo-3-(pentylamino)propyl]benzoic acid;

Methyl-2-[4-{(2S)-benzoylamino)-3-oxo-3-[(4-phenylbutyl)amino]propyl}-2-(2H-1,2,3,4-tetrazol-5-yl)phenoxy]acetate;

2-[4-{(2S)-2-benzoylamino-3-oxo-3-[(4-phenylbutyl)amino]propyl}-2-(2H-1,2,3,4-tetrazol-5-yl)phenoxy] acetic acid;

2-[4-{(2S)-3-furoylamino)-3-oxo-3-[(4-phenylbutyl)amino]propyl}-2-(2H-1,2,3,4-tetrazol-5-yl)phenoxy] acetic acid;

5-{(2S)-2-({(2S)-2-[(tert-butoxycarbonyl)amino]-3-phenylpropanoyl}amino)-3-oxo-3-[(3-phenylpropoxy)amino]propyl}-2-(carboxymethoxy)benzoic acid;

5-{(2S)-2-({(2S)-2-[(tert-butoxycarbonyl)amino]-3-phenylpropanoyl}amino)-3-oxo-3-[(4-phenylbutyl)amino]propyl}-2-(carboxymethoxy)benzoic acid;

5-{(2S)-2-({(2S)-2-[(tert-butoxycarbonyl)amino]-3-phenylpropanoyl}amino)-3-[(2-hydroxyethyl)amino]-3-oxopropyl}-2-(carboxymethoxy)benzoic acid;

5-{(2S)-2-({(2S)-2-[(tert-butoxycarbonyl)amino]-3-phenylpropanoyl}amino)-3-oxo-3-[(3-phenylpropyl)amino]propyl}-2-(carboxymethoxy)benzoic acid;

5-[(2S)-2-({(2S)-2-[(tert-butoxycarbonyl)amino]-3-phenylpropanoyl}amino)-3-hydroxypropy]-2-(carboxymethoxy)benzoic acid;

2-(carboxymethoxy)-5-[(2S)-2-{[(5,6-dichloro-3-pyridinyl)carbonyl]amino}-3-oxo-3-(pentylamino)propyl]benzoic acid;

5-{(2S)-2-benzoylamino)-3-oxo-3-[(4-phenylbutyl)amino]propyl}-2-(carboxymethoxy)benzoic acid;

2-(carboxymethoxy)-5-{(2S)-2-[(4-chlorobenzoyl)amino]-3-oxo-3-[(4-phenylbutyl)amino]propyl}benzoic acid;

2-(carboxymethoxy)-5-{(2S)-3-oxo-3-[(4-phenylbutyl)amino]-2-[(3-pyridinylcarbonyl)amino]propyl}benzoic acid;

2-(carboxymethoxy)-5-{(2S)-2-(3-furoylamino)-3-oxo-3-[(4-phenylbutyl)amino]propyl}benzoic acid;

5-((2S)-2-(benzoylamino)-3-{[4-(4-chlorophenyl)butyl]amino}-3-oxopropyl)-2-(carboxymethoxy)benzoic acid;

2-(carboxymethoxy)-5-((2S)-2-[(4-chlorobenzoyl)amino]-3-{[4-(4-chlorophenyl)butyl]amino}-3-oxopropyl)benzoic acid;

2-(carboxymethoxy)-5-[(2S)-3-{[4-(4-chlorophenyl)butyl]amino}-2-(3-furoylamino)-3-oxopropyl]benzoic acid;

2-(carboxymethoxy)-5-((2S)-2-{[(6-chloro-3-pyridinyl)carbonyl]amino}-3-{[4-(4-methoxyphenyl)butyl]amino}-3-oxopropyl)benzoic acid;

2-(carboxymethoxy)-5-((2S)-3-{[4-(4-chlorophenyl)butyl]amino}-2-{[(2,4-diflurophenyl)sulfonyl]amino}-3-oxopropyl)benzoic acid;

2-(carboxymethoxy)-5-[(2S)-3-{[4-(4-chlorophenyl)butyl]amino}-3-oxo-2-({[(E)-2-phenylethenyl]sulfonyl}amino)propyl]benzoic acid; and 2-(carboxymethoxy)-5-{(2S)-3-oxo-3-[(3-phenoxypropyl)amino]-2-[(phenylsulfonyl)amino]propyl}benzoic acid.

DESCRIPTION OF PREFERRED EMBODIMENTS

EXAMPLE 1

(S)-4-Oxo-4-[[2-oxo-2-(pentylamino)-1-[[4-(sulfooxy)phenyl]-methyl]ethyl]amino]butanoic Acid (Formula F-2, Chart F)

PREPARATION OF E-2 (Chart E): To a 0° C. mixture of Boc-L-tyrosine (2.04 g) and amylamine (0.93 mL) in methylene chloride (30 mL) is added 1-(3-dimethylaminopropyl)-3-ethylcarbodiimide (EDC) (1.53 g). The white mixture is stirred at 0 C for 5 min and at room temp for 23 hrs. The resulting solution is diluted with methylene chloride (30 mL) and washed successively with 0.5 M HCl (40 mL), water (20 mL) and sat aq sodium bicarbonate (25 mL). The organic phase is dried over magnesium sulfate and concentrated to a foam (1.84 g), sufficiently pure to carry into the next step. An analytical sample is obtained by flash chromatography (1/1 ethyl acetate/hexane) as a glass.

Physical characteristics are as follows: $^1$H NMR (CDCl$_3$) δ 7.01, 6.74, 5.90, 5.17, 4.21, 3.13, 2.93, 1.41, 1.1–1.4, 0.85; IR (mull) 3341, 3318, 3004, 1684, 1651, 1615, 1595, 1517, 1393, 1293, 1267, 1248, 1170, 1048, 828; MS (EI) m/z 350 (M+), 234, 233, 188, 180, 177, 147, 143, 136, 107, 57 cm$^{-1}$; HRMS (EI) found 350.2209. Anal. Found: C, 64.27; H, 8.54; N, 7.82.

PREPARATION OF E-3 (Chart E): To a solution of E-2 (5.28 g) in dioxane (40 mL) chilled in an ice bath is added a freshly prepared solution of HCl in dioxane (about 3 M, 25 mL). The solution is then stirred at room temp for 1.5 hrs when a TLC indicates the reaction is done. The solution is diluted rapidly with ether (350 mL) until no further precipitation is evident. The mixture is stirred vigorously until all insoluble material is adhering to the sides of the flask. After decanting the supernatant, the crude material is taken up in more ether (200 mL) and sonicated until a fine solid (required about 1 hr). Filtration gives a hygroscopic white powder (4.32 g).

Physical characteristics are as follows: $^1$H NMR (DMSO) δ 9.3, 8.40, 8.25, 6.98, 6.68, 3.08, 2.9, 1.0–1.35, and 0.83.

PREPARATION OF F-1 (Chart F): Triethylamine (307 uL) is added to a 0 C mixture of E-3 (287 mg) in methylene chloride (4 mL), causing rapid dissolution. To this solution is added succinic anhydride (100 mg), and the reaction is stirred at room temp for 25 h. The reaction is then diluted with ethyl acetate (20 mL) and washed successively with 0.5 M HCl (10 mL) and brine (10 mL). The organic phase is dried over magnesium sulfate and concentrated to a viscous oil (350 mg) that solidified on standing and is analytically pure.

Physical characteristics are as follows: $^1$H NMR (DMSO) δ 9.1, 7.98, 7.74, 6.96, 6.60, 4.30, 2.9–3.1, 2.8, 2.60, 2.3, 1.1–1.4, 0.83; $^{13}$C NMR (CDCl$_3$) 175.1, 173.1, 172.2, 155.9, 129.8, 127.8, 114.8, 55.3, 39.2, 39.0, 36.7, 30.0, 28.8, 28.7, 28.5, 22.0, 13.0; IR (mull) 3296, 3102, 2728, 1715, 1642, 1615, 1596, 1548, 1516, 1401; 1239, 1173, 1117, 832, 722; MS (EI) m/z 350 (M+), 233, 177, 162, 147, 144, 143, 136, 107, 91, 55 cm$^{-1}$; MS (FAB) m/z 351 (M+H), 352, 351, 350, 236, 233, 136, 121, 107, 88, 43. HRMS (FAB) found 351.1928. Anal. Found: C, 60.34; H, 7.48; N, 7.72.

PREPARATION OF F-2 (Chart F): A solution of F-1 (100 mg) and pyridine sulfur trioxide complex (500 mg) in DMF:pyridine (1:1, 10 mL) is stirred under nitrogen at room temp for 20 hrs. NMR analysis of an aliquot indicates complete conversion to product. Solvent is removed under vacuum, leaving a solid that is purified by reverse phase HPLC.

Physical characteristics are as follows: $^1$H NMR (DMSO) δ 8.03, 7.79, 7.06, 7.01, 4.33, 2.99, 2.87, 2.68, 2.3, 1.1–1.3, 0.83; ES MS m/z (negative ion) 429, 214.

EXAMPLE 2

(S)-[4-[2-[[1,4-Dioxo-4-(phenylmethoxy)butyl]amino]-3-oxo-3-(pentylamino)propyl]phenoxy]propanedioic Acid (Formula I-2, Chart I)

PREPARATION OF E-4 (Chart E): EDC (368 mg) is added to a 0 C solution of E-3 (500 mg), (mono)benzyl succinate (368 mg) and triethylamine (270 uL) in methylene chloride (7 mL). The reaction is stirred at room temp for 24 h. After dilution with ethyl acetate (40 mL), the mixture is washed successively with 0.5 M HCl, water and sat aq sodium bicarbonate (20 mL each). The organic phase is dried over magnesium sulfate and concentrated to a white amorphous solid (694 mg) that is analytically pure.

Physical characteristics are as follows: $[δ]^{25}_D$–5.4° (c 0.017, methanol); $^1$H NMR (CDCl$_3$) δ 7.33, 7.05, 6.74, 6.21, 5.90, 5.68, 5.13, 5.09, 4.54, 3.12, 3.06, 2.90, 2.4–2.85, 1.1–1.4, 0.86; IR (mull) 3379, 3285, 1706, 1640, 1617, 1552, 1517, 1339, 1271, 1218, 1196, 1181, 1174, 749, 694; MS (EI) m/z 440 (M+), 233, 226, 208, 147, 136, 108, 107, 91, 79, 77. Anal. Found: C, 67.89; H, 7.23; N, 6.38.

PREPARATION OF I-1 (Chart I): A solution of di-tert-butyl diazomalonate (396 mg) in benzene (2 mL) is added over 6 h to an 80 C mixture of E-4 (342 mg) and rhodium (II) acetate (7 mg) in benzene (33 mL) via syringe pump, during which time most of the starting material goes into solution. The blue-green solution is stirred at that temp for an additional hour and then overnight at room temp. The reaction is filtered through a medium frit and then concentrated in vacuo. Flash chromatography (80 g silica, 70% ethyl acetate/hexane) provides the title material (232 mg) as a foam (Rf=0.45).

Physical characteristics are as follows: $^1$H NMR (CDCl$_3$) δ 7.33, 7.12, 6.89, 6.10, 5.81, 5.12, 5.08, 4.94, 4.52, 3.1, 2.6–2.95, 2.45, 1.49, 1.1–1.4, 0.86; MS (FAB) m/z 655 (M+H), 655, 599, 447, 92, 91, 88, 86, 57, 41, 29. HRMS (FAB) found 655.3588.

PREPARATION OF I-2 (Chart I): Trifluoroacetic acid (5 mL) is added to a solution of I-1 (225 mg) in methylene chloride (5 mL) with ice bath chilling. The solution is stirred at room temp for 2 h. Concentration in vacuo affords the title compound as a light amber foam, sufficiently pure to carry into the next step.

Physical characteristics are as follows: $^1$H NMR (CD$_3$OD) δ 7.33, 7.15, 6.89, 5.23, 5.10, 4.48, 3.05, 2.80, 2.35–2.7, 1.1–1.5, 0.88; MS (FAB) m/z 543 (M+H), 544, 543, 542, 441, 92, 91, 88, 86, 43. HRMS (FAB) found 543.2332.

EXAMPLE 3

(S)-[4-[2-[(3-Carboxy-1-oxopropyl)amino]-3-oxo-3-(pentylamino)propyl]phenoxy]propanedioic Acid (Formula I-3, Chart I)

Crude I-2 (approx. 0.29 mmol) is dissolved in ethyl acetate and concentrated in vacuo three times to get rid of traces of trifluoroacetic acid. The residue is then dissolved in methanol (10 mL) and subjected to three cycles of evacuation and nitrogen purge at 0 C before the introduction of 10% Pd/C (20 mg). The mixture is then hydrogenated at 1 atm for 1.5 h. The mixture is filtered through Celite and concentrated in vacuo. The crude glass is taken up in methylene chloride (40 mL) and sonicated until it is all suspended. Filtration gives a brittle white amorphous solid (116 mg) that is analytically pure (m.p. 117–120 C, dec).

Physical characteristics are as follows: $[a]^{25}_D$=−0.70 (c 0.0058, methanol); $^1$H NMR (CD$_3$OD) δ 8.13, 7.81, 7.17, 6.90, 5.23, 4.48, 3.1, 2.81, 2.3–2.6, 1.2–1.5, 0.89; MS (FAB) m/z 453 (M+H), 453, 238, 194, 136, 133, 101, 88, 86, 55, 43. HRMS (FAB) found 453.1859. Anal. Found: C, 54.25; H, 6.31; N, 5.97.

EXAMPLE 4

(S)-[4-[2-[[[(Carboxymethyl)amino]carbonyl]amino]-3-oxo-3-(pentylamino)propyl]phenoxy]propanedioic Acid (Formula C-1 (R$^2$=CH$_2$CO$_2$H), Chart C)

To a solution of amine hydrochloride B-4 (50 mg) and triethylamine (16 uL) in methylene chloride (1 mL) is added ethyl isocyanatoacetate (13 uL) neat. TLC analysis shows reaction is nearly done after 5 min. After stirring for a total of 1 hr at room temp., the reaction is diluted with ethyl acetate (5 mL) and washed successively with 1 M HCl, water, and brine (2 mL each). The organic layer is dried over magnesium sulfate and concentrated in vacuo to a colorless oil (58 mg).

Physical characteristics are as follows: $^1$H NMR (CDCl$_3$) δ 7.11, 6.82, 6.57, 6.48, 6.11, 5.10, 4.49, 4.28, 4.15, 3.94, 3.82, 2.8–3.2, 1.1–1.4, 0.83; MS (ES+): 537.9 (M+H), 559.8 (M+Na).

To a solution of the crude triester from above in 3:1:1 THF:MeOH:water (1 mL) at room temp is added lithium hydroxide monohydrate (21 mg). The solution is stirred for 3 hrs. The solvent is evaporated in vacuo, and the residue is acidified with 1M HCl (1 mL). To the slightly cloudy mixture is added brine (2 mL), resulting in a copious ppt. The mixture is extracted with ethyl acetate, and the extracts are dried over magnesium sulfate. Concentration gives a glass (50 mg). This material is sonicated with methylene chloride (20 mL) for 30 min, and the resulting fine white solid is collected by filtration, giving the title product as an amorphous powder (32 mg).

Physical characteristics are as follows: $^1$H NMR (DMSO) δ 7.84, 7.06, 6.79, 6.33, 6.29, 5.25, 4.25, 3.65, 2.85–3.05, 2.78, 2.63, 1.1–1.4, 0.82; MS (ES−): 451.7; HRMS (FAB) found 454.1820. Anal. Found: C, 51.50; H, 5.94; N, 8.89.

EXAMPLE 5

(S)-[4-[2-[[[(5-Carboxypentyl)amino]carbonyl]amino]-3-oxo-3-(pentylamino)propyl]phenoxy]propanedioic Acid (Formula C-1, Chart C)

By the two-step procedure described for Example 4, the title product is obtained as a foam (44 mg). Saponification is effected in 3:1 THF:MeOH (2 mL) with added 2.5 M aq LiOH (0.3 mL). Sonication does not produce a filtratable solid, so the methylene chloride is decanted, and the residue is dried under vacuum.

Physical characteristics are as follows: $^1$H NMR (DMSO) δ 7.82, 7.04, 6.79, 6.00, 5.90, 5.25, 4.25, 2.8–3.0, 2.76, 2.65, 2.16, 1.45, 1.1–1.35, 0.82; MS (ES−): 508.1; HRMS (FAB) found 510.2446. Anal. Found: C, 54.63; H, 6.93; N, 8.02.

EXAMPLE 6

(S)-[4-[2-[[[(4-Carboxyphenyl)amino]carbonyl]amino]-3-oxo-3-(pentylamino)propyl]phenoxy]propanedioic Acid (Formula C-1, Chart C)

By the procedure described for Example 5 is obtained the title product as a glass that slowly solidifies (57 mg).

Physical characteristics are as follows: $^1$H NMR (DMSO) δ 9.06, 8.05, 7.77, 7.42, 7.07, 6.81, 6.42, 5.26, 4.38, 3.01, 2.7–2.9, 1.1–1.4, 0.82; MS (ES−): 514.0; HRMS (FAB): Found=516.1979.

EXAMPLE 7

(S)-[4-[2-[[[(2-Carboxyethyl)amino]carbonyl]amino]-3-oxo-3-(pentylamino)propyl]phenoxy]propanedioic Acid (Formula C-1, Chart C)

By the procedure described for Example 5 is obtained the title compound (43 mg) as a glass. Sonication in methylene chloride was not performed.

Physical characteristics are as follows: $^1$H NMR (DMSO) δ 7.83, 7.04, 6.79, 6.11, 5.25, 4.22, 3.13, 2.96, 2.76, 2.61, 2.27, 1.1–1.4, 0.82; MS (ES−): 465:8; HRMS (FAB) found 468.1982.

EXAMPLE 8

(S)-5-[[[[1-[[4-(Dicarboxymethoxy)phenyl]methyl]-2-oxo-2-(pentylamino)ethyl]amino]carbonyl]amino]-1,3-benzene-dicarboxylic Acid (Formula C-1, Chart C)

By the procedure described for Example 5 is obtained the title compound as a glass (61 mg).

Physical characteristics are as follows: $^1$H NMR (DMSO) δ 8.15, 8.04, 7.99, 7.08, 6.82, 6.32, 5.26, 4.37, 2.7–3.1, 1.1–1.4, 0.82; MS (ES−): 557.8; HRMS (FAB) 560.1880. Anal. Found: C, 54.21; H, 5.28; N, 6.89.

EXAMPLE 9

(S)-N-[[[1-[[4-(Dicarboxymethoxy)phenyl]methyl]-2-oxo-2-(pentylamino)ethyl]amino]carbonyl]-L-glutamic Acid (Formula C-1, Chart C)

(S)-(−)-2-isocyanatoglutaric acid, diethyl ester (24 uL) is added to a 0 C mixture of B-4 (50 mg) and triethylamine (16 uL) in THF (1 mL). After 1 hr, 2.5 M aq LiOH (0.4 mL) is added directly to the reaction mixture, and the two-phase mixture is stirred vigorously for 1.5 hrs. The mixture is diluted with 1 M HCl (2 mL), saturated with solid NaCl, and extracted with ethyl acetate (3×2 mL). Drying of the extracts over magnesium sulfate and concentration leaves a glass (68 mg), which is sonicated with methylene chloride (20 mL) for 1 h. Filtration and drying in vacuo leaves the title compound as a white powder (52 mg).

Physical characteristics are as follows: $^1$H NMR (DMSO) δ 7.84, 7.05, 6.79, 6.44, 6.14, 5.25, 4.22, 4.05, 2.95, 2.80, 2.68, 2.21, 1.85, 1.65, 1.1–1.4, 0.82; MS (ES–): 523.9. IR (mull) 3358, 2670, 2605, 1727, 1625, 1564, 1512, 1416, 1341, 1230, 1185, 1114, 855, 833, 805, cm$^{-1}$. HRMS (FAB) found 526.2051. Anal. Found: C, 51.54; H, 6.06; N, 7.85.

EXAMPLE 10

(S)-[4-[2-[[[(Carboxymethyl)(phenylmethyl)amino] carbonyl]-amino]-3-oxo-3-(pentylamino)propyl] phenoxy]propanedioic Acid (Formula D-2, Chart D)

To a 0 C solution of B-4 (50 mg), and Proton Sponge (71 mg) in methylene chloride (1 mL) is added diphosgene (8 uL). The solution is stirred at 0 C for 45 min before dilution with more methylene chloride (2 mL) and washing successively with 1 M HCl, water, and sat aq sodium bicarbonate (2 mL each). The extracts are dried over magnesium sulfate and concentrated in vacuo, leaving D-1 as an oil.

Physical characteristics are as follows: $^1$H NMR (CDCl$_3$) δ 7.17, 6.94, 6.15, 5.18, 4.30, 3.2–3.32, 2.92, 1.5, 1.3, 0.90.

To a solution of D-1 in THF (1 mL) is added N-benzylglycine ethyl ester (21 uL). The solution is stirred at room temp for 1.5 h before the addition of 2.5 M aq LiOH (0.3 mL). The resulting mixture is stirred vigorously at room temp for 1.5 h. The mixture is diluted with 1M HCl (2 mL), saturated with brine, and extracted with ethyl acetate. The extracts are dried over magnesium sulfate and concentrated in vacuo, leaving a glass (65 mg). Sonication with methylene chloride (20 mL) for 30 min followed by filtration afforded the title compound as a white solid (41 mg).

Physical characteristics are as follows: $^1$H NMR (DMSO) δ 7.69, 7.25, 7.10, 6.77, 6.48, 5.25, 4.40, 4.27, 3.81, 2.7–3.1, 1.1–1.4, 0.84; MS (ES–): 541.9. HRMS (FAB) found 544.2293. Anal. Found: C, 58.10; H, 6.08; N, 7.56.

EXAMPLE 11

(S)-[4-[2-[[[(Carboxymethyl)[[4-(phenylmethoxy) phenyl]methyl]-amino]carbonyl]amino]-3-oxo-3- (pentylamino)propyl]phenoxy]-propanedioic Acid (Refer to Chart D)

4-(4-benzyloxy)benzylglycine methyl ester is prepared from 4-(benzyloxy)-benzaldehyde and glycine methyl ester by the method of Zydowsky et al (J. Org. Chem. 1988, 53:5607). Using the method described for Example 10, this material affords the title compound as a white powder (54 mg). Sonication with methylene chloride does not provide the product as a filterable solid; it is isolated by decantation and drying of the insoluble residue.

Physical characteristics are as follows: $^1$H NMR (DMSO) δ 7.69, 7.25–7.5, 7.10, 7.04, 6.91, 6.79, 6.45, 5.27, 5.06, 4.32, 4.25, 3.77, 3.0, 2.85, 2.75, 1.1–1.4, 0.84; MS (ES–): 647.9. IR (mull) 3346, 3063, 3032, 1732, 1612, 1587, 1538, 1511, 1422, 1341, 1297, 1230, 1177, 1113, 697, cm$^{-1}$. Anal. Found: C, 61.89; H, 6.05; N, 6.30.

EXAMPLES 12–24

(General Synthesis of Formula J-6, Chart J)

PREPARATION OF J-3: To a stirring solution of E-2 (2.0 g) in acetone (50 ml) is added K$_2$CO$_3$ (1.57 g) at ambient temperature. To the resulting heterogeneous mixture is added dibenzyl bromomalonate (2.89 g) and the mixture stirred at ambient temperature overnight. The resulting amber suspension is diluted with H$_2$O (100 ml) and extracted with EtOAc (2×100 ml). The combined organic layers are dried over MgSO$_4$ and solvent removed in vacuo. The residue is purified via SiO$_2$ flash chromatography (eluant 2:1 EtOAc/hexane) to afford 1.26 g title compound as a white solid.

Physical characteristics are as follows: $^1$H NMR (CDCl$_3$) δ 0.84, 1.16–1.38, 1.39, 2.96, 3.13, 4.21, 5.20, 5.08, 5.23, 5.85, 6.83, 7.07, 7.25; IR (mull) 3346, 3326, 1748, 1683, 1657, 1540, 1522, 1510, 1313, 1297, 1238, 1221, 1188, 1173, 698, cm$^{-1}$. MS (FAB) m/z 633 (MH$^+$), 633, 578, 577, 533, 515, 92, 91, 88, 86, 57. Anal. Found: C, 68.06; H, 6.91; N, 4.33.

PREPARATION OF J-4: To a stirring solution of J-3 (2.85 g) in HOAc (25 ml) at ambient temperature, is added 1.5N HCl/HOAc (20 ml) and the resulting solution is stirred at ambient temperature for 2 h). The solvent is evaporated to 30 ml and triturated with Et$_2$O (400 ml). The resulting turbid suspension is stirred at ambient temperature for 30 min, sonicated and filtered to afford 2.50 g title compound as a white solid.

Physical characteristics are as follows: $^1$H NMR (DMSO) δ 0.80, 1.18, 2.93, 3.04, 3.87, 5.20, 5.83, 6.91, 7.13, 7.32, 8.39; IR (liq.) 3035, 2957, 2932, 2872, 2861, 1763, 1748, 1661, 1511, 1500, 1456, 1224, 1185, 1167, 697, cm$^{-1}$. MS (FAB) m/z 533 (MH$^+$), 1067, 1066, 535, 534, 533, 418, 143, 92, 91, 88. Anal. Found: C, 64.74; H, 6.54; N, 4.88.

GENERAL PREPARATION OF J-5: To a stirring solution of J-4 (0.20 g) in CH$_2$Cl$_2$ (10 ml) is added triethylamine (0.078 g) at 0 C. The requisite cyclic anhydride (0.35 mmol) is added in one portion and the resulting solution allowed to stir for 16 h while warming to ambient temperature. The solution is diluted with CH$_2$Cl$_2$ (50 ml) and washed with 10% HCl/H$_2$O (2×50 ml). The combined organic phases are dried over MgSO$_4$ and solvent removed in vacuo to afford material suitable for subsequent transformations.

GENERAL PREPARATION OF J-6: To a solution of the requisite dibenzylester J-5 in MeOH (~0.02 M) at ambient temperature is added 10% Pd/C (10 weight %) and the resulting mixture hydrogenated at atmospheric pressure for 3 h. The mixture is filtered through Celite and solvent removed to afford analytically pure material.

The following examples (12–24) are prepared by the general synthesis of J-6 outlined above, using the appropriate commercially available anhydrides (Chart J).

EXAMPLE 12

(S)-[4-[2-[(4-Carboxy-1-oxobutyl)amino]-3-oxo-3- (pentylamino)-propyl]phenoxy]propanedioic Acid 0.115 g as an amorphous white solid. $^1$H NMR (DMSO) δ 0.84, 1.15–1.36, 1.61, 2.06, 2.68, 2.84, 3.00, 4.38, 5.25, 6.80, 7.13, 7.86, 8.00; IR (mull) 3305, 3070, 2729, 2669, 2599, 1730, 1626, 1551, 1512, 1341, 1231, 1185, 1112, 855, 831, cm$^{-1}$. MS (FAB) m/z 467 (MH$^+$), 481, 468, 467, 423, 238, 194, 91, 88, 59, 43. Anal. Found: C, 54.90; H, 6.52; N, 5.47.

EXAMPLE 13

[1R-[1(S*),2]]-[4-[2-[[(2-Carboxycyclohexyl) carbonyl]amino]-3-oxo-3-(pentylamino)propyl] phenoxy]propanedioic Acid 0.068 g as an amorphos white solid. $^1$H NMR (DMSO) δ 0.84, 1.12–1.50, 1.80, 2.4–3.15, 3.35, 5.22, 6.65, 6.78, 7.0, 7.08, 7.22, 7.62, 7.75; IR (mull) 3336, 2731, 2674, 2595, 1727, 1630, 1537, 1512, 1338, 1296, 1229, 1184, 1130, 1103, 854, cm$^{-1}$. MS (FAB) m/z 507 (MH$^+$), 508, 507, 238, 194, 136, 102, 91, 88, 81, 43. Anal. Found: C, 57.50; H, 6.67; N, 5.33.

EXAMPLE 14

(S)-[4-[2-[[(Carboxymethoxy)acetyl]amino]-3-oxo-3-(pentylamino)propyl]phenoxy]propanedioic Acid 0.096 g as an amorphous solid. $^1$H NMR (DMSO) δ 0.83, 1.20–1.32, 2.76–3.01, 3.89, 4.03, 4.45, 5.23, 6.78, 7.08, 7.77, 7.95; IR (mull) 3340, 2730, 2670, 2596, 1745, 1632, 1543, 1512, 1346, 1230, 1184, 1144, 833, 721, 668, cm$^{-1}$. MS (FAB) m/z 469 (MH$^+$), 497, 483, 469, 107, 88, 86, 75, 43, 39, 23. Anal. Found: C, 52.07; H, 5.98; N, 5.67.

EXAMPLE 15

(S)-[4-[2-[[[1-(Carboxymethyl)cyclopentyl]acetyl]amino]-3-oxo-3-(pentylamino)propyl]phenoxy]propanedioic Acid 0.108 g as an amorphous solid. $^1$H NMR (DMSO) δ 0.82, 1.20–1.47, 2.18–2.35, 2.60–2.92, 2.99, 4.40, 5.22, 7.79, 7.11, 7.83, 8.00; IR (mull) 3294, 3069, 2728, 2668, 2604, 1732, 1629, 1613, 1554, 1512, 1331, 1280, 1229, 1182, 1110 cm$^{-1}$. MS (FAB) m/z 462 (MH$^+$), 535, 521, 143, 136, 109, 88, 81, 67, 43, 39. Anal. Found: C, 58.00; H, 6.87; N, 5.06.

EXAMPLE 16

(S)-[4-[2-[(Carboxyacetyl)amino]-3-oxo-3-(pentylamino)propyl]-phenoxy]propanedioic Acid 0.101 g as an amorphous solid. $^1$H NMR (DMSO) δ 0.82, 1.19–1.31, 2.69, 2.85–3.21, 4.37, 5.23, 6.78, 7.09, 7.86, 8.27; IR (mull) 3326, 3079, 3041, 2591, 1740, 1634, 1557, 1513, 1441, 1424, 1231, 1185, 1115, 855, 833, cm$^{-1}$. MS (FAB) m/z 439 (MH$^+$, 99), 453, 440, 439, 395, 331, 177, 133, 118, 88, 23. Anal. Found 53.18; H, 5.86; N, 5.91.

EXAMPLE 17

(S)-[4-[2-[(4-Carboxy-3,3-dimethyl-1-oxobutyl)amino]-3-oxo-3-(pentylamino)propyl]phenoxy]propanedioic Acid 0.96 g as an amorphous solid. $^1$H NMR (DMSO) δ 0.85, 1.11–1.40, 2.12, 2.67, 2.85, 2.98, 5.22, 5.73, 6.78, 7.11, 7.84, 7.97. R (mull) 3296, 3069, 2729, 2670, 2606, 1727, 1612, 1557, 1512, 1329, 1231, 1184, 1115, 830, 720, cm$^{-1}$. Anal. Found: C, 55.71; H, 6.90; N, 5.32.

EXAMPLE 18

(S)-[4-[2-[(2-Carboxybenzoyl)amino]-3-oxo-3-(pentylamino)-propyl]phenoxy]propanedioic Acid 0.070 g as an amorphous solid. $^1$H NMR (DMSO) δ 0.83, 1.22, 1.40, 2.73, 3.08, 4.50, 5.27, 6.83, 6.97, 7.15, 7.50, 7.70, 7.89, 8.52; IR (mull) 3341, 3065, 3033, 1720, 1627, 1599, 1580, 1538, 1512, 1488, 1271, 1232, 1185, 1147, 1103, cm$^{-1}$. MS (FAB) m/z 501 (MH$^+$), 501, 154, 149, 137, 117, 109, 92, 59, 45, 41. MS (FAB) m/z 501 (MH$^+$), 501, 154, 149, 137, 117, 109, 59, 57, 43, 41. Anal. Found: C, 57.36; H, 5.74; N, 5.30.

EXAMPLE 19

[2(S)]-[4-[2-[[(3-Carboxybicyclo[2.2.2]oct-2-yl)carbonyl]amino]-3-oxo-3-(pentylamino)propyl]phenoxy]propanedioic Acid 10.072 g as a white amorphous solid. $^1$H NMR (DMSO) δ 0.83, 0.98–1.60, 1.76, 2.00, 2.47–3.11, 4.35, 5.20, 6.75, 7.06, 7.5–7.9; IR (mull) 3326, 1772, 1732, 1704, 1639, 1547, 1512, 1355, 1340, 1292, 1228, 1183, 1106, 1085, 907, cm$^{-1}$. MS (FAB) m/z 533 (MH$^+$), 353, 309, 194, 136, 107, 88, 43, 41, 39, 23. Anal. Found: C, 59.26; H, 6.77; N, 4.84.

EXAMPLE 20

(S)-[4-[2-[[(1,1-Dimethylethoxy)carbonyl]amino]-3-oxo-3-(pentylamino)propyl]phenoxy]propanedioic Acid 0.203 g as a low melting white solid. $^1$H NMR (MeOH) δ 0.88, 1.16–1.58, 2.80, 2.97, 3.10, 4.19, 5.23, 6.89, 7.16, 7.80; IR (mull) 3326, 1738, 1693, 1639, 1614, 1588, 1512, 1393, 1297, 1233, 1169, 1114, 1085, 1051, 1022, cm$^{-1}$. MS (FAB) m/z 453 (MH$^+$), 453, 409, 397, 370, 353, 194, 88, 57, 41, 29. Anal. Found: C, 59.08; H, 7.15; N, 6.23.

EXAMPLE 21

(S)-3-[[[1-[[4-(Dicarboxymethoxy)phenyl]methyl]-2-oxo-2-(pentylamino)ethyl]amino]carbonyl]pentanedioic Acid 0.037 g as an amorphous solid. $^1$H NMR (DMSO) δ 0.83, 1.22, 2.24, 2.69, 2.98, 4.30, 5.21, 6.77, 7.08, 7.60, 8.10; HRMS (FAB) found 511.1933. Anal. Found: C, 51.39; H, 6.18; N, 5.42.

EXAMPLE 22

[1(S)]-[4-[2-[[(2-Carboxycyclopropyl)carbonyl]amino]-3-oxo-3-(pentylamino)-propyl]-phenoxy]propanedioic Acid 0.068 g as an amorphous solid. $^1$H NMR (DMSO) δ 0.82, 1.22, 1.92, 2.72, 2.98, 4.32, 5.24, 6.78, 7.09, 7.82, 8.40; IR (mull) 3330, 2730, 2598, 1729, 1612, 1554, 1512, 1229, 1184, 1114, 979, 855, 834, 808, 623, cm$^{-1}$. MS (FAB) m/z 465 (MH$^+$), 466, 465, 421, 238, 194, 113, 107, 102, 88, 63. Anal. Found: C, 55.01; H, 6.18; N, 5.74.

EXAMPLE 23

[2(S)]-[4-[2-[[(3-Carboxybicyclo[2.2.1]hept-2-yl)carbonyl]amino]-3-oxo-3-(pentylamino)propyl]phenoxy]propanedioic Acid 0.049 g. (quant). $^1$H NMR (DMSO) δ 0.80, 1.21, 1.43–2.10, 2.12–2.42, 2.60–3.10, 4.34, 5.15, 6.75, 7.05, 7.60, 7.80; IR (mull) 3311, 2727, 2670, 1722, 1632, 1543, 1511, 1295, 1228, 1184, 1113, 1083, 846, 831, 721, cm$^{-1}$. MS (FAB) m/z 519 (MH$^+$), 519, 353, 238, 194, 177, 167, 88, 67, 43, 23. Anal. Found: C, 58.39; H, 6.52; N, 4.81.

EXAMPLE 24

[1R-[1(S*),2]]-[4-[2-[[(2-Carboxycyclohexyl)carbonyl]amino]-3-oxo-3-(pentylamino)propyl]phenoxy]propanedioic Acid 0.109 g as a waxy white solid. $^1$H NMR (DMSO) δ 0.82, 1.20, 1.53–1.96, 2.40, 2.54–2.89, 3.00, 4.29, 5.23, 6.76, 7.08, 7.52, 7.90; IR (mull) 3307, 2729, 2671, 1727, 1631, 1543, 1511, 1299, 1226, 1184, 1113, 910, 855, 832, 721, cm$^{-1}$. MS (FAB) m/z 507 (MH$^+$), 508, 507, 353, 238, 194, 143, 109, 88, 81, 43. Anal. Found: C, 56.11; H, 6.65; N, 5.31.

EXAMPLE 25

N-[(1,1-Dimethylethoxy)carbonyl]-L-α-aspartyl-O-(dicarboxymethyl)-N-pentyl-L-tyrosinamide
(Formula O-1 (n=1), Chart O)

PREPARATION OF L-2 (n=1, Chart L): To a stirring solution of J-4 (0.25 g) and triethylamine (0.044 g) is added Boc-Asp(OBn)OSu (0.185 g) at 0 C. The resulting solution is stirred for 16 h allowing the mixture to warm to ambient temperature. The resulting solution is diluted with CH$_2$Cl$_2$ (50 ml) and washed with 10% aqueous HCl (3×50 ml). the organic layer is dried over MgSO$_4$ and solvent removed to afford 0.33 g title compound as a white solid. $^1$H NMR (CDCl$_3$) δ 0.84, 1.15–1.43, 2.76, 2.93, 3.09, 4.41, 4.48, 5.10, 5.23, 5.29, 5.44, 5.91, 6.89, 6.85, 7.10, 7.30; IR (mull) 3308, 1744, 1694, 1646, 1527, 1511, 1500, 1355, 1280, 1223, 1169, 1115, 749, 738, 697, cm$^{-1}$. MS (FAB) m/z 838 (MH$^+$), 783, 739, 515, 178, 92, 91, 88, 86, 57, 41. Anal. Found: C, 66.86; H, 6.59; N, 5.00.

PREPARATION OF O-1 (n=1): To a solution of L-2 (0.317 g) in MeOH (15 ml) at ambient temperature is added 10% Pd-C (50 mg) and the resulting mixture hydrogenated at atmospheric pressure for 2 h. The mixture is filtered through Celite and solvent removed to afford 0.208 g title compound as a white solid. $^1$H NMR (DMSO) δ 0.82, 1.12–1.40, 2.30–2.52, 2.70–3.06, 4.16, 4.32, 5.20, 6.76, 7.60, 7.12, 7.69, 7.78. IR (mull) 3334, 2729, 1726, 1668, 1637, 1512, 1395, 1341, 1280, 1233, 1180, 1165, 1114, 1053, 855, cm$^{-1}$. MS (FAB) m/z 568 (MH$^+$), 512, 468, 88, 88, 86, 57, 43, 41, 29, 23. Anal. Found: C, 52.55; H, 6.53; N, 7.08.

EXAMPLE 26

N-(3-Carboxy-1-oxopropyl)-L-α-aspartyl-O-(dicarboxymethyl)-N-pentyl-L-tyrosinamide
(Formula L-5, n=1, Chart L)

PREPARATION OF L-3: To a solution of L-2 (0.263 g) in HOAc (5 ml) is added 1.5 M HCl/HOAc (5 ml) and the resulting solution allowed to stand for 2 h. The solvent is removed in vacuo to afford 0.24 g (quant) title compound as a white solid. $^1$H NMR (DMSO) δ 0.79, 1.17, 2.94, 4.05, 4.40, 5.12, 5.19, 5.81, 6.86, 7.14, 7.34, 8.02, 8.70; IR (mull) 3300, 3034, 1744, 1671, 1649, 1554, 1510, 1500, 1305, 1285, 1221, 1188, 1099, 746, 697, cm$^{-1}$. MS (FAB) m/z 738 (MH$^+$), 741, 740, 739, 178, 92, 91, 88, 88, 86, 43.

PREPARATION OF L-4: To a stirring solution of L-3 (0.10 g) and triethylamine (0.028 g) in CH$_2$Cl$_2$ (8 ml) at 0 C is added succinic anhydride (0.015 g, 0.13 mmol). The resulting solution is stirred for 16 h allowing the solution to warm to ambient temperature. The mixture is diluted with CH$_2$Cl$_2$ (50 ml) and washed with 10% aqueous HCl (2×50 ml). The organic layer is dried over MgSO$_4$ and solvent removed to afford 0.076 g title compound as a white solid. $^1$H NMR (CDCl$_3$) δ 0.85, 1.23, 1.40, 2.37, 2.68, 3.14, 4.57, 4.72, 5.01, 5.16, 5.21, 6.36, 6.80, 7.05, 7.25; MS (FAB) m/z 838 (MH$^+$), 839, 838, 533, 516, 515, 418, 178, 92, 91, 88. Anal. Found: C, 65.53; H, 6.01; N, 4.98.

PREPARATION OF L-5 (n=1): To a stirring solution of L-4 (0.07 g) in MeOH (5 ml) is added 10% Pd-C (10 mg). The resulting mixture is hydrogenated at atmospheric pressure for 2 h and filtered through celite. The solvent is removed to afford 0.044 g title compound as a white amorphous solid. $^1$H NMR (DMSO) δ 0.82, 1.20, 2.33, 2.43, 2.72, 2.96, 4.27, 4.42, 5.2, 6.74, 7.06, 7.60, 7.70, 8.30; IR (mull) 3326, 3069, 3036, 2601, 1726, 1638, 1544, 1512, 1407, 1342, 1231, 1183, 1115, 832, 637, cm$^{-1}$. MS (FAB) m/z 568 (MH$^+$), 582, 569, 568, 238, 177, 102, 88, 88, 39, 23. Anal. Found: C, 51.15; H, 5.79; N, 6.64.

EXAMPLE 27

N-[(1,1-Dimethylethoxy)carbonyl]-L-α-glutamyl-O-(dicarboxymethyl)-N-pentyl-L-tyrosinamide
(Formula O-1 (n=2), Chart O)

By an analogous procedure as described for Example 25 is obtained 0.21 g title compound as a white amorphous solid. $^1$H NMR (DMSO) δ 0.81, 1.18, 1.71, 2.12, 2.96–3.10, 3.82, 4.38, 5.19, 6.76, 6.96, 7.08, 7.77, 7.84; IR (mull) 3316, 3067, 2730, 2604, 1720, 1639, 1512, 1395, 1341, 1232, 1168, 1106, 1056, 855, 832, cm$^{-1}$. MS (FAB) m/z 582 (MH$^+$), 133, 102, 88, 84, 57, 43, 41, 39, 29, 23. Anal. Found: C, 53.72; H, 6.75; N, 6.96.

EXAMPLE 28

N-(3-Carboxy-1-oxopropyl)-L-α-glutamyl-O-(dicarboxymethyl)-N-pentyl-L-tyrosinamide
(Formula L-5 (n=2), Chart L)

By a procedure analogous to that described for Example 26 is obtained 0.082 g title compound as a white solid. $^1$H NMR (DMSO) δ 0.82, 1.20, 1.32, 1.55–1.90, 2.14, 2.38, 2.72, 2.92, 4.11, 4.30, 5.21, 6.77, 7.67, 7.77, 8.08; IR (mull) 3316, 3069, 2730, 2605, 1722, 1634, 1546, 1512, 1414, 1341, 1231, 1183, 1116, 834, 721, cm$^{-1}$. MS (FAB) m/z 582 (MH$^+$), 582, 238, 133, 102, 102, 88, 84, 43, 39, 23. Anal. Found: C, 51.51; H, 6.00; N, 6.89.

EXAMPLES 29–35

(General Synthesis of Formula K-6, Chart K)

PREPARATION OF K-2: To a stirring solution of H-Tyr-OBu$^t$ (3.0 g) in CH$_2$Cl$_2$ (150 ml) at 0 C is added EDC (2.42 g) and mono-benzyl succinate (2.62 g). The mixture is stirred for 16 h allowing the solution to warm to ambient temperature. The resulting solution is washed with 10% HCl/H$_2$O (150 ml), the solvent dried over Na$_2$SO$_4$ and evaporated in vacuo. The residue is purified via flash column chromatography (eluant 2:1 hexane/EtOAc) to afford 5.06 g. $^1$H NMR (CDCl$_3$) δ 1.41, 2.50, 2.67, 2.99, 4.68, 5.11, 5.54, 6.12, 6.71, 6.98, 7.33; IR (liq.) 3351, 2979, 1734, 1654, 1615, 1595, 1516, 1455, 1393, 1369, 1356, 1232, 1155, 752, 698, cm$^{-1}$. MS (EI) m/z 427 (M$^+$), 226, 209, 208, 164, 136, 108, 107, 92, 91, 57.). Anal. Found: C, 67.17; H, 6.80; N, 3.27.

PREPARATION OF K-3: To a stirring solution of K-2 (3.55 g) in acetone (175 ml) at ambient temperature is added K$_2$CO$_3$ (2.29 g). Dibenzylbromomalonate (3.31 g) is added and the mixture stirred at ambient temperature overnight. The solvent is removed in vacuo and the residue suspended between EtOAc/H$_2$O (100 ml each). The layers are shaken, the organic layer separated, dried over Na$_2$SO$_4$, and the solvent removed. The residue is purified vie flash column chromatography to afford 1.72 g title compound as a yellow oil. $^1$H NMR (CDCl$_3$) δ 1.39, 2.49, 2.68, 3.00, 4.66, 5.11, 5.23, 5.24, 6.05, 6.82, 7.03, 7.33; MS (EI) m/z 709 (M$^+$), 368, 312, 108, 107, 91, 79, 77, 57, 56, 55. Anal. Found: C, 69.21; H, 6.15; N, 2.03.

PREPARATION OF K-4: To a stirring solution of K-3 (1.56 g) in $CH_2Cl_2$ (40 ml) is added trifluoroacetic acid (100 ml). The resulting solution is stirred for 2 h and solvent removed in vacuo to afford 1.42 g (quant) title compound as a slightly pink oil. $^1$H NMR ($CDCl_3$) δ 2.52, 2.67, 3.07, 4.81, 5.10, 5.20, 5.25, 6.43, 6.83, 7.40, 7.31, 7.80; IR (liq.) 3035, 1741, 1641, 1612, 1535, 1511, 1500, 1456, 1388, 1351, 1219, 1180, 1118, 751, 698, cm$^{-1}$. MS (FAB) m/z 654 (MH$^+$), 656, 655, 654, 564, 447, 446, 181, 107, 92, 91.

GENERAL PREPARATION OF K-5: To a stirring solution of K-4 in $CH_2Cl_2$ (0.035 M) at 0 C is added EDC (1 eq) followed by the requisite amine. The mixture is stirred for 16 h, allowing the solution to warm to ambient temperature. The mixture is diluted with $CH_2Cl_2$ (50 ml), washed with 10% HCl/$H_2O$ (2×50 ml) and saturated $NaHCO_3$. The solvent is dried over $Na_2SO_4$ and removed in vacuo. Purification from $SiO_2$ flash column chromatography (eluant 1:1 EtOAc/hexane) is done to afford title compound.

GENERAL PREPARATION OF K-6: To a stirring solution of requisite ester K-5 in MeOH (0.03M) is added 10% Pd-C (10% w/w). The resulting mixture is hydrogenated at atmospheric pressure for 3 h and filtered through celite. The solvent is removed in vacuo to afford desired material.

The following examples (29–35) are prepared by the general synthesis of K-6 outlined above, using the appropriate commercially available amines (Chart K).

EXAMPLE 29

(S)-[4-[2-[(3-Carboxy-1-oxopropyl)amino]-3-(hexylamino)-3-oxopropyl]phenoxy]propanedioic Acid 0.052 g as a waxy solid. $^1$H NMR (DMSO) δ 0.82, 1.19, 2.32, 2.66, 2.90, 4.32, 5.22, 6.76, 7.09, 7.77, 8.03; IR (mull) 3308, 3069, 3034, 2730, 2597, 1728, 1630, 1550, 1511, 1402, 1341, 1229, 1183, 1111, 833, cm$^{-1}$. HRMS (FAB) found 467.2040. Anal. Found: C, 55.39; H, 6.56; N, 5.62.

EXAMPLE 30

(S)-[4-[2-[(3-Carboxy-1-oxopropyl)amino]-3-[(cyclohexylmethyl)-amino]-3-oxopropyl]phenoxy]propanedioic Acid 0.048 g as a waxy solid. $^1$H NMR (DMSO) δ 0.78, 1.12, 1.32, 1.62, 2.30, 2.62–2.92, 4.32, 5.22, 6.78, 7.09, 7.76, 8.02; IR (mull) 3318, 3068, 3034, 2730, 2665, 2599, 1728, 1629, 1550, 1512, 1402, 1350, 1228, 1184, 1108, cm$^{-1}$. MS (FAB) m/z 479 (MH$^+$), 480, 479, 435, 331, 177, 127, 114, 71, 57, 55. HRMS (FAB) found 479.2029. Anal. Found: C, 56.68; H, 6.46; N, 5.59.

EXAMPLE 31

(S)-[4-[2-[(3-Carboxy-1-oxopropyl)amino]-3-[(2,2-diethoxyethyl)-amino]-3-oxopropyl]phenoxy]propanedioic Acid 0.062 g as a waxy solid. $^1$H NMR (DMSO) δ 1.07, 2.30, 2.66, 2.85, 3.15, 3.42, 3.55, 4.38, 5.25, 5.73, 6.78, 7.12, 7.92, 8.06; IR (mull) 3327, 2728, 2669, 2606, 1732, 1638, 1546, 1512, 1351, 1230, 1183, 1116, 1053, 833, 721, cm$^{-1}$. MS (FAB) m/z 499 (MH$^+$), 453, 251, 194, 177, 136, 107, 101, 88, 57, 23. Anal. Found: C, 50.80; H, 6.05; N, 5.57.

EXAMPLE 32

(S)-[4-[2-[(3-Carboxy-1-oxopropyl)amino]-3-[(3-methylbutyl)-amino]-3-oxopropyl]phenoxy]propanedioic Acid 0.061 g as an amorphous solid. $^1$H NMR (DMSO) δ 0.83, 1.22, 1.48, 2.32, 2.75, 2.82, 3.00, 4.35, 5.22, 6.78, 7.09, 7.74, 8.04; IR (mull) 3315, 3065, 2728, 2669, 2603, 1729, 1630, 1549, 1512, 1341, 1229, 1182, 1111, 833, 721, cm$^{-1}$. MS (FAB) m/z 453 (MH$^+$), 475, 453, 431, 194, 136, 88, 86, 55, 43, 23. Anal. Found: C, 54.45; H, 6.36; N, 5.85.

EXAMPLE 33

(S)-[4-[2-[(3-Carboxy-1-oxopropyl)amino]-3-oxo-3-[[2-(1-piperidinyl)ethyl]amino]propyl]phenoxy]propanedioic Acid 0.047 g as a white solid. $^1$H NMR (DMSO) δ 1.47, 1.66, 2.33, 2.76, 3.05, 4.30, 5.04, 6.64, 7.01, 8.02, 8.16; IR (mull) 3300, 3032, 2729, 2687, 2587, 1722, 1649, 1541, 1512, 1299, 1234, 1182, 1096, 833, 638, cm$^{-1}$. MS (FAB) m/z 494 (MH$^+$), 495, 494, 450, 392, 133, 98, 71, 57, 45, 43. Anal. Found: C, 53.22; H, 6.63; N, 7.88.

EXAMPLE 34

(S)-[4-[2-[(3-Carboxy-1-oxopropyl)amino]-3-[[3-(4-morpholinyl)-propyl]amino]-3-oxopropyl]phenoxy]propanedioic Acid 0.059 g as a waxy solid. $^1$H NMR (DMSO) δ 2.32, 2.50–2.80, 2.97, 3.76, 4.31, 5.10, 6.68, 7.00, 7.79, 8.05; IR (mull) 3303, 2728, 2620, 1725, 1646, 1545, 1512, 1298, 1234, 1183, 1140, 1107, 1049, 834, 638, cm$^{-1}$. MS (FAB) m/z 510 (MH$^+$), 511, 510, 466, 463, 308, 241, 177, 100, 57, 39. Anal. Found: C, 50.54; H, 6.12; N, 7.35.

EXAMPLE 35

(S)-[4-[2-[(3-Carboxy-1-oxopropyl)amino]-3-[[3-(1H-imidazol-1-yl)propyl]amino]-3-oxopropyl]phenoxy]propanedioic Acid 0.049 g as an amorphous solid. $^1$H NMR (DMSO/DCl) δ 0.93, 1.80–1.93, 2.28, 3.03, 4.02, 5.00, 6.78, 7.12, 7.30, 7.63, 7.71; IR (mull) 3283, 3132, 3032, 1717, 1644, 1565, 1511, 1406, 1332, 1300, 1235, 1181, 1089, 834, 633, cm$^{-1}$. MS (FAB) m/z 491 (MH$^+$), 505, 383, 357, 236, 222, 174, 127, 124, 118, 107.

EXAMPLE 36

N-(3-Carboxy-1-oxopropyl)-O-(dicarboxymethyl)-L-tyrosyl-L-norleucinamide (Formula M-6, Chart M)

PREPARATION OF M-2: To a stirring solution of CBZ-L-Tyr-OH (0.50 g) in $CH_2Cl_2$ (25 ml) at 0 C is added H-L-Nle-NH$_2$ HCl (0.264 g), N-methyl morpholine (0.16 g) and EDC (0.303 g). The resulting turbid mixture is stirred for 16 h and allowed to warm to ambient temperature in which time a solid forms. The solid is collected, washed with $CH_2Cl_2$ and dried in vacuo to afford 0.374 g title compound as a white solid. $^1$H NMR (DMSO) δ 0.82, 1.22, 1.40–1.80, 2.59, 2.87, 4.15, 4.92, 6.62, 7.02, 7.28, 7.41, 7.85.

PREPARATION OF M-3: To a stirring solution of M-2 (0.30 g) in acetone (30 ml) at ambient temperature is added diethyl chloromalonate (0.149 g) and $K_2CO_3$ (0.194 g). The resulting mixture is stirred for 16 h and solvent removed in vacuo. The residue is suspended between EtOAc/$H_2O$ (100 ml each), the layers shaken, the organic layer separated, dried over $Na_2SO_4$, and solvent removed in vacuo. The residue is suspended in hexane, sonicated and filtered, to afford 0.295 g title compound as a white solid. $^1$H NMR (DMSO) δ 0.83, 1.15, 1.50, 2.68, 2.95, 4.21, 4.92, 5.61, 6.83, 7.26, 7.49, 7.91; IR (mull) 3286, 1747, 1696, 1674, 1643, 1538, 1510, 1334, 1296, 1290, 1260, 1225, 1186, 1028, 698, cm$^{-1}$. MS (FAB) m/z 586 (MH$^+$), 586, 569, 434, 384, 305, 265, 176, 92, 91, 86. Anal. Found: C, 61.09; H, 6.56; N, 7.03.

PREPARATION OF M-4: To a solution of M-3 (0.25 g) in MeOH is added 10% Pd-C (25 mg) and the mixture hydrogenated at atmospheric pressure for 3 h. The mixture is filtered through celite and solvent removed in vacuo to afford 0.168 g title compound as a clear yellow oil. $^1$H NMR (DMSO) δ 0.89, 1.13, 1, 62, 2.82, 2.75, 3.16, 3.60, 4.32, 5.16, 5.40, 6.11, 6.90, 7.13, 7.75; IR (liq.) 3327, 2959, 2935, 1767, 1746, 1666, 1612, 1511, 1445, 1371, 1298, 1226, 1183, 1097, 1027, cm$^{-1}$. MS (EI) m/z 451 (M$^+$), 434, 295, 294, 266, 265, 186, 169, 141, 107, 86.

PREPARATION OF M-5: To a stirring solution of M-4 (0.157 g) in CH$_2$Cl$_2$ (5 ml) at 0 C is added triethyl amine (0.039 g) followed by succinic anhydride (0.035 g). The resulting solution is stirred overnight allowing the solution to warm to ambient temperature. CH$_2$Cl$_2$ (20 ml) is added and the organics washed with 10% HCl/H$_2$O (2×50 ml). The organic layer is dried over Na$_2$SO$_4$ and solvent removed to afford 0.090 g title compound as a waxy solid. $^1$H NMR (DMSO) δ 0.083, 1.17, 1.50, 1.65, 2.29, 2.65, 2.95, 4.20, 4.42, 5.60, 6.83, 6.97, 7.14, 7.82, 8.10; IR (mull) 3280, 3206, 1745, 1716, 1676, 1666, 1631, 1548, 1511, 1424, 1324, 1300, 1228, 1184, 1098, cm$^{-1}$. MS (FAB) m/z 552 (MH$^+$), 566, 553, 552, 434, 305, 294, 265, 131, 115, 86. Anal. Found: C, 55.96; H, 6.73; N, 7.41.

PREPARATION OF M-6: To a stirring solution of M-5 (0.050g) in THF/MeOH (1:3 v/v, 5 ml) is added LiOH/H$_2$O (2.5 M, 0.18 ml). H$_2$O (3 ml) is added and the mixture is stirred for 3 h. The solution is diluted with H$_2$O (20 ml) and extracted with EtOAc (2×25 ml). The organic layers are combined, dried over Na$_2$SO$_4$ and the solvent removed to afford 0.036 g title compound as a waxy solid. $^1$H NMR (DMSO) δ 0.83, 1.19, 1.53, 1.68, 2.30, 2.71, 2.95, 4.02, 4.40, 5.30, 6.79, 6.99, 7.09, 7.13, 7.80, 8.10; HRMS (FAB) found 496.1929.

EXAMPLE 37

N-(1-Oxohexyl)-L-α-aspartyl-O-(dicarboxymethyl)-N-pentyl-L-tyrosinamide (Formula P-2, Chart P)

PREPARATION OF P-1: To a stirring solution of L-3 (0.25 g) in CH$_2$Cl$_2$ (8 ml) at 0 C is added hexanoyl chloride (0.043 g, 0.32). The resulting solution is stirred for 16 h, allowing the mixture to warm to ambient temperature. The solution is diluted with CH$_2$Cl$_2$ (20 ml) and washed with 10% HCl/H$_2$O (3×50 ml). The organic layer is dried over Na$_2$SO$_4$ and solvent removed to afford 0.164 g title compound as a white solid. $^1$H NMR (DMSO) δ 0.81, 1.20, 2.03, 2.54, 2.73, 2.79, 4.32, 4.60, 5.04, 5.19, 5.77, 6.82, 7.06, 7.31, 7.81, 8.11; IR (mull) 3286, 1765, 1739, 1663, 1639, 1543, 1511, 1499, 1299, 1276, 1223, 1170, 749, 733, 695, cm$^{-1}$. MS (FAB) m/z 836 (MH$^+$), 837, 533, 515, 418, 178, 92, 91, 88, 88, 43. Anal. Found: C, 68.75; H, 6.95; N, 5.01.

PREPARATION OF P-2: To a stirring solution of P-1 (0.175 g) in MeOH (15 ml) is added 10% Pd-C (25 mg). The mixture is hydrogenated at atmospheric pressure for 3 h, and filtered through celite. The solvent is removed to afford 0.113 g title compound as a white solid. $^1$H NMR (DMSO) δ 0.82, 1.22, 1.44, 2.04, 2.38, 2.62, 2.63–3.10, 4.32, 4.51, 5.19, 6.75, 7.04, 7.74, 8.10; IR (mull) 3308, 3069, 3035, 2731, 2597, 1729, 1636, 1541, 1512, 1418, 1341, 1230, 1183, 1114, 637, cm$^{-1}$. MS (FAB) m/z 566 (MH$^+$), 588, 566, 177, 99, 88, 88, 71, 43, 39, 23. Anal. Found: C, 55.95; H, 7.05; N, 7.24.

EXAMPLE 38

(S)-[[4-[3-[[1-[[4-(Dicarboxymethoxy)phenyl]methyl]-2-oxo-2-(pentylamino)ethyl]amino]-3-oxopropyl]phenyl]methyl]propanedioic Acid (Formula N-4, Chart N)

PREPARATION OF N-2: To a stirring suspension of 4-formyl cinnamic acid (N-1, 0.50 g) and dibenzylmalonate (0.806 g) is added piperidine (0.290 g) and acetic acid (3 drops). The mixture is refluxed for 16 h, cooled to ambient temperature, and solvent diluted with EtOAc (50 ml). The organics are washed with 10% HCl/H$_2$O (2×50 ml), solvent dried over Na$_2$SO$_4$ and evaporated to afford 0.485 title compound as a white solid. $^1$H NMR (DMSO) δ 5.25, 5.27, 6.54, 7.35, 7.50, 7.75; IR (mull) 1724, 1696, 1680, 1628, 1442, 1426, 1414, 1315, 1260, 1224, 1215, 1202, 1185, 699, 694, cm$^{-1}$. MS (EI) m/z 442 (M$^+$), 442, 246, 245, 227, 127, 114, 92, 91, 77, 65. Anal. Found: C, 70.77; H, 4.87.

PREPARATION OF N-3: To a stirring suspension of N-2 (0.194 g) and J-4 (0.25 g) at 0 C is added triethyl amine (0.045 g) and EDC (0.085 g). The mixture is stirred for 16 h allowing the solution to warm to ambient temperature. The mixture is diluted with CH$_2$Cl$_2$ (50 ml) and washed with 10% HCl/H$_2$O (2×50 ml). The organic layer is dried over Na$_2$SO$_4$ and evaporated to dryness. The residue is purified via flash column chromatography (eluant 1:1 EtOAc/hexane) to afford 0.038 g title compound as a white solid. $^1$H NMR (CDCl$_3$) δ 0.84, 1.25, 3.00, 3.20, 4.62, 5.21, 5.25, 5.27, 5.28, 5.51, 6.38, 6.87, 7.13, 7.32, 7.54, 7.73; MS (ES+) 957.

PREPARATION OF N-4: To a stirring solution of N-3 (0.030 g) in MeOH/THF (5:3 v/v, 8 ml) is added 10% Pd-C (10 mg). The mixture is hydrogenated at atmospheric pressure for 16 h. The solvent is filtered and evaporated to afford 0.016 g title compound as a white solid. $^1$H NMR (DMSO) δ 0.82, 1.33, 2.28, 2.63, 2.80–3.10, 3.2–4.0, 4.40, 5.12, 6.75, 7.06, 7.73, 8.03; MS (FAB) m/z 601 (MH$^+$), 601, 219, 193, 177, 107, 88, 57, 43, 39, 23.

EXAMPLE 39

(S)-[[4-[2-[(3-Carboxy-1-oxopropyl)amino]-3-oxo-3-(pentylamino)-propyl]phenyl]methyl]propanedioic Acid (Formula G-7, Chart G)

PREPARATION OF G-1: To a stirring solution of E-2 (5.0 g) and pyridine (2.58 g) in CH$_2$Cl$_2$ (50 ml) at 0 C is added trifluoromethane sulfonic anhydride (4.42 g) dropwise over 15 min. After addition, the mixture is stirred for 1 h at 0 C and diluted with CH$_2$Cl$_2$ (50 ml). The organics are washed with 10% HCl/H$_2$O (2×50 ml), separated and dried over Na$_2$SO$_4$. The solvent is filtered through a pad of SiO$_2$ (50 g) and washed with CH$_2$Cl$_2$ (75 ml). The solvent is removed to afford 2.54 g title compound as a yellow solid. $^1$H NMR (CDCl$_3$) δ 0.86, 1.18–1.50, 1.40, 3.09, 4.27, 5.07, 5.90, 7.19, 7.28; IR (mull) 3346, 1683, 1651, 1540, 1523, 1504, 1429, 1271, 1252, 1211, 1169, 1144, 901, 638, 607, cm$^{-1}$. MS (EI) m/z 482 (M$^+$), 426, 409, 312, 268, 243, 232, 143, 135, 107, 57. Anal. Found: C, 50.10; H, 5.83; N, 5.88.

PREPARATION OF G-2: To stirring mixture of G-1 (0.60 g), LiCl (0.158 g) and tributylvinyl tin (0.591 g) in DMF (10 ml) at ambient temperature is added dichlorobis (triphenylphosphine)palladium(II) (0.087 g). The mixture is heated to 90 C and stirred for 16 h. The resulting black mixture is cooled to ambient temperature, poured into ice/H$_2$O, and extracted with EtOAc (3×75 ml). The organic layers are combined, dried over Na$_2$SO$_4$, and solvent removed. The residue is purified via $SiO_2$ flash column chromatography (eluant 2:1 hexane/EtOAc) to afford 0.365 g title compound as a white solid. $^1H$ NMR ($CDCl_3$) δ 0.84, 1.13–1.40, 1.36, 3.06, 4.23, 5.06, 5.22, 5.68, 5.70, 6.67, 7.15, 7.33; IR (mull) 3337, 1690, 1680, 1656, 1540, 1523, 1331, 1321, 1309, 1299, 1269, 1251, 1170, 906, 631, $cm^{-1}$. MS (EI) m/z 360 ($M^+$), 304, 244, 243, 190, 187, 146, 143, 118, 117, 57.

PREPARATION OF G-3: $O_3$ (g) is bubbled through a stirring solution of G-2 (0.30 g) in $CH_2Cl_2$ (50 ml) at −78 C until the blue endpoint is observed. The reaction mixture is capped with a septum and stirred an additional 1.5 h at −78 C. Dimethylsulfide (0.78 g) is added at −78 C and the mixture allowed to warm to ambient temperature (over 1 h). The solvent is removed, the residue taken up in $Et_2O$ (50 ml) and washed with $H_2O$ (2×50 ml). The organic layer is dried over $Na_2SO_4$, solvent removed in vacuo, and residue purified via $SiO_2$ flash column chromatography (eluant 2:1 hexane/EtOAc) to afford 0.172 g title compound as a white solid. $^1H$ NMR ($CDCl_3$) δ 0.85, 1.15–1.36, 1.39, 3.14, 4.30, 5.05, 5.08, 7.38, 7.81, 10.00; IR (mull) 3324, 1700, 1689, 1651, 1607, 1576, 1529, 1333, 1313, 1300, 1270, 1253, 1224, 1214, 1170, $cm^{-1}$. MS (EI) m/z 362 ($M^+$), 306, 289, 243, 193, 192, 149, 148, 143, 120, 57. Anal. Found: C, 65.39; H, 8.43; N, 7.47.

PREPARATION OF G-4: G-3 (0.50 g), dibenzyl malonate (0.47 g), piperidine (0.023 g), and HOAc (3 drops) in benzene (15 ml) are heated to reflux for 2 h. The mixture is cooled to ambient temperature, diluted with EtOAc (50 ml) and washed with 10% $HCl/H_2O$ (2×50 ml). The organic layer is dried over $Na_2SO_4$, the solvent removed, and the residue purified via $SiO_2$ flash column chromatography (eluant 2:1 hexane/EtOAc)to afford 0.060 g title compound as a slightly yellow oil. $^1H$ NMR ($CDCl_3$) δ 0.84, 1.17–1.39, 1.40, 3.02, 3.13, 4.21, 5.00, 5.28, 5.67, 7.09, 7.32, 7.72; IR (mull) 3328, 1726, 1685, 1653, 1632, 1542, 1527, 1321, 1267, 1234, 1213, 1200, 1185, 749, 696, $cm^{-1}$. MS (EI) m/z 628 ($M^+$), 571, 511, 420, 414, 386, 278, 143, 92, 91, 57. Anal. Found: C, 70.21; H, 7.05; N, 4.48.

PREPARATION OF G-5: To a stirring solution of G-4 (0.65 g) in HOAc (10 ml) is added 1.5 M HCl/HOAc (10 ml). The mixture is allowed to stand at ambient temperature for 2 h and the solvent removed to afford 0.58 g (quant) title compound as a slightly yellow amorphous solid. $^1H$ NMR (DMSO) δ 0.76, 1.03, 1.17, 2.89, 3.02, 3.94, 5.25, 5.29, 7.22, 7.36, 7.73, 8.34, 8.41; IR (liq.) 3065, 3034, 2957, 2933, 2872, 2861, 1730, 1669, 1629, 1499, 1456, 1260, 1204, 1185, 697, $cm^{-1}$. MS (FAB) m/z 529 ($MH^+$), 1058, 531, 530, 529, 414, 143, 92, 91, 88, 43. Anal. Found: C, 67.22; H, 6.81; N, 4.94.

PREPARATION OF G-6: To a stirring solution of G-5 (0.507 g) in $CH_2Cl_2$ (15 ml) at 0 C is added triethylamine (0.20 g) followed by succinic anhydride (0.089 g). The mixture is stirred for 16 h allowing to warm to ambient temperature. The mixture is diluted with $CH_2Cl_2$ (50 ml) and washed with 10% $HCl/H_2O$ (2×50 ml). The organic layer is dried over $Na_2SO_4$ and solvent removed to afford 0.557 title compound as a yellow amorphous solid. $^1H$ NMR ($CDCl_3$) δ 0.83, 1.11–1.28, 2.47, 2.63, 3.03, 4.57, 5.25, 5.27, 5.93, 6.88, 7.09, 7.27, 7.70; IR (mull) 3287, 3089, 3064, 3032, 1726, 1640, 1610, 1543, 1356, 1260, 1213, 1198, 1181, 745, 695, $cm^{-1}$. MS (FAB) m/z 629 ($MH^+$), 631, 630, 629, 521, 414, 92, 91, 88, 86, 43. Anal. Found: C, 68.45; H, 6.50; N, 4.50.

PREPARATION OF G-7: To a stirring solution of G-6 (0.15 g) in MeOH (20 ml) is added 10% Pd-C (15 mg) and the mixture hydrogenated at atmospheric pressure for 3 h. The solvent is filtered through celite and removed in vacuo to afford 0.105 g title compound as an amorphous solid. $^1H$ NMR (DMSO) δ 0.82, 1.15–1.30, 2.31, 2.71, 2.96, 3.09, 4.35, 7.07, 7.77, 8.06; IR (mull) 3300, 2730, 2618, 1716, 1632, 1551, 1517, 1422, 1404, 1244, 1212, 1171, 956, 853, 655, $cm^{-1}$. MS (FAB) m/z 451 ($MH^+$), 604, 452, 451, 407, 236, 192, 102, 88, 86, 43. Anal. Found: C, 57.00; H, 6.74; N, 6.06.

EXAMPLE 40

(S)-[[4-[2-[(3-Carboxy-1-oxopropyl)amino]-3-oxo-3-(pentylamino)-propyl]phenyl]methylene] propanedioic Acid (Formula H-1, Chart H)

To a stirring solution of G-6 (0.15 g) in THF/MeOH (3:1 v/v, 5 ml) at ambient temperature is added $LiOH/H_2O$ (2.5 M, 0.52 ml). The mixture is stirred for 3 h and acidified to pH~4 with 10% $HCl/H_2O$. The aqueous layer is extracted with EtOAc (2×50 ml), the organic layers combined and dried over $Na_2SO_4$. The solvent is removed to afford 0.062 g title compound as a waxy solid. $^1H$ NMR (DMSO) δ 0.82, 1.13–1.17, 2.30, 2.78, 2.96, 7.20, 7.29, 7.45, 7.81, 8.10; IR (mull) 3302, 3066, 3031, 2624, 1715, 1630, 1550, 1515, 1442, 1422, 1243, 1212, 1187, 699, 665, $cm^{-1}$. MS (FAB) m/z 449 ($MH^+$), 481, 450, 449, 363, 177, 133, 118, 88, 86, 43.

EXAMPLES 41–50:

(General Synthesis of Formula A-5, Chart A)

PREPARATION OF A-2: To a mixture of L-tyrosine benzyl ester p-toluenesulfonate salt (5.0 g) and triethylamine in $CH_2Cl_2$ (25 mL) at 0 C is added EDC (2.2 g) and monomethyl succinate (1.5 g). The mixture is warmed to room temperature and stirred overnight. The mixture is diluted with EtOAc (150 mL), and washed with 1 M HCl (50 mL), sat. $NaHCO_3$ (50 mL), and sat. NaCl (50 mL). The organic phase is dried ($MgSO_4$), and the solvent is removed under reduced pressure. The residue is purified by flash chromatography ($SiO_2$, 60% EtOAc/hexane) to provide 3.4 g of title compound as a colorless oil which slowly solidified to a white solid: $^1H$ NMR ($CDCl_3$) δ 7.33, 6.84, 6.65, 6.15, 5.62, 5.14, 4.87, 3.67, 3.01, 2.64, 2.47; MS (EI) m/z 385 ($M^+$), 254, 209, 208, 147, 136, 132, 115, 107, 91, 55; Anal. Found: C, 65.41; H, 6.00; N, 3.61.

PREPARATION OF A-3: To a mixture of A-2 (2.64 g) and $K_2CO_3$ (1.9 g) in acetone (20 mL) is added diethyl chloromalonate (2.2 mL). The mixture is stirred vigorously for 18 h. The mixture is partitioned between EtOAc and $H_2O$. The organic phase is washed with sat. $NaHCO_3$ and sat. NaCl. After drying ($MgSO_4$), the solvent is removed under reduced pressure. The residue is purified by flash chromatography (150 g $SiO_2$, 50% EtOAc/hexane) to provide 2.9 g of A-3 as a colorless oil; $^1H$ NMR ($CDCl_3$) δ 7.37, 7.29, 6.90, 6.80, 6.06, 5.12, 4.86, 4.31, 3.67, 3.05, 2.62, 2.48, 1.30; MS (ES−) 542.

PREPARATION OF A-4: A Parr flask is charged with A-3 (150 mg), 10% Pd/C (25 mg) qnd abs. EtOH (25 mL), and the mixture is hydrogenated (35 psi) for 45 minutes. The mixture is filtered through Celite and concentrated to provide 110 mg (87%) of A-4 as a colorless oil: $^1H$ NMR ($CDCl_3$) δ 7.11, 6.88, 6.23, 5.17, 4.79, 4.30, 3.67, 3.15, 3.06, 2.63, 2.28, 1.30; MS (ES−) 452.

GENERAL PREPARATION OF A-5: To a mixture of A-4 (1 eq.) in $CH_2Cl_2$ (0.2 M) at 0 C is added EDC (1 eq.)

followed by the requisite amine. The reaction is warmed to room temperature and stirred for 18 h. The mixture is diluted with EtOAc and washed with 1 M HCl, sat NaHCO$_3$, and sat. NaCl. The organic phase is dried (MgSO$_4$) and concentrated under reduced pressure. The residue is dissolved in THF (3 mL), and a solution of LiOH H$_2$O (6–8 eq.) in H$_2$O (1 mL) is added. The mixture is stirred for 2–4 h. The mixture is acidified with 1M HCl, and extracted with EtOAc (3×). The combined organic phase is washed with sat. NaCl and dried (MgSO$_4$). The solvent is removed in vacuo to provide A-5.

EXAMPLE 41

(S)-[4-[2-[(3-Carboxy-1-oxopropyl)amino]-3-[(3,3-diphenylpropyl)-amino]-3-oxopropyl]phenoxy] propanedioic Acid (Chart A, A-5)

$^1$H NMR (DMSO) δ 8.04, 7.90, 7.25, 7.12, 6.77, 5.22, 4.34, 3.92, 2.89, 2.65, 2.31, 2.10; MS (ES+) 577; Anal. Found: C, 62.82; H, 5.77; N, 4.75.

EXAMPLE 42

(S)-[4-[3-[(1,3-Benzodioxol-5-ylmethyl)amino]-2-[(3-carboxy-1-oxopropyl)amino]-3-oxopropyl] phenoxy]propanedioic Acid (Chart A, A-5)

$^1$H NMR (DMSO) δ 8.32, 8.11, 7.10, 6.78, 5.59, 5.95, 5.23, 4.40, 4.14, 3.92, 2.70, 2.30; MS (ES−) 515.

EXAMPLE 43

(S)-[4-[2-[(3-Carboxy-1-oxopropyl)amino]-3-oxo-3-[(3-phenylpropyl)amino]propyl]phenoxy] propanedioic Acid (Chart A, A-5)

$^1$H NMR (DMSO) δ 8.10, 7.89, 7.25, 7.15, 6.80, 5.23, 4.33, 3.01, 2.89, 2.70, 2.32, 1.61; MS (ES−) 499; Anal. Found: C, 58.46; H, 5.68; N, 5.47.

EXAMPLE 44

(S)-[4-[2-[(3-Carboxy-1-oxopropyl)amino]-3-[(1-naphthalenyl-methyl)amino]-3-oxopropyl]phenoxy] propanedioic Acid (Chart A, A-5)

$^1$H NMR (DMSO) δ 8.45, 8.17, 8.00, 7.92, 7.81, 7.41, 7.41, 7.25, 7.11, 6.77, 5.25, 4.70, 4.50, 3.94, 2.72, 2.32; MS (ES−) 521; HRMS (FAB) found 523.1722.

EXAMPLE 45

(S)-[4-[2-[(3-Carboxy-1-oxopropyl)amino]-3-(decylamino)-3-oxopropyl]phenoxy]propanedioic Acid (Chart A, A-5)

$^1$H NMR (DMSO) δ 8.06, 7.80, 7.10, 6.78, 5.24, 3.33, 2.98, 2.85, 2.65, 2.30, 1.21, 0.83; HRMS (FAB) found 523.2634; Anal. Found: C, 59.64; H, 7.88; N, 5.25.

EXAMPLE 46

(S)-[4-[3-[[2-[4-(Aminosulfonyl)phenyl]ethyl] amino]-2-[(3-carboxy-1-oxopropyl)amino]-3-oxopropyl]phenoxy]propanedioic Acid (Chart A, A-5)

$^1$H NMR (DMSO) δ 8.09, 8.00, 7.71, 7.35, 7.27, 5.27, 4.33, 2.84, 2.60–2.77, 2.31; MS (ES−) 564; Anal. Found: C, 48.88; H, 4.95; N, 7.04.

EXAMPLE 47

(S)-[4-[2-[(3-Carboxy-1-oxopropyl)amino]-3-oxo-3-[[[4-(trifluoromethyl)phenyl]methyl]amino]propyl]-phenoxy]-propanedioic Acid (Chart A, A-5)

$^1$H NMR (DMSO) δ 8.50, 8.18, 7.62, 7.31, 7.12, 6.80, 5.27, 4.43, 7.32, 3.91, 3.71, 2.33; MS (ES−) 539; Anal. Found: C, 52.27; H, 4.68; N, 5.12.

EXAMPLE 48

(S)-[4-[2-[(3-Carboxy-1-oxopropyl)amino]-3-oxo-3-[(2-phenoxyethyl)amino]propyl]phenoxy] propanedioic Acid (Chart A, A-5)

$^1$H NMR (DMSO) δ 8.15, 8.09, 7.27, 7.10, 6.92, 7.76, 5.23, 4.40, 3.90, 2.87, 2.65, 2.30; MS (FAB) m/z 503 (MH$^+$), 392, 391, 149, 113, 71, 69, 57, 55, 43, 41; HRMS (FAB) found 503.1656; Anal. Found: C, 57.51; H, 5.79; N, 4.96.

EXAMPLE 49

(S)-[4-[2-[(3-Carboxy-1-oxopropyl)amino]-3-[[2-(4-hydroxyphenyl)-ethyl]amino]-3-oxopropyl]phenoxy] propanedioic Acid (Chart A, A-5)

$^1$H NMR (DMSO) δ 8.06, 7.90, 7.09, 6.95, 6.79, 6.64, 5.27, 4.31, 3.15, 2.85, 2.63, 2.52, 2.33; MS (ES−) 501; HRMS (FAB) found 503.1656.

EXAMPLE 50

(S)-[4-[2-[(3-Carboxy-1-oxopropyl)amino]-3-[[(4-carboxyphenyl)-methyl]amino]-3-oxopropyl] phenoxy]propanedioic Acid (Chart A, A-5)

$^1$H NMR (DMSO) δ 8.49, 8.20, 7.85, 7.27, 7.13, 6.80, 5.28, 4.45, 4.31, 2.95, 2.71, 2.34; MS (FAB) m/z 517 (MH$^+$), 517, 391, 149, 113, 71, 69, 57, 55, 43, 41; HRMS (FAB) found 517.1451; Anal. Found: C, 54.60; H, 5.25; N, 4.82.

EXAMPLE 51

(S)-[4-[2-[(4-Amino-1,4-dioxobutyl)amino]-3-oxo-3-(pentylamino)-propyl]phenoxy]propanedioic Acid (Chart B, B-5)

PREPARATION OF B-2: To a mixture of Cbz-Try-OH (2 g) in CH$_2$Cl$_2$ (75 mL) and DMF (5 mL) at 0 C is added EDC (1.21 g). After a few minutes, amylamine (0.74 mL) is added, and the mixture is warmed to room temperature and stirred for 4.5 h. 10% HCl (50 mL) is added, and the phases are separated. The organic phase is washed with sat. NaCl (30 mL), dried (MgSO$_4$), and concentrated. The residue is purified by flash chromatography (75 g SiO$_2$, 50% EtOAc/ hexane) to give 1.7 g of title compound as a white solid: $^1$H NMR (CDCl$_3$) δ 7.34, 7.06, 6.74, 5.53, 5.35, 5.09, 5.05, 4.25, 3.14, 3.15, 2.92, 1.14–1.35, 0.86; MS (EI) m/z 384 (M$^+$), 234, 233, 226, 177, 162, 147, 127, 107, 92, 91; Anal. Found: C, 68.53; H, 7.14; N, 7.25.

PREPARATION OF B-3: To a mixture of B-2 (200 mg) and K$_2$CO$_3$ (146 mg) in acetone (1.5 mL) is added diethyl chloromalonate (0.17 mL). The mixture is stirred vigorously for 18 h. The mixture is partitioned between EtOAc (10 mL) and H$_2$O (5 mL). The organic phase is washed with H$_2$O (1×5 mL) and sat. NaCl (1×5 mL). After drying (MgSO$_4$), the solvent is removed under reduced pressure. The residue is purified by flash chromatography (30 g SiO$_2$, 40% EtOAc/ hexane) to provide 140 mg (49%) of title compound (B-3)

as a white solid: $^1$H NMR (CDCl$_3$) δ 7.33, 7.10, 6.88, 5.55, 5.31, 5.14, 5.08, 4.30, 3.12, 2.93, 1.30, 0.86; MS (ES–) 541.

PREPARATION OF B-4: To a solution of B-3 (2.9 g) in abs. EtOH (100 mL) and THF (10 mL) is added 10% Pd/C (0.29 g, moistened with abs. EtOH). The mixture is hydrogenated (40 psi) for 1 h. The mixture is filtered through Celite and concentrated under reduced pressure. The residue is dissolved in a 1 M solution of HCl in HOAc (10 mL). After stirring for several minutes, the mixture is concentrated to 2–3 mL. A large amount of Et$_2$O is added, and the mixture is cooled to 0 C. The Et$_2$O is decanted from the oil which had settled on the flask. The oil is washed with Et$_2$O, and the Et$_2$O is decanted again. To the oil is added Et$_2$O again, and the mixture is sonicated. The oil gradually crystallizes, and the solid is collected to provide 2.0 g of B-4 as an off-white solid: $^1$H NMR (DMSO) δ 8.39, 8.23, 7.14, 6.90, 5.63, 4.20, 3.88, 3.05, 2.93, 1.19, 1.1–1.4, 0.82; MS (ES+) 409.1.

PREPARATION OF B-5: To a suspension of succinamic acid (40 mg) in CH$_2$Cl$_2$ (1 mL) at 0 C is added EDC (65 mg) and HOBT (46 mg), and the mixture is stirred for a few minutes. B4 (150 mg) and triethylamine (48 mL) are added, and the mixture is warmed to room temperature and stirred overnight. The mixture is partitioned between EtOAc and 1 M HCl. The organic phase is washed with sat. NaHCO$_3$, sat. NaCl, and dried (MgSO$_4$). After the solvent is removed under reduced pressure, the residue is purified by flash chromatography (11 g SiO$_2$, 6% MeOH/CH$_2$Cl$_2$) to yield 72 mg of a white solid. To a solution of the solid dissolved in THF (3 mL) and MeOH (1 mL) is added a solution of LiOH H$_2$O (30 mg) in H$_2$O (1 mL). The mixture is stirred at room temperature for 2.5 h. The mixture is neutralized with 1 M HCl and extracted with EtOAc (3×). The combined organic phase is washed with sat. NaCl and dried (MgSO$_4$). The solvent is removed in vacuo to give 27 mg of B-5 as a white solid: $^1$H NMR (DMSO) δ 8.05, 7.85, 7.27, 1.12, 6.79, 6.75, 5.26, 4.30, 2.89–3.03, 2.89–3.03, 2.60–2.71, 2.12–2.32, 1.11–1.38, 0.83; MS (ES–) 450; HRMS (FAB) found 452.2051.

EXAMPLES 52–54

(General Synthesis of Formulae BB-2 and BB-3, Chart BB)

GENERAL PREPARATION OF BB-1: To a mixture of the N-protected amino acid (0.34 mmol) in CH$_2$Cl$_2$ (1 mL) at 0 C is added EDC (0.34 mmol). After stirring for a few minutes, the compound (B-4) (150 mg) and triethylamine (48 mL) are added, and the mixture is warmed to room temperature and stirred overnight. The mixture is partitioned between EtOAc and 1 M HCl. The organic phase is washed with sat. NaHCO$_3$, sat. NaCl, and dried (MgSO$_4$). The solvent is removed under reduced pressure to provide BB-1 which used directly in the next step.

GENERAL PREPARATION OF BB-2: BB-1 (0.34 mmol) is dissolved in a 1 M solution of HCl in acetic acid (4 mL), and stirred at room temperature for 3 h. The solvent is removed under reduced pressure, and the residue is dissolved in a mixture of triethylamine (0.75 mmol) in CH$_2$Cl$_2$ (1.5 mL). The mixture is cooled to 0 C, and succinic anhydride (0.34 mmol) is added. The mixture is warmed to room temperature and stirred overnight. The mixture is partitioned between EtOAc and 1 M HCl, and the organic phase is washed with sat. NaCl and dried (MgSO$_4$). After the solvent is removed, the residue is dissolved in THF (3 mL), and a solution of LiOH H$_2$O (1–2 mmol) in H$_2$O (1 mL) is added. The mixture is stirred for 2–5 h. The mixture is neutralized with 1 M HCl and extracted with EtOAc (2×). The combined organic phase is washed with sat. NaCl and dried (MgSO$_4$). The solvent is removed in vacuo to provide BB-2.

GENERAL PREPARATION OF BB-3: Prepared by direct LiOH saponification of BB-1 with isolation as described in the general synthesis of BB-2.

EXAMPLE 52

N-[(Phenylmethoxy)carbonyl]-L-α-aspartyl-O-(dicarboxymethyl)-N-pentyl-L-tyrosinamide (Chart BB, BB-3)

Obtained 130 mg of title compound (BB-3) as a white solid. 1H NMR (DMSO) δ 8.10, 7.80, 7.45, 7.31, 7.00, 6.78, 5.24, 5.00, 4.32, 2.80–3.00, 2.55–2.70, 1.10–1.35, 0.82; MS (FAB) m/z 602 (MH$^+$), 602, 392, 391, 149, 113, 91, 74, 71, 57, 43; HRMS (FAB) found 602.2363.

EXAMPLE 53

N-[(1,1-Dimethylethoxy)carbonyl]-D-α-aspartyl-O-(dicarboxymethyl)-N-pentyl-L-tyrosinamide (Chart BB, BB-3)

Obtained 90 mg of title compound (BB-3) as a white solid. $^1$H NMR (DMSO) δ 8.04, 7.80, 7.09, 6.85, 7.78, 5.24, 4.35, 4.19, 2.81–3.09, 2.70, 1.34, 110–1.40, 0.82; MS (FAB) m/z 568 (MH$^+$), 468, 238, 194, 136, 133, 88, 57, 43, 41, 29, HRMS (FAB) found 568.2498; Anal. Found: C, 53.89; H, 6.58; N, 7.23.

EXAMPLE 54

4-Benzoyl-N-(3-carboxy-1-oxopropy)-L-phenylalanyl-O-(dicarboxymethyl)-N-pentyl-L-tyrosinamide (Chart BB, BB-2)

Obtained 169 mg of title compound (BB-2) as an off-white solid. $^1$H NMR (DMSO) δ 8.12, 8.05, 7.75, 7.70–7.75, 7.35, 7.11, 6.81, 5.25, 4.51, 4.35, 2.70–3.05, 2.32, 1.10–1.35, 0.80; MS (FAB) m/z 704 (MH$^+$), 705, 704, 353, 238, 224, 194, 136, 107, 105, 88; HRMS (FAB) found 704.2804; Anal. Found: C, 62.15; H, 6.03; N, 5.87.

EXAMPLE 55

(S)-2-[4-[2-[(3-Carboxy-1-oxopropyl)amino]-3-oxo-3-(pentylamino)propyl]phenoxy]-2-butenedioic Acid (Chart E, E-9)

To a mixture of E-5 (0.37 g) and triethylamine (0.17 ml) in THF (5 mL) is added dimethylacetylene dicarboxylate (0.25 mL), and the mixture is heated at 50 C overnight. The mixture is diluted with Et$_2$O, and washed with 1 M HCl and sat. NaCl. The organic phase is dried (Na$_2$SO$_4$) and concentrated. The residue is purified by flash chromatography (SiO$_2$, 90% EtOAc/hexane) to yield 0.41 g of E-7 as a 1:1 mixture of isomers. To a mixture of (E-7, Chart E) (100 mg) in MeOH (5 mL) is added a solution of LiOH H$_2$O (50 mg) in H$_2$O (1.5 mL), and the mixture is stirred at room temperature overnight. The reaction mixture is concentrated in vacuo, and the residue is dissolved in H$_2$O. After cooling to 0 C, 1 M HCl is added until pH=1. The solid which slowly precipitates over several hours at 0 C is collected and dried to provide 30 mg of E-9 (6:1 mixture of isomers) as a slight yellow solid: $^1$H NMR (MeOH) δ 7.18, 6.86, 6.55, 5.10, 4.49, 3.10, 2.87, 2.39–2.54, 1.27–1.45, 0.90; HRMS (FAB) found 465.1856; Anal. Found: C, 54.20; H, 6.04; N, 5.77.

EXAMPLE 56

[2(S)]-[4-[2-[(3-Carboxy-1-oxopropyl)amino]-3-oxo-3-(pentylamino)propyl]phenoxy]butanedioic Acid (Chart E, E-8)

To a suspension of E-4 (50 mg) and triethylamine (18 mL) in THF (0.3 mL) is added a solution of dibenzylacetylene dicarboxylate (35 mg) in THF (0.2 mL). The reaction mixture is heated at 50 C for 20 h. The mixture is diluted with $Et_2O$, and washed with 1 M HCl and sat. NaCl. The organic phase is dried ($Na_2SO_4$), and the solvent is removed in vacuo. The residue is purified by flash chromatography (9 g $SiO_2$, 60% EtOAc/hexane) to provide 48 mg of E-6 as a 1:1 mixture of isomers. A mixture of E-6 (48 mg) and 10% Pd/C (5 mg) in MeOH (2 mL) is stirred under a hydrogen atmosphere (balloon) for 1 h. The mixture is filtered through Celite and concentrated to provide 27 mg of E-8 as a glass: $^1$H NMR (DMSO) δ 8.02, 7.78, 7.08, 6.76, 4.92, 4.32, 2.6–3.0, 2.25–2.35, 1.1–1.4, 0.83; MS (FAB) m/z 467 ($MH^+$), 489, 468, 467, 349, 252, 136, 107, 88, 86, 43; HRMS (FAB) found 467.2040.

EXAMPLE 57

(R)-[4-[2-[(3-Carboxy-1-oxopropyl)amino]-3-oxo-3-(pentylamino)-propyl]phenoxy]propanedioic Acid (Chart J, J-6)

Prepared by general method of Chart J from N-t-Boc-D-tyrosine. $^1$H NMR (MeOH) δ 7.83, 7.16, 6.90, 5.21, 4.48; MS (ES−) 451; Anal. Found: C, 54.36; H, 6.41; N, 6.22.

EXAMPLE 58

(S)-2-(Carboxymethoxy)-5-[2-[(3-carboxy-1-oxopropyl)amino]-3-oxo-3-(pentylamino)propyl] benzoic Acid (Chart Q, Q-6)

PREPARATION OF Q-2: To a stirring mixture of 3-iodo-L-tyrosine (10.0 g) in dioxane (100 mL), $H_2O$ (50 mL) and 1 M aqueous NaOH (50 mL) is added di-t-butyl dicarbonate (7.8 g) at 0° C. The mixture is stirred for 2 h allowing the solution to warm to ambient temperature, and is then washed with EtOAc (2×50 mL). The water layer is separated and carefully acidified with 4 M $NaHSO_4H_2O$ in a beaker, and is then extracted with EtOAc (2×100 mL). The organic layer is dried ($NaSO_4$) and concentrated to afford 15.1 g of the crude acid as a yellow oil. The acid is suspended in $CH_2Cl_2$ (200 mL) and cooled with ice to 0° C. 1-(3-Dimethylaminopropyl)-3-ethylcarbodiimide hydrochloride (EDC, 6.2 g) is added and the mixture is stirred for 10 min at 0° C. 1-Pentylamine (3.8 mL) is added, and the mixture is stirred for 16 h allowing the solution to warm to ambient temperature. The mixture is washed with 10% aqueous HCl (2×100 mL), the organic layer dried ($MgSO_4$), and concentrated. The residue is purified by column chromatography ($SiO_2$, EtOAc), which furnishes 10.0 g of Q-2 as a white solid. $^1$H NMR 400 MHz ($CDCl_3$) δ 0.87, 1.21, 1.30, 1.41, 1.43, 2.93, 3.09–3.20, 4.17, 5.20, 6.00, 6.85, 7.05, 7.50; $^{13}$C NMR ($CDCl_3$) δ 13.95, 22.28, 28.26, 28.89, 29.04, 37.34, 39.54, 54.80, 80.37, 85.24, 115.04, 130.47, 130.86, 139.00, 154.27, 155.52, 171.01. Anal. Found: C, 47.5; H, 6.1.

PREPARATION OF Q-3: Triethylamine (0.61 mL) is added to a stirring suspension of Q-2 (1.05 g), palladium (II) acetate (14 mg) and 1,1'-bis(diphenylphosphino)-ferrocene (DPPF, 73 mg) in DMF/MeOH 4:1 (5 mL). The mixture is saturated with CO (1 atm) and stirred at 70° C. for 16 h. The mixture is extracted with EtOAc (5 mL), and the organic layer is washed with 10% aqueous HCl (2×2 mL), dried ($MgSO_4$) and concentrated. The residue is purified by column chromatography ($SiO_2$, EtOAc/n-hexane 1:2), which furnishes 0.54 g of Q-3 as a white solid. $^1$H NMR 500 MHz ($CDCl_3$) δ 0.86, 1.17, 1.25, 1.36, 1.41, 2.97, 3.12–3.21, 3.92, 4.21, 5.11, 5.81, 6.91, 7.30, 7.67; $^{13}$C NMR ($CDCl_3$) δ 13.86, 22.24, 28.26, 28.90, 29.05, 37.77, 39.47, 52.23, 54.69, 80.37, 112.25, 117.82, 127.54, 130.34, 136.76, 160.56, 170.32, 170.74. Anal. Found: C, 61.6; H, 7.7.

PREPARATION OF Q-4: A mixture of Q-3 (259 mg), methyl bromoacetate (66 mL) and freshly ground $K_2CO_3$ (96 mg) is suspended in acetone (5 mL). After being stirred for 24 h at ambient temperature, TLC (EtOAc/n-hexane 1:1) indicates that not all starting material has been consumed, and additional methyl bromoacetate (60 mL, 0.63 mmol) is added. After stirring for 24 h, $H_2O$ (2 mL) is added and the mixture is extracted with EtOAc (3 mL). The organic layer is dried ($MgSO_4$) and concentrated. The residue is purified by column chromatography ($SiO_2$, EtOAc/n-hexane 1:1), which furnishes 163 mg of Q-4 as a white solid. $^1$H NMR 500 MHz ($CDCl_3$) δ 0.87, 1.21, 1.28, 1.38, 1.41, 3.00, 3.16, 3.79, 3.88, 4.23, 4.70, 5.10, 6.81, 7.29, 7.66; $^{13}$C NMR ($CDCl_3$) δ 13.86,.22.21, 28.22, 28.88, 29.02, 37.51, 39.46, 52.04, 52.20, 55.87, 66.68, 80.19, 114.61, 121.21, 130.35, 132.59, 134.24, 154.25, 156.44, 165.97, 168.95, 170.69. Anal. Found: C, 60.6; H, 7.5.

PREPARATION OF Q-5: Trifluoroacetic acid (0.38 mL) is carefully added to a stirring solution of Q-4 (159 mg) in $CH_2Cl_2$ (3 mL) at 0° C. The mixture is stirred for 4 h allowing the solution to warm to ambient temperature. The volatiles are removed in vacuo and the residue is partitioned between EtOAc (3 mL) and saturated $NaHCO_3$ (3 mL). The organic layer is dried ($MgSO_4$), and concentrated to dryness to afford 130 mg of the crude amine as a colorless oil. The amine is dissolved in $CH_2Cl_2$ (3 mL) and cooled with ice to 0° C. Succinic anhydride (33 mg) and triethylamine (101 mL) is added and the mixture is stirred for 16 h allowing the solution to warm to ambient temperature. The mixture is diluted with $CH_2Cl_2$ (3 mL) and the organic phase is washed with 10% aqueous HCl (2×3 ml), dried ($MgSO_4$), and concentrated. The residue is purified by column chromatography ($SiO_2$, mobile impurities are eluted with 5% MeOH in $CH_2Cl_2$, and then 5% MeOH/1% HOAc in $CH_2Cl_2$ to bring of product). The collected fractions are concentrated, and the remaining HOAc is removed by azeotroping with toluene on a rotavapor and then drying over night under high vacuum, which furnishes 109 mg of Q-5 as a white solid. $^1$H NMR 400 MHz (MeOH-$d_4$) δ 0.95, 1.29, 1.38, 1.48, 2.43–2.64, 2.91, 3.13–3.22, 3.82, 3.92, 4.55, 4.83, 7.00, 7.43, 7.72, 7.97; $^{13}$C NMR (MeOH-$d_4$) δ 14.75, 23.78, 30.35, 30.52, 30.57, 31.81, 38.19, 40.99, 52.95, 53.00, 56.62, 67.31, 115.68, 122.18, 132.22, 133.74, 135.87, 158.12, 168.53, 171.27, 173.51, 174.98, 176.81. MS (ESI) 481 (M+H). Anal. Found: C, 57.3; H, 6.7.

PREPARATION OF Q-6: A solution of Q-5 (87 mg) and 2.5 M aqueous LiOH (435 mL) in THF/MeOH/$H_2O$ 3:1:1 (3 mL) is stirred at ambient temperature for 16 h. The reaction mixture is acidified with 10% aqueous HCl and extracted with EtOAc (4×2 mL). The organic layer is dried ($MgSO_4$) and concentrated to dryness which furnished 68 mg of Q-6 as a white solid. $^1$H NMR 400 MHz (MeOH-$d_4$) δ 0.66, 1.00, 1.08, 2.13–2.40, 2.65, 2.84–2.93, 4.28, 4.58, 6.79, 7.20, 7.56, 7.69; $^{13}$C NMR (MeOH-$d_4$) δ 14.75, 23.78, 30.34, 30.47, 30.52, 31.74, 38.22, 40.87, 56.58, 67.67, 115.90, 121.69, 132.74, 134.38, 136.40, 158.14, 169.50, 172.65, 173.41, 174.97, 176.76. MS (ESI) 453 (M+H). Anal. Found: C, 54.3; H, 6.3

Examples 59–64 were prepared according to the general procedure described for BB-2.

EXAMPLE 59

2-{4-[(2S)-2-({(2S)-3-[4-(benzyloxy)phenyl]-2-[(3-carboxypropanoyl)amino]propanoyl}amino)-3-oxo-3-(pentylamino)propyl]phenoxy}malonic Acid
(Chart BB, BB-2)

$^1$H NMR (DMSO-d$_6$) δ 8.05 (d, 1H), 7.95 (d, 1H), 7.66 (t, 1H), 7.36 (m, 5H), 7.09 (t, 4H), 6.82 (dd, 4H), 5.25 (s, 1H), 5.02 (s, 2H), 4.34 (m, 2H), 2.97 (m, 2H), 2.95–2.90 (m, 2H), 2.90 (dd, 1H), 2.61 (dd, 1H), 2.30 (m, 4H), 1.33–1.13 (m, 6H), 0.8 (t, 3H); MS (FAB) m/z (rel. intensity) 706 (MH$^+$, 36), 707 (15), 706 (36), 353 (15), 238 (13), 226 (28), 91 (99), 88 (16), 57 (20), 55 (15), 43 (20); HRMS (FAB) calcd for C$_{37}$H$_{43}$N$_3$O$_{11}$+H$_1$ 706.2975; found 706.2986.

EXAMPLE 60

2-{4-[(2S)-2-({(2R)-3-(4-benzoylphenyl)-2-[(3-carboxypropanoyl)amino]propanoyl}amino)-3-oxo-3-(pentylamino)propyl]phenoxy}malonic Acid
(Chart BB, BB-2)

$^1$H NMR (DMSO-d$_6$) δ 8.38 (d, 1H), 8.10 (d, 1H), 7.90 (t, 1H), 7.67 (m, 3H), 7.55 (m, 4H), 7.25 (d, 2H), 7.25 (d, 2H), 7.79 (d, 2H), 5.21 (s, 1H), 4.52 (m, 1H), 4.38 (m, 1H), 3.00 (m, 2H), 2.75–2.90 (m, 2H), 2.60 (dd, 2H), 2.27 (m, 4H), 1.21 (m, 6H), 0.83 (t, 3H); MS (FAB) m/z (rel. intensity) 704 (MH$^+$, 99), 705 (42), 704 (99), 353 (20), 238 (35), 224 (70), 219 (27), 194 (19), 107 (28), 105 (34), 88 (49); HRMS (FAB) calcd for C$_{37}$H$_{41}$N$_3$O$_{11}$+H$_1$ 704.2819, found 704.2822.

EXAMPLE 61

(Chart BB, BB-2) 2-{4-[(2S)-2-[((2S)-2-[(3-carboxypropanoyl)amino]-3-{4-[(2,6-dichlorobenzyl)oxy]phenyl}propanoyl]amino]-3-oxo-3-(pentylamino)propyl]phenoxy}malonic Acid $^1$H NMR (DMSO-d$_6$) δ 8.10 (d, 1H), 7.95 (d, 1H), 7.67 (t, 1H), 7.54 (m, 2H), 7.45 (dd, 1H), 7.11 (m, 4H), 6.91 (d, 2H), 6.81 (d, 2H), 5.26 (s, 1H), 5.15 (s, 2H), 4.35 (m, 2H), 2.98 (m, 2H), 2.85 (m, 2H), 2.73 (dd, 1H), 2.62 (dd, 1H), 2.33 (m, 4H), 1.33–1.12 (m, 6H), 0.81 (t, 3H); MS (FAB) m/z (rel. intensity) 774 (MH$^+$, 99), 776 (70), 775 (53), 774 (99), 391 (97), 294(48), 161 (54), 159 (80), 149 (63), 136 (39), 88 (46); HRMS (FAB) calcd for C$_{37}$H$_{41}$CL$_2$N$_3$O$_{11}$+H$_1$ 774.2196, found 774.2224.

EXAMPLE 62

(Chart BB, BB-2) 2-{4-[(2S)-2-({(2S)-3-[4-(tert-butoxy)phenyl]-2-[(3-carboxypropanoyl)amino]propanoyl}amino)-3-oxo-3-(pentylamino)propyl]phenoxy}malonic Acid $^1$H NMR (DMSO-d$_6$) δ 8.05 (d, 1H), 7.90 (d, 1H), 7.62 (t, 1H), 7.10 (d, 2H), 6.94 (d, 2H), 6.80 (d, 2H), 6.58 (d, 2H), 5.26 (s, 1H), 4.33 (m, 2H), 2.95 (m, 2H), 2.90–2.70 (m, 3H), 2.51 (dd, 1H), 2.40 (m, 9H), 2.32 (m, 4H), 1.35–1.10 (m, 6H), 0.82 (t, 3H); MS (FAB) m/z (rel. intensity) 672 (MH$^+$, 2), 616 (56), 149 (99), 136 (55), 135 (67), 71 (48), 69 (48), 57 (83), 55 (60), 43 (66), 41 (48); HRMS (FAB) calcd for C$_{34}$H$_{45}$N$_3$O$_{11}$+H$_1$ 672.3132, found 672.3110.

EXAMPLE 63

(Chart BB, BB-2) 2-{4-[(2S)-2-({(2S)-2-[(3-carboxypropanoyl)amino]-3-phenylpropanoyl}amino)-3-oxo-3-(pentylamino)propyl]phenoxy}malonic Acid $^1$H NMR (DMSO-d$_6$) δ 8.10 (d, 1H), 7.96 (d, 1H), 7.69 (t, 1H), 7.15 (m, 7H), 6.80 (d, 2H), 5.26 (s, 1H), 4.35 (m, 2H), 2.92 (m, 4H), 2.71 (m, 2H), 2.80 (m, 4H), 1.25 (m, 6H), 0.82 (t, 3H); MS (FAB) m/z (rel. intensity) 600 (MH$^+$, 35), 600 (35), 155 (22), 149 (50), 136 (20), 120 (99), 88 (27), 73 (32), 71 (23), 57 (34), 43 (26); HRMS (FAB) calcd for C$_{30}$H$_{37}$N$_3$O$_{10}$+H$_1$ 600.2557, found 600.2579.

EXAMPLE 64

(Chart BB, BB-2) 2-{4-[(2S)-2-{[(2S)-2-[(3-carboxypropanoyl)amino]-3-(4-methoxyphenyl)propanoyl]amino}-3-oxo-3-(pentylamino)propyl]phenoxy}malonic Acid $^1$H NMR (DMSO-d$_6$) δ 8.02 (d, 1H), 7.90 (d, 1H), 7.64 (t, 1H), 7.09 (m, 4H), 6.78 (m, 4H), 5.25 (s, 1H), 4.35 (m, 2H), 3.68 (s, 3H), 2.98 (m, 2H), 2.9–2.70 (m, 3H), 2.60 (dd, 1H), 2.30 (m, 4H), 1.35–1.10 (m, 6H), 0.82 (t, 3H); MS (FAB) m/z (rel. intensity) 630 (MH$^+$, 81), 631 (28), 630 (81), 353 (25), 250 (25), 238 (23), 177 (30), 161 (28), 150 (99), 121 (44), 88 (39); HRMS (FAB) calcd for C$_{31}$H$_{39}$N$_3$O$_{11}$+H$_1$ 630.2662, found 630.2661.

Examples 65–71 were prepared according to the general procedure described for BB-3.

EXAMPLE 65

(Chart BB, BB-3) 2-{4-[(2S)-2-({(2S)-3-(4-benzoylphenyl)-2-[(tert-butoxycarbonyl)amino]propanoyl}amino)-3-oxo-3-(pentylamino)propyl]phenoxy}malonic Acid $^1$H NMR (DMSO-d$_6$) δ 8.00 (d, 1H), 7.88 (t, 1H), 7.66 (m, 5H), 7.53 (t, 2H), 7.12 (d, 2H), 7.00 (d, 1H), 6.80 (d, 2H), 5.23 (s, 1H), 4.40 (m, 1H), 4.30 (m, 1H), 2.70–3.05 (m, 6H), 1.10–1.30 (m, 15H), 0.80 (t, 3H); MS (FAB) m/z (rel. intensity) 704 (MH$^+$, 6), 648 (30), 238 (23), 224 (49), 194 (30), 136 (20), 105 (33), 88 (99), 57 (88), 43 (24), 41 (22); HRMS (FAB) calcd for C$_{38}$H$_{45}$N$_3$O$_{10}$+H$_1$ 704.3183, found 704.3171.

EXAMPLE 66

(Chart BB, BB-3) 2-{4-[(2S)-2-[((2S)-2-[(tert-butoxycarbonyl)amino]-3-{4-[(2,6-dichlorobenzyl)oxy]phenyl}propanoyl)amino]-3-oxo-3-(pentylamino)propyl]phenoxy}malonic Acid $^1$H NMR (DMSO-d$_6$) δ 7.87 (m, 2H), 7.53 (m, 2H), 7.46 (m, 1H), 7.11 (d, 2H), 6.91 (d, 2H), 6.89 (m, 1H), 6.80 (d, 2H), 5.23 (s, 1H), 5.15 (s, 2H), 4.40 (m, 1H), 4.05 (m, 1H), 2.97 (m, 2H), 2.78 (m, 3H), 2.60 (m, 1H), 1.35–1.14 (m, 15H), 0.81 (t, 3H); MS (FAB) m/z (rel. intensity) 774 (MH$^+$, 8), 296 (28), 294 (41), 238 (39), 194 (31), 161 (52), 159 (81), 136 (31), 88 (56), 57 (99), 41 (24); HRMS (FAB) calcd for C$_{38}$H$_{45}$Cl$_2$N$_3$O$_{10}$+H$_1$ 774.2560, found 774.2557.

EXAMPLE 67

(Chart BB, BB-3) 2-{4-[(2S)-2-({(2S)-2-[(tert-butoxycarbonyl)amino]-3-[4-(tert-butoxy)phenyl]propanoyl}amino)-3-oxo-3-(pentylamino)propyl]phenoxy}malonic Acid $^1$H NMR (DMSO-d$_6$) δ 7.90 (d, 2H), 7.09 (t, 2H), 6.85 (d, 1H), 6.81 (t, 2H), 5.23 (s, 1H), 4.40 (m, 1H), 4.08 (m, 1H), 2.97 (m, 2H), 2.77 (m, 3H), 2.60 (m, 1H), 1.27–1.14 (m, 24H), 0.82 (t, J=7 Hz, 3H); MS (FAB) m/z (rel. intensity) 672 (MH$^+$, 2), 238 (25), 194 (22), 192 (19), 136 (79), 107 (39), 88 (48), 57 (99), 41 (26), 39 (23), 29 (25); HRMS (FAB) calcd for C$_{35}$H$_{49}$N$_3$O$_{10}$+H$_1$ 672.3496, found 672.3491.

EXAMPLE 68

(Chart BB, BB-3) 2-{4-[(2S)-2-{[(2S)-2-[(tert-butoxycarbonyl)amino]-3-(4-methoxyphenyl)propanoyl]amino}-3-oxo-3-(pentylamino)propyl]phenoxy}malonic Acid $^1$H NMR (DMSO-d$_6$) δ 7.85 (m, 2H), 7.09 (m, 4H), 6.78 (m, 5H), 5.22 (s, 1H), 4.40 (m, 1H), 4.02 (m, 1H), 3.68 (s, 3H), 2.97 (m, 2H), 3.90–3.70 (m, 3H), 2.60 (m, 1H), 1.34–1.12 (m, 15H), 0.82 (t, 3H); MS (FAB) m/z (rel. intensity) 630 (MH$^+$, 11), 574 (24), 238 (29), 194 (31), 177 (34), 161 (29), 150 (99), 136 (24), 121 (65), 88 (64), 57 (87); HRMS (FAB) calcd for $C_{32}H_{43}N_3O_{10}+H_1$ 630.3026, found 630.3015.

EXAMPLE 69

(Chart BB, BB-3) 2-{4-[(2S)-2-({(2S)-2-[(tert-butoxycarbonyl)amino]-3-phenylpropanoyl}amino)-3-oxo-3-(pentylamino)propyl]phenoxy}malonic Acid $^1$H NMR (DMSO-d$_6$) δ 7.87 (m, 2H), 7.17 (m, 5H), 6.90 (d, 1H), 6.80 (d, 2H), 5.22 (s, 1H), 4.41 (m, 1H), 4.10 (m, 1H), 2.97 (m, 2H), 2.83 (m, 2H), 2.70–2.50 (m, 2H), 1.34–1.12 (m, 15H), 0.82 (t, J=3 Hz, H); MS (FAB) m/z (rel. intensity) 600 (MH$^+$, 27), 600 (27), 544 (33), 238 (22), 136 (22), 133 (22), 120 (99), 88 (61), 57 (87), 43 (18), 41 (20); HRMS (FAB) calcd for $C_{31}H_{41}N_3O_9+H_1$ 600.2921, found 600.2923.

EXAMPLE 70

(Chart BB, BB-3) 2-{4-[(2S)-2-({(2S)-2-[(tert-butoxycarbonyl)amino]propanoyl}amino)-3-oxo-3-(pentylamino)propyl]phenoxy}malonic Acid $^1$H NMR (DMSO-d$_6$) δ 7.80 (m, 1H), 7.69 (d, 1H), 7.08 (d, 2H), 6.95 (d, 1H), 6.77 (d, 2H), 5.22 (s, 1H), 4.35 (m, 1H), 3.80 (m, 1H), 2.95 (m, 2H), 2.95–2.85 (m, 1H), 2.75 (m, 1H), 1.35–1.15 (m, 15H), 1.05 (d, 3H), 0.82 (t, 3H); MS (FAB) m/z (rel. intensity) 524 (MH$^+$, 13), 468 (39), 238 (25), 136 (21), 133 (20), 88 (99), 86 (19), 57 (71), 44 (58), 41 (19), 29 (18); HRMS (FAB) calcd for $C_{25}H_{37}N_3O_9+H_1$ 524.2607, found 524.2612.

EXAMPLE 71

(Chart BB, BB-3) 2-{4-[(2S)-2-({(2S)-3-[4-(benzyloxy)phenyl]-2-[(tert-butoxycarbonyl)(methyl)amino]propanoyl}amino)-3-oxo-3-(pentylamino)propyl]phenoxy}malonic Acid Prepared from B4 and Boc-N-Me-Try(Bzl)-OH by general procedure for BB-3. $^1$H NMR (DMSO-d$_6$) δ 7.85 (br m, 2H), 7.35 (m, 5H), 7.10 (m, 4H), 7.88 (br m, 2H), 6.78 (d, 2H), 5.24 (s, 1H), 5.02 (s, 2H), 5.72 (br m, 1H), 4.40 (br m, 1H), 2.95 (m, 4H), 2.80–7.70 (m, 2H), 2.42 (br s, 3H), 1.25 (m, 15H), 0.83 (t, 3H); MS (FAB) m/z (rel. intensity) 720 (MH$^+$, 3), 620 (15), 253 (9), 241 (12), 240 (73), 238 (10), 237 (9), 91 (99), 57 (51), 41 (13), 29 (9); HRMS (FAB) calcd for $C_{39}H_{49}N_3O_{10}+H_1$ 720.3496, found 720.3511.

GENERAL PROCEDURE FOR THE PREPARATION OF BB-4 (Chart BB):

Where R6 is t-butyloxycarbonyl (Boc), the Boc group is removed with HCl/acetic acid or HCl/dioxane, and the resulting amine is acylated with the appropriate acid chloride, isocyanate, sulfonyl chloride, or carboxylic acid via standard procedures. Final saponification (as described for BB-2) affords the diacids BB-4.

EXAMPLE 72

(Chart BB, BB-4) 2-{4-[(2S)-2-[((2S)-3-(4-benzoylphenyl)-2-{[3-(4-hydroxyphenyl)propanoyl]amino}propanoyl)amino]-3-oxo-3-(pentylamino)propyl]phenoxy}malonic Acid $^1$H NMR (DMSO-d$_6$) δ 8.10 (d, 1H), 8.05 (d, 1H), 7.83 (t, 1H), 7.65 (m, 3H), 7.60 (m, 2H), 7.51 (t, 2H), 7.41 (d, 2H), 7.11 (d, 2H), 6.90 (d, 2H), 6.80 (d, 2H), 6.58 (d, 2H), 5.24 (s, 1H), 4.57 (m, 1H), 4.48 (m, 1H), 2.96 (m, 3H), 2.80 (m, 3H), 2.50 (m, 2H), 2.25 (m, 2H), 1.31–1.10 (m, 6H), 0.79 (t, 3H); MS (FAB) m/z (ret. intensity) 752 (MH$^+$, 45), 753 (21), 752 (45), 353 (41), 238 (25), 224 (99), 136 (23), 107 (74), 88 (39), 57 (20), 43 (19); HRMS (FAB) calcd for $C_{42}H_{45}N_3O_{10}+H_1$ 752.3183, found 752.3186.

EXAMPLE 73

(Chart BB, BB-4) 2-{4-[(2S)-2-{[(2S)-2-(acetylamino)-3-(4-benzoylphenyl)propanoyl]amino}-3-oxo-3-(pentylamino)propyl]phenoxy}malonic Acid $^1$H NMR (DMSO-d$_6$) δ 8.06 (d, 2H), 7.79 (t, 1H), 7.68 (dd, 2H), 7.62 (m, 3H), 7.55 (t, 2H), 7.35 (d, 2H), 7.10 (d, 2H), 6.79 (d, 2H), 5.24 (s, 1H), 4.65 (m, 1H), 4.38 (m, 1H), 3.00 (m, 3H), 2.88–3.70 (m, 3H), 1.74 (s, 3H), 1.33–1.10 (m, 6H), 0.80 (t, 3H); MS (FAB) m/z (rel. intensity) 646 (MH$^+$, 99), 647 (42), 646 (99), 353 (28), 238 (42) 224 (58), 194 (24), 136 (15), 105 (27), 88 (45), 43 (15); HRMS (FAB) calcd for $C_{35}H_{39}N_3O_9+H_1$ 646.2764, found 646.2770.

EXAMPLE 74

(Chart BB, BB-4) 2-{4-[(2S)-2-[((2S)-2-{[(tert-butylamino)carbonyl]amino}-3-phenylpropanoyl)amino]-3-oxo-3-(pentylamino)propyl]phenoxy}malonic Acid $^1$H NMR (DMSO-d$_6$) δ 7.94 (d, 1H), 7.80 (t, 1H), 7.18 (m, 3H), 7.08 (m, 4H), 6.78 (d, 2H), 5.73 (d, 1H), 5.23 (s, 1H), 4.35 (m, 1H), 4.22 (m, 1H), 2.97 (m, 2H), 2.85 (m, 2H), 2.65 (m, 2H), 1.38–1.14 (m, 6H), 1.13 (s, 9H), 0.82 (t, 3H); MS (FAB) m/z (rel. intensity) 599 (MH$^+$, 6), 500 (13), 247 (9), 121 (10), 120 (99), 102 (9), 88 (15), 58 (7), 57 (15), 43 (7), 41 (7); HRMS (FAB) calcd for $C_{31}H_{42}N_4O_8+H_1$ 599.3080, found 599.3088.

EXAMPLE 75

(Chart BB, BB-4) 2-{4-[(2S)-2-({(2S)-2-[(methylsulfonyl)amino]-3-phenylpropanoyl}amino)-3-oxo-3-(pentylamino)propyl]phenoxy}malonic Acid $^1$H NMR (DMSO-d$_6$) δ 8.33 (d, 1H), 7.86 (t, 1H), 7.41 (d, 1H), 7.23 (m, 5H), 7.14 (d, 2H), 6.79 (d, 2H), 5.24 (s, 1H), 4.45 (m, 1H), 4.01 (m, 1H), 2.99 (m, 2H), 2.85 (m, 2H), 2.65 (m, 2H), 2.20 (s, 3H), 1.35–1.15 (m, 6H), 0.83 (t, 3H); MS (FAB) m/z (rel. intensity) 578 (MH$^+$, 50), 578 (50), 238 (29), 198 (20), 136 (27), 120 (59), 119 (24), 118 (30), 91 (28), 88 (99), 43 (29); HRMS (FAB) calcd for $C_{27}H_{35}N_3O_9S+H_1$ 578.2172, found 578.2197.

EXAMPLE 76

(Chart BB, BB-4) 2-{4-[(2S)-2-[((2S)-2-{[3-(diethylamino)propanoyl]amino}-3-phenylpropanoyl)amino]-3-oxo-3-(pentylamino)propyl]phenoxy}malonic Acid Hydrochloride $^1$H NMR (DMSO-d$_6$) δ 8.39 (d, 1H), 8.23 (d, 1H), 7.86 (t, 1H), 7.21 (m, 5H), 7.11 (d, 2H), 6.78 (d, 2H), 5.25 (s, 1H), 4.52 (m, 1H), 4.39 (m, 1H), 3.10 (t, 2H), 2.95 (m, 10H), 2.75–2.60 (m, 2H), 1.33–1.15 (m, 6H), 1.10 (t, 6H), 0.82 (t, 3H); MS (FAB) m/z (rel. intensity) 627 (MH$^+$, 19), 627 (19), 583 (13), 123 (37), 120 (10), 105 (32), 103 (32), 91 (29), 86 (99), 58 (9), 57 (12); HRMS (FAB) calcd for $C_{33}H_{46}N_4O_8$+$H_1$ 627.3394, found 627.3402.

EXAMPLE 77

(Chart BB, BB-4) 2-(4-{(2S,5S)-5-benzyl-13,13-dimethyl-4,7,11-trioxo-2-[(pentylamino)carbonyl]-12-oxa-3,6,10-triazatetradec-1-yl}phenoxy)malonic Acid $^1$H NMR (DMSO-d$_6$) δ 8.03 (d, 1H), 7.98 (d, 1H), 7.76 (t, 1H), 7.17 (m, 5H), 7.10 (d, 2H), 6.80 (d, 2H), 7.60 (br s, 1H), 5.24 (s, 1H), 4.40 (m, 2H), 2.98 (m, 4H), 2.88 (m, 2H), 3.75–3.62 (m, 2H), 2.17 (m, 2H), 1.34 (s, 9H), 1.33–1.13 (m, 6H), 0.82 (t, 3H); MS (FAB) m/z (rel. intensity) 671 (MH$^+$, 6), 572 (13), 571 (39), 219 (11), 191 (13) 136 (11), 121 (10), 120 (99), 88 (16), 57 (33), 41 (11); HRMS (FAB) calcd for $C_{34}H_{46}N_4O_{10}$+$H_1$ 671.3292, found 671.3300.

EXAMPLE 78

(Chart BB, BB-4) 2-{4-[(2S)-2-({(2S)-2-[(benzylsulfonyl)amino]-3-phenylpropanoyl}amino)-3-oxo-3-(pentylamino)propyl]phenoxy}malonic Acid $^1$H NMR (DMSO-d$_6$) δ 8.25 (d, 1H), 7.82 (t, 1H), 7.50 (d, 1H), 7.23 (m, 9H), 7.11 (m, 3H), 6.76 (d, 2H), 5.13 (s, 1H), 4.45 (m, 1H), 4.10 (m, 1H), 3.80 (d, 1H), 3.65 (d, 1H), 3.90 (m, 4H), 3.80–33.63 (m, 2H), 1.33–1.10 (m, 6H), 0.81 (t, 3H); MS (FAB) m/z (rel. intensity) 654 (MH$^+$, 31), 654 (31), 210 (26), 120 (40), 91 (99), 88 (31), 69 (21), 57 (21), 55 (20), 43 (26), 41 (15); HRMS (FAB) calcd for $C_{33}H_{39}N_3O_9S$+$H_1$ 654.2485, found 654.2488.

EXAMPLE 79

(Chart BB, BB-4) 2-{4-[(2S)-2-({(2S)-2-[(3-methoxypropanoyl)amino]-3-phenylpropanoyl}amino)-3-oxo-3-(pentylamino)propyl]phenoxy}malonic Acid $^1$H NMR (DMSO-d$_6$) δ 7.98 (t, 2H), 7.73 (br s, 1H), 7.17 (m, 5H), 7.08 (d, 2H), 6.80 (d, 2H), 5.23 (s, 1H), 4.45 (m, 1H), 4.35 (m, 1H), 3.38 (m, 2H), 3.11 (s 3H), 2.96 (m, 4H), 2.72 (m, 2H), 2.25 (m, 2H), 1.22 (m, 6H), 0.83 (t, 3H); MS (FAB) m/z (rel. intensity) 586 (MH$^+$, 69), 587 (26), 586 (69), 542 (18), 353 (28), 251 (19), 234 (31), 206 (35), 121 (18), 120 (99), 88 (24); HRMS (FAB) calcd for $C_{30}H_{39}N_3O_9$+$H_1$ 586.2764, found 586.2757.

EXAMPLES 80–96

(General Synthesis of R-1, R-2, R-3 and R-4, Chart R)

GENERAL PREPARATION OF R-1: Q-4 (0.50 g, 1.0 mmol) was dissolved in a 4 M solution of HCl in dioxane (5 mL). Stirred at room temperature for 2 h. The solvent was removed under reduced pressure. The residue was dissolved in CH$_2$Cl$_2$ (5 mL) and triethylamine (0.43 mL, 3.1 mmol), and N-(tert-Butoxycarbonyl)-L-phenylalanine (0.28 g, 1.0 mmol) was added. After the mixture was cooled to 0° C., EDC (0.20 g, 1.0 mmol) and HOBT (0.14 g, 1.0 mmol) was added. The mixture was warmed to room temperature and stirred overnight. The mixture was partitioned between EtOAc and 1 M HCl. The organic phase was washed with sat. NaHCO$_3$, sat. NaCl and dried (MgSO$_4$) and concentrated to a glassy solid (0.54 g). The residue was purified by flash chromatography (40 g SiO$_2$, 60% EtOAc/heptane) to obtain 0.42 g (67%) of R-1 (R=PhCH$_2$) as a white powder. PNU-178773 $^1$H NMR (CDCl$_3$) δ 7.48 (br s, 1H), 7.30 (m, 3H), 7.18 (m, 3H), 6.76 (d, 1H), 6.32 (br s, 1H), 6.00 (br s, 1H), 4.90 (br s, 1H), 4.68 (s, 3H), 4.55 (m, 1H), 4.25 (m, 1H), 3.88 (s, 3H), 3.78 (s, 3H), 3.07 (m, 4H), 2.90 (m, 2H), 1.40–1.20 (m, 15H), 0.86 (t, 3H);

MS (ESI–) for $C_{33}H_{45}N_3O_9$ m/z 626 (M–H)$^-$; HRMS (FAB) calcd for $C_{33}H_{45}N_3O_9$+$H_1$ 628.3234, found 628.3233.

GENERAL PREPARATION OF R-2: R-2 was prepared by LiOH saponification of R-1 with isolation as described in the general synthesis of BB-2.

EXAMPLE 80

(Chart R, R-2) 5-[(2S)-2-({(2S)-2-[(tert-butoxycarbonyl)amino]propanoyl}amino)-3-oxo-3-(pentylamino)propyl]-2-(carboxymethoxy)benzoic Acid $^1$H NMR (DMSO-d$_6$) δ 7.87 (br s, 1H), 7.54 (d, 1H), 7.52 (br s, 1H), 7.29 (dd, 1H), 6.99 (d, 1H), 6.89 (d, 1H), 4.71 (s, 2H), 4.39 (m, 1H), 3.84 (m, 1H), 2.97 (m, 3H), 2.77 (m, 1H), 1.40–1.15 (m, 15H), 1.07 (d, 3H), 0.84 (t, 3H); MS (ESI–) for $C_{25}H_{37}N_3O_9$ m/z 522 (M–H)$^-$; MS (FAB) m/z (rel. intensity) 524 (MH$^+$, 1), 546 (45), 525 (22), 446 (16), 425 (23), 424 (99), 88 (60), 57 (56), 44 (46), 41 (18), 29 (17); HRMS (FAB) calcd for $C_{25}H_{37}N_3O_9$+$NA_1$ 546.2427, found 546.2438.

EXAMPLE 81

(Chart R, R-2) 5-[(2S)-2-({(2S)-2-[(tert-butoxycarbonyl)amino]-3-phenylpropanoyl}amino)-3-oxo-3-(pentylamino)propyl]-2-(carboxymethoxy) benzoic Acid $^1$H NMR (DMSO-d$_6$) δ 7.92 (br s, 1H), 7.54 (br s, 1H), 7.30 (d, 1H), 7.18 (m, 6H), 6.90 (d, 1H), 4.68 (s, 2H), 4.40 (m, 1H), 4.05 (m, 1H), 2.98 (m, 2H), 2.83 (m, 2H), 2.65 (m, 2H), 1.33–1.10 (m, 15H), 0.82 (t, 3H); MS (FAB) m/z (rel. intensity) 600 (MH$^+$, 21), 622 (15), 600 (21), 501 (30), 500 (99), 238 (11), 120 (73), 88 (34), 57 (52), 43 (12), 41 (14); HRMS (FAB) calcd for $C_{31}H_{41}N_3O_9$+$H_1$ 600.2921, found 600.2923.

GENERAL PREPARATION OF R-3: R-3 was prepared by removal of the Boc group from R-1 with HCl/dioxane followed by coupling with the appropriate carboxylic acid with EDC and HOBT as described for R-1. Final saponification then affords R-3.

EXAMPLE 82

(Chart R, R-3) 2-(carboxymethoxy)-5-[(2S)-2-({(2S)-2-[(3-carboxypropanoyl)amino]-3-phenylpropanoyl}amino)-3-oxo-3-(pentylamino)propyl]benzoic Acid $^1$H NMR (DMSO-d$_6$) δ 8.10 (d, 1H), 8.00 (d, 1H), 7.78 (t, 1H), 7.53 (d, 1H), 7.29 (dd, 1H), 7.16 (m, 5H), 6.90 (d, 1H), 4.71 (s, 2H), 4.37 (m, 2H), 2.95 (m, 4H), 2.70 (m, 2H), 2.29 (m, 4H), 1.35–1.15 (m, 6H), 0.82 (t, 3H); MS (FAB) m/z (rel. intensity) 600 (MH$^+$, 20), 600 (20), 353 (12), 248 (11), 238 (12), 220 (15), 131 (9), 121 (10), 120 (99), 88 (32), 43 (11); HRMS (FAB) calcd for $C_{30}H_{37}N_3O_{10}$+$H_1$ 600.2557, found 600.2564.

EXAMPLE 83

(Chart R, R-3) 2-(carboxymethoxy)-5-[(2S)-2-[((2S)-2-{[2-(1H-indol-3-yl)acetyl]amino}-3-phenylpropanoyl)amino]-3-oxo-3-(pentylamino)propyl]benzoic Acid $^1$H NMR (DMSO-d$_6$) δ 8.09 (d, 1H), 7.97 (d, 1H), 7.88 (t, 1H), 7.53 (br s, 1H), 7.31 (m, 3H), 7.14 (br s, 5H), 7.01 (m, 2H), 6.90 (t, 2H), 4.71 (s, 2H), 4.48 (m, 1H), 4.39 (m, 1H), 3.46 (d, 2H), 2.97 (m, 4H), 2.75 (m, 2H), 1.35–1.15 (m, 6H), 0.84 (t, 3H); MS (ESI–) for C$_{36}$H$_{40}$N$_4$O$_8$MS m/z 655 (M–H)$^-$; MS (EI) m/z (rel. intensity) 304 (67), 157 (62), 131 (59), 130 (99), 128 (37), 117 (46), 103 (52), 91 (94), 77 (68), 55 (37); HRMS (FAB) calcd for C$_{36}$H$_{40}$N$_4$O$_8$+H$_1$ 657.2924, found 657.2894.

EXAMPLE 84

(Chart R, R-3) 2-(carboxymethoxy)-5-[(2S)-3-oxo-3-(pentylamino)-2-({(2S)-3-phenyl-2-[(2-phenylacetyl)amino]propanoyl}amino)propyl] benzoic Acid $^1$H NMR (DMSO-d$_6$) δ 8.20 (d, 1H), 8.10 (d, 1H), 7.90 (t, 1H), 7.55 (d, 1H), 7.29 (dd, 1H), 7.18 (m, 8H), 6.90 (d, 2H), 6.90 (d, 1H), 4.71 (s, 2H), 4.45 (m, 2H), 3.33 (m, 2H), 2.97 (m, 4H), 2.73 (m, 2H), 1.35–1.15 (m, 6H), 0.85 (t, 3H); MS (ESI–) for C$_{34}$H$_{39}$N$_3$O$_8$ m/z 616 (M–H)$^-$; MS (EI) m/z (rel. intensity) 265 (40), 120 (56), 118 (26), 117 (29), 92 (50), 91 (99), 89 (30), 77 (28), 65 (54), 51 (25); HRMS (FAB) calcd for C$_{34}$H$_{39}$N$_3$O$_8$+H$_1$ 618.2815, found 618.2799.

EXAMPLE 85

(Chart R, R-3) 2-(carboxymethoxy)-5-[(2S)-3-oxo-3-(pentylamino)-2-({(2S)-3-phenyl-2-[(4-phenylbutanoyl)amino]propanoyl}amino)propyl] benzoic Acid $^1$H NMR (DMSO-d$_6$) δ 8.00 (br d, 2H), 7.90 (br s, 1H), 7.55 (br s, 1H), 7.20 (m, 11H), 6.90 (br d, 1H), 4.70 (s, 2H), 4.45 (m, 2H), 2.97 (m, 4H), 2.75 (m, 2H), 2.36 (t, 2H), 2.03 (t, 2H), 1.62 (m, 2H), 1.36–1.10 (m, 6H), 0.83 (t, 3H); MS (ESI–) for C$_{36}$H$_{43}$N$_3$O$_8$ m/z 644 (M–H)$^-$; MS (EI) m/z (rel. intensity) 189 (41), 120 (63), 119 (82), 104 (41), 91 (93), 73 (49), 65 (50), 64 (99), 63 (73), 59 (35); HRMS (FAB) calcd for C$_{36}$H$_{43}$N$_3$O$_8$+H$_1$ 646.3128, found 646.3113.

EXAMPLE 86

(Chart R, R-3) 5-[(2S)-2-{[(2S)-2-(acetylamino)-3-phenylpropanoyl]amino}-3-oxo-3-(pentylamino)propyl]-2-(carboxymethoxy)benzoic Acid $^1$H NMR (DMSO-d$_6$) δ 8.04 (m, 2H), 7.84 (t, 1H), 7.53 (d, 1H), 7.30 (dd, 1H), 7.19 (m, 5H), 6.91 (d, 1H), 4.71 (s, 2H), 2.95 (m, 4H), 2.70 (m, 2H), 1.73 (s, 3H), 1.35–1.15 (m, 6H), 0.85 (t, 3H); MS (ESI–) for C$_{28}$H$_{35}$N$_3$O$_8$ m/z 540 (M–H)$^-$; MS (EI) m/z (rel. intensity) 120 (22), 91 (99), 86 (14), 73 (82), 65 (18), 59 (17), 58 (18), 57 (15), 55 (17), 51 (19); HRMS (FAB) calcd for C$_{28}$H$_{35}$N$_3$O$_8$+H$_1$ 542.2502, found 542.2507.

EXAMPLE 87

(Chart R, R-3) 2-(carboxymethoxy)-5-[(2S)-2-({(2S)-2-[(3-methoxypropanoyl)amino]-3-phenylpropanoyl}amino)-3-oxo-3-(pentylamino)propyl]benzoic Acid $^1$H NMR (DMSO-d$_6$) δ 8.01 (d, 2H), 7.85 (t, 2H), 7.52 (d, 1H), 7.30 (dd, 1H), 7.22 (m, 5H), 6.93 (d, 1H), 4.69 (s, 2H), 4.02 (m, 2H), 3.39 (t, 2H), 3.12 (s, 3H), 2.96 (m, 4H), 2.76 (m, 2H), 2.27 (t, 2H), 1.37–1.15 (m, 6H), 0.85 (t, 3H); MS (ESI–) for C$_{30}$H$_{39}$N$_3$O$_9$ m/z 584 (M–H)$^-$; MS (EI) m/z (rel. intensity) 120 (72), 119 (30), 91 (95), 86 (54), 84 (78), 73 (33), 57 (34), 55 (51), 51 (99), 50 (34); HRMS (FAB) calcd for C$_{30}$H$_{39}$N$_3$O$_9$+H$_1$ 586.2764, found 586.2757.

EXAMPLE 88

(Chart R, R-3) 2-(carboxymethoxy)-5-[(2S)-2-({(2S)-2-[(4-hydroxybutanoyl)amino]-3-phenylpropanoyl}amino)-3-oxo-3-(pentylamino)propyl]benzoic Acid $^1$H NMR (DMSO-d$_6$) δ 7.99 (m, 2H), 7.86 (br s, 1H), 7.53 (d, 1H), 7.31 (m, 1H), 7.19 (m, 5H), 6.90 (d, 1H), 4.71 (s, 2H), 4.40 (m, 2H), 3.30 (m, 2H), 2.95 (m, 4H), 2.72 (m, 2H), 2.05 (m, 2H), 1.50 (m, 2H), 1.38–1.15 (m, 6H), 0.84 (t, 3H); MS (ESI–) for C$_{30}$H$_{39}$N$_3$O$_9$ m/z 584 (M–H)$^-$; MS (FAB) m/z (rel. intensity) 586 (MH$^+$, 1), 587 (15) 188 (11), 131 (10), 120 (99), 118 (18), 88 (21), 79 (14), 77 (11), 59 (10), 43 (14); HRMS (FAB) calcd for C$_{30}$H$_{39}$N$_3$O$_9$+H$_1$ 586.2764, found 586.2791.

EXAMPLE 89

(Chart R, R-3) 5-{(2S,5S)-5-benzyl-13,13-dimethyl-4,7,11-trioxo-2-[(pentylamino)carbonyl]-12-oxa-3,6,10-triazatetradec-1-yl}-2-(carboxymethoxy)benzoic Acid $^1$H NMR (DMSO-d$_6$) δ 8.03 (t, 1H), 7.86 (t, 1H), 7.56 (d, 1H), 7.30 (dd, 1H), 7.21 (m, 5H), 6.92 (d, 1H), 6.58 (br s, 1H), 4.72 (s, 2H), 4.42 (m, 2H), 2.95 (m, 6H), 2.73 (m, 2H), 2.17 (m, 2H), 1.36 (s, 9H), 1.35–1.15 (m, 6H), 0.84 (t, 3H); MS (ESI–) for C$_{34}$H$_{46}$N$_4$O$_{10}$ m/z 669 (M–H)$^-$; MS (FAB) m/z (rel. intensity) 671 (MH$^+$, 2), 673 (16), 672 (38), 573 (24), 572 (67), 133 (12), 121 (12), 120 (99), 89 (17), 88 (20), 57 (24); HRMS (FAB) calcd for C$_{34}$H$_{46}$N$_4$O$_{10}$+H$_1$ 671.3292, found 671.3324.

EXAMPLE 90

(Chart R, R-3) 5-{(2S,5S)-5-benzyl-4,7,11,11-tetraoxo-2-[(pentylamino)carbonyl]-11lambda~6~thia-3,6,10-triazadodec-1-yl}-2-(carboxymethoxy)benzoic Acid $^1$H NMR (DMSO-d$_6$) δ 8.10 (m, 2H), 7.85 (t, 1H), 7.56 (d, 1H), 7.32 (dd, 1H), 7.20 (m, 5H), 6.90 (m, 2H), 4.72 (s, 2H), 4.45 (m, 2H), 2.98 (m, 6H), 2.82 (s, 3H), 2.71 (m, 2H), 2.27 (m, 2H), 1.35–1.15 (m, 6H), 0.85 (t, 3H); MS (ESI–) for C$_{30}$H$_{40}$N$_4$O$_{10}$S m/z 647 (M–H)$^-$; MS (FAB) m/z (rel. intensity) 649 (MH$^+$, 41), 650 (15), 649 (41), 297 (14) 269 (25), 133 (15), 131 (12), 120 (99), 88 (30), 79 (40), 43 (18); HRMS (FAB) calcd for C$_{30}$H$_{40}$N$_4$O$_{10}$S+H$_{1\ 649.2543}$, found 649.2544.

EXAMPLE 91

(Chart R, R-3) 2-(carboxymethoxy)-5-[(2S)-2-[((2S)-2-{[2-(3-hydroxyphenyl)acetyl]amino}-3-phenylpropanoyl)amino]-3-oxo-3-(pentylamino)propyl]benzoic Acid $^1$H NMR (DMSO-d$_6$) δ 8.10 (m, 2H), 7.86 (t, 1H), 7.55 (d, 1H), 7.30 (d, 1H), 7.16 (m, 5H), 7.00 (t, 1H), 6.90 (d, 1H), 6.59 (m, 2H), 6.49 (d, 1H), 4.72 (s, 2H) 7.42 (m, 2H), 3.32 (m, 2H), 2.95 (m, 4H), 2.75 (m, 2H), 1.35–1.15 (m, 6H), 0.85 (t, 3H); MS (ESI+) for C$_{34}$H$_{39}$N$_3$O$_9$ m/z 634

(M+H)+; MS (FAB) m/z (rel. intensity) 634 (MH+, 7), 120 (99), 107 (31), 91 (27), 74 (46), 69 (28), 57 (29), 55 (28), 43 (36), 41 (26), 23 (28); HRMS (FAB) calcd for $C_{34}H_{39}N_3O_9$+$H_1$ 634.2764, found 634.2787.

EXAMPLE 92

(Chart R, R-3) 2-(carboxymethoxy)-5-[(2S)-2-[((2S)-2-{[2-(4-hydroxyphenyl)acetyl]amino}-3-phenylpropanoyl)amino]-3-oxo-3-(pentylamino) propyl]benzoic Acid $^1$H NMR (DMSO-$d_6$) δ 8.05 (t, 2H), 7.86 (t, 1H), 7.55 (d, 1H), 7.30 (dd, 1H), 7.17 (m, 5H), 6.91 (d, 1H), 6.84 (d, 2H), 6.58 (d, 2H), 4.72 (s, 2H), 4.45 (m, 2H), 3.35 (m, 2H), 2.98 (m, 4H), 2.75 (m, 2H), 1.35–1.15 (m, 6H), 0.85 (t, 3H); MS (ESI+) for $C_{34}H_{39}N_3O_9$ m/z 634 (M+H)+; MS (FAB) m/z (rel. intensity) 634 (MH+, 10), 219 (15), 120 (99), 107 (32), 91 (20), 88 (22), 57 (16), 55 (13), 43 (22), 41 (15), 23 (19); HRMS (FAB) calcd for $C_{34}H_{39}N_3O_9$+$H_1$ 634.2764, found 634.2769.

EXAMPLE 93

(Chart R, R-3) 2-(carboxymethoxy)-5-[(2S)-2-[((2S)-2-{[2-(4-methylphenyl)acetyl]amino}-3-phenylpropanoyl)amino]-3-oxo-3-(pentylamino) propyl]benzoic Acid $^1$H NMR (DMSO-$d_6$) δ 8.11 (d, 1H), 8.06 (d, 1H), 7.86 (t, 1H), 7.55 (d, 1H), 7.28 (dd, 1H), 7.18 (m, 5H), 7.00 (d, 2H), 6.92 (m, 3H), 4.71 (s, 2H), 4.42 (m, 2H, 3.33 (m, 2H), 2.98 (m, 4H), 2.73 (m, 3H), 2.24 (s, 3H), 1.35–1.15 (m, 6H), 0.85 (t, 3H); MS (FAB) m/z (rel. intensity) 632 (MH+, 25), 632 (25), 280 (13), 252 (13), 121 (12), 120 (99), 105 (57), 103 (12), 91 (15), 88 (15), 23 (14); HRMS (FAB) calcd for $C_{35}H_{41}N_3O_8$+$H_1$ 632.2972, found 632.2980.

EXAMPLE 94

(Chart R, R-3) 2-(carboxymethoxy)-5-((2S)-3-oxo-3-(pentylamino)-2-{[(2S)-3-phenyl-2-({2-[4-(trifluoromethyl)phenyl]acetyl}amino)propanoyl] amino}propyl)benzoic Acid $^1$H NMR (DMSO-$d_6$) δ 8.32 (d, 1H), 8.13 (d, 1H), 7.87 (t, 1H), 7.57 (m, 3H), 7.28 (m, 3H), 7.16 (m, 5H), 6.90 (d, 1H), 4.72 (s, 2H), 4.51 (m, 1H), 4.41 (m, 1H), 4.48 (m, 2H), 2.98 (m, 4H), 2.75 (m, 2H), 1.35–1.15 (m, 6H), 0.84 (t, 3H); MS (FAB) m/z (rel. intensity) 686 (MH+, 28), 686 (28), 159 (23), 139 (36), 121 (17), 120 (99), 105 (25), 103 (26), 91 (30), 88 (26), 23 (19); HRMS (FAB) calcd for $C_{35}H_{38}F_3N_3O_8$+$H_1$ 686.2689, found 686.2719.

EXAMPLE 95

(Chart R, R-3) 2-(carboxymethoxy)-5-[(2S)-2-[((2S)-2-{[2-(4-methoxyphenyl)acetyl]amino}-3-phenylpropanoyl)amino]-3-oxo-3-(pentylamino) propyl]benzoic Acid $^1$H NMR (DMSO-$d_6$) δ 8.08 (t, 2H), 7.86 (t, 1H), 7.55 (d, 1H), 7.29 (dd, 1H), 7.17 (m, 5H), 6.98 (d, 2H), 6.89 (d, 1H), 6.76 (d, 2H), 4.71 (s, 2H), 4.43 (m, 2H), 3.70 (s, 3H), 3.20 (m, 2H), 2.98 (m, 4H), 2.75 (m, 2H), 1.35–1.15 (m, 6H), 0.85 (t, 3H); MS (FAB) m/z (rel. intensity) 648 (MH+, 28), 648 (28), 148 (16), 139 (29), 123 (18), 121 (83), 120 (99), 105 (21), 103 (21), 91 (25), 88 (16); HRMS (FAB) calcd for $C_{35}H_{41}N_3O_9$+$H_1$ 648.2921, found 648.2915.

EXAMPLE 96

(Chart R, R-3) 2-(carboxymethoxy)-5-[(2S)-3-oxo-3-(pentylamino)-2-({(2S)-3-phenyl-2-[(3-phenylpropanoyl)amino]propanoyl}amino)propyl] benzoic Acid $^1$H NMR (DMSO-$d_6$) δ 8.03 (t, 2H), 7.85 (t, 1H), 7.56 (d, 1H), 7.31 (dd, 1H), 7.14 (m, 10H), 6.91 (d, 1H), 4.71 (s, 2H), 4.45 (m, 2H), 2.96 (m, 4H), 2.72 (m, 4H), 2.32 (t, 2H), 1.35–1.15 (m, 6H), 0.84 (t, 3H); MS (ESI–) for $C_{35}H_{41}N_3O_8$ m/z 630 (M–H)−; MS (FAB) m/z (rel. intensity) 632 (MH+, 3), 634 (15), 633 (38), 353 (7), 335 (6), 280 (12), 252 (10), 131 (7), 120 (99), 88 (18), 79 (17); HRMS (FAB) calcd for $C_{35}H_{41}N_3O_8$+$H_1$ 632.2972, found 632.2986.

EXAMPLE 97

(Chart R, R-4) 2-(carboxymethoxy)-5-{(2S)-3-oxo-3-(pentylamino)-2-[(3-phenylpropanoyl)amino] propyl}benzoic Acid Prepared from Q-4 and hydrocinnamic acid according to the general procedure for R-1.

$^1$H NMR (DMSO-$d_6$) δ 8.08 (d, 1H), 7.91 (t, 1H), 7.55 (d, 1H), 7.19 (m, 3H), 7.13 (t, 3H), 6.87 (d, 1H), 4.70 (s, 2H), 4.40 (m, 1H), 2.98 (m, 2H), 2.85 (dd, 1H), 2.68 (m, 3H), 2.32 (t, 2H), 1.35–1.15 (m, 6H), 0.83 (t, 3H); MS (FAB) m/z (rel. intensity) 485 (MH+, 99), 971 (10), 970 (16), 638 (8), 486 (30), 485 (99), 398 (9), 238 (23), 105 (8), 91 (11), 88 (70); HRMS (FAB) calcd for $C_{26}H_{32}N_2O_7$+$H_1$ 485.2288, found 485.2303.

EXAMPLE 98

PNU-176703 (Chart S, S-4) 2-{4-[2-({(2S)-3-(4-benzoylphenyl)-2-[(3-carboxypropanoyl)amino] propanoyl}amino)ethyl]phenoxy}malonic Acid PREPARATION OF S-2: To a suspension of N-(tert-Butoxycarbonyl)tyramine (S-1, 0.20 g, 0.84 mmol) and $K_2CO_3$ (0.23 g, 1.7 mmol) in acetone (3 mL) was added diethyl chloromalonate (0.27 mL, 1.7 mmol). The mixture was stirred vigorously at room temperature for 24 h. The mixture was partitioned between EtOAc and $H_2O$. The organic phase was washed with sat. NaCl and dried (MgSO$_4$). After the solvent was removed, the residue was purified by flash chromatography (45 g SiO$_2$, 3% EtOAc/$CH_2Cl_2$) to provide 0.24 g of S-2 as a colorless oil.

$^1$H NMR (CDCl$_3$) δ 7.11 (d, 2H), 6.90 (d, 2H), 5.16 (s, 1H), 4.51 (br s, 1H), 4.32 (m, 4H), 3.33 (q, 2H), 2.73 (t, 2H), 1.42 (s, 9H), 1.30 (t, 6H); MS (ESI–) for $C_{20}H_{29}NO_7$ m/z 394 (M–H)−.

PREPARATION OF S-3: S-2 (239 mg, 0.6 mmol) was dissolved in 1 M HCl/acetic acid (4 mL) and stirred at room temperature for 4 h. The solvent was removed under reduced pressure. The residue was dissolved in $CH_2Cl_2$ (2 mL), and triethylamine (0.25 mL, 1.8 mmol) and Boc-p-Bz-Phe-OH (222 mg, 0.60 mmol) was added. The mixture was cooled to 0° C., and EDC (115 mg, 0.6 mmol) and HOBT (81 mg, 0.6 mmol) was added. The mixture was warmed to room temperature and stirred overnight. The mixture was partitioned between EtOAc and 1 M HCl. The organic phase was washed with sat. NaHCO$_3$, sat. NaCl, and dried (MgSO$_4$). After the solvent was removed under reduced pressure, the residue was purified by flash chromatography (25 g SiO$_2$, 15% EtOAc/$CH_2Cl_2$) to provide 108 mg of S-3 as a colorless glass.

$^1$H NMR (CDCl$_3$) δ 7.76 (t, 4H), 7.59 (t, 1H), 7.46 (t, 2H), 7.31 (d, 2H), 7.01 (d, 2H), 6.87 (d, 2H), 5.90 (br s, 1H), 5.16 (s, 1H), 4.95 (br s, 1H), 4.30 (q, 4H), 3.40 (m, 2H), 3.12 (m, 2H), 2.66 (m, 2H), 1.40 (s, 9H), 1.30 (t, 6H); MS (ESI–) for $C_{36}H_{42}N_2O_9$ m/z 645 (M–H)−.

PREPARATION OF S-4: S-3 (108 mg, 0.17 mmol) was dissolved in 1 M HCl/acetic acid (2 mL) and stirred at room temperature for 3 h. The solvent was removed under reduced pressure. The residue was dissolved in $CH_2Cl_2$ (2 mL) and triethylamine (70 μL, 0.51 mmol). The mixture was cooled to 0° C., and succinic anhydride (17 mg, 0.17 mmol) was added. The mixture was warmed to room temperature and stirred overnight. The mixture was partitioned between EtOAc and 1 M HCl. The organic phase was washed with sat. NaCl, dried (MgSO$_4$), and concentrated. The residue was dissolved in THF (3 mL), and a solution of LiOH.H$_2$O (28 mg, 0.68 mmol) in H$_2$O (1 mL) was added. The mixture was stirred at room temperature for 3 h. The mixture was acidified (1 M HCl) and extracted with EtOAc. The organic phase was washed sat. NaCl and dried (MgSO$_4$). The solvent was removed in vacuo to provide 89 mg of S-4 as an off-white solid.

$^1$H NMR (DMSO-d$_6$) δ 8.18 (d, 1H), 8.04 (t, 1H), 7.65 (m, 5H), 7.55 (t, 2H), 7.37 (d, 2H), 7.10 (d, 2H), 6.82 (d, 2H), 5.28 (s, 1H), 4.45 (m, 1H), 3.22 (m, 2H), 3.03 (dd, 1H), 2.80 (dd, 1H), 2.57 (t, 2H), 2.31 (m, 4H); MS (FAB) m/z (rel. intensity) 591 (MH$^+$, 27), 591 (27), 391 (83), 149 (99), 113 (29), 71 (48), 69 (37), 57 (39), 55 (39), 43 (52), 41 (35); HRMS (FAB) calcd for C$_{31}$H$_{30}$N$_2$O$_{10}$+H$_1$ 591.1978, found 591.1981.

EXAMPLE 99

(Chart A, A-5) 2-[4-((2S)-2-[(3-carboxypropanoyl) amino]-3-{[(1S)-1-(hydroxymethyl)-3-methylbutyl] amino}-3-oxopropyl)phenoxy]malonic Acid Prepared by the general procedure described for A-5.

$^1$H NMR (DMSO-d$_6$) δ 7.99 (d, 1H), 7.43 (d, 1H), 7.11 (d, 2H), 6.78 (d, 2H), 5.25 (s, 1H), 4.35 (m, 1H), 7.72 (m, 1H), 3.25 (dd, 1H), 3.12 (dd, 1H), 2.87 (dd, 1H), 2.65 (dd, 1H), 2.31 (m, 4H), 1.52 (m, 1H), 1.26 (m, 2H), 0.82 (q, 6H); MS (FAB) m/z (rel. intensity) 483 (MH$^+$, 91), 484 (22), 483 (91), 139 (25), 123 (18), 118 (99), 105 (17), 103 (15), 91 (18), 86 (16), 55 (15); HRMS (FAB) calcd for C$_{22}$H$_{30}$N$_2$O$_{10}$+H$_1$ 483.1978, found 483.1999.

Examples 100–113 were prepared according to the general procedure described for BB-3.

EXAMPLE 100

(Chart BB, BB-3) 2-{4-[(2S)-2-({(2S)-2-[(tert-butoxycarbonyl)amino]-3-phenylpropanoyl}amino)-3-oxo-3-(pentylamino)propyl]phenoxy}malonic Acid $^1$H NMR (DMSO-d$_6$) δ 8.22 (bd, J=8 Hz, 1H), 7.8 (bt, 1H), 7.0–7.3 (m, 7H), 6.80 (d overlapping m, J=8 Hz, 3H), 5.21 (s, 1H); 4.39 (m, 1H), 4.15 (m, 1H), 2.6–3.1 (m, 6H), 1.1–1.4 (m, 6H), 1.31 (s, 9H), 0.86 (t, J=7 Hz, 3H).

EXAMPLE 101

(Chart BB, BB-3) 2-{4-[(2S)-2-({(2R)-3-(benzylsulfanyl)-2-[(tert-butoxycarbonyl)amino] propanoyl}amino)-3-oxo-3-(pentylamino)propyl] phenoxy}malonic Acid $^1$H NMR (DMSO-d$_6$) δ 7.98 (d, J=8 Hz, 1H), 7.85 (bt, J=6 Hz, 1H), 7.15–7.3 (m, 5H), 7.07 (d, J=8 Hz, 2H), 6.76 (d, J=8 Hz, 2H), 5.22 (s, 1H), 4.38 (m, 1H), 4.12 (m, 1H), 3.71 (bs, 2H), 2.4–3.0 (m, 6H), 1.1–1.4 (m, 6H), 1.38 (s, 9H), 0.81 (t, J=7 Hz, 3H); MS (FAB) m/z (rel. intensity) 646 (MH$^+$, 11), 590 (16), 546 (21), 238 (17), 194 (18), 166 (22), 136 (27), 91 (99), 88 (69), 57 (60), 43 (16). HRMS (FAB) calcd for C$_{32}$H$_{43}$N$_3$O$_9$S+H$_1$ 646.2798, found 646.2769.

EXAMPLE 102

(Chart BB, BB-3) 2-{4-[(2S)-2-{[(2S)-2-[(tert-butoxycarbonyl)amino]-3-(2-naphthyl)propanoyl] amino}-3-oxo-3-(pentylamino)propyl] phenoxy}malonic Acid $^1$H NMR (DMSO-d$_6$) δ 7.99 (bd, J=8 Hz, 1H), 7.8 (m, 3H), 7.66 (bs, 1H), 7.3–7.5 (m, 3H), 7.1 (d, J=8 Hz, 2H), 6.80 (d, J=8 Hz, 2H), 5.24 (s, 1H), 4.4 (m, 1H), 4.17 (m, 1H), 2.7–3.1 (m, 6H), 1.1–1.4 (m, 6H), 1.22 (s, 9H), 0.82 (t, J=7 Hz, 3H); Anal. Calcd for C$_{35}$H$_{43}$N$_3$O$_9$: C, 64.70; H, 6.67; N, 6.47. Found: C, 64.76; H, 6.86; N, 6.14. MS (ESI–) for C$_{35}$H$_{43}$N$_3$O$_9$ m/z 648 (M–H)$^-$.

EXAMPLE 103

(Chart BB, BB-3) 2-{4-[(2S)-2-{[(2S)-2-[(tert-butoxycarbonyl)amino]-3-(1-naphthyl)propanoyl] amino}-3-oxo-3-(pentylamino)propyl] phenoxy}malonic Acid $^1$H NMR (DMSO-d$_6$) δ 8.08 (bd, J=8 Hz, 1H), 7.9 (m, 2H), 7.75 (d, J=7 Hz, 1H), 7.5 (m, 2H), 7.35 (t, J=7 Hz, 1H), 7.25 (m, 1H), 7.15 (d, J=8 Hz, 2H), 6.82 (d, J=8 Hz, 2H), 5.24 (s, 1H), 4.44 (m, 1H), 4.2 (m, 1H), 2.7–3.1 (m, 6H), 1.1–1.4 (m, 6H), 1.22 (s, 9H), 0.82 (t, J=7 Hz, 3H); MS (FAB) m/z (rel. intensity) 650 (MH+, 37), 606 (38), 391 (27), 294 (83), 170 (80), 153 (90), 141 (39), 136 (27), 88 (83), 57 (99). Anal. Calcd for C$_{35}$H$_{43}$N$_3$O$_9$.0.6H$_2$O C, 63.64; H, 6.75; N, 6.36. Found: C, 63.94; H, 6.86; N, 5.97.

EXAMPLE 104

(Chart BB, BB-3) 2-{4-[(2S)-2-({(2S)-6-{[(benzyloxy)carbonyl]amino}-2-[(tert-butoxycarbonyl)amino]hexanoyl}amino)-3-oxo-3-(pentylamino)propyl]phenoxy}malonic Acid $^1$H NMR (DMSO-d$_6$) δ 7.82 (bt, J=7 Hz, 1H), 7.72 (d, J=8 Hz, 1H), 7.32 (m, 5H), 7.17 (bt, J=6 Hz, 1H), 7.08 (d, J=8 Hz, 2H), 6.87 (d, J=7 Hz, 1H), 6.78 (d, J=8 Hz, 2H), 5.22 (s, 1H), 4.98 (s, 2H), 4.35 (m, 1H), 3.77 (m, 1H), 2.7–3.1 (m, 6H), 1.1–1.5 (m, 12H), 1.35 (s, 9H), 0.82 (t, J=7 Hz, 3H); MS (FAB) m/z (rel. intensity) 715 (MH$^+$, 5), 615 (10), 133 (8), 92 (9), 91 (99), 88 (16), 84 (24), 57 (31), 43 (6), 41 (8), 29 (7). HRMS (FAB) calcd for C$_{36}$H$_{50}$N$_4$O$_{11}$+H$_1$ 715.3554, found 715.3562. Anal. Calcd for C$_{36}$H$_{50}$N$_4$O$_{11}$.1.2H$_2$O: C, 58.72; H, 7.17; N, 7.61. Found: C, 58.68; H, 7.05; N, 7.35.

EXAMPLE 105

(Chart BB, BB-3) 2-{4-[(2S)-2-{[(2S)-2-[(tert-butoxycarbonyl)amino]-4-(methylsulfanyl)butanoyl] amino}-3-oxo-3-(pentylamino)propyl] phenoxy}malonic Acid $^1$H NMR (DMSO-d$_6$) δ 7.84 (bt, J=6 Hz, 1H), 7.75 (d, J=8 Hz, 1H), 7.09 (d, J=8 Hz, 2H), 6.77 (d, J=8 Hz, 2H), 7.01 (d, J=7 Hz, 1H), 5.21 (s, 1H), 4.38 (m, 1H), 3.90 (m, 1H), 2.7–3.1 (m, 4H), 2.31 (bt, J=7 Hz, 2H), 1.97 (s, 3H), 1.66 (m, 2H), 1.1–1.14 (m, 6H), 1.35 (s, 9H), 0.82 (t, J=7 Hz, 3H); MS (FAB) m/z (rel. intensity) 584 (MH$^+$, 12), 484 (33), 238 (29), 194 (30), 104 (68), 88 (99), 61 (43), 57 (99), 56 (33), 43 (26), 41 (31). HRMS (FAB) calcd for C$_{27}$H$_{41}$N$_3$O$_9$S+H$_1$ 584.2642, found 584.2620.

EXAMPLE 106

(Chart BB, BB-3) 2-{4-[(2S)-2-{[(2S)-2-[(tert-butoxycarbonyl)amino]-4-(methylsulfmyl)butanoyl] amino}-3-oxo-3-(pentylamino)propyl] phenoxy}malonic Acid $^1$H NMR (DMSO-d$_6$) δ 7.9 (bm, 2H), 7.10 (d, J=8 Hz, 2H), 7.05 (bm, 1H), 6.78 (d, J=8 Hz, 2H), 5.23 (s, 1H), 4.4 (m, 1H), 3.95 (m, 1H), 2.5–3.1 (m, 6H), 2.47 (s, 3H), 1.8 (m, 2H), 1.1–1.4 (m, 6H), 1.36 (s, 9H), 0.82 (t, J=7 Hz, 3H); MS (FAB) m/z (rel. intensity) 600 (M+, 48), 556 (41), 500 (40), 100 (30), 88 (50), 59 (64), 57 (71), 56 (99), 41 (32). Anal. Calcd for $C_{27}H_{41}N_3O_{10}S \cdot 0.6H_2O$: C, 53.12; H, 6.97; N, 6.88. Found: C, 53.13; H, 6.95; N, 6.72.

EXAMPLE 107

(Chart BB, BB-3) 2-{4-[(2S)-2-{[(2S)-2-[(tert-butoxycarbonyl)amino]-3-(2,3,4,5,6-pentafluorophenyl)propanoyl]amino}-3-oxo-3-(pentylamino)propyl]phenoxy}malonic Acid $^1$H NMR (DMSO-d$_6$) δ 7.98 (bm, 1H), 7.91 (bt, J=6 Hz, 1H), 7.10 (bd, J=8 Hz, 2H), 6.78 (d, J=8 Hz, 2H), 5.21 (s, 1H), 4.4 (m, 1H), 4.15 (m, 1H), 2.6–3.1 (m, 6H), 1.28 (s, 9H), 1.1–1.4 (m, 6H), 0.82 (t, J=7 Hz, 3H); MS (FAB) m/z (rel. intensity) 690 (MH$^+$, 14), 294 (28), 210 (24), 136 (29), 133 (49), 88 (95), 86 (33), 57 (99), 43 (18), 41 (29), 29 (27). HRMS (FAB) calcd for $C_{31}H_{36}F_5N_3O_9+H_1$ 690.2449, found 690.2457. Anal. Calcd for $C_{31}H_{36}F_5N_3O_9 \cdot 0.48H_2O$: C, 53.32; H, 5.34; N, 6.02. Found: C, 53.33; H, 5.49; N, 5.70.

EXAMPLE 108

(Chart BB, BB-3) 2-{4-[(2S)-2-({(2S)-2-[(tert-butoxycarbonyl)amino]-4-methylpentanoyl}amino)-3-oxo-3-(pentylamino)propyl]phenoxy}malonic Acid $^1$H NMR (DMSO-d$_6$) δ 7.83 (bt, J=6 Hz, 1H), 7.69 (bd, J=8 Hz, 1H), 7.07 (d, J=8 Hz, 2H), 6.91 (m, 1H), 6.77 (d, J=8 Hz, 2H), 5.19 (s, 1H), 4.38 (m, 1H), 3.82 (m, 1H), 2.6–3.0 (m, 4H), 1.35 (s, 9H), 1.1–1.6 (m, 9H), 0.8 (overlapping t and d, 9H); MS (ESI–) for $C_{28}H_{43}N_3O_9$ m/z 564.1 (M–H)$^-$. Anal. Calcd for $C_{28}H_{43}N_3O_9$: C, 59.45; H, 7.66; N, 7.43. Found: C, 59.56; H, 7.71; N, 7.06.

EXAMPLE 109

(Chart BB, BB-3) 2-{4-[(2S)-2-({(2S)-3-(benzyloxy)-2-[(tert-butoxycarbonyl)amino]propanoyl}amino)-3-oxo-3-(pentylamino)propyl]phenoxy}malonic Acid $^1$H NMR (DMSO-d$_6$) δ 7.94 (bd, J=6 Hz, 1H), 7.83 (bt, 1H), 7.31 (bs, 5H), 7.09 (d, J=8 Hz, 2H), 6.95 (bd, J=8 Hz, 1H), 6.78 (d, J=8 Hz, 2H), 5.22 (s, 1H), 4.45 (s, 2H), 4.4 (m, 1H), 4.2 (m, 1H), 3.51 (m, 2H), 2.6–3.1 (m, 4H), 1.1–1.4 (m, 15H), 0.84 (t, J=7 Hz, 3H); MS (ESI–) for $C_{32}H_{43}N_3O_{10}$ m/z 628.1 (M–H)$^-$. Anal. Calcd for $C_{32}H_{43}N_3O_{10}$: C, 61.04; H, 6.88; N, 6.67. Found: C, 60.98; H, 7.14; N, 6.33.

EXAMPLE 110

(Chart BB, BB-3) 2-{4-[(2S)-2-({(2S)-4-amino-2-[(tert-butoxycarbonyl)amino]-4-oxobutanoyl}amino)-3-oxo-3-(pentylamino)propyl]phenoxy}malonic Acid $^1$H NMR (DMSO-d$_6$) δ 7.85 (bt, J=6 Hz, 1H), 7.80 (d, J=8 Hz, 1H), 7.3 (bs, 1H), 7.08 (d, J=8 Hz, 2H), 6.9 (m, 2H), 6.78 (d, J=8 Hz, 2H), 5.21 (s, 1H), 4.3 (m, 1H), 4.16 (m, 1H), 2.65–3.1 (m, 4H), 2.40 (dd, J=15, 7 Hz, 1H), 2.28 (dd, J=15, 8 Hz), 1.35 (s, 9H), 1.1–1.4 (m, 6H), 0.83 (t, J=7 Hz, 3H); MS (FAB) m/z (rel. intensity) 567 (MH$^+$, 19), 467 (43), 238 (26), 194 (30), 88 (76), 87 (47), 73 (34), 57 (99), 43 (27), 41 (31), 29 (33).

EXAMPLE 111

(Chart BB, BB-3) 2-{4-[(2S)-2-[(2-{[(benzyloxy)carbonyl]amino}acetyl)amino]-3-oxo-3-(pentylamino)propyl]phenoxy}malonic Acid $^1$H NMR (DMSO-d$_6$) δ 8.00 (d, J=8 Hz, 1H), 7.88 (bt, 1H), 7.32 (m, 5H), 7.10 (d, J=8 Hz, 2H), 6.79 (d, J=8 Hz, 8H), 5.23 (s, 1H), 5.00 (s, 2H), 4.38 (m, 1H), 3.4–3.7 (m, 2H), 2.6–3.1 (m, 4H), 1.1–1.4 (m, 6H), 0.82 (t, J=7 Hz, 3H); MS (ESI–) for $C_{27}H_{33}N_3O_9$ m/z 542.2 (M–H)$^-$. Anal. Calcd for $C_{27}H_{33}N_3O_9 \cdot 0.4H_2O$: C, 58.87; H, 6.19; N, 7.63. Found: C, 58.86; H, 6.33; N, 7.41.

EXAMPLE 112

(Chart BB, BB-3) 2-{4-[(2S)-2-{[(2S)-2-[(tert-butoxycarbonyl)amino]-3-(4-hydroxyphenyl)propanoyl]amino}-3-oxo-3-(pentylamino)propyl]phenoxy}malonic Acid $^1$H NMR (DMSO-d$_6$) δ 7.8–8.0 (m, 2H), 7.10 (d, J=8 Hz, 2H), 6.94 (d, J=8 Hz, 2H), 6.79 (d, J=8 Hz, 2H), 6.59 (d overlapping m, J=8 Hz, 3H), 5.22 (s, 1H), 4.38 (m, 1H), 4.0 (m, 1H), 2.5–3.1 (m, 6H), 1.1–1.4 (m, 6H), 0.82 (t, J=7 Hz, 3H); MS (FAB) m/z (rel. intensity) 616 (MH$^+$, 77), 616 (77), 560 (66), 516 (25), 336 (32), 238 (37), 194 (25), 136 (98), 133 (25), 88 (92), 57 (99). HRMS (FAB) calcd for $C_{31}H_{41}N_3O_{10}+H_1$ 616.2870, found 616.2860. Anal. Calcd for $C_{31}H_{41}N_3O_{10} \cdot 1.1H_2O$: C, 58.52; H, 6.86; N, 6.61. Found: C, 58.52; H, 6.80; N, 6.52.

EXAMPLE 113

(Chart BB, BB-3) 2-{4-[(2S)-2-({(2S)-2-[(tert-butoxycarbonyl)amino]-4-phenylbutanoyl}amino)-3-oxo-3-(pentylamino)propyl]phenoxy}malonic Acid $^1$H NMR (DMSO-d$_6$) δ 7.84 (t, J=6 Hz, 1H), 7.77 (d, J=8 Hz, 1H), 7.21 (d, J=8 Hz, 2H), 7.1 (m, 6H), 6.79 (d, J=8 Hz, 2H), 5.17 (s, 1H), 4.4 (m, 1H), 3.8 (m, 1H), 2.7–3.0 (m, 4H), 2.45 (m, 2H), 1.71 (m, 2H), 1.37 (s, 9H), 1.1–1.4 (m, 6H), 0.79 (t, J=7 Hz, 3H); MS (FAB) m/z (rel. intensity) 614 (MH$^+$, 27), 558 (53), 514 (37), 238 (52), 194 (41), 134 (85), 117 (38), 91 (78), 88 (90), 57 (99), 41 (31). HRMS (FAB) calcd for $C_{32}H_{43}N_3O_9+H_1$ 614.3077, found 614.3073.

Examples 114–115 were prepared by the general procedure described for R-2 (Chart R).

EXAMPLE 114

(Chart R, R-2) 5-[(2S)-2-({(2S)-2-[(tert-butoxycarbonyl)amino]-3-phenylpropanoyl}amino)-3-oxo-3-(pentylamino)propyl]-2-(carboxymethoxy)benzoic Acid $^1$H NMR (DMSO-d$_6$) δ 8.30 (d, J=8 Hz, 1H), 7.84 (bt, J=6 Hz, 1H), 7.58 (bs, 1H), 7.27 (bd, J=8 Hz, 1H), 7.15 (m, 5H), 6.88 (d, J=9 Hz, 1H), 6.79 (d, J=8 Hz, 1H), 4.66 (s, 2H), 4.38 (m, 1H), 4.11 (m, 1H), 2.5–3.1 (m, 6H), 1.1–1.4 (m, 6H), 1.27 (s, 9H), 0.83 (t, J=7 Hz, 3H); MS (ESI–) for $C_{31}H_{41}N_3O_9$ m/z 598.4 (M–H)$^-$. HRMS (FAB) calcd for $C_{31}H_{41}N_3O_9+H_1$ 600.2921, found 600.2930.

EXAMPLE 115

(Chart R, R-2) 5-[(2S)-2-{[(2S)-2-[(tert-butoxycarbonyl)amino]-3-(4-hydroxyphenyl)propanoyl]amino}-3-oxo-3-(pentylamino)propyl]-2-(carboxymethoxy)benzoic Acid $^1$H NMR (DMSO-d$_6$) δ 7.85 (m, 2H), 7.52 (bs, 1H), 7.28 (dm, J=8 Hz, 1H), 6.9 (m, 3H), 6.78 (d, J=8 Hz, 1H), 6.59 (d, J=8 Hz, 2H), 4.68 (s, 2H), 4.39 (m, 1H), 3.97 (m, 1H), 2.5–3.1 (m, 6H), 1.1–1.4 (m, 6H), 1.28 (s, 9H), 0.82 (t, J=7 Hz, 3H); MS (ESI–) for $C_{31}H_{41}N_3O_{10}$ m/z 614.3 (M–H)$^-$. HRMS (FAB) calcd for $C_{31}H_{41}N_3O_{10}+H_1$ 616.2870, found 616.2866.

Examples 116–124 were prepared by procedures analogous to that described for Example 10 (Chart D).

EXAMPLE 116

2-{4-[(2S)-2-({[(1-carboxy-2-phenylethyl)amino]carbonyl}amino)-3-oxo-3-(pentylamino)propyl]phenoxy}malonic Acid Major diastereomer. $^1$H NMR (DMSO-d$_6$) δ 7.79 (bt, J=7 Hz, 1H), 7.1–7.3 (m, 5H), 7.04 (d, J=8 Hz, 2H), 6.78 (d, J=8 Hz, 2H), 6.35 (d, J=7 Hz, 1H), 6.30 (d, J=7 Hz, 1H), 5.26 (s, 1H), 4.23 (m, 2H), 2.6–3.1 (m, 6H), 1.1–1.4 (m, 6H), 0.82 (t, J=7 Hz, 3H); MS (FAB) m/z (rel. intensity) 544 (MH$^+$, 99), 545 (31), 544 (99), 353 (24), 238 (21), 194 (18), 166 (23), 136 (16), 120 (42), 88 (20), 43 (17). Minor diastereomer (apparent peaks): $^1$H NMR (DMSO-d$_6$) δ 6.96 (d, J=8 Hz), 5.22 (s); HRMS (FAB) calcd for $C_{27}H_{33}N_3O_9+H_1$ 544.2295, found 544.2310. Anal. Calcd for $C_{27}H_{33}N_3O_9$.1.9H$_2$O: C, 56.13; H, 6.42; N, 7.27. Found: C, 56.13; H, 6.06; N, 7.26.

EXAMPLE 117

2-{4-[(2S)-2-({[benzyl(4-carboxybenzyl)amino]carbonyl}amino)-3-oxo-3-(pentylamino)propyl]phenoxy}malonic Acid $^1$H NMR (DMSO-d$_6$) δ 7.85 (d, J=8 Hz, 2H), 7.24 (m, 5H), 7.06 (m, 4H), 6.77 (d, J=8 Hz, 2H), 5.27 (s, 1H), 4.4 (m, 5H), 2.7–3.1 (m, 4H), 1.1–1.4 (m, 6H), 0.83 (t, J=7 Hz, 3H); MS (FAB) m/z (rel. intensity) 620 (MH$^+$, 25), 621 (9), 620 (25), 139 (10), 135 (13), 107 (7), 105 (8), 103 (8), 92 (8), 91 (99), 43 (7). HRMS (FAB) calcd for $C_{33}H_{37}N_3O_9+H_1$ 620.2607, found 620.2621. Anal. Calcd for $C_{33}H_{37}N_3O_9$.0.81H$_2$O: C, 62.49; H, 6.14; N, 6.63. Found: C, 62.49; H, 6.10; N, 6.73.

EXAMPLE 118

2-{4-[(2S)-2-[({[4-(carboxymethyl)benzyl][3-(trifluoromethyl)benzyl]amino}carbonyl)amino]-3-oxo-3-(pentylamino)propyl]phenoxy}malonic Acid $^1$H NMR (DMSO-d$_6$) δ 7.76 (bt, J=7 Hz, 1H), 7.4–7.6 (m, 4H), 7.3 (bd, J=7 Hz, 1H), 7.15 (d, J=8 Hz, 2H), 7.07 (d, J=9 Hz, 2H), 7.01 (d, J=8 Hz, 2H), 6.75 (d, J=9 Hz, 2H), 5.24 (s, 1H), 4.2–4.5 (m, 5H), 3.52 (s, 2H), 2.7–3.1 (m, 4H), 1.1–1.4 (m, 6H), 0.83 (t, J=7 Hz, 3H);

MS (FAB) m/z (rel. intensity) 702 (MH$^+$, 21), 702 (21), 324 (14), 322 (8), 159 (27), 150 (10), 149 (99), 107 (11), 105 (19), 104 (18), 91 (10). HRMS (FAB) calcd for $C_{35}H_{38}F_3N_3O_9+H_1$ 702.2638, found 702.2637. Anal. Calcd for $C_{35}H_{38}F_3N_3O_9$.0.44H$_2$O: C, 59.24; H, 5.52; N, 5.92. Found: C, 59.24; H, 5.56; N, 5.89.

EXAMPLE 119

2-{4-[(2S)-2-{[({1-[4-(benzyloxy)benzyl]-2-hydroxy-2-oxoethyl}amino)carbonyl]amino}-3-oxo-3-(pentylamino)propyl]phenoxy}malonic Acid $^1$H NMR (major isomer peaks)(DMSO-d$_6$) δ 7.3–7.5 (m, 5H), 7.0–7.1 (m, 4H), 6.88 (d, J=8 Hz, 2H), 6.78 (d, J=8 Hz, 2H), 5.26 (s, 1H), 5.04 (s, 2H), 4.2 (m, 2H), 2.6–3.0 (m, 6H), 1.1–1.4 (m, 6H), 0.81 (t, J=7 Hz, 3H); MS (FAB) m/z (rel. intensity) 544 (MH$^+$, 99), 545 (31), 544 (99), 353 (24), 238 (21), 194 (18), 166 (23), 136 (16), 120 (42), 88 (20), 43 (17). HRMS (FAB) calcd for $C_{27}H_{33}N_3O_9+H_1$ 544.2295, found 544.2310.

EXAMPLE 120

2-{4-[(2S)-2-[({[4-(aminosulfonyl)benzyl][3-(trifluoromethyl)benzyl]amino}carbonyl)amino]-3-oxo-3-(pentylamino)propyl]phenoxy}malonic Acid $^1$H NMR (DMSO-d$_6$) δ 7.83 (bt, J=6 Hz, 1H), 7.72 (d, J=8 Hz, 2H), 7.45–7.6 (m, 3H), 7.3 (m, 4H), 7.08 (d, J=8.5 Hz, 2H), 6.76 (d, J=8.5 Hz, 2H), 6.67 (bd, J=8 Hz, 1H), 5.27 (s, 1H), 4.3–4.55 (m, 5H), 2.7–3.1 (m, 4H), 1.1–1.4 (m, 6H), 0.83 (t, J=7 Hz, 3H); MS (FAB) m/z (rel. intensity) 723 (MH$^+$, 37), 724 (15), 723 (37), 345 (16), 170 (81), 159 (99), 107 (28), 106 (17), 91 (29), 88 (16), 43 (29). HRMS (FAB) calcd for $C_{33}H_{37}F_3N_4O_9S+H_1$ 723.2311, found 723.2315. Anal. Calcd for $C_{33}H_{37}F_3N_4O_9S$.2.2H$_2$O: C, 51.99; H, 5.48; N, 7.48. Found: C, 51.99; H, 5.35; N, 7.34.

EXAMPLE 121

2-{4-[(2S)-2-[({(3-carboxybenzyl)[3-(trifluoromethyl)benzyl]amino}carbonyl)amino]-3-oxo-3-(pentylamino)propyl]phenoxy}malonic Acid $^1$H NMR (DMSO-d$_6$) δ 7.75 (m, 3H), 7.2–7.6 (m, 6H), 7.05 (d, J=8 Hz, 2H), 6.73 (d, J=8 Hz, 2H), 6.6 (bd, J=8 Hz, 1H), 5.23 (s, 1H), 4.2–4.6 (m, 5H), 3.0 (m, 2H), 2.7–2.9 (m, 2H), 1.1–1.4 (m, 6H), 0.82 (t, J=7 Hz, 3H); MS (FAB) m/z (rel. intensity) 688 (MH$^+$, 19), 689 (8), 688 (19), 601 (7), 310 (15), 160 (6), 159 (38), 136 (11), 135 (99), 91 (11), 43 (8). HRMS (FAB) calcd for $C_{34}H_{36}F_3N_3O_9+H_1$ 688.2482, found 688.2489. Anal. Calcd for $C_{34}H_{36}F_3N_3O_9$.1.05H$_2$O: C, 57.80; H, 5.44; N, 5.95. Found: C, 57.79; H, 5.21; N, 5.77.

EXAMPLE 122

2-{4-[(2S)-2-[({benzyl[1-(carboxymethyl)-3-phenylpropyl]amino}carbonyl)amino]-3-oxo-3-(pentylamino)propyl]phenoxy}malonic Acid NMR analysis indicated a 1:1 mixture of diastereomers. $^1$H NMR (DMSO-d$_6$) δ 7.7 (m, 1H), 7.0–7.3 (m, 10H), 6.93 (t, J=8 Hz, 2H), 6.7 (overlapping t, J=8 Hz, 2H), 5.19, 5.14 (two s, 1H), 4.2–4.5 (m, 3H), 2.2–3.1 (m, 9H), 1.6 (m, 2H), 1.1–1.4 (m, 6H), 0.81, 0.80 (two t, J=7 Hz, 3H); MS (FAB) m/z (rel. intensity) 662 (MH$^+$, 27), 663 (11), 662 (27), 575 (9), 327 (6), 285 (8), 284 (34), 282 (6), 238 (8), 92 (9), 91 (99). HRMS (FAB) calcd for $C_{36}H_{43}N_3O_9+H_1$ 662.3077, found 662.3080. Anal. Calcd for $C_{36}H_{43}N_3O_9$.0.7H$_2$O: C, 64.12; H, 6.64; N, 6.23. Found: C, 64.12; H, 6.62; N, 6.11.

EXAMPLE 123

2-{4-[(2S)-2-{[(dibenzylamino)carbonyl]amino}-3-oxo-3-(pentylamino)propyl]phenoxy}malonic Acid $^1$H NMR (DMSO-d$_6$) δ 7.71 (bt, J=6 Hz, 1H), 7.25 (m, 6H), 7.05 (m, 6H), 6.77 (d, J=8.6 Hz, 2H), 5.27 (s, 1H), 4.38, 4.25 (ABq, J=17 Hz, 4H), 4.35 (m, 1H), 2.7–3.1 (m, 4H), 1.1–1.4 (m, 6H), 0.84 (t, J=7 Hz, 3H). MS (FAB) m/z (rel. intensity) 576 (MH$^+$, 51), 577 (17), 576 (51), 575 (8), 489 (9), 241 (9), 177 (8), 92 (10), 91 (99), 63 (9), 43 (8). HRMS (FAB) calcd for $C_{32}H_{37}N_3O_7+H_1$ 576.2709, found 576.2706. Anal. Calcd for $C_{32}H_{37}N_3O_7$.0.85H$_2$O: C, 65.04; H, 6.00; N, 7.11. Found: C, 65.03; H, 6.51; N, 7.29.

EXAMPLE 124

2-{4-[(2S)-2-({[4-(tert-butoxycarbonyl)-1-piperazinyl]carbonyl}amino)-3-oxo-3-(pentylamino)propyl]phenoxy}malonic Acid $^1$H NMR (DMSO-d$_6$) δ 7.85 (bt, J=6 Hz, 1H), 7.15 (d, J=8.6 Hz, 2H), 6.79 (d, J=8.6 Hz, 2H), 5.28 (s, 1H), 4.16 (m, 1H), 3.20 (bs, 8H), 2.55–3.1 (m, 4H), 1.38 (s, 9H), 1.1–1.4 (m, 6H), 0.83 (t, J=7 Hz, 3H); MS (FAB) m/z (rel. intensity) 565 (MH$^+$, 60), 566 (18), 565 (60), 157 (41), 131 (23), 129 (16), 113 (45), 87 (61), 57 (99), 43 (19), 41 (16). HRMS (FAB) calcd for $C_{27}H_{40}N_4O_9+H_1$ 565.2873, found 565.2896. Anal. Calcd for $C_{27}H_{40}N_4O_9 \cdot 0.58H_2O$: C, 56.38; H, 7.21; N, 9.74. Found: C, 56.39; H, 6.93; N, 9.43.

EXAMPLE 125

2-{4-[(2S)-2-{[(3-carboxyanilino)carbonyl]amino}-3-oxo-3-(pentylamino)propyl]phenoxy}malonic Acid Prepared by a procedure analogous to that described for Example 4 (Chart C).

$^1$H NMR (DMSO-d$_6$) δ 8.86 (s, 1H), 8.03 (bt, J=6 Hz, 1H), 8.00 (s, 1H), 7.45 (m, 2H), 7.30 (t, J=8 Hz, 1H), 7.08 (d, J=9 Hz, 2H), 6.82 (d, J=9 Hz, 2H), 6.30 (2, J=8 Hz, 1H), 5.27 (s, 1H), 4.36 (m, 1H), 2.7–3.1 (m, 4H), 1.1–1.4 (m, 6H), 0.83 (t, J=7 Hz, 3H); MS (FAB) m/z (rel. intensity) 516 (MH$^+$, 99), 517 (29), 516 (99), 515 (15), 414 (20), 353 (19), 194 (14), 136 (12), 107 (13), 88 (22), 43 (13). HRMS (FAB) calcd for $C_{25}H_{29}N_3O_9+H_1$ 516.1982, found 516.1965.

EXAMPLE 126

2-(carboxymethoxy)-5-[(2S)-2-{[(dibenzylamino)carbonyl]amino}-3-oxo-3-(pentylamino)propyl] benzoic Acid Prepared by a procedure analogous to that described for Example 10 (Chart D), using Q-4 as a starting material instead of B-4 as follows. Q-4 (54 mg, 0.11 mmole) was dissolved in 4 M HCl/dioxane (1 mL) and stirred at room temp. for 1 h. The solution was concentrated in vacuo, and the resulting residue was taken up in dry THF (2 mL). To the mixture was added triethylamine (47 μL, 0.34 mmol), and the reaction was cooled to 0° C. before the addition of diphosgene (7 μL, 0.06 mmol). The reaction was stirred at 0° C. for 15 minutes before the addition of dibenzylamine (29 μL, 0.15 mmol). Stirring was continued at room temperature for 3 h, followed by the addition of 2.5 M aq LiOH (0.6 mL). The mixture was stirred vigorously for 2 h, at which point MS analysis indicated saponification was complete. The reaction was acidified with 1 M HCl (3 mL), saturated with solid NaCl, and extracted with ethyl acetate. Drying of the extracts over MgSO$_4$ and concentration in vacuo left a glass (67 mg). The crude material was sonicated with CH$_2$Cl$_2$ (20 mL) for 30 min, diluted with hexane (approx. 5 mL), and allowed to stand at room temperature for 1 h, affording a white powder (43 mg, 68% overall). $^1$H NMR (DMSO-d$_6$) δ 7.82 (t, J=7 Hz, 1H), 7.62 (bs, 1H), 7.15–7.3 (m, 7H), 7.06 (d, J=7 Hz, 4H), 6.83 (d, J=9 Hz, 1H), 6.54 (d, J=7 Hz, 1H), 4.71 (s, 2H), 4.35 (m, 1H), 4.35, 4.25 (ABq, J=16 Hz, 4H), 2.7–3.1 (m, 4H), 1.1–1.4 (m, 6H), 0.84 (t, J=7 Hz, 3H); IR (mull) 3289 (b) 3088, 3064, 3030, 1735 (s), 1614 (s), 1585 (s), 1536 (s), 1496 (s), 1438 (s), 1340, 1301, 1247 (s), 1153, 700, cm$^{-1}$. MS (FAB) m/z (rel. intensity) 576 (MH$^+$, 40), 577 (14), 576 (40), 490 (4), 489 (14), 198 (7), 196 (6), 106 (6), 92 (8), 91 (99), 43 (5). HRMS (FAB) calcd for $C_{32}H_{37}N_3O_7+H_1$ 576.2709, found 576.2704. Anal. Calcd for $C_{32}H_{37}N_3O_7 \cdot 0.84H_2O$: C, 65.06; H, 6.60; N, 7.11. Found: C, 65.06; H, 6.47; N, 7.24.

EXAMPLE 127

2-{4-[(2S)-2-{[(2S)-2-[(tert-butoxycarbonyl)amino]-3-(1H-indol-3-yl)propanoyl]amino}-3-oxo-3-(pentylamino)propyl]phenoxy}malonic Acid Prepared according to the general procedure described for BB-3 (Chart BB).

$^1$H NMR (DMSO-d$_6$) δ 10.75 (s, 1H), 7.84 (d, J=8 Hz, 1H), 7.80 (bt, 1H), 7.51 (d, J=7 Hz, 1H), 7.29 (d,J=8 Hz, 1H), 6.95–7.15 (m, 4H), 6.94 (t, J=7 Hz, 1H), 6.79 (d overlapping m, J=8 Hz, 3H), 5.22 (s, 1H), 4.4 (m, 1H), 4.12 (m, 1H), 2.6–3.1 (m, 6H), 1.1–1.4 (m, 6H), 1.28 (s, 9H), 0.82 (t, J=7 Hz, 3H); MS (FAB) m/z (rel. intensity) 639 (MH$^+$, 7), 194 (13), 186 (17), 170 (25), 159 (42), 131 (13), 130 (99), 88 (27), 57 (48), 43 (12), 41 (14). HRMS (FAB) calcd for $C_{33}H_{42}N_4O_9+H_1$ 639.3030, found 639.3026. Anal. Calcd for $C_{33}H_{42}N_4O_9 \cdot 0.72H_2O$: C, 60.82; H, 6.72; N, 8.60. Found: C, 60.81; H, 6.70; N, 8.35.

EXAMPLE 128

(Chart R, R-3) 2-(carboxymethoxy)-5-{(2S)-3-oxo-3-(pentylamino)-2-[((2S)-3-phenyl-2-{[2-(4H-1,2,4-triazol-3-ylsulfanyl)acetyl]amino}propanoyl)amino] propyl}benzoic Acid A solution of R-1 (R==(S)—CH$_2$Ph) 0.5 g, 0.8 mmol) and 4N HCl/dioxane (20 mL) was stirred at room temp for 1.5 h. The reaction was concentrated to dryness in vacuo, and the resulting residue was taken up in DMF (50 mL). To the solution was added sequentially diisopropylethylamine (1.03 g, 0.8 mmol), 1,2,4-triazole-5-ylthioacetic acid (Drysdale et al, *J. Med. Chem.* 1992, 35, 2573)(159 mg, 1 mmol), HOBT monohydrate (135 mg, 1 mmol) and EDC hydrochloride (153 mg, 0.8 mmol). The mixture was stirred overnight at room temp. Solvent was removed in vacuo, and the residue was partitioned taken up in water and extracted with ethyl acetate. The organic extracts were dried over MgSO$_4$ and concentrated in vacuo. The residue was triturated with ether and dried again in vacuo, leaving the crude diester (190 mg) as a white solid. The diester was saponified by dissolving in DMF (10 mL) and adding 5.0 mL of 1.0 N aq NaOH. After stirring for 2 h, the reaction was neutralized by the addition of 1.0 N aq HCl (5.0 mL). The solvent was removed in vacuo, and the residue was taken up in water. The insoluble solid was filtered, air-dried and washed with ether, affording the title compound (136 mg) as an off-white solid after drying in vacuo. $^1$H NMR (DMSO-d$_6$) δ 8.37 (bs, 1H), 8.23 (d, J=8 Hz, 1H), 8.14 (d, J=8 Hz, 1H), 7.81 (bt, 1H), 7.43 (bs, 1H), 7.25 (bd, J=7 Hz, 1H), 7.1 (m, 5H), 7.01 (d, J=7 Hz, 1H), 4.56 (bs, 2H), 4.45 (m, 1H), 4.37 (m, 1H), 3.81, 3.72 (ABq, J=15 Hz, 2H), 2.8–3.1 (m, 4H), 2.6–2.8 (m, 2H), 1.1–1.4 (m, 6H), 0.82 (t, J=7 Hz, 3H); MS (ESI–) for $C_{30}H_{36}N_6O_8S$ m/z 639.2 (M–H)$^-$. HRMS (FAB) calcd for $C_{30}H_{36}N_6O_8S+H_1$ 641.2393, found 641.2388.

EXAMPLE 129

(Chart R, R-3) 2-(carboxymethoxy)-5-{(2S)-3-oxo-3-(pentylamino)-2-[((2S)-3-phenyl-2-{[2-(5-sulfanyl-1H-1,2,3,4-tetraazol-1-yl)acetyl] amino}propanoyl)amino]propyl}benzoic Acid Prepared by a procedure analogous to that described for Example 128. $^1$H NMR (DMSO-d$_6$) δ 8.55 (d, J=9 Hz, 1H), 8.22 (d, J=8 Hz, 1H), 7.77 (bt, J=6 Hz, 1H), 7.55 (d, J=1 Hz, 1H), 7.29 (dd, J=7, 1 Hz, 1H), 7.17 (m, 5H), 6.90 (d, J=7 Hz, 1H), 4.94, 4.84 (ABq, J=15 Hz, 2H), 4.70 (bs, 2H), 4.5 (m, 1H), 4.37 (m, 1H), 2.8–3.1 (m, 4H), 2.65–2.8 (m, 2H), 1.1–1.4 (m, 6H), 0.82 (t, J=7 Hz, 3H); MS (ESI–) for $C_{29}H_{35}N_7O_8S$ m/z 640.2 (M–H)$^-$. HRMS (FAB) calcd for $C_{29}H_{35}N_7O_8S+H_1$ 642.2346, found 642.2322.

EXAMPLE 130

(Chart R, R-3) $^2$-(carboxymethoxy)-5-{(2S)-3-oxo-3-(pentylamino)-2-[((2S)-3-phenyl-2-{[2-(1H-1,2,3-triazol-5-ylsulfanyl)acetyl]amino}propanoyl)amino] propyl}benzoic Acid Prepared by a procedure analogous to that described for Example 128. $^1$H NMR (DMSO-d$_6$) δ 8.25 (d, J=8 Hz, 1H), 8.21 (d, J=8 Hz, 1H), 7.83 (bt, 1H), 7.73 (bs, 1H), 7.43 (bs, 1H), 7.26 (dm, J=7 Hz, 1H), 7.15 (m, 5H), 7.04 (d, J=7 Hz, 1H), 4.56 (bs, 2H), 4.48 (m, 1H), 4.38 (m, 1H), 3.56 (bs, 2H), 2.6–3.1 (m, 6H), 1.1–1.4 (m, 6H), 0.84 (t, J=7 Hz, 3H); MS (FAB) m/z (rel. intensity) 641 (MH$^+$, 18), 685 (17), 665 (11), 664 (20), 663 (47), 641 (18), 195 (19), 120 (99), 114 (17), 88 (25), 30 (17). HRMS (FAB) calcd for $C_{30}H_{36}N_6O_8S+H_1$ 641.2393, found 641.2388.

EXAMPLE 131

2-{4-[(2S)-2-{[({$^2$-[(carboxymethyl)amino]-2-oxoethyl}amino)carbonyl]amino}-3-oxo-3-(pentylamino)propyl]phenoxy}malonic Acid Prepared by a procedure analogous to that described for Example 10 (Chart D). $^1$H NMR (DMSO-d$_6$) δ 8.08 (bt, J=7 Hz, 1H), 7.82 (bt, J=7 Hz, 1H), 7.07 (d, J=8.5 Hz, 2H), 6.80 (d, J=8.5 Hz, 2H), 5.27 (s, 1H), 4.22 (m, 1H), 3.73 (s, 2H), 3.65 and 3.55 (ABq, J=15 Hz, 2H), 2.6–3.1 (m, 4H), 1.1–1.4 (m, 6H), 0.82 (t, J=7 Hz, 3H); MS (FAB) m/z (rel. intensity) 511 (MH$^+$, 99), 512 (25), 511 (99), 409 (17), 371 (30), 133 (25), 129 (16), 107 (22), 88 (30), 59 (27), 43 (22). HRMS (FAB) calcd for $C_{22}H_{30}N_4O_{10}+H_1$ 511.2040, found 511.2057.

EXAMPLE 132

(Chart T, Formula T-5) 2-[4-[(2S)-2-({(2S)-2-[(tert-butoxycarbonyl)amino]-3-phenylpropanoyl}amino)-3-oxo-3-(pentylamino)propyl]-2-(2H-1,2,3,4-tetraazol-5-yl)phenoxy]acetic Acid PREPARATION OF T-1: To a solution of Q-2 (5.94 g, 12.47 mmol) in DMF (anhydrous, 30 mL) in a Heck vial was added Pd(PPh$_3$)$_4$ (0.58 g, 0.50 mmol) and zink cyanide (1.61 g, 13.72 mmol). The vial was flushed with nitrogen, tightly sealed and stirred at 80° C. for 16 h. After cooling to room temperature, the mixture was partitioned between EtOAc (50 mL) and 2 M aqueous ammonium hydroxide (50 mL). The organic layer was dried (Na$_2$SO$_4$), and concentrated. The residue was purified by column chromatography (SiO$_2$, EtOAc/n-hexane 1:1) to afford 1.76 g (38%) of T-1 as a white solid. $^1$H NMR 400 MHz (MeOH) δ 0.91 (t, 3H, J=7.3, 14.4), 1.18–1.48 (m, 6H), 1.39 (s, 9H), 2.77 (dd, 1H, J=8.6, 13.7), 2.98 (dd, 1H, J=6.45, 13.7), 3.08–3.21 (m, 2H), 4.20 (m, 1H), 6.88 (d, 1H, J=8.5), 7.34 (dd, 1H, J=2.2, 8.5), 7.38 (d, 1H, 2.2).

PREPARATION OF T-2: Prepared from T-1 (0.61 g, 1.63 mmol) by the general method described for U-2 and U-3, which afforded 0.69 g (94%) of the title compound as a white solid. $^1$H NMR 400 MHz (CDCl$_3$) δ 0.90 (t, 3H, J=7.1, 14.4), 1.22–1.45 (m, 6H), 1.38 (s, 9H), 2.79 (dd, 1H, J=8.8, 13.7), 3.01 (m, 1H), 3.11–3.18 (m, 2H), 3.77 (s, 3H), 4.87 (s, 2H), 7.00 (d, 1H, J=8.7), 7.46 (dd, 1H, J=2.2, 8.7), 7.51 (d, 1H, J=2.2).

PREPARATION OF T-3: Prepared from T-2 (0.55 mg, 1.23 mmol) by the general method described for U4 and U-5, which afforded 0.61 g (84%) of the title compound as a white solid. Mp=121.4–123.0° C. $^1$H NMR 400 MHz (MeOH) δ 0.90 (t, 3H, J=7.2, 14.5), 1.21 (m, 2H), 1.29 (m, 2H), 1.37 (s, 9H), 1.40 (m, 2H), 2.75 (dd, 1H, J=9.2, 13.5), 2.91 (dd, 1H, J=7.7, 13.5), 2.97–3.06 (m, 3H), 3.12 (m, 1H), 3.75 (s, 3H), 4.24 (dd, 1H, J=5.3, 9.2), 4.51 (app t, 1H, J=7.1, 14.1), 4.87 (s, 2H), 6.98 (d, 1H, J=8.6), 7.14–7.27 (m, 5H), 7.44 (dd, 1H, J=1.9, 8.6), 7.49 (d, 1H, J=1.9).

PREPARATION OF T-4: To a suspension of T-3 (0.45 g, 0.75 mmol) in toluene in a Heck vial was added trimethyl-silyl azide (0.30 mL, 2.25 mmol) and dibutyltin oxide (19 mg, 0.075 mmol). The mixture was flushed with nitrogen, tightly sealed and stirred at 110° C. for 16 h. The reaction mixture was cooled to room temperature and the volatiles were evaporated in vacuo. The residue was purified by column chromatography (SiO$_2$, EtOAc) which afforded 90 mg (19%) of T-4 as a white solid. Mp=189.5–192.8° C. $^1$H NMR 400 MHz (MeOH) δ 0.85 (t, 3H, J=6.9, 14.1), 1.16–1.41 (m, 6H), 1.33 (s, 9H), 2.69 (dd, 1H, J=9.4, 13.7), 2.95–3.17 (m, 5H), 3.79 (s, 3H), 4.22 (dd, 1H, J=4.9, 9.4), 4.58 (m, 1H), 4.99 (s, 2H), 7.09–7.24 (m, 6H), 7.42 (d, 1H, J=1.7, 6.9), 8.09 (d, 1H, J=1.7).

PREPARATION OF T-5: Prepared from T-4 (19 mg, 0.029 mmol) by the general method described for U-10 and U-11, which afforded 16 mg (90%) of the title compound as a white solid. $^1$H NMR 400 MHz (MeOH) δ 0.85 (t, 3H, J=7.0, 14.2), 1.18 (m, 2H), 1.24 (m, 2H), 1.33 (s, 9H), 1.38 (m, 2H), 2.70 (dd, 1H, J=9.4, 13.8), 2.96–3.08 (m, 3H), 3.14 (m, 2H), 4.22 (dd, 1H, J=5.1, 9.4), 4.58 (m, 1H), 4.95 (s, 2H), 7.12–7.29 (m, 6H), 7.44 (dd, 1H, J=1.9, 8.5), 7.86 (br m, 0.5H), 8.01 (br m, 1H), 8.10 (d, 1H, J=1.9); $^{13}$C NMR (MeOH) δ 14.3, 23.4, 28.7, 30.0, 30.2, 38.2, 39.0, 40.6, 55.8, 67.0, 80.9, 114.0, 114.9, 127.8, 129.5, 130.3, 131.5, 132.8, 135.4, 138.5, 155.9, 157.9, 172.5, 173.1, 174.1. MS (ESI) 622 (M–H). HRMS (EI) calcd for $C_{31}H_{41}N_7O_7$ 623.3068, found 623.3071. Anal. Calcd for $C_{31}H_{41}N_7O_7$: C, 59.70; H, 6.63; N, 15.72. Found: C, 59.5; H, 6.7; N, 14.0.

EXAMPLES 133–135 (Chart U)

PREPARATION OF U-1: Triethylamine (1.71 mL, 12.5 mmol) and benzyl alcohol (6.45 mL, 62 mmol) is added to a stirring suspension of Q-2 (2.97 g, 6.23 mmol) palladium (II)acetate (42 mg, 0.19 mmol) and 1,1'-bis (diphenylphosphino)ferrocene (DPPF, 207 mg, 0.37 mmol) in DMF (15 mL). The mixture is saturated with CO (1 atm) and stirred at 70° C. for 16 h. The mixture is allowed to reach room temperature and extracted with EtOAc (40 mL), the organic layer is washed with 10% aqueous HCl (20 mL) and brine (20 mL), dried (Na$_2$SO$_4$) and concentrated. The residue is purified by column chromatography (SiO$_2$, EtOAc/n-hexane 1:2), which furnished 5.7 g of a yellow oil. This crude material still contains some benzyl alcohol. Crystallization in EtOAc/n-hexane gives 0.82 g (27%) of pure U-1 as a white solid. $^1$H NMR 400 MHz (CDCl$_3$) δ 0.84 (t, 3H, J=7.1, 14.4), 1.13 (m, 2H), 1.23 (m, 2H,), 1.35 (m, 2H), 1.39 (s, 9H), 2.95 (d, 2H, J=6.7), 3.11 (m, 2H), 4.18 (m, 1H), 5.07 (br m, 1H), 5.37 (d, 2H, J=1,7), 5.77 (br m, 1H), 6.91 (d, 1H, J=8.5), 7.30 (dd, 1H, J=2.2, 8.5), 7.35–7.47 (m, 5H), 7.69 (d, 1H, J=2.2), 10.69.

PREPARATION OF U-2: Methyl bromoacetate (0.35 mL, 3.75 mmol) and freshly grounded K$_2$CO$_3$ (0.52 g, 3.75 mmol) is added to a stirring solution of U-1 (0.61 g, 1.25 mmol) in acetone (15 mL). The mixture is stirred at 50° C. over night. After cooling to ambient temperature, H$_2$O (10 mL) is added and the mixture is extracted with EtOAc (10 mL). The organic layer is dried (Na$_2$SO$_4$), and concentrated. The residue is purified by column chromatography (SiO$_2$, EtOAc/n-hexane 1:1) which furnished 0.46 g (66%) of U-2 as a white solid. $^1$H NMR 400 MHz (MeOH) δ 0.87 (t, 3H, J=7.1, 14.3), 1.17–1.40 (m, 6H), 1.35 (s, 9H), 2.79 (dd, 1H, J=8.4, 13.6), 2.98–3.14 (m, 3H), 3.74 (s, 3H), 4.19 (m, 1H), 4.75 (s, 2H), 5.33 (s, 2H), 6.95 (d, 1H, J=8.5), 7.32–7.39 (m, 5H), 7.46 (dd, 1H, J=1.9 8.5), 7.67 (d, 1H, J=1.9).

PREPARATION OF U-3: From Q-3 as described for the preparation of U-2. $^1$H NMR 400 MHz (MeOH) δ 0.89 (t, 3H, J=6.8, 13.9), 1.22 (m, 2H), 1.29 (m, 2H), 1.37 (s, 9H), 1.39 (m, 2H), 2.81 (dd, 1H, J=8.5, 13.3), 3.00 (dd, 1H, J=7.4, 13.3), 3.07–3.15 (m, 2H), 3.82 (s, 3H), 4.20 (m, 1H), 4.79 (s, 2H), 5.21 (s, 2H), 6.91 (d, 1H, J=8.5), 7.31–7.35 (m, 6H), 7.66 (s, 1H).

PREPARATION OF U-4: Trifluoroacetic acid (0.90 mL) is carefully added to a stirring solution of U-2 (0.44 mg, 0.78 mmol) in $CH_2Cl_2$ at 0° C. The mixture is stirred for 4 h allowing the solution to warm to ambient temperature. The volatiles are removed by vacuo and the residue is partitioned between EtOAc (15 mL) and saturated aqueous $NaHCO_3$ (2×10 mL). The organic layer is dried ($Na_2SO_4$) and concentrated to give 0.35 g (98%) of the crude amine as a yellowish oil. The amine is dissolved in $CH_2Cl_2$ (7 mL) and cooled with ice. Boc-(L)-phenylalanine (0.20 g, 0.77 mmol), 1-hydroxybenzotriazole (0.10 g, 0.77 mmol) and 1-(3-dimethylaminopropyl)-3-ethylcarbodiimide hydrochloride (EDC, 0.15 g, 0.77 mmol) is added to the solution, which is then stirred at room temperature over night. The reaction mixture is diluted with $CH_2Cl_2$ (5 mL) and washed with saturated aqueous $NaHCO_3$ (5 mL), brine (5 mL) and 10% aqueous HCl. The organic layer is dried ($Na_2SO_4$) and concentrated. The residue is purified by column chromatography ($SiO_2$, EtOAc) which gave 0.46 g (86%) of U-4 as a white solid. $^1$H NMR 400 MHz (MeOH) δ 0.86 (t, 3H, J=7.2, 14.5), 1.18 (m, 2H), 1.24 (m, 2H), 1.34 (s, 9H), 1.38 (m, 2H), 2.72 (dd, 1H, J=9.4, 13.8), 2.89–3.11 (m, 3H), 3.71 (s, 3H), 4.22 (m, 1H), 4.49 (m, 1H), 4.74 (s, 2H), 5.31 (s, 2H), 6.94 (d, 1H, J=8.6), 7.14–7.46 (m, 6H), 7.65 (d, 1H, J=1.7).

PREPARATION OF U-5: From U-3 as described for U-4. $^1$H NMR 400 MHz (MeOH) δ 0.88 (t, 3H, J=7.1, 14.4), 1.18 (m, 2H), 1.28 (m, 2H), 1.34 (s, 9H), 1.37 (m, 2H), 2.74 (dd, 1H, J=9.4, 13.8), 2.93 (dd, 1H, J=7.5, 13.8), 2.97–3.05 (m, 3H), 3.12 (m, 1H), 3.82 (s, 3H), 4.23 (m, 1H), 4.50 (m, 1H), 4.79 (s, 2H), 5.18 (s, 2H), 6.69 (br d, 0.6H), 6.91 (d, 1H, J=8.6).

EXAMPLE 133

(Chart U, Formula U-6) 5-[(2S)-2-({(2S)-2-[(tert-butoxycarbonyl)amino]-3-phenylpropanoyl}amino)-3-oxo-3-(pentylamino)propyl]-2-(2-methoxy-2-oxoethoxy)benzoic Acid A mixture of U-4 (0.41 g, 0.58 mmol) and 10% Pd/C (80 mg) in methanol (25 mL) is hydrogenated at atmospheric pressure for 2h. The mixture is filtered through Celite and solvent removed in vacuo to afford 0.34 g (96%) of U-6 as a white solid. $^1$H NMR 400 MHz (MeOH) δ 0.89 (t, 3H, J=7.1, 14.4), 1.19–1.42 (m, 6H), 1.36 (s, 9H), 2.73 (dd, 1H, J=9.5, 13.8), 2.93–3.07 (m, 3H), 3.14 (m, 1H), 3.75 (s, 2H), 4.23 (m, 1H), 4.51 (br m, 1H), 4.81 (s, 2H), 6.96 (d, 1H, J=8.5), 7.17–7.27 (m, 5H), 7.35 (dd, 1H, J=1.8, 8.5), 7.72 (d, 1H, J=1.8), 7.84 (br m, 0.5H), 7.98 (br m, 0.2H); $^{13}$C NMR (MeOH) δ 14.6, 23.7, 28.9, 30.2, 30.2, 30.4, 38.3, 39.3, 40.8, 53.0, 56.1, 58.0, 67.4, 81.1, 115.6, 122.7, 128.0, 129.7, 130.6, 132.0, 134.2, 135.9, 138.8, 157.9, 158.2, 169.7, 171.2, 172.7, 172.8, 174.3. MS (ESI) 612 (M–H).

Anal. Calcd for $C_{32}H_{43}N_3O_9$: C, 62.63; H, 7.06; N, 6.85. Found: C, 62.0; H, 7.0; N, 6.8.

PREPARATION OF U-7: From U-5 as described for U-6. $^1$H NMR 400 MHz (MeOH) δ 0.89 (t, 3H, J=7.1, 14.4), 1.21 (m, 2H), 1.29 (m, 2H), 1.35 (s, 9H), 1.37 (m, 2H), 2.75 (dd, 1H, J=9.3, 13.8), 2.94 (dd, 1H, J=7.4, 13.8), 2.98–3.05 (m, 3H), 3.13 (m, 1H), 3.86 (s, 3H), 4.24 (m, 1H), 4.50 (m, 1H), 4.69 (s, 2H), 6.95 (d, 1H, J=8.6), 7.17–7.27 (m, 5H), 7.35 (dd, 1H, J=1.5, 8.6), 7.64 (d, 1H, J=1.5), 7.83 (br m, 1H), 7.98 (br d, 0.6H).

PREPARATION OF U-8: To a solution of U-6 (116 mg, 0.19 mmol) in a mixture of THF (2.5 mL) and DMF (0.2 mL) was added 1.1'-carbonyldiimidazole (CDI, 61 mg, 0.38 mmol), and the mixture was refluxed at 80° C. for 1 h. The mixture was cooled to ambient temperature and hydroxylamine hydrochloride (39 mg, 0.57 mmol) was added. The reaction mixture was refluxed at 80° C. for 4h. After cooling to room temperature the mixture was partitioned between EtOAc (3 mL) and 3 M aqueous HCl (3 mL), the organic layer was dried ($Na_2SO_4$) and concentrated. The residue was purified by column chromatography ($SiO_2$, 5% MeOH in $CH_2Cl_2$) to afford 76 mg of a red/brownish solid. This material could be further purified by crystallization in EtOAc to give 34 mg (28%). of U-8 as a white solid. $^1$H NMR 400 MHz (MeOH) δ 0.89 (t, 3H, J=7.1, 14.4), 1.20 (m, 2H), 1.29 (m, 2H), 1.35 (s, 9H), 1.38 (m, 2H), 2.70 (dd, 1H, J=9.4, 13.3), 2.91–3.17 (m, 5H), 3.81 (s, 3H), 4.21 (m, 1H), 4.54 (m, 1H), 4.86 (s, 2H, obscured by solvent peak), 6.98 (d, 1H, J=8.1), 7.16 (m, 5H), 7.34 (br d, 1H, J=8.1), 7.84 (br s, 1H).

PREPARATION OF U-9: From U-7 as described for U-8. $^1$H NMR 400 MHz (MeOH) δ 0.88 (t, 3H, J=7.1, 14.5), 1.19 (m, 2H), 1.28 (m, 2H), 1.35 (s, 9H), 1.37 (m, 2H), 2.77 (dd, 1H, J=9.2, 13.7), 2.93 (dd, 1H, J=7.5), 2.98–3.06 (m, 3H), 3.13 (m, 1H), 3.90 (s, 3H), 4.22 (dd, 1H, J=5.3, 9.1), 4.50 (app t, 1H), 4.66 (s, 2H), 7.06 (d, 1H, J=8.5), 7.17–7.27 (m, 5H), 7.43 (dd, 1H, J=1.8, 8.5), 7.75 (d, 1H, 1.8).

EXAMPLE 134

(Chart U, Formula U-10) 2-{4-[(2S)-2-({(2S)-2-[(tert-butoxycarbonyl)amino]-3-phenylpropanoyl}amino)-3-oxo-3-(pentylamino)propyl]-2-[(hydroxyamino)carbonyl]phenoxy}acetic Acid To a solution of U-8 (10 mg, 0.0165 mmol) in THF (200 μL) was added a 2.5 M aqueous solution of LiOH (9.9 μL, 0.0248 mmol). The mixture was stirred at ambient temperature for 2 h. The reaction mixture was acidified with 3 M HCl and extracted with EtOAc (2 mL). The organic layer was dried ($Na_2SO_4$), and concentrated to afford 8.0 mg (79%) of U-10 as a white solid. $^1$H NMR 400 MHz (MeOH) δ 0.88 (t, 3H, J=7.1, 14.5), 1.19 (m, 2H), 1.29 (m, 2H), 1.35 (s, 9H), 1.38 (m, 2H), 2.71 (dd, 1H, J=9.5, 13.5), 2.94 (m, 1H), 2.98–3.07 (m, 3H), 3.12 (m, 2H), 4.22 (dd, 1H, J=5.1, 9.5), 4.54 (m, 1H), 4.81 (s, 2H), 6.99 (d, 1H, J=8.5), 7.17–7.27 (m, 5H), 7.35 (dd, 1H, J=1.8, 8.5), 7.85 (d, 1H, J=1.8); $^{13}$C NMR (MeOH) δ 14.6, 23.7, 28.9, 30.2, 30.4, 38.4, 39.2, 40.7, 56.1, 58.0, 67.3, 81.1, 114.8, 121.9, 128.0, 129.7, 130.6, 132.4, 133.4, 135.4, 138.8, 156.3, 158.1, 165.7, 172.4, 172.8, 174.3. MS (ESI) 613 (M–H). Anal. Calcd for $C_{31}H_{42}N_4O_9 \cdot \frac{1}{2} H_2O$: C, 59.70; H, 6.95; N, 8.98. Found: C, 59.5; H, 7.0; N, 8.8.

EXAMPLE 135

(Chart U, Formula U-11) 5-[(2S)-2-({(2S)-2-[(tert-butoxycarbonyl)amino]-3-phenylpropanoyl}amino)-3-oxo-3-(pentylamino)propyl]-2-[2-(hydroxyamlino)-2-oxoethoxy]benzoic Acid Prepared from U-9 (10 mg, 0.016 mmol) by the above method which afforded 8.1 mg (83%) of the title compound as a white solid. $^1$H NMR 400 MHz (MeOH) δ 0.88 (t, 3H, J=7.1, 14.5), 1.19 (m, 2H), 1.29 (m, 2H), 1.35 (s, 9H), 1.38 (m, 2H), 2.78 (dd. 1H), 2.95 (dd, 1H), 3.14 (m, 1H), 4.23 (dd, 1H, 5.2, 9.2), 4.51 (m, 1H), 4.68 (s, 2H), 7.04 (d, 1H, J=8.5), 7.17–7.27 (m, 5H), 7.42 (dd, 1H, J=2.1, 8.5), 7.78 (d, 1H, 2.1); $^{13}$C NMR (MeOH) δ 14.3, 23.4, 286, 29.9, 30.1, 38.1, 39.0, 40.5, 55.8, 57.7, 68.9, 80.9, 115.8, 121.2, 127.7, 129.4, 130.3, 131.9, 134.2, 136.4, 138.4, 158.2, 167.6, 169.0, 172.4, 172.5, 174.0. MS (ESI) 613 (M−H). Anal. Calcd for $C_{31}H_{42}N_4O_9 \cdot \frac{1}{2} H_2O$: C, 59.70; H, 6.95; N, 8.98. Found: C, 59.6; H, 7.2; N, 8.8.

EXAMPLE 136

(Chart V, Formula V-6) 2-(4-{(2S,3E,Z)-2-[(3-carboxypropanoyl)amino]-3-nonenyl}phenoxy) malonic Acid PREPARATION OF V-2: Diisobutylaluminium hydride (DIBAL-H, 20 wt. % in toluene, 72.2 mL, 101.6 mmol) was added dropwise, during 10 min, to a stirred solution of N-Boc-L-tyrosine methyl ester (V-1, 6.0 g, 20.3 mmol) in diethylether (dried over molecular sieves, 120 mL) kept at −78° C., under nitrogen atmosphere. After being stirred at −78° C. for 1 h, the reaction was quenched with MeOH (20 mL) and the mixture was poured into a saturated aqueous solution of potassium sodium tartrate (Rochelle salt, 500 mL). The mixture was allowed to warm to ambient temperature and diethylether (100 mL) was added. The ethereal layer was separated, dried ($MgSO_4$) and concentrated. The crude product was passed through a short pad of silica gel, eluting with EtOAc/n-hexane 1:1, which furnished 4.9 g (91%) of V-2 as a slightly yellow oil. $^1$H NMR 400 MHz ($CDCl_3$) δ 1.44 (s, 9H), 3.02 (d, 2H, J=6.5), 4.41 (dd, 1H, J=6.5, 13.3), 5.14 (m, 1H), 6.75 (d, 2H, J=8.1), 7.00 (d, 2H, J=8.1), 9.61 (s, 1H).

PREPARATION OF V-3: Potassium-tert-butoxide (12.5 g, 111.2 mmol) was added to solution of N-hexyl-triphenylphosphonium bromide (5.9 g, 22.2 mmol) in THF (dried over molecular sieves, 60 mL) at −5° C. (ice/acetone bath), under nitrogen atmosphere. After 10 min stirring, the aldehyde V-2 (5.9 g, 22.2 mmol) dissolved in THF (30 mL) was added dropwise. The mixture was stirred at 0° C. for 10 min, and then at ambient temperature for an additional 25 min. The reaction was quenched with crushed ice and the pH was adjusted to 3–4 with 10% aqueous HCl. The mixture was extracted with EtOAc (50 mL), washed with brine (2×50 mL), dried ($MgSO_4$), and concentrated. The residue was purified by flash chromatography ($SiO_2$, EtOAc/n-hexane 1:1.5), which furnished 4.31 g (58%) of V-3 as a yellow oil. $^1$H NMR 400 MHz ($CDCl_3$) δ 0.85 (t, 3H, J=6.8, 14.0), 1.19–1.28 (m, 6H), 1.43 (s, 9H), 1.85–1.97 (m, 2H), 2.64 (m, 1H), 2.82 (br m, 2H), 4.45 (br s, 1H), 5.18 (dd, 1H, J=8.9, 10.7), 5.42 (ddd, 1H, J=7.4, 10.7. 14.8), 6.73 (d, 2H, J=8.5), 7.00 (d, 2H, J=8.5).

PREPARATION OF V-4: Dibenzyl bromomalonate (4.6 g, 13.7 mmol) and potassium carbonate (2.71 g, 19.6 mmol) were added to a solution of V-3 (3.27 g, 9.81 mmol) in acetone (40 mL). The mixture was stirred at ambient temperature for 16 h. The reaction was quenched with $H_2O$ (100 ML) and the mixture was extracted with EtOAc (2×50 mL). The organic layer was dried ($MgSO_4$) and concentrated. The residue was purified by flash chromatography ($SiO_2$, EtOAc/n-hexane 1:5) which furnished 5.86 g (97%) of V-4 as a yellow oil. $^1$H NMR 400 MHz ($CDCl_3$) δ 0.88 (t, 3H), 1.15–1.29 (m, 6H), 1.42 (s, 9H), 1.80–2.00 (m, 2H), 1.63 (m, 1H), 1.72 (m, 1H), 3.59 (s, 1H), 4.52 (br s, 1H), 5.02–5.42 (m, 7H), 6.7–7.3 (m, 14H).

PREPARATION OF V-5: Trifluoroacetic acid (2.4 mL, 31.1 mmol) was carefully added to a stirring solution of V-4 (1.74 g, 2.83 mmol) in $CH_2Cl_2$ (20 mL) at 0° C. The mixture was stirred for 2 h allowing the solution to warm to ambient temperature. The volatiles were removed in vacuo and the residue was partitioned between diethylether (20 mL) and saturated aqueous $NaHCO_3$ (2×10 mL). The organic layer was dried ($MgSO_4$), and concentrated to dryness to afford 1.49 g (>100%) of the crude amine as a brown/yellow oil. The amine was dissolved in $CH_2Cl_2$ (20 mL) and cooled with ice to 0° C. Benzylhydrogen succinate (0.59 g, 2.83 mmol) and N'-(3-dimethylaminopropyl)-N-ethylcarbodiimide hydrochloride (EDC, 0.54 g, 2.83 mmol) was added and the mixture was stirred for 16 h allowing the solution to warm to ambient temperature. The mixture was diluted with $CH_2Cl_2$ (10 mL) and the organic phase was washed with 10% aqueous HCl (2×20 ml), dried ($MgSO_4$), and concentrated. TLC indicated that the product was a mixture of 4 compounds. By repeated flash chromatography, ($SiO_2$, EtOAc/n-hexane 1:3), 0.57 g (28%) of V-5 as a colorless oil could be isolated. $^1$H NMR 400 MHz ($CDCl_3$) δ 0.83 (t, 3H, J=6.8, 14.0), 1.14–1.26 (m, 8H), 1.77 (m, 1H), 1.94 (m, 1H), 2.41 (t, 2H), 2.69 (m, 2H), 2.83 (dd, 1H, J=5.1, 13.4), 4.86 (br m, 1H), 5.11 (s, 2H), 5.21 (s, 4H), 5.24 (s, 1H), 5.43 (m, 1H), 5.58 (br d, 1H), 6.82 (d, 2H, J=8.5), 7.05 (d, 2H, J=8.5), 7.25–7.34 (m, 15H).

PREPARATION OF V-6: A solution of V-5 (172 mg, 0.25 mmol) and 2.5 M aqueous LiOH (609 μL, 1.52 mmol) in THF (4 mL) was stirred at ambient temperature for 16 h. The reaction mixture was partitioned between EtOAc (5 mL) and saturated aqueous $NaHCO_3$ (5 mL). The water layer was acidified with 10% aqueous HCl and extracted with EtOAc (4×2 mL). The organic layer was dried ($MgSO_4$) and concentrated to dryness which furnished 96 mg (87%) of V-6 as a white solid. $^1$H NMR 400 MHz ($CDCl_3$) δ 0.85 (t, 3H, J=6.8, 14.0), 1.19–1.28 (m, 6H), 1.43 (s, 9H), 1.85–1.97 (m, 2H), 2.64 (m, 1H), 2.82 (br m, 2H), 4.54 (br s, 1H), 5.18 (dd, 1H, J=8.9, 10.7), 5.42 (ddd, 1H, J=7.4, 10.7, 14.8), 6.73 (d, 2H, J=8.5), 7.00 (d, 2H, J=8.5); $^{13}$C NMR ($CDCl_3$) δ 14.0, 22.5, 27.7, 28.4, 29.0, 31.4, 41.4, 60.5, 80.3, 115.2, 128.9, 129.1, 130.6, 133.0, 154.7, 173.2. MS (ESI) 434 (M−H). Anal. Calcd. for $C_{22}H_{29}O_8N \cdot \frac{1}{4} H_2O$: C, 60.06; H, 6.76; N, 3.18; O, 30.0. Found: C, 60.1; H, 6.7; N, 3.0; O, 29.8.

EXAMPLE 137

(Chart W, W-6) 2-[4-[(2S)-2-({(2S)-2-[(tert-butoxycarbonyl)amino]-3-phenylpropanoyl}amino)-3-oxo-3-(pentylamino)propyl](carboxymethyl) anilino]acetic Acid PREPARATION OF W-2: To a stirring solution of Boc-Phe (4-$NO_2$)-OH (1.0 g, 3.22 mmol) and amyl amine (0.0.280 g, 3.22 mmol) in $CH_2Cl_2$ at 0° C. was added EDC (0.617 g, 3.22 mmol) and the resulting solution stirred overnight allowing the solution to warm to ambient temperature. $CH_2Cl_2$ (100 ml) was added and the solution washed with 10% $HCl/H_2O$ (3×100 ml). The organic layer was further washed with saturated aqueous $NaHCO_3$ (3×100 ml) dried over $MgSO_4$ and solvent removed under reduced pressure to afford 0.856 g title compound as a white solid. m.p. 151–152° C. $^1$H NMR δ 0.86 (t, 3H), 1.22 (m, 6H), 1.40 (s, 9H), 3.16 (m, 4H), 4.31 (q, 1H), 5.02 (brs, 1H), 5.87 (brs, 1H), 7.38 (d, 2H), 8.14 (d, 2H).

PREPARATION OF W-3: A mixture of W-2 (3.43 g, 9.04 mmol) and 10% Pd/C (0.9 g) in abs. EtOH (125 mL) was hydrogenated at atmospheric pressure and room temperature for 4 h. The reaction mixture was filtered over diatomaceous earth and evaporated in vacuo leaving a off-white solid, that was purified on a silica gel flash-column eluting with ethyl acetate/n-hexane (2:1 v/v). A pinkish solid (3.01 g, 95% was isolated after pooling and evaporating pure fractions. $^1$H NMR δ 0.86 (t, 3H), 1.17–1.41 (m, 15H), 2.84–2.97 (m, 2H), 3.06–3.19 (m, 2H), 3.69 (s, 2H), 4.22 (m, 1H), 5.28 (br s, NH), 6.08 (t, NH), 6.59 (d, 2H), 6.96 (d, 2H).

PREPARATION OF W-4: A magnetically stirred mixture of W-3 (410 mg, 1.17 mmol), methyl bromoacetate (300 μL, 2.2 eq.), $K_2CO_3$ (500 mg) and KI (100 mg) in acetonitrile (4 mL) was heated at 60° C. for 15 h and then for 6 h at ambient temperature under $N_2$-atmosphere. The reaction mixture was treated with $H_2O$ (20 mL), extracted with ethyl acetate (3×15 mL) and washed with brine (30 mL). The combined organic layers were dried over $Na_2SO_4$, filtered and reduced to dryness giving 0.83 g of a yellow oil. Purification with flash-chromatography on silica gel eluting with ethyl acetate/n-hexane (1:1 v/v) gave 429 mg (74%) of a yellow waxy solid. $^1$H NMR δ 0.87 (t, 3H), 1.16–1.42 (m, 15H), 2.85–3.04 (m, 2H), 3.08–3.22 (m, 2H), 3.75 (s, 6H), 4.13 (s, 4H), 4.25 (m, 1H), 5.05 (br s, NH), 5.76 (br s, NH), 7.04 (d, 2H), 7.53 (d, 2H).

PREPARATION OF W-5: At 0° C., TFA (0.5 mL) was added dropwise to a solution of W-4 (200 mg, 0.41 mmol) in DCM (4 mL). The resulting solution was stirred for 4 h at room temperature. Evaporation in vacuo gave a red oil that was taken up in methanol and heated shortly with activated carbon. Filtration over diatomaceous earth and removal of the solvent gave 246 mg (97%) of the title compound di-TFA salt as a yellow oil. This oil was dissolved in DCM (3 mL) in stirred at 0° C. Then, HOBT (54 mg, 1 eq), Boc-L-Phe (106 mg, 1 eq), EDC (77 mg, 1 eq) and TEA (166 μL, 3 eq) were added, and this mixture was stirred for 16 h at room temperature. Ethyl acetate (30 mL) was added and washed with 2% aqueous HCl (20 mL) and saturated aqueous $NaHCO_3$ (20 mL). The organic layer was dried ($Na_2SO_4$) and reduced to dryness giving 210 mg of a yellow oil. Purification with flash-chromatography on silica gel eluting with ethyl acetate/n-hexane (1:1 v/v) gave 132 mg (50%) after two steps of a colorless oil. A small fraction was recrystallized from toluene giving a white solid. $^1$H NMR δ 0.87 (t, 3H), 1.16–1.42 (m, 15H), 2.74–2.79 (m, 1H), 2.97–3.14 (m, 5H), 3.74 (s, 6H), 4.11 (s, 4H), 4.28 (m, 1H), 4.51 (m, 1H), 4.91 (br s, NH), 5.99 (br s, NH), 6.41 (m, NH), 6.48 (d, 2H), 6.94 (d, 2H), 7.16 (d, 2H), 7.23–7.32 (m, 3H).

PREPARATION OF W-6: To a stirred solution of W-5 (88 mg, 137 mmol) in THF (2 mL), aqueous LiOH (2.5 M, 400 μL, 7.3 eq) was added. After 3 h the reaction mixture was acidified with 10% aqueous HCl until pH 5. The milky suspension was extracted with warm ethyl acetate (3×15 mL). The combined organic layers were dried ($Na_2SO_4$) and evaporated in vacuo leaving a white solid (64 mg, 76%). A small portion was recrystallized from acetonitrile giving white flakes. $^1$H NMR ($CD_3OD$) δ 0.91 (t, 3H), 1.20–1.42 (m, 15H), 2.01 (m, 1H), 2.79 (dd, 2H), 2.90–3.14 (m, 3H), 4.17 (s, 4H), 4.26 (dd, 1H), 4.46 (m, 1H), 6.53 (d, 2H), 7.05 (d, 2H), 7.20–7.30 (m, 5H); MS (Ionspray, [M−H]$^+$) m/z 611.0; Anal. Calcd. (found) for $C_{32}H_{46}N_4O_9 \cdot H_2O$: C 60.9 (60.8)% H 7.4 (7.1)% N 8.9 (9.0)%.

EXAMPLE 138

(Chart X, Formula X-7) 5-[(2S)-2-({(2S)-2-[(tert-butoxycarbonyl)amino]-3-phenylpropanoyl}amino)-3-hydroxypropyl]-2-(carboxymethoxy)benzoic Acid PREPARATION OF X-1: 3-Iodo-L-tyrosine (5.0 g, 16.3 mmol) was suspended in benzyl alcohol (100 mL) and at 0° C., thionyl chloride (20 mL) was added dropwise over a 20-min period. The temperature was raised to 80° C. and HCl (g) started to evolve. The reaction mixture became yellow turbid and turned to clear colorless after 30 min. After 8 h of heating, the mixture was stirred overnight at ambient temperature. Dry diethyl ether (150 mL) was added and the flask was stored overnight at −10° C. The white product was collected on a glass-sintered funnel and dried (1.91 g). An additional amount of 2.65 g (product/start. mat. 3:1) was obtained after the addition of i-hexane and storage at −10° C. The combined material was taken up in 5% $NaHCO_3$ (200 mL) and extracted with ethyl acetate (3×150 mL). The combined organic layers were dried ($Na_2SO_4$) and evaporated in vacuo leaving a crude yellow oil (4.00 g; 64%). $^1$H NMR (HCl salt, $CD_3OD$) δ 3.02 (d, J=6.83, 2H), 4.22 (t, J=6.83, 1H), 5.15 (?,J=3.93, 2H), 6.68 (d, J=8.28, 1H), 6.91 (dd, J=8.28, $J_2$=2.18, 1H), 7.23–7.31 (m, 5H), 7.51 (d, J=2.18, 1H).

PREPARATION OF X-2: The free base of X-1 (3.97 g, 10.0 mmol) was dissolved in dichloromethane (75 mL) and stirred at 0° C. under $N_2$-atmosphere. Then, EDC (1.92 g, 10.0 mmol), HOBT (1.35 g, 10.0 mmol) and BOC-L-Phe (2.65 g, 10.0 mmol) were added simultaneously and triethylamine 1.39 mL, 10.0 mmol) was added dropwise. This reaction mixture was stirred for 15 h allowing to warm to ambient temperature. Ethyl acetate (200 mL) was added and the organic layer was washed with 5% HCl (2×200 mL). The combined aqueous phases were extracted with ethyl acetate (100 mL) after which the combined organic layers were washed with 10% $NaHCO_3$ (100 mL). Drying ($Na_2SO_4$), filtration and evaporation in vacuo gave an off-white foam (6.01 g, 93%). The product was purified by flash column chromatography on silica gel eluting with chloroform: white foam C.Y. 78%). $^{13}$C NMR ($CDCl_3$) δ 28.24, 36.52, 38.26, 53.34, 55.85, 67.36, 85.47, 115.02, 127.06, 128.59, 128.66, 128.71, 128.75, 129.30, 129.58, 131.04, 134.86, 136.39, 138.79, 151.04, 170.58, 170.91. (Rf 0.30/i-hexane/ethyl acetate 3:1).

PREPARATION OF X-3: A mixture of X-2 (4.43 g, 6.87 mmol), Pd(OAc)$_2$ (50 mg, 3.3 mol %) and DPPF (230 mg, 6.2 mol %) in acetonitrile (20 mL) was treated with triethylamine (1.9 mL, 13.74 mmol) and methanol (4.4 mL). A carbon monoxide atmosphere was established and the reaction mixture was heated at 70° C. (Essential! Solvent vapor displaces CO if temperature is too high) for 16 h. The dark brown reaction mixture was directly coated on silica gel and subjected to column chromatography (3×20 cm) eluting with chloroform. Pure fractions were pooled giving 2.45 g (62%) off-white solid after evaporation of the eluent. Pure material can be obtained by recrystallization from abs. ethanol. (Rf 0.15/chloroform).

PREPARATION OF X-4: A mixture of X-3 (1.68 g, 2.91 mmol), methyl bromoacetate (0.83 uL, 3 eq.) and $K_2CO_3$ (activated, 1.20 g, 3 eq.) in acetone (20 mL) was heated at 50° C. overnight. TLC showed complete conversion and water (20 mL) was added. Extraction with dichloromethane (3×25 mL), drying ($Na_2SO_4$) and removal of the solvent at the rotavapor afforded 2.27 g of a yellow oil. Flash column chromatography on silica gel (2×20 cm) eluting with chloroform gave 1.17 g (62%) of a pure colorless oil, that solidified on standing. An additional amount (0.45 g) impure colorless oil was isolated. (Rf 0.12/chloroform).

PREPARATION OF X-5: X-4 (0.97 g, 1.50 mmol) was hydrogenated (atmospheric pressure) in abs ethanol (30 mL) using 10% Pd/C (100 mg) for 3 h. Filtration over diatomaceous earth and evaporation in vacuo of the filtrate yielded 0.76 g (91%) of a light-grey foam.

PREPARATION OF X-6: To a solution of X-5 (1.24 g, 2.24 mmol) in dry THF (10 mL) is added 1,1'- carbonyldiimidazole (CDI, 0.54 g, 3.35 mmol). The solution is stirred at room temperature over night under nitrogen atmosphere. The reaction mixture is cooled with ice and a solution of $NaBH_4$ (0.21 g, 5.59 mmol) in $H_2O$ (5 mL) is slowly added. After addition is complete, the mixture is stirred at room temperature for 10 min. The mixture is quenched with 10% aqueous HCl, and extracted with EtOAc. The organic layer is dried ($Na_2SO_4$) and concentrated. The residue is purified by flash chromatography ($SiO_2$, EtOAc) with furnished 160 mg (13%) of X-6 as a sticky foam. $^1H$ NMR 400 MHz ($CDCl_3$) δ 1.38, 2.49, 2.68, 2.73, 3.00, 3.42, 3.57, 3.78, 3.87, 4.05, 4.27, 4.68, 6.80, 7.13–7.30, 7.61.

PREPARATION OF X-7: To a solution of X-6 (36 mg, 0.066 mmol) in THF (1.5 mL) was added a 2.5 M aqueous solution of LiOH (106 μL, 0.26 mmol). The mixture was stirred at room temperature for 4 h, and then acidified with 10% aqueous HCl and extracted with EtOAc. The organic layer was dried ($Na_2SO_4$) and concentrated to afford 33 mg (96%) of X-7 as a white solid. Mp=168.8–172.3° C. $^1H$ NMR 400 MHz (MeOH) δ 1.35, 2.31, 2.64–2.97, 3.52, 4.06, 4.22, 4.78, 7.00, 7.11–7.27, 7.43, 7.77; $^{13}C$ NMR (MeOH) δ 20.7, 28.6, 30.9, 36.8, 39.5, 57.3, 67.5, 80.6, 111.0115.6, 12.1.3, 127.6, 129.3, 130.3, 133.6, 134.0, 136.1, 138.6, 157.5, 169.1, 172.2, 174.1. MS (ESI) 516 (M−H). Anal. Calcd for $C_{26}H_{32}N_2O_9 \cdot H_2O$: C, 59, 42; H, 6.33; N, 5.33. Found; C, 59.4; H, 6.3; N, 5.35.4.

EXAMPLE 139

(Chart Y, Formula Y-6) 2-{4-[2-[(3-carboxypropanoyl)amino]-2-methyl-3-oxo-3-(pentylamino)propyl]phenoxy}malonic Acid PREPARATION OF Y-2: To a solution of DL-a-methyl tyrosine (2.72 g; 13.9 mmol) and tetramethylammonium hydroxide pentahydrate (5.62 g; 31.0 mmol) in acetonitrile (270 mL) was added di-tert-butyldicarbonate (3.79 g; 17.4 mmol) and the resulting solution was allowed to stir 18 h at rt and concentrated [Khalil, E. M.; Subasinghe, N. L.; Johnson, R. L. Tet. Lett. 1996, 37, 3441]. The residue was partitioned between $Et_2O/H_2O$; the phases were separated and the aqueous phase extracted twice more with $Et_2O$. The aqueous phase was brought to pH 4 with solid citric acid and extracted with $CHCl_3$ (3×100 mL). The organic extracts were combined, dried ($Na_2SO_4$) and concentrated to afford 2.58 g (63%) 9 as a white foam. $^1H$ NMR ($CDCl_3$) δ 6.95 (d, J=8 Hz, 2H), 6.70 (d, J=8 Hz, 2H), 5.17 (brs, 1H), 3.29 (brm, 1H), 3.11 (brm, 1H), 1.56 (s, 3H), 1.47 (s, 9H).

PREPARATION OF Y-3: To a solution of Y-2 (3.23 g; 10.9 mmol), diisopropylethylamine (2.09 mL; 12.0 mmol), and amylamine (1.39 mL; 12.0 mmol) in $CH_2Cl_2$ (250 mL) was added N-[(dimethylamino)-1H-1,2,3-triazolo[4,5-b]pyridin-1-ylmethylene]-N-methylmethanammonium hexafluorophosphonate N-oxide (4.63 g; 12.2 mmol), and the reaction was allowed to stir 18 h at rt. The reaction was washed with 1 M HCl (3×100 mL), saturated aq. $NaHCO_3$ (3×100 mL), and dried ($Na_2SO_4$). Upon concentration in vacuo, the residue was dissolved in a minimum of hot EtOAc and cooled to 4° C. The resulting precipitate was collected to afford 1.92 g (5.26 mmol; 48%) Y-3 as a white solid. Mp 170–2° C.; UV $λ_{max}$ 225 (9820, 95% EtOH); $^1H$ NMR (300 MHz, DMSO) δ 0.84 (t, J=7 Hz, 3H), 1.17–1.24 (m, 7H), 1.38 (s, 9H), 2.90–3.10 (m, 4H), 3.35 (s, 2H), 6.32 (br s, 1H), 6.60 (d, J=8 Hz, 2H), 6.82 (d, J=8 Hz, 2H), 7.67 (br t, 1H), 9.10 (s, 1H).

PREPARATION OF Y-4: To a solution of Y-3 (1.94 g; 5.33 mmol) in acetone (100 mL) was added finely ground $K_2CO_3$ (2.28 g; 16.5 mmol) and dibenzyl bromomalonate (3.07 g; 8.46 mmol). After 18 h at rt, the reaction was diluted with $H_2O$ (250 mL), extracted with EtOAc (3×100 mL), and dried ($Na_2SO_4$). Chromatography (mplc, E. Merck silica 60, 230–400) with 30% EtOAc/hexane afforded 1.11 g (32%) y-4 as a colorless oil. UV $λ_{max}$ 222 (13000, 95% EtOH); $^1H$ NMR (300 MHz, $CDCl_3$) δ 7.34–7.25 (m, 10 H), 7.01 (d, J=9 Hz, 2H), 6.83 (d, J=9 Hz, 2H), 6.33 (br s, 1H), 5.26 (s, 1H), 5.22 (s, 4H), 3.31 (d, J=14 Hz, 1H), 3.24–3.20 (m, 2H), 3.00 (d, J=14 Hz, 1H), 1.45 (s, 9H), 1.36 (s, 3H), 1.38–1.29 (m, 6H), 0.88 (t, J=7 Hz, 3H).

PREPARATION OF Y-5: HCl gas was bubbled into a solution of Y-4 (1.044 g; 1.61 mmol) for 15 min. After 4 h, the reaction was concentrated in vacuo and the residue dissolved in $CH_2Cl_2$ and triethylamine (0.49 mL; 3.54 mmol). Succinic anhydride (0.186 g; 1.86 mmol) was added and the reaction was allowed to stir 20 h at rt. An additional 0.186 g of succinic anhydride and 0.49 mL of triethylamine were added and the reaction allowed to stir an additional 20 h. The reaction was washed with 1 M HCl (2×20 mL), dried ($MgSO_4$), and chromatographed (mplc, E. Merck silica gel 60, 230–400 mesh) with 2% MeOH/$CH_2Cl_2$/0.5% AcOH to afford 0.567 g (54%) Y-5 as a colorless oil. $^1H$ NMR (300 MHz, $CDCl_3$) δ 7.33–7.25 (m, 10H), 6.98 (d, J=9 Hz, 2H), 6.81 (d, J=9 Hz, 2H), 6.32 (br s, 1H), 6.26 (br t, 1H), 5.26 (s, 1H), 5.22 (s, 4H), 3.31–3.14 (m, 4H), 2.70–2.67 (m, 2H), 2.42–2.39 (m, 2H), 1.50 (s, 3H), 1.50–1.43 (m, 2H), 1.30–1.24 (m, 4H), 0.88 (t, J=7 Hz, 3H).

PREPARATION OF Y-6: A solution of Y-5 (0.225 g; 0.348 mmol) and 10% Pd/C (0.031 g) in MeOH (10 mL) was hydrogenated at atmospheric pressure for 18 h. The reaction was filtered through Celite, concentrated, and purified by preparative RP HPLC using the conditions outlined below to afford 0.088 g (54%) Y-6 as a hygroscopic white solid after lyophilization. UV $λ_{max}$ 223 (11400, 95% EtOH); $^1H$ NMR (300 MHz, DMSO-$d_6$) δ 7.59 (brs, 1H), 7.45 (brt, 1H), 6.96 (d, J=8 Hz, 2H), 6.79 (d, J=8 Hz, 2H), 5.24 (s, 1H), 3.26 (d, J=13 Hz, 1H), 3.05–2.93 (m, 3H), 2.45–2.42 (m, 2H), 2.35–2.29 (m, 2H), 1.38–1.29 (m, 2H), 1.24–1.14 (m, 4H), 1.13 (s, 3H), 0.84 (t, J=7 Hz, 3H); $^{13}C$ NMR (75 MHz, DMSO-$d_6$) δ 174.8, 173.8, 171.3, 167.9, 155.9, 131.9, 130.8, 114.6, 76.1, 59.7, 30.9, 29.4, 29.1, 29.0, 24.1, 22.3, 14.1; IR (mull) 3362, 2729, 2669, 2592, 1732, 1631, 1612, 1544, 1511, 1299, 1226, 1184, 1120, 855, 839 $cm^{-1}$; MS (FAB) m/z 467 ($MH^+$), 468, 467, 252, 208, 177, 157, 88, 43, 42, 23; HRMS (FAB) calcd for $C_{22}H_{30}N_2O_9+H_1$ 467.2029, found 467.2040.

EXAMPLE 140

(Chart Z, Formula Z-6) 2-{4-[2-[(3-carboxypropanoyl)amino]-3-oxo-3-(pentylamino)propyl]-2-fluorophenoxy}malonic Acid PREPARATION OF Z-2: To a suspension of commercially available 3-fluoro-DL-tyrosine (1.58 g; 7.93 mmol) in 0.5 M NaOH (19 mL) was added di-tert-butyl dicarbonate (2.12 g; 9.72 mmol) in THF (19 mL). After 26 h at rt, and additional 1.5 g of di-tert-butyl dicarbonate was added and the reaction stirred for an additional 2 h. The reaction was concentrated in vacuo to remove THF, and the residue was washed with $Et_2O$. The aqueous phase was acidified with 1 M citric acid, extracted with $CHCl_3$, and dried ($Na_2SO_4$) to afford 2.05 g (86%) Z-2 as a white foam. UV $λ_{max\ 223}$ (8000, 95% EtOH); $^1H$ NMR (300 MHz, DMSO-$d_6$) δ 7.04 (d, J=8 Hz, 1H), 6.98 (d, J=13 Hz, 1H), 6.82–6.78 (m, 2H), 3.99 (ddd, J=5, 10, 14 Hz, 1H), 2.88 (dd, J=5, 14 Hz, 1H), 2.68 (dd, J=10, 14 Hz, 1H), 1.30 (s, 9H).

PREPARATION OF Z-3: N-Ethyl-N'-3-dimethylaminopropylcarbodiimide hydrochloride (1.38 g; 7.20 mmol) was added to a solution of Z-2 (1.78 g; 5.96 mmol) in $CH_2Cl_2$ (50 mL). After 10 min, amyl amine (0.83 mL; 7.2 mmol) was added and the reaction was allowed to stir 18 h at rt. The reaction was washed with 1 M citric acid (3×25 mL), dried ($Na_2SO_4$), and concentrated in vacuo to afford 1.50 g (68%) Z-3 as a white solid. Mp. 63–4° C.; UV $\lambda_{max}$ 272 (1600, 95% EtOH); $^1$H NMR (300 MHz, $CDCl_3$) δ 6.94–6.79 (m, 3H), 6.07 (t, J=6 Hz, 1H), 5.19 (br s, 1H), 4.23 (q, J=8 Hz, 1H), 3.35–3.04 (m, 2H), 2.93 (d, J=7 Hz, 2H), 1.40 (s, 9H), 1.32–1.18 (m, 6H), 0.84 (t, J=7 Hz, PREPARATION OF Z-4: To a solution of Z-3 (1.49 g; 4.04 mmol) in acetone (60 mL) was added finely ground $K_2CO_3$ (1.72 g; 12.5 mmol) and dibenzyl bromomalonate (1.75 g; 4.83 mmol). After 18 h at rt, the reaction was diluted with $H_2O$ (250 mL), extracted with EtOAc (3×100 mL), and dried ($Na_2SO_4$). Chromatography (mplc, E. Merck silica 60, 230–400) with 30% EtOAc/hexane afforded 0.799 g (30%) Z-4 as a colorless oil which solidified upon standing. Mp. 77–78.5° C.; UV $\lambda_{max}$ 223 (12200, 95% EtOH); $^1$H NMR (300 MHz, $CDCl_3$) δ 7.34–7.29 (m, 10H), 6.97–6.81 (m, 3H), 5.74 (br t, 1H), 5.24 (s, 4H), 5.23 (s, 4H), 4.96 (br s, 1H), 4.22–4.15 (m, 1H), 3.15 (q, J=7 Hz, 2H), 2.97 (d, J=7 Hz, 2H), 1.41 (s, 9H), 1.43–1.34 (m, 2H), 1.29–1.16 (m, 4H), 0.86 (t, J=7 Hz, 3H).

PREPARATION OF Z-5: HCl gas was bubbled into a solution of Z-4 (0.490 g; 0.753 mmol) for 10 min. After 18 h, the reaction was concentrated in vacuo and the residue dissolved in $CH_2Cl_2$ (15 mL) and triethylamine (0.25 mL; 1.8 mmol). Succinic anhydride (0.088 g; 0.879 mmol) was added and the reaction was allowed to stir 18 h at rt. The reaction was diluted with $CH_2Cl_2$ (50 ML), washed with 1 M HCl (2×30 mL), dried ($MgSO_4$), and chromatographed (mplc, E. Merck silica gel 60, 230–400 mesh) with 2% $MeOH/CH_2Cl_2$/1% AcOH to afford 0.0.167 g (34%) Z-5 as a colorless oil. UV $\lambda_{max}$ 223 (11500, 95% EtOH); $^1$H NMR (300 MHz, $CDCl_3$) δ 7.56 (d, J=8 Hz, 1H), 7.32–7.23 (m, 10H), 6.95–6.78 (m, 3H), 5.25 (s, 1H), 5.19 (dd, J=12, 14 Hz, 4H), 4.69–4.61 (m, 1H), 3.21–3.09 (m, 1H), 3.05–2.86 (m, 3H), 2.59–2.54 (m, 2H), 2.47–2.40 (m, 2H), 1.35–1.07 (m, 6H), 0.82 (t, J=7 Hz, 3H).

PREPARATION OF Z-6: A solution of Z-5 (0.145 g; 0.223 mmol) and 10% Pd/C (0.026 g) in MeOH (10 mL) was hydrogenate at atmospheric pressure for 18 h. The reaction was filtered through Celite, concentrated, and purified by preparative RP HPLC using the conditions outlined below to afford 0.068 g (65%) Z-6 as a hygroscopic white solid after lyophilization. UV $\lambda_{max}$ 222 (10200, 95% EtOH); $^1$H NMR (300 MHz, DMSO-$d_6$) δ 8.08 (d, J=8 Hz, 1H), 7.82 (br t, 1H), 7.07 (d, J=12 Hz, 1H), 6.96–6.89 (m, 2H), 5.33 (s, 1H), 4.39–4.32 (m, 1H), 3.06–2.94 (m, 2H), 2.90–2.84 (m, 1H), 2.99–2.63 (m, 1H), 2.35–2.21 (m, 4H), 1.46–1.11 (m, 6H), 0.82 (t, J=7 Hz, 3H); IR (mull) 3333, 2727, 2670, 26 1733, 1626, 1549, 1516, 1341, 1278, 1216, 1174, 1134, 1091, 722 $cm^{-1}$; MS (FAB) m/z 471 ($MH^+$), 471, 193, 171, 167, 153, 135, 133, 121, 103, 89; HRMS (FAB) calcd for $C_{21}H_{27}FN_2O_9+H_1$ 471.1779, found 471.1797.

EXAMPLE 141

(Chart AA, Formula AA-#) 2-(4-{3-[(2-carboxyethyl)amino]-3-oxo-2-[(pentylamino)carbonyl]propyl}phenoxy)malonic Acid PREPARATION OF AA-2: To a solution of 4-hydroxybenzaldehyde (5.04 g, 41.3 mmol) was added finely ground $K_2CO_3$ (17.3 g; 125 mmol) and diethyl chloromalonate (7.34 mL; 45.4 mmol). After 18 h at rt, the reaction was concentrated in vacuo, and the residue taken up in water (200 mL). This was extracted with EtOAc (3×100 mL), dried ($Na_2SO_4$) and chromatographed (mplc, E. Merck silica gel 60, 230–400 mesh) to afford 7.97 g (69%) AA-2 as a pale yellow oil UV $\lambda_{max}$ 267 (15300, 95% EtOH); $^1$H NMR (300 MHz, $CDCl_3$) δ 9.76 (s, 1H), 7.73 (d, J=9 Hz, 2H), 6.96 (d, J=9 Hz, 2H), 5.24 (s, 1H), 4.28–4.15 (m, 4H), 1.18 (t, J=7 Hz, 6H).

PREPARATION OF AA-4: To a solution of commercially available ethyl hydrogen malonate (12.1 g; 91.7 mmol) and amyl amine (10.6 mL; 91.7 mmol) in $CH_2Cl_2$ (100 mL) was added diethyl cyanophosphonate (13.9 mL; 91.7 mmol) over 15 min. After 1.5 h at rt, the reaction was washed with 1 M citric acid (2×50 mL); $H_2O$ (50 mL), saturated aqueous $NaHCO_3$ (2×50 mL), and dried ($Na_2SO_4$). Chromatography (mplc, E. Merck silica gel 60, 230400 mesh) with 30% EtOAc/heptane afforded 8.9 g (48%) AA-4 as a pale yellow oil. $^1$H NMR (300 MHz, $CDCl_3$) δ 7.28 (br s, 1H), 4.00 (q, J=7 Hz, 2H), 3.12 (s, 2H), 3.06 (q, J=7 Hz, 2H), 1.35 (quintet, J=7 Hz, 2H), 1.16–1.11 (m, 4H), 1.10 (t, J=7 Hz, 3H), 0.71 (t, J=6 Hz, 3H).

PREPARATION OF AA-5: A solution of AA-4 (7.2 g; 36 mmol), 1.0 M NaOH (35.8 mL) and THF (100 mL) was allowed to stir at rt for 1 h. The reaction was concentrated in vacuo to remove THF, diluted with $H_2O$ (200 mL), and washed with $Et_2O$ (3×100 mL). The aqueous phase was brought to pH 1 with 3 M HCl and extracted with $CH_2Cl_2$ (3×100 mL). Upon drying ($Na_2SO_4$) and concentrating, 5.02 g (81%) AA-5 was obtained as a white solid. Mp. 66–7° C.; $^1$H NMR (300 MHz, $CDCl_3$) δ 12.23 (br s, 1H), 7.53 (br t, 1H), 3.34 (s, 2H), 3.25 (q, J=7 Hz, 2H), 1.51 (quintet, J=7 Hz, 2H), 1.33–1.27 (m, 4H), 0.86 (t, J=7 Hz, 3H).

PREPARATION OF AA-6: To a solution of β-alanine ethyl ester hydrochloride (1.76 g; 11.5 mmol) and triethylamine (1.60 mL; 11.5 mmol) was added AA-5 (1.99 g; 11.5 mmol) and diethyl cyanophosphonate (1.74 mL; 11.5 mmol). After 18 h at rt, the reaction was washed with 1 M citric acid (3×50 mL) and dried ($MgSO_4$). Chromatography (mplc, E. Merck silica gel 60, 230–400 mesh) with 5% $MeOH/CH_2Cl_2$ afforded 1.65 g (53%) AA-6 as a white solid. Mp. 102–3° C.; UV $\lambda_{max}$ 331 (8.99, 95% EtOH); $^1$H NMR (300 MHz, $CDCl_3$) δ 7.52 (br s, 1H), 7.26 (br s, 1H), 4.12 (q, J=7 Hz, 2H), 3.50 (q, J=6 Hz, 2H), 3.20 (q, J=7 Hz, 2H), 3.13 (s, 2H), 2.51 (s, 2H), 1.48 (quintet, J=7 Hz, 2H), 1.29–1.26 (m, 4H), 1.23 (t, J=7 Hz, 3H), 0.86 (t, J=7 Hz, 3H).

PREPARATION OF AA-7: A solution of AA-67 (0.981 g; 3.60 mmol), AA-2 (1.02 g; 3.62 mmol) and piperidine (1 mL) in toluene (100 mL) was brought to reflux under a Dean-Stark trap. After 21 h, the reaction was cooled, concentrated, and chromatographed (mplc, E. Merck silica gel 60, 230–400 mesh) with 1:1 EtOAc/heptane to afford 0.593 g (31%) AA-7 as an orange oil which solidified upon standing. A second chromatography using 20%–50% EtOAc/heptane separated the two isomers. Earlier eluting isomer: $^1$H NMR (300 MHz, $CDCl_3$) δ 7.72 (s, 1H), 7.40 (br t, 1H), 7.33 (d, J=9 Hz, 2H), 6.91 (d, J=9 Hz, 2H), 6.33 (br rt, 1H), 5.18 (s, 1H), 4.34–4.27 (m, 4H), 4.00 (q, J=7 Hz, 2H), 3.49 (q, J=6 Hz, 2H), 3.29 (q, J=7 Hz, 2H), 2.43 (t, J=6 Hz, 2H), 1.54 (quintet, J=7 Hz, 2H), 1.33–1.27 (m, 4H), 1.30 (t, J=7 Hz, 6H), 1.17 (t, J=7 Hz, 3H), 0.89 (t, J=7 Hz, 3H). Later eluting isomer: $^1$H NMR (300 MHz, $CDCl_3$) δ 7.79 (br t, 1H), 7.69 (s, 1H), 7.37 (d, J=9 Hz, 2H), 6.91 (d, J=9 Hz, 2H), 5.78 (br t, 1H), 5.19 (s, 1H), 4.35–4.27 (m, 4H), 4.16 (q, J=7 Hz, 2H), 3.59 (q, J=6 Hz, 2H), 3.21 (q, J=7 Hz, 2H), 2.57 (t, J=6 Hz, 2H), 1.38 (quintet, J=7 Hz, 2H), 1.35–1.24 (m, 11 H), 1.24–1.14 (m, 2H), 0.84 (t, J=7 Hz, 3H).

PREPARATION OF AA-8: A mixture of E and Z AA-7 (0.580 g; 1.08 mmol) in MeOH (25 mL) was hydrogenated at atmospheric pressure with 10% Pd/C (0.059 g) for 18 h. The reaction was filtered through a pad of Celite, concentrated, and chromatographed (flash, silica gel) with 60% EtOAc/heptane to afford 0.408 g (70%) AA-8 as a white solid. Mp. 88–90° C.; UV $\lambda_{max}$ 222 (11900, 95% EtOH); $^1$H NMR (300 MHz, CDCl$_3$) δ 7.07 (d, J=9 Hz, 2H), 7.00 (br t, 1H), 6.82 (d, J=9 Hz, 2H), 6.71 (br t, 1H), 5.12 (s, 1H), 4.32–4.25 (m, 4H), 4.10 (q, J=7 Hz, 2H), 3.39 (q, J=6 Hz, 2H), 3.14–3.02 (m, 5H), 2.45–2.30 (m, 2H), 1.38 (quintet, J=7 Hz, 2H), 1.34–1.18 (m, 13 H), 0.85 (t, J=7 Hz, 3H).

PREPARATION OF AA-9: A solution of AA-8 (0.313 g; 0.583 mmol), 1.0 M NaOH (2.92 mL), H$_2$O (7 mL) and THF (10 mL) was stirred at rt. After 3 hr, the reaction was concentrated in vacuo to remove THF, diluted with H$_2$O (10 mL) and washed with CH$_2$Cl$_2$ (5 mL). The aqueous phase was brought to pH 2 with 1 M HCl, and allowed to stir until a white precipitate appeared (approx. 1 h). This was collected, washed with H$_2$O and dried to afford 0.216 g (82%) AA-9. UV $\lambda_{max}$ 225 (10700, 95% EtOH); $^1$H NMR (300 MHz, DMSO-d$_6$) δ 7.86 (br t, 1H), 7.75 (br t, 1H), 6.99 (d, J=9 Hz, 2H), 6.78 (d, J=9 Hz, 2H), 5.12 (s, 1H), 3.23–3.17 (m, 3H), 2.99–2.95 (m, 2H), 2.87–2.85 (m, 2H), 2.27 (t, J=7 Hz, 2H), 1.31–1.11 (m, 6H), 0.81 (t, J=7 Hz, 3H); $^{13}$C NMR (75 MHz, DMSO-d$_6$) δ 173.3, 169.4, 169.0, 168.7, 156.2, 131.9, 129.8, 115.0, 75.6, 55.4, 32.2, 34.8, 34.1, 29.0, 28.9, 22.2, 14.4; IR (drift) 3283, 3053, 2953, 2928, 2871, 2859, 1768, 1725, 1663, 1639, 1551, 1512, 1275, 1245, 1205 cm$^{-1}$; MS (FAB) m/z 453 (MH$^+$), 475, 454, 453, 431, 139, 107, 105, 103, 91, 23; HRMS (FAB) calcd for C$_{21}$H$_{28}$N$_2$O$_9$+H$_1$ 453.1873, found 453.1859.

EXAMPLE 142

(Chart CC, Formula CC-7) 2-[4-[2-({(2R)-2-[(tert-butoxycarbonyl)amino]-3-phenylpropanoyl}amino)-3-oxo-3-(pentylamino)propyl]-2-(2-hydroxy-2-oxoethoxy)phenoxy]acetic Acid PREPARATION OF CC-2: K$_2$CO$_3$ (0.776 g; 5.61 mmol) and ethyl bromoacetate (0.63 mL; 5.6 mmol) were added to a solution of benzyl 2-[(tert-butoxycarbonyl)amino]-3-(3,4-dihydroxyphenyl)propanoate (CC-1) [Kaiser, Ado; Koch, Wolfgang; Scheer, Marcel; Woelcke, Uwe. N-Acyl-3,4-dihydroxy-L-phenylalanines. Ger. Offen., 32 pp. DE 2153811 720504] (0.997 g; 2.57 mmol) in acetone (100 mL). After 18 h at rt, the reaction was concentrated in vacuo, and the residue partitioned between H$_2$O (100 mL)/EtOAc (50 mL). The phases were separated, the aqueous phase was extracted with EtOAc (50 mL) and the organic phases were combined and dried (Na$_2$SO$_4$). Chromatography (mplc, E. Merck silica gel 60, 230–400 mesh) with 30% EtOAc/hexane afforded 0.691 g (48%) benzyl 3-[3,4-bis(2-ethoxy-2-oxoethoxy)phenyl]-2-[(tert-butoxycarbonyl)amino]propanoate (CC-2) as a colorless oil. UV $\lambda_{max}$ 224 (8550, 95% EtOH); $^1$H NMR (300 MHz, CDCl$_3$) δ 7.36–7.28 (m, 5H), 6.73 (d, J=8 Hz, 1H), 6.62 (m, 2H), 5.16–5.10 (m, 2H), 4.94 (br d, 1H), 4.67–4.51 (m, 5H), 4.28–4.21 (m, 4H), 2.92–2.88 (m, 2H), 1.41 (s, 9H), 1.32–1.26 (m, 6H).

PREPARATION OF CC-3: 10% Pd/C (554 mg) was added to CC-2 (2.94 g, 5.25 mmol) followed by the addition of 100 mL of MeOH. The reaction mixture was stirred at rt under a H$_2$ atmosphere$_{for}$ 14 h, filtered through celite, concentrated and purified by column chromatography (1% AcOH, 5% MeOH/CH$_2$Cl$_2$) to afford CC-3 as a clear oil (1.86 g, 3.75 mmol, 71% yield). UV $\lambda_{max}$ 221 (7890, 95% Ethanol); (400 MHz, CDCl$_3$) δ 6.74–6.85 (m, 3H), 4.97 (s, 1H), 4.70 (s, 2H), 4.69 (s, 2H), 4.53 (s, 1H), 4.27 (m, 4H), 3.06 (s, 2H), 1.44 (s, 9H), 1.29 (m, 6H).

PREPARATION OF CC-4: CC-3 (1.64 g, 3.50 mmol) was dissolved in 75 mL of CH$_2$Cl$_2$, to the solution was added amylamine (450 μL, 3.88 mmol), triethylamine (610 μL, 4.02 mmol), and diethyl cyanophosphonate (610 mL, 4.38 mmol). The reaction mixture was stirred for 18 h, quenched with 10% aq citric acid, extracted with CH$_2$Cl$_2$ and washed with water. The organic layer was dried over NaSO$_4$, filtered and condensed. The residue was purified by flash chromatography (30% EtOAc-50% EtOAc/heptane) to afford CC-4 as a white solid (964 mg, 1.79 mmol, 51% yield). UV $\lambda_{max}$ 221 (8920,95% ETHANOL; $^1$H NMR (400 MHz, CDCl$_3$) δ 7.28 (s, 1H), 6.76–6.84 (m, 3H), 5.75 (s, 1H), 5.05 (s, 1H), 4.70 (s, 2H), 4.68 (s, 2H), 4.21–4.30 (m, 4H), 4.19 (m, 1H), 3.14 (m, 2H), 3.02 (dd, J=14, 6 Hz, 1H), 2.90 (dd, J=14, 8 Hz, 1H), 1.43 (s, 9H), 1.15–1.41 (m, 12H), 0.87 (t, J=7 Hz, 3H).

PREPARATION OF CC-5: CC-4 (765 mg, 1.42 mmol) was dissolved in 25 mL of 20% TFA/CH$_2$Cl$_2$ solution, the reaction mixture was stirred for 1 h at rt then condensed to afford a yellow oil. The oil was redissolved in CH$_2$Cl$_2$, washed with NaHCO$_3$ and water. The organic layer was dried over NaSO$_4$, filtered and condensed. The residue was purified by flash chromatography (5% MeOH sat. NH$_3$/CH$_2$Cl$_2$) to afford CC-5 as a clear oil. $^1$H NMR (400 MHz, CDCl$_3$) δ 6.76–6.84 (m, 3H), 4.69 (s, 4H), 4.25 (q, J=10 Hz, 4H), 3.54 (m, 1H), 3.13–3.25 (m, 3H), 2.60 (dd, J=18, 13 Hz, 1H), 1.50 (m, 2H), 1.26–1.32 (m, 10H), 0.89 (t, J=9 Hz, 3H).

PREPARATION OF CC-6: CC-5 (362 mg, 0.826 mmol) was dissolved in 50 mL of CH$_2$Cl$_2$ to the solution was added triethylamine (160 μL, 1.18 mmol), diethylcyanophosphonate (160 μL, 1.06) and Boc-L-Phe (262 mg, 0.99 mmol). The reaction mixture was stirred at rt for 16 h, quenched with 10% aq citric acid, extracted with CH$_2$Cl$_2$ and washed with water. The organic layer was dried over NaSO$_4$, filtered, and condensed. The residue was purified by column chromatography (5% MeOH/CH$_2$Cl$_2$) to afford CC-6 (1:1 mixture of diastereomers) as a white solid (418 mg, 0.610 mmol, 74% yield). UV $\lambda_{max}$ 224 (10300, MeOH); $^1$H NMR (400 MHz, CDCl$_3$) δ 7.18–7.32 (m, 5H), 6.63–6.46 (m, 3H), 6.34 (m, 1H), 5.98–6.07 (m, 1H), 5.00–5.07 (m, 1H), 4.67–4.71 (m, 4H), 4.55 (m, 1H), 4.09–4.28 (m, 5H), 2.90–3.18 (m, 5H), 2.52–2.82 (m, 1H), 1.15–1.43 (m, 21 H), 0.86 (m, 3H).

PREPARATION OF CC-7: CC-6 (160 mg, 0.243 mmol) was dissolved in 15 mL of THF, to the solution was added 1.0 N NaOH (800 μL, 0.800 mmol), the reaction mixture was stirred for 16 h at rt. The reaction was quenched with 10% citric acid, extracted with CH$_2$Cl$_2$, the organic layer was dried over NaSO$_4$, filtered and condensed to afford CC-7 as a white solid (122 mg, 0.201 mmol, 83% yield). UV $\lambda_{max}$ 226 (9460, MeOH; $^1$H NMR (400 MHz, DMSO-d6) δ 12.90 (s, 2H), 7.76–8.24 (m, 2H), 7.10–7.24 (m, 5H), 6.65–6.90 (m, 4H), 4.61 (m, 4H), 4.40 (m, 1H), 4.11 (m, 1H), 2.63–2.87 (m, 6H), 1.15–1.35 (m, 15H), 0.84 (m, 3H); $^{13}$C NMR (100 MHz, DMSO-d6) δ 180.9, 180.8, 180.7, 179.9, 179.8, 179.7, 179.7, 179.6, 164.9, 164.6, 156.5, 155.5, 155.4, 147.5, 147.5, 147.4, 140.7, 140.3, 138.6, 138.5, 137.5, 137.4, 135.6, 131.6, 131.4, 124.8, 123.6, 123.6, 87.7, 87.6, 81.9, 74.9, 74.7, 74.6, 65.4, 65.2, 63.6, 63.3, 52.2, 48.0, 47.9, 46.9, 46.7, 39.9, 38.1, 38.0, 38.0, 37.9, 37.6, 37.2, 31.3, 23.3; IR (drift) 3316, 2958, 2931, 1756, 1710, 1688, 1646, 1614, 1551, 1517, 1271, 1250, 1192, 1168, 1145 cm$^{-1}$. HRMS (FAB) calcd for $C_{32}H_{43}N_3O_{10}+H_1$ 630.3026, found 630.3038.

EXAMPLE 143

(Chart DD, Formula DD-3) 2-(carboxymethoxy)-5-[[(2S)-3-oxo-2-{[(2R)-2-(2-oxo-1-pyrrolidinyl)-3-phenylpropanoyl]amino}-3-(pentylamino)propyl] benzoic Acid PREPARATION OF DD-1: Q-4 (2.30 g, 4.53 mmol) was dissolved in 20 mL of 20% TFA/CH$_2$Cl$_2$ solution, the reaction mixture was stirred at rt for 5 h. The solution was condensed, dissolved in CH$_2$Cl$_2$, washed with saturated aq NaHCO$_3$, organics dried over NaSO$_4$. Purified by column chromatography (5%MeOH (sat. NH$_3$)/CH$_2$Cl$_2$) to afford DD-1 as a clear oil (1.48 g, 3.62 mmol, 80% yield). $[\alpha]^{25}{}_D$=18° (c 0.64, methanol); UV $\lambda_{max}$ 226 (9750, MeOH); $^1$H NMR (300 MHz, CDCl$_3$) δ 7.65 (d, J=2 Hz, 1H), 7.32 (d, J=2 Hz, 1H), 7.29 (d, J=2 Hz, 1H), 6.85 (d, J=9 Hz, 1H), 4.68 (s, 2H), 4.35 (q, J=7 Hz, 2H), 4.25 (q, J=7 Hz, 2H), 3.56 (dd, J=9, 4 Hz, 1H), 3.21 (m, 3H), 2.71 (dd, J=14, 9 Hz, 1H), 1.25–1.50 (m, 12H), 0.89 (t, J=7 Hz, 3H).

PREPARATION OF DD-3: (2S)-2-(2-Oxo-1-pyrrolidinyl)-3-phenylpropanoic acid [Ocain, T. D.; Deininger, D. D., U.S. Pat. No. 5,023,338] (124 mg, 0.532 mmol) was added to 15 ml of CH$_2$Cl$_2$, to the reaction mixture was added triethyl amine (75 µL, 0.54 mmol), DD-1 (225 mg, 0.551 mmol) and diethyl cyanophosphonate (90 µL, 0.59 mmol). The reaction mixture was stirred at rt for 12 h, diluted with CH$_2$Cl$_2$, quenched with 10% aq citric acid, washed with water, organics dried over NaSO$_4$, filtered and condensed. The resulting product DD-2 was dissolved in 10 mL THF/water (1:1), to the reaction mixture was added 1 N NaOH solution (600 µL, 0.600 mmol), the reaction mixture was stirred at rt for 2 h then quenched with 10% aq citric acid, extracted with EtOAc, washed with water, dried organics over NaSO$_4$, filtered, and condensed. Purified by column chromatography (10% MeOH/CH$_2$Cl$_2$, 1% AcOH, to give a white solid as a diastereomer mixture 7:1, (175 mg, 0.31 mmol, 56% yield). Separated major diastereomers by HPLC to give DD-3 as a white solid. Mp. 96–97° C.; $^1$H NMR (400 MHz, DMSO) δ 7.98 (d, J=8 Hz, 1H), 7.87 (t, J=4 Hz, 1H), 7.56 (d, J=2 Hz, 1H), 7.32 (dd, J=10, 2 Hz, 1H), 7.20 (m, 2H), 7.12 (m, 3H), 6.91 (d, J=9 Hz, 1H), 4.80 (dd, J=10, 5 Hz, 1H), 4.71 (s, 3H), 4.45 (m, 1H), 2.90–3.12 (m, 5H), 2.72–2.83 (m, 3H), 2.07 (m, 1H), 1.89 (m, 1H), 1.75 (m, 1H), 1.62 (m, 1H), 1.36 (m, 2H), 1.14–1.23 (m, 5H), 0.85 (t, J=7 Hz, 3H); $^{13}$C NMR (100 MHz, DMSO) δ 174.2, 170.5, 170.1, 169.2, 167.0, 155.3, 137.7, 133.6, 131.6, 130.4, 128.7, 128.0, 126.2, 121.0, 113.4, 65.5, 54.6, 54.2, 43.0, 38.5, 36.3, 33.8, 30.2, 28.6, 28.5, 21.8, 17.6, 13.9; MS (ESI+) for $C_{30}H_{37}N_3O_8$ m/z 568.2 (M+H)$^+$.

EXAMPLE 144

(Chart EE, Formula EE-4) 5-[(2S)-2-({(2S)-2-[(tert-butoxycarbonyl)amino]-3-phenylpropanoyl}amino)-3-oxo-3-(pentylamino)propyl]-2-[carboxy(fluoro) methoxy]benzoic Acid PREPARATION OF EE-1: Triethylamine (3.37 mL; 24.2 mmol) was added to a solution of Q-2 (5.76 g; 12.1 mmol), 1,1'-bis(diphenylphosphino)ferrocene (0.400 g; 0.721 mmol) and palladium (II) acetate (0.0814 g; 0.362 mmol) in 25 mL DMF/10 mL benzyl alcohol. The reaction was placed under a CO atmosphere and heated to 60° C. for 12 h. The reaction was diluted with EtOAc (75 mL), washed with 1 M HCl (3×25 mL), and dried (Na$_2$SO$_4$). The organic phase was filtered, absorbed onto silica gel, and chromatographed (flash, silica gel) with 20% EtOAc/heptane. The white precipitate which formed in the resulting fractions was collected and washed with 20% EtOAc/heptane to afford 1.47 g EE-1. The filtrate was combined with the remaining product-containing fractions and rechromatographed with 10%–20% EtOAc/heptane to afford an additional 0.902 g EE-1 as a solid. The mixed cuts (containing residual benzyl alcohol) were evaporated to dryness at 70° C./1 Torr to afford an additional 0.527 g EE-1 as a solid. Total yield: 2.90 g (49%). $^1$H NMR (300 MHz, CDCl$_3$) δ 10.70 (s, 1H), 7.68 (d, J=2 Hz, 1H), 7.46–7.35 (m, 5H), 7.30 (dd, J=2, 9 Hz, 1H), 6.89 (d, J=9 Hz, 1H), 6.12 (br t, 1H), 5.36 (s, 2H), 5.25 (br d, 1H), 4.25–4.22 (m, 1H), 3.15–3.07 (m, 2H), 2.97–2.92 (m, 2H), 1.37 (s, 9H), 1.41–1.14 (m, 6H), 0.85 (t, J=7 Hz, 3H).

PREPARATION OF EE-2: Ethyl bromofluoroacetate (0.26 mL; 2.2 mmol) was added to EE-1 (0.902 g; 1.86 mmol) and finely ground K$_2$CO$_3$ (1.28 g; 9.24 mmol) in acetone (100 mL) and the reaction was stirred 18 h at rt. The reaction was filtered throught Whatman 42 paper, concentrated, and chromatographed (flash, silica) with 30%–50% EtOAc/heptane to afford 0.809 g (74%) EE-2 as a white solid. Mp. 88–90° C.; $[\alpha]^{25}{}_D$=1° (c 0.91, chloroform); UV $\lambda_{max}$ 229 (10300, 95% EtOH); $^1$H NMR (300 MHz, CDCl$_3$) δ 7.73 (t, J=3 Hz, 1H), 7.42–7.28 (m, 6H), 7.16 (d, J=8 Hz, 1H), 6.27(brs, 1H), 5.88 (dd, J=1, 60 Hz, 1H), 5.35–5.30 (m, 3H), 4.28–4.21 (m, 3H), 3.12–3.08 (m, 3H), 2.99–2.94 (m, 1H), 1.39–1.17 (m, 6H), 1.36 (s, 9H), 1.29 (t, J=7 Hz, 3H), 0.85 (t, J=7 Hz, 3H).

PREPARATION OF EE-3: Trifluoroacetic acid (12 mL) was added to a solution of EE-2 (0.659 g; 1.12 mmol) in CH$_2$Cl$_2$ (36 mL) and allowed to stir at rt for 20 min. The reaction was concentrated, and the residue was dissolved in CH$_2$Cl$_2$ (70 mL), washed with 5% NaHCO$_3$ (12 mL), water (2×12 mL), and dried (MgSO$_4$). Removal of the solvent in vacuo afforded (0.543 g) of a yellow oil, which was used without further purification. A 0.438 g portion of this oil in CH$_2$Cl$_2$ (40 mL) was treated with triethylamine (0.187 g; 1.34 mmol), N-tert-butyl-L-phenylalanine (0.286 g; 1.08 mmol), and diethylcyanophosphonate (0.203 g; 1.34 mmol). After 18 h at rt, the reaction was diluted with CH$_2$Cl$_2$ (40 mL), washed with 1 M citric acid (2×20 mL), and dried (MgSO$_4$). Chromatography (flash, silica) with 50% EtOAc/heptane) afforded 0.504 g (76%) EE-3 as a white solid. $[\alpha]^{25}{}_D$=−24° (c 1.02, chloroform); UV $\lambda_{max}$ 230 (10500, 95% EtOH); $^1$H NMR (300 MHz, CDCl$_3$) δ 7.42–7.14 (m, 13 H), 6.74 (br s, 1H), 6.36 (br s, 1H), 5.88 (dd, J =5, 60 Hz, 1H), 5.31 (s, 2H), 5.14 (br t, 1H), 4.65–4.61 (m, 1H), 4.35–4.32 (m, 1H), 4.26–4.22 (m, 2H), 3.20–2.89 (m, 6H), 1.33–1.16 (m, 18 H), 0.85 (t, J=7 Hz, 3H).

PREPARATION OF EE-4: A solution of EE-3 (0.389 g; 0.529 mmol) in MeOH (25 mL) was hydrogenated at atmospheric pressure with 10% Pd/C (80.3 mg), After 23 h the catalyst was removed by filtration through Whatman 42 paper, and the filtrate concentrated to a white solid. Mass spectroscopy showed a mixture of methyl and ethyl esters: MS (ESI−) for $C_{39}H_{48}FN_3O_9$ m/z 630.1 (M−H)$^−$. MS (ESI−) for $C_{40}H_{50}FN_3O_9$ m/z 644.1 (M−H)$^−$. A 99.3 mg portion of this mixture was treated with 0.0509 M LiOH (6.35 mL) in THF (6 mL). After 15 min, rxn concentrated in vacuo to remove THF, acidified with 1 M citric acid. The resulting solid was purified by preparative RP HPLC to afford 21 mg EE-4 as a white solid after lyophilization. UV $\lambda_{max}$ 229 (8470, 95% EtOH); $^1$H NMR (300 MHz, DMSO-$d_6$) δ 7.96–7.94 (m, 2H), 7.62 (s, 1H), 7.6–7.4 (m, 1H), 7.24–7.17 (m, 6H), 9.91 (br d, 1H), 6.17 (d, J=59 Hz, 1H), 4.50–4.40 (m, 1H), 4.14–4.04 (m, 1H), 3.08–2.91 (m, 3H), 2.86–2.79 (m, 2H), 2.71–2.61 (m, 1H), 1.37–1.12 (m, 15H), 0.84 (t, J=7 Hz, 3H); IR (drift) 3311, 2959, 2931, 2871, 2860, 1689, 1646, 1525, 1498, 1450, 1441, 1368, 1291, 1242, 1166 cm$^{-1}$; MS (FAB) m/z 618 (MH$^+$), 518, 120, 88, 86, 57, 43, 41, 39, 29, 23; HRMS (FAB) calcd for $C_{31}H_{40}FN_3O_9+H_1$ 618.2827, found 618.2851.

EXAMPLE 145

(Chart FF, Formula FF-2) 5-{(2S)-2-({(2S)-2-[(tert-butoxycarbonyl)amino]-3-phenylpropanoyl}amino)-3-oxo-3-[(4-phenylbutyl)amino]propyl}-2-(carboxymethoxy)benzoic Acid To a solution of X-5 (100 mg, 0.18 mmol) in dichloromethane (500 uL) was added 1-hydroxybenzotriazole (31 mg, 0.23 mmol) in N,N-dimethylformamide (100 uL) and 4-phenylbutylamine (46 uL, 0.29 mmol). The mixture was cooled in an ice bath and 1-(3-dimethylaminopropyl)-3-ethylcarbodiimide hydrochloride (44 mg, 0.23 mmol) in dichloromethane (2 mL) was added. The mixture was stirred in room temperature for 3 h. The reaction mixture was applied on a small silica gel column (5 mL) packed in dichloromethane and the amide FF-1 was eluted using a stepwise gradient of dichloromethane-acetonitrile. The amide was then dissolved in tetrahydrofuran-methanol (3 mL, 2:1) and aqueous sodium hydroxide (1.5 mL, 2%) was added. The mixture was stirred at room temperature for 6 h. Acetic acid (40 uL) was added and the mixture was concentrated. The material was purified by reversed phase HPLC (Vydac C-18 column) using a water-acetonitrile gradient and lyophilized to give FF-2 (34 mg) as a white solid. $^1$H-NMR (400 MHz, CD$_3$OD) δ 7.76 (s, 1H), 7.38 (d, J=8.5 Hz, 1H), 7.26–7.11 (m, 10H), 6.98 (d, J=8.5 Hz, 1H), 4.76 (s, 2H), 4.50 (t, J=6.9 Hz, 1H), 4.23 (dd, J=5.2 Hz, J=9.3 Hz, 1H), 3.21–2.72 (m, 6H), 2.58 (t, J=7.5 Hz, 2H), 1.54 (m, 2H), 1.42 (m 2H), 1.34 (s, 9H); IR (KBr) 3296, 2925, 1738, 1687, 1643 cm$^{-1}$; HRMS m/z 661.2987 (calc. of monoisotopic mass for $C_{36}H_{43}N_3O_9$ gives 661.2999).

EXAMPLE 146

(Chart GG, Formula GG-7) 2-[4-{(2S)-2-(benzoylamino)-3-oxo-3-[(4-phenylbutyl)amino]-propyl}-2-(2H-1,2,3,4-tetrazol-5-yl)phenoxy]acetic Acid PREPARATION OF GG-2: To stirring solution of GG-1 (0.25 g, 0.61 mmol) in CH$_2$Cl$_2$ (4 mL) was added 1-(3-dimethylaminopropyl)-3-ethylcarbodiimide hydrochloride (EDC, 0.13 g, 0.67 mmol) and 4-phenylbutylamine (107 μL, 0.67 mmol) at 0° C. The mixture was stirred at ambient temperature over night, and then extracted with 1 M aqueous HCl (2×2 mL) and brine (4 mL). The organic layer was dried (Na$_2$SO$_4$) and concentrated. The crude material was purified by flash chromatography (SiO$_2$, EtOAc/iso-hexane 1:1) which furnished 0.28 g (85%) of GG-2 as a colorless oil. $^1$H NMR 500 Mz (CDCl$_3$) δ 1.41 (s, 9H), 1.43 (m, 2H), 1.54 (m, 2H), 2.59 (dd, 2H), 2.92 (m, 2H), 3.18 (m, 2H), 4.18 (m, 1H), 5.07 (br s, 1H), 5.81 (br s, 1H), 6.85 (d, 1H, J=8,1 Hz), 7.05 (dd, 1H, J=8.1, 1.6 Hz), 7.13–7.49 (m, 6H); $^{13}$C NMR (CDCl$_3$) δ 28.3, 28.4, 29.0, 35.4, 37.3, 39.4, 40.5, 56.1, 65.3, 80.4, 85.4, 115.1, 125.8, 128.3, 128.4, 131.0, 138.9, 141.9, 154.2, 155.4, 170.9. IR 3312, 3010, 2932, 1660, 1500, 1367 cm$^{-1}$. MS (ESI) 537 (M–H). HRMS (EI) calcd for $C_{24}H_{31}IN_2O_4$ 538.1329, found 538.1315.

PREPARATION OF GG-3: To a solution of GG-2 (7.0 g, 13 mmol) in THF (50 mL) was added zinc cyanide (1.83 g, 15.6 mmol), Pd(PPh$_3$)$_4$ (0.75 g, 0.65 mmol) and copper(I) iodide (0.25 g, 1.30 mmol). The mixture was refluxed (75° C.) over night, under nitrogen atmosphere. The reaction mixture was cooled to ambient temperature, diluted with EtOAc and filtered through a pad of celite. The filtrate was concentrated and purified by flash chromatography (SiO$_2$, gradient: EtOAc/iso-hexan 1:3 to EtOAc/iso-hexane 1:1) which furnished 1.40 g of a mixture of starting material and product, and 2.51 g of GG-3 (44%) as a white solid. $^1$H NMR 400 MHz (MeOH) δ 1.37 (s, 9H), 1.46 (m, 2H), 1.57 (m, 2H), 2.60 (m, 2H), 2.74 (dd, 1H, J=8.8, 13.8), 2.96 (dd, 1H, J=6.3, 13.8), 3.12 and 3.18 (m, 2H), 4.16 (m, 1H), 6.87 (d, 1H, J=8.5), 7.11–7.36 (m, 7H); $^{13}$C NMR (MeOH) δ 28.6, 29.9, 30.94, 36.4, 38.2, 40.2, 40.8, 57.3, 80.7, 100.5, 117.1, 117.9, 126.7, 129.3, 129.4, 130.2, 134.9, 136.8, 143.5, 157.5, 160.4, 173.7. MS 436 (M–H).

PREPARATION OF GG-4: To a solution of GG-3 (2.51 g, 5.74 mmol) in acetone (30 mL) was added methyl bromoacetate (1.09 mL, 11.47 mmol) and grounded K$_2$CO$_3$ (1.59 g, 11.47). The mixture was stirred at 50° C. over night and then cooled to ambient temperature. Water (20 mL) was added and the mixture was extracted with EtOAc (2×20 mL), the organic layer was dried (Na$_2$SO$_4$) and concentrated. The crude material was purified by flash chromatography (SiO$_2$, EtOAc/iso-hexane 1:1) which furnished 2.21 g (76%) of GG-4 as a white solid. Mp 94–96° C. $^1$H NMR 500 MHz (CDCl$_3$) δ 1.40 (s, 9H), 1.46 (m, 2H), 1.58 (m, 2H), 2.61 (m, 2H), 2.95 (dd, 1H, J=6.9, 14.1), 3.05 (dd, 1H, J=6.9, 14.1), 3.22 (m, 2H), 3.79 (s, 3H), 4.21 (m, 1H), 4.71 (s, 2H), 5.01 (br s, 1H), 5.96 (br m, 1H), 6.73 (d, 1H, J=8.5), 7.14–7.28 (m, 5H), 7.35 (dd, 1H, J=8.5, 2.2), 7.42 (d, 1H, J=2.2); $^{13}$C NMR (CDCl$_3$) δ 28.2, 28.4, 29.0, 29.8, 35.3, 35.5, 37.1, 39.4, 40.5, 52.4, 55.6, 65.7, 80.5, 102.7, 112.5, 115.8, 125.8, 128.4, 130.9, 134.5, 135.2, 142.1, 158.4, 168.2, 170.4. IR 3338, 2932, 2863, 2224 (CN signal), 1754, 1681, 1646. MS (ESI) 508 (M–H). Anal. Calcd for $C_{28}H_{35}N_3O_6$: C, 65.99; H, 6.92; N, 8.25. Found: C, 66.9; H, 7.0; N, 8.2.

PREPARATION OF GG-5: Trifluoroacetic acid (2.1 mL) was carefully added to a stirring solution of GG-4 (0.93 g, 1.82 mmol) in CH$_2$Cl$_2$ (17 mL) at 0° C. The mixture was stirred for 3 h allowing the solution to warm to ambient temperature. The volatiles were removed by evaporation in vacuo, and the residue was partitioned between EtOAc (15 mL) and saturated aqueous NaHCO$_3$ (2×10 mL). The organic layer was dried (Na$_2$SO$_4$) and concentrated to give 0.90 g (>100%) of the crude amine as a yellowish oil. The amine was dissolved in CH$_2$Cl$_2$ (15 mL) and cooled with ice. Bensoic acid (0.22 g, 1.82 mmol), 1-hydroxybenzotriazole (0.25 g, 1.82 mmol) and 1-(3-dimethylaminopropyl)-3-ethylcarbodiimide hydrochloride (EDC, 0.35 g, 1.82 mmol) was added to the solution, which was then stirred at room temperature over night. The reaction mixture was diluted with CH$_2$Cl$_2$ (10 mL) and washed with saturated aqueous NaHCO$_3$ (10 mL) and brine (10 mL). The organic layer was dried (Na$_2$SO$_4$) and concentrated. The residue was purified by column chromatography (SiO$_2$, EtOAc) which gave 0.65 g (69%) of GG-5 as a white solid. Mp=125–128° C. $^1$H NMR 500 MHz(CDCl$_3$) δ 1.43 (m, 2H), 1.54 (m, 2H), 2.55 (t, 2H, J=7.2, 15.1 Hz), 3.13 (m, 3H), 3.21 (m, 1H), 3.77 (s, 3H), 4.68 (s, 2H), 4.86 (m, 1H), 6.48 (br t, 1H), 6.71 (d, 1H, J=8.8 Hz), 7.10 (d, 3H), 7.15 (m, 1H), 7.24 (m, 2H), 7.39 (m, 3H), 7.49 (m, 1H), 7.71 (m, 2H); $^{13}$C NMR (CDCl3) δ 28.4, 28.9, 35.3, 37.4, 39.4, 52.4, 54.7, 65.6, 102.6, 112.5, 115.8, 125.8, 127.0, 128.3, 128.7, 130.8, 132.0, 133.4, 134.7, 135.2, 141.9, 158.5, 167.4, 168.1, 170.4. IR 3278, 2932, 2855, 2224 (CN signal), 1750, 1630, 1500. MS (ESI) 512 (M−H). Anal. Calcd for $C_{30}H_{31}N_3O_5$: C, 70.16; H, 6.08; N, 8.18. Found: C, 70.3; H, 6.1; N, 8.2.

PREPARATION OF GG-6: To a suspension of GG-5 (0.21 g, 0.42 mmol) in toluene (4 mL) in a Heck vial was added trimethylsilyl azide (165 μL, 1.25 mmol) and dibutyltin oxide (10.3 mg, 0.042 mmol). The flask was flushed with nitrogen, tightly sealed, and stirred at 95° C. over night. Some more trimethylsilyl azide (3 eq.) and dibutyltin oxide (0.1 eq.) was added two times and the mixture was continuously stirred at 95° C. After 48 h the reaction mixture was cooled to ambient temperature, and the volatiles were evaporated in vacuo. The residue was partitioned between EtOAc (5 mL) and 1 M aqueous HCl (3 mL). The organic layer was washed with brine (3 mL), dried ($Na_2SO_4$), and concentrated. The material was purified by flash chromatography ($SiO_2$, gradient system: EtOAc/iso-hexane 1:1 to 3:1) which furnished 49 mg (21%) of GG-6 as a white solid. Mp=183–186° C. $^1$H NMR 500 MHz (MeOH) δ 1.46 (m, 2H), 1.53 (m, 2H), 2.53 (t, 2H, J=7.2, 14.8), 3.07–3.16 (m, 2H), 3.23 (m, 2H), 3.79 (s, 3H), 4.80 (m, 1H, hidden behind solvent peak), 4.93 (s, 2H), 7.06 (d, 1H), 7.11 (m, 3H), 7.19 (m, 2H), 7.40 (m, 2H), 7.45–7.51 (m, 2H), 7.75 (m, 2H), 8.18 (d, 1H); $^{13}$C NMR (MeOH) δ 29.7, 29.9, 36.3, 38.2, 40.2, 53.0, 56.7, 66.8, 114.3, 115.5, 126.7, 128.5, 129.3, 129.4, 129.5, 131.7, 132.8, 135.0, 135.2, 143.5, 153.3, 155.6, 170.1, 171.5, 173.2. IR 3286, 2924, 2855, 1742, 1634, 1500. MS (ESI) 555 (M−H). Anal. Calcd for $C_{30}H_{32}N_6O_5$: C, 64.74; H, 5.79; N, 15.10. Found: C, 64.8; H, 5.8; N, 15.1.

PREPARATION OF GG-7: To a solution of GG-6 (33 mg, 0.060 mmol) in THF (0.8 mL) was added 2.5 M aqueous LiOH (72 μL, 0.18 mmol). The mixture was stirred at room temperature for 4 h, and then quenched with 1 M aqueous HCl. The mixture was diluted with EtOAc (3 mL). Some precipitate was formed which was filtered off by a glass funnel. The filtrate was washed with brine (3 mL) and the organic layer was dried ($Na_2SO_4$), and concentrated in vacuo, which furnished a white solid. This material was combined with the precipitate, which totally gave 28 mg (84%) of GG-7 as a white solid. Mp=223–225° C. $^1$H NMR 500 MHz (MeOH) δ 1.44 (m, 2H), 1.53 (m, 2H), 2.53 (t, 2H, J=7.5, 15.3 Hz), 3.08–3.17 (m, 2H), 3.21–3.26 (m, 2H), 4.79 (m, 1H, partly hidden behind solvent peak), 4.89 (s, 2H), 7.09 (m, 4H), 7.19 (m, 2H), 7.40 (m, 2H), 7.49 (m, 2H), 7.76 (m, 2H), 8.20 (d, 1H); $^{13}$C NMR (MeOH) δ 29.7, 29.9, 36.3, 38.2, 40.2, 56.7, 67.0, 114.1, 114.8, 126.7, 128.5, 129.3, 129.5, 131.5, 132.8, 133.0, 135.2, 135.3, 143.5, 153.1, 155.8, 170.1, 173.1, 173.2. IR 3286, 3062, 2924, 1655, 1630, 1539, 1496, 1242. MS (ESI) 541 (M−H). Anal. Calcd for $C_{29}H_{30}N_6O_5 \cdot \frac{1}{4}H_2O$: C, 62.13; H, 5.75; N, 14.99. Found: C, 62.4; H, 5.4; N, 14.8.

EXAMPLE 147

(Chart HH, Formula HH-4) 2-[4-{(2S)-2-(3-furoylamino)-3-oxo-3-[(4-phenylbutyl)amino]-propyl}-2-(2H-1,2,3,4-tetrazol-5-yl)phenoxy]acetic Acid PREPARATION OF HH-2: Trifluoroacetic acid (1.9 mL) was carefully added to a stirring solution of GG-4 (0.85 g, 1.66 mmol) in $CH_2Cl_2$ (10 mL) at 0° C. The mixture was stirred for 3 h allowing the solution to warm to ambient temperature. The volatiles were removed by evaporation in vacuo, and the residue was partitioned between EtOAc (10 mL) and saturated aqueous $NaHCO_3$ (2×5 mL). The organic layer was dried ($Na_2SO_4$) and concentrated to give 0.71 g (>100%) of the crude amine as a yellowish oil. The amine was dissolved in $CH_2Cl_2$ (8 mL) and cooled with ice. 3-Furoic acid (0.21 g, 1.83 mmol), 1-hydroxybenzotriazole (0.25 g, 1.83 mmol) and 1-(3-dimethylaminopropyl)-3-ethylcarbodiimide hydrochloride (EDC, 0.35 g, 1.82 mmol) was added to the solution, which was then stirred at room temperature over night. The reaction mixture was diluted with $CH_2Cl_2$ (5 mL) and washed with saturated aqueous $NaHCO_3$ (5 mL) and brine (5 mL). The organic layer was dried ($Na_2SO_4$) and concentrated. The residue was purified by column chromatography ($SiO_2$, EtOAc/iso-hexane 1:1 to 3:1), which gave 0.51 g (62%) of HH-2 as a colorless oil. $^1$H NMR 500 MHz (CDCl$_3$) δ 1.44 (m, 2H), 1.56 (m, 2H), 2.57 (t, 2H, J=7.3, 15.1 Hz), 3.06 (t, 2H, partly hidden behind multiplet), 3.13 (m, 1H), 3.24 (m, 1H), 3.76 (s, 3H), 4.68 (s, 2H), 4.82 (m, 1H), 6.61 (d, 1H), 6.72 (m, 1H), 7.11–7.17 (m, 3H), 7.24 (t, 2H), 7.34–7.38 (m, 2H), 7.48 (d, 1H), 7.91 (d, 1H); 13C NMR (CDCl$_3$) δ 28.5, 28.9, 35.3, 37.1, 39.5, 52.4, 54.6, 65.6, 102.6, 108.3, 112.5, 115.8, 121.8, 125.8, 128.3, 130.9, 134.7, 135.2, 141.9, 143.8, 145.3, 158.4, 162.8, 168.1, 171.0. MS (ESI) 502 (M−H). Anal. Calcd for $C_{28}H_{29}N_3O_6$: C, 66.79; H, 5.80; N, 8.34. Found: C, 66.6; H, 5.9; N, 8.3.

PREPARATION OF HH-3: To a suspension of HH-2 (0.44 g, 0.88 mmol) in toluene (5 mL) in a Heck vial was added trimethylsilyl azide (349 μL, 2.64 mmol) and dibutyltin oxide (22 mg, 0.088 mmol). The flask was flushed with nitrogen, tightly sealed, and stirred at 95° C. over night. Some more trimethylsilyl azide (3 eq.) and dibutyltin oxide (0.1 eq.) was added two times and the mixture was continuously stirred at 95° C. After 48 h the reaction mixture was cooled to ambient temperature, and the volatiles were evaporated in vacuo. The residue was partitioned between EtOAc (5 mL) and 1 M aqueous HCl (3 mL). The organic layer was washed with brine (3 mL), dried ($Na_2SO_4$), and concentrated. The material was purified by flash chromatography ($SiO_2$, gradient system: EtOAc/iso-hexane 1:1 to 3:1) which furnished 52 mg (11%) of HH-3 as a white solid. Mp=152–154° C. $^1$H NMR 500 MHz (MeOH) δ 1.44 (m, 2H), 1.53 (m, 2H), 2.53 (t, 2H), 3.05–3.25 (m, 4H), 3.81 (s, 3H), 4.78 (m, 1H), 4.91 (s, 2H), 6.79 (s, 1H), 7.05–7.23 (m, 6H), 7.48 (m, 2H), 8.07 (s, 1H), 8.21 (s, 1H); $^{13}$C NMR (MeOH) δ 29.7, 29.8, 36.3, 38.1, 40.2, 53.0, 56.2, 66.7, 109.7, 113.9, 114.4, 123.2, 126.7, 129.2, 129.3, 131.5, 132.9, 135.1, 143.4, 145.1, 146.8, 152.9, 155.5, 164.9, 171.4, 173.1. IR 3140, 2933, 2860, 2367, 1736, 1653, 1617, 1493. MS (ESI) 545 (M−H). Anal. Calcd for $C_{28}H_{30}N_6O_6$: C, 61.53; H, 5.53; N, 15.38. Found: C, 61.4; H, 5.8; N, 15.4.

PREPARATION OF HH-4: To a solution of HH-3 (40 mg, 0.073 mmol) in THF (0.8 mL) was added 2.5 M aqueous LiOH (88 μL, 0.22 mmol). The mixture was stirred at room temperature for 4 h, and then washed with EtOAc (2 mL). The aqueous layer was acidified with 1 M aqueous HCl and extracted with EtOAc (2×3 mL). Some precipitate was formed which was filtered off by a glass funnel. The filtrate was washed with brine (3 mL) and the organic layer was dried ($Na_2SO_4$), and concentrated in vacuo, which furnished a white solid. This material was combined with the precipitate, which totally gave 14 mg (37%) of HH-4 as a white solid. Mp=230–233° C. $^1$H NMR 500 MHz (MeOH) δ 1.42 (m, 2H), 1.50 (m, 2H), 2.51 (t, 2H, J=7.5, 15.1 Hz), 3.07–3.13 (m, 2H), 3.19–3.23 (m, 2H), 4.75 (m, 1H), 4.91 (s, 2H), 6.78 (d, 1H, J=2.5), 7.07–7.20 (m, 2H), 7.47 (dd, 1H), 7.53 (t, 1H), 8.06 (s, 1H), 8.17 (d, 1H, J=2.5); $^{13}$C NMR δ 29.7, 29.8, 36.3, 38.1, 40.2, 56.2, 66.9, 109.7, 111.0, 114.0, 114.7, 123.2, 126.7, 129.3, 129.4, 131.4, 132.9, 135.2, 143.5, 145.2, 146.8, 155.7, 173.0, 173.1. IR 3300, 2940, 2867, 1637, 1543, 1497, 1173. MS (ESI) 531 (M–H). Anal. Calcd for $C_{27}H_{28}N_6O_6 \cdot \frac{1}{4} H_2O$: C, 60.38; H, 5.25; N, 15.65. Found: C, 60.2; H, 5.2; N, 15.4.

EXAMPLE 148

(Chart II, Formula 11–3) 5-[(2S)-2-({(2S)-2-[(tert-butoxycarbonyl)amino]-3-phenylpropanoyl}amino)-3-hydroxypropyl]-2-(carboxymethoxy)benzoic Acid PREPARATION OF II-2: Methyl 5-[(2S)-2-({(2S)-2-[(tert-butoxycarbonyl)amino]-3-phenylpropanoyl}amino)-3-hydroxypropyl]-2-(2-methoxy-2-oxoethoxy)benzoate: To a solution of II-1 (1.24 g, 2.24 mmol) in dry THF (10 mL) is added 1,1'-carbonyldiimidazole (CDI, 0.54 g, 3.35 mmol). The solution is stirred at room temperature over night under nitrogen atmosphere. The reaction mixture is cooled with ice and a solution of $NaBH_4$ (0.21 g, 5.59 mmol) in $H_2O$ (5 mL) is slowly added. After addition is complete, the mixture is stirred at room temperature for 10 min. The mixture is quenched with 10% aqueous HCl, and extracted with EtOAc. The organic layer is dried ($Na_2SO_4$) and concentrated. The residue is purified by flash chromatography ($SiO_2$, EtOAc) with furnished 160 mg (13%) of II-2 as a sticky foam. $^1H$ NMR 400 MHz ($CDCl_3$) δ 1.38, 2.49, 2.68, 2.73, 3.00, 3.42, 3.57, 3.78, 3.87, 4.05, 4.27, 4.68, 6.80, 7.13–7.30, 7.61; $^{13}C$ NMR ($CDCl_3$) δ 28.2, 33.2, 38.5, 52.1, 56.2, 58.2, 60.9, 62.8, 66.7, 71.9, 80.6, 114.6, 121.0, 126.9, 128.6, 128.9, 131.1, 131.5, 132.5, 134.1, 136.6, 156.2, 166.2, 169.0, 171.6. MS (ESI) 543 (M–H). Anal. Calcd for $C_{28}H_{36}N_2O_9$: C, 61.75; H, 6.66; N, 5.14. Found; C, 61.5; H, 6.6; N, 5.3.

PREPARATION OF II-3: 5-[(2S)-2-({(2S)-2-[(tert-butoxycarbonyl)amino]-3-phenylpropanoyl}amino)-3-hydroxypropyl]-2-(carboxymethoxy)benzoic acid: To a solution of II-2 (36 mg, 0.066 mmol) in THF (1.5 mL) was added a 2.5 M aqueous solution of LiOH (106 μL, 0.26 mmol). The mixture was stirred at room temperature for 4 h, and then acidified with 10% aqueous HCl and extracted with EtOAc. The organic layer was dried ($Na_2SO_4$) and concentrated to afford 33 mg (96%) of II-3 as a white solid. Mp=168.8–172.3° C. $^1H$ NMR 400 MHz (MeOH) δ 1.35, 2.31, 2.64–2.97, 3.52, 4.06, 4.22, 4.78, 7.00, 7.11–7.27, 7.43, 7.77; $^{13}C$ NMR (MeOH) δ 20.7, 28.6, 30.9, 36.8, 39.5, 57.3, 67.5, 80.6, 111.0115.6, 121.3, 127.6, 129.3, 130.3, 133.6, 134.0, 136.1, 138.6, 157.5, 169.1, 172.2, 174.1. MS (ESI) 516 (M–H). Anal. Calcd for $C_{26}H_{32}N_2O_9 \cdot H_2O$: C, 59,42; H, 6.33; N, 5.33. Found; C, 59.4; H, 6.3; N, 5.35.4.

EXAMPLE 149

(Chart JJ, Formula JJ-5) 2-[4-[(2S)-2-({(2S)-2-[(Tert-butoxycarbonyl)amino]-3-phenylpropanoyl}amino)-3-oxo-3-(pentylamino)propyl]-2-(3-hydroxy-5-isoxazolyl)phenoxy]acetic Acid PREPARATION OF JJ-2: Methyl 2-{4-[(2S)-2-[(tert-butoxycarbonyl)amino]-3-oxo-3-(pentylamino)propyl]-2-iodophenoxy}acetate: Prepared from JJ-1 (2.24 g, 4.70 mmol) by the general method as described for GG-4, which afforded 2.29 g (89%) of the title compound as a white solid. $^1H$ NMR 400 MHz ($CDCl_3$) δ 0.88 (t, 3H, J=7.1, 14.4), 1.20 (m, 2H), 1.29 (m, 2H), 1.38 (m, 2H), 1.43 (s, 9H), 2.96 (m, 2H), 3.17 (m, 2H), 3.81 (s, 3H), 4.19 (m, 1H), 4.67 (s, 2H), 5.06 (br s, 1H), 5.79 (br s, 1H), 6.63 (d, 1H, J=8.4), 7.12 (dd, 1H, J=2.1, 8.4), 7.64 (d, 1H, J=2.1); $^{13}C$ NMR ($CDCl_3$) δ 14.0, 22.3, 28.3, 28.9, 29.1, 37.2, 39.5, 52.4, 56.0, 66.3, 80.3, 86.6, 112.3, 130.4, 132.3, 140.5, 155.4, 155.7, 168.8, 170.6. MS (ESI) 544 (M–H). Anal. Calcd for $C_{22}H_{33}N_2O_6I$: C, 48.18; H, 6.06. Found: C, 48.3; H, 6.2.

PREPARATION OF JJ-3: Ethyl 3-[5-[(2S)-2-[(tert-butoxycarbonyl)amino]-3-oxo-3-(pentylamino)propyl]-2-(2-methoxy-2-oxoethoxy)phenyl]-2-propynoate: Ethyl propiolate (1.94 mL, 19.2 mmol) is added to a suspension of copper(I)oxide (0.61 g, 6.39 mmol) in anhydrous DMF (3 mL) under nitrogen atmosphere. A solution of JJ-2 (4.38 g, 7,99 mmol) in DMF (40 mL) is added. The reaction flask is flushed with nitrogen, tightly sealed, and stirred at 110° C. for 16 h. The reaction mixture is filtered through a short pad of $SiO_2$ and washed with EtOAc. The organic layer is washed with 1 M aqueous HCl (20 mL), brine (20 mL), saturated aqueous $NaHCO_3$ (20 mL), dried ($Na_2SO_4$) and concentrated. The residue is purified by column chromatography ($SiO_4$, EtOAc/hexane 1:2 to 1:1) which afforded 1.93 g (47%) of JJ-3 as a white solid. Mp=133.9–135.1° C. $^1H$ NMR 400 MHz ($CDCl_3$) δ 0.87 (t, 3H, J=7.1, 14.4), 1.22 (m, 2H), 1.29 (m, 2H), 1.35 (t, 3H, J=7.1), 1.41 (s and m, 11H), 2.97 (app t, 2H, J=6.7, 13.2), 3.17 (m, 2H), 3.80 (s, 3H), 4.21 (m, 1H), 4.29 (q, 2H, J=7.1), 4.72 (s, 2H), 5.06 (br s, 1H), 5.91 (m, 1H), 6.70 (d, 1H, J=8.6), 7.22 (dd, 1H, J=2.1, 8.6), 7.38 (d, 1H, J=2.1); $^{13}C$ NMR ($CDCl_3$) δ 13.9, 14.1, 22.2, 28.2, 28.9, 29.1, 37.4, 39.5, 52.3, 55.9, 62.0, 65.9, 80.3, 82.1, 85.0, 109.9, 112.6, 130.3, 133.0, 135.7, 154.0, 155.3, 158.8, 168.7, 170.6. MS (ESI) 517 (M–H). Anal. Calcd for $C_{27}H_{38}N_2O_8 \cdot H_2O$: C, 60.43; H, 7.33; N, 5.22. Found: C, 60.7; H, 7.4; N, 5.3.

PREPARATION OF JJ-4: Ethyl 3-[5-[(2S)-2-({(2S)-2-[(tert-butoxycarbonyl)amino]-3-phenylpropanoyl}amino)-3-oxo-3-(pentylamino)propyl]-2-(2-methoxy-2-oxoethoxy)phenyl]-2-propynoate: Prepared from JJ-3 (1.01 g, 1.95 mmol) by the general method as described for GG-5, which afforded 1.09 g (84%) of the title compound as a white solid. Mp=121.8–123.1° C. $^1H$ NMR 400 MHz ($CDCl_3$) δ 0.87 (t, 3H, J=7.1, 14.4), 1.14–1.41 (m, 6H), 1.34 (t, 3H, J=7.1), 1.35 (s, 9H), 2.81 (m, 1H), 3.01–3.09 (m, 4H), 3.15 (m, 1H), 3.77 (s, 3H), 4.27 (m, 1H), 4.29 (q, 2H, J=7.1), 4.56 (m, 1H), 4.69 (s, 2H), 4.97 (d, 1H, J=6.3), 6.17 (br m, 1H), 6.41 (br m, 1H), 6.66 (d, 1H, J=8.6), 7.10–7.19 (m, 4H), 7.25–7.34 (m, 3H); $^{13}C$ NMR ($CDCl_3$) δ 13.9, 14.1, 22.2, 28.1, 28.9, 36.4, 37.7, 39.6, 52.2, 53.6, 56.1, 62.0, 65.8, 80.6, 82.0, 85.0, 109.8, 112.6, 127.2, 128.8, 129.2, 129.9, 133.1, 135.5, 136.0, 153.9, 158.8, 168.6, 169.6, 170.9. MS (ESI) 664 (M–H). Anal. Calcd for $C_{36}H_{47}N_3O_9$: C, 64.95; H, 7.12; N, 6.31. Found: C, 64.9; H, 7.0; N, 6.3.

PREPARATION OF JJ-5: 2-[4-[(2S)-2-({(2S)-2-[(Tert-butoxycarbonyl)amino]-3-phenylpropanoyl}amino)-3-oxo-3-(pentylamino)propyl]-2-(3-hydroxy-5-isoxazolyl)phenoxy]acetic acid: 2.5 M aqueous NaOH (670 μL, 1.68 mmol) is added to hydroxylamine hydrochloride (61 mg, 0.87 mmol). This mixture is added to a solution of JJ-4 (446 mg, 0.67 mmol) in ethanol/THF (1 mL: 2mL). The clear yellow solution is stirred over night at ambient temperature, and then acidified with 1 M aqueous HCl. The reaction mixture is extracted with EtOAc (2×4 mL), and the organic layer is washed with brine (4 mL), dried ($Na_2SO_4$) and concentrated which afforded 418 mg of a crude material as a yellowish solid. This material is a mixture of the target compound and the corresponding hydroxamic acid analogs. Separation by reversed phase HPLC furnished 82 mg (19%) of pure title compound JJ-5 as a white solid. Melting point: sublimentet above 260° C. Accurate mass: Calculated 638.2952; Found 638.2957. MS (ESI) 637 (M–H). Anal. Calcd for $C_{33}H_{42}N_4O_9 \cdot H_2O$: C, 60.35; H, 6.75; N, 8.53. Found: C, 60.2; H, 6.6; N, 8.6.

EXAMPLE 150

(Chart KK, Formula KK-6) 2-[4-[(2S)-2-({(2S)-2-[(tert-butoxycarbonyl)amino]-3-phenylpropanoyl}amino)-3-oxo-3-(pentylamino)propyl]-2-(2-hydroxy-3,4-dioxo-1-cyclobuten-1-yl)phenoxy]acetic Acid PREPARATION OF KK-2: (2S)-2-amino-3-(4-hydroxy-3-iodophenyl)-N-pentylpropanamide (KK-1) (8.64 g, 14.30 mmol) was dissolved in $CH_2Cl_2$ and stirred at 0° C. under $N_2$. Then EDC (2.74 g, 14.30 mmol), HOBt (1.93 g, 14.30 mmol) and Boc-L-Phe (3.79 g, 14.30 mmol) were added simultaneously. $Et_3N$ (3.98 mL, 28.6 mmol) was added dropwise. The resulting mixture was stirred overnight. EtOAc (200 mL) was added and the organic layer was washed with 5% aqueous HCl (2×100 mL). The aqueous phases were combined and extracted with EtOAc (100 mL). The combined organic phases were washed with 10% aqueous $NaHCO_3$, (100 mL). Drying ($Na_2SO_4$), filtration and evaporation of volatiles gave an yellowish solid. Column chromatography of the crude product on silica using $CHCl_3$/MeOH (95:5) and then EtOAc/light petroleum (1:1) as eluent gave 3.58 g 43% of a pale white solid: TLC Rf=0.08 ($SiO_2$, $CHCl_3$/MeOH 99:1); Mp 162–164° C. $^1H$ NMR ($CDCl_3$) δ 7.38–7.16 (m, 6H), 6.92–6.87 (m, 1H), 6.84 (d, J=8.16 Hz, 1H), 6.28 (brs, 1H), 6.13 (brs, 1H), 6.0 (brs, 1H) 4.89 (d, J=5.97 Hz, 1H), 4.57–4.50 (m, 1H), 4.29–4.23 (m, 1H), 3.20–2.95 (m, 5H), 2.72–2.62 (m, 1H), 1.45–1.15 (m, 15H), 0.87 (tr, J=7.22 Hz, 3H); $^{13}C$ NMR ($CDCl_3$) δ 170.80, 169.87, 155.73, 154.25, 138.82, 135.92, 131.09, 130.09, 129.24, 128.97, 127.37, 115.19, 85.49, 80.89, 56.19, 53.53, 39.76, 37.59, 36.07, 28.99, 28.95, 28.10, 22.29, 13.94; IR (KBr disc) 1690, 1655 $cm^{-1}$; MS (ESI) m/z 624 (m+H),; Anal. Calcd for $C_{28}H_{38}IN_3O_5 \cdot 0.25 H_2O$: C, 53.17; H, 6.06; N, 6.64; Found: C, 52.95; H, 5.95; N, 6.00.

PREPARATION OF KK-3: A mixture of KK-2 (463 mg 0.742 mmol), methyl bromoacetate (206 μL, 2.23 mmol) and $K_2CO_3$ (308 mg, 2.23 mmol) in $CH_3CN$ (4 mL) was stirred at 40° C. overnight. The reaction mixture was filtered and the solid was washed with $CH_3CN$. The organic phase was concentrated to give a crude solid. The solid was dissolved in $CHCl_3$ and purified by column chromatography on $SiO_2$ using EtOAc/pentane (1:1) as eluent to give 0.446 g (86%) of the product as a white solid: TLC Rf=0.11 ($SiO_2$, $CHCl_3$/MeOH 99:1); Mp 141–142° C. $^1H$ NMR ($CDCl_3$) δ 7.45–7.25 (m, partly obscured by solvent signal, 6H), 7.02 (m, 2H), 7.02 (d,d, J=1.89 and 8.48 Hz, 1H) 6.60 (d, J=8.48 Hz, 1H), 6.24 (brs, 1H), 610 (brs, 1H), 4.83 (m, 1H), 4.64 (s, 2H), 4.57–4.47 (m, 1H), 4.30–4.21 (m, 1H), 3.79 (s, 3H), 3.20–2.95 (m, 5H), 2.78–2.70 (m, 1H), 1.43–1.15 (m, 15H), 0.87 (tr, J=7.22 Hz, 3H); $^{13}C$ NMR ($CDCl_3$) δ 170.74, 169.65, 168.59, 155.90, 140.35, 135.97, 131.82, 130.43, 129.21, 128.97, 128.85, 127.35, 112.44, 86.54, 80.83, 66.34, 56.27, 53.54, 52.28, 39.71, 39.58, 37.65, 36.14, 28.99, 28.95, 28.12, 22.27; IR (KBr disc) 1690, 1645 $cm^{-1}$; MS (ESI) m/z 694 (m–H),; Anal. Calcd for $C_{31}H_{42}IN_3O_7$: C, 53.53; H, 6.09; N, 6.04; Found: C, 53.40; H, 6.15; N, 6.00.

PREPARATION OF KK-4: A mixture of KK-3 (508.0 mg 0.7303 mmol), 3-isopropoxy4-(tri-n-butylstannyl)-3-cyclobutene-1,2-dione (prepared from 3,4-diisopropoxycyclobutenediones using the protocol of Liebeskind, L. S.; Fengl, R. W., *J. Org. Chem.*, 1990, 55, 5359–5364. 313.4 mg, 0.7303 mmol), $Pd_2(dba)_3$ (16.7 mg, 0.0292 mmol), and $AsPh_3$ (35.8 mg, 0.1168 mmol) in degassed DMF was stirred at room temperature. After 5 min, CuI (11.12 mg, 0.058 mmol), and the mixture was stirred at 50° C. for 24 h. Additional $Pd_2(dba)_3$ (16.7 mg, 0.0292 mmol), and $AsPh_3$ (35.8 mg, 0.1168 mmol), CuI (11.12 mg, 0.058 mmol) were added and the reaction was run for another 48 h. The reaction mixture was diluted with EtOH (10 mL) and filtered through celite. The mixture was concentrated and partioned between water and $CHCl_3$. The organic phase was filtered and concentrated. The crude residue was purified by flash chromatography on silica by first using gradient elution ($CHCl_3$→$CHCl_3$/MeOH) and then by using $CHCl_3$+2.5% MeOH. This gave 215 mg (44%) of the product as yellowish solid: TLC Rf=0.1 ($SiO_2$, $CHCl_3$/MeOH 99:1); Mp 175–178° C. $^1H$ NMR ($CDCl_3$) δ 7.74–7.71 (m, 1H) 7.35–7.16 (m., partly obscured by solvent signal, 7H), 6.78 (d, J=8.48 Hz, 1H), 6.57–6.50 (m, 1H), 5.65 (h, J=6.28 Hz, 1H), 5.46 (brs, 1H), 4.68 (d, J=3.77 Hz, 2H), 4.28–4.23 (m, 1H), 3.79 (s, 3H), 3.26–2.86 (m, 7H), 1.49 (d, J=6.28 Hz, 6H), 1.45–1.17 (m, 15H), 0.87 (tr, J=7.22 Hz, 3H); $^{13}C$ NMR ($CDCl_3$) δ 194.23, 193.12, 193.03, 171.91, 171.28, 169.74, 168.33, 154.28, 136.53, 135.15, 130.28, 129.73, 129.24, 128.75, 128.68, 127.01, 117.77, 113.11, 79.44, 65.71, 57.04, 52.26, 39.75, 37.54, 28.91, 28.12, 28.03, 22.90, 22.26, 13.91. not all signals are visible in the $^{13}C$ NMR spectrum; IR (KBr disc) 3291, 1644 $cm^{-1}$; MS (ESI) m/z 694 (M-isopropyl); HPLC: chemical purity 90.6%; Anal. Calcd for $C_{38}H_{49}N_3O_{10} \cdot 1.0 H_2O$: C, 62.88; H, 7.08; N, 5.78; Found: C, 62.85; H, 6.90; N, 5.90.

PREPARATION OF KK-5: KK-4 was dissolved in warm THF (10 mL). 6M aqueous HCl (0.5 mL) was added and the solution was stirred at room temperature 3 days and then at 50° C. for 2 h. The reaction mixture was concentrated to give 1.48 g of a yellow solid. The solid was triturated first with ether then with acetone/water to give 503 mg of a yellow solid. The solid was then purified on a reverse phase preparative HPLC system to give 406 mg (71%) of the pure compound: Mp 210-decomp. $^1H$ NMR (DMSO-d6) δ 15.14 (brs, 1H), 8.75 (d, J=8.48 Hz, 1H), 8.16 (d, J=2.20 Hz, 1H), 8.03 (m, 3H), 7.35–7.13 (m, 5H), 6.97 (d, J=8.48 Hz, 1H), 4.69 (s, 2H), 4.48 (m, 1H), 4.10 (m, 1H), 3.15–2.70 (m, 5H), 1.40–1.10 (m, 5H), 0.83 (tr, J=7.54 Hz, 3H); $^{13}C$ NMR (DMSO-d6) δ 210.87, 196.94, 172.81, 169.68, 169.42, 167.72, 155.16, 151.39, 139.50, 134.79, 131.26, 129.48, 128.40, 127.01, 126.67, 120.82, 111.76, 65.53, 54.39, 53.23, 38.46, 37.31, 36.95, 28.58, 28.53, 21.74, 13.80; MS (ESI) m/z 552 (M+H); HPLC: 97% chemical purity.

PREPARATION OF KK-6: To a stirred solution of KK-5 (386.4 mg, 0.657 mmol), in 1M NaOH (3 mL), dioxane (5 mL) and water (4 mL) was added di-t-butyldicarbonate at 0° C. The reaction mixture was then stirred for 10 h. The mixture was acidified with 2M $KHSO_4$, and the dioxane was evaporated (precipitation of starting material). The reaction mixture was filtered and extracted with EtOAc. The organic phase was dried ($Na_2SO_4$) and concentrated. The purity of the crude residue on a reversed phase HPLC system shows a purity of 64% with no major side products. Ms (ESI) shows the right molecular ion 650 (M–H). The solid was then purified on a reverse phase preparative HPLC system using the same conditions as in the analytical experiment (mobile phase CHCN/aq. 0.1% TFA gradient 10:90→95:5). An analytical sample was then run on the purest fraction (96% purity). Something happens with the product during workup. The worked up fraction seem to be more impure than the crude fraction. The workup consisted of carefully evaporate the organic phase and then lyophilize the product. The product seem to be very sensitive towards TFA.

EXAMPLE 151

(Chart LL, R=pyridine, Formula LL-2) Methyl 2-(2-methoxy-2-oxoethoxy)-5-{(2S)-3-oxo-3-(pentylamino)-2-[(3-pyridinylcarbonyl)amino]propyl}benzoate PREPARATION OF LL-2 (General Procedure A: Amide Coupling): Triethylamine was added dropwise to a stirred solution of LL-1 (200 mg, 0.44 mmol) in dichloromethane (3.3 ml) at 0° C. until neutral. EDC (85 mg, 0.44 mmol), HOBT (60 mg, 0.44 mmol) and nicotinic acid (47 mg, 0.44 mmol) were then added in single portions to the stirred solution again at 0° C. under nitrogen. The mixture was then allowed to warm to room temperature where it was stirred for 3 hr. The yellow mixture was then diluted with EtOAc (20 ml) and the organic solution washed with HCl (2M, 10 ml). The acidic layer was basified with NaOH and extracted with EtOAc (3×10 ml) and the combined organic layers washed with NaHCO$_3$ (1×10 ml), dried (MgSO$_4$) and concentrated under reduced pressure to give a cloudy oil. The crude product was purified by column chromatography on silica gel using petrol:EtOAc:MeOH (4:2:1) as eluent to give a white solid, LL-2 (120 mg), $^1$H NMR (270 MHz, MeOH) δ 8.90 (1H, s), 8.66 (1H, d, J=4.95 Hz), 8.15 (1H, dt, J=2.31, 8.04 Hz), 7.72 (1H, d, J=2.3 1 Hz), 7.51 (1H, dd, J=4.95, 7.92 Hz), 7.41 (1H, dd, J=2.31, 6.27 Hz), 6.93 (1H, d, J=8.58 Hz), 4.75 (2H, s), 4.73 (1H, obscured m), 3.83 (3H, s), 3.74 (3H, s), 3.58–2.97 (4H, m), 1.45–1.20 (6H, m), 0.88 (3H, t, J=6.93 Hz).

EXAMPLE 152

(Chart LL, R=pyridine, Formula LL-3) 5-[(2S)-2-({(2R)-2-[(tert-butoxycarbonyl)amino]-3-phenylpropyl}amino)-3-oxo-3-(pentylamino)propyl]-2-(carboxymethoxy)benzoic Acid Dihydrochloride PREPARATION OF LL-3 (General Procedure B: Ester Hydrolysis): Lithium hydroxide (15 mg, 0.64 mmol) was added to a stirred solution of LL-2 (100 mg, 0.21 mmol) in THF (20 ml) and the mixture stirred at room temperature for 3 hr. The solvent was removed in vacuo and the residue dissolved in water (20 ml) and acidified with HCl (10% aqueous). The solution became cloudy and was extracted with EtOAc (3×10 ml). The combined organic phases were dried (NaSO$_4$) and concentrated under reduced pressure to give a white solid LL-3 (40 mg, 0.09 mmol, 42%) m.p. 168–170° C.; $\lambda_{max}$ (cm$^{-1}$) 3288, 3073, 2931, 1731, 1639, 1545, 1498; $^1$H NMR (500 MHz, DMSO) δ 8.96 (1H, s), 8.80 (1H, d, J=8.17 Hz), 8.71 (1H, br s), 8.16 (1H, d, J=7.85 Hz), 8.08 (1H, t, J=5.65 Hz), 7.70 (1H, d, J=2.20 Hz), 7.5o (1H, dd, J4.71, 7.85 Hz), 7.43 (1H, dd, J2.51, 8.79 Hz), 6.92 (1H, d, J=8.47 Hz), 4.70 (2H, s), 4.64–4.55 (1H, m), 3.12–3.01 (4H, m), 1.44–1.16 (6H, m), 0.85 (3H, t, J=7.22 Hz); $^{13}$C NMR (500 MHz, CD$_3$OD) 172.90, 167.81, 157.65, 152.58, 149.00, 137.36, 136.06, 133.87, 132.10, 115.83, 67.95, 56.76, 40.51, 37.95, 30.89, 30.02, 29.80, 23.25, 14.30; MS (ESI) 456.2 (M−H$^+$), 458.2 (M+H$^+$).

EXAMPLE 153

(Chart LL, R=2-methoxybenzyl, Formula LL-5) 2-(carboxymethoxy)-5-[(2R)-2-{[2-(2-methoxyphenyl)acetyl]amino}-3-oxo-3-(pentylamino)propyl]benzoic Acid (a) PREPARATION OF LL-4: Methyl 2-(2-methoxy-2-oxoethoxy)-5-[(2R)-2-{[2-(2-methoxyphenyl)acetyl]amino}-3-oxo-3-(pentylamino)propyl]benzoate: By general procedure A, a solution of LL-1 (500 mg, 1.2 mmol) in dichloromethane (8ml) was treated with EDC (230 mg, 1.2 mmol), HOBT (162 mg, 1.2 mmol), triethylamine (243 mg, 2.4 mmol) 2-(2-methoxyphenyl)acetic acid (199 mg, 1.2 mmol) at room temperature overnight. The mixture was then diluted with EtOAc (20 ml) and the organic layer washed with HCl (5%, 1×5 ml). The aqueous layer was then extracted with EtOAc (3×10 ml) and the combined organic layers washed with NaHCO$_3$ (sat. aq.), dried (MgSO$_4$) and concentrated to give a yellow oil. The crude product was purified by column chromatography using dichoromethane-:MeOH (20:1) as eluent to give a white solid, LL-4 (320 mg, 0.6 mmol, 50%) m.p. 145–6; $\lambda_{max}$ (cm$^{-1}$). 3282, 2954, 1755, 1731, 1642, 1547, 1497, 1437; $^1$H NMR (500 MHz, CD$_3$OD) δ 7.57 (1H, d, J=2.2 Hz), 7.24–7.19 (2H, m), 7.08 (1H, d, J7.22 Hz), 6.92–6.84 (3H, m), 4.75 (2H, s), 4.52 (1H, m), 3.85 (3H, s), 3.77 (3H, s), 3.74 (3H, s), 3.52 (1H, d (AB), J=14.76 Hz), 3.45 (1H, d (AB), J=14.76 Hz), 3.16–3.03 (2H, m), 3.00 (1H, dd, J6.6, 14.3 Hz), 2.86 (1H, dd, J7.84, 13.82 Hz), 1–43–1.17 (6H, m), 0.88 (3H, t, J7.22 Hz); $^3$C NMR (500 MHz, CD$_3$OD) δ 173.83, 172.80, 170.84, 168.04, 158.75, 157.76, 135.45, 133.36, 131.87, 131.36, 129.72, 124.75, 121.87, 121.76, 115.38, 111.80, 67.09, 55.96, 55.74, 52.60, 52.52, 40.44, 38.69, 38.17, 30.11, 29.93, 23.33, 14.29; MS (ESI) 529.1 (M+H$^+$); Anal. Calculated for C28H36N2O8: C, 63.6; H, 6.9; N, 5.3; Found: C, 63.6; H, 6.9; N, 5.3%.

(b) PREPARATION OF LL-5: By general procedure B, a solution of LL-4 (280 mg, 0.53 mmol) in THF (5 ml) and water (5 ml) was treated with lithium hydroxide (100 mg, 1.1 mmol) at room temperature overnight. The crude product was recrystallized from acetonitrile to give a white crystalline solid, LL-5 (130 mg, 0.26 mmol, 50%) m.p. 146–8° C.; $\lambda_{max}$(cm$^{-1}$). 3296, 2929, 1736, 1643, 1547, 1495; $^1$H NMR (500 MHz, CD$_3$OD) δ 7.71 (1H, br d, J=6.2 Hz), 7.23 (2H, m), 7.09 (1H, d, J=7.04 Hz), 6.93–6.86 (3H, m), 4.79 (2H, s), 4.55 (1H, br t, J=7.45 Hz), 3.75 (3H, s), 3.55 (1H, d (AB), J=14.48 Hz), 3.45 (1H, d (AB), J=15.3 Hz), 3.18–3.06 (2H, m), 3.02 (1H, dd, J=6.20, 14.07 Hz), 2.87 (1H, dd, J=7.45, 13.66 Hz), 1.44–1.20 (6H, m), 0.88 (3H, t, J=7.45 Hz); $^1$H NMR (500 MHz, CD$_3$OD) δ 172.84, 172.75, 172.20, 168.96, 158.71, 157.73, 135.99, 134.03, 131.88, 131.84, 129.77, 124.70, 121.79, 121.30, 115.50, 111.84, 67.41, 55.98, 55.67, 40.45, 38.70, 38.19, 30.11, 29.94, 23.32, 14.29; MS (ESI) 499.0 (M−H$^+$); Anal. Calculated for C$_{26}$H$_{32}$N$_2$O$_8$: C, 62.4; H, 6.4; N, 5.6; Found: C, 62.2; H, 6.4; N, 5.6%.

EXAMPLE 154

Two-dimensional library of 5-substituted-2-carbomethoxybenzoic Acids

Scheme 1

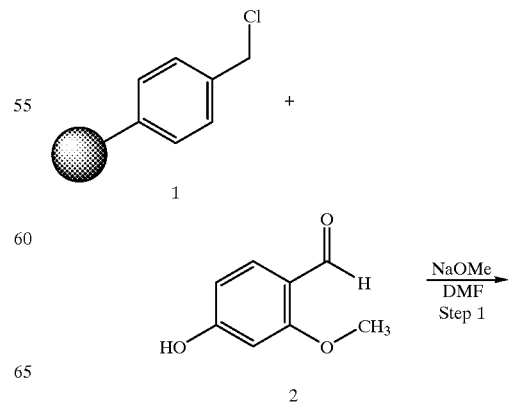

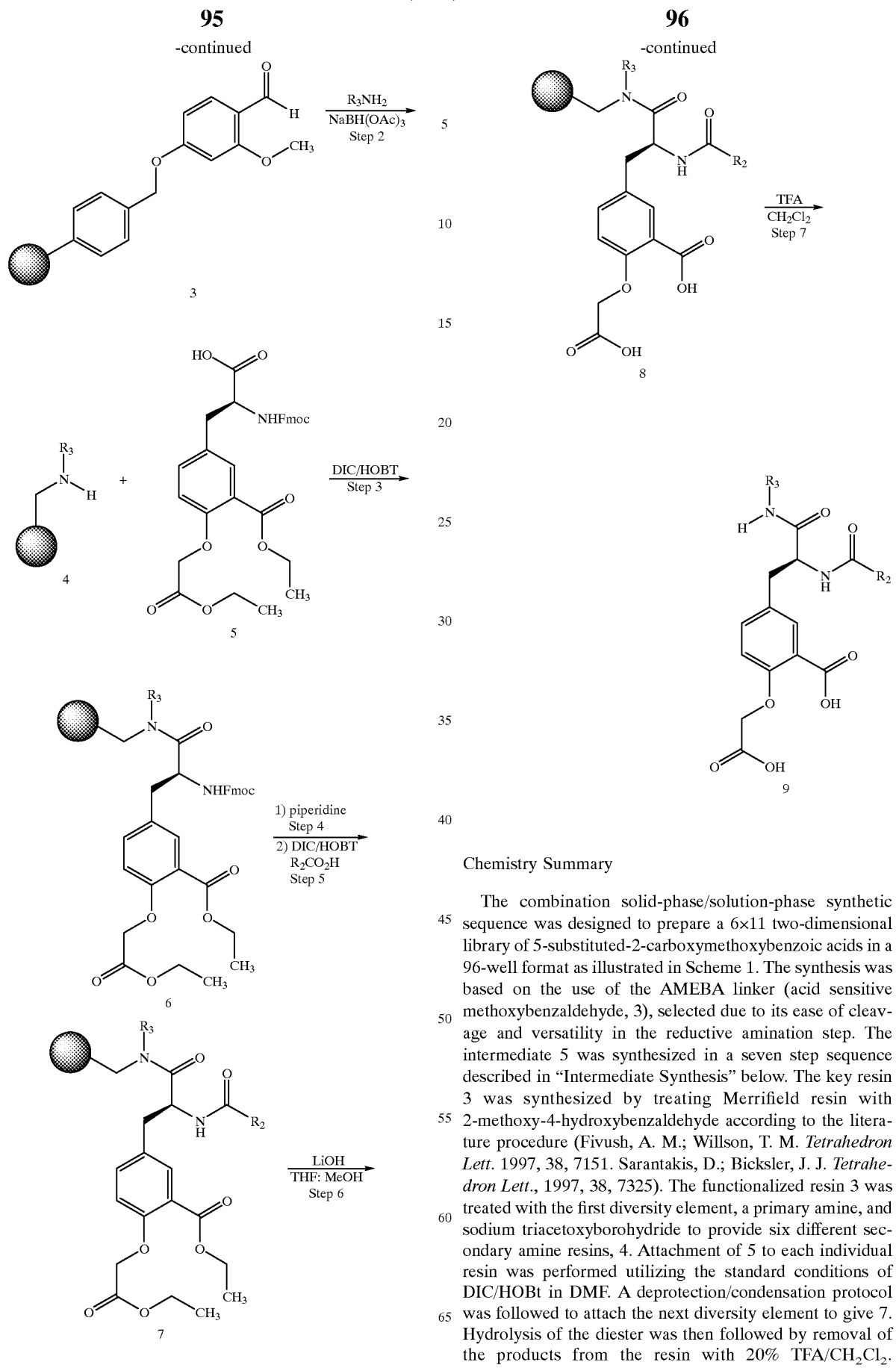

Chemistry Summary

The combination solid-phase/solution-phase synthetic sequence was designed to prepare a 6×11 two-dimensional library of 5-substituted-2-carboxymethoxybenzoic acids in a 96-well format as illustrated in Scheme 1. The synthesis was based on the use of the AMEBA linker (acid sensitive methoxybenzaldehyde, 3), selected due to its ease of cleavage and versatility in the reductive amination step. The intermediate 5 was synthesized in a seven step sequence described in "Intermediate Synthesis" below. The key resin 3 was synthesized by treating Merrifield resin with 2-methoxy-4-hydroxybenzaldehyde according to the literature procedure (Fivush, A. M.; Willson, T. M. *Tetrahedron Lett.* 1997, 38, 7151. Sarantakis, D.; Bicksler, J. J. *Tetrahedron Lett.*, 1997, 38, 7325). The functionalized resin 3 was treated with the first diversity element, a primary amine, and sodium triacetoxyborohydride to provide six different secondary amine resins, 4. Attachment of 5 to each individual resin was performed utilizing the standard conditions of DIC/HOBt in DMF. A deprotection/condensation protocol was followed to attach the next diversity element to give 7. Hydrolysis of the diester was then followed by removal of the products from the resin with 20% TFA/CH$_2$Cl$_2$.

Scheme 2-Intermediate Synthesis

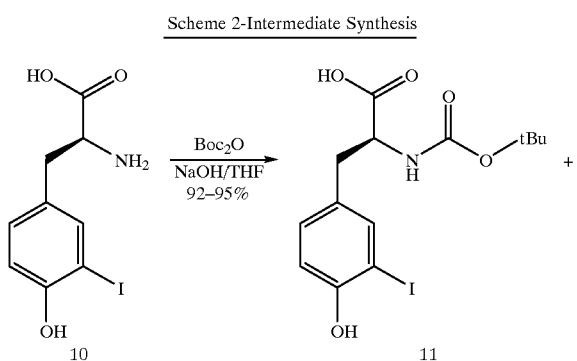

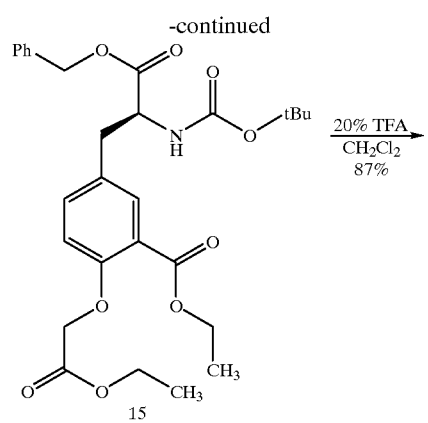

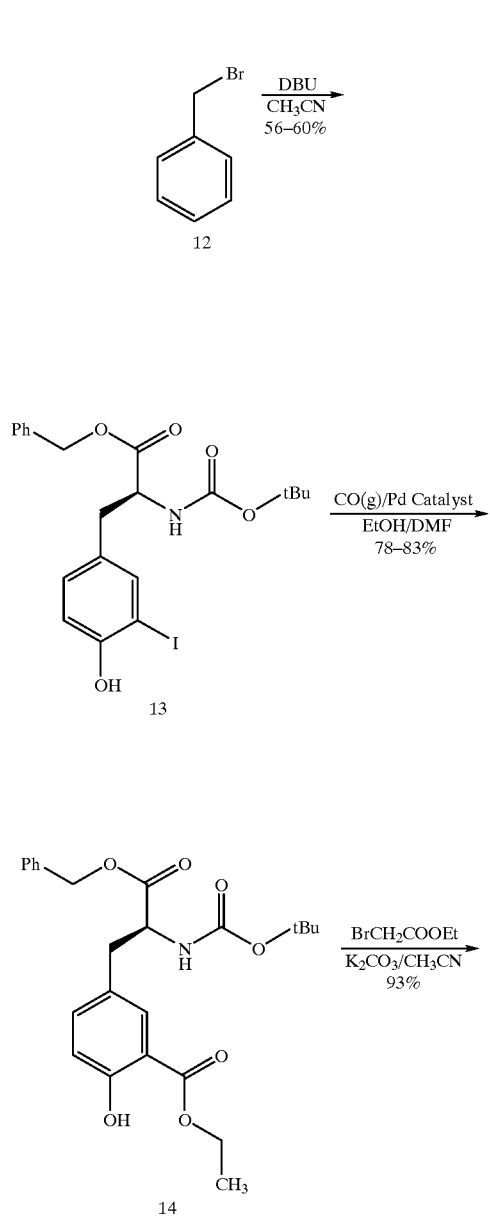

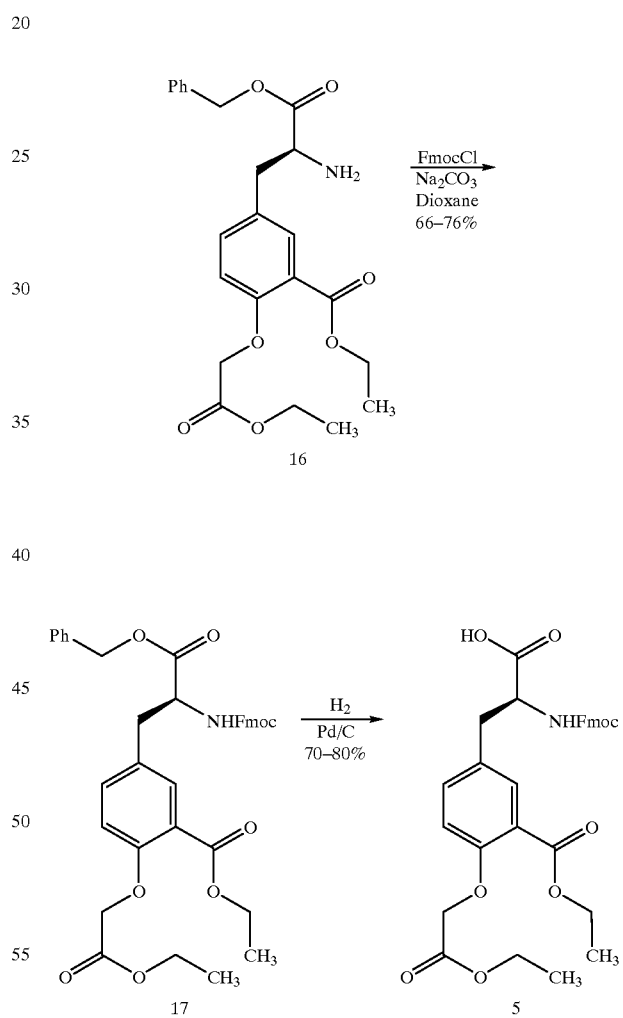

The tyrosine scaffold (5) was prepared in seven steps with an overall yield of 23% on a multi-gram scale. Commercially available 3-iodotyrosine (10) was treated with di-t-butylcarbonate to afford 11 (92–95%), treatment of 11 with DBU (1,5-diazobicyclo[5.4.0.]-undec-5-ene) and benzyl bromide (12) gave 13 (56–60%). Carbonylation of 13 in ethanol gave the corresponding ethyl ester 14 in 93% yield. Treatment of 14 with ethyl bromoacetate in potassium carbonate gave the diethyl ester 15 (93%). Deprotection of the Boc group was carried out using 20% TFA to afford the amine 16 (87%), which was protected with Fmoc-Cl to give 17 (66–76%), followed by hydrogenation to afford the acid 5 (70–80%).

(2S)-2-[(tert-Butoxycarbonyl)amino]-3-(4-hydroxy-3-iodophenyl)propanoic Acid (11) To a solution of 3-iodo-L-tyrosine (10) (5.00 g, 16.3 mmol) in 1.0 M NaOH (16.3 mL), $H_2O$ (16 mL) and THF 32 mL was added di-tert-butyl dicarbonate (3.95 g, 18.1 mmol). After 1.5 hr at rt, the reaction was concentrated in vacuo to remove THF, diluted with $H_2O$ (25 mL), and washed with $Et_2O$ (3×25 mL). The aqueous phase was brought to pH 4 with 1 M citric acid, extracted with $CH_2Cl_2$ (3×50 mL), and dried ($Na_2SO_4$). Removal of the solvent in vacuo afforded 11 (6.30 g, 95%) as a white foam (Rzeszotarska, B.; Nadolska, B.; Tarnawski, J. *Liebigs Ann. Chem.* 1981, 7, 1294). $^1$H NMR (300 MHz, DMF-$d_7$) δ 7.67 (s, 1H), 7.18 (d, J=8 Hz, 1H), 6.92 (d, J=8 Hz, 1H), 4.29–4.24 (m, 1H), 3.08 (dd, J=9, 14 Hz, 1H), 2.88–2.84 (m, 1H), 1.37 (s, 9H).

Benzyl (2S)-2-[(tert-Butoxycarbonyl)amino]-3-(4-hydroxy-3-iodophenyl)propanoate (13). A solution of acid 11 (17.6 g, 43.3 mmol) in 150 mL of $CH_3CN$ was treated DBU (6.8 mL, 45 mmol) and benzylbromide (12) (5.4 mL, 45 mmol). The reaction mixture was stirred at rt for 18 h, then concentrated to remove $CH_3CN$, diluted with 300 mL of $CH_2Cl_2$, washed with 1 N HCl (2×150 mL), 100 mL of water, dried over $NaSO_4$ and condensed. Purified by chromatography (20% EtOAc: Heptane) to yield 13 as an oil (21.5 g, 24.3 mmol, 56% yield). UV $\lambda_{max}$ 228 (10800, 95% ETHANOL); $^1$H NMR (CDCl$_3$) δ 7.41–7.31 (m, 6H), 6.88 (d, J=8 Hz, 1H), 6.79 (d, J=8 Hz, 1H), 5.95 (br s, 1H), 5.22–5.10 (m, 3H), 4.59–4.13 (m, 1H), 3.02–2.96 (m, 2H), 1.45 (s, 9H); $^{13}$C NMR (75 MHz, CDCl$_3$) δ 171.6, 155.2, 154.2, 139.1, 135.0, 131.0, 129.8, 128.7, 128.6, 115.1, 85.4, 80.3, 67.3, 54.6, 36.9, 28.4; IR (drift) 3457, 3362, 1737, 1683, 1528, 1503, 1350, 1294, 1281, 1206, 1195, 1169, 810, 753, 701 cm$^{-1}$; MS (EI) m/z 497 (M$^+$), 380, 233, 107, 106, 92, 91, 77, 65, 57, 51. Anal. Calcd for $C_{21}H_{24}INO_5$: C, 50.72; H, 4.86; N, 2.82. Found: C, 50.87; H, 4.70; N, 2.72.

Ethyl 5-{(2S)-3-(Benzyloxy)-2-[(tert-butoxycarbonyl)amino]-3-oxopropyl}-2-hydroxybenzoate (14) A solution of 13 (12.1 g, 24.3 mmol) in 50 mL of EtOH and 120 mL of DMF was treated with Pd(II)Acetate (270 mg, 1.20 mmol), triethylamine (6.8 mL, 48.8 mmol). The reaction atmosphere was replaced with CO (g) at 1 atm. and stirred at 60–70° C. for 18 h. The reaction mixture was diluted with 300 mL of EtOAc, washed with 1 N HCl (3×100 mL) and 100 mL of water. The organics were dried over $Na_2SO_4$ and condensed. Purified by chromatography (20% EtOAc: heptane) to give product 14 as white crystals (8.44 g, 19.0 mmol, 78% yield). UV $\lambda_{max}$ 228 (10800, 95% EtOH); $^1$H NMR (CDCl$_3$) δ 10.73 (s, 1H), 7.61 (d, J=2 Hz, 1H), 7.38–7.36 (m, 3H), 7.32–7.28 (m, 2H), 7.11 (br d, J=8 Hz, 1H), 6.84 (d, J=8 Hz, 1H), 5.18 (d, J=12 Hz, 1H), 5.13 (d, J=12 Hz, 1H), 5.06 (br d, 1H), 4.62–4.59 (m, 1H), 4.39 (q, J=7 Hz, 2H), 3.09–3.00 (m, 2H), 1.43 (s, 9H), 1.41 (t, J=7 Hz, 3H); $^{13}$C NMR (75 MHz, CDCl$_3$) δ 171.6, 170.0, 160.7, 155.0, 136.6, 135.0, 130.4, 128.6, 128.6, 128.5, 126.5, 117.8, 112.5, 80.0, 67.2, 61.5, 54.5, 37.4, 28.3, 14.2; IR (drift) 3357, 1732, 1687, 1528, 1493, 1371, 1292, 1270, 1252, 1207, 1191, 1169, 1088, 792, 699 cm$^{-1}$; MS (E) m/z 443 (M$^+$), 326, 180, 179, 134, 133, 91, 77, 65, 57, 51. Anal. Calcd for $C_{24}H_{29}NO_7$: C, 65.00; H, 6.59; N, 3.16. Found: C, 64.93; H, 6.48; N, 3.11.

Ethyl 5-{(2S)-3-(Benzyloxy)-2-[(tert-butoxycarbonyl)amino]-3-oxopropyl}-2-(2-ethoxy-2-oxoethoxy)benzoate (15) A solution of 14 (5.76 g, 13.0 mmol) in 100 mL of $CH_3CN$ was treated with solid $K_2CO_3$ (9.0 g, 65.1 mmol), ethylbromoacetate (1.7 mL, 15.3 mmol). The reaction mixture was stirred at rt for 14 h, additional ethylbromoacetate (0.5 mL, 4.5 mmol) added, then refluxed for 1 h. The reaction solution was filtered to remove $K_2CO_3$ with fine filter paper to yield 15 as an orange oil. Purified by chromatography (20% EtOAc/heptane) to yield a clear colorless oil (6.37 g, 12.0 mmol, 93%). $[\alpha]^{25}_D$=5° (c 0.78, chloroform); UV $\lambda_{max}$ 228 (10800, 95% EtOH); $^1$H NMR (CDCl$_3$) δ 7.58 (s, 1H), 7.36–7.28 (m, 5H), 7.10 (d, J=8 Hz, 1H), 6.74 (d, J=8 Hz, 1H), 5.12 (d, J=2 Hz, 2H), 5.06 (d, J=9 Hz, 1H), 4.64 (s, 2H), 4.60–4.57 (m, 1H), 4.34 (q, J=7 Hz, 2H); 4.25 (q, J=7 Hz, 2H), 3.10–3.01 (m, 2H), 1.40 (s, 9H), 1.36 (t, J=7 Hz, 3H), 1.27 (t, J=7 Hz, 3H); $^{13}$C NMR (75 MHz, CDCl$_3$) δ 171.5, 168.5, 165.6, 156.6, 155.0, 135.1, 134.0, 132.6, 129.4, 128.6, 128.5, 121.5, 114.7, 79.9, 67.2, 66.9, 61.3, 60.9, 54.4, 37.2, 31.9, 28.3, 22.7, 14.2; IR (liq.) 2980, 1717, 1500, 1456, 1446, 1392, 1379, 1367, 1303, 1254, 1200, 1166, 1090, 1068, 1022 cm$^{-1}$; MS (El) m/z 529 (M$^+$), 266, 265, 220, 192, 179, 133, 91, 59, 57, 56. Anal. Calcd for $C_{28}H_{35}NO_9$: C, 63.50; H, 6.66; N, 2.64. Found: C, 63.86; H, 6.76; N, 2.63.

Ethyl 5-[(2S)-2-Amino-3-(benzyloxy)-3-oxopropyl]-2-(2-ethoxy-2-oxoethoxy)benzoate (16) A solution of 15 (10.0 g, 18.9 mmol) in 100 mL of 20% TFA/$CH_2Cl_2$ was stirred at rt for 2 h. The reaction mixture was condensed; the oil was redissolved in 400 mL of $CH_2Cl_2$ and washed with $NaHCO_3$ and dried over $NaSO_4$, condensed to yield product 16 as an oil (8.12 g, 17.0 mmol, 90% yield). $[\alpha]^{25}_D$=−3° (c 0.52, methanol); UV $\lambda_{max}$ 227 (9410, MeOH); $^1$H NMR (400 MHz, CDCl$_3$) δ 7.66 (d, J=2 Hz, 1H), 7.32 (m, 6H), 6.78 (d, 1H), 5.14 (s, 2H), 4.66 (s, 2H), 4.35 (q, J=7 Hz, 2H), 4.26 (q, J=7 Hz, 2H), 3.75 (dd, J=6, 8 Hz, 1H), 3.05 (dd, J=5, 14 Hz, 2H), 2.87 (dd, J=8, 14 Hz, 2H), 1.38 (t, J=7 Hz, 3H), 1.29 (t, J=7 Hz, 3H); $^{13}$C NMR (100 MHz, CD$_3$OD) δ 174.6, 169.3, 166.7, 156.7, 136.0, 138.4, 132.1, 130.4, 128.6, 128.4, 128.3, 121.5, 114.6, 66.7, 66.3, 61.3, 61.2, 55.7, 39.7, 13.6, 13.5; IR (liq.) 2982, 1757, 1731, 1500, 1455, 1445, 1367, 1302, 1254, 1200, 1172, 1091, 1023, 754, 700 cm$^{-1}$; MS (FAB) m/z (rel. intensity) 430 (MH$^+$, 4), 430 (4), 265 (4), 133 (7), 92 (8), 91 (99), 81 (4), 69 (8), 55 (5), 41 (4), 29 (4). HRMS (FAB) calcd for $C_{23}H_{27}NO_7+H_1$ 430.1866, found 430.1860.

Ethyl 5-((2S)-3-(Benzyloxy)-2-{[(9H-fluoren-9-ylmethoxy)carbonyl]amino}-3-oxopropyl)-2-(2-ethoxy-2-oxoethoxy)benzoate (17) A solution of 16 (6.93 g, 16.1 mmol) in 50 mL of dioxane was treated with $Na_2CO_3$ (5.47 g 44.1 mmol) and 44 mL of water and then cooled to 0° C. To the cooled reaction mixture was added 9-fluorenylcarbonylchloride (4.57 g, 17.7 mmol) portionwise. After 30 min the reaction mixture was warmed to rt for 5 h. The reaction mixture was concentrated to remove dioxane, then partitioned between water and $CH_2Cl_2$, organics dried over $Na_2SO_4$, and condensed. Purified by chromatography (20% EtOAc/heptane to 50% EtOAc/heptane) to yield 17 as a gummy clear oil (6.97 g, 10.7 mmol, 66% yield). $^1$H NMR (400 MHz, CDCl$_3$) δ 7.77 (d, J=8 Hz, 2H), 7.63 (s, 1H), 7.59 (t, J=6 Hz, 1H), 7.36 (m, 9H), 7.08 (d, J=8 Hz, 1H), 6.75 (d, J=9 Hz, 2H), 5.38 (d, J=8 Hz, 1H), 5.17 (s, 2H), 4.72 (m, 1H), 4.65 (s, 2H), 4.36 (m, 4H), 4.24 (q, J=9 Hz, 2H), 4.21 (m, 1H), 3.11 (m, 2H), 1.35 (t, J=7 Hz, 3H), 1.27 (t, J=5 Hz, 3H).

(2S)-3-[3-(Ethoxycarbonyl)-4-(2-ethoxy-2-oxoethoxy)phenyl]-2-{[(9H-fluoren-9-ylmethoxy)carbonyl]amino}propanoic acid (5) To 17 (6.97 g, 10.7 mmol) was added 504 mg of Pd/C followed by the addition of 250 mL of MeOH. The reaction mixture was stirred at rt under 1 atm of $H_2$ (g) for 18 h. The reaction mixture was filtered through celite, condensed. Purified by chromatography (1% AcOH, 5% MeOH, CH$_2$Cl$_2$) to yield 5 as a white solid (4.19 g, 7.45 mmol, 70% yield). The product can be recrystallized in intoluene/heptane. [α]$^{25}_D$=3° (c 0.99, methanol); UV λ$_{max}$ 264(18800, MeOH); $^1$H NMR (400 MHz, CDCl$_3$) δ 8.95 (s, 1H), 7.75 (d, J=7 Hz, 2H), 7.67 (s, 1H), 7.55 (t, J=8 Hz, 2H), 7.39 (t, J=7 Hz, 2H), 7.24 (m, 3H), 7.22 (m, 1H), 6.79 (d, J=8 Hz, 1H), 5.41 (d, J=8 Hz, 1H), 4.68 (m, 1H), 4.64 (s, 2H), 4.26 (m, 6H), 3.20 (m, 1H), 3.08 (m, 1H), 1.34 (t, J=7 Hz, 3H), 1.27 (t, J=7 Hz, 3H); $^{13}$C NMR (100 MHz, CDCl$_3$) δ 174.8, 168.6, 166.1, 156.5, 155.8, 143.7, 141.2, 134.1, 132.6, 129.1, 127.7, 127.1, 125.0, 121.6, 119.9, 114.6, 67.2, 66.8, 61.4, 61.2, 54.5, 47.1, 36.7, 14.2, 14.1; IR (drift) 3337, 3318, 1754, 1744, 1694, 1543, 1445, 1295, 1269, 1255, 1203, 1167, 1090, 764, 741 cm$^{-1}$; HRMS (FAB) calcd for C$_{31}$H$_{31}$NO$_9$+H$_1$ 562.2077, found 562.2070.

| Diversity Elements | |
| --- | --- |
| N-Terminal Carboxylic Acids (commercially available): | |
| Name | Cpd # |
| nicotinic acid | 18 |
| 2-pyrazinecarboxylic acid | 19 |
| 4-chlorobenzoic acid | 20 |
| 6-chloronicotinic acid | 21 |
| 2,3,5,6-tetrafluorobenzoic acid | 22 |
| 5-methoxyindole-2-carboxylic acid | 23 |
| 3-furoic acid | 24 |
| 5,6-dichloronicotinic acid | 25 |
| cycloheptanecarboxylic acid | 26 |
| benzoic acid | 27 |
| N-acetyl-(L)-phenylalanine | 28 |
| (S)-(-)-3-(benzyloxycarbonyl) 4-oxazolidinecarboxylic acid | 29 |
| C-Terminal Amines: | |
| Name | Cpd # |
| a) Commercially available: | |
| n-propylamine | 30 |
| n-amylamine | 31 |
| 4-phenylbutylamine | 32 |
| b) Synthesized: | |

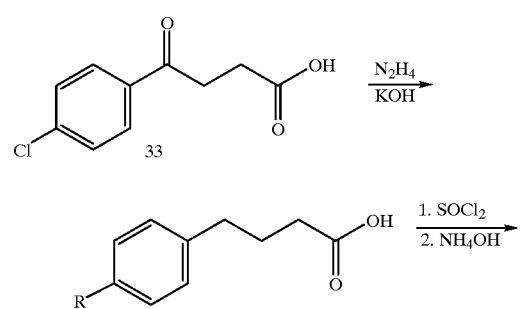

34a: R = Cl (96%)
34b: R = OCH$_3$

-continued

| Diversity Elements |
| --- |

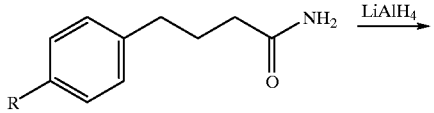

35a: R = Cl (55%)
35b: R = OCH$_3$ (57–79%)

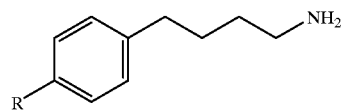

36a: R = Cl (98%)
36b: R = OCH$_3$ (95%)

Three of the six amines used in this library were commercially available, the remaining three amines 36a, 36b and 38 were prepared synthetically. Wolff-Kishner reduction of 4-(p-chlorophenyl)-4-oxobutanoic acid gave 4-(p-chlorophenyl)butanoic acid (34a) in 96% yield, which was converted to 35a (55%). 4-(p-Methoxyphenyl)butylamine (36b) was similarly synthesized with equal results from commercially available 34b. Benzyl ethylamine ether (38) was prepared in one step from ethanolamine and benzyl chloride in 10% yield.

4-(p-chlorophenyl)butanoic acid (34a)

A mixture of 3-(4-chlorobenzoyl) propionic acid (33) (2.50 g, 12.0 mmol), KOH (s) (1.75 g, 31.2 mmol), and hydrazine monohydrate (1.25 mL, 25.8 mmol) in 12.5 mL of diethylene glycol was refluxed azeotropically at 120–130° C. for 90 min to remove water. The reaction mixture was then refluxed at 170° C. for 3 h, cooled to RT, diluted with 12.5 mL of water, and poured into 15 mL 2.5 N HCl(aq). The precipate was filtered off, dissolved in CH$_2$Cl$_2$, and the solvent removed to give 34a (2.23 g, 96%) as a white solid. UV λ$_{max}$ 223 (8980, 95% ETHANOL); $^1$H NMR (400 MHz, CDCl$_3$) δ 7.26 (d, J=7 Hz, 2H), 7.12 (d, J=8 Hz, 2H), 2.66 (t, J=4 Hz, 2H), 2.38 (t, J=4 Hz, 2H), 1.96 (m, 2H); $^{13}$C NMR (CDCl$_3$) δ 179.3, 140.0, 132.2, 130.2, 128.9, 34.7, 33.4, 26.4; IR (drift) 3063 (s), 3051 (s), 2955 (s), 2923 (s,b), 2905 (s), 2814, 2797, 2493 (b), 2466, 2413, 2367 (b), 2321, 1706 (s), 1492 (s), 1212 (s), cm$^{-1}$; MS (EI ) m/z (rel. intensity) 198 (M+, 22), 200 (7), 198 (22), 140 (32), 139 (17), 138 (99), 127 (15), 125 (48), 103 (10), 89 (13), 60 (9); HRMS (EI) calcd for 198.0448, found 198.0441.

4-(p-chlorophenyl)butanamide (35a)

A mixture of 34a (1.880 g, 10.1 mmol) and thionyl chloride (3.0 mL, 40.9 mmol) in 15 mL CHCl$_3$ was stirred at reflux (75° C.) for 4 h. Solvent and excess thionyl chloride were removed in vacuo, and residue was twice diluted with 7.5 mL toluene and evaporated to remove traces of thionyl chloride. To a solution of the residue in 3 mL toluene was slowly added 9 mL of cold concentrated NH$_4$OH. The precipitate was filtered off and recrystallized in CHCl$_3$/heptane to give 35a (1.02 g, 55%) as a white solid. UV λ$_{max}$ 224 (9300, 95% ETHANOL). $^1$H NMR (400 MHz, CDCl$_3$) δ 7.25 (d, J=8 Hz, 2H), 7.12 (d, J=8 Hz, 2H), 5.31 (s, 2H), 2.66 (t, J=8 Hz, 2H), 2.23 (t, J=7 Hz, 2H), 1.98 (m, 2H); $^{13}$C NMR (CDCl$_3$) δ 175.4, 140.2, 134.5, 130.2, 128.9, 35.1, 34.8, 27.0; IR (drift) 3434, 2948, 2282 (w), 1901 (w), 1655 (s), 1607, 1491, 1420, 1306, 1094, 1016, 836 (s), 825, 804, 666, cm$^{-1}$. Calcd for C$_{10}$H$_{12}$ClNO: C, 60.76; H, 6.12; N, 7.09; Cl, 17.94. Found: C, 60.60; H, 6.11; N, 6.96.

4-(p-chlorophenyl)butylamine (36a) (Ali, F. E.; Dandridge, P. A.; Gleason, J. G.; Krell, R. D.; Kruse, C. H.; Lavanchy, P. G; Snader, K. M. *J. Med Chem.*, 1982, 25, 947) To a stirred suspension of lithium aluminum hydride (2.40 g, 63.2 mmol) in 65 mL diethyl ether was added slowly a solution of (3.12 g 15.8 mmol) of 35a in 28 mL THF, and stirred at rt for 1 h. To the reaction mixture was slowly added 4 mL water, 4 mL 5 N NaOH(aq), and 12 mL water. The organics were removed from the emulsion which was dissolved in water and extracted with ether. The organic portions were dried over $Na_2SO_4$(s), and condensed to give 36a (2.76 g, 95%) as an oil. UV $\lambda_{max}$ 224 (7600, 95% ETHANOL). $^1$H NMR (400 MHz, $CDCl_3$) δ 7.23 (m, 2H), 7.10 (d, J=8 Hz, 2H), 2.74 (t, J=7 Hz, 2H), 2.60 (t, J=8 Hz, 2H), 2.25 (s, 2H), 1.64 (m, 2H), 1.49 (m, 2H). $^{13}$C NMR ($CDCl_3$) δ 141.2, 131.8, 130.1, 128.8, 42.3, 35.4, 33.6, 29.0; IR (liq.) 3365 (b), 3296 (b), 3026, 2933 (s), 2858 (s), 2170 (w), 1996 (w), 1576, 1492 (s), 1460, 1093 (s), 1016 (s), 831, 821, 804, $cm^{-1}$; HRMS (FAB) calcd for $C_{10}H_{14}ClN+H_1$ 184.0893, found 184.0879.

4-(p-methoxyphenyl)butanamide (35b)

A mixture of 4-(p-methoxyphenyl)butyric acid (34b) (6.50 g, 33.5 mmol) and thionyl chloride (10.0 mL, 137 mmol) in 50 mL $CHCl_3$ was stirred at reflux for 5.5 h. Solvent and excess thionyl chloride were removed in vacuo, and residue was twice diluted with 25 mL toluene and evaporated to remove traces of thionyl chloride. To a solution of the residue in 10 mL toluene was added slowly 30 mL of cold concentrated $NH_4OH$. The precipitate was filtered off and recrystallized in $CHCl_3$/heptane to give 35b (3.68 g, 57%) as a white solid. UV $\lambda_{max}$ 223 (10200, 95% EtOH); $^1$H NMR (400 MHz, CDCl3) δ 7.10 (d, J=9 Hz, 2H), 6.84 (d, J=9 Hz, 2H), 5.44 (s, 2H), 3.80 (s, 3H), 2.63 (t, J=7 Hz, 2H), 2.23 (d, J=8 Hz, 2H), 1.96 (m, 2H); 13C NMR (CDCl3) δ 175.5, 158.3, 133.8, 129.7, 114.2, 55.6, 35.4, 34.5, 27.4; IR (drift) 3366 (s), 2479 (w), 2355 (w), 2285 (w), 2053 (w), 1993 (w), 1656 (s), 1628 (s), 1512 (s), 1416 (s), 1304 (s), 1243 (s), 1230 (s), 1031 (s), 838 (s), $cm^{-1}$. Anal. Calcd for $C_{11}H_{15}NO_2$: C, 68.37; H, 7.82; N, 7.25. Found: C, 68.42; H, 8.03; N, 7.24.

4-(p-methoxyphenyl)butylamine (36b) (Ali, F. E.; Dandridge, P. A.; Gleason, J. G.; Krell, R. D.; Kruse, C. H.; Lavanchy, P. G; Snader, K. M. *J. Med Chem.*, 1982, 25, 947)

To a stirred suspension of lithium aluminum hydride (4.40 g, 116 mmol) in 120 mL diethyl ether was added dropwise a solution of 35b (5.60 g, 29.0 mmol) in 10 mL THF, and stirred at rt for 1 h. To the reaction mixture was added 7.5 mL water, 7.5 mL 5 N NaOH(aq), and 20 mL water. The organics were removed from the emulsion which was dissolved in water and extracted with ether. The organic portions were dried over $Na_2SO_4$(s), and condensed to give 36b (5.10 g, 98%) as an oil. UV $\lambda_{max}$ 223 (9410, 95% EtOH). (400 MHz, $CDCl_3$) δ 7.10 (d, J=9 Hz, 2H), 6.83 (d, J=9 Hz, 2H), 3.79 (s, 3H), 2.71 (t, J=7 Hz, 2H), 2.58 (t, J=7 Hz, 2H), 1.63 (m, 2H), 1.48 (m, 2H); IR (liq.) 2933 (s), 2856, 2145 (w), 2059 (w), 1996 (w), 1612 (s), 1584, 1513 (s), 1461, 1442, 1246 (s), 1178, 1034 (s), 827, 822, $cm^{-1}$ HRMS (FAB) calcd for $C_{11}H_{17}NO+H_1$ 180.1388, found 180.1387.

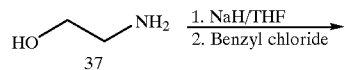

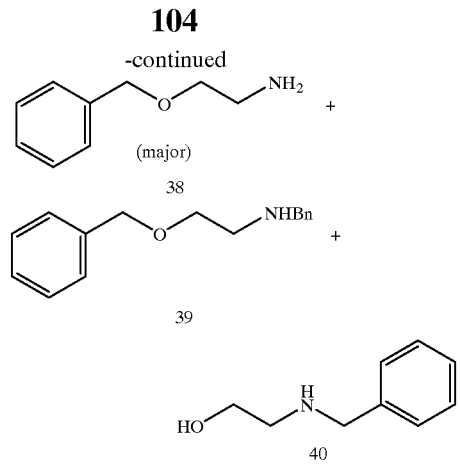

2-(benzyloxy)ethylamine (38) (Hu, X. E.; Cassady, J. M. *Synthetic Comm.*, 1995, 25, 907) To a solution of distilled ethanolamine (37) (1.81 mL, 30.0 mmol) in 30 mL of dry THF, was added NaH (1.2 g 30.0 mmol) as a 60% dispersion in mineral oil, in small portions at rt. The mixture was stirred at reflux for 30 min., benzyl chloride (2.88 mL, 25.0 mmol) was added, and stirred at reflux for an additional 4.5 h. The mixture was cooled to rt, 10 mL water was added, and solvent evaporated in vacuo. The residue was partitioned between 1 N HCl(aq) and $CH_2Cl_2$. The aqueous layer was extracted with $CH_2Cl_2$ to remove side product 39. The aqueous portion was adjusted to pH 13 with 10% NaOH(aq) and extracted with $CH_2Cl_2$. The extracts were condensed and purified by flash chromatography (10% MeOH (saturated with $NH_3$)/$CH_2Cl_2$) to give 38 (0.24 g, 10%) as a yellow oil. $R_f$(10% MeOH(saturated with $NH_3$)/$CH_2Cl_2$)= 0.47; UV $\lambda_{max}$ 251 (162, 95% ETHANOL); 1H NMR (400 MHz, $CDCl_3$) δ 7.31 (m, 5H), 4.55 (s, 2H), 3.53 (t, J=5 Hz, 2H), 2.90 (t, J=5, 2H), 1.68 (s, 2H); $^{13}$C NMR ($CDCl_3$) δ 138.7, 128.8, 128.1, 128.0, 73.5, 72.9, 42.3; IR (liq.) 3371, 3302 (b), 3030, 2924 (b), 2860 (s), 2202 (w), 1955 (w), 1496, 1453 (s), 1356, 1101 (s), 1069, 1028, 739 (s), 698 (s), $cm^{-1}$. HRMS (FAB) calcd for $C_9H_{13}NO+H_1$ 152.1075, found 152.1074.

Library Synthesis

The production of this library required seven steps using solid support. Three steps were carried out in a 96 well format. The AMEBA (acid sensitive methoxy benzaldehyde) linker was prepared by reacting Merrifield resin and 4-hydroxy-2-methoxybenzaldehyde with sodium methoxide (see Scheme I). The AMEBA resin was then treated with the corresponding amine and $NaBH(OAc)_3$ to give the corresponding reductive amination product. The tyrosine scaffold (5) was then coupled to the various amine resins using DIC and HOBT in DMF. The Fmoc protecting group was then removed with piperidine/DMF (1:1). The resin was then plated in a 96 well Robbins block then coupled to the corresponding acid with DIC and HOBT in DMF. The diethyl ester was hydrolyzed with excess LiOH in THF: MeOH (1:1) for 5–14 h at rt to yield the dicarboxylic acid on resin. The use of THF: MeOH (1:1) is crucial for this hydrolysis. The use of excess LiOH and neat MeOH, THF and DMF failed to yield the diacid. The product was then cleaved from the resin with 20% TFA/$CH_2Cl_2$ solution. The resin was cleaved twice to yield the maximum possible product. The second cleavage resulted in approximately 10–20% more product without any change in purity levels.

Step 1: Preparation of AMEBA Linker A suspension of Merrifield resin (2.10 g, 3.47 mmol) in 50 mL of DMF was treated with solid sodium methoxide (560 mg, 10.4 mmol).

To the solution was added 4-hydroxy-2-methoxybenzaldehyde (1.58 g, 10.4 mmol). The reaction mixture was heated to 60–70° C. for 24 h. The resin was then washed with DMF, MeOH, water, MeOH, $CH_2Cl_2$, and MeOH (3×10 mL). IR indicated strong absorption at 1681 $cm^{-1}$.

Step 2: Reductive Amination A suspension of AMEBA (1.04 g 1.12 mmol) in 25 mL of $C_2H_4Cl_2$ was treated with phenylbutyl amine (0.36 mL, 2.3 mmol) and $NaBH(OAc)_3$ (479 mg, 2.26 mmol). The reaction mixture was stirred at rt for 3 h. The resin was then washed with $CH_2Cl_2$, DMF, MeOH and $CH_2Cl_2$ (3×10 mL). IR indicated disappearance of strong absorption at 1681 $cm^{-1}$.

Step 3: Coupling Resin to Intermediate 5 A suspension of resin (734 mg, 0.751 mmol) in 20 mL of DMF was treated with tyrosine scaffold 5 (632 mg, 1.13 mmol), hydroxybenzotriazole (HOBT) (24 mg, 0.18 mmol), diisopropyl carbodiimide (DIC) (175 $\mu$L, 1.12 mmol). The reaction mixture was stirred at rt for 2 h. The resin was tested for the presence of any secondary amine using the choranil test. A sample of resin 1–5 mg was mixed with one drop of 2% acetaldehyde in DMF and one drop of 2% chloranil in DMF. After 5 min the resin showed no color change; a control containing a secondary amine stained blue (Rzeszotarska, B.; Nadolska, B.; Tarnawski, J. *Liebigs Ann. Chem.* 1981, 7, 1294). The resin was washed with DMF, $CH_2Cl_2$, MeOH, $CH_2Cl_2$ (3×10 mL).

Step 4: Fmoc Removal Resin (1.14 g, 0.751 mmol) was suspended in 10 mL of piperidine/DMF (1:5) and stirred for 30 min. at rt. The resin was washed with DMF, $CH_2Cl_2$, MeOH, $CH_2Cl_2$ (3×10 mL).

Step 5: Coupling Resin to Acid The resin was plated in a 96 well Robbins block (approx. 35 mg, 0.027 mmol). To each well was added as a slurry of DMF/$CH_2Cl_2$ and the resin was dried. Standard solutions of acid (1.26 mmol) in 7.5 mL of DMF, HOBT (119 mg, 0.88 mmol) in 20 mL of DMF and DIC (1.3 mL, 8.4 mmol) in 20 mL DMF were prepared. To the resin in each well was added the standard acid solution (0.50 mL, 0.084 mmol), DIC (0.20 mL DMF, 0.084 mmol) and HOBT (0.20 mL DMF, 0.009 mmol). The Robbins plate was then rotated for 5 h. The resin was washed with DMF, $CH_2Cl_2$, MeOH, $CH_2Cl_2$ (3×1 mL).

Step 6: Hydrolysis of Esters A standard solution of LiOH (2.26 g, 53.9 mmol) in 25 mL of MeOH and 25 mL of THF was prepared. The resin (approx. 35 mg, 0.027 mmol) in each well was treated with 0.5 mL of standard LiOH solution (0.62 mmol). The Robbins plate was rotated for 14 h. The resin was washed with DMF, $CH_2Cl_2$, MeOH, $CH_2Cl_2$ (3×1 mL).

Step 7: Cleavage The resin (approx. 35 mg, 0.027 mmol) in each well was treated with 0.50 mL of TFA/$CH_2Cl_2$ (1:5). The robbins block was rotated for 30 min. The resin was washed with $CH_2Cl_2$ (3×0.2 mL) and the filtrate collected. This process was repeated to insure all the product was cleaved from the resin.

Purification

The entire library was purified by reverse phase HPLC. The average purity after purification of the eleven samples was >99%. All samples tested indicated a purity >98% by analytical HPLC. The average yield after purification was 17% (2–3 mg per well on average). The preparative HPLC system used a Gilson 215 liquid robotics autosampler/fraction collector. The chromatography utilized a three-pump system of Rainin pump heads equipped with 10 mL/min or 50 mL/min pump solvent delivery heads and a Gilson solvent mixing chamber. Two pumps were used for solvent delivery, and one was used for flushing the system at the completion of the series of chromatography runs. UV absorbance was monitored using a Knauer variable wavelength UV detector equipped with a 10 mm path length analytical flow cell. The entire system was controlled by Gilson Unipoint software v. 1.65 which was used for data acquisition and analysis.

Samples were prepared for injection by dissolving each in 1–2 mL MeOH and housing them in 96 deep-well microtiter plates (2 mL/well). Injections for the chromatography loaded the entire sample into a 2.0 mL injection loop installed on the Gilson 819/Rheodyne Injector Module.

The HPLC method used in this study is as follows:

Column: YMC GuardPack C8 (20×50 mm, 5 $\mu$, 120 A)

Mobile A: water+0.05% trifluoroacetic acid (TFA)

Mobile B: acetonitrile

Flow Rate. 10 mL/min

Gradient: 10% B 0–2 min, 10–100% B 2–23 min, 100% B 23–25 min, re-equilibrate for 3 min Detection cell: UV absorbance at 220 nm, Knauer UV detector with 10 mm flow Fraction Collection: Gilson 215, 15% AUFS threshold, 9 mL maximum/tube in 13×100 mm disposable tubes Mass Spectrometry The entire library was analyzed by mass spectrometry after reverse phase HPLC. All of the 64 recovered compounds were positively identified by a molecular ion peak.

Library Compounds (Examples 154-1 to 154-64)

TABLE A

| Ex. No. | Compound Name | Mol. Wt. | Mass Data (M+) | Post Purification HPLC Analysis | Retention Time (min) | 1H NMR |
|---|---|---|---|---|---|---|
| 154-1 | 2-(carboxymethoxy)-5-{[(2S)-2-[(6-chloro-3-pyridinyl)carbonyl]amino}-3-oxo-3-(pentylamino)propyl]benzoic acid | 491.93 | 492.1 | | | Y |
| 154-2 | 2-(carboxymethoxy)-5-[(2S)-2-{[(5,6-dichloro-3-pyridinyl)carbonyl]amino}-3-oxo-3-(pentylamino)propyl]benzoic acid | 526.38 | 544 (M + NH3)+ | | | Y |
| 154-3 | 2-(carboxymethoxy)-5-{(2S)-3-oxo-3-(pentylamino)-2-[(2-pyrazinylcarbonyl)amino]propyl}benzoic acid | 458.48 | 459.1 | | | Y |
| 154-4 | 2-(carboxymethoxy)-5-[(2S)-2-(3-furoylamino)-3-oxo-3-(pentylamino)propyl]benzoic acid | 446.46 | 447.2 | | | Y |
| 154-5 | 2-(carboxymethoxy)-5-[(2S)-2-{[(5-methoxy-1H-indol-2-yl)carbonyl]amino}-3-oxo-3-(pentylamino)propyl]benzoic acid | 525.56 | 526.1 | >98% | 3.67 | |

TABLE A-continued

| Ex. No. | Compound Name | Mol. Wt. | Mass Data (M+) | Post Purification HPLC Analysis | Retention Time (min) | 1H NMR |
|---|---|---|---|---|---|---|
| 154-6 | 5-[(2S)-2-{[(2S)-2-(acetylamino)-3-phenylpropanoyl]amino}-3-oxo-3-(pentylamino)propyl]-2-(carboxymethoxy)benzoic acid | 541.61 | 542.2 | | | |
| 154-7 | 2-(carboxymethoxy)-5-{(2S)-2-[(cycloheptylcarbonyl)amino]-3-oxo-3-[(4-phenylbutyl)amino]propyl}benzoic acid | 538.65 | 539.2 | | | |
| 154-8 | 5-{(2S)-2-(benzoylamino)-3-oxo-3-[(4-phenylbutyl)amino]propyl}-2-(carboxymethoxy)benzoic acid | 518.57 | 519.2 | | | |
| 154-9 | 2-(carboxymethoxy)-5-{(2S)-2-[(4-chlorobenzoyl)amino]-3-oxo-3-[(4-phenylbutyl)amino]propyl}benzoic acid | 553.02 | 554.1 | >98% | 4.71 | |
| 154-10 | 2-(carboxymethoxy)-5-{(2S)-3-oxo-3-[(4-phenylbutyl)amino]-2-[(2,3,5,6-tetrafluorobenzoyl)amino]propyl}benzoic acid | 590.53 | 591.0 | | | |
| 154-11 | 2-(carboxymethoxy)-5-{(2S)-3-oxo-3-[(4-phenylbutyl)amino]-2-[(3-pyridinylcarbonyl)amino]propyl}benzoic acid | 519.56 | 520.2 | | | |
| 154-12 | 2-(carboxymethoxy)-5-{(2S)-2-{[(6-chloro-3-pyridinyl)carbonyl]amino}-3-oxo-3-[(4-phenylbutyl)amino]propyl}benzoic acid | 554 | 555.1 | | | |
| 154-13 | 2-(carboxymethoxy)-5-{(2S)-2-{[(5,6-dichloro-3-pyridinyl)carbonyl]amino}-3-oxo-3-[(4-phenylbutyl)amino]propyl}benzoic acid | 588.45 | 589.9 | | | |
| 154-14 | 2-(carboxymethoxy)-5-{(2S)-3-oxo-3-[(4-phenylbutyl)amino]-2-[(2-pyrazinylcarbonyl)amino]propyl}benzoic acid | 520.55 | 521.1 | | | |
| 154-15 | 2-(carboxymethoxy)-5-{(2S)-2-(3-furoylamino)-3-oxo-3-[(4-phenylbutyl)amino]propyl}benzoic acid | 508.53 | 509.1 | >98% | 4.29 | |
| 154-16 | 2-(carboxymethoxy)-5-{(2S)-2-[(5-methoxy-1H-indol-2-yl)carbon-yl]amino]-3-oxo-3-[(4-phenylbutyl)amino]propyl}benzoic acid | 587.64 | 588.1 | | | |
| 154-17 | 5-{(2S)-2-{[(2S)-2-(acetylamino)-3-phenylpropanoyl]amino}-3-oxo-3-[(4-phenylbutyl)amino]propyl}-2-(carboxymethoxy)benzoic acid | 603.68 | 604.1 | | | |
| 154-18 | 2-(carboxymethoxy)-5-{(2S)-3-{[4-(4-chlorophenyl)butyl]amino}-2-[(cycloheptylcarbonyl)amino]-3-oxopropyl}benzoic acid | 573.09 | 574.1 | | | |
| 154-19 | 5-((2S)-2-(benzoylamino)-3-{[4-(4-chlorophenyl)butyl]amino}-3-oxopropyl)-2-(carboxymethoxy)benzoic acid | 553.02 | 554.2 | | | |
| 154-20 | 2-(carboxymethoxy)-5-((2S)-2-[(4-chlorobenzoyl)amino]-3-{[4-(4-chlorophenyl)butyl]amino}-3-oxopropyl)benzoic acid | 587.46 | 589.0 | | | |
| 154-21 | 2-(carboxymethoxy)-5-{(2S)-3-{[4-(4-chlorophenyl)butyl]amino}-3-oxo-2-[(2,3,5,6-tetrafluorobenzoyl)amino]propyl}benzoic acid | 624.98 | 626.2 | >98% | 3.99 | |
| 154-22 | 2-(carboxymethoxy)-5-{(2S)-3-{[4-(4-chlorophenyl)butyl]amino}-3-oxo-2-[(3-pyridinylcarbonyl)amino]propyl}benzoic acid | 554 | 555.1 | | | |
| 154-23 | 2-(carboxymethoxy)-5-((2S)-3-{[4-(4-chlorophenyl)butyl]amino}-2-{[(6-chloro-3-pyridinyl)carbonyl]amino}-3-oxopropyl)benzoic acid | 588.45 | 589.1 | | | |
| 154-24 | 2-(carboxymethoxy)-5-((2S)-3-{[4-(4-chlorophenyl)butyl]amino}-2-{[(5,6-dichloro-3-pyridinyl)carbonyl]amino}-3-oxopropyl)benzoic acid | 622.89 | 623.9 | | | |
| 154-25 | 2-(carboxymethoxy)-5-{(2S)-3-{[4-(4-chlorophenyl)butyl]amino}-3-oxo-2-[(2-pyrazinylcarbonyl)amino]propyl}benzoic acid | 554.99 | 556.1 | >98% | 4.43 | |
| 154-26 | 2-(carboxymethoxy)-5-[(2S)-3-{[4-(4-chlorophenyl)butyl]amino}-2-(3-furoylamino)-3-oxopropyl]benzoic acid | 542.98 | 544.1 | | | |
| 154-27 | 2-(carboxymethoxy)-5-((2S)-3-{[4-(4-chlorophenyl)butyl]amino}-2-{[(5-methoxy-1H-indol-2-yl)carbonyl]amino}-3-oxopropyl)benzoic acid | 622.08 | 623.1 | | | |
| 154-28 | 5-((2S)-2-{[(2S)-2-(acetylamino)-3-phenylpropanoyl]amino}-3-{[4-(4-chlorophenyl)butyl]amino}-3-oxopropyl)-2-(carboxymethoxy)benzoic acid | 638.12 | 639.2 | | | |

TABLE A-continued

| Ex. No. | Compound Name | Mol. Wt. | Mass Data (M+) | Post Purification HPLC Analysis | Retention Time (min) | 1H NMR |
|---|---|---|---|---|---|---|
| 154-29 | 2-(carboxymethoxy)-5-((2S)-2-[(cycloheptylcarbonyl)amino]-3-{[4-(4-methoxyphenyl)butyl]amino}-3-oxopropyl)benzoic acid | 568.67 | 569.1 | | | |
| 154-30 | 5-((2S)-2-(benzoylamino)-3-{[4-(4-methoxyphenyl)butyl]amino}-3-oxopropyl)-2-(carboxymethoxy)benzoic acid | 548.6 | 549.1 | | | |
| 154-31 | 2-(carboxymethoxy)-5-((2S)-2-[(4-chlorobenzoyl)amino]-3-{[4-(4-methoxyphenyl)butyl]amino}-3-oxopropyl)benzoic acid | 583.04 | 584.3 | | | |
| 154-32 | 2-(carboxymethoxy)-5-{(2S)-3-[4-(4-methoxyphenyl)butyl]amino}-3-oxo-2-[(2,3,5,6-tetrafluorobenzoyl)amino]propyl}benzoic acid | 620.56 | 621.0 | | | |
| 154-33 | 2-(carboxymethoxy)-5-{(2S)-3-{[4-(4-methoxyphenyl)butyl]amino}-3-oxo-2-[(3-pyridinylcarbonyl)amino]propyl}benzoic acid | 549.59 | 550.1 | >98% | 3.83 | |
| 154-34 | 2-(carboxymethoxy)-5-((2S)-2-{[(6-chloro-3-pyridinyl)carbonyl]amino}-3-{[4-(4-methoxyphenyl)butyl]amino}-3-oxopropyl)benzoic acid | 584.03 | 585.2 | | | |
| 154-35 | 2-(carboxymethoxy)-5-((2S)-2-{[(5,6-dichloro-3-pyridinyl)carbonyl]amino}-3-[4-(4-methoxyphenyl)butyl]amino}-3-oxopropyl)benzoic acid | 618.48 | 619.9 | >98% | 4.59 | |
| 154-36 | 2-(carboxymethoxy)-5-{(2S)-3-[4-(4-methoxyphenyl)butyl]amino}-3-oxo-2-[(2-pyrazinylcarbonyl)amino]propyl}benzoic acid | 550.57 | 551.1 | | | |
| 154-37 | 2-(carboxymethoxy)-5-((2S)-2-(3-furoylamino)-3-{[4-(4-methoxyphenyl)butyl]amino}-3-oxopropyl)benzoic acid | 538.56 | 539.1 | | | |
| 154-38 | 2-(carboxymethoxy)-5-((2S)-2-{[(5-methoxy-1H-indol-2-yl)carbonyl]amino}-3-{[4-(4-methoxyphenyl)butyl]amino}-3-oxopropyl)benzoic acid | 617.66 | 618.1 | | | |
| 154-39 | 5-((2S)-2-{[(2S)-2-(acetylamino)-3-phenylpropanoyl]amino}-3-{[4-(4-methoxyphenyl)butyl]amino}-3-oxopropyl)-2-(carboxymethoxy)benzoic acid | 633.7 | 634.1 | | | |
| 154-40 | 5-{(2S)-3-{[2-(benzyloxy)ethyl]amino}-2-[(cycloheptylcarbonyl)amino]-3-oxopropyl}-2-(carboxymethoxy)benzoic acid | 540.62 | 541.2 | | | |
| 154-41 | 5-((2S)-2-(benzoylamino)-3-{[2-(benzyloxy)ethyl]amino}-3-oxopropyl)-2-(carboxymethoxy)benzoic acid | 520.54 | 521.1 | | | |
| 154-42 | 5-{(2S)-3-{[2-(benzyloxy)ethyl]amino}-2-[(4-chlorobenzoyl)amino]-3-oxopropyl}-2-(carboxymethoxy)benzoic acid | 554.99 | 556.0 | | | |
| 154-43 | 5-{(2S)-3-{[2-(benzyloxy)ethyl]amino}-3-oxo-2-[(2,3,5,6-tetrafluorobenzoyl)amino]propyl}-2-(carboxymethoxy)benzoic acid | 592.51 | 593.0 | | | |
| 154-44 | 5-{(2S)-3-{[2-(benzyloxy)ethyl]amino}-3-oxo-2-[(3-pyridinylcarbonyl)amino]propyl}-2-(carboxymethoxy)benzoic acid | 521.53 | 522.1 | | | |
| 154-45 | 5-((2S)-3-{[2-(benzyloxy)ethyl]amino}-2-{[(6-chloro-3-pyridinyl)carbonyl]amino}-3-oxopropyl)-2-(carboxymethoxy)benzoic acid | 555.98 | 557.1 | >98% | 3.83 | |
| 154-46 | 5-((2S)-3-{[2-(benzyloxy)ethyl]amino}-2-{[(5,6-dichloro-3-pyridinyl)carbonyl]amino}-3-oxopropyl)-2-(carboxymethoxy)benzoic acid | 590.42 | 592.0 | | | |
| 154-47 | 5-{(2S)-3-{[2-(benzyloxy)ethyl]amino}-3-oxo-2-[(2-pyrazinylcarbonyl)amino]propyl}-2-(carboxymethoxy)benzoic acid | 522.52 | 523.1 | | | |
| 154-48 | 5-[(2S)-3-{[2-(benzyloxy)ethyl]amino}-2-(3-furoylamino)-3-oxopropyl]-2-(carboxymethoxy)benzoic acid | 510.51 | 511.1 | | | |
| 154-49 | 5-((2S)-3-{[2-(benzyloxy)ethyl]amino}-2-{[(5-methoxy-1H-indol-2-yl)carbonyl]amino}-3-oxopropyl)-2-(carboxymethoxy)benzoic acid | 589.61 | 590.0 | | | |
| 154-50 | 5-((2S)-2-{[(2S)-2-acetylamino)-3-phenylpropanoyl]amino}-3-{[2-(benzyloxy)ethyl]amino}-3-oxopropyl)-2-(carboxymethoxy)benzoic acid | 605.65 | 606.0 | | | |
| 154-51 | 4-[(2S)-2-(benzoylamino)-3-oxo-3-(propylamino)propyl]-2-(carboxymethoxy)benzoic acid | 428.45 | 429.2 | | | |

TABLE A-continued

| Ex. No. | Compound Name | Mol. Wt. | Mass Data (M+) | Post Purification HPLC Analysis | Retention Time (min) | 1H NMR |
|---|---|---|---|---|---|---|
| 154-52 | 2-(carboxymethoxy)-5-[(2S)-2-[(4-chlorobenzoyl)amino]-3-oxo-3-(propylamino)propyl]benzoic acid | 462.89 | 463.1 | | | |
| 154-53 | 2-(carboxymethoxy)-5-{(2S)-3-oxo-3-(propylamino)-2-[(2,3,5,6-tetrafluorobenzoyl)amino]propyl}benzoic acid | 500.41 | 501.1 | | | |
| 154-54 | 2-(carboxymethoxy)-5-{(2S)-3-oxo-3-(propylamino)-2-[(3-pyridinylcarbonyl)amino]propyl}benzoic acid | 429.43 | 430.2 | | | |
| 154-55 | 2-(carboxymethoxy)-5-[(2S)-2-{[(6-chloro-3-pyridinyl)carbonyl]amino}-3-oxo-3-(propylamino)propyl]benzoic acid | 463.88 | 464.1 | | | |
| 154-56 | 2-(carboxymethoxy)-5-[(2S)-2-{[(5,6-dichloro-3-pyridinyl)carbonyl]amino}-3-oxo-3-(propylamino)propyl]benzoic acid | 498.32 | 516 (M + NH3)+ | | | |
| 154-57 | 2-(carboxymethoxy)-5-{(2S)-3-oxo-3-(propylamino)-2-[(2-pyrazinylcarbonyl)amino]propyl}benzoic acid | 430.42 | 431.2 | | | |
| 154-58 | 2-(carboxymethoxy)-5-[(2S)-2-(3-furoylamino)-3-oxo-3-(propylamino)propyl]benzoic acid | 418.41 | 419.1 | | | |
| 154-59 | 2-(carboxymethoxy)-5-[(2S)-2-{[(5-methoxy-1H-indol-2-yl)carbonyl]amino}-3-oxo-3-(propylamino)propyl]benzoic acid | 497.51 | 498.1 | | | |
| 154-60 | 2-(carboxymethoxy)-5-[(2S)-2-[(cycloheptylcarbonyl)amino]-3-oxo-3-(pentylamino)propyl]benzoic acid | 476.57 | 477.2 | | | |
| 154-61 | 5-[(2S)-2-(benzoylamino)-3-oxo-3-(pentylamino)propyl]-2-(carboxymethoxy)benzoic acid | 456.5 | 457.2 | >98% | 3.77 | |
| 154-62 | 2-(carboxymethoxy)-5-[(2S)-2-[(4-chlorobenzoyl)amino]-3-oxo-3-(pentylamino)propyl]benzoic acid | 490.94 | 491.1 | | | |
| 154-63 | 2-(carboxymethoxy)-5-{(2S)-3-oxo-3-(pentylamino)-2-[(2,3,5,6-tetrafluorobenzoyl)amino]propyl}benzoic acid | 528.46 | 529.1 | | | |
| 154-64 | 2-(carboxymethoxy)-5-{(2S)-3-oxo-3-(pentylamino)-2-[(3-pyridinylcarbonyl)amino]propyl}benzoic acid | 457.49 | 458.2 | | | |

The following NMR data were determined

Ex. 154-64; $^1$H NMR (300 MHz, DMSO-d$_6$) δ 8.97 (d, J=5 Hz, 1H), 8.77 (d, J=3 Hz, 2H), 8.12 (t, J=2 Hz, 1H), 7.81 (m, 2H), 7.40 (dd, J=2, 6 Hz, 1H), 6.89 (d, J=6 Hz, 1H), 4.69 (s, 2H), 4.62 (m, 1H), 3.07 (m, 3H), 2.94 (m, 1H), 1.40 (m, 2H), 1.26 (m, 4H), 0.85 (J=5 Hz, 3H).

Ex-154-3; $^1$H NMR (300 MHz, DMSO-d$_6$) δ 9.10 (s, 1H), 8.87 (d, J=2 Hz, 1H), 8.72 (m, 1H), 8.65 (d, J=6 Hz, 1H), 8.15 (m, 1H), 7.53 (d, J=2 Hz, 1H), 7.30 (dd, J=2, 6 Hz, 1H), 6.87 (d, J=6 Hz, 1H), 4.69 (s, 2H), 4.65 (m, 1H), 3.06 (m, 4H), 1.38 (m, 2H), 12.3 (m, 4H), 0.84 (t, J=6 Hz, 3H).

Ex. 154-62; $^1$H NMR (300 MHz, DMSO-d$_6$) δ 8.62 (d, J=6 Hz, 1H), 8.05 (m, 1H), 7.80 (d, J=9 Hz, 2H), 7.66 (d, J=2 Hz, 1H), 7.49 (d, J=8 Hz, 2H), 7.41 (dd, J=2, 6 Hz, 1H), 6.88 (d, J=6 Hz, 1H), 4.68 (s, 2H), 4.58 (m, 1H), 3.00 (m, 4H), 1.38 (m, 2H), 1.23 (m, 4H), 0.83 (t, J=6 Hz, 3H).

Ex. 154-1; $^1$H NMR (300 MHz, DMSO-d$_6$) δ 8.88 (d, J=5 Hz, 1H), 8.73 (d, J=2 Hz, 1H), 8.16 (dd, J=3, 6 Hz, 1H), 8.10 (m, 1H), 7.66 (s, 1H), 7.59 (d, J=8 Hz, 1H), 7.39 (dd, J=2, 7 Hz, 1H), 6.88 (d, J=9 Hz, 1H), 4.68 (s, 2H), 4.58 (m, 1H), 2.90 (m, 4H), 1.37 (m, 2H), 1.23 (m, 4H), 0.83 (t, J=5 Hz, 3H)

Ex. 154-2; $^1$H NMR (300 MHz, DMSO-d$_6$) δ 8.70 (d, J=6 Hz, 1H), 8.53 (s, 1H), 8.26 (s, 1H), 8.07 (m, 1H), 7.68 (s, 1H), 7.40 (m, 1H), 6.90 (d, J=6 Hz, 1H), 4.70 (s, 2H), 4.58 (m, 1H), 3.03 (m, 2H), 2.89 (m, 1H), 1.38 (m, 1H), 1.25 (m, 4H), 0.84 (t, J=6 Hz, 3H).

Ex. 154-4; $^1$H NMR (400 MHz, DMSO-d$_6$) δ 8.27 (d, J=10 Hz, 1H), 8.16 (s, 1H), 8.03 (m, 1H), 7.67 (m, 2H), 7.39 (m, 1H), 6.89 (d, J=10 Hz, 1H), 6.83 (s, 1H), 4.70 (s, 2H), 4.56 (m, 1H), 3.03 (m, 2H), 2.96 (m, 1H), 2.85 (m, 1H), 1.37 (m, 2H), 1.23 (m, 4H), 0.84 (t, 3H). $^1$H NMR.

EXAMPLE 155

One-dimensional library of 5-substituted-2-carbomethoxybenzoic Acids

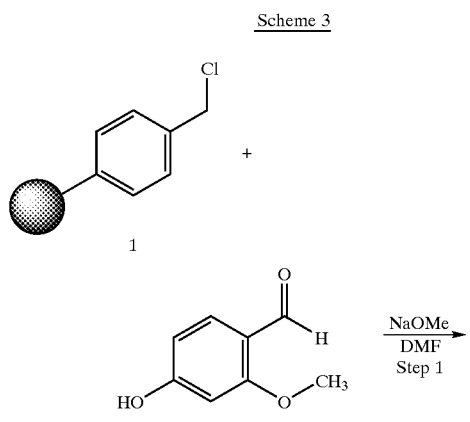

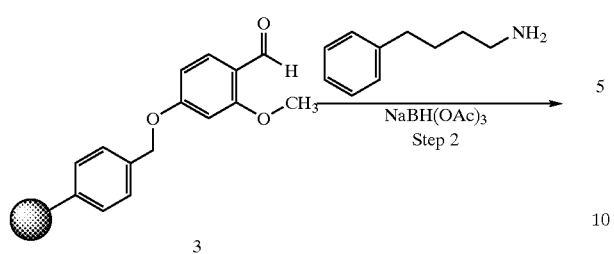
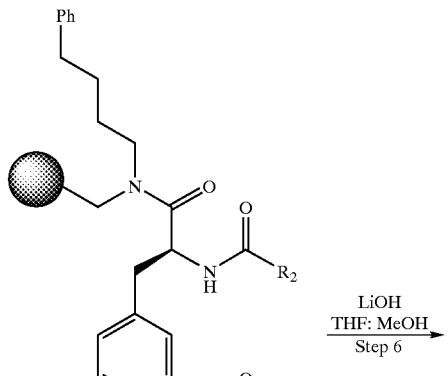
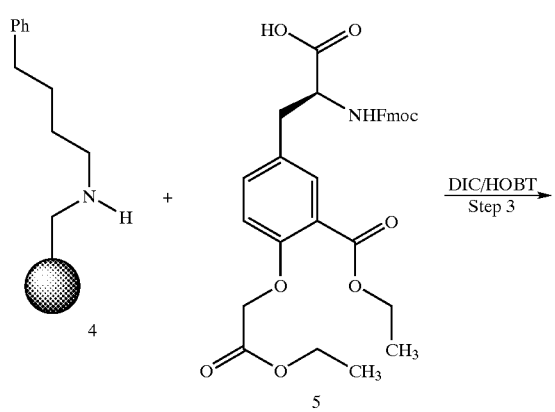
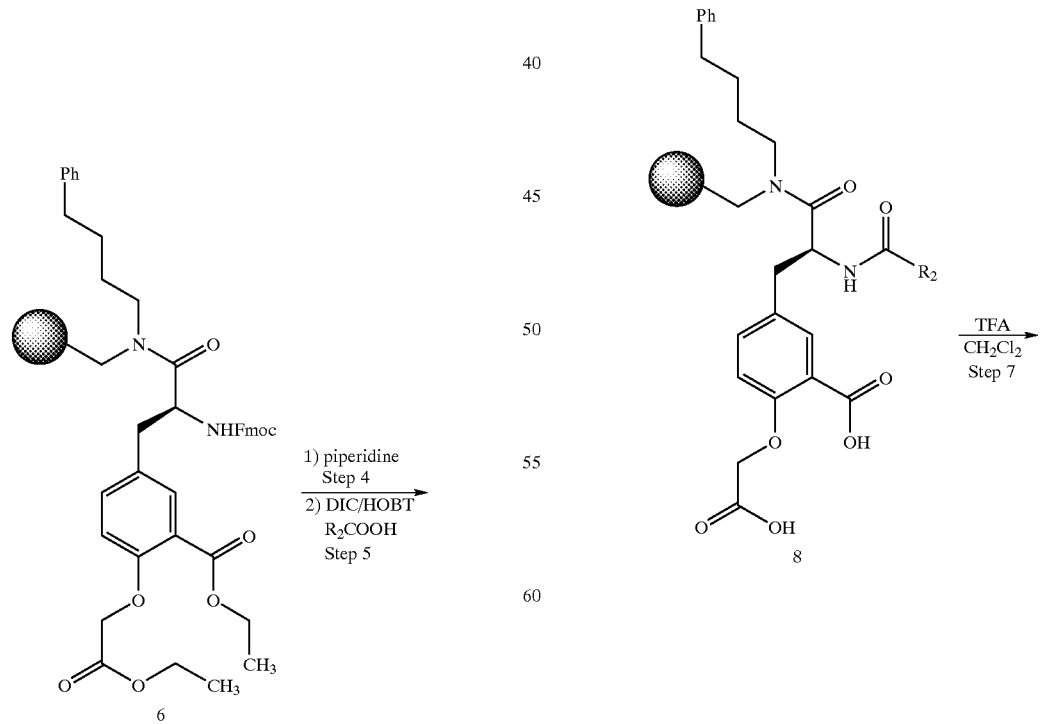

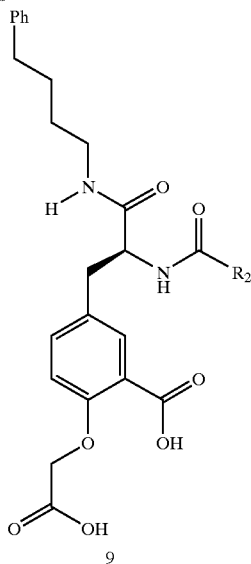

9

Chemistry Summary

The combination solid-phase/solution-phase synthetic sequence was designed to prepare an 88-member one-dimensional library of 5-substituted-2-carboxymethoxybenzoic acids in a 96-well format as illustrated in Scheme 3. The synthesis was based on the use of the AMEBA linker (acid sensitive methoxybenzaldehyde, 3), selected due to its ease of cleavage and versatility in the reductive amination step, and the intermediate 5, synthesized in a seven step sequence as described below. The key resin 3 was synthesized by treating Merrifield resin with 2-methoxy4-hydroxybenzaldehyde according to the literature procedure (Fivush, A. M.; Willson, T. M. *Tetrahedron Lett.* 1997, 38, 7151. Sarantakis, D.; Bicksler, J. J. *Tetrahedron Lett.*, 1997, 38, 7325e). The functionalized resin 3 was treated with 4-phenylbutyl amine and sodium triacetoxyborohydride to provide resin 4. Attachment of the scaffold 5 to the resin was performed utilizing the standard conditions of DIC/HOBt in DMF. A deprotection/condensation protocol was followed to attach the diversity element to give 7. Hydrolysis of the diester was then followed by removal of the products from the resin with 20% TFA/$CH_2Cl_2$.

Intermediate Synthesis

Scaffold 5 (see Scheme 3 above), (2S)-3-[3-ethyoxycarbonyl)-4-(2-ethoxy-2-oxoethoxy)phenyl]-2-{[(9H-fluoren-9-ylmethoxy)carbonyl]amino}propanoic acid, was prepared as described in Example 154 above.

Diversity Elements

Compound Name benzoic acid
diethylphosphonoacetic acid
pentafluoropropionic acid
S-benzylthioglycolic acid
2-methyl-6-nitrobenzoic acid
2-formylphenoxyacetic acid
4-cyanocinnamic acid
benzoylformic acid
1-phenyl-1-cyclopentylcarboxylic acid
2-cyanobenzoic acid
4-oxo-2-thioxo-3-thiazolidineacetic acid
pivalic acid
p-chlorophenylpropiolic acid
2-benzoylbenzoic acid
3,4-dihydro-2,2-dimethyl-4-oxo-2H-pyran-6-carboxylic acid
isonicotinic acid
cyclopropanecarboxylic acid
3-cyclopentylpropionic acid
1-methyl-1-cyclohexanecarboxylic acid
2,5-dimethoxybenzoic acid
2-biphenylcarboxylic acid
2-acetylbenzoic acid
o-toluic acid
3-fluorobenzoic acid
3,4-dichlorobenzoic acid
m-anisic acid
3,4-dimethoxybenzoic acid
3,4,5-trimethoxybenzoic acid
3,5-dimethoxybenzoic acid
4-bromobenzoic acid
4-chloro-o-anisic acid
4-dimethylaminobenzoic acid
4-(trifluoromethoxy)benzoic acid
4-butoxybenzoic acid
4-biphenylcarboxylic acid
4-acetylbenzoic acid
$\alpha,\alpha,\alpha$-trifluoro-p-toluic acid
4-tert-butylbenzoic acid
ptoluic acid
3-methoxy-4-methylbenzoic acid
hydrocinnamic acid
3-(4-methoxyphenyl)propionic acid
3-benzoylpropionic acid
1-methylpyrrole-2-carboxylic acid
5-bromo-2-furoic acid
2-naphthoic acid
(R)-(+)-$\alpha$-methoxy-$\alpha$-(trifluoromethyl)phenylacetic acid
(R)-(−)-$\alpha$-methoxyphenylacetic acid
4-fluorophenoxyacetic acid
phenylacetic acid
2-chlorophenylacetic acid
2-methoxyphenylacetic acid
o-tolylacetic acid
3-chlorophenylacetic acid
m-methoxyphenylacetic acid
($\alpha,\alpha,\alpha$-trifluoro-m-tolyl)acetic acid
p-chlorophenylacetic acid
4-methoxyphenylacetic acid
($\alpha,\alpha,\alpha$-trifluoro-p-tolyl)acetic acid
4-phenylbutyric acid
4-(4-methoxyphenyl)butyric acid
4-benzoylbutyric acid
5-phenylvaleric acid
undecylenic acid
3-methyl-2-thiophenecarboxylic acid
4-(2-thienyl)butyric acid
3-thiophenecarboxylic acid
1-methylindole-2-carboxylic acid
piperonylic acid
picolinic acid
3-quinolinecarboxylic acid
coumarin-3-carboxylic acid
4-(methylsulfonyl)benzoic acid
2-methoxy-4-(methylthio)benzoic acid
(2-pyrimidylthio)acetic acid
2-fluoro-4-(trifluoromethyl)benzoic acid
3-pyridylacetic acid hydrochloride
2-methylnicotinic acid
2,3,5,6-tetramethyl-benzoic acid β-(p-chlorophenyl)propionic acid
(3,5-dimethoxyphenyl)acetic acid
3-(3,4-methylenedioxyphenyl)propionic acid
6-methylpicolinic acid
1-acetylpiperidine-4-carboxylic acid
4-cyclohexylbenzoic acid
5-chloro-2-thiophenecarboxylic acid
3-methylindene-2-carboxylic acid
8-quinolinecarboxylic acid
3,5-dimethylisoxazole-4-carboxylic acid
2,4-dimethylthiazole-5-carboxylic acid
3-(4-fluorophenyl)propionic acid
7-chlorobenzofuran-2-carboxylic acid
(S)-(−)-α-methoxy-α-(trifluoromethyl)phenylacetic acid
(±)-camphorcarboxylic acid
pinonic acid
1-adamantanecarboxylic acid
tetrahydro-3-furoic acid
3-fluoro-2-methyl-benzoic acid
2,6-dimethoxynicotinic acid
1,4-benzodioxan-2-carboxylic acid
2-fluoro-5-methylbenzoic acid
2-norbomaneacetic acid
2-phenoxypropionic acid
anti-3-oxotricyclo(2.2.1.02,6)heptane-7-carboxylic acid Library Synthesis The production of the library required seven steps using solid support. Three steps were carried out in a 96 well format. The AMEBA (acid sensitive methoxy benzaldehyde) linker was prepared by reacting Merrifield resin and 4-hydroxy-2-methoxybenzaldehyde with sodium methoxide (see Scheme 3). The AMEBA resin was then treated with 4-phenylbutyl amine and $NaBH(OAc)_3$ to give the corresponding reductive amination product. The tyrosine scaffold (5) was then coupled to this amine resin using DIC and HOBT in DMF. The Fmoc protecting group was then removed with piperidine/DMF (1:1). The resin was then plated in a 96 well Robbins block and coupled to the corresponding acid with DIC and HOBT in DMF. After thorough washing, the resin was subjected to the coupling conditions a second time. The diethyl ester was hydrolyzed with excess LiOH in THF: MeOH (1:1) for 5–14 h at rt to yield the dicarboxylic acid on resin. The product was then cleaved from the resin with 20% $TFA/CH_2Cl_2$ solution. The resin was cleaved twice to yield the maximum possible product. The second cleavage resulted in approximately 10–20% more product without any change in purity levels.

Step 1: Preparation of AMEBA Linker A suspension of Merrifield resin (10.3 g, 12.9 mmol) in 200 mL of DMF was treated with solid sodium methoxide (2.08 g, 38.5 mmol) and 4-hydroxy-2-methoxybenzaldehyde (5.81 g, 38.2 mmol). The reaction mixture was heated to 60° C. for 24 h. The resin was then washed with DMF, MeOH, water, MeOH, $CH_2Cl_2$, and MeOH (3×50 mL), and dried to a constant weight (9.31 g) under high vacuum. IR indicated strong absorption at 1681 $cm^{-1}$.

Step 2: Reductive Amination A suspension of AMEBA (0.804 g 0.878 mmol) in 25 mL of 1,2-dichloroethane was treated with 4-phenylbutyl amine (0.29 mL, 1.8 mmol) and $NaBH(OAc)_3$ (394 mg, 1.86 mmol). After stirring at room temperature for 4 h, the resin was washed with $CH_2Cl_2$, DMF, MeOH and $CH_2Cl_2$ (3×each) and dried under high vacuum to a constant mass (0.807 g). IR indicated disappearance of strong absorption at 1681 $cm^{-1}$.

Step 3: Coupling Resin to Intermediate 5 A suspension of resin (0.724 g, 0.689 mmol) in 20 mL of DMF was treated with tyrosine scaffold 5 (0.584 g, 1.04 mmol), hydroxybenzotriazole (HOBt) (32 mg, 0.24 mmol), diisopropyl carbodiimide (DIC) (0.13 mL, 0.24 mmol). The reaction mixture was stirred at rt for 2.5 h. The resin was tested for the presence of any secondary amine using the choranil test (a sample of resin 1–5 mg was mixed with one drop of 2% acetaldehyde in DMF and one drop of 2% chloranil in DMF). After 5 min the resin showed no color change; a control containing a secondary amine stained blue (Vojkovsky T. *Peptide Research* 1995, 4, 236). The resin was washed with DMF, $CH_2Cl_2$, MeOH, $CH_2Cl_2$ (3×each) and dried under high vacuum to constant mass (0.857 g).

Step 4: Fmoc Removal Resin (0.855 g, 0.0.537 mmol) was suspended in 10 mL of piperidine/DMF (1:5) and stirred for 45 min. at rt. The resin was washed with DMF, $CH_2Cl_2$, MeOH, $CH_2Cl_2$ (3×10 mL) and dried under high vacuum to constant mass (0.528 g).

Step 5: Coupling Resin to Acid The resin was plated into a 96 well Robbins block (approx. 60 mg, 0.045 mmol/well) as a suspension in $DMF/CH_2Cl_2$ and dried. Standard solutions of acid (0.50 mL of a 0.27M stock in DMF), HOBt (200 μL of a 0.0675M stock in DMF) and DIC (200 μL of a 0.675M stock in DMF) were added to each well. The Robbins block was then rotated for 18 h at ambient temperature. The resin was washed with DMF, $CH_2Cl_2$, MeOH, $CH_2Cl_2$ (3×each). The coupling was repeated by adding the same amounts of reagents as above, rotating for an additional 18 h, and washing as above.

Step 6: Hydrolysis of Esters A standard solution of 0.90M LiOH in 1:1 MeOH/THF was prepared. The resin (approx. 60 mg, 0.045 mmol) in each well was treated with 1.0 mL of standard LiOH solution (0.90 mmol). The Robbins plate was rotated for 6 h, and the resin was washed with MeOH/$CH_2Cl_2$ (3×).

Step 7: Cleavage The resin (approx. 60 mg, 0.045 mmol) in each well was treated with 0.50 mL of $TFA/CH_2Cl_2$ (1:5). The Robbins block was rotated for 30 min. The resin was washed with $CH_2Cl_2$ (3×0.2 mL) and the filtrate collected. This process was repeated to ensure complete cleavage from the resin.

Purification

The entire library from the first cleavage iteration was purified by reverse phase HPLC. Based on HPLC analysis of 54 randomly chosen samples, the average purity of these compounds was 98%. The average yield after purification was 3% (0.6 mg per well on average). The recovered weight of each compound was determined by transferring the appropriate fraction(s) to a tared vial and removing the solvent in a Savant concentrator. The preparative HPLC system used a Gilson 215 liquid robotics autosampler/fraction collector. The chromatography utilized a three-pump system of Rainin pump heads equipped with 10 mL/min or 50 mL/min pump solvent delivery heads and a Gilson solvent mixing chamber. Two pumps were used for solvent delivery, and one was used for flushing the system at the completion of the series of chromatography runs. UV absorbance was monitored using a Knauer variable wavelength UV detector equipped with a 10 mm path length analytical flow cell. The entire system was controlled by Gilson Unipoint software v. 1.65 which was used for data acquisition and analysis.

Samples were prepared for injection by dissolving each in 1–2 mL MeOH and housing them in 96 deep-well microtiter plates (2 mL/well). No filtering was performed on those samples. Injections for the chromatography loaded the entire sample into a 2.0 mL injection loop installed on the Gilson 819/Rheodyne Injector Module.

The HPLC method used in this study is as follows:

Column: YMC GuardPack C8 (20×50 mm, 5 μ, 120 A)

Mobile A: water+0.05% trifluoroacetic acid (TFA)

Mobile B: acetonitrile

Flow Rate. 10 mL/min

Gradient: 10% B 0–2 min, 10–100% B 2–23 min, 100% B 23–25 min, re-equilibrate for 3 min Detection cell: UV absorbance at 220 nm, Knauer UV detector with 10 mm flow Fraction Collection: Gilson 215, 15% AUFS threshold, 9 mL maximum/tube in 13×100 mm disposable tubes Mass Spectrometry The entire library was analyzed by mass spectrometry after reverse phase HPLC. All but five of the 85 recovered compounds were positively identified by a molecular ion peak.

Library Compounds (Examples 155-1 to 155-80)

The following compounds were obtained in the library.

TABLE B

| Ex. No. | Compound Name | M.W. | Observed Molecular ion (ES−) | Amount of compound (g) (after HPLC) | Purity by HPLC (220 nm) | Ret. Time (min.) |
|---|---|---|---|---|---|---|
| 155-1 | 2-(carboxymethoxy)-5-{(2S)-2-[(3-cyclopentylpropanoyl)amino]-3-oxo-3-[(4-phenylbutyl)amino]propyl}benzoic acid | 538.64 | 537.3 | 0.0010 | | |
| 155-2 | 2-(carboxymethoxy)-5-{(2S)-2-{[(1-methylcyclohexyl)carbonyl]amino}-3-oxo-3-[(4-phenylbutyl)amino]propyl}benzoic acid | 538.64 | 537.3 | 0.0012 | 99 | 7.06 |
| 155-3 | 2-(carboxymethoxy)-5-{(2S)-2-[(2,5-dimethoxybenzoyl)amino]-3-oxo-3-[(4-phenylbutyl)amino]propyl}benzoic acid | 578.62 | 577.2 | 0.0013 | 99 | 6.52 |
| 155-4 | 5-{(2S)-2-[([1,1′-biphenyl]-2-ylcarbonyl)amino]-3-oxo-3-[(4-phenylbutyl)amino]propyl}-2-(carboxymethoxy)benzoic acid | 594.67 | 593.3 | 0.0022 | 99 | 7.32 |
| 155-5 | 2-(carboxymethoxy)-5-{(2S)-2-[(2-methylbenzoyl)amino]-3-oxo-3-[(4-phenylbutyl)amino]propyl}benzoic acid | 532.60 | 531.2 | 0.0008 | | |
| 155-6 | 2-(carboxymethoxy)-5-{(2S)-2-[(3-fluorobenzoyl)amino]-3-oxo-3-[(4-phenylbutyl)amino]propyl}benzoic acid | 536.56 | 535.1 | 0.0006 | 99 | 6.48 |
| 155-7 | 2-(carboxymethoxy)-5-{(2S)-2-[(3,4-dichlorobenzoyl)amino]-3-oxo-3-[(4-phenylbutyl)amino]propyl}benzoic acid | 587.46 | 585.0 | 0.0019 | 99 | 7.61 |
| 155-8 | 2-(carboxymethoxy)-5-{(2S)-2-[(3-methoxybenzoyl)amino]-3-oxo-3-[(4-phenylbutyl)amino]propyl}benzoic acid | 548.59 | 547.2 | 0.0015 | 99 | 6.38 |
| 155-9 | 2-(carboxymethoxy)-5-{(2S)-2-[(3,4-dimethoxybenzoyl)amino]-3-oxo-3-[(4-phenylbutyl)amino]propyl}benzoic acid | 578.62 | 577.0 | 0.0008 | 97.3 | 5.91 |
| 155-10 | 2-(carboxmethoxy)-5-{(2S)-3-oxo-3-[(4-phenylbutyl)amino]-2-[(3,4,5-trimethoxybenzoyl)amino]propyl}benzoic acid | 608.65 | 607.2 | 0.0004 | 99 | 6.21 |
| 155-11 | 2-(carboxymethoxy)-5-{(2S)-2-[(3,5-dimethoxybenzoyl)amino]-3-oxo-3-[(4-phenylbutyl)amino]propyl}benzoic acid | 578.62 | 576.9 | 0.0001 | 99 | 6.67 |
| 155-12 | 5-{(2S)-2-[(4-bromobenzoyl)amino]-3-oxo-3-[(4-phenylbutyl)amino]propyl}-2-(carboxymethoxy)benzoic acid | 597.47 | 596.8 | 0.0008 | 99 | 7.13 |
| 155-13 | 2-(carboxymethoxy)-5-{(2S)-2-[(4-chloro-2-methoxybenzoyl)amino]-3-oxo-3-[(4-phenylbutyl)amino]propyl}benzoic acid | 583.04 | 581.0 | 0.0011 | 99 | 7.18 |
| 155-14 | 2-(carboxymethoxy)-5-{(2S)-2-{[4-(dimethylamino)benzoyl]amino}-3-oxo-3-[(4-phenylbutyl)amino]propyl}benzoic acid | 561.64 | 560.0 | 0.0004 | 99 | 6.54 |
| 155-15 | 2-(carboxymethoxy)-5-((2S)-3-oxo-3-[(4-phenylbutyl)amino]-2-{[4-(trifluoromethoxy)benzoyl]amino}propyl)benzoic acid | 602.57 | 600.9 | 0.0003 | 99 | 7.62 |
| 155-16 | 5-{(2S)-2-[(4-butoxybenzoyl)amino]-3-oxo-3-[(4-phenylbutyl)amino]propyl}-2-(carboxymethoxy)benzoic acid | 590.68 | 589.2 | 0.0008 | 99 | 8.07 |
| 155-17 | 5-{(2S)-2-[([1,1′-biphenyl]-4-ylcarbonyl)amino]-3-oxo-3-[(4-phenylbutyl)amino]propyl-2-(carboxymethoxy)benzoic acid | 594.67 | 539.0 | 0.0005 | 99 | 7.96 |
| 155-18 | 5-{(2S)-2-[(4-acetylbenzoyl)amino]-3-oxo-3-[(4-phenylbutyl)amino]propyl}-2-(carboxymethoxy)benzoic acid | 560.61 | 559.1 | 0.0005 | 99 | 5.99 |
| 155-19 | 2-(carboxymethoxy)-5-((2S)-3-oxo-3-[(4-phenylbutyl)amino]-2-{[4-(trifluoromethyl)benzoyl]amino}propyl)benzoic acid | 586.57 | 585.0 | 0.0002 | | |
| 155-20 | 5-{(2S)-2-{[4-(tert-butyl)benzoyl]amino}-3-oxo-3-[(4-phenylbutyl)amino]propyl}-2-(carboxymethoxy)benzoic acid | 574.68 | 573.1 | 0.0015 | | |
| 155-21 | 2-(carboxymethoxy)-5-{(2S)-2-[(4-methylbenzoyl)amino]-3-oxo-3-[(4-phenylbutyl)amino]propyl}benzoic acid | 532.60 | 531.1 | 0.0010 | | |
| 155-22 | 2-(carboxymethoxy)-5-{(2S)-2-[(3-methoxy-4-methylbenzoyl)amino]-3-oxo-3-[(4-phenylbutyl)amino]propyl}benzoic acid | 562.62 | 561.0 | 0.0005 | 99 | 7.01 |
| 155-23 | 2-(carboxymethoxy)-5-{(2S)-3-oxo-3-[(4-phenylbutyl)amino]-2-[(3-phenylpropanoyl)amino]propyl}benzoic acid | 546.62 | 544.9 | 0.0006 | | |
| 155-24 | 2-carboxmethoxy)-5-{(2S)-2-{[3-(4-methoxyphenyl)propanoyl]amino}-3-oxo-3-[(4-phenylbutyl)amino]propyl}benzoic acid | 576.65 | 575.0 | 0.0001 | | |
| 155-25 | 2-(carboxymethoxy)-5-{(2S)-3-oxo-2-[(4-oxo-4-phenylbutanoyl)amino]-3-[(4-phenylbutyl)amino]propyl}benzoic acid | 574.63 | 573.1 | 0.0007 | 99 | 6.47 |
| 155-26 | 2-(carboxymethoxy)-5-{(2S)-2-{[(1-methyl-1H-pyrrol-2-yl)carbonyl]amino}-3-oxo-3-[(4-phenylbutyl)amino]propyl}benzoic acid | 521.57 | 520.1 | 0.0002 | | |
| 155-27 | 5-{(2S)-2-[(5-bromo-2-furoyl)amino]-3-oxo-3-[(4-phenylbutyl)amino]propyl}-2-(carboxymethoxy)benzoic acid | 587.43 | 585.0 | 0.0007 | | |
| 155-28 | 2-(carboxymethoxy)-5-{(2S)-2-(2-naphthoylamino)-3-oxo-3-[(4-phenylbutyl)amino]propyl}benzoic acid | 568.63 | 567.0 | 0.0005 | | |
| 155-29 | 2-(carboxymethoxy)-5-((2S)-3-oxo-3-[(4-phenylbutyl)amino]-2-{[(2R)-3,3,3-trifluoro-2-methoxy-2-phenylpropanoyl]amino}propyl)benzoic acid | 630.62 | 628.9 | 0.0001 | | |
| 155-30 | 2-(carboxymethoxy)-5-{(2S)-2-{[(2R)-2-methoxy-2-phenylethanoyl]amino}-3-oxo-3-[(4-phenylbutyl)amino]propyl}benzoic acid | 562.62 | 561.1 | 0.0005 | 99 | 6.6 |

TABLE B-continued

| Ex. No. | Compound Name | M.W. | Observed Molecular ion (ES−) | Amount of compound (g) (after HPLC) | Purity by HPLC (220 nm) | Ret. Time (min.) |
|---|---|---|---|---|---|---|
| 155-31 | 2-(carboxymethoxy)-5-{(2S)-2-{[2-(4-fluorophenoxy)acetyl]amino}-3-oxo-3-[(4-phenylbutyl)amino]propyl}benzoic acid | 566.59 | 565.2 | 0.0005 | 95.2 | 6.78 |
| 55-32 | 2-(carboxymethoxy)-5-{(2S)-3-oxo-2-[(2-phenylacetyl)amino]-3-[(4-phenylbutyl)amino]propyl}benzoic acid | 532.60 | 531.2 | 0.0004 | 99 | 6.21 |
| 155-33 | 2-(carboyxmethoxy)-5-{(2S)-2-{[2-(2-chlorophenyl)acetyl]amino}-3-oxo-3-[(4-phenylbutyl)amino]propyl}benzoic acid | 567.04 | 565.1 | 0.0013 | 96.9 | 6.6 |
| 155-34 | 2-(carboxymethoxy)-5-{(2S)-2-{[2-(2-methoxyphenyl)acetyl]amino}-3-oxo-3-[(4-phenylbutyl)amino]propyl}benzoic acid | 562.62 | 561.0 | 0.0003 | | |
| 155-35 | 2-(carboxymethoxy)-5-{(2S)-2-{[2-(2-methylphenyl)acetyl]amino}-3-oxo-3-[(4-phenylbutyl)amino]propyl}benzoic acid | 546.62 | 545.2 | 0.0007 | 99 | 6.6 |
| 155-36 | 2-(carboxymethoxy)-5-{(2S)-2-{[2-(3-chlorophenyl)acetyl]amino}-3-oxo-3-[(4-phenylbutyl)amino]propyl}benzoic acid | 567.04 | 565.1 | 0.0005 | 99 | 6.84 |
| 155-37 | 2-(carboxymethoxy)-5-{(2S)-2-{[2-(3-methoxyphenyl)acetyl]amino}-3-oxo-3-[(4-phenylbutyl)amino]propyl}benzoic acid | 562.62 | 561.0 | 0.0001 | 99 | 6.29 |
| 155-38 | 2-(carboxymethoxy)-5-[(2S)-3-oxo-3-[(4-phenylbutyl)amino]-2-({2-[3-(trifluoromethyl)phenyl]acetyl}amino)propyl]benzoic acid | 600.59 | 599.0 | 0.0002 | 99 | 7.27 |
| 155-39 | 2-(carboxymethoxy)-5-{(2S)-2-{[2-(4-chlorophenyl)acetyl]amino}-3-oxo-3-[(4-phenylbutyl)amino]propyl}benzoic acid | 567.04 | 565.0 | 0.0002 | | |
| 155-40 | 2-(carboxymethoxy)-5-{(2S)-2-{[2-(4-methoxyphenyl)acetyl]amino}-3-oxo-3-[(4-phenylbutyl)amino]propyl}benzoic acid | 562.62 | 561.0 | 0.0003 | 99 | 6.21 |
| 155-41 | 2-(carboxymethoxy)-5-{(2S)-3-oxo-3-[(4-phenylbutyl)amino]-2-({2-[4-(trifluoromethyl)phenyl]acetyl}amino)propyl]benzoic acid | 600.59 | 589.9 | 0.0002 | | |
| 155-42 | 2-(carboxymethoxy)-5-{(2S)-3-oxo-2-[(4-phenylbutanoyl)amino]-3-[(4-phenylbutyl)amino]propyl}benzoic acid | 560.65 | 559.1 | 0.0017 | | |
| 155-43 | 2-(carboxymethoxy)-5-{(2S)-2-{[4-(4-methoxyphenyl)butanoyl]amino}-3-oxo-3-[(4-phenylbutyl)amino]propyl}benzoic acid | 590.68 | 589.1 | 0.0005 | 99 | 6.89 |
| 155-44 | 2-(carboxymethoxy)-5-{(2S)-3-oxo-2-[(5-oxo-5-phenylpentanoyl)amino]-3-[(4-phenylbutyl)amino]propyl}benzoic acid | 588.66 | 586.9 | 0.0001 | | |
| 155-45 | 2-(carboxymethoxy)-5-{(2S)-3-oxo-3-[(4-phenylbutyl)amino]-2-[(5-phenylpentanoyl)amino]propyl}benzoic acid | 574.68 | 573.0 | 0.0001 | | |
| 155-46 | 2-(carboxymethoxy)-5-[(2S)-3-oxo-3-[(4-phenylbutyl)amino]-2-(10-undecenoylamino)propyl]benzoic acid | 580.72 | 579.1 | 0.0005 | | |
| 155-47 | 2-(carboxymethoxy)-5-{(2S)-2-{[(3-methyl-2-thienyl)carbonyl]amino}-3-oxo-3-[(4-phenylbutyl)amino]propyl}benzoic acid | 538.62 | 537.0 | 0.0005 | 99 | 6.46 |
| 155-48 | 2-(carboxymethoxy)-5-((2S)-3-oxo-3-[(4-phenylbutyl)amino]-2-{[4-(2-thienyl)butanoyl]amino}propyl)benzoic acid | 566.68 | 565.0 | 0.0004 | | |
| 155-49 | 2-(carboxymethoxy)-5-{(2S)-3-oxo-3-[(4-phenylbutyl)amino]-2-[(3-thienylcarbonyl)amino]propyl}benzoic acid | 524.59 | 523.0 | 0.0004 | 99 | 5.93 |
| 155-50 | 5-{(2S)-2-[(1,3-benzodioxol-5-ylcarbonyl)amino]-3-oxo-3-[(4-phenylbutyl)amino]propyl}-2-(carboxymethoxy)benzoic acid | 562.58 | 561.1 | 0.0002 | 95.9 | 6.19 |
| 155-51 | 2-(carboxymethoxy)-5-{(2S)-3-oxo-3-[(4-phenylbutyl)amino]-2-[(3-quinolinylcarbonyl)amino]propyl}benzoic acid | 569.62 | 568.0 | 0.0003 | 99 | 5.95 |
| 155-52 | 2-(carboxymethoxy)-5-{(2S)-3-oxo-2-{[(2-oxo-2H-chromen-3-yl)carbonyl]amino}-3-[(4-phenylbutyl)amino]propyl}benzoic acid | 586.60 | 585.0 | 0.0007 | 96.1 | 6.75 |
| 155-53 | 2-(carboxymethoxy)-5-{(2S)-2-{[4-(methylsulfonyl)benzoyl]amino}-3-oxo-3-[(4-phenylbutyl)amino]propyl}benzoic acid | 596.66 | 594.9 | 0.0001 | 99 | 5.62 |
| 155-54 | 2-(carboxymethoxy)-5-{(2S)-2-{[2-methoxy-4-(methylsulfanyl)benzoyl]amino}-3-oxo-3-[(4-phenylbutyl)amino]propyl}benzoic acid | 594.69 | 593.1 | 0.0013 | 97.4 | 7.02 |
| 155-55 | 2-(carboxymethoxy)-5-{(2S)-3-oxo-3-[(4-phenylbutyl)amino]-2-{[2-(2-pyrimidinylsulfanyl)acetyl]amino}propyl)benzoic acid | 566.63 | 565.0 | 0.0004 | | |
| 155-56 | 2-(carboxymethoxy)-5-{(2S)-2-{[3-(4-chlorophenyl)propanoyl]amino}-3-oxo-3-[(4-phenylbutyl)amino]propyl}benzoic acid | 581.07 | 579.0 | 0.0002 | 99 | 7.21 |
| 155-57 | 2-(carboxymethoxy)-5-{(2S)-2-{[2-(3,5-dimethoxyphenyl)acetyl]amino}-3-oxo-3-[(4-phenylbutyl)amino]propyl}benzoic acid | 592.65 | 590.9 | 0.0001 | 99 | 6.39 |
| 155-58 | 5-{(2S)-2-[3-(1,3-benzodioxol-5-yl)propanoyl]amino}-3-oxo-3-[(4-phenylbutyl)amino]propyl}-2-(carboxymethoxy)benzoic acid | 590.63 | 589.1 | 0.0001 | 99 | 6.46 |
| 155-59 | 2-(carboxymethoxy)-5-{(2S)-2-{[(6-methyl-2-pyridinyl)carbonyl]amino}-3-oxo-3-[(4-phenylbutyl)amino]propyl}benzoic acid | 533.58 | 532.0 | 0.0000 | | |
| 155-60 | 5-{(2S)-2-{[(1-acetyl-4-pipendinyl)carbonyl]amino}-3-oxo-3-[(4-phenylbutyl)amino]propyl}-2-(carboxymethoxy)benzoic acid | 567.64 | 566.0 | 0.0002 | | |
| 155-61 | 2-(carboxymethoxy)-5-{(2S)-2-[(4-cyclohexylbenzoyl)amino]-3-oxo-3-[(4-phenylbutyl)amino]propyl}benzoic acid | 600.71 | 599.2 | 0.0014 | 99 | 9.01 |
| 155-62 | 2-(carboxymethoxy)-5-{(2S)-2-{[(5-chloro-2-thienyl)carbonyl]amino}-3-oxo-3-[(4-phenylbutyl)amino]propyl}benzoic acid | 559.04 | 557.0 | 0.0002 | 99 | 7.07 |
| 155-63 | 2-(carboxymethoxy)-5-{(2S)-2-{[(3-methyl-1H-inden-2-yl)carbonyl]amino}-3-oxo-3-[(4-phenylbutyl)amino]propyl}benzoic acid | 570.64 | 569.0 | 0.0001 | 99 | 7.44 |
| 155-64 | 2-(carboxymethoxy)-5-{(2S)-3-oxo-3-[(4-phenylbutyl)amino]-2-[(8-quinolinylcarbonyl)amino]propyl}benzoic acid | 569.62 | 568.1 | 0.0011 | 96.9 | 6.4 |
| 155-65 | 2-(carboxymethoxy)-5-{(2S)-2-{[(3,5-dimethyl-4-isoxazolyl)carbonyl]amino}-3-oxo-3-[(4-phenylbutyl)amino]propyl}benzoic acid | 537.57 | 536.0 | 0.0001 | 99 | 5.67 |
| 155-66 | 2-(carboxymethoxy)-5-{(2S)-2-{[(2,4-dimethyl-1,3-thiazol-5-yl)carbonyl]amino}-3-oxo-3-[(4-phenylbutyl)amino]propyl}benzoic acid | 553.64 | 554.0 (ES+) | 0.0001 | | |

TABLE B-continued

| Ex. No. | Compound Name | M.W. | Observed Molecular ion (ES−) | Amount of compound (g) (after HPLC) | Purity by HPLC (220 nm) | Ret. Time (min.) |
|---|---|---|---|---|---|---|
| 155-67 | 2-(carboxymethoxy)-5-{(2S)-2-{[3-(4-fluorophenyl)propanoyl]amino}-3-oxo 3-[(4-phenylbutyl)amino]propyl}benzoic acid | 564.61 | 563.1 | 0.0002 | 99 | 6.75 |
| 155-68 | 2-(carboxymethoxy)-5-{(2S)-2-{[(7-chloro-1-benzofuran-2-yl)carbonyl]amino}-3-oxo-3-[(4-phenylbutyl)amino]propyl}benzoic acid | 593.03 | 590.9 | 0.0007 | 99 | 7.57 |
| 155-69 | 2-(carboxymethoxy)-5-((2S)-3-oxo-3-[(4-phenylbutyl)amino]-2-{[(2S)-3,3,3 trifluoro-2-methoxy-2-phenylpropanoyl]amino}propyl)benzoic acid | 630.62 | 629.0 | 0.0004 | | |
| 155-70 | 2-(carboxymethoxy)-5-((2S)-3-oxo-3-[(4-phenylbutyl)amino]-2-{[(4,7,7-trimethyl-3-oxobicyclo[2.2.1]hept-2-yl)carbonyl]amino}propyl)benzoic acid | 592.69 | 591.1 | 0.0009 | | |
| 155-71 | 5-{(2S)-2-{[2-(3-acetyl-2,2-dimethylcyclobutyl)acetyl]amino}-3-oxo-3-[(4-phenylbutyl)amino]propyl}-2-(carboxymethoxy)benzoic acid | 580.68 | 579.1 | 0.0001 | 99 | 5.86 |
| 155-72 | 5-{(2S)-2-[(1-adamantylcarbonyl)amino]-3-oxo-3-[(4-phenylbutyl)amino]propyl}-2-(carboxymethoxy)benzoic acid | 576.69 | 575.2 | 0.0014 | 96.1 | 7.72 |
| 155-73 | 2-(carboxymethoxy)-5-{(2S)-3-oxo-3-[(4-phenylbutyl)amino]-2-[(tetrahydro 3-furanylcarbonyl)amino]propyl}benzoic acid | 512.56 | 511.1 | 0.0004 | 99 | 4.74 |
| 155-74 | 2-(carboxymethoxy)-5-{(2S)-2-[(3-fluoro-2-methylbenzoyl)amino]-3-oxo-3-[(4-phenylbutyl)amino]propyl}benzoic acid | 550.59 | 549.2 | 0.0020 | 69.7 | 6.8 |
| 155-75 | 2-(carboxymethoxy)-5-{(2S)-2-{[(2,6-dimethoxy-3-pyridinyl)carbonyl]amino}-3-oxo-3-[(4-phenylbutyl)amino]propyl}benzoic acid | 579.61 | 578.2 | 0.0029 | 98.7 | 6.69 |
| 155-76 | 2-(carboxymethoxy)-5-{(2S)-2-[(2,3-dihydro-1,4-benzodioxin-2-ylcarbonyl)amino]-3-oxo-3-[(4-phenylbutyl)amino]propyl}benzoic acid | 576.61 | 575.0 | 0.0006 | 99 | 7.06/7.21 |
| 155-77 | 2-(carboxymethoxy)-5-{(2S)-2-[(2-fluoro-5-methylbenzoyl)amino]-3-oxo-3-[(4-phenylbutyl)amino]propyl}benzoic acid | 550.59 | 549.2 | 0.0007 | 95.5 | 6.86 |
| 155-78 | 5-{(2S)-2-({2-[(1S,4S)bicyclo[2.2.1]hept-2-yl]acetyl}amino)-3-oxo-3-[(4-phenylbutyl)amino]propyl}-2-(carboxymethoxy)benzoic acid | 550.65 | 549.1 | 0.0004 | | |
| 155-79 | 2-(carboxymethoxy)-5-{(2S)-3-oxo-2-[(2-phenoxypropanoyl)amino]-3-[(4-phenylbutyl)amino]propyl}benzoic acid | 562.62 | 561.2 | 0.0009 | 99 | 6.98/7.14 |
| 155-80 | 2-(carboxymethoxy)-5-{(2S)-3-oxo-2-({[(1R,2S,3S,4S)-5-oxotricyclo[2.2.1.0~2,6~]hept-3-yl]carbonyl}amino)-3-[(4-phenylbutyl)amino]propyl}benzoic acid | 548.59 | 547.1 | 0.0012 | 99 | 5.15 |

EXAMPLE 156 Two-dimensional library of 5-substituted-2-carbomethoxybenzoic Acids

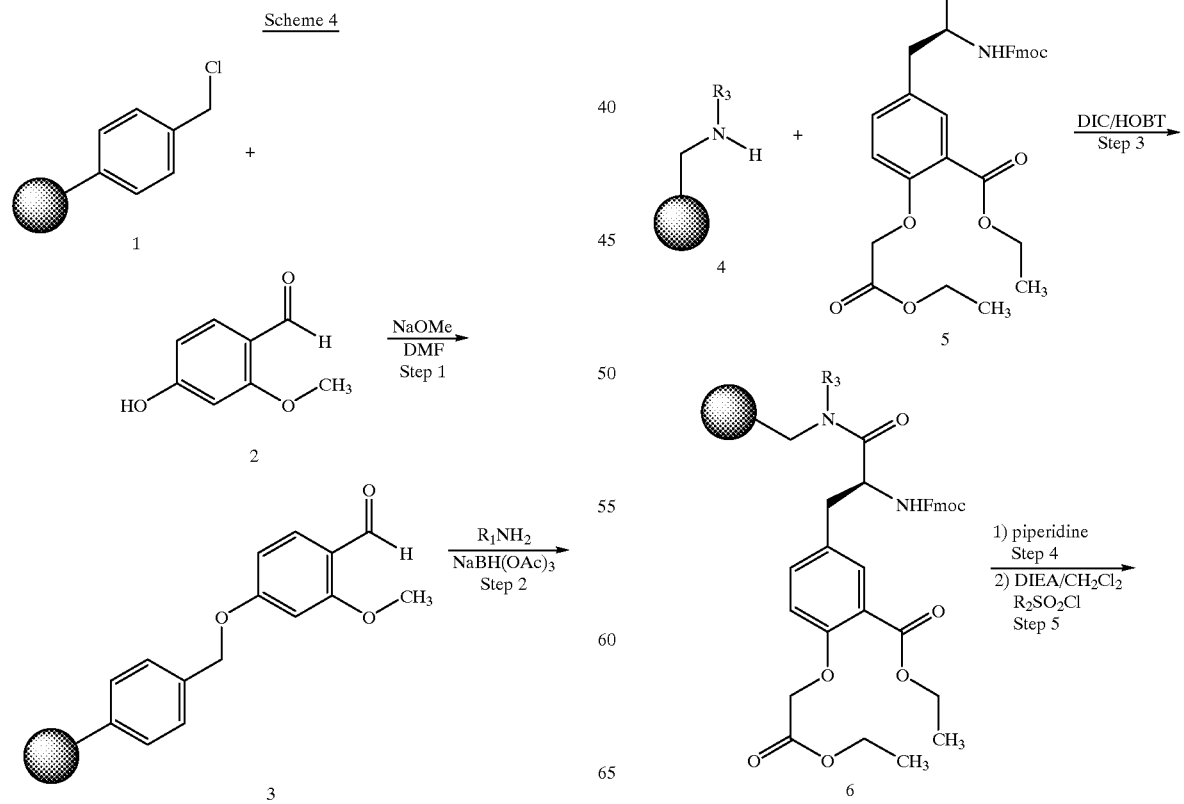

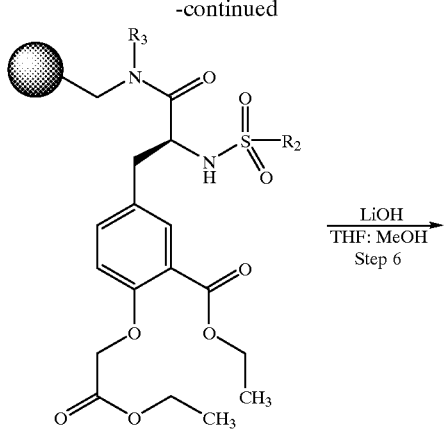

7

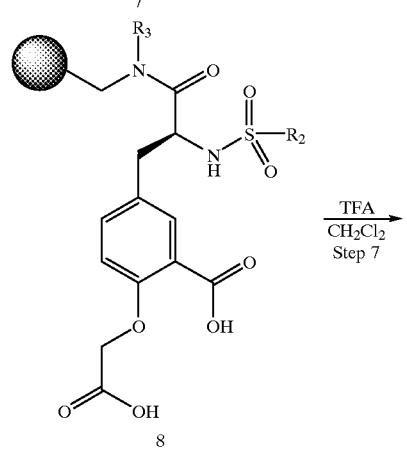

8

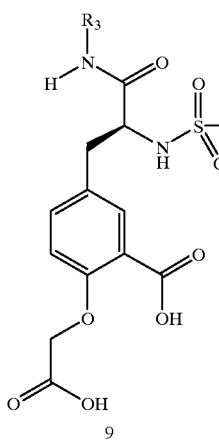

9

Chemistry Summary

The combination solid-phase/solution-phase synthetic sequence was designed to prepare a 6×10 two-dimensional library of 5-substituted-2-carboxymethoxybenzoic acids in a 96-well format as illustrated in Scheme 4. The synthesis was based on the use of the AMEBA linker (acid sensitive methoxybenzaldehyde, 3), selected due to its ease of cleavage and versatility in the reductive amination step, and the intermediate 5, synthesized in a seven step sequence as described below. The key resin 3 was synthesized by treating Merrifield resin with 2-methoxy-4-hydroxybenzaldehyde according to the literature procedure (Fivush, A. M.; Willson, T. M. *Tetrahedron Lett.* 1997, 38; 7151. Sarantakis, D.; Bicksler, J. J. *Tetrahedron Lett.*, 1997, 38, 7325). The functionalized resin 3 was treated with the first diversity element, a primary amine, and sodium triacetoxyborohydride to provide six different secondary amine resins, 4. Attachment of 5 to each individual resin was performed utilizing the standard conditions of DIC/HOBt in DMF. A deprotection/sulfonamide formation (Kim, S. W.; Hong, C. Y.; Lee, K.; Lee, E. J.; Koh, J. S. *Bio. and Med Chem. Letters*. 1998, 8, 735) protocol was followed to attach the next diversity element to give 7. Hydrolysis of the diester was then followed by removal of the products from the resin with 20% TFA/CH$_2$Cl$_2$.

Intermediate Synthesis

Scaffold 5 (see Scheme 4 above), (2S)-3-[3-ethyoxycarbonyl)-4-(2-ethoxy-2-oxoethoxy)phenyl]-2-{[(9H-fluoren-9-ylmethoxy)carbonyl]amino}propanoic acid, was prepared as described in Example 154 above.

| Diversity Elements | |
|---|---|
| N-Terminal Sulfonyl Chlorides (commercially available): | |
| Name | Cpd # |
| benzene sulfonyl chloride | 18 |
| 2,4-difluorobenzene sulfonyl chloride | 19 |
| 1-methylimidazole-4-sulfonyl chloride | 20 |
| 4-(n-butoxy)benzene sulfonyl chloride | 21 |
| naphthalene sulfonyl chloride | 22 |
| 2-nitrobenzene sulfonyl chloride | 23 |
| octane sulfonyl chloride | 24 |
| 8-quinoline sulfonyl chloride | 25 |
| 2,3,5,6-tetramethylbenzene sulfonyl chloride | 26 |
| trans-β-styrene sulfonyl chloride | 27 |
| N-acetylsulfanilylchloride | 28 |
| benzo-2,1,3-thiadiazole-4-sulfonyl chloride | 29 |
| 4-cyanobenzene sulfonyl chloride | 30 |
| 3,4-dimethoxybenzene sulfonyl chloride | 31 |
| C-Terminal Amines: | |
| Name | Cpd # |
| a) Commercially available: | |
| n-amylamine | 32 |
| 4-phenylbutyamine | 33 |
| b) Synthesized | |

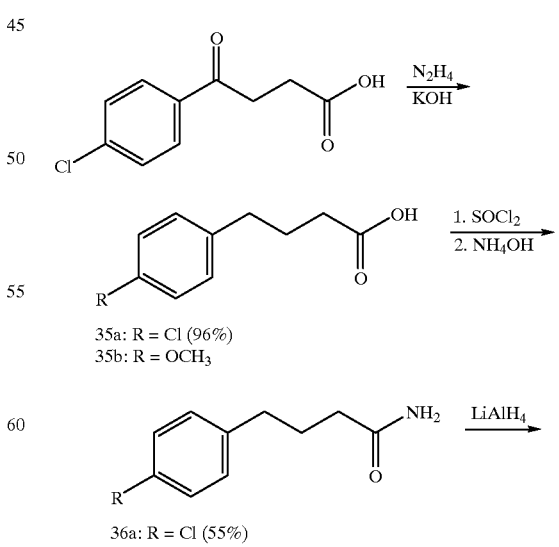

35a: R = Cl (96%)
35b: R = OCH$_3$

36a: R = Cl (55%)
36b: R = OCH$_3$ (57–79%)

-continued

Diversity Elements

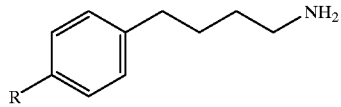

37a: R = Cl (98%)
37b: R = OCH₃ (95%)

Two of the six amines used in this library were commercially available, the remaining four amines 37a, 37b, 39 and 44 were prepared synthetically. Wolff-Kishner reduction of 4-(p-chlorophenyl)-4-oxobutanoic acid gave 4-(p-chlorophenyl)butanoic acid (35a) in 96% yield, which was converted to 36a (55%). 4-(p-Methoxyphenyl)butylamine (37b) was similarly synthesized with equal results from commercially available 35b. Benzyl ethylamine ether (39) was prepared in one step from ethanolamine and benzyl chloride in 10% yield.

4-(p-chlorophenyl)butanoic acid (35a). A mixture of 3-(4-chlorobenzoyl) propionic acid (34) (2.50 g, 12.0 mmol), KOH (s) (1.75 g, 31.2 mmol), and hydrazine monohydrate (1.25 mL, 25.8 mmol) in 12.5 mL of diethylene glycol was refluxed azeotropically at 120–130° C. for 90 min to remove water. The reaction mixture was then refluxed at 170° C. for 3 h, cooled to RT, diluted with 12.5 mL of water, and poured into 15 mL 2.5 N HCl(aq). The precipitate was filtered off, dissolved in $CH_2Cl_2$, and the solvent removed to give 35a (2.23 g, 96%) as a white solid. UV $\lambda_{max}$ 223 (8980, 95% ETHANOL); $^1$H NMR (400 MHz, $CDCl_3$) δ 7.26 (d, J=7 Hz, 2H), 7.12 (d, J=8 Hz, 2H), 2.66 (t, J=4 Hz, 2H), 2.38 (t, J=4 Hz, 2H), 1.96 (m, 2H); $^{13}$C NMR ($CDCl_3$) δ 179.3, 140.0, 132.2, 130.2, 128.9, 34.7, 33.4, 26.4; IR (drift) 3063 (s), 3051 (s), 2955 (s), 2923 (s,b), 2905 (s), 2814, 2797, 2493 (b), 2466, 2413, 2367 (b), 2321, 1706 (s), 1492 (s), 1212 (s), $cm^{-1}$; MS (EI) m/z (rel. intensity) 198 (M+, 22), 200 (7), 198 (22), 140 (32), 139 (17), 138 (99), 127 (15), 125 (48), 103 (10), 89 (13), 60 (9); HRMS (EI) calcd for 198.0448, found 198.0441.

4-(p-chlorophenyl)butanamide (36a). A mixture of 35a (1.880 g, 10.1 mmol) and thionyl chloride (3.0 mL, 40.9 mmol) in 15 mL $CHCl_3$ was stirred at reflux (75° C.) for 4 h. Solvent and excess thionyl chloride were removed in vacuo, and residue was twice diluted with 7.5 mL toluene and evaporated to remove traces of thionyl chloride. To a solution of the residue in 3 mL toluene was slowly added 9 mL of cold concentrated $NH_4OH$. The precipitate was filtered off and recrystallized in $CHCl_3$/heptane to give 36a (1.02 g, 55%) as a white solid. UV $\lambda_{max}$ 224 (9300, 95% ETHANOL). $^1$H NMR (400 MHz, $CDCl_3$) δ 7.25 (d, J=8 Hz, 2H), 7.12 (d, J=8 Hz, 2H), 5.31 (s, 2H), 2.66 (t, J=8 Hz, 2H), 2.23 (t, J=7 Hz, 2H), 1.98 (m, 2H); $^{13}$C NMR ($CDCl_3$) δ 175.4, 140.2, 134.5, 130.2, 128.9, 35.1, 34.8, 27.0; IR (drift) 3434, 2948, 2282 (w), 1901 (w), 1655 (s), 1607, 1491, 1420, 1306, 1094, 1016, 836 (s), 825, 804, 666, $cm^{-1}$. Calcd for $C_{10}H_{12}ClNO$: C, 60.76; H, 6.12; N, 7.09; Cl, 17.94. Found: C, 60.60; H, 6.11; N, 6.96.

4-(p-chlorophenyl)butylamine (37a). (Ali, F. E.; Dandridge, P. A.; Gleason, J. G.; Krell, R. D.; Kruse, C. H.; Lavanchy, P. G; Snader, K. M. *J. Med Chem.*, 1982, 25, 947). To a stirred suspension of lithium aluminum hydride (2.40 g, 63.2 mmol) in 65 mL diethyl ether was added slowly a solution of (3.12 g 15.8 mmol) of 36a in 28 mL THF, and stirred at rt for 1 h. To the reaction mixture was slowly added 4 mL water, 4 mL 5 N NaOH(aq), and 12 mL water. The organics were removed from the emulsion which was dissolved in water and extracted with ether. The organic portions were dried over $Na_2SO_4$(s), and condensed to give 37a (2.76 g, 95%) as an oil. UV $\lambda_{max}$ 224 (7600, 95% ETHANOL). $^1$H NMR (400 MHz, $CDCl_3$) δ 7.23 (m, 2H), 7.10 (d, J=8 Hz, 2H), 2.74 (t, J=7 Hz, 2H), 2.60 (t, J=8 Hz, 2H), 2.25 (s, 2H), 1.64 (m, 2H), 1.49 (m, 2H). $^{13}$C NMR ($CDCl_3$) δ 141.2, 131.8, 130.1, 128.8, 42.3, 35.4, 33.6, 29.0; IR (liq.) 3365 (b), 3296 (b), 3026, 2933 (s), 2858 (s), 2170 (w), 1996 (w), 1576, 1492 (s), 1460, 1093 (s), 1016 (s), 831, 821, 804, $cm^{-1}$; HRMS (FAB) calcd for $C_{10}H_{14}ClN+H_1$ 184.0893, found 184.0879.

4-(p-methoxyphenyl)butanamide (36b). A mixture of 4-(p-methoxyphenyl)butyric acid (35b) (6.50 g, 33.5 mmol) and thionyl chloride (10.0 mL, 137 mmol) in 50 mL $CHCl_3$ was stirred at reflux for 5.5 h. Solvent and excess thionyl chloride were removed in vacuo, and residue was twice diluted with 25 mL toluene and evaporated to remove traces of thionyl chloride. To a solution of the residue in 10 mL toluene was added slowly 30 mL of cold concentrated $NH_4OH$. The precipitate was filtered off and recrystallized in $CHCl_3$/heptane to give 36b (3.68 g, 57%) as a white solid. UV $\lambda_{max}$ 223 (10200, 95% EtOH); $^1$H NMR (400 MHz, CDCl3) δ 7.10 (d, J=9 Hz, 2H), 6.84 (d, J=9 Hz, 2H), 5.44 (s, 2H), 3.80 (s, 3H), 2.63 (t, J=7 Hz, 2H), 2.23 (d, J=8 Hz, 2H), 1.96 (m, 2H); 13C NMR (CDCl3) δ 175.5, 158.3, 133.8, 129.7, 114.2, 55.6, 35.4, 34.5, 27.4; IR (drift) 3366 (s), 2479 (w), 2355 (w), 2285 (w), 2053 (w), 1993 (w), 1656 (s), 1628 (s), 1512 (s), 1416 (s), 1304 (s), 1243 (s), 1230 (s), 1031 (s), 838 (s), $cm^{-1}$. Anal. Calcd for $C_{11}H_{15}NO_2$: C, 68.37; H, 7.82; N, 7.25. Found: C, 68.42; H, 8.03; N, 7.24.

4-(p-methoxyphenyl)butylamine (37b). (Ali, F. E.; Dandridge, P. A.; Gleason, J. G.; Krell, R. D.; Kruse, C. H.; Lavanchy, P. G; Snader, K. M. *J. Med Chem.*, 1982, 25, 947). To a stirred suspension of lithium aluminum hydride (4.40 g, 116 mmol) in 120 mL diethyl ether was added dropwise a solution of 36b (5.60 g, 29.0 mmol) in 10 mL THF, and stirred at rt for 1 h. To the reaction mixture was added 7.5 mL water, 7.5 mL 5 N NaOH(aq), and 20 mL water. The organics were removed from the emulsion which was dissolved in water and extracted with ether. The organic portions were dried over $Na_2SO_4$(s), and condensed to give 37b (5.10 g, 98%) as an oil. UV $\lambda_{max}$ 223 (9410, 95% EtOH). (400 MHz, $CDCl_3$) δ 7.10 (d, J=9 Hz, 2H), 6.83 (d, J=9 Hz, 2H), 3.79 (s, 3H), 2.71 (t, J=7 Hz, 2H), 2.58 (t, J=7 Hz, 2H), 1.63 (m, 2H), 1.48 (m, 2H); IR (liq.) 2933 (s), 2856, 2145 (w), 2059 (w), 1996 (w), 1612 (s), 1584 (s), 1513 (s), 1461, 1442, 1246 (s), 1178, 1034 (s), 827, 822, $cm^{-1}$. $^1$HRMS (FAB) calcd for $C_{11}H_{17}NO+H_1$ 180.1388, found 180.1387.

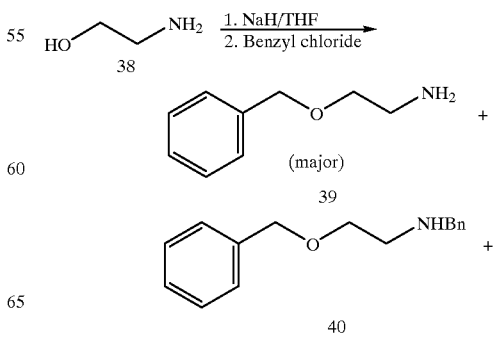

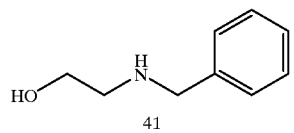

2-(benzyloxy)ethylamine (39). (Hu, X. E.; Cassady, J. M. Synthetic Comm., 1995, 25, 907). To a solution of distilled ethanolamine (38) (1.81 mL, 30.0 mmol) in 30 mL of dry THF, was added NaH (1.2 g 30.0 mmol) as a 60% dispersion in mineral oil, in small portions at rt. The mixture was stirred at reflux for 30 min., benzyl chloride (2.88 mL, 25.0 mmol) was added, and stirred at reflux for an additional 4.5 h. The mixture was cooled to rt, 10 mL water was added, and solvent evaporated in vacuo. The residue was partitioned between 1 N HCl(aq) and $CH_2Cl_2$. The aqueous layer was extracted with $CH_2Cl_2$ to remove side product 40. The aqueous portion was adjusted to pH 13 with 10% NaOH(aq) and extracted with $CH_2Cl_2$. The extracts were condensed and purified by flash chromatography (10% MeOH (saturated with $NH_3$)/$CH_2Cl_2$) to give 39 (0.24 g, 10%) as a yellow oil. $R_f$(10% MeOH(saturated with $NH_3$)/$CH_2Cl_2$)= 0.47; UV $\lambda_{max}$ 251 (162, 95% ETHANOL); $^1$H NMR (400 MHz, $CDCl_3$) δ 7.31 (m, 5H), 4.55 (s, 2H), 3.53 (t, J=5 Hz, 2H), 2.90 (t, J=5, 2H), 1.68 (s, 2H); $^{13}$C NMR (CDCl3) δ 138.7, 128.8, 128.1, 128.0, 73.5, 72.9, 42.3; IR (liq.) 3371, 3302 (b), 3030, 2924 (b), 2860 (s), 2202 (w), 1955 (w), 1496, 1453 (s), 1356, 1101 (s), 1069, 1028, 739 (s), 698 (s), $cm^{-1}$. HRMS (FAB) calcd for $C_9H_{13}NO+H_1$ 152.1075, found 152.1074.

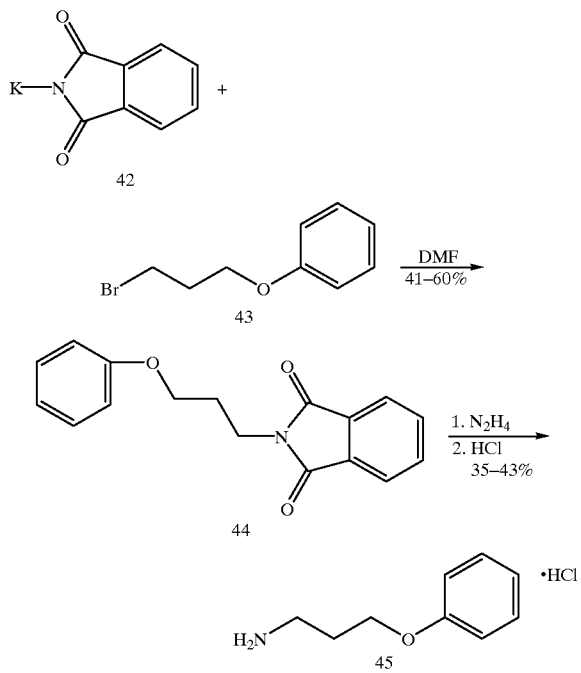

3-Phenoxypropylphthalimide (44). A mixture of 7.41 g (40.0 mmol) of potassium phthalimide and 6.30 mL (40.0 mmol) of 3-phenoxypropylbromide in 100 mL DMF was stirred at reflux (165° C.) under $N_2$(g) for 90 min. Mixture was cooled and filtered, filtrate was condensed in vacuo. Residue was recrystallized from 95% ethanol to give 44 (6.68 g, 58%) as a white solid. UV $\lambda_{max}$ 222 (41700, 95% ETHANOL). $^1$H NMR (400 MHz, CDCl3) δ 7.85 (m, 2H), 7.72 (m, 2H), 7.24 (t, J=10 Hz, 2H), 6.92 (t, J=7 Hz, 4H), 6.82 (d, J=4 Hz, 2H), 4.03 (t, J=6 Hz, 2H), 3.92 (t, J=4 Hz, 2H), 2.20 (t, J=3 Hz, 2H); $^{13}$C NMR (CDCl3) δ 168.7, 134.7, 134.3, 132.6, 129.7, 124.0, 123.6, 121.1, 114.9, 65.9, 35.9, 28.7; IR (drift) 2474 (w), 2431 (w), 2417 (w), 2339 (w), 2305 (w), 1770, 1705 (s), 1600, 1397, 1388, 1249 (s), 1233, 756, 721 (s), 712, $cm^{-1}$. HRMS (FAB) calcd for $C_{17}H_{15}NO_3+H_1$ 282.1130, found 282.1129.

3-Phenoxypropylamine hydrochloride(45). (Lever, O. W., Jr.; Bell, L. N.; McGuire, H. M.; Ferone, R. J. Med. Chem., 1985, 28I, 1873). A mixture of 6.95 g (24.8 mmol) of 44 and 3.12 mL (99.3 mmol) of 98% hydrazine in 80 mL 95% ethanol was stirred at reflux (85° C.) under $N_2$(g) for 3 h. Mixture was cooled and white precipitate was dissolved in 250 mL water, mixed with 20 mL 10% NaOH(aq), extracted with diethyl ether. Ether extracts were washed with water, acidified with 60 mL 1 N HCl(aq), and condensed in vacuo. Residue was recrystallized from ethanol-ether to give 45 (2.02 g, 43%) as a white solid. UV $\lambda_{max}$ 222 (41700, 95% ETHANOL). $^1$H NMR (400 MHz, DMSO-$d_6$) δ 8.00 (s), 7.29 (t, J=4 Hz, 2H), 6.93 (m, 3H), 4.05 (t, J=3 Hz, 2H), 3.31 (s, 2H), 2.94 (s, 2H), 2.02 (m, 2H); $^{13}$C NMR (DMSO-d6) δ 159.1, 130.3, 121.5, 115.3, 65.3, 37.1, 27.7; IR (drift) 3036 (s), 3029 (s,b), 3009 (s,b), 2963 (s,b), 2938 (s), 2925 (s), 2428 (w), 2351 (w), 2256 (w), 2203 (w), 2052 (w), 1598 (s), 1258 (s), 749 (s), 696 (s), $cm^{-1}$. Anal. Calcd for $C_9H_{13}NO\cdot HCl$: C, 57.60; H, 7.52; N, 7.46; Cl, 18.89. Found: C, 57.45; H, 7.75; N, 7.36.

Library Synthesis

The production of the library required seven steps using solid support. Three steps were carried out in a 96 well format. The AMEBA (acid sensitive methoxy benzaldehyde) linker was prepared by reacting Merrifield resin and 4-hydroxy-2-methoxybenzaldehyde with sodium methoxide (see Scheme 4). The AMEBA resin was then treated with the corresponding amine and NaBH(OAc)$_3$ to give the corresponding reductive amination product. The tyrosine scaffold (5) was then coupled to the various amine resins using DIC and HOBT in DMF. The Fmoc protecting group was then removed with piperidine/DMF (1:1). The resin was then plated in a 96 well Robbins block then coupled to the corresponding sulfonyl chloride with DIEA in $CH_2Cl_2$. The diethyl ester was hydrolyzed with excess LiOH in THF: MeOH (1:1) for 16 h at rt to yield the dicarboxylic acid on resin. The use of THF: MeOH (1:1) is believed to be crucial for this hydrolysis. The product was then cleaved from the resin with 20% TFA/$CH_2Cl_2$ solution. The resin was cleaved twice to yield the maximum possible product. The second cleavage resulted in approximately 10–20% more product without any change in purity levels.

Step 1: Preparation of AMEBA Linker A suspension of Merrifield resin (2.10 g, 3.47 mmol) in 50 mL of DMF was treated with solid sodium methoxide (560 mg, 10.4 mmol). To the solution was added 4-hydroxy-2-methoxybenzaldehyde (1.58 g, 10.4 mmol). The reaction mixture was heated to 60–70° C. for 24 h. The resin was then washed with DMF, MeOH, water, MeOH, $CH_2Cl_2$, and MeOH (3×10 mL). IR indicated strong absorption at 1681 $cm^{-1}$.

Step 2: Reductive Amination A suspension of AMEBA (1.04 g 1.12 mmol) in 25 mL of $C_2H_4Cl_2$ was treated with phenylbutyl amine (0.36 mL, 2.3 mmol) and NaBH(OAc)$_3$ (479 mg, 2.26 mmol). The reaction mixture was stirred at rt for 3 h. The resin was then washed with $CH_2Cl_2$, DMF, MeOH and $CH_2Cl_2$ (3×10 mL). IR indicated disappearance of strong absorption at 1681 $cm^{-1}$.

Step 3: Coupling Resin to Intermediate 5 A suspension of resin (734 mg, 0.751 mmol) in 20 mL of DMF was treated with tyrosine scaffold 5 (632 mg, 1.13 mmol), hydroxybenzotriazole (HOBT) (24 mg, 0.18 mmol), diisopropyl carbodiimide (DIC) (175 µL, 1.12 mmol). The reaction mixture was stirred at rt for 2 h. The resin was tested for the presence of any secondary amine using the choranil test. A sample of resin 1–5 mg was mixed with one drop of 2% acetaldehyde in DMF and one drop of 2% chloranil in DMF. After 5 min the resin showed no color change; a control containing a secondary amine stained blue (Vojkovsky T. *Peptide Research* 1995, 4,236). The resin was washed with DMF, $CH_2Cl_2$, MeOH, $CH_2Cl_2$ (3×10 mL).

Step 4: Fmoc Removal Resin (1.14 g, 0.751 mmol) was suspended in 10 mL of piperidine/DMF (1:5) and stirred for 30 min. at rt. The resin was washed with DMF, $CH_2Cl_2$, MeOH, $CH_2Cl_2$ (3×10 mL).

Step 5: Coupling Resin to Sulfonyl Chloride The resin was plated in a 96 well Robbins block (approx. 62 mg, 0.045 mmol), added to each well as a slurry in DMF/$CH_2Cl_2$. The resin was filtered and dried. Standard solutions of sulfonyl chloride (0.9 M in $CH_2Cl_2$) and DIEA (1.8 M in $CH_2Cl_2$) were prepared. To the resin in each well was added 0.5 mL $CH_2Cl_2$, 0.25 mL DIEA solution, and then 0.25 mL of the standard sulfonyl chloride solution. The Robbins block was then rotated at rt for 2.5 h. The resin was filtered and washed with $CH_2Cl_2$, DMF, MeOH (2×1 mL), then 1 mL $CH_2Cl_2$.

Step 6: Hydrolysis of Esters A standard solution of LiOH (0.9 M in 1:1 THF/MeOH) was prepared. The resin in each well was treated with 1 mL of standard LiOH solution. The Robbins block was rotated at rt for 16 h. The resin was filtered and washed with $CH_2Cl_2$, DMF, MeOH (2×1 mL), then 1 mL $CH_2Cl_2$.

Step 7: Cleavage The resin (approx. 62 mg, 0.045 mmol) in each well was treated with 0.50 mL of TFA/$CH_2Cl_2$ (1:5). The Robbins block was rotated for 30 min. The resin was washed with $CH_2Cl_2$ (0.75 mL) collecting the filtrate. Resin was rinsed a second time into a second collection plate with $CH_2Cl_2$ (1.0 mL).

Purification

The entire library was purified by reverse phase HPLC. Half of the library was, however, lost during purification. The average purity, based on four original and six different standards, after purification of the library average purity was 75±13% by analytical HPLC. The average yield after purification was 10% (1–2 mg per well on average). The preparative HPLC system used a Gilson 215 liquid robotics autosampler/fraction collector. The chromatography utilized a three-pump system of Rainin pump heads equipped with 10 mL/min or 50 mL/min pump solvent delivery heads and a Gilson solvent mixing chamber. Two pumps were used for solvent delivery, and one was used for flushing the system at the completion of the series of chromatography runs. UV absorbance was monitored using a Knauer variable wavelength UV detector equipped with a 10 mm path length analytical flow cell. The entire system was controlled by Gilson Unipoint software v. 1.65 which was used for data acquisition and analysis.

Samples were prepared for injection by dissolving each in 1 mL MeOH and housing them in 96-well microtiter plates (2 mL/well). Injections for the chromatography loaded the entire sample into a 2.0 mL injection loop installed on the Gilson 819/Rheodyne Injector Module.

The HPLC method used in this study is as follows:

Column: YMC GuardPack C8 (20×50 mm, 5 µ, 120 A)

Mobile A: water+0.05% trifluoroacetic acid (TFA)

Mobile B: acetonitrile

Flow Rate. 10 mL/min

Gradient: 10% B 0–2 min, 10–100% B 2–23 min, 100% B 23–25 min, re-equilibrate for 3 min Detection cell: UV absorbance at 220 nm, Knauer UV detector with 10 mm flow Fraction Collection: Gilson 215, 15% AUFS threshold, 9 mL maximum/tube in 13×100 mm disposable tubes Mass Spectrometry Each of the recovered compounds was analyzed by mass spectrometry after reverse phase HPLC. Only 28 compound having a covered mass greater than 0.1 mg were positively identified by a molecular ion peak.

Library Compounds (Examples 156-1 to 156-28)

The following compounds were obtained in the library

TABLE C

| Ex. No. | Compound Name | Mol Wt. | MS (ES+) Ion Observed | Mass Recovered, g | Final HPLC Purity at 220 nm | Retention Time, min |
|---|---|---|---|---|---|---|
| 156-1 | 2-(carboxymethoxy)-5-((2S)-3-{[4-(4-chlorophenyl)butyl]amino}-2-{[(2,4-difluorophenyl)sulfonyl]amino}-3-oxopropyl)benzoic acid | 625.05 | 626.3 | 0.0014 | | |
| 156-2 | 5-((2S)-2-{[(4-butoxyphenyl)sulfonyl]amino}-3-{[4-(4-chlorophenyl)butyl]amino}-3-oxopropyl)-2-(carboxymethoxy)benzoic acid | 661.17 | 662.4 | 0.0015 | | |
| 156-3 | 2-(carboxymethoxy)-5-{(2S)-3-{[4-(4-chlorophenyl)butyl]amino}-2-[(1-naphthylsulfonyl)amino]-3-oxopropyl}benzoic acid | 639.13 | 640.3 | 0.0018 | | |
| 156-4 | 2-(carboxymethoxy)-5-((2S)-3-{[4-(4-chlorophenyl)butyl]amino}-2-{[(2-nitrophenyl)sulfonyl]amino}-3-oxopropyl)benzoic acid | 634.06 | 635.3 | 0.0015 | | |
| 156-5 | 2-(carboxymethoxy)-5-{(2S)-3-{[4-(4-chlorophenyl)butyl]amino}-3-oxo-2-[(8-quinolinylsulfonyl)amino]propyl}benzoic acid | 640.11 | 641.2 | 0.0018 | | |
| 156-6 | 2-(carboxymethoxy)-5-((2S)-3-{[4-(4-chlorophenyl)butyl]amino}-3-oxo-2-{[(2,3,5,6-tetramethylphenyl)sulfonyl]amino}propyl)benzoic acid | 645.17 | 646.4 | 0.0009 | 78.316 | 5.71 |
| 156-7 | 2-(carboxymethoxy)-5-[(2S)-3-{[4-(4-chlorophenyl)butyl]amino}-3-oxo-2-({[(E)-2-phenylethenyl]sulfonyl}amino)propyl]benzoic acid | 615.10 | 616.3 | 0.0009 | 59.937 | 5.32 |
| 156-8 | 2-(carboxymethoxy)-5-{(2S)-3-{[4-(4-methoxyphenyl)butyl]amino}-3-oxo-2-[(phenylsulfonyl)amino]propyl}benzoic acid | 584.65 | 585.2 | 0.0014 | 82.814 | 4.55 |
| 156-9 | 2-(carboxymethoxy)-5-((2S)-2-{[(2,4-difluorophenyl)sulfonyl]amino}-3-{[4-(4-methoxyphenyl)butyl]amino}-3-oxopropyl)benzoic acid | 620.63 | 621.2 | 0.0018 | 83.333 | 4.70 |
| 156-10 | 4-((2S)-2-{[(4-butoxyphenyl)sulfonyl]amino}-3-{[4-(4-methxoyphenyl)butyl]amino}-3-oxopropyl)-2-(carboxymethoxy)benzoic acid | 656.75 | 657.2 | 0.0015 | | |
| 156-11 | 2-(carboxymethoxy)-5-{(2S)-3-{[4-(4-methoxyphenyl)butyl]amino}-2-[(1- | 634.71 | 635.2 | 0.0010 | | |

TABLE C-continued

| Ex. No. | Compound Name | Mol Wt. | MS (ES+) Ion Observed | Mass Recovered, g | Final HPLC Purity at 220 nm | Retention Time, min |
|---|---|---|---|---|---|---|
| 156-12 | 2-(carboxymethoxy)-5-((2S)-3-{[4-(4-methoxyphenyl)butyl]amino}-2-{[(2-nitrophenyl)sulfonyl]amino}-3-oxopropyl}benzoic acid naphthylsulfonyl)amino]-3-oxopropyl}benzoic acid | 629.65 | 630.1 | 0.0011 | | |
| 156-13 | 2-(carboxymethoxy)-5-{(2S)-3-{[4-(4-methxoyphenyl)butyl]amino}-3-oxo-2-[(8-quinolinylsulfonyl)amino]propyl}benzoic acid | 635.70 | 636.2 | 0.0020 | 71.512 | 4.48 |
| 156-14 | 2-(carboxymethoxy)-5-((2S)-3-{[4-(4-methoxyphenyl)butyl]amino}-3-oxo-2-{[(2,3,5,6-tetramethylphenyl)sulfonyl]amino}propyl)benzoic acid | 640.76 | 641.2 | 0.0012 | | |
| 156-15 | 2-(carboxymethoxy)-5-[(2S)-3-{[4-(4-methoxyphenyl)butyl]amino}-3-oxo-2-({[(E)-2-phenylethenyl]sulfonyl}amino)propyl]benzoic acid | 610.69 | 611.2 | 0.0011 | | |
| 156-16 | 2-(carboxymethoxy)-5-{(2S)-3-oxo-3-[(3-phenoxypropyl)amino]-2-[(phenylsulfonyl)amino]propyl}benzoic acid | 556.59 | 557.2 | 0.0012 | | |
| 156-17 | 2-(carboxymethoxy)-5-{(2S)-2-{[(2,4-difluorophenyl)sulfonyl]amino}-3-oxo-3-[(3-phenoxypropyl)amino]propyl}benzoic acid | 592.57 | 593.1 | 0.0002 | | |
| 156-18 | 5-{(2S)-2-{[(4-butoxyphenyl)sulfonyl]amino}-3-oxo-3-[(3-phenoxypropyl)amino]propyl}-2-(carboxymethoxy)benzoic acid | 628.70 | 629.2 | 0.0010 | 98.744 | not available |
| 156-19 | 2-(carboxymethoxy)-5-{(2S)-2-[(1-naphthylsulfonyl)amino]-3-oxo-3-[(3-phenoxypropyl)amino]propyl}benzoic acid | 606.65 | 607.2 | 0.0007 | | |
| 156-20 | 2-(carboxymethoxy)-5-{(2S)-2-{[2-nitrophenyl)sulfonyl]amino}-3-oxo-3-[(3-phenoxypropyl)amino]propyl}benzoic acid | 601.59 | 602.1 | 0.0010 | 95.316 | 4.48 |
| 156-21 | 2-(carboxymethoxy)-5-((2S)-3-oxo-3-[(3-phenoxypropyl)amino]-2-{[(2,3,5,6-tetramethylphenyl)sulfonyl]amino}propyl)benzoic acid | 612.70 | 613.2 | 0.0006 | | |
| 156-22 | 2-(carboxymethoxy)-5-((2S)-3-oxo-3-[(4-phenylbutyl)amino]-2-{[2,3,5,6-tetramethylphenyl)sulfonyl]amino}propyl)benzoic acid | 610.73 | 611.2 | 0.0005 | 41.633 | not available |
| 156-23 | 5-{(2S)-3-{[2-(benzyloxy)ethyl]amino}-3-oxo-2-[(phenylsulfonyl)amino]propyl}-2-(carboxymethoxy)benzoic acid | 556.59 | 557.2 | 0.0012 | | |
| 156-24 | 5-((2S)-3-{[2-(benzyloxy)ethyl]amino}-2-{[(2,4-difluorophenyl)sulfonyl]amino}-3-oxopropyl)-2-(carboxymethoxy)benzoic acid | 595.57 | 595.1 | 0.0004 | | |
| 156-25 | 5-{(2S)-3-{[2-(benzyloxy)ethyl]amino}-2-[(1-naphthylsulfonyl)amino]-3-oxopropyl}-2-(carboxymethoxy)benzoic acid | 606.65 | 607.1 | 0.0002 | 85.214 | 4.13 |
| 156-26 | 4-((2S)-2-{[2-(benzyloxy)ethyl]amino}-2-{[(2-nitrophenyl)sulfonyl]amino}-3-oxopropyl)-2-(carboxymethoxy)benzoic acid | 601.59 | 602.2 | 0.0008 | | |
| 157-27 | 5-{(2S)-3-{[2-(benzyloxy)ethyl]amino}-3-oxo-2-[(8-quinolinylsulfonyl)amino]propyl}-2-(carboxymethoxy)benzoic acid | 607.64 | 608.2 | 0.0003 | | |
| 156-28 | 5-((2S)-3-{[2-(benzyloxy)ethyl]amino}-3-oxo-2-{[(2,3,5,6-tetramethylphenyl)sulfonyl]amino}propyl)-2-(carboxymethoxy)benzoic acid | 612.70 | 613.2 | 0.0002 | | |

EXAMPLE 157

General Methods. NMR spectra were recorded on a Varian-spectrometer and chemical shifts are given in ppm using $CD_3OD$ d 3.31 as an internal standard at 25° C. Only selected data are reported. HPLC analysis was performed using a Hypersil C-18 column (50×4.6 mm, 3 m) with a flow of 1 ml/min on a HP 1100 system with monitoring at 214 and 254 nm. For preparative HPLC purification a Vydac C-18 column (250×22 mm, 10 u) was used on a Gilson system with a flow of 15 ml/min. LCMS chromatograms and spectra were recorded on a Perkin Elmer Sciex system using a YMC-Pack FL-ODS column (50×4.6 mm, 5 u, 120A) with a flow of 4 ml/min. IR spectra were recorded on a Perkin Elmer Spectrum 1000 FTIR spectrometer. HRMS and FRMS spectra were recorded on a LCT instrument with electrospray.

Synthetic Method A. (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl]propanoic acid (100 mg, 0.18 mmol) was weighed into 10 screw-capped tubes and dissolved in dichloromethane (500 uL). 1-Hydroxybenzotriazole (0.23 mmol) in dimethylformamide (100 uL) was added to each tube followed by a set of 10 amines (0.29 mmol). The mixtures were cooled in an ice bath and 1-ethyl-3-(3-dimethylaminopropyl)carbodiimide hydrochloride (0.23 mmol) in dichloromethane (2 mL) was added to each tube. The mixtures were left in room temperature for 3 h and were then applied on small silica gel columns (5 ml) packed in dichloromethane. The products were eluted with dichloromethane followed by, dichloromethane-acetonitrile (1:1) and finally acetonitrile. The amide containing fractions were concentrated and dried under vacuum. The amides were then dissolved in tetrahydrofuran-methanol (2:1, 3 mL) and sodium hydroxide (1.5 mL, 2%, aq) was added. The mixtures were shaken at room temperature 5–7 h. Acetic acid (40 uL) was added and the mixtures were concentrated until approximately 2 mL was left in each tube. The materials were analyzed by HPLC and LC-MS and were then purified by reversed phase HPLC (Vydac C-18 column) using acetonitrile-water gradients containing 0.1% trifluoroacetic acid. After HPLC analysis the purest fractions were collected and lyophilized.

Synthetic Method B. To eight solutions of (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl]propanoic acid (100 mg, 0.18 mmol) in dichloromethane (500 μL) in screw-capped tubes was added a set of eight amines (0.29 mmol). 1-Hydroxybenzotriazole (0.23 mmol) in dimethylformamide (100 uL) was added and the mixtures were cooled in an ice bath. 1-Ethyl-3-(3-dimethylaminopropyl)carbodiimide hydrochloride (0.23 mmol) in dichloromethane (2 ml) was added to each tube and the reaction mixtures were left in room temperature over night. The mixtures were then applied on small silica gel columns (6 ml) packed in chloroform. The products were eluted with a step-wise chloroform-methanol gradient. The amide containing fractions were concentrated and dried under vacuum. The amides were then dissolved in methanol (1 mL) and sodium hydroxide (1.2 mL, 2%, aq) was added. When necessary tetrahydrofuran (500 uL) was added. The mixtures were left in room temperature for 5–7 h. Dowex H+ was added and after analysis by HPLC and LC/MS the materials were purified by reversed phase HPLC (Vydac C-1 8 column) using acetonitrile-water gradients. After HPLC analysis the purest fractions were collected and lyophilized.

Synthetic Method C. (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl] propanoic acid (typically 100 mg, 1 eq) was weighed into 10 screw-capped tubes and dissolved in dichloromethane (500 uL). A set of 10 amines (1.2 eq) was dissolved in dichloromethane (1 mL) and triethylamine (2 equivalents to the amines) was added. The amine solutions were added to the carboxylic acid solutions and the mixtures were cooled in an ice bath. 1-Hydroxybenzotriazole (1.2 eq) in dimethylformamide (100 uL) was added followed by 1-ethyl-3-(3-dimethylaminopropyl)carbodiimide hydrochloride (0.23 mmol) in dichloromethane (2 mL). The mixtures were left in room temperature over night. The mixtures were then applied on small silica gel columns (5–7 ml) packed in chloroform. The products were eluted with a stepwise chloroform-methanol gradient. The amide containing fractions were concentrated and dried under vacuum. The amides were then dissolved in tetrahydrofuran-methanol (1:1, 2 mL) and sodium hydroxide (1 mL, 2%, aq) was added. The mixtures were left in room temperature over night. Dowex H+ was added and the mixtures were concentrated until approximately 2 mL was left. The materials were either lyophilized directly or purified by reversed phase HPLC (Vydac C-1 8 column) using acetonitrile-water gradients. After HPLC analysis the purest fractions were collected and lyophilized.

Example 157-1

5-{(2S)-2-({(2S)-2-[(tert-Butoxycarbonyl)amino]-3-phenylpropanoyl}amino)-3-oxo-3-[(3-phenylpropyl) amino]propyl}-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl] propanoic acid and 3-phenylpropylamine (41 uL) according to Method A to give the title compound (48 mg). $^1$H-NMR (400 MHz, CD$_3$OD) d 7.79 (s, 1H), 7.40 (d, J=8.5 Hz, 1H), 7.26–7.13 (m, 10H), 6.99 (d, J=8.5 Hz, 1H), 4.72 (s, 2H), 4.52 (t, J=6.8 Hz, 1H), 4.25 (dd, J=5.3 Hz, J=9.2 Hz, 1H), 3.18 (m, 1H), 3.09–2.92 (m, 4H), 2.77 (dd, J=9.5 Hz, J=13.5 Hz, 1H), 2.50 (t, J=7.7 Hz, 2H), 1.69 (m, 2H), 1.34 (s, 9H); IR (KBr) 3302, 2926, 1736, 1686, 1646 cm$^{-1}$; HRMS m/z 647.2823 (calc. of monoisotopic mass for C$_{35}$H$_{41}$N$_3$O$_9$ gives 647.2823).

Example 157-2

5-{(2S)-2-({(2S)-2-[(tert-Butoxycarbonyl)amino]-3-phenylpropanoyl}amino)-3-oxo-3-[(4-phenylbutyl) amino]propyl}-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl] propanoic acid and 4-phenylbutylamine (46 uL) according to Method A to give the title compound (34 mg). $^1$H-NMR (400 MHz, CD$_3$OD) d 7.76 (s, 1H), 7.38 (d, J=8.5 Hz, 1H), 7.26–7.11 (m, 10H), 6.98 (d, J=8.5 Hz, 1H), 4.76 (s, 2H), 4.50 (t, J=6.9 Hz, 1H), 4.23 (dd, J=5.2 Hz, J=9.3 Hz, 1H), 3.17 (m, 1H), 3.09–2.91 (m, 4H), 2.75 (dd, J=9.4 Hz, J=13.6 Hz, 1H), 2.58 (t, J=7.5 Hz, 2H), 1.54 (m, 2H), 1.42 (m, 2H), 1.34 (s, 9H); IR (KBr) 3296, 2925, 1738, 1687, 1643 cm$^{-1}$; HRMS m/z 661.2987 (calc. of monoisotopic mass for C$_{36}$H$_{43}$N$_3$O$_9$ gives 661.2999).

Example 157-3

5-{(2S)-2-({(2S)-2-[(tert-Butoxycarbonyl)amino]-3-phenylpropanoyl}amino)-3-[(2-hydroxyethyl) amino]-3-oxopropyl}-2-(carboxymethoxy)benzoic Synthesis was performed from PNU-181049 and ethanolamine (18 uL) according to Method A to give the title compound (58 mg). $^1$H-NMR (400 MHz, CD$_3$OD) d 7.76 (s, 1H), 7.41 (d, J=8.6 Hz, 1H), 7.27–7.17 (m, 5H), 7.02 (d, J=8.5 Hz, 1H), 4.80 (s, 2H), 4.55 (m, 1H), 4.24 (dd, J=5.0 Hz, J=9.4 Hz, 1H), 3.52 (m, 2H), 3.25 (m, 2H), 3.10 (dd, J=6.1 Hz, J=13.7 Hz, 1H), 3.02 (dd, J=4.9 Hz, J=13.9 Hz, 1H), 2.95 (dd, J=7.9 Hz, J=13.8 Hz, 1H), 2.74 (dd, J=9.5 Hz, J=13.4 Hz, 1H), 1.35 (s, 9H); IR (KBr) 3339, 3298, 2961, 1743, 1714, 1686 cm$^{-1}$; HRMS m/z 573.2325 (calc. of monoisotopic mass for C$_{28}$H$_{35}$N$_3$O$_{10}$ gives 573.2322).

Example 157-4

{(2S)-2-({(2S)-2-[(tert-Butoxycarbonyl)amino]-3-phenylpropanoyl}amino)-3-[(2,3-dihydroxypropyl) amino]-3-oxopropyl}-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl] propanoic acid and 3-amino-1,2-propanediol 22 (uL) according to Method A to give the title compound (46 mg). $^1$H-NMR (400 MHz, CD$_3$OD) d 7.78 (s, 1H), 7.42 (d, J=8.3 Hz, 1H), 7.28–7.20 (m, 5H), 7.03 (d, J=8.5 Hz, 1H), 4.81 (s, 2H), 4.57 (m, 1H), 4.24 (dd, J=4.8 Hz, J=9.3 Hz, 1H), 3.69–3.56 (m, 2H), 2.74 (dd, J=9.0 Hz, J=13.4 Hz, 1H), 1.34 (s, 9H); IR (KBr) 3292, 2932, 1686, 1652 cm$^{-1}$; HRMS m/z 603.2412 (calc. of monoisotopic mass for C$_{29}$H$_{37}$N$_3$O$_{11}$ gives 603.2428).

Example 157-5

Disodium 5-{(2S)-2-({(2S)-2-[(tert-butoxycarbonyl) amino]-3-phenylpropanoyl}amino)-3-oxo-3-[(1-phenylethyl)amino]propyl}-2-(2-oxido-2-oxoethoxy) benzoate Synthesis was performed from (2S)-2-({(2S)-2-[(tert-butoxycarbonyl)amino]-3-phenylpropanoyl}amino)-3-[3-(methoxycarbonyl)-4-(2-methoxy- 2-oxoethoxy)phenyl] propanoic acid and 1-phenylethylamine (38 uL) according to Method A to give a material which was re-purified by reversed phase C-18 HPLC in absence of trifluoroacetic acid and then passed through a column with Dowex Na+. After lyophilizing, the title compound (34 mg) was obtained as a diasteromeric mixture with a 2:1 ratio of the components (HPLC). (KBr) 3291, 2971, 1691, 1642 cm$^{-1}$; HRMS m/z 633.2682 (calc. of monoisotopic mass for C$_{34}$H$_{39}$N$_3$O$_9$ gives 633.2686).

Example 157-6

5-((2S)-2-({(2S)-2-[(tert-Butoxycarbonyl)amino]-3-phenylpropanoyl}amino)-3-{[1-(hydroxymethyl) pentyl]amino}-3-oxopropyl)-2-(carboxymethoxy) benzoic Acid Synthesis was performed from (2S)-2-({(2S)-2-[(tert-butoxycarbonyl)amino]-3-phenylpropanoyl}amino)-3-[3-

(methoxycarbonyl)-4-(2-methoxy-2-oxoethoxy)phenyl] propanoic acid and D,L-2-amino-1-hexanol (37 uL) according to Method A with the difference that after the hydrolysis, the reaction mixture was neutralized by Dowex H+. Thereafter the obtained solution was lyophilized to give the title compound (95 mg) as a diasteromeric mixture with a 1:1 ratio of the components (HPLC). $^1$H-NMR (400 MHz, CD$_3$OD) d 7.76 (s, 1H), 7.40 (d, J=8.5 Hz, 1H), 7.27–7.17 (m, 5H), 7.02 (d, J=8.5 Hz, 1H), 4.82 (s, 2H), 4.51 (t, J=6.8 Hz, 1H), 4.23 (m, 1H), 3.16 (m, 1H), 2.76 (dd, J=9.3 Hz, J=13.8 Hz, 1H), 1.51 (m, 2H), 1.34 (s, 9H); (KBr) 3293, 2931, 1689, 1645 cm$^{-1}$; HRMS m/z 629.2943 (calc. of monoisotopic mass for C$_{32}$H$_{43}$N$_3$O$_{10}$ gives 629.2948).

Example 157-7

5-[(2S)-3-(Benzylamino)-2-({(2S)-2-[(tert-butoxycarbonyl)amino]-3-phenyl-propanoyl}amino)-3-oxopropyl]-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl] propanoic acid and benzylamine (31 μL) according to Method A to give a material which was re-purified by reversed phase C-18 HPLC in absence of trifluoroacetic acid to give the title compound (29 mg). $^1$H-NMR (400 MHz, CD$_3$OD) d 7.78 (s, 1H), 7.36 (dd, J=2.0 Hz, J=8.6 Hz, 1H), 7.30–7.13 (m, 10H), 6.96 (d, J=8.5 Hz, 1H), 4.79 (s, 2H), 4.58 (t, J=6.9 Hz, 1H), 3.11–2.94 (m, 4H), 2.76 (dd, J=10 Hz, J=13.4 Hz, 1H), 1.33 (s, 9H); IR (KBr) 3304, 2979, 1694, 1640 cm$^{-1}$; HRMS m/z 619.2511 (calc. of monoisotopic mass for C$_{33}$H$_{37}$N$_3$O$_9$ gives 619.2530).

Example 157-8

5-{(2S)-2-({(2S)-2-[(tert-Butoxycarbonyl)amino]-3-phenylpropanoyl}amino)-3-[(6-hydroxyhexyl)amino]-3-oxopropyl}-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl] propanoic acid and 6-amino-1-hexanol (34 mg) according to Method A to give the title compound (64 mg). $^1$H-NMR (400 MHz, CD$_3$OD) d 7.79 (s, 1H), 7.43 (d, J=8.1 Hz, 1H), 7.27–7.18 (m, 5H), 7.02 (dd, J=7.0 Hz, J=8.5 Hz, 1H), 4.80 (s, 2H), 4.57 (m, 1H), 4.25 (dd, J=4.8 Hz, J=9.5 Hz, 1H), 3.77 (m, 1H), 2.74 (dd, J=10.2 Hz, J=13.2 Hz, 1H), 1.34 (s, 9H); IR (KBr) 3291, 2932, 1691, 1647 cm$^{-1}$; HRMS m/z 629.2948 (calc. of monoisotopic mass for C$_{32}$H$_{43}$N$_3$O$_{10}$ gives 629.2948).

Example 157-9

5-((2S)-2-({(2S)-2-[(tert-Butoxycarbonyl)amino]-3-phenylpropanoyl}amino)-3-{[(1R)-1-(hydroxymethyl)-3-methylbutyl]amino}-3-oxopropyl)-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl] propanoic acid and D-leucinol (37 uL) according to Method A to give the title compound (51 mg). $^1$H-NMR (400 MHz, CD$_3$OD) d 7.79 (s, 1H), 7.44 (d, J=8.1 Hz, 1H), 7.29–7.18 (m, 5H), 7.04 (d, J=8.5 Hz, 1H), 4.80 (s, 2H), 4.55 (t, J=7.0 Hz, 1H), 4.25 (dd, J=4.8 Hz, J=9.5 Hz, 1H), 3.86 (m, 1H), 2.75 (dd, J=9.5 Hz, J=13.5 Hz, 1H), 1.35 (s, 9H), 0.82 (m, 6H); IR (KBr) 3312, 2958, 1639 cm$^{-1}$; HRMS m/z 629.2926 (calc. of monoisotopic mass for C$_{32}$H$_{43}$N$_3$O$_{10}$ gives 629.2948).

Example 157-10

5-[(2S)-2-({(2S)-2-[(tert-Butoxycarbonyl)amino]-3-phenylpropanoyl}amino)-3-oxo-3-(phenethylamino)propyl]-2-(carboxymethoxy)benzoic Acid Synthesis was performed performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl]propanoic acid and phenetylamine (38 uL) according to Method A to give the title compound (57 mg). $^1$H-NMR (400 MHz, CD$_3$OD) d 7.76 (s, 1H), 7.36 (dd, J=1.9 Hz, J=8.3 Hz, 1H), 7.28–7.15 (m, 10H), 7.00 (d, J=8.7 Hz, 1H), 4.79 (s, 2H), 4.50 (t, J=6.8 Hz, 1H), ), 4.25 (dd, J=5.1 Hz, J=9.4 Hz, 1H), 3.40 (m, 1H), 3.02 (m 2H), 2.90 (dd, J=7.7 Hz, J=13.6 Hz, 1H), 1.36 (s, 9H); (KBr) 3297, 2979, 1728, 1688, 1645 cm$^{-1}$; HRMS m/z 633.2660 (calc. of monoisotopic mass for C$_{34}$H$_{39}$N$_3$O$_9$ gives 633.2686).

Example 157-11

Disodium 5-{(2S)-2-({(2S)-2-[(tert-butoxycarbonyl)amino]-3-phenylpropanoyl}amino)-3-[(5-hydroxypentyl)amino]-3-oxopropyl}-2-(2-oxido-2-oxoethoxy)benzoate Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl] propanoic acid and 5-amino-1-pentanol (31 mg) according to Method A to give a material which was re-purified by reversed phase C-18 HPLC in absence of trifluoroacetic acid and then passed through a column with Dowex Na+. After lyophilizing, the title compound (34 mg) was obtained. $^1$H-NMR (400 MHz, CD$_3$OD) d 7.56 (s, 1H), 7.30–7.17 (m, 6H), 7.04 (d, J=8.5 Hz, 1H), 4.57–4.50 (m, 3H), 4.24 (dd, J=5.0 Hz, J=9.7 Hz, 1H), 3.52 (t, J=13.2 Hz, 2H), 3.14 (m, 1H), 3.07–2.92 (m, 4H), 2.72 (dd, J=9.8 Hz, J=13.6 Hz, 1H), 1.50 (m, 2H), 1.35 (s, 9H), 1.28 (m, 2H); (KBr) 3318, 2934, 1686, 1647 cm$^{-1}$; HRMS m/z 615.2821 (calc. of monoisotopic mass for C$_{31}$H$_{41}$N$_3$O$_{10}$ gives 615.2792).

Example 157-12

5-((2R)-2-({(2S)-2-[(tert-Butoxycarbonyl)amino]-3-phenylpropanoyl}amino)-3-oxo-3-{[3-(2-oxo-1-pyrrolidinyl)propyl]amino}propyl)-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy- 2-oxoethoxy)phenyl] propanoic acid (100 mg, 0.18 mmol) and N-(3'-aminopropyl)-2-pyrrolidinone (42 mg, 0.29 mmol) according to Method C with HPLC purification to give the title compound (26 mg). $^1$H-NMR (400 MHz, CD$_3$OD) δ 1.35 (s, 9H) 1.6 (m, 2H) 2.03 (m, 2H) 2.37 (t, 2H) 2.76 (m, 1H) 2.92–3.10 (m, 5H) 3.14 (t, 2H) 3.42 (t, 2H) 4.25 (m, 1H) 4.5 (m, 1H) 4.78 (s, 2H) 7.05 (d, 1H) 7.23 (dd, 5H) 7.42 (d, 1H) 7.72 (s, 1H); HR-MS m/z 654.2880 (calc. Of monoisotopic mass for C$_{33}$H$_{42}$N$_4$O$_{10}$ gives 654.2901).

Example 157-13

5-((2S)-2-({(2S)-2-[(tert-butoxycarbonyl)amino]-3-phenylpropanoyl}amino)-3-{[2-(dimethylamino)ethyl]amino}-3-oxopropyl)-2-(carboxymethoxy)benzoic Acid Synthesis was performed from (2S)-2-({(2S)-2-[(tert-butoxycarbonyl)amino]-3-phenylpropanoyl}amino)-3-[3-

(methoxycarbonyl)-4-(2-methoxy-2-oxoethoxy)phenyl]propanoic acid and N,N-dimethylenediamine (26 mg) according to Method B to give the title compound (7.2 mg). $^{1}$H-NMR (400 MHz, CD$_3$OD) d 7.50 (s, 1H), 7.35 (m, 1H), 7.29–7.20 (m, 5H), 7.13 (d, J=8.5 Hz, 1H), 4.69 (s, 2H), 4.39 (t, J=7.3 Hz, 1H), 4.29 (dd, J=5.3 Hz, J=9.2 Hz, 1H), 3.37 (m, 2H), 3.07 (dd, J=5.1 Hz, J=13.9 Hz, 1H), 2.99 (m, 4H), 2.85 (s, 6H), 2.79 (dd, J=9.0 Hz, J=13.6 Hz, 1H), 1.36 (s, 9H); HRMS m/z 600.2774 (calc. of monoisotopic mass for C$_{30}$H$_{40}$N$_4$O$_9$ gives 600.2795).

Example 157-14

5-{(2S)-2-({(2S)-2-[(tert-Butoxycarbonyl)amino]-3-phenylpropanoyl}amino)-3-oxo-3-[(3-pyridinylmethyl)amino]propyl}-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl]propanoic acid and 3-(aminomethyl)pyridine (31 mg) according to Method B to give the title compound (14 mg). HRMS m/z 620.2471 (calc. of monoisotopic mass for C$_{32}$H$_{36}$N$_4$O$_9$ gives 620.2482).

Example 157-15

5-((2S)-2-({(2S)-2-[(tert-Butoxycarbonyl)amino]-3-phenylpropanoyl}amino)-3-{[3-(isopropylamino)propyl]amino}-3-oxopropyl)-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl]propanoic acid and N-isopropyl-1,3-propanediamine (34 mg) according to Method B to give the title compound (26 mg). $^{1}$H-NMR (400 MHz, CD$_3$OD) d 7.46 (d, J=2.2 Hz, 1H), 7.36 (dd, J=2.2 Hz, J=6.2 Hz, 1H), 7.29–7.20 (m, 5H), 7.08 (d, J=8.4 Hz, 1H), 4.68 (s, 2H), 4.44 (dd, J=5.7 Hz, J=9.9 Hz, 1H), 4.30 (dd, J=5.5 Hz, J=9.2 Hz, 1H), 3.27 (m, 2H), 3.06 (m, 2H), 2.89 (dd, J=10.1 Hz, J=13.0 Hz, 1H), 2.80 (m, 2H), 2.65 (m, 2H), 1.30 (dd, J=2.9 Hz, J=6.6 Hz); IR (KBr) cm$^{-1}$; HRMS m/z 628.3082 (calc. of monoisotopic mass for C$_{32}$H$_{44}$N$_4$O$_9$ gives 628.3108).

Example 157-16

5-{(2S)-2-({(2S)-2-[(tert-Butoxycarbonyl)amino]-3-phenylpropanoyl}amino)-3-[(3-isopropoxypropyl)amino]-3-oxopropyl}-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl]propanoic acid and 3-isopropoxypropylamine (34 mg) according to Method B to give the title compound (34 mg). $^{1}$H-NMR (400 MHz, CD$_3$OD) d 7.76 (s, 1H), 7.40 (d, J=8.3 Hz, 1H), 7.28–7.17 (m, 5H), 7.03 (d, J=8.6 Hz, 1H), 4.80 (s, 2H), 4.50 (m, 1H), 4.24 (dd, J=5.1 Hz, J=9.3 Hz, 1H), 3.54 (t, J=6.1 Hz, 1H), 3.35 (m, 2H), 3.23 (m, 1H), 3.14 (m, 1H), 3.08–2.91 (m, 3H), 2.75 (dd, J=9.6 Hz, J=13.5 Hz, 1H), 1.63 (m, 2H), 1.35 (s, 9H), 1.12 (dd, J=2.0 Hz, J=6.1 Hz); IR (KBr) cm$^{-1}$; HRMS m/z 629.2946 (calc. of monoisotopic mass for C$_{32}$H$_{43}$N$_3$O$_{10}$ gives 629.2948).

Example 157-17

5-((2S)-2-({(2S)-2-[(tert-Butoxycarbonyl)amino]-3-phenylpropanoyl}amino)-3-oxo-3-{[2-(2-pyridinyl)ethyl]amino}propyl)-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl]propanoic acid and 2-(2-aminoethyl)pyridine (35 mg) according to Method B to give the title compound (56 mg). $^{1}$H-NMR (400 MHz, CD$_3$OD) d 8.52 (d, J=4.6 Hz, 1H), 7.97 (m, 1H), 7.69 (d, J=2.0 Hz, 1H), 7.46–7.17 (m, 8H), 7.03 (d, J=8.6 Hz, 1H), 4.78 (s, 2H), 4.46 (m, 1H), 4.23 (dd, J=5.2 Hz, J=9.4 Hz, 1H), 3.41 (m, 1H), 2.74 (dd, J=8.9 Hz, J=13.6 Hz, 1H), 1.35 (s, 9H); HRMS m/z 634.2651 (calc. of monoisotopic mass for C$_{33}$H$_{38}$N$_4$O$_9$ gives 634.2639).

Example 157-18

5-((2S)-2-({(2S)-2-[(tert-Butoxycarbonyl)amino]-3-phenylpropanoyl}amino)-3-oxo-3-{[2-(1-piperazinyl)ethyl]amino}propyl)-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl]propanoic acid and N-2-aminoethyl)piperazine (37 mg) according to Method B to give the title compound (5.8 mg). $^{1}$H-NMR (400 MHz, CD$_3$OD) d 7.58 (s, 1H), 7.37 (dd, J=2.0 Hz, J=8.4 Hz, 1H), 7.26–7.18 (m, 5H), 7.13 (d, J=8.5 Hz, 1H), 4.68 (s, 2H), 4.50 (t, J=7.3 Hz, 1H), 4.28 (dd, J=5.3 Hz, J=9.0 Hz, 1H), 3.68 (m, 1H), 3.56 (m, 1H), 2.80 (dd, J=9.3 Hz, J=13.2 Hz, 1H), 2.37 (m, 1H), 1.37 (s, 9H); HRMS m/z 641.3032 (calc. of monoisotopic mass for C$_{32}$H$_{43}$N$_5$O$_9$ gives 641.3061).

Example 157-19

5-[(2S)-2-({(2S)-2-[(tert-Butoxycarbonyl)amino]-3-phenylpropanoyl}amino)-3-({2-[(2-hydroxypropyl)amino]ethyl}amino)-3-oxopropyl]-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl]propanoic acid and N-(2-hydroxypropyl)ethylenediamine (34 mg) according to Method B to give the title compound (26 mg). $^{1}$H-NMR (400 MHz, CD$_3$OD) d 7.56 (d, J=2.4 Hz, 1H), 7.32 (d, J=8.8 Hz, 1H), 7.28–7.17 (m, 5H), 7.05 (d, J=8.5 Hz, 1H), 4.37 (m, 1H), 4.27 (dd, J=5.2 Hz, J=8.9 Hz, 1H), 1.35 (s, 9H), 1.22 (dd, J=1.8 Hz, J=6.3 Hz, 3H); HRMS m/z 630.2883 (calc. of monoisotopic mass for C$_{31}$H$_{42}$N$_4$O$_{10}$ gives 630.2901).

Example 157-20

5-{(2S)-2-({(2S)-2-[(tert-Butoxycarbonyl)amino]-3-phenylpropanoyl}amino)-3-[(4-methoxybenzyl)amino]-3-oxopropyl}-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl]propanoic acid and 4-methoxybenzylamine (40 mg) according to Method B to give the title compound (33 mg). $^{1}$H-NMR (400 MHz, CD$_3$OD) d 7.75 (s, 1H), 7.34 (dd, 1H), 7.26–7.18 (m, 5H), 7.05 (d, J=8.6 Hz, 1H), 6.94 (d, J=8.6 Hz, 2H), 6.82 (m, 2H), 4.77 (s, 2H), 4.56 (m, 1H), 4.15 (dd, J=5.1 Hz, J=14.7 Hz, 1H), 3.76 (s, 3H), 3.08–2.94 (m, 3H), 2.76 (dd, J=9.6 Hz, J=13.7 Hz, 1H), 1.33 (s, 9H); HRMS m/z 649.2615 (calc. of monoisotopic mass for C$_{34}$H$_{39}$N$_3$O$_{10}$ gives 649.2635).

Example 157-1

5-{(2S)-2-({(2S)-2-[(tert-Butoxycarbonyl)amino]-3-phenylpropanoyl}amino)-3-[(3-hydroxypropyl)amino]-3-oxopropyl}-2-(carboxymethoxy)benzoic Acid Synthesis was performed from (2S)-2-({(2S)-2-[(tert-butoxycarbonyl)amino]-3-phenylpropanoyl}amino)-3-[3-

(methoxycarbonyl)-4-(2-methoxy-2-oxoethoxy)phenyl] propanoic acid and 3-amino-1-propanol (18 ul) according to Method A to give material was re-purified by reversed phase HPLC in absence of trifluoroacetic acid to give the title compound (11 mg). $^1$H-NMR (400 MHz, CD$_3$OD) d 7.84 (s, 1H), 7.39 (d, J=8.3 Hz, 1H), 7.27–7.17 (m, 5H), 7.04 (d, J=8.5 Hz, 1H), 4.79 (s, 2H), 4.51 (m, 1H), 4.23 (dd, J=5.2 Hz, J=9.3 Hz, 1H), 3.25 (m, 1H), 3.15 (m, 1H), 2.75 (m, 1H), 1.62 (m, 2H), 1.36 (s, 9H); HRMS m/z 587.2493 (calc. of monoisotopic mass for C$_{29}$H$_{37}$N$_3$O$_{10}$ gives 587.2479).

Example 157-22

5-{(2S)-2-({(2S)-2-[(tert-Butoxycarbonyl)amino]-3-phenylpropanoyl}amino)-3-[2-(3-hydroxy-3-phenylpropanoyl)hydrazino]-3-oxopropyl}-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl] propanoic acid (100 mg, 0.18 mmol) and 3-phenylhydracrylic acid hydrazide (39 mg, 0.22 mmol) according to Method C with HPLC purification to give the title compound (58 mg) as a diasteromeric mixture. $^1$H-NMR (400 MHz, CD$_3$OD) d 7.77 (1H), 5.11 (dd, J=4.6 Hz, J=8.6 Hz, 1H), 4.78 (2H), 4.70 (m, 1H), 4.24 (dd, J=5.0 Hz, J=9.3 Hz, 1H), 1.34 (s, 9H); IR (KBr) 3274, 1681, 1652, 1608 cm$^{-1}$; HRMS m/z 692.2670 (calc. of monoisotopic mass for C$_{35}$H$_{40}$N$_4$O$_{11}$ gives 692.2694).

Example 157-23

5-((2S)-2-({(2S)-2-[(tert-Butoxycarbonyl)amino]-3-phenylpropanoyl}amino)-3-{2-[(2-hydroxy[1,1'-biphenyl]-3-yl)carbonyl]hydrazino}-3-oxopropyl)-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl] propanoic acid (93 mg, 0.17 mmol) and 3-phenylsalicylic acid hydrazide (45 mg, 0.20 mmol) according to Method C with HPLC purification to give the title compound (30 mg). $^1$H-NMR (400 MHz, CD$_3$OD) d 4.80 (s, 2H), 4.27 (dd, J=4.9 Hz, J=9.8 Hz, 1H), 3.04 (m, 1H), 2.94 (m, 1H), 2.72 (dd, J=9.3 Hz, J=13.7 Hz, 1H), 1.34 (s, 9H); IR (KBr) 3280, 1694, 1653 cm$^{-1}$; HRMS m/z 740.2666 (calc. of monoisotopic mass for C$_{39}$H$_{40}$N$_4$O$_{11}$ gives 740.2694).

Example 157-24

5-[(2S)-3-{2-[2-(Benzoylamino)acetyl]hydrazino}-2-({(2S)-2-[(tert-butoxycarbonyl)amino]-3-phenylpropanoyl}amino)-3-oxopropyl]-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl] propanoic acid (100 mg, 0.18 mmol) and hippuric acid hydrazide (42 mg, 0.22 mmol) according to Method C with HPLC purification to give the title compound (24 mg). IR (KBr) 3274, 1652, 1616 cm$^{-1}$; HRMS m/z 705.2640 (calc. of monoisotopic mass for C$_{35}$H$_{39}$N$_5$O$_{11}$ gives 705.2646).

Example 157-25

5-[(2S)-3-({2-[5-(Benzyloxy)-1H-indol-3-yl]-1-methylethyl}amino)-2-({(2S)-2-[(tert-butoxycarbonyl)amino]-3-phenylpropanoyl}amino)-3-oxopropyl]-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl] propanoic acid (68 mg, 0.12 mmol) and 3-(2-aminopropyl)-5-(benzyloxy)-indole hydrochloride (46 mg, 0.15 mmol) according to Method C with HPLC purification to give the title compound (32 mg) as a diasteromeric mixture. IR (KBr) 3409, 1681, 1652 cm$^{-1}$; HRMS m/z 792.3360 (calc. of monoisotopic mass for C$_{44}$H$_{48}$N$_4$O$_{10}$ gives 792.3370).

Example 157-26

5-{(2S)-2-({(2S)-2-[(tert-Butoxycarbonyl)amino]-3-phenylpropanoyl}amino)-3-[(3,3-diphenylpropoxy)amino]-3-oxopropyl}-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl] propanoic acid (85 mg, 0.15 mmol) and 3,3-diphenylpropoxyamine hydrochloride (48 mg, 0.18 mmol) according to Method C with HPLC purification to give the title compound (29 mg). 7.75 (s, 1H), 7.33 (d, J=9.5 Hz, 1H), 6.87 (d, J=8.3 Hz, 1H), 4.71 (s, 2H), 4.39 (dd, 1H), 4.25 (m, 1H), 4.11 (t, J=8.0 Hz, 1H), 3.57 (m, 2H), 3.01 (m, 2H), 2.93 (m, 1H), 2.75 (m, 1H), 2.24 (m, 2H), 1.35 (s, 9H); IR (KBr) 3274, 2978, 1684 1651 cm$^{-1}$; HRMS m/z 739.3126 (calc. of monoisotopic mass for C$_{41}$H$_{45}$N$_3$O$_{10}$ gives 739.3105).

Example 157-27

5-[(2S)-3-{[3-(Benzylanilino)-2-hydroxypropyl]amino}-2-({(2S)-2-[(tert-butoxycarbonyl)amino]-3-phenylpropanoyl}amino)-3-oxopropyl]-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl] propanoic acid (85 mg, 0.15 mmol) and 1-amino-3-(N-benzylanilino)-2-propanol (47 mg, 0.18 mmol) according to Method C with HPLC purification to the title compound (23 mg) as a diasteromeric mixture. IR (KBr) 3414, 1654 cm$^{-1}$; HRMS m/z 768.3382 (calc. of monoisotopic mass for C$_{42}$H$_{48}$N$_4$O$_{10}$ gives 768.3370).

Example 157-28

5-{(2S)-2-({(2S)-2-[(tert-Butoxycarbonyl)amino]-3-phenylpropanoyl}amino)-3-oxo-3-[(3-phenylpropoxy)amino]propyl}-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl] propanoic acid (100 mg, 0.18 mmol) and 3-phenylpropoxyamine (41 mg, 0.22 mmol) according to Method C with HPLC purification to give the title compound (53 mg). $^1$H-NMR (400 MHz, CD$_3$OD) d 7.57 (s, 1H), 6.94 (d, J=8.3 Hz, 1H), 4.28 (m, 1H), 3.65 (m, 2H), 3.04 (dd, J=4.9 Hz, J=13.9 Hz, 1H), 2.97 (m, 1H), 2.73 (dd, J=9.6 Hz, J=13.8 Hz, 1H), 2.65 (t, J=7.7 Hz, 2H), 1.78 (m, 2H), 1.37 (s, 3H), 1.36 (s, 6H); IR (KBr) 3293, 2949, 1681, 1651 cm$^{-1}$; HRMS m/z 663.2806 (calc. of monoisotopic mass for C$_{35}$H$_{41}$N$_3$O$_{10}$ gives 663.2792).

Example 157-29

5-((2S)-2-({(2R)-2-[(tert-Butoxycarbonyl)amino]-3-phenylpropanoyl}amino)-3-oxo-3-{[2-(1-pyrrolidinyl)ethyl]amino}propyl)-2-(carboxymethoxy)benzoic Acid Synthesis was performed from (2S)-2-({(2S)-2-[(tert-butoxycarbonyl)amino]-3-phenylpropanoyl}amino)-3-[3-

(methoxycarbonyl)-4-(2-methoxy-2-oxoethoxy)phenyl]propanoic acid (100 mg, 0.18 mmol) and N-(2-aminoethyl)-pyrrolidinone (33 mg, 0.29 mmol) according to Method C with HPLC purification to give the title compound (10 mg). $^1$H-NMR (400 MHz, CD$_3$OD) δ 1.36 (s, 9H) 2.05 (s, 4H) 2.68–3.20 (m, 8H) 3.39 (m, 4H) 4.28 (m, 1H) 4.39 (m, 1H) 4.69 (s, 2H) 7.05–7.40 (m, 7H) 7.52 (s, 1H); HRMS m/z 626.2929 (calc. of monoisotopic mass for C$_{32}$H$_{42}$N$_4$O$_9$ gives 626.2952).

Example 157-30

5-{(2S)-2-({(2R)-2-[(tert-Butoxycarbonyl)amino]-3-phenylpropanoyl}amino)-3-[(3,4-dimethoxyphenethyl)amino]-3-oxopropyl}-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl]propanoic acid (100 mg, 0.18 mmol) and 3,4-dimethoxyphenethylamine (52 mg, 0.29 mmol) according to Method C with HPLC purification to give the title compound (12 mg). $^1$H-NMR (400 MHz, CD$_3$OD) δ 1.38 (s, 9H) 2.68 (t, 2H) 2.72–3.09 (m, 4H) 3.29–3.44 (m, 3H) 3.80 (s, 3H) 3.85 (s, 3H) 4.25 (m, 1H) 4.52 (m, 1H) 4.79 (s, 2H) 6.74 (d, 1H) 6.84 (s, 1H) 6.87 (d, 1H) 7.06 (d, 1H) 7.17–7.38 (m, 6H) 7.73 (s, 1H); HRMS m/z 693.2904 (calc of monoisotopic mass for C$_{36}$H$_{43}$N$_3$O$_{11}$ gives 693.2898).

Example 157-31

5-((2S)-2-({(2R)-2-[(tert-Butoxycarbonyl)amino]-3-phenylpropanoyl}amino)-3-{[2-hydroy-2-(1-phenyl-1H-indol-3-yl)ethyl]amino}-3-oxopropyl)-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl]propanoic acid(49 mg, 0.08 mmol) and N-phenyl-3-(1-hydroxy-2-aminoethyl)indole malonate (45 mg, 0.14 mmol) according to Method C with HPLC purification to give the title compound (13 mg). $^1$H-NMR (400 MHz, CD$_3$OD) δ 1.30–1.31 (d, 9H) 2.65 (m, 1H) 2.80–3.06 (m, 3H) 3.45 (m, 1H) 3.72 (m, 1H) 4.19 (m, 1H) 4.52 (m, 1H) 4.67 (d, 2H) 5.03 (m, 1H) 7.0–7.8 (m, 18H); HRMS m/z 764.3073 (calc. of monoisotopic mass for C$_{42}$H$_{44}$N$_4$O$_{10}$ gives 764.3057).

Example 157-32

5-[(2S)-2-({(2R)-2-[(tert-Butoxycarbonyl)amino]-3-phenylpropanoyl}amino)-3-oxo-3-({5-[(phenylsulfonyl)amino]pentyl}amino)propyl]-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl]propanoic acid (45 mg) and N-(5-aminopentyl)-benzenesulphonamide malonate (45 mg, 0.08 mmol) according to Method C with HPLC purification to give the title compound (4.2 mg, 0.13 mmol). $^1$H-NMR (400 MHz, CD$_3$OD) δ 0.97 (m, 1H) 1.16–1.49 (m, 16H) 2.73–3.16 (m, 6H) 4.26 (m, 1H) 4.50 (m, 1H) 4.68 (s, 2H) 7.09–7.9 (m, 13H); HRMS 754.2859 (calc of monoisotopic mass for C$_{37}$H$_{46}$N$_4$O$_{11}$S gives 754.2884).

Example 157-33

5-[(2S)-3-{2-[2-(Benzoylamino)-3-methylbutanoyl]hydrazino}-2-({(2R)-2-[(tert-butoxycarbonyl)amino]-3-phenylpropanoyl}amino)-3-oxopropyl]-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl]propanoic acid (66 mg, 0.12 mmol) and N-benzoylvaline hydrazide (45 mg, 0.19 mmol) according to Method C with HPLC purification to give the title compound (3.5 mg). $^1$H-NMR (400 MHz, CD$_3$OD) δ 1.10 (m, 6H) 1.35 (s, 9H) 1.43 (m, 1H) 2.25 (m, 1H) 2.68 (m, 1H) 2.90 (m, 2H) 3.51 (m, 1H) 4.24 (m, 1H) 4.51 (m, 1H) 4.70 (m, 2H), 7.02–8.0 (m, 13H); HRMS m/z 747.3098 (calc of monoisotopic mass for C$_{38}$H$_{45}$N$_5$O$_{11}$ gives 747.3116).

Example 157-34

5-[2-({2-[(tert-Butoxycarbonyl)amino]-3-phenylpropanoyl}amino)-3-(dipentylamino)-3-oxopropyl]-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl]propanoic acid (100 mg, 0.18 mmol) and dipentylamine (46 mg, 0.29 mmol) according to Method C with HPLC purification to give the title compound (64 mg). $^1$H-NMR (400 MHz, CD$_3$OD) δ 0.90 (m, 6H) 1.14–1.53 (m, 21H) 2.65–2.82 (m, 1H) 2.86–3.38 (m, 7H) 4.30 (m, 1H) 4.80 (d, 2H) 4.94 (m, 1H) 7.02 (m, 1H) 7.21 (m, 5H) 7.35–7.35 (dd, 1H) 7.76 (dd, 1H); HRMS m/z 669.3634 (calc. of monoisotopic mass for C$_{36}$H$_{51}$N$_3$O$_9$ gives 669.3625); mp 87–90° C.

Example 157-35

5-{(2S)-2-({(2S)-2-[(tert-Butoxycarbonyl)amino]-3-phenylpropanoyl}amino)-3-[(4-hydroxybutyl)amino]-3-oxopropyl}-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl]propanoic acid and 4-amino-1-butanol (21 ul) according to Method A to give a material which was re-purified by reversed phase C-18 HPLC in absence of trifluoroacetic acid to give the title compound (19 mg). $^1$H-NMR (400 MHz, CD$_3$OD) d 7.75 (s, 1H), 7.40 (d, J=8.3 Hz, 1H), 7.28–7.18 (m, 5H), 7.04 (d, J=8.8 Hz, 1H), 4.79 (s, 2H), 4.51 (m, 1H), 4.24 (dd, J=5.2 Hz, J=9.2 Hz, 1H), 3.52 (m, 1H), 3.18 (m, 1H), 3.09–2.92 (m, 4H), 2.75 (m, 1H), 1.45 (m, 4H), 1.36 (s, 9H); HRMS m/z 601.2616 (calc. of monoisotopic mass for C$_{30}$H$_{39}$N$_3$O$_{10}$ gives 601.2635).

Example 157-36

5-((2S)-2-({(2S)-2-[(tert-Butoxycarbonyl)amino]-3-phenylpropanoyl}amino)-3-{[2-(2-fluoro[1,1'-biphenyl]-4-yl)propyl]amino}-3-oxopropyl)-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl]propanoic acid (79 mg, 0.14 mmol) and 2-fluoro-β-methyl-4-biphenylethylamine hydrochloride (45 mg, 0.17 mmol) according to Method C to give the title compound (44 mg). $^1$H-NMR (400 MHz, CD$_3$OD) d 7.75 (s, 1H), 4.78 (s, 1H), 4.57 (s, 1H), 4.51 (m, 1H), 4.22 (m, 1H), 3.52 (m, 1H), 3.41 (m, 1H), 3.22 (m, 1H), 3.06–2.85 (m, 4H), 2.72 (m, 1H), 1.35 (s, 9H), 1.20 (dd, J=7.0 Hz, J=15.7 Hz, 4H); HRMS m/z 741.3094 (calc. of monoisotopic mass for C$_{41}$H$_{44}$FN$_3$O$_9$ gives 741.3062).

Example 157-37

5-((2S)-2-({(2S)-2-[(tert-butoxycarbonyl)amino]-3-phenylpropanoyl}amino)-3-{[2-hydroxy-2-(3-phenoxyphenyl)ethyl]amino}-3-oxopropyl)-2-(carboxymethoxy)benzoic Acid Synthesis was performed from (2S)-2-({(2S)-2-[(tert-butoxycarbonyl)amino]-3-phenylpropanoyl}amino)-3-[3-

(methoxycarbonyl)-4-(2-methoxy-2-oxoethoxy)phenyl] propanoic acid (96 mg, 0.16 mmol) and 2-amino-1-(3-phenoxyphenyl)-1-ethanol (45 mg, 0.20 mmol) according to Method C with HPLC purification to give the title compound (25 mg) as a diasteromeric mixture. $^1$H-NMR (400 MHz, CD$_3$OD) d 7.59 (d, J=1.7 Hz, 1H), 6.87 (dd, J=1.2 Hz, J=8.3 Hz, 1H), 4.66 (m, 3H), 4.55 (t, J=7.0 Hz, 1H), 4.23 (m, 1H), 3.02 (m, 2H), 3.52 (m, 1H), 2.90 (m, 1H), 2.69 (m, 1H), 1.34 (s, 9H); HRMS m/z 741.2925 (calc. of monoisotopic mass for C$_{40}$H$_{43}$N$_3$O$_{11}$ gives 741.2898).

Example 157-38

5-((2S)-2-({(2S)-2-[(tert-butoxycarbonyl)amino]-3-phenylpropanoyl}amino)-3-{[(4-hydroxy-2-phenyl-3,4-dihydro-2H-chromen-4-yl)methyl]amino}-3-oxopropyl)-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl] propanoic acid (82 mg, 0.15 mmol) and 4-(aminomethyl)-2-phenyl-4-chromanol (45 mg, 0.18 mmol) according to Method C with HPLC purification to give the title compound (15 mg). $^1$H-NMR (400 MHz, CD$_3$OD) d 7.64 (s, 1H), 6.84 (dd, J=1.0 Hz, J=8.3 Hz, 1H), 5.33 (d, J=12.0 Hz, 1H), 4.64 (s, 2H), 4.63 (m, 1H), 4.28 (m, 1H), 3.95 (m, 1H), 3.19 (m, 1H), 1.35 (s, 3H), 1.32 (s, 6H); HRMS m/z 767.3084 (calc. of monoisotopic mass for C$_{42}$H$_{45}$N$_3$O$_{11}$ gives 767.3054).

Example 157-39

5-[(2S)-3-({2-[2-(benzyloxy)-5-chlorophenyl]-2-hydroxyethyl}amino)-2-({(2S)-2-[(tert-butoxycarbonyl)amino]-3-phenylpropanoyl}amino)-3-oxopropyl]-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl] propanoic acid (75 mg, 0.13 mmol) and 2-amino-1-[2-(benzyloxy)-5-chlorophenyl]-1-ethanol (45 mg, 0.16 mmol) according to Method C to give the title compound (66 mg) as a diasteromeric mixture. $^1$H-NMR (400 MHz, CD$_3$OD) d 4.77 (s, 1H), 4.75 (s, 1H), 4.55 (m, 1H), 4.22 (m, 1H), 1.33–1.32 (9H); HRMS m/z 789.2713 (calc. of monoisotopic mass for C$_{41}$H$_{44}$ClN$_3$O$_{11}$ gives 789.2664).

Example 157-40

5-[(2S)-3-{[2-(1-benzyl-1H-indol-3-yl)ethyl]amino}-2-({(2S)-2-[(tert-butoxycarbonyl)amino]-3-phenylpropanoyl}amino)-3-oxopropyl]-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl] propanoic acid (73 mg, 0.13 mmol) and 2-(1-benzyl-1H-indol-3-yl)ethylamine hydrochloride (45 mg, 0.16 mmol) according to Method C to give the title compound (48 mg). $^1$H-NMR (400 MHz, CD$_3$OD) d 7.56 (d, J=7.6 Hz, 1H), 6.81 (d, J=8.5 Hz, 1H), 5.28 (s, 2H), 4.69 (s, 2H), 4.48 (m, 1H), 4.22 (dd, J=5.2 Hz, J=9.2 Hz, 1H), 3.52 (m, 1H), 3.38 (m, 1H), 2.98 (m, 2H), 2.86 (m, 3H), 2.72 (dd, J=9.3 Hz, J=13.8 Hz, 1H), 1.33 (s, 9H); HRMS m/z 762.3292 (calc. of monoisotopic mass for C$_{43}$H$_{46}$N$_4$O$_9$ gives 762.3265).

Example 157-41

5-{2-({2-[(tert-Butoxycarbonyl)amino]-3-phenylpropanoyl}amino)-3-[methyl(pentyl)amino]-3-oxopropyl}-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl] propanoic acid (100 mg, 0.18 mmol) and N-methylamylamine (29 mg, 0.29 mmol) according to Method C with HPLC purification to give the title compound (33 mg). $^1$H-NMR (400 MHz, CD$_3$OD) d 7.76 (s, 1H), 7.5–7.15 (m, 6H), 7.04 (d, 1H), 5.02 (m, 1H), 4.81 (s, 2H), 4.28 (m, 1H), 3.25–2.7 (m, 9H), 1.10–1.5 (m, 15H), 0.89 (t, 3H); HRMS m/z 613.2982 (calc. of monoisotopic mass for C$_{32}$H$_{43}$N$_3$O$_9$ gives 613.2999).

Example 157-42

5-[(2S)-3-{[2-(Benzylsulfanyl)ethyl]amino}-2-({(2S)-2-[(tert-butoxycarbonyl)amino]-3-phenylpropanoyl}amino)-3-oxopropyl]-2-(carbomethoxy)benzoic Acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl] propanoic acid (100 mg, 0.18 mmol) and 2-(benzylsulfanyl)-1-ethanamine hydrochloride (44 mg, 0.22 mmol) according to Method C with HPLC purification to give the title compound (15 mg). $^1$H-NMR (400 MHz, CD$_3$OD) d 7.76 (s, 1H), 6.97 (d, J=8.6 Hz, 1H), 4.77 (s, 2H), 4.51 (m, 1H), 4.24 (dd, J=5.1 Hz, J=9.3 Hz, 1H), 3.71 (s, 2H), 3.19 (m, 1H), 2.74 (m, 1H), 2.41 (m, 2H), 1.35 (s, 9H); HRMS m/z 679.2542 (calc. of monoisotopic mass for C$_{34}$H$_{41}$N$_3$O$_9$S gives 679.2564).

Example 157-43

5-[(2S)-3-[([1,1'-Biphenyl]-4-ylmethoxy)amino]-2-({(2S)-2-[(tert-butoxycarbonyl)amino]-3-phenylpropanoyl}amino)-3-oxopropyl]-2-(carboxymethoxy)benzoic Acid Synthesis was performed from (2S)-2-({(2S)-2-[(tert-butoxycarbonyl)amino]-3-phenylpropanoyl}amino)-3-[3-(methoxycarbonyl)4-(2-methoxy-2-oxoethoxy)phenyl] propanoic acid (91 mg, 0.16 mmol) and 4-[(aminooxy)methyl]-1,1'-biphenyl hydrochloride (46 mg, 0.20 mmol) according to Method C with HPLC purification to give the title compound (47 mg). $^1$H-NMR (400 MHz, CD$_3$OD-Me$_2$SO-d6) d 7.74–7.16 (17H), 4.84 (1H), 4.76 (1H), 4.64 (s, 2H), 4.32 (m, 1H), 3.03 (m, 3H), 1.41 (s, 9H); IR (KBr) 3272, 2978, 1681, 1652 cm$^{-1}$; HRMS m/z 711.2831 (calc. of monoisotopic mass for C$_{39}$H$_{41}$N$_3$O$_{10}$ gives 711.2792).

Example 157-44

5-[(2S)3-{[2-(Benzylamino)-2-phenylethyl]amino}-2-({(2S)-2-[(tert-butoxycarbonyl)amino]-3-phenylpropanoyl}amino)-3-oxopropyl]-2-(carboxymethoxy)benzoic acid Synthesis was performed from (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl] propanoic acid (70 mg, 0.13 mmol) and N$^1$-benzyl-1-phenyl-1,2-ethandiamine dihydrochloride (45 mg, 0.15 mmol) according to Method C with HPLC purification to give the title compound (11 mg) as a diastereomeric mixture. $^1$H-NMR (400 MHz, CD$_3$OD) d 7.50 (1H), 7.45–7.03 (17H), 4.40 (m, 1H), 4.25 (m, 1H), 4.06 (m, 1H), 3.80 (s, 2H), 3.03 (m, 1H), 1.33 (s, 9H); HRMS m/z 738.3281 (calc. of monoisotopic mass for C$_{41}$H$_{46}$N$_4$O$_9$ gives 738.3265).

Example 157-45

5-[(2S)-2-({(2S)-2-[(tert-butoxycarbonyl)amino]-3-phenylpropanoyl}amino)-3-[(1-methyl-3,3-diphenylpropyl)amino]-3-oxopropyl]-2-(carboxymethoxy)benzoic acid Synthesis was performed from (2S)-2-({(2S)-2-[(tert-butoxycarbonyl)amino]-3-phenylpropanoyl}amino)-3-[3-

(methoxycarbonyl)-4-(2-methoxy-2-oxoethoxy)phenyl]propanoic acid (88 mg, 0.16 mmol) and 1-methyl-3,3-diphenylpropylamine (45 mg, 0.19 mmol) according to Method C with HPLC purification to give the title compound (31 mg) as a diastereomeric mixture in a 2:1 ratio. HRMS m/z 737.3312 (calc. of monoisotopic mass for $C_{42}H_{47}N_3O_9$ gives 737.3329).

Preparation of Starting Material (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl]propanoic acid General. All experiments were carried out under $N_2$-atmosphere, except the hydrogenation and carbonylation reactions. Melting points were determined in open glass capillaries on a Gallenkamp apparatus and were not corrected. $^1H$ NMR and $^{13}C$ NMR were recorded on a Bruker Avance DPX 400 spectrometer at 400.1 and 100.6 MHz, respectively or on a Bruker DRX 500 at 500 MHz and at 125.7 MHz, respectively. $^1H$ NMR and $^{13}C$ NMR spectra were referenced to internal tetramethylsilane. IR spectra were recorded on a Perkin-Elmer Spectrum 1000 FT-IR spectrophotometer. Ionspray MS spectra were obtained on a Perkin Elmer API 150EX mass spectrometer. Thin-layer chromatography was carried out using pre-coated silica gel F-254 plates (thickness 0.25 mm). Column chromatography was performed on silica using Kieselgel 60 (230–400 mesh), E. Merck. The elemental analyses were performed by Mikro Kemi AB, Uppsala, Sweden.

a) Benzyl (2S)-2-amino-3-(4-hydroxy)-3-iodophenyl)propanoate Hydrochloride

3-Iodo-L-tyrosine (5.0 g, 16.3 mmol) was suspended in benzyl alcohol (100 mL) and at 0° C., thionyl chloride (20 mL) was added dropwise over a 20-min period. The temperature was raised to 80° C. and HCl (g) started to evolve. The reaction mixture became yellow turbid and turned to clear colorless after 30 min. After 8 h of heating, the mixture was stirred overnight at ambient temperature. Dry diethyl ether (150 mL) was added and the flask was stored overnight at −10° C. The white product was collected on a glass-sintered funnel and dried (1.91 g). An additional amount of 2.65 g was obtained after the addition of i-hexane and storage at −10° C. The combined material was taken up in 5% $NaHCO_3$ (200 mL) and extracted with ethyl acetate (3×150 mL). The combined organic layers were dried ($Na_2SO_4$) and evaporated in vacuo leaving a crude yellow oil (4.00 g; 64%). Mp (HCl salt): 187–188° C.; $^1H$ NMR (HCl salt, $CD_3OD$) δ 3.02 (d, J=6.8, 2H), 4.22 (t, J=6.8, 1H), 5.15 (q, $J_1$=15.9, $J_2$=3.9, 2H), 6.68 (d, J=8.3, 1H), 6.91, (dd, $J_1$=8.3, $J_2$=2.2, 1H), 7.23–7.31 (m, 5H), 7.51 (d, J=2.2, 1H); $^{13}C$ NMR (HCl salt, $CD_3OD$) δ 36.44, 55.61, 69.60, 85.56, 116.48, 128.11, 130.14, 130.22, 130.28, 131.99, 136.49, 141.55, 158.35, 170.34; MS (Ionspray, [M+H]$^+$) m/z 396.2; Anal. Calcd. (found) for $C_{16}H_{16}INO_3$·HCl: C, 44.3 (44.7) % H, 4.0 (3.9) % N, 3.2(3.2) %.

b) Benzyl (2S)-2-({(2S)-2-[(tert-butoxycarbonyl)amino]-3-phenylpropanoyl}amino)-3-(4-hydroxy-3-iodophenyl)propanoate The free base of benzyl (2S)-2-amino-3-(4-hydroxy)-3-iodophenyl)propanoate hydrochloride (3.97 g, 10.0 mmol) was dissolved in dichloromethane (75 mL) and stirred at 0° C. under $N_2$-atmosphere. Then, EDC (1.92 g, 10.0 mmol), HOBT (1.35 g, 10.0 mmol) and BOC-L-Phe (2.65 g, 10.0 mmol) were added simultaneously and triethylamine 1.39 mL, 10.0 mmol) was added dropwise. This reaction mixture was stirred for 15 h allowing to warm to ambient temperature. Ethyl acetate (200 mL) was added and the organic layer was washed with 5% HCl (2×200 mL). The combined aqueous phases were extracted with ethyl acetate (100 mL) after which the combined organic layers were washed with 10% $NaHCO_3$ (100 mL). Drying ($Na_2SO_4$), filtration and evaporation in vacuo gave an off-white foam (6.01 g, 93%). The product was purified by flash column chromatography on silica gel eluting with chloroform giving a 4.88 g (76%) of a white foam. Mp: 81.6–82.7° C.; $^1H$ NMR δ 1.39 (s, 9H), 2.89–2.98 (m, 2H), 3.03 (d, J=6.5, 2H), 4.33 (m, 1H), 4.75 (m, 1H), 4.94 (br s, 1H), 5.10 (s, 2H), 5.60 (br s, 1H), 6.37 (d, J=8.0, 1H), 6.73, (s, 1H), 7.17–7.39 (m, 11H); $^{13}C$ NMR δ 28.24, 36.52, 38.26, 53.34, 55.85, 67.36, 85.47, 115.02, 128.59, 128.66, 128.71, 128.75, 129.30, 129.58, 131.04, 134.86, 136.39, 138.79, 154.04, 170.58, 170.91; MS (Ionspray, [M−H]$^+$) m/z 643.2; Anal. Calcd. (found) for $C_{30}H_{33}IN_2O_6$: C, 55.9 (56.3) % H, 5.5 (5.2) % N, 4.4 (4.7) %.

c) Methyl 5-[(2S)-3-(benzyloxy)-2-({(2S)-2-[(tert-butoxycarbonyl)amino]-3-phenylpropanoyl}amino)-3-oxopropyl]-2-hydroxybenzoate A mixture of benzyl (2S)-2-({(2S)-2-[(tert-butoxycarbonyl)amino]-3-phenylpropanoyl}amino)-3-(4-hydroxy-3-iodophenyl)propanoate (4.43 g, 6.87 mmol), Pd(OAc)$_2$ (50 mg, 3.3 mol %) and DPPF (230 mg, 6.2 mol %) in acetonitrile (20 mL) was treated with triethylamine (1.9 mL, 13.74 mmol) and methanol (4.4 mL). A carbon monoxide atmosphere was established and the reaction mixture was heated at 70° C. (Essential! Solvent vapour displaces CO if temperature is too high) for 16 h. The dark brown reaction mixture was directly coated on silica gel and subjected to column chromatography (3×20 cm) eluting with chloroform. Pure fractions were pooled giving 2.45 g (62%) off-white solid after evaporation of the eluent. Pure material can be obtained by recrystallization from abs. ethanol. $^1H$ NMR δ 1.38 (s, 9H), 2.98–3.05 (m, 4H), 3.87 (s, 3H), 4.37 (br s, 1H), 4.78 (q, $J_1$=13.2, $J_2$=7.2, 1H), 4.99 (br s, 1H), 5.08 (s, 2H), 6.43 (d, J=7.5, 1H), 6.76 (d, J=8.5, 1H), 6.95 (dd, $J_1$=8.5, $J_2$=2.2, 1H), 7.16–7.37 (m, 10H) 7.46 (d, J=2.2, 1H), 10.62 (s, 1H); $^{13}C$ NMR δ 28.19, 36.97, 38.19, 52.30, 53.35, 55.71, 67.28, 80.27, 112.11, 117.77, 126.20, 126.99, 128.50, 128.60, 128.66, 129.28, 130.30, 134.84, 136.45, 136.68, 155.33, 160.58, 170.20, 170.65, 170.87; MS (Ionspray, [M−H]$^+$) m/z 575.2; Anal. Calcd. (found) for $C_{32}H_{36}N_2O_8$·0.25 $H_2O$: C, 66.1 (66.0) % H, 6.3 (6.5) % N, 4.8 (4.9) % d) Methyl 5-[(2S)-3-(benzyloxy)-2-({(2S)-2-[(tert-butoxycarbonyl)amino]-3-phenylpropanoyl}amino)-3-oxopropyl]-2-(2-methoxy-2-oxoethoxy)benzoate A mixture of methyl 5-[(2S)-3-(benzyloxy)-2-({(2S)-2-[(tert-butoxycarbonyl)amino]-3-phenylpropanoyl}amino)-3-oxopropyl]-2-hydroxybenzoate (1.68 g, 2.91 mmol), methyl bromoacetate (0.83 uL, 3 eq.) and $K_2CO_3$ (activated, 1.20 g, 3 eq.) in acetone (20 mL) was heated at 50° C. overnight. TLC showed complete conversion and water (20 mL) was added. Extraction with dichloromethane (3×25 mL), drying ($Na_2SO_4$) and removal of the solvent at the rotavapor afforded 2.27 g of a yellow oil. Flash column chromatography on silica gel (2×20 cm) eluting with chloroform gave 1.17 g (62%) of a pure colorless oil, that solidified on standing. An additional amount (0.45 g) impure colorless oil was isolated. $^1H$ NMR δ 1.36 (s, 9H), 2.95–3.11 (m, 4H), 3.78 (s, 3H), 3.85 (s, 3H), 4.36 (br s, 1H), 4.66 (s, 2H), 4.80 (q, 1H), 5.09 (s, 2H), 5.11 (br s, 1H), 6.57 (d, 1H), 6.66 (d, 1H), 7.00 (dd, 1H), 7.17–7.37 (m, 10H) 7.48 (d, 1H); $^{13}C$ NMR δ 28.06, 36.69 38.01, 52.02, 52.15, 53.12, 55.62, 66.45, 67.20, 80.05, 114.27, 120.75, 126.79, 128.34, 128.43, 128.48, 128.50, 128.90, 129.16, 132.65, 134.12, 136.49, 156.40, 165.86, 168.82, 170.48, 170.87; MS (Ionspray, [M-H]$^+$) m/z 647.4; Anal. Calcd. (found) for $C_{35}H_{40}N_2O_{10}\cdot 0.25\ H_2O$: C, 64.4(64.1) % H, 6.3 (6.2) % N, 4.3(4.3) %.

e) (2S)-2-({(2S)-2-[(tert-butoxycarbonyl)amino]-3-phenylpropanoyl}amino)-3-[3-(methoxycarbonyl)-4-(2-methoxy-2-oxoethoxy)phenyl]propanoic Acid Methyl 5-[(2S)-3-(benzyloxy)-2-({(2S)-2-[(tert-butoxycarbonyl)amino]-3-phenylpropanoyl}amino)-3-oxopropyl]-2-(2-methoxy-2-oxoethoxy)benzoate (0.97 g, 1.50 mmol) was hydrogenated (atmospheric pressure) in abs ethanol (30 mL) over 10% Pd/C (100 mg) for 3 h. Filtration over diatomaceous earth and evaporation in vacuo of the filtrate yielded 0.76 g (91%) of a light-grey foam. $^1$H NMR (CD$_3$OD) δ 1.33 (s, 9H), 2.62–2.75 (m, 1H), 2.98–3.08 (m, 2H), 3.17–3.22 (m, 1H), 3.74 (s, 3H), 3.83 (s, 3H), 4.27 (m, 1H), 4.64 (m, 1H), 4.76 (s, 2H), 6.93 (d, 1H), 7.18–7.27 (m, 5H) 7.35 (d, 1H), 7.64 (s, 1H), $^{13}$C NMR (CD$_3$OD) δ 28.12, 36.82, 38.71, 52.08, 54.32, 56.96, 66.52, 80.16, 114.89, 121.30, 127.15, 128.87, 129.81, 130.92, 133.06, 135.20, 138.16, 157.31, 167.67, 170.37, 173.49, 173.66; MS (Ionspray, [M-H]$^+$) m/z 557.2; Anal. Calcd. (found) for $C_{28}H_{34}N_2O_{10}\cdot 0.25\ H_2O$: C, 59.7 (59.6) % H, 6.2 (6.1) % N, 5.0 (4.9) %

EXAMPLE 158

2-(Carboxymethoxy)-5-[(2S)-3-oxo-3-(pentylamino)-2-({(2S)-2-[(phenoxycarbonyl)amino]-3-phenylpropanoyl}amino)propyl]benzoic Acid The title compound was prepared in analogy with the preparation of the compound of Example 151 above. MS (FAB) m/z (rel. intensity) 620 (MH+, 18), 620 (18), 231 (52), 155 (33), 154 (99), 137 (65), 109 (18), 91 (16), 57 (11), 45 (11), 43 (11). Anal. Calcd for $C_{33}H_{37}N_3O_9$: C, 63.96, H, 6.02; N, 6.78. Found: C, 64.06, H, 6.27; N, 6.53.

EXAMPLE 159

2-(Carboxymethoxy)-5-[(2S)-2-{[(3R)-3-carboxy-4-phenylbutanoyl]amino}-3-oxo-3-(pentylamino)propyl]benzoic Acid The title compound was prepared in analogy with the preparation of the compound of Example 151 above. MS (FAB) m/z (rel. intensity) 543 (MH+, 25), 544 (9), 543 (25), 309 (15), 263 (9), 233 (10), 231 (48), 154 (99), 137 (58), 109 (15), 91 (16). MS (FAB) m/z (rel. intensity) 543 (MH+, 99), 565 (20), 544 (33), 543 (99), 238 (25), 117 (16), 107 (16), 88 (58), 43 (23), 41 (16), 23 (17). HRMS (FAB) calcd for $C_{28}H_{34}N_2O_9$+H1 543.2343, found 543.2353. Anal. Calcd for $C_{28}H_{34}N_2O_9$: C, 61.98; H, 6.32; N, 5.16. Found: C, 60.35; H, 6.35; N, 4.89.

CHART A

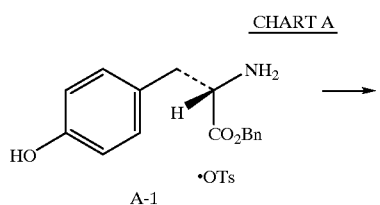

A-1

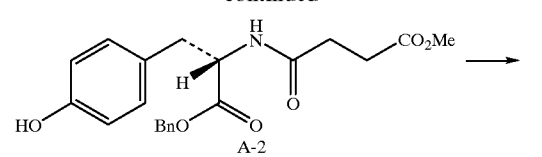

A-2

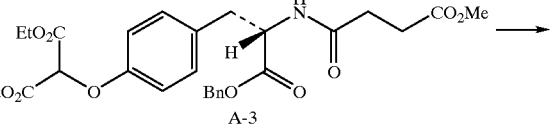

A-3

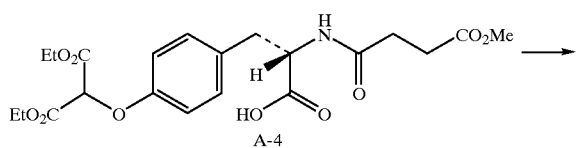

A-4

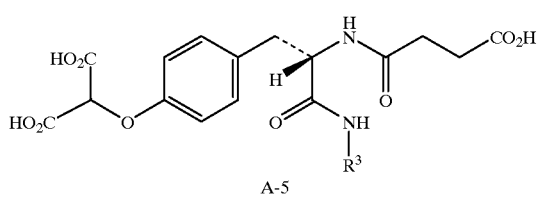

A-5

CHART B

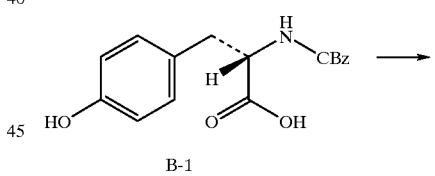

B-1

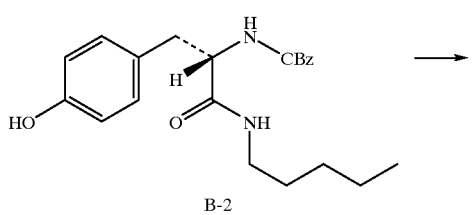

B-2

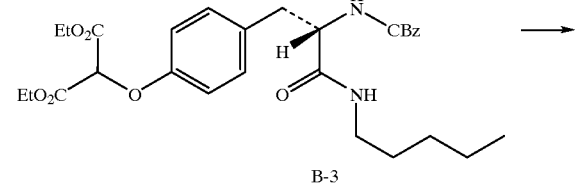

B-3

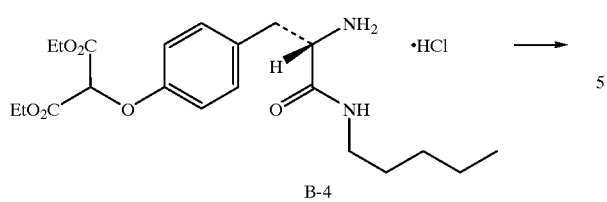
B-4
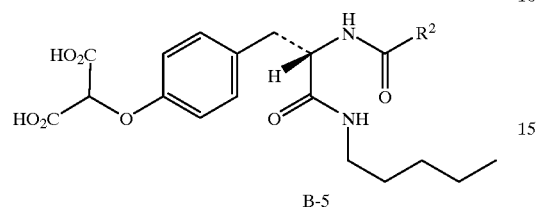
B-5
CHART C
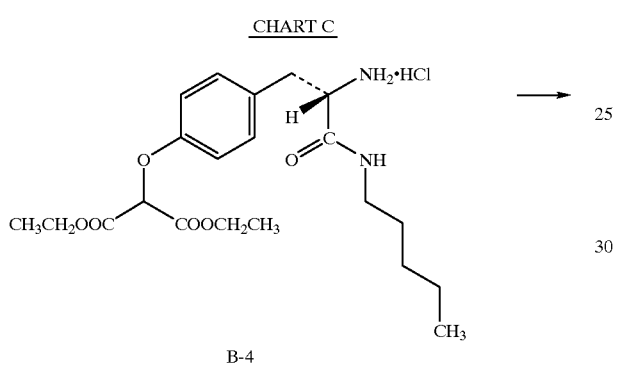
B-4
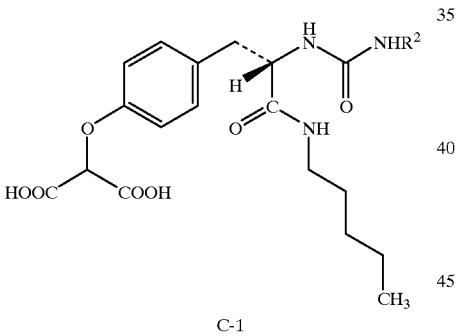
C-1
CHART D
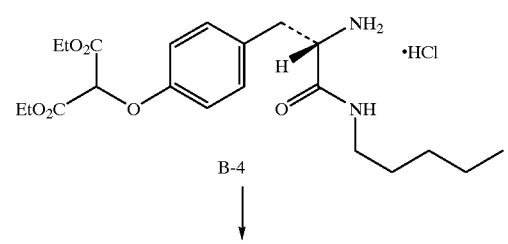
B-4
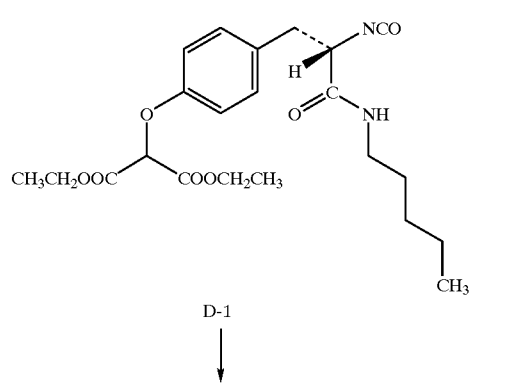
D-1
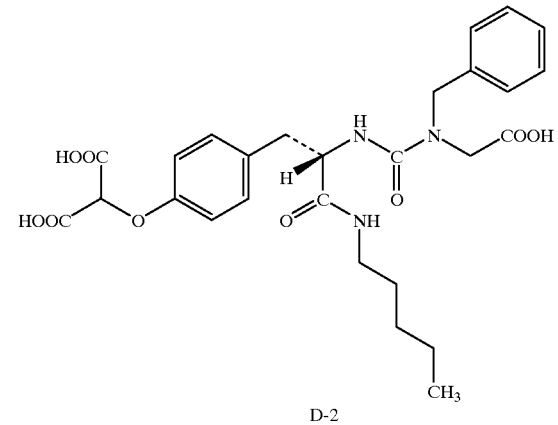
D-2
CHART E
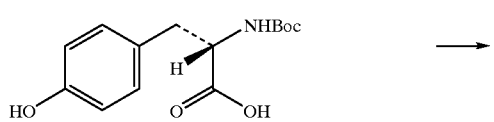
E-1
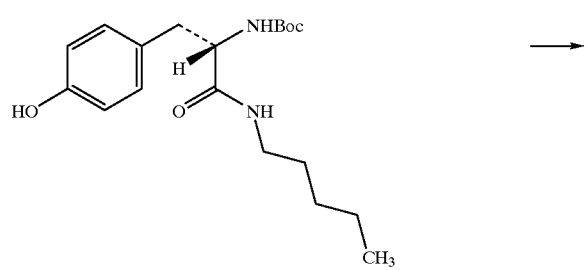
E-2

153
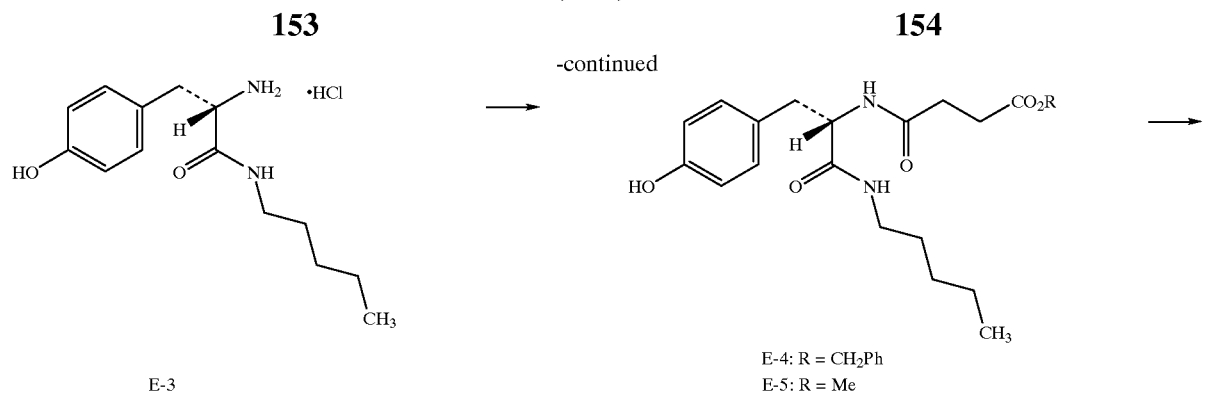
154
-continued
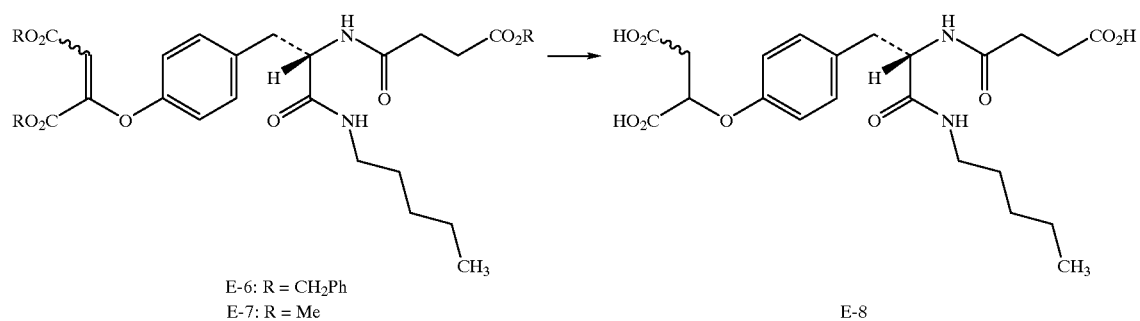
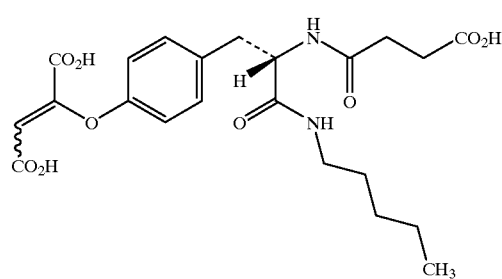
CHART F
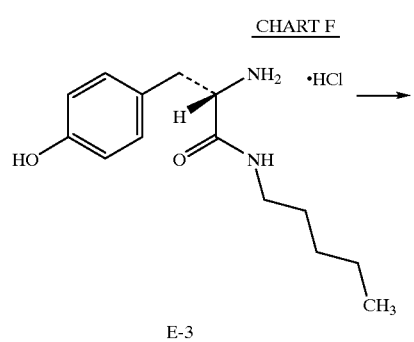
-continued
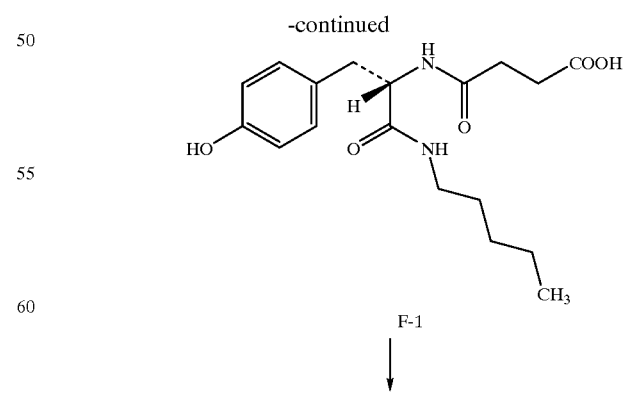

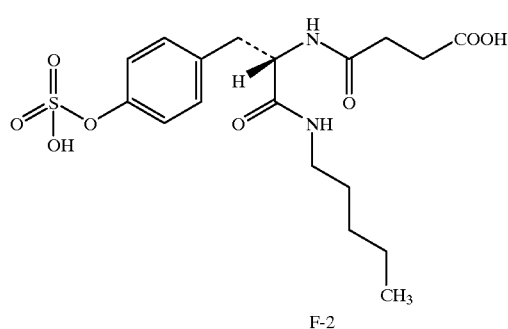
F-2
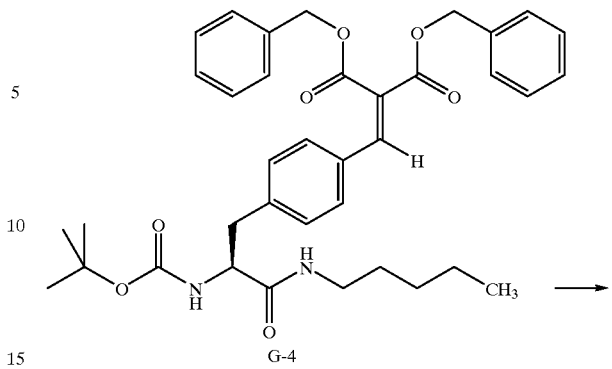
G-4
CHART G
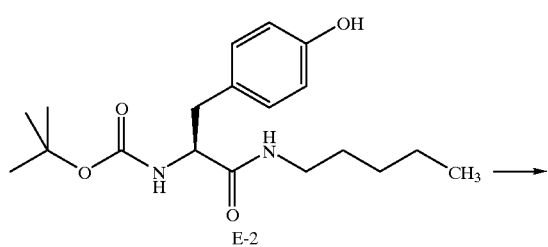
E-2
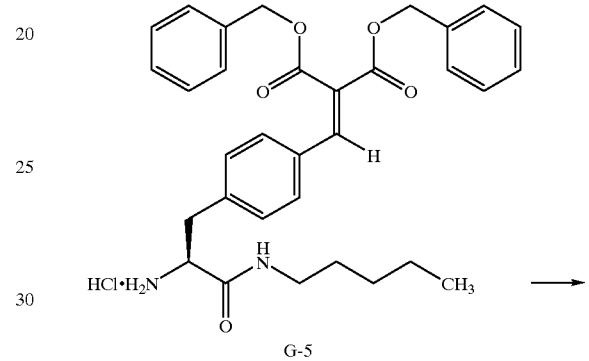
G-5
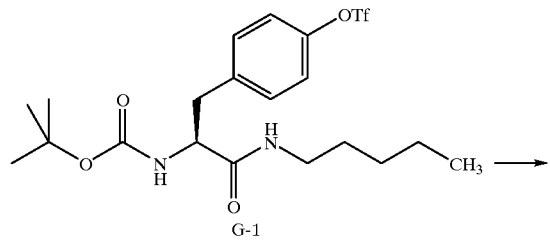
G-1
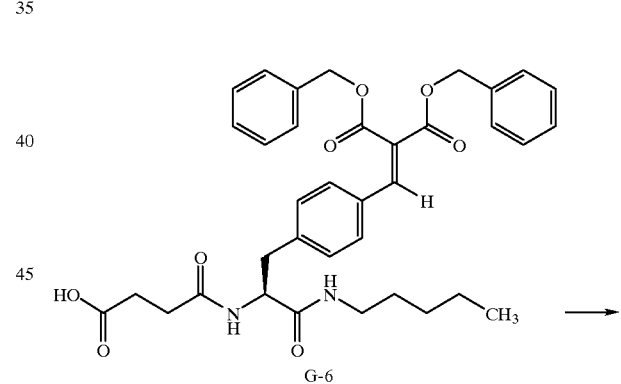
G-6
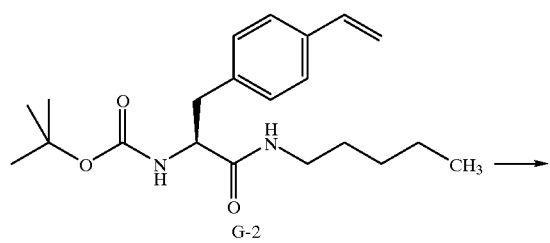
G-2
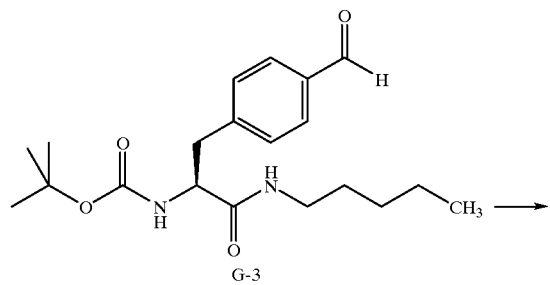
G-3
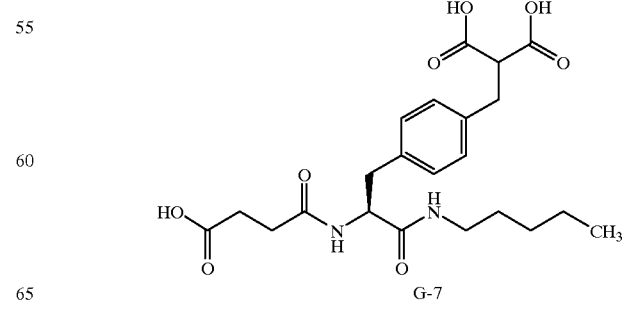
G-7

CHART H
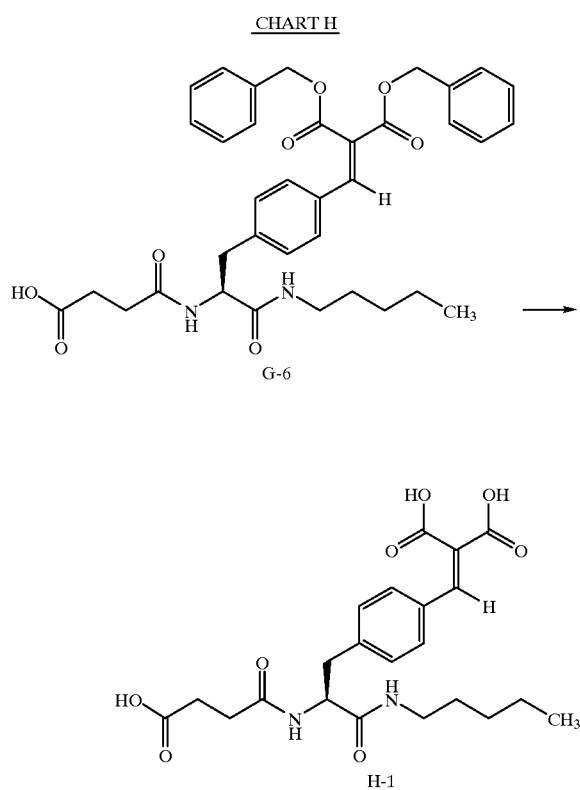
CHART I
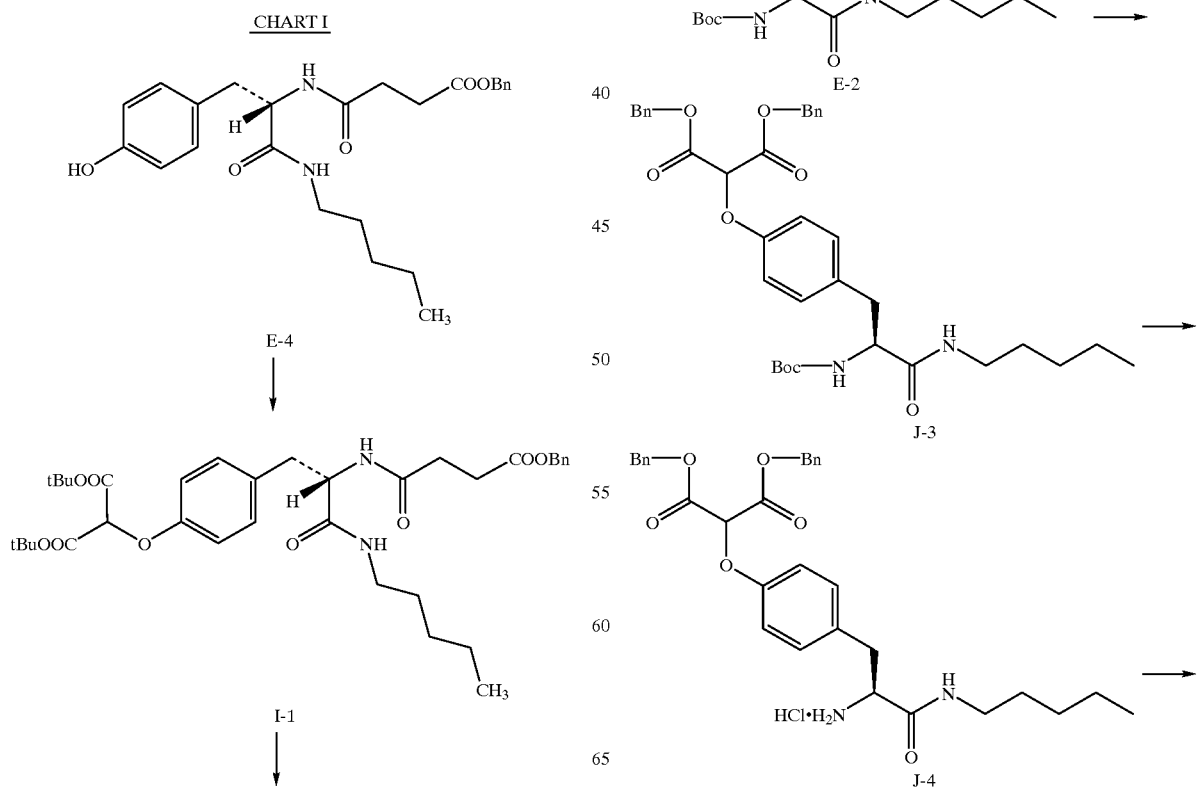

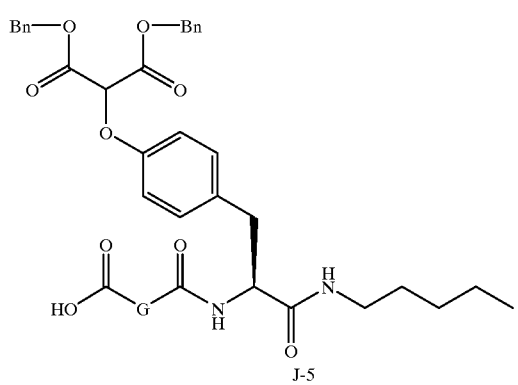
J-5
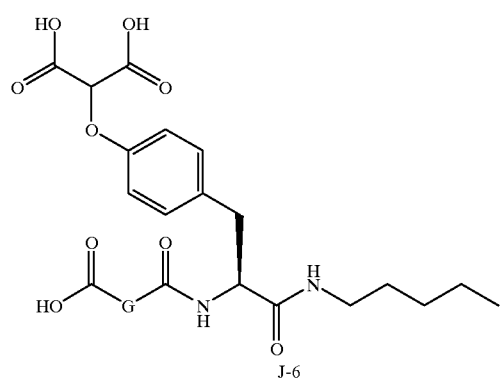
J-6
CHART K
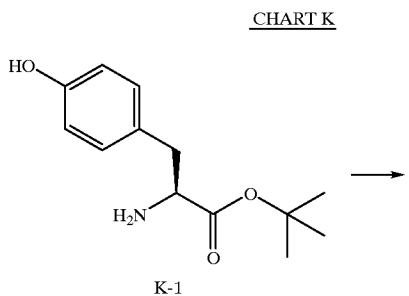
K-1
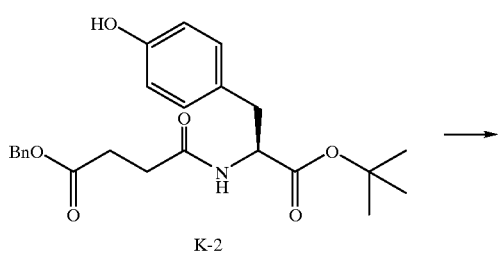
K-2
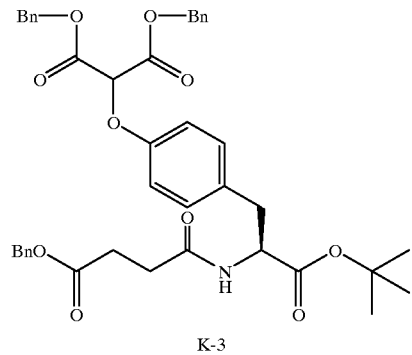
K-3
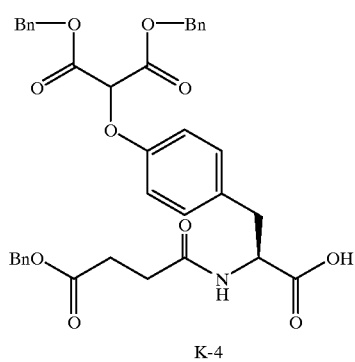
K-4
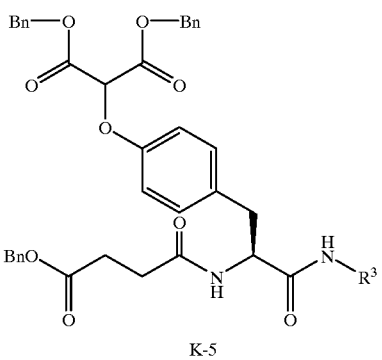
K-5
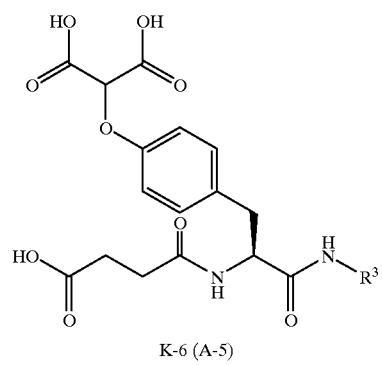
K-6 (A-5)

CHART L
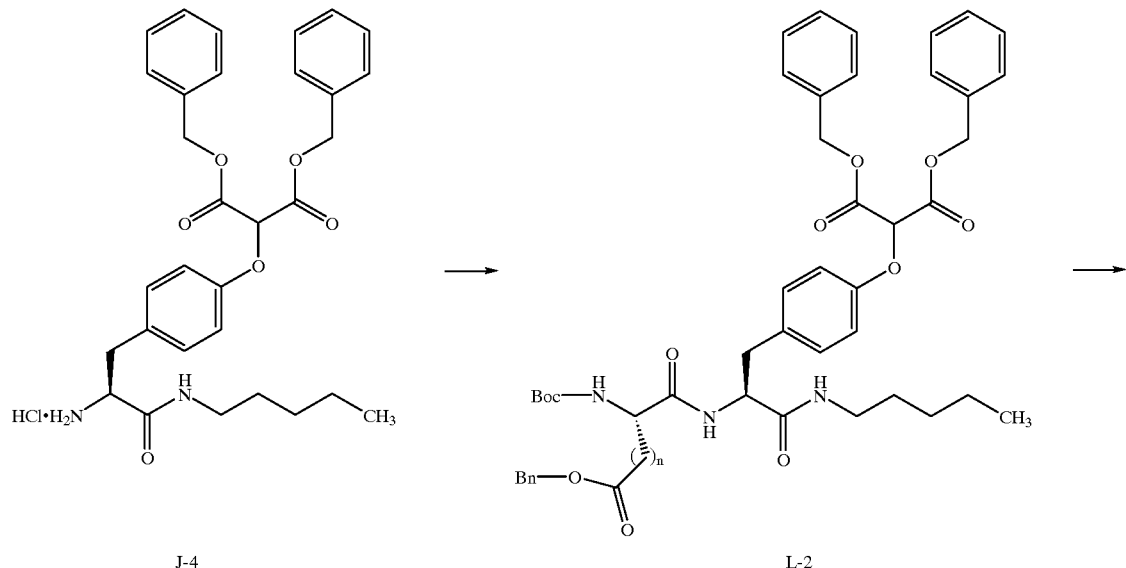
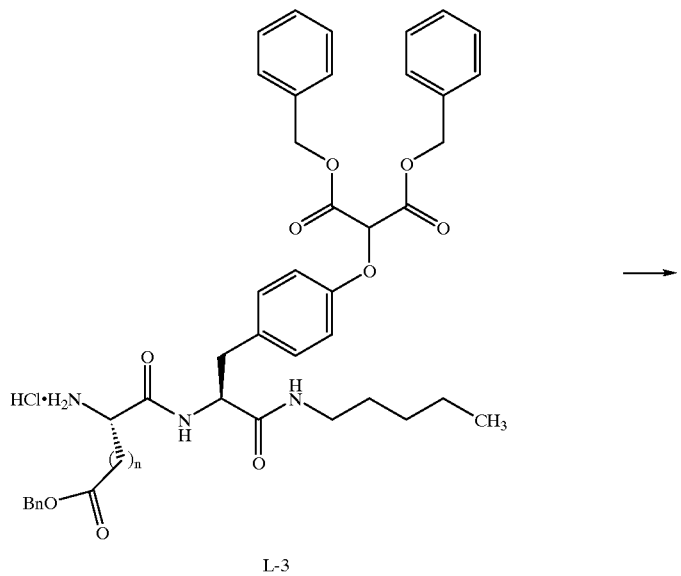

-continued
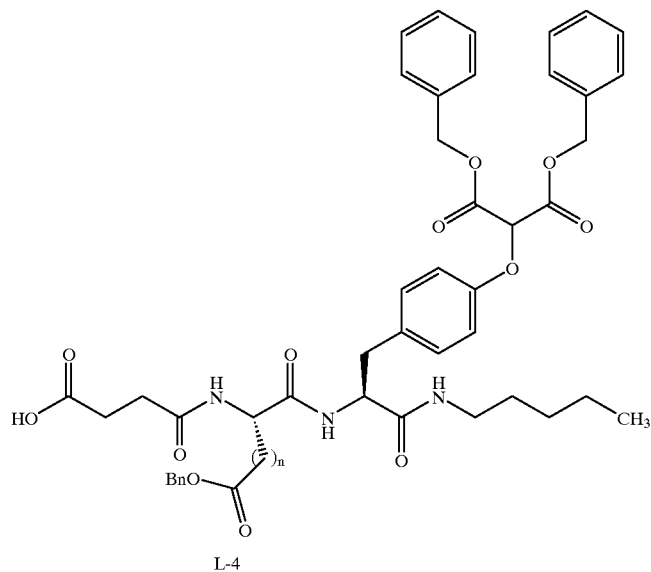 
L-4
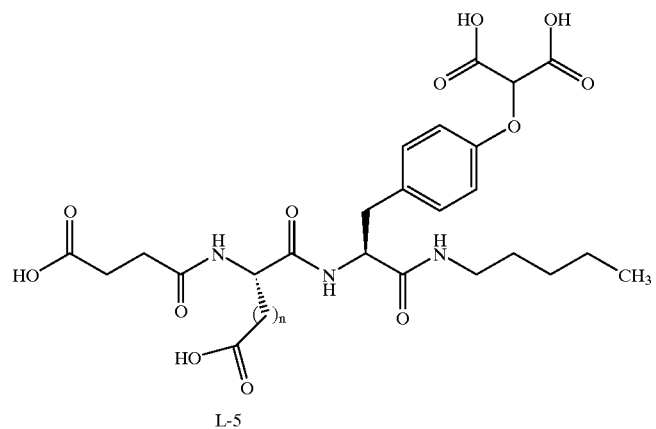
L-5
CHART M
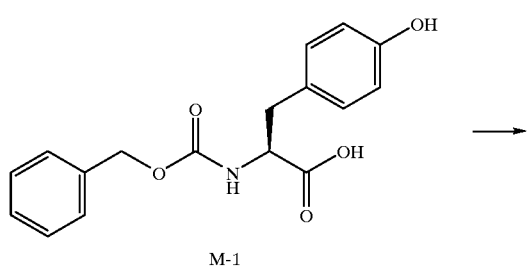 
M-1
-continued
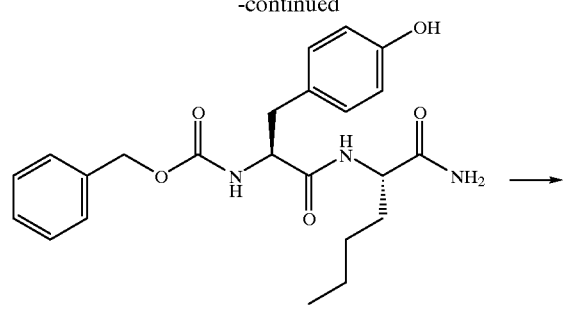
M-2

165
-continued
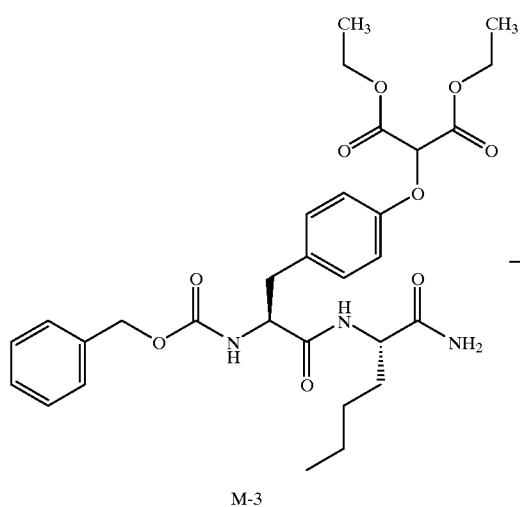
M-3
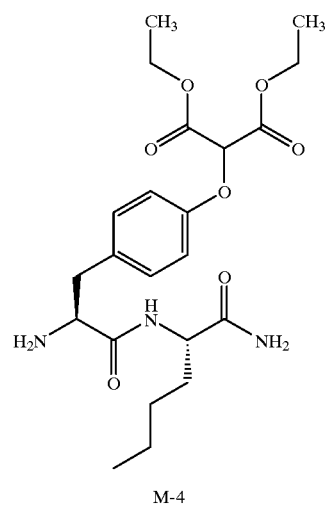
M-4
166
-continued
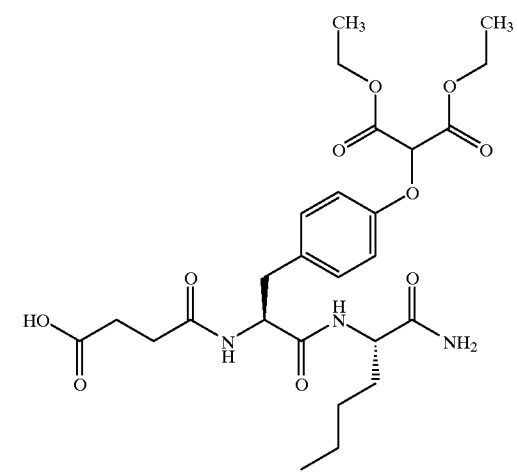
M-5
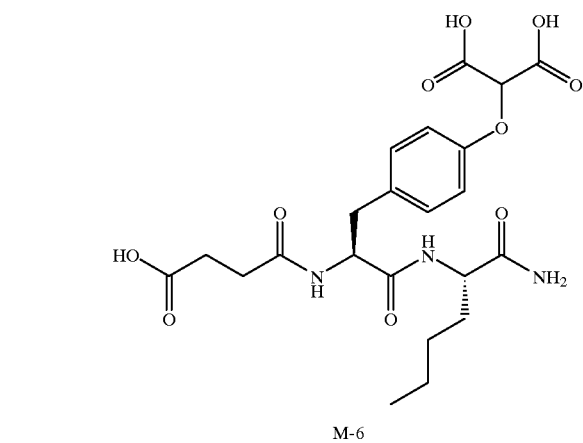
M-6

CHART N
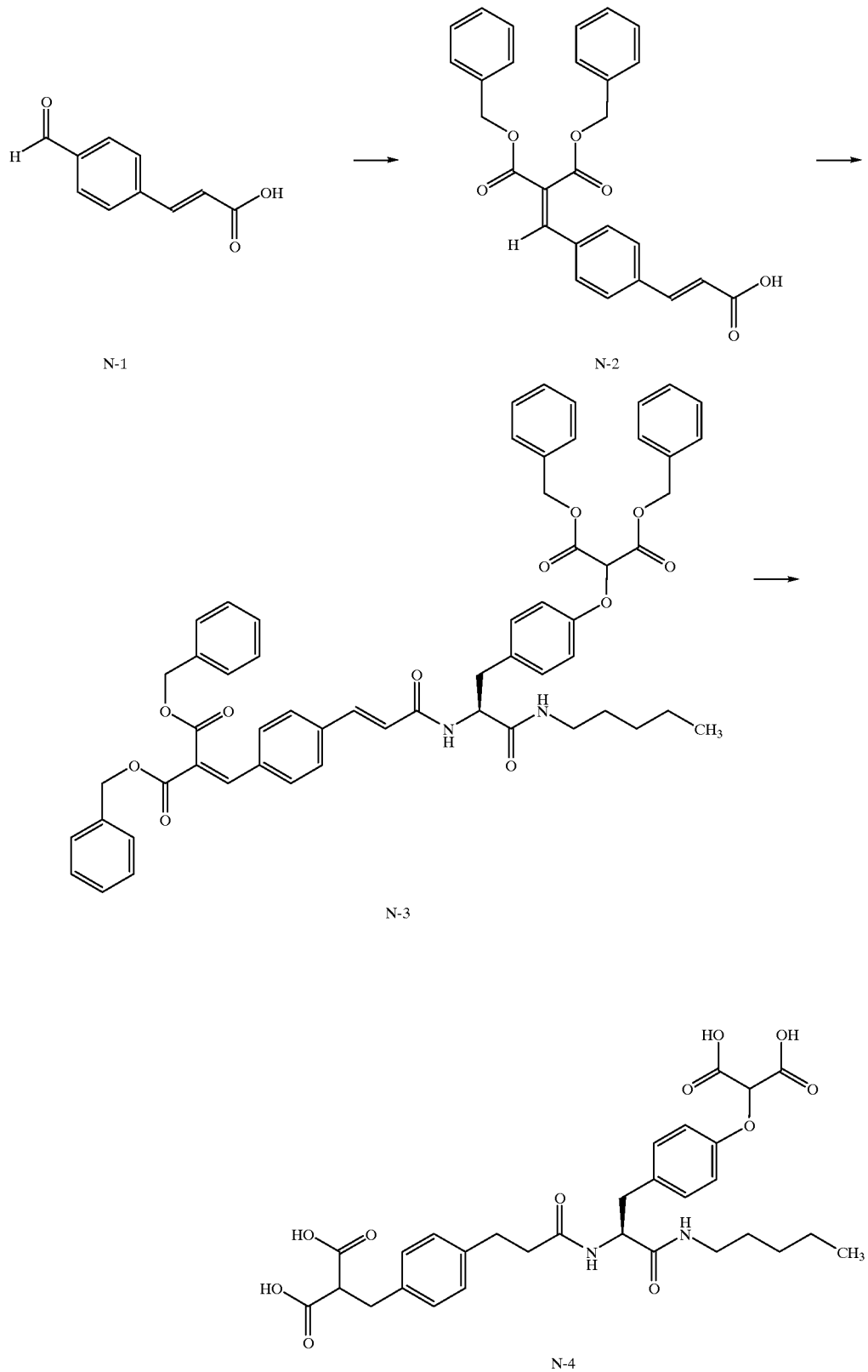

CHART O
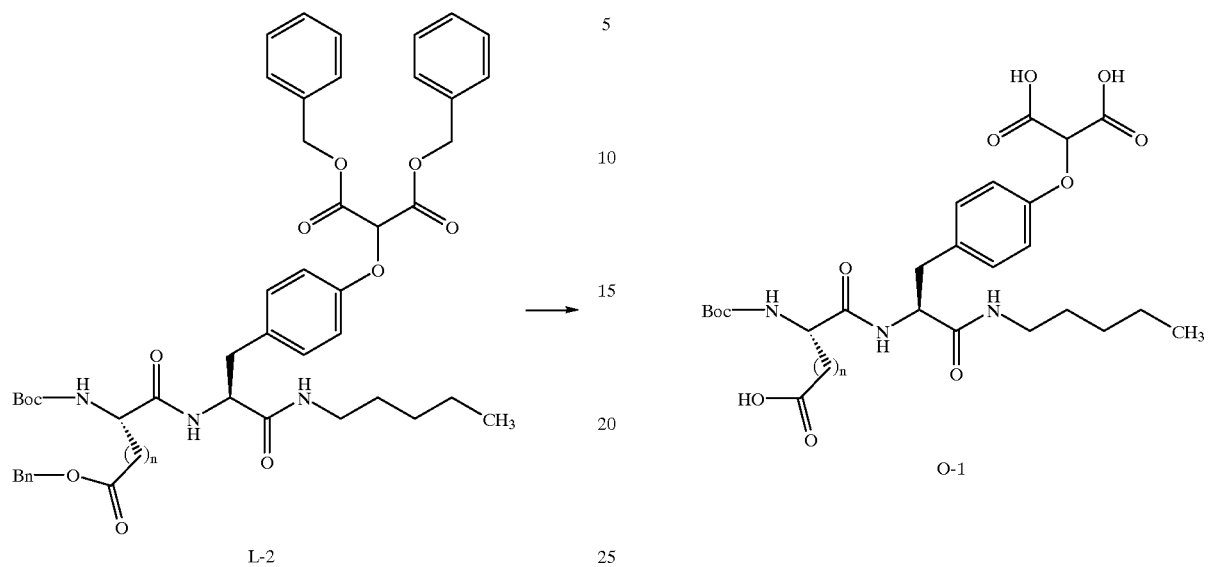
CHART P
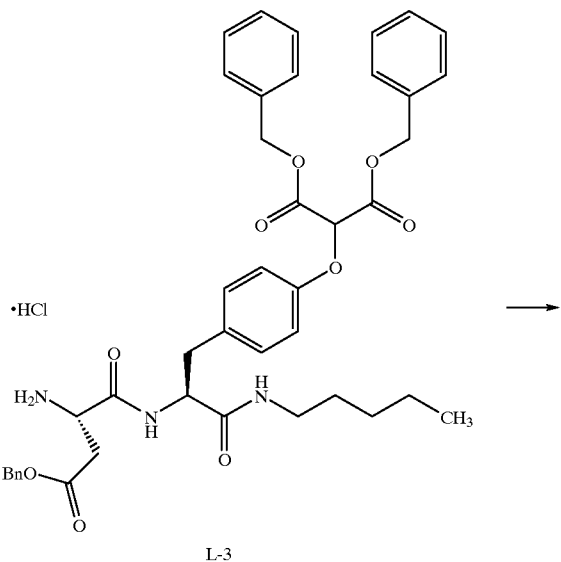

-continued
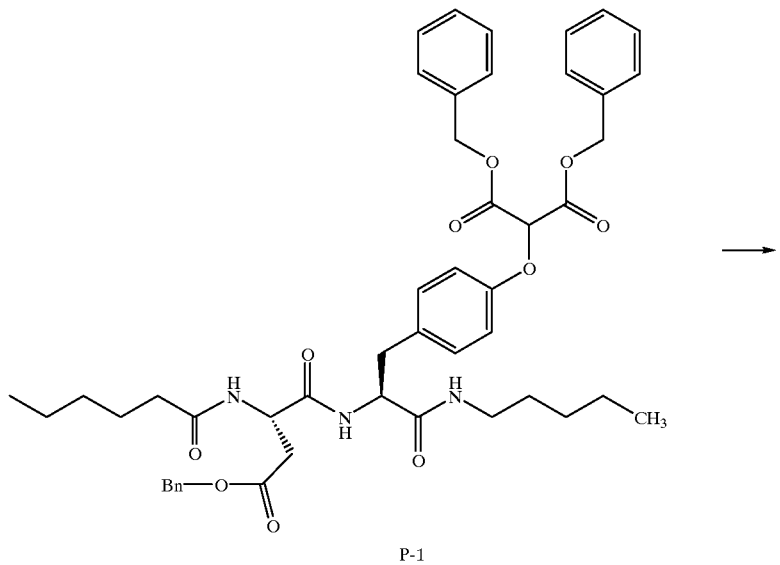
P-1
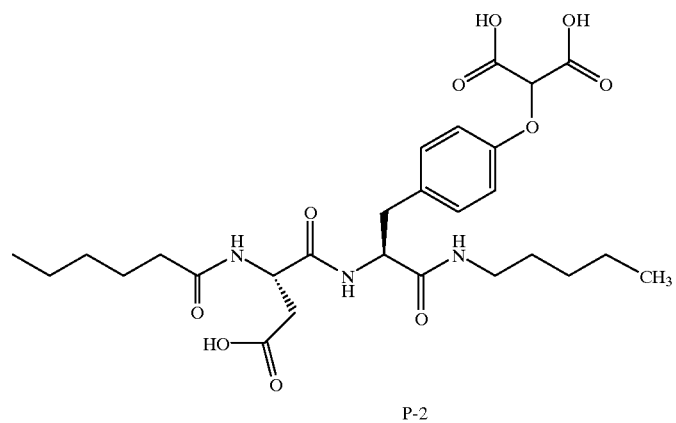
P-2
CHART Q
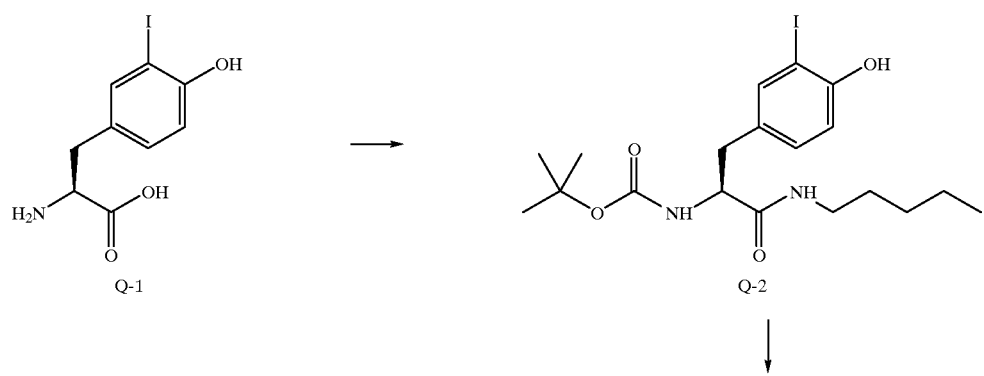
Q-1    Q-2

173 174
-continued
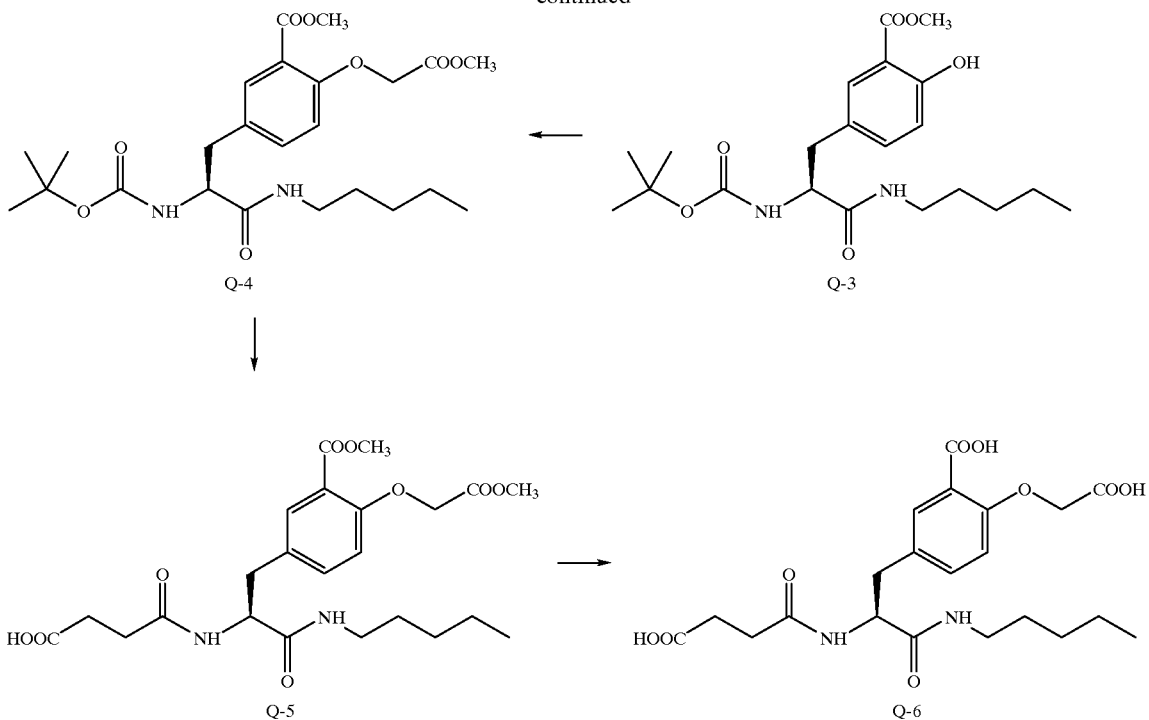
CHART R
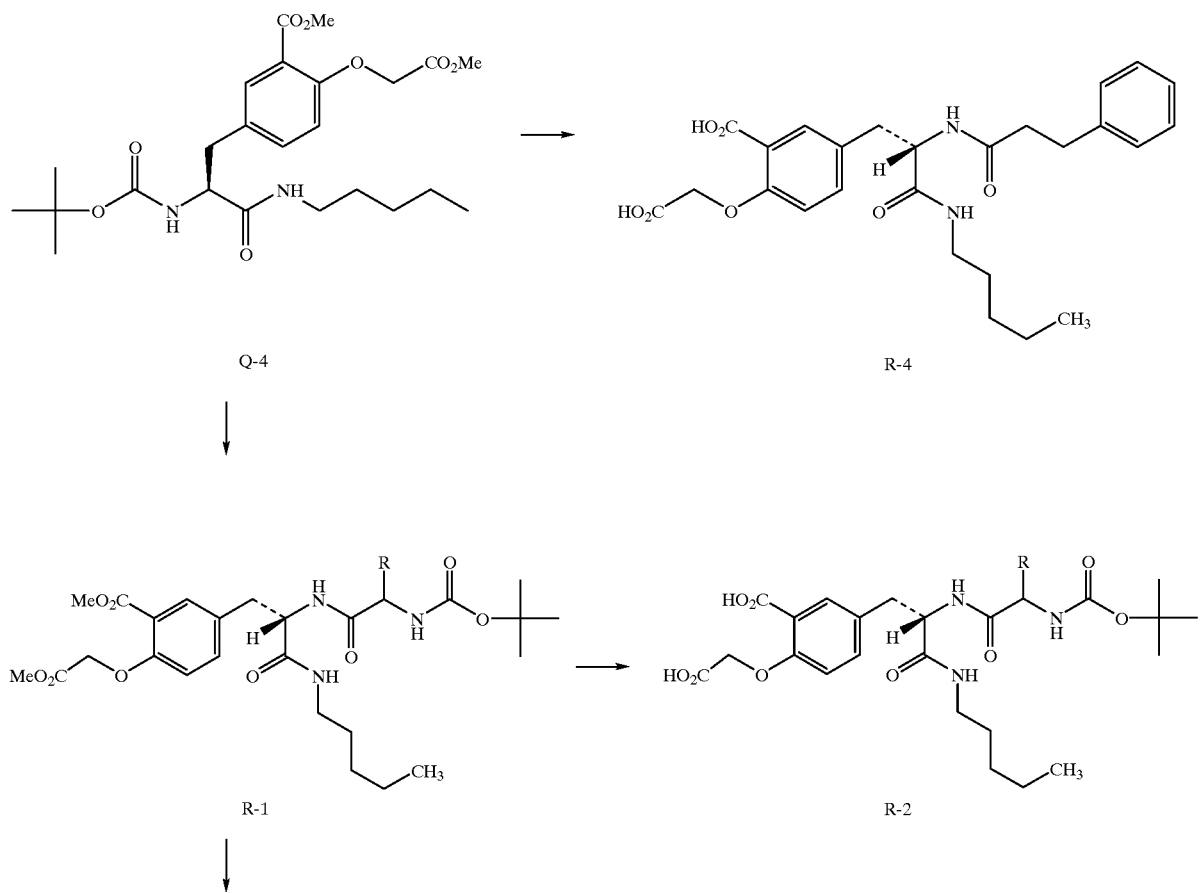

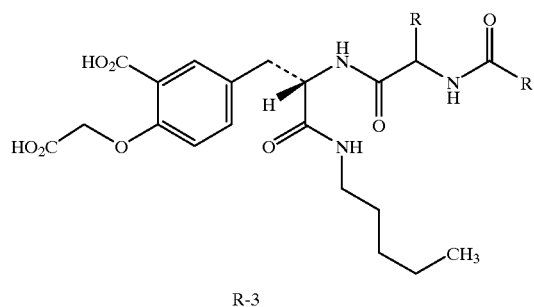
R-3
CHART S
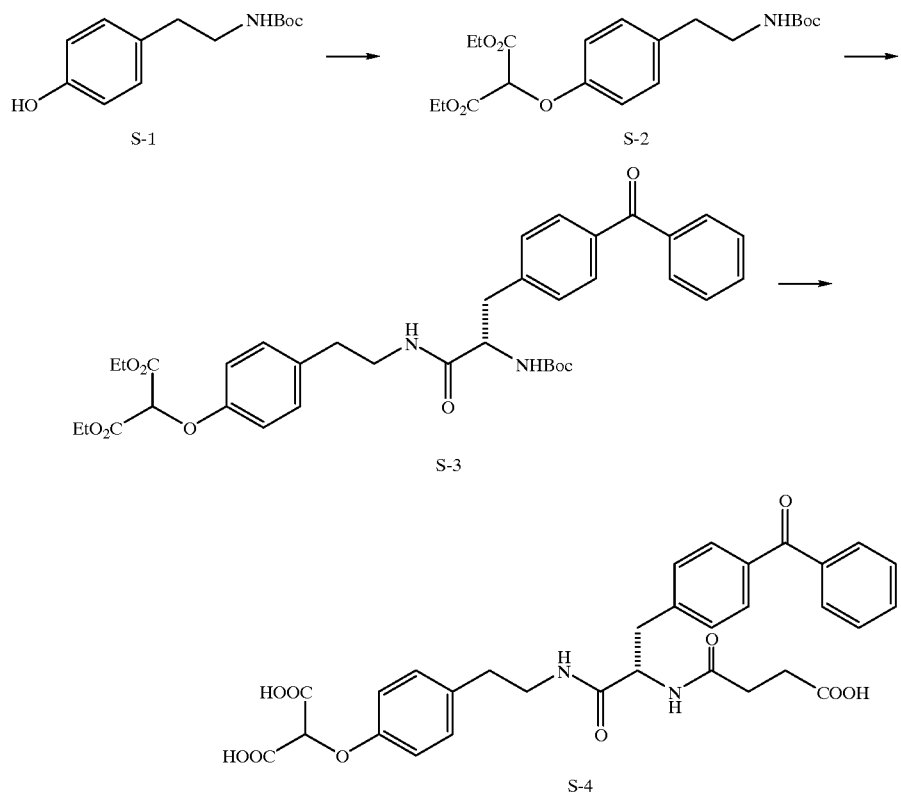
CHART T
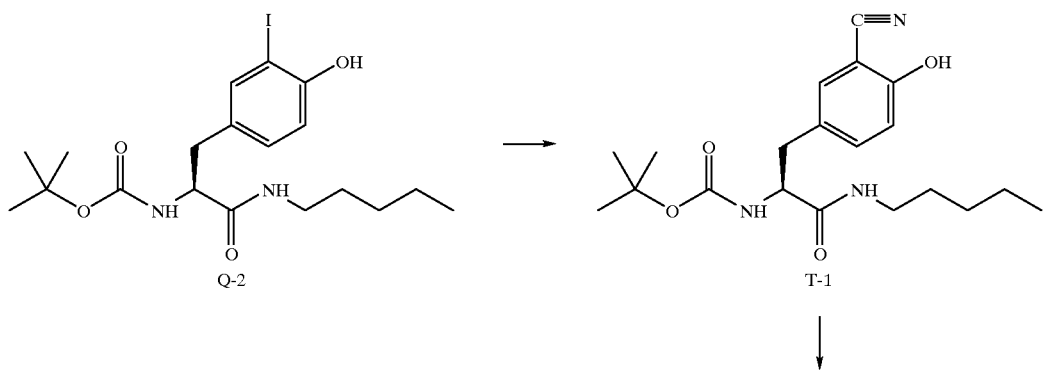

177
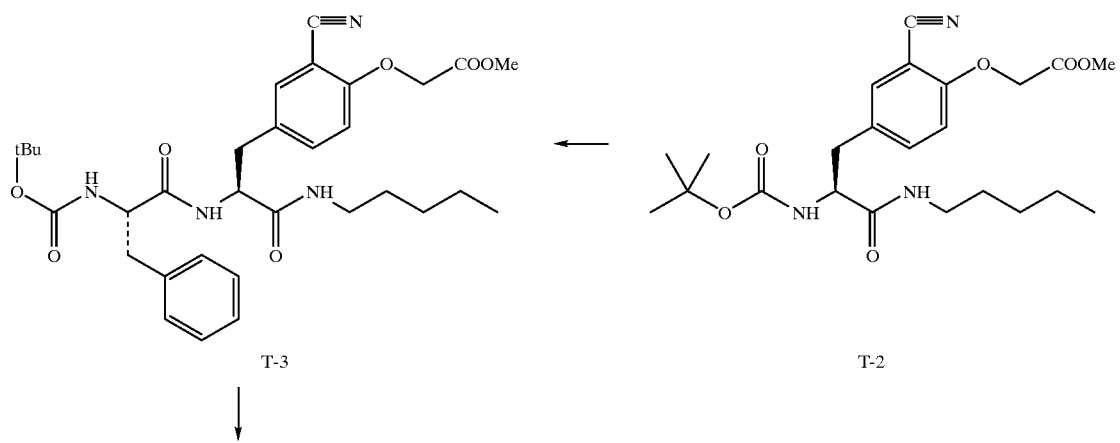
T-3
178
-continued
T-2
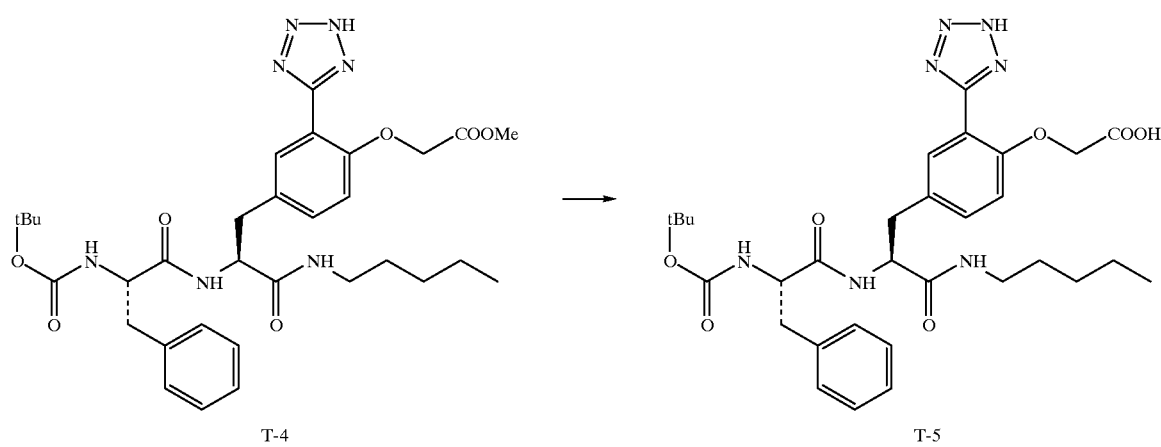
T-4
T-5
CHART U
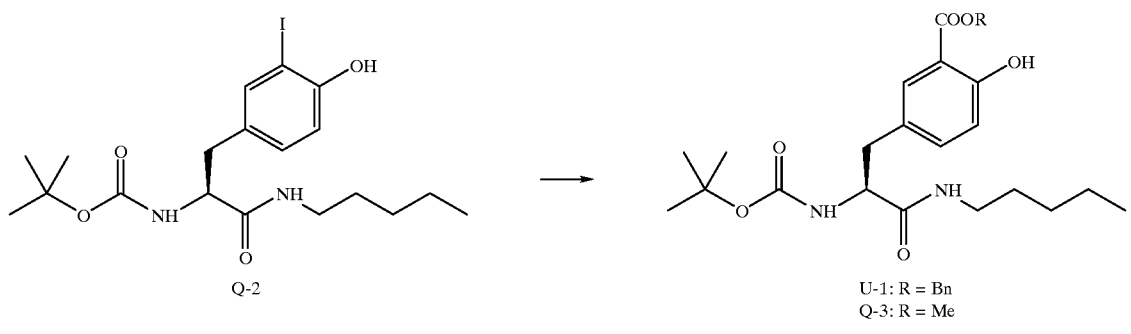
Q-2
U-1: R = Bn
Q-3: R = Me

179 180
-continued
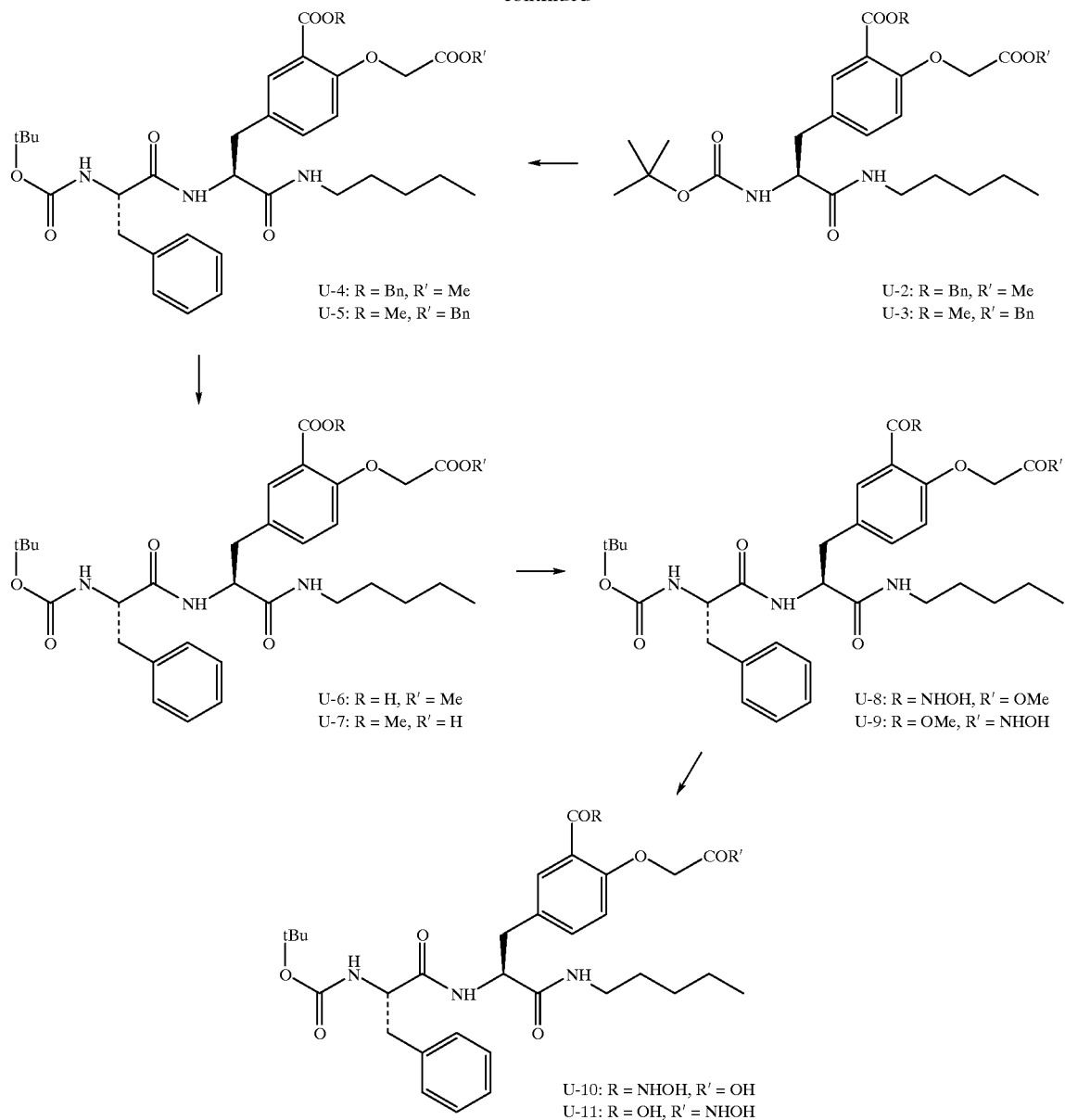
CHART V
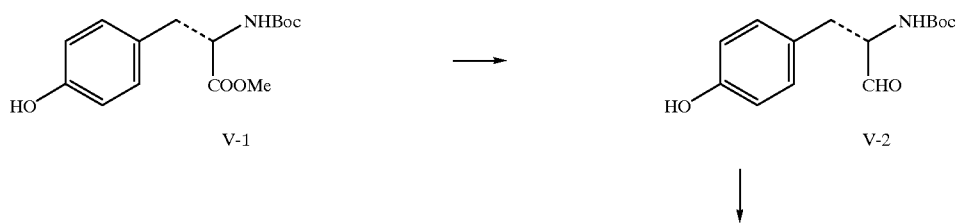

181 182
-continued
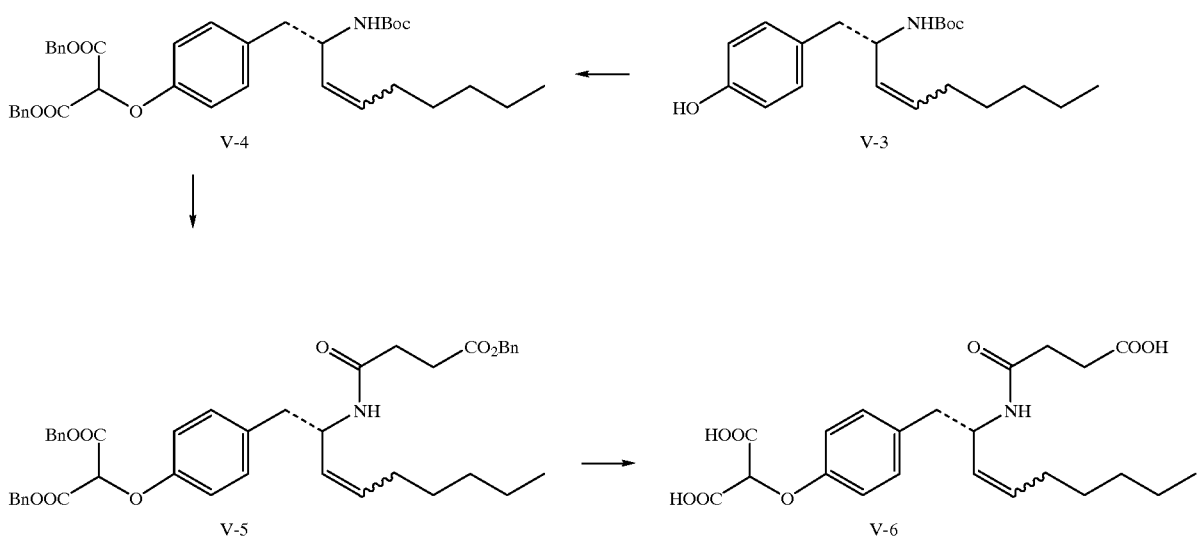
CHART W
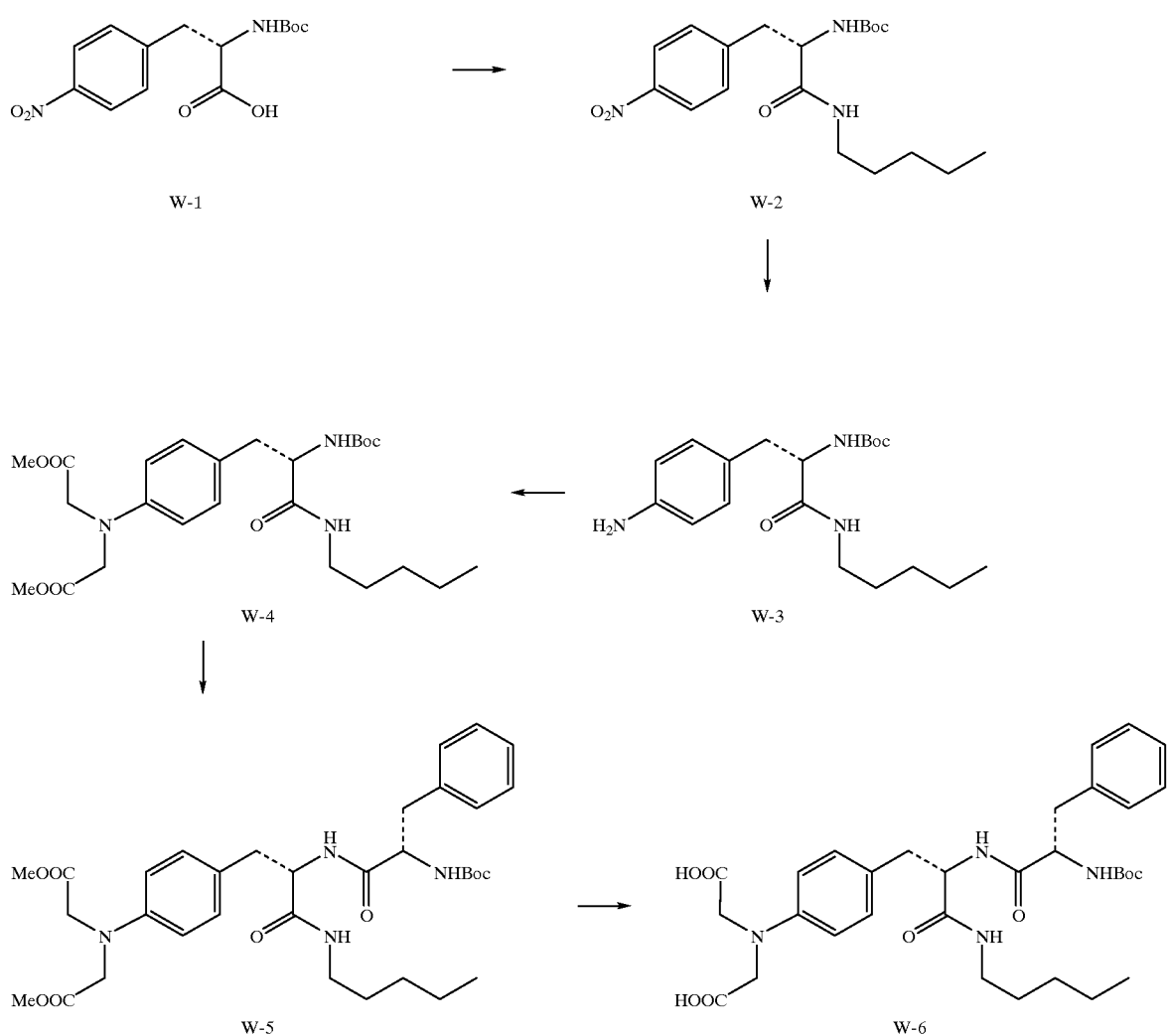

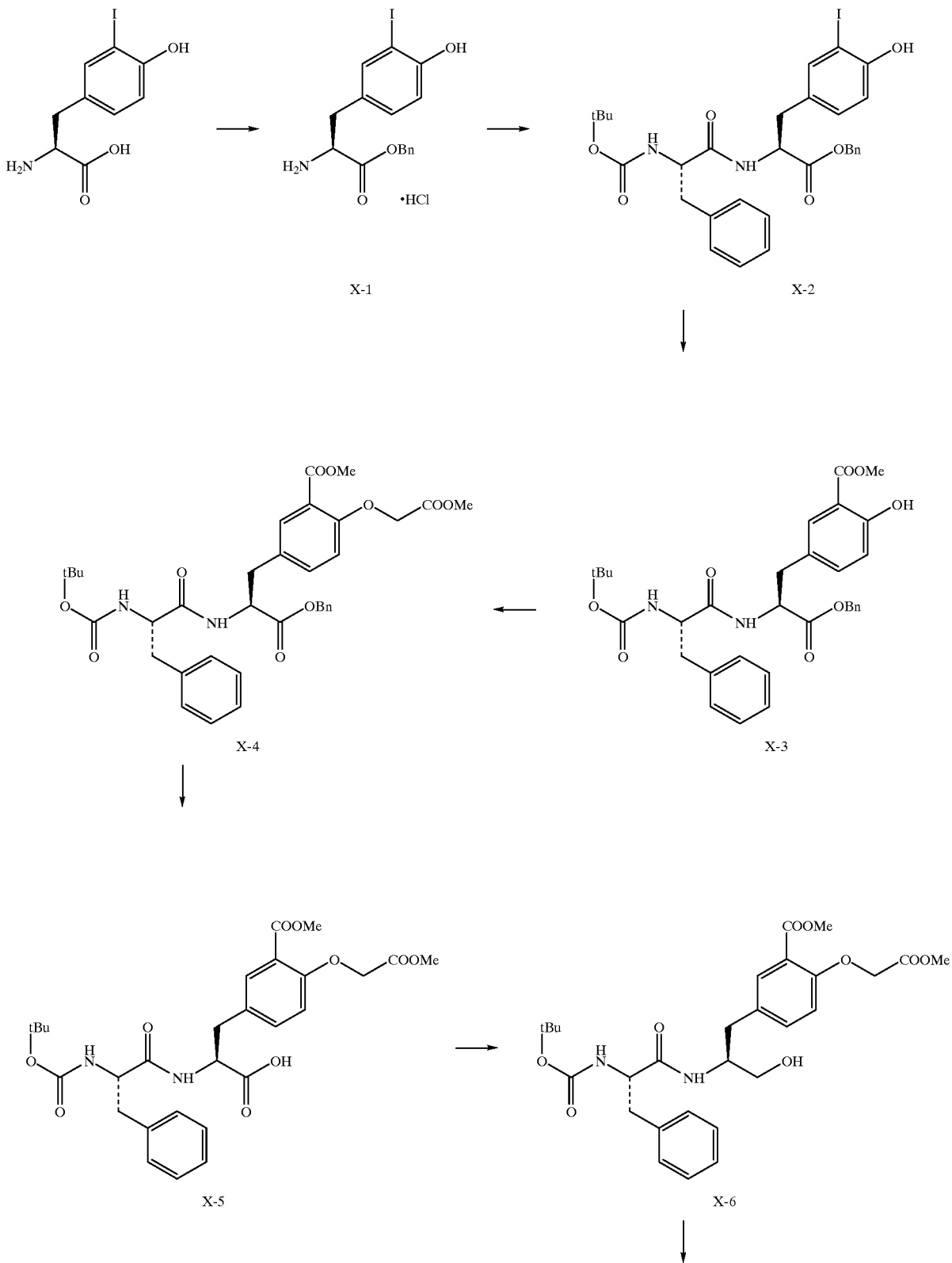
CHART X

-continued
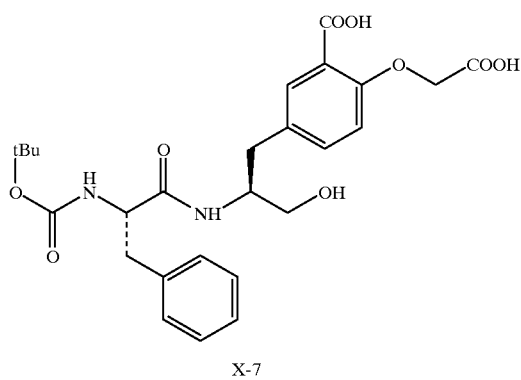
X-7
CHART Y
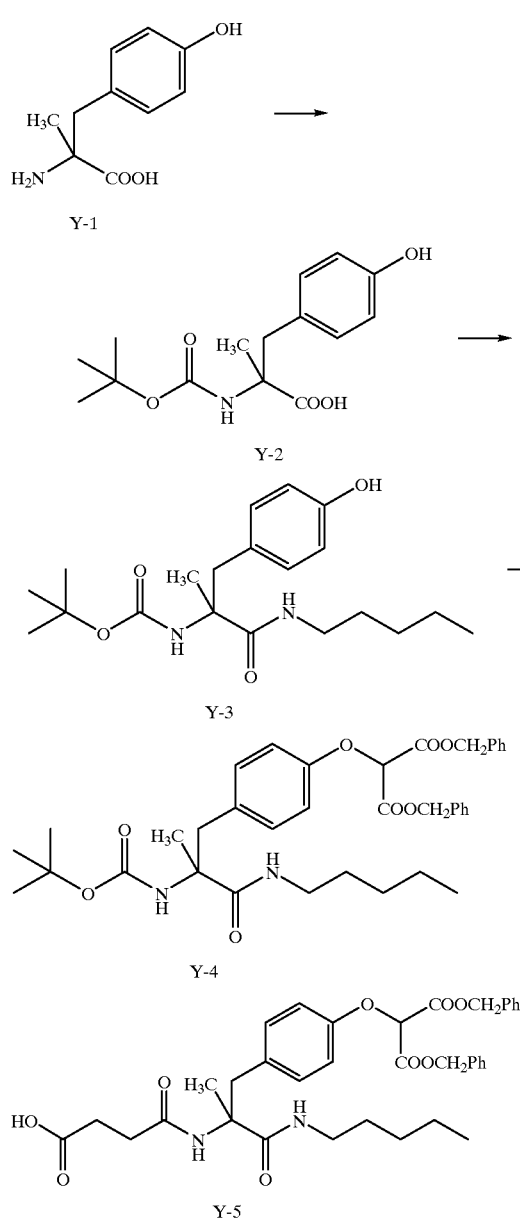
-continued
Y-6
CHART Z

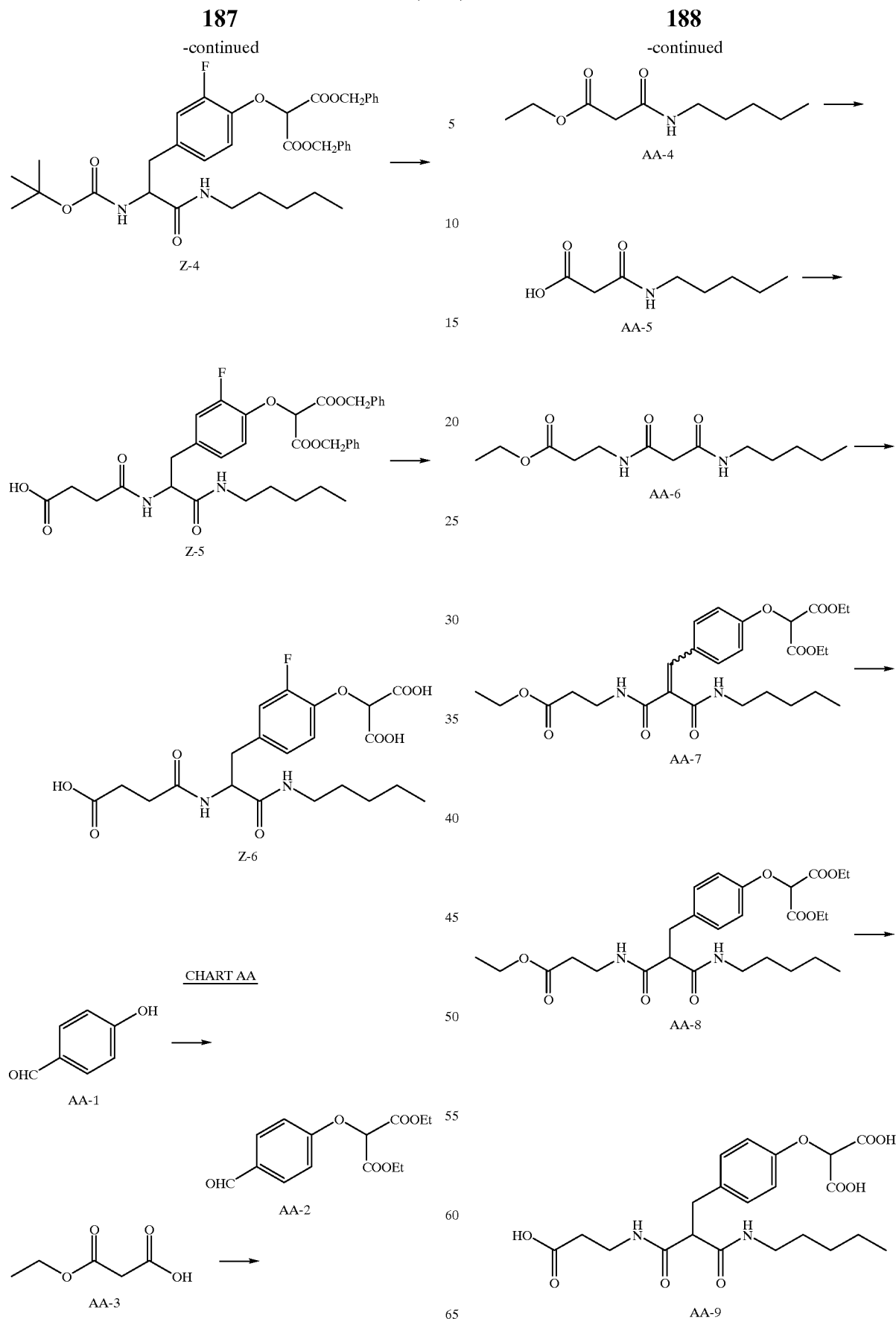

CHART BB
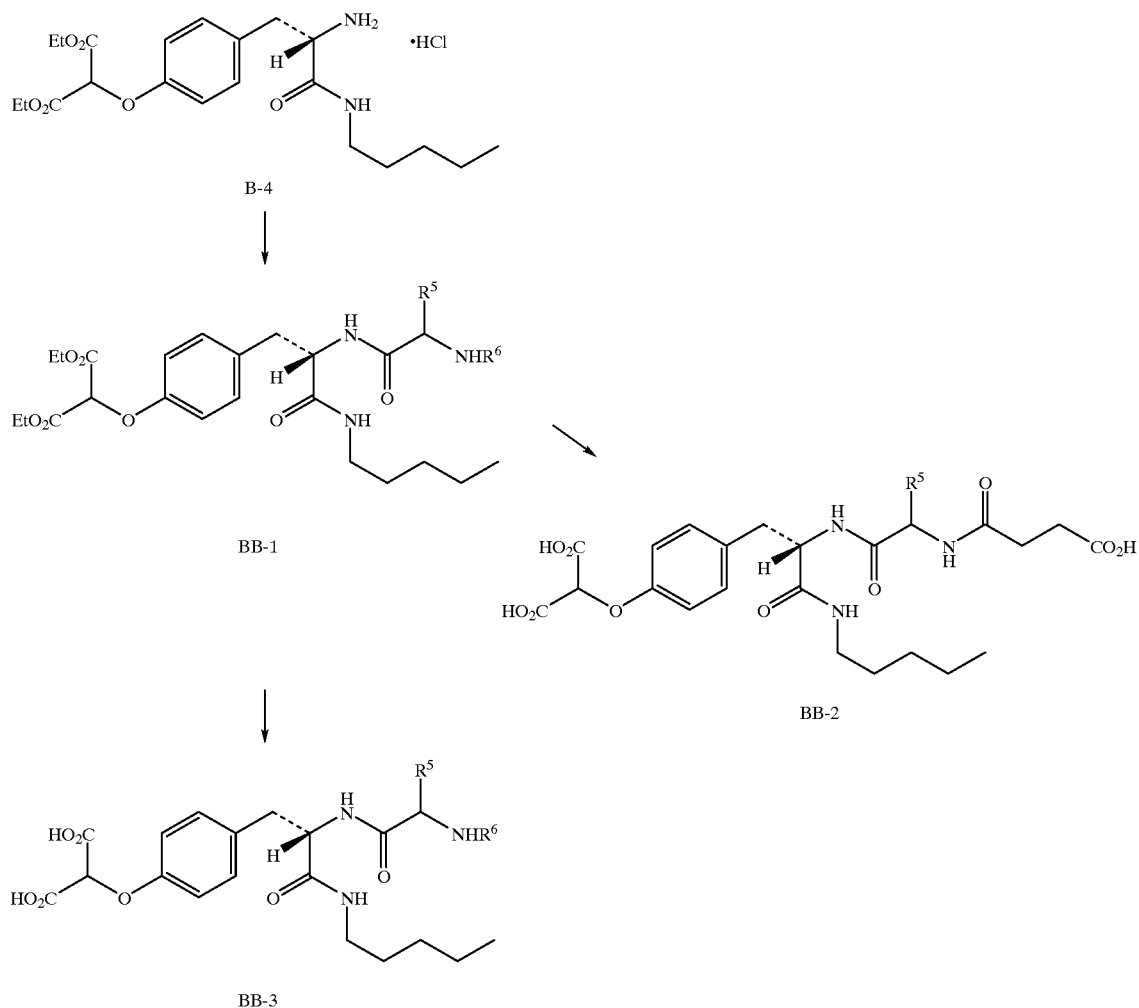
CHART CC
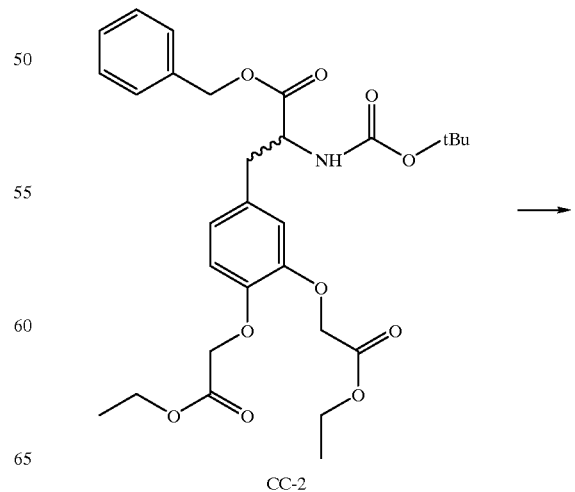

-continued
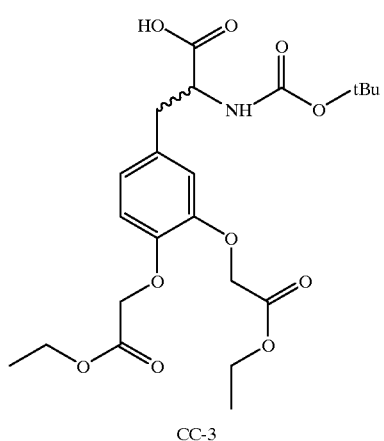
CC-3
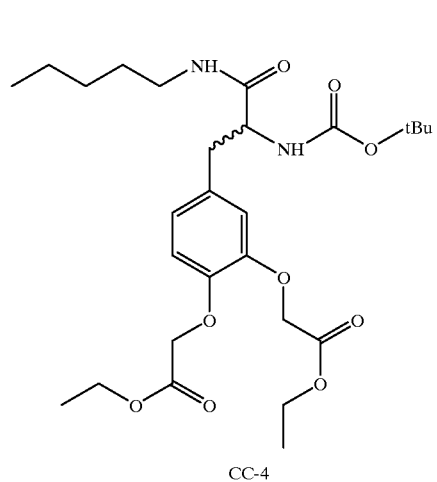
CC-4
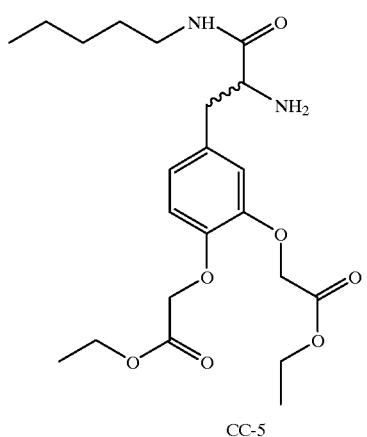
CC-5
-continued
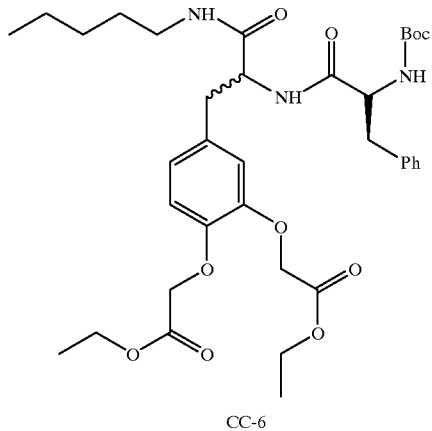
CC-6
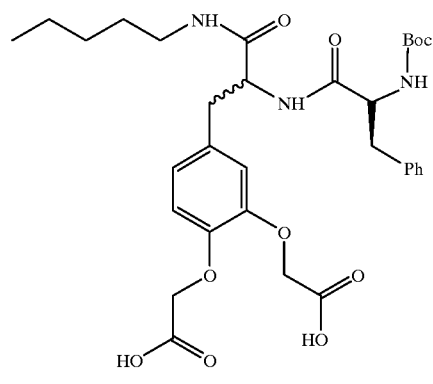
CC-7
CHART DD
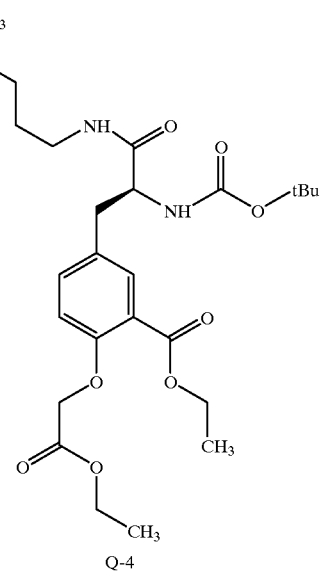
Q-4

193 194
-continued
CHART EE
Q-2 →
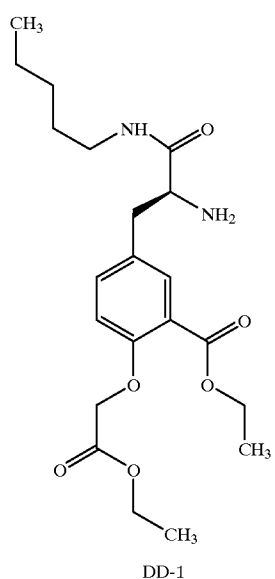
DD-1
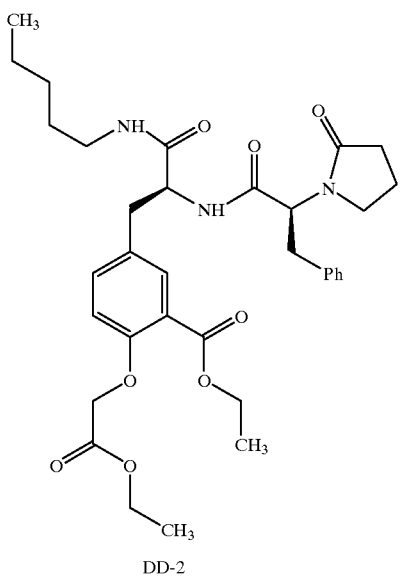
DD-2
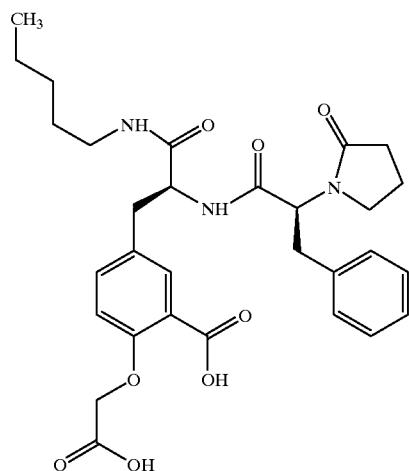
DD-3
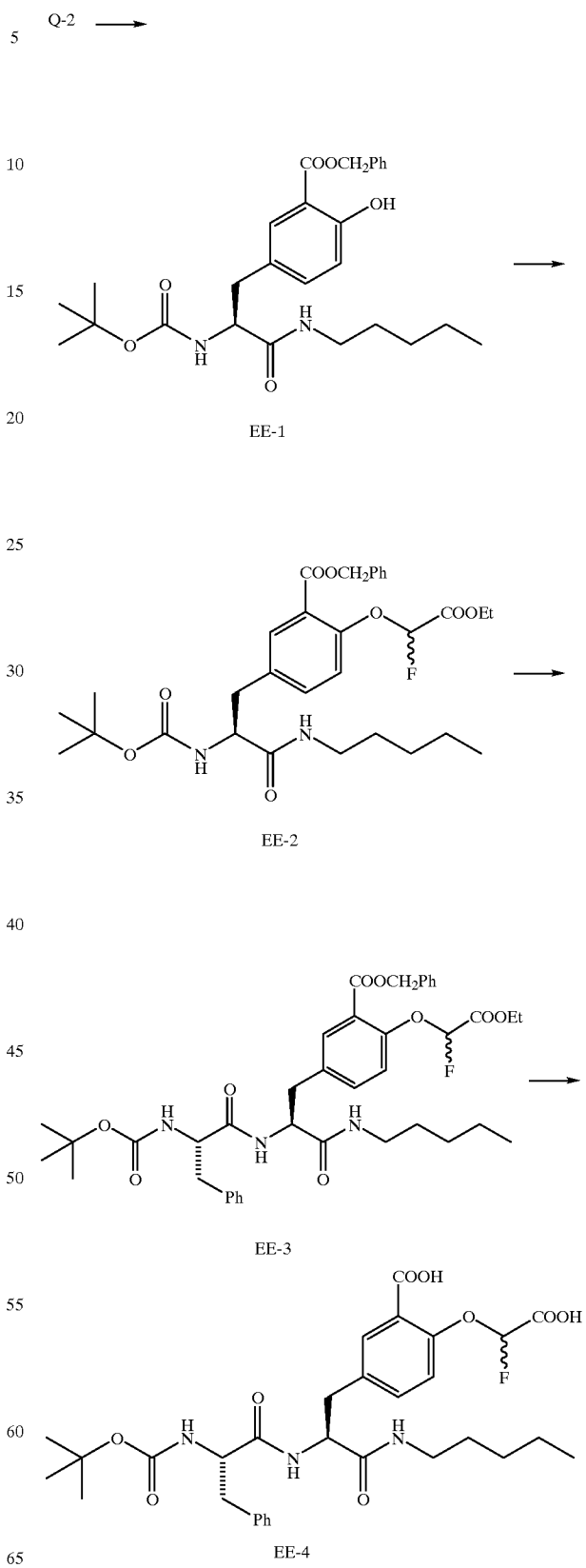
EE-1
EE-2
EE-3
EE-4

CHART FF
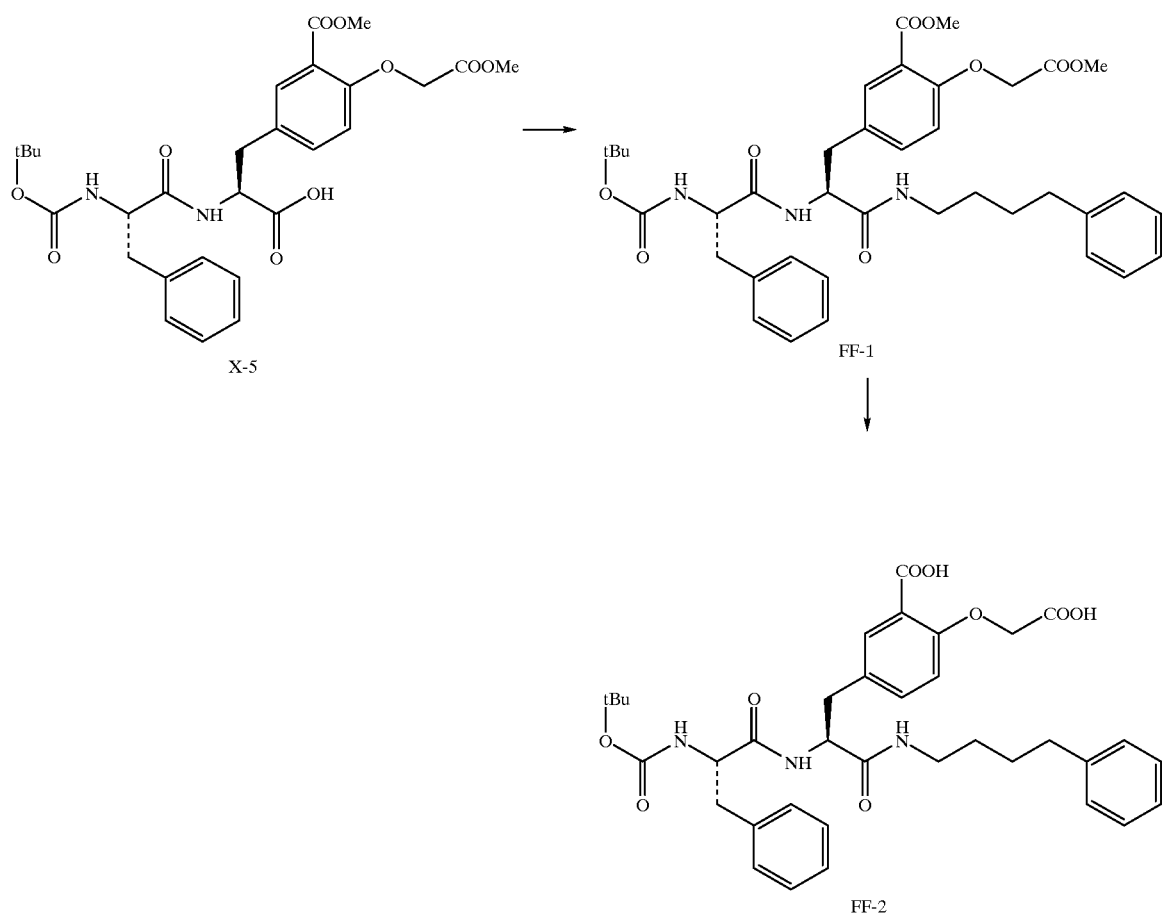
CHART GG
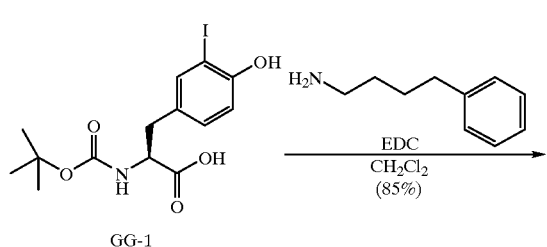
-continued
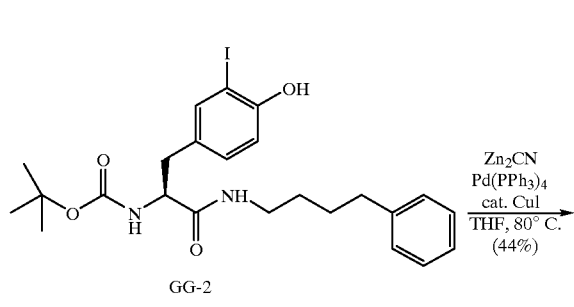

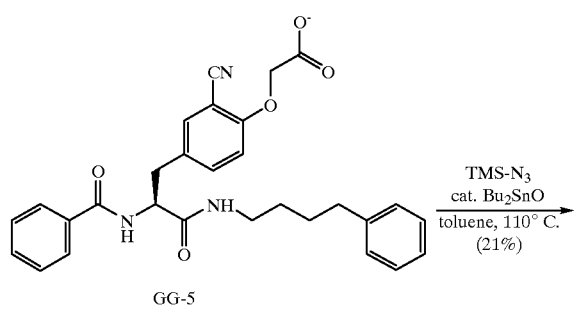
GG-5
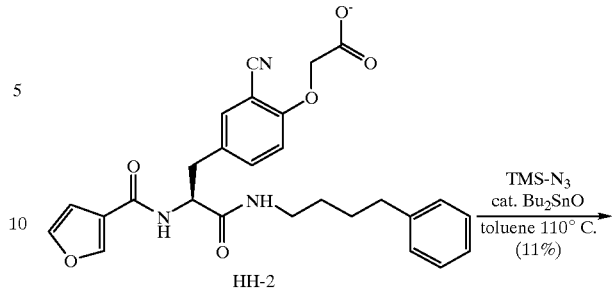
HH-2
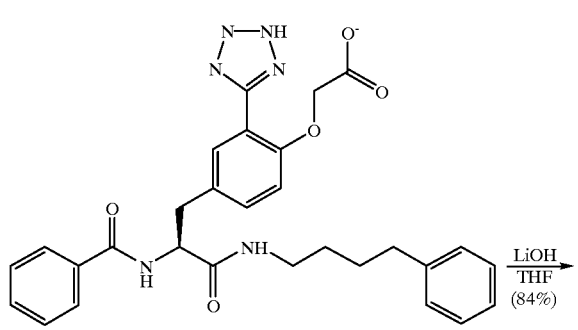
GG-6
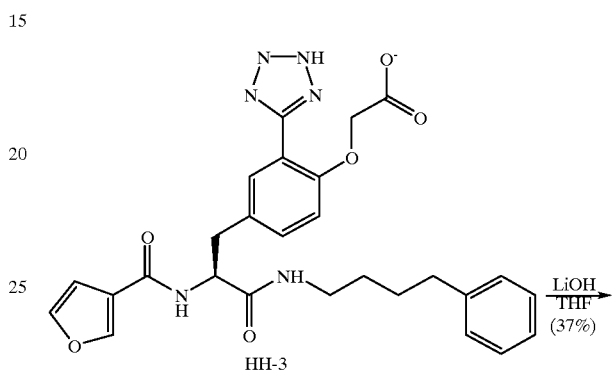
HH-3
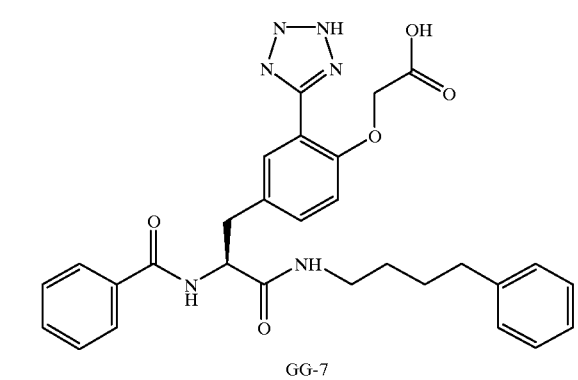
GG-7
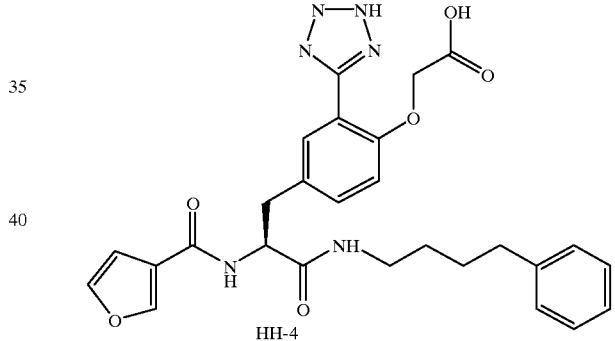
HH-4
CHART HH
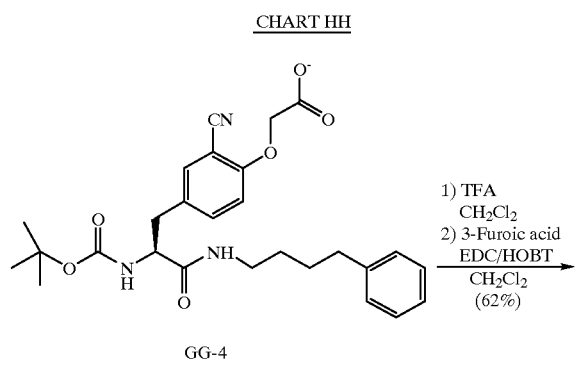
GG-4
CHART II
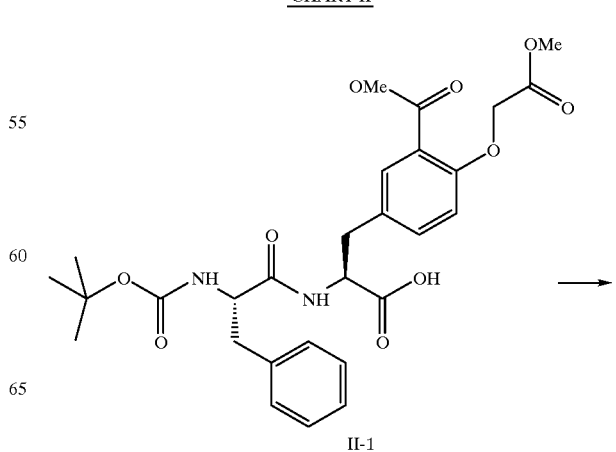
II-1

199
-continued
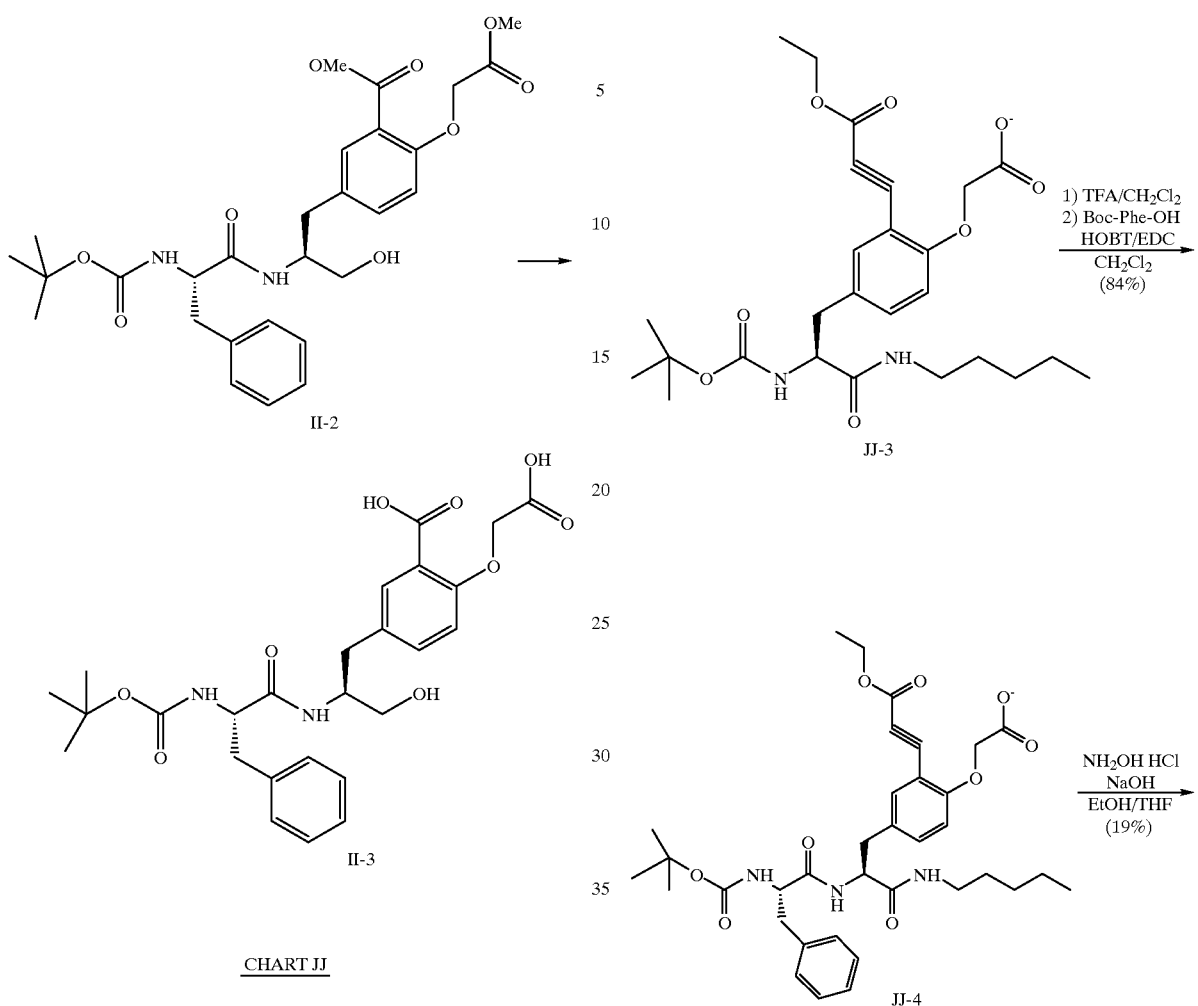
CHART JJ
200
-continued
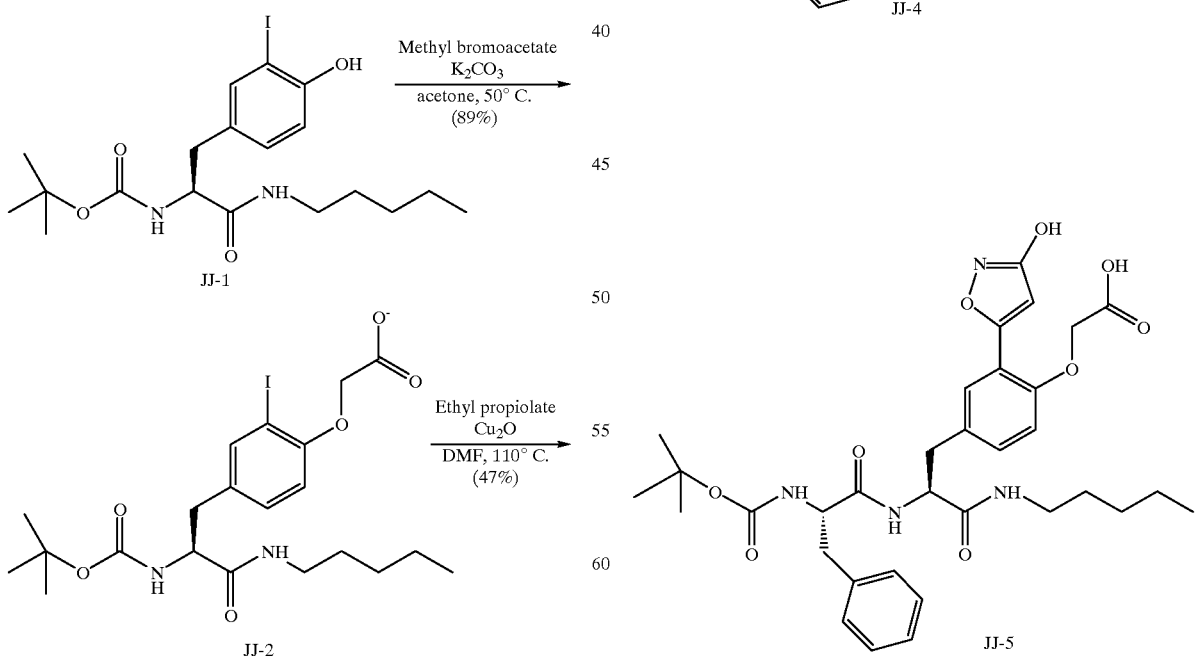

CHART KK
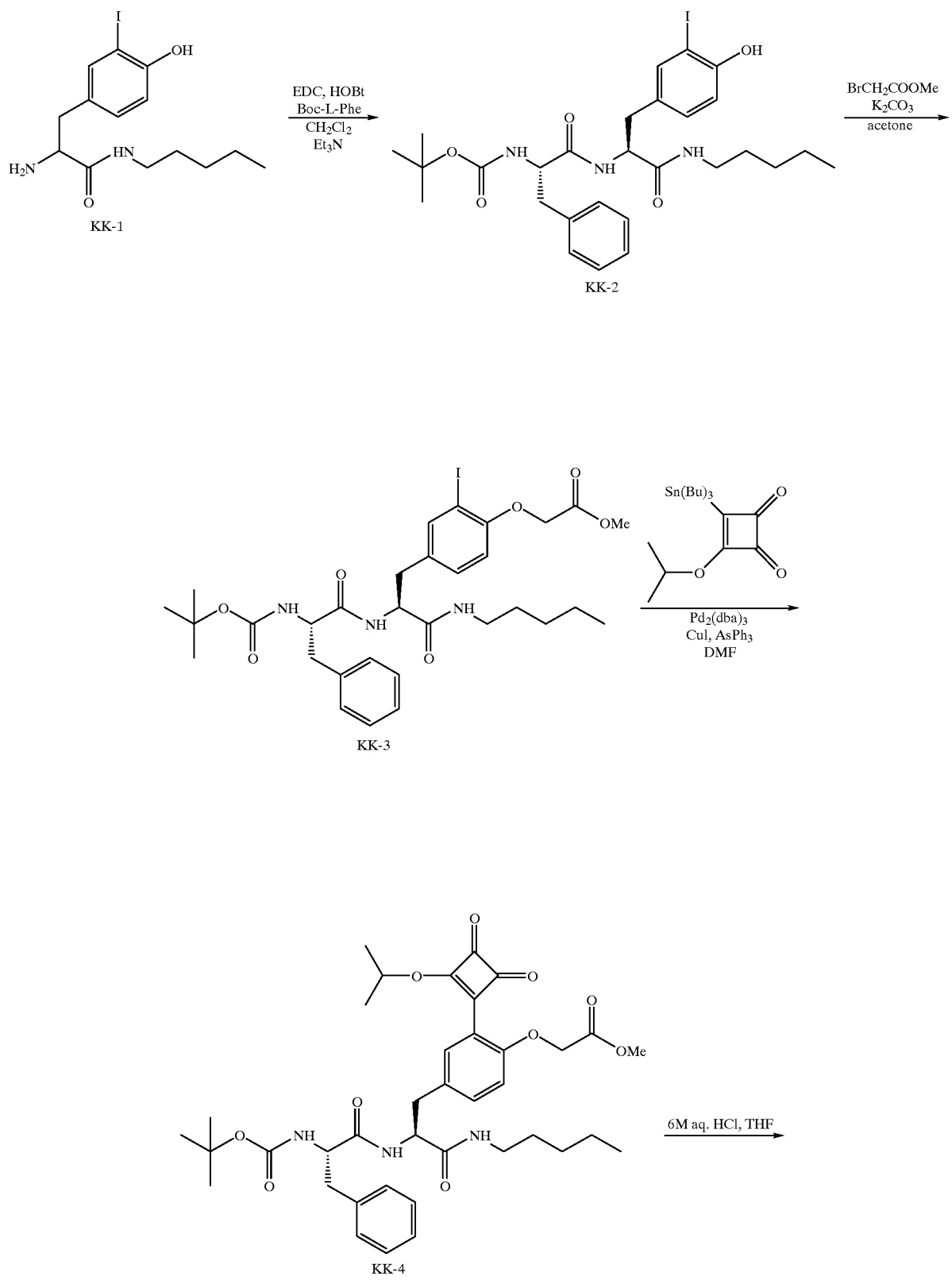

-continued
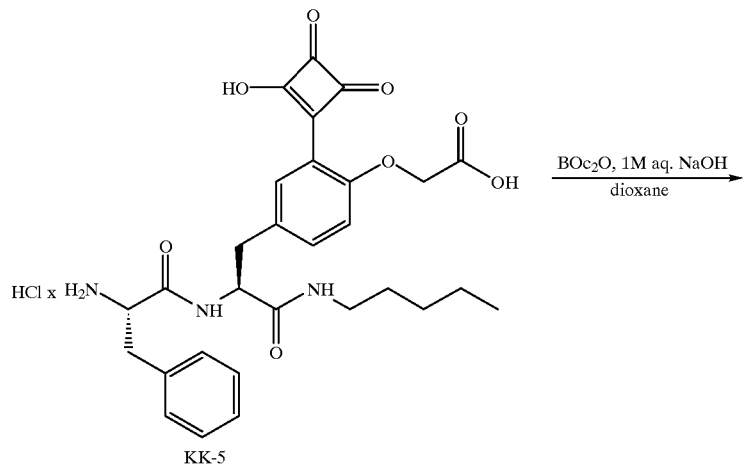
KK-5
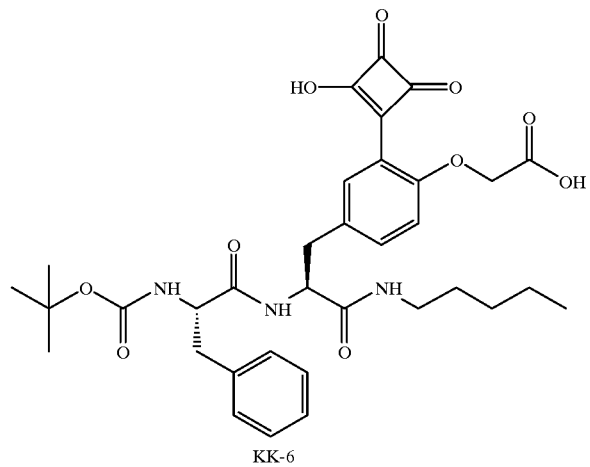
KK-6
CHART LL
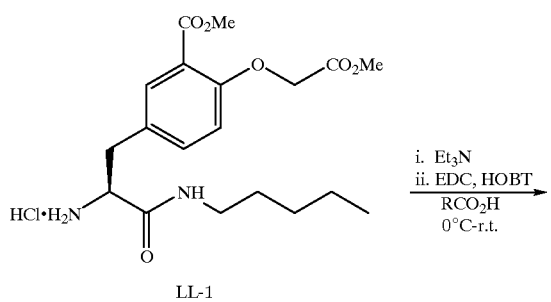
LL-1
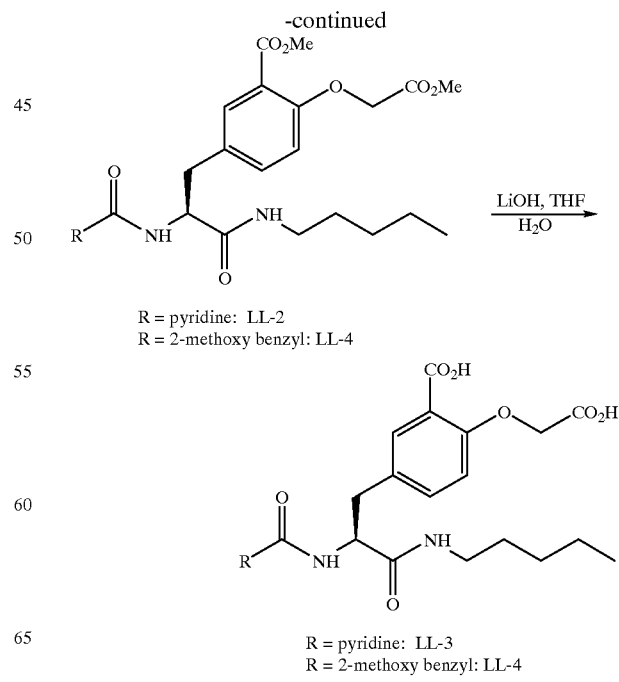
R = pyridine: LL-2
R = 2-methoxy benzyl: LL-4
R = pyridine: LL-3
R = 2-methoxy benzyl: LL-4

TABLE 1

| Example Number, Structure | PTP1 Inhib Conc (uM) | % Inhib |
|---|---|---|
| Example 1 | 100 | 80 |
|  | 10 | 8 |
|  | 1 | 3 |
| Example 3 | 100 | 81 |
|  | 100 | 76 |
|  | 10 | 25 |
|  | 1 | 1 |
| Example 2 | 10 | 9 |
|  | 1 | 4 |
|  | 100 | 39 |
| Example 12 | 10 | 17 |
|  | 1 | 2 |
|  | 100 | 67 |

TABLE 1-continued

| Example Number, Structure | PTP1 Inhib | |
|---|---|---|
| | Conc (uM) | % Inhib |
| Example 13 | 10 | 13 |
| | 1 | 3 |
| | 100 | 62 |
| Example 14 | 10 | 12 |
| | 1 | 3 |
| | 100 | 53 |
| Example 15 | 10 | 20 |
| | 1 | 2 |
| | 100 | 72 |
| Example 16 | 10 | 20 |
| | 100 | 74 |
| | 1 | 4 |

TABLE 1-continued

| Example Number, Structure | PTP1 Inhib | |
|---|---|---|
| | Conc (uM) | % Inhib |
| Example 56 | 100 | 34 |
| | 10 | 1 |
| | 1 | 0 |
| Example 17 | 100 | 67 |
| | 10 | 18 |
| | 1 | 0 |
| Example 18 | 100 | 63 |
| | 10 | 14 |
| | 1 | 2 |
| Example 19 | 100 | 41 |
| | 10 | 5 |
| | 1 | 4 |

TABLE 1-continued

| Example Number, Structure | PTP1 Inhib | |
|---|---|---|
| | Conc (uM) | % Inhib |
| Example 29 | 100 | 74 |
| | 10 | 17 |
| | 1 | 3 |
| Example 30 | 100 | 73 |
| | 10 | 21 |
| | 1 | 0 |
| Example 21 | 100 | 83 |
| | 10 | 33 |
| | 1 | 1 |
| Example 22 | 100 | 57 |
| | 10 | 11 |
| | 1 | 0 |

TABLE 1-continued

| Example Number, Structure | PTP1 Inhib Conc (uM) | % Inhib |
|---|---|---|
| Example 31 | 100 | 46 |
| | 10 | 7 |
| | 1 | 0 |
| Example 32 | 100 | 48 |
| | 10 | 6 |
| | 1 | 0 |
| Example 33 | 100 | 23 |
| | 10 | 2 |
| | 1 | 0 |
| Example 55 | 10 | 9 |
| | 100 | 50 |
| | 1 | 0 |

TABLE 1-continued

| Example Number, Structure | PTP1 Inhib | |
|---|---|---|
| | Conc (uM) | % Inhib |
| Example 34 | 100 | 35 |
| | 10 | 6 |
| | 1 | 0 |
| Example 57 | 100 | 39 |
| | 10 | 4 |
| | 1 | 3 |
| Example 41 | 100 | 45 |
| | 10 | 3 |
| | 1 | 0 |
| Example 35 | 100 | 26 |
| | 10 | 3 |
| | 1 | 2 |

TABLE 1-continued

| Example Number, Structure | PTP1 Inhib | |
|---|---|---|
| | Conc (uM) | % Inhib |
| Example 23 | 100 | 37 |
| | 10 | 4 |
| | 1 | 0 |
| Example 24 | 100 | 72 |
| | 10 | 20 |
| | 1 | 1 |
| Example 4 | 10 | 23 |
| | 100 | 75 |
| | 1 | 4 |
| Example 5 | 10 | 18 |
| | 100 | 63 |
| | 1 | 6 |

TABLE 1-continued

| Example Number, Structure | PTP1 Inhib | |
|---|---|---|
| | Conc (uM) | % Inhib |
| Example 26 | 100 | 96 |
| | 10 | 75 |
| | 1 | 27 |
| Example 25 | 100 | 90 |
| | 10 | 53 |
| | 1 | 13 |
| Example 42 | 100 | 63 |
| | 10 | 24 |
| | 1 | 12 |
| Example 43 | 100 | 72 |
| | 10 | 23 |
| | 1 | 8 |

TABLE 1-continued

| Example Number, Structure | PTP1 Inhib Conc (uM) | % Inhib |
|---|---|---|
| Example 44 | 100<br>10<br>1 | 61<br>18<br>7 |
| Example 45 | 100<br>10<br>1 | 51<br>3<br>4 |
| Example 46 | 100<br>10<br>1 | 63<br>19<br>4 |
| Example 6 | 100<br>10<br>1 | 81<br>34<br>8 |

TABLE 1-continued

| Example Number, Structure | PTP1 Inhib | |
| --- | --- | --- |
| | Conc (uM) | % Inhib |
| Example 39 | 10 | 3 |
| | 100 | 34 |
| | 1 | 0 |
| Example 7 | 100 | 72 |
| | 10 | 21 |
| | 1 | 2 |
| | 100 | 74 |
| | 10 | 21 |
| | 1 | 3 |
| Example 8 | 10 | 64 |
| | 100 | 94 |
| | 1 | 16 |
| Example 47 | 10 | 15 |
| | 100 | 66 |
| | 1 | 4 |

TABLE 1-continued

| Example Number, Structure | PTP1 Inhib | |
|---|---|---|
| | Conc (uM) | % Inhib |
| Example 27 | 100 | 83 |
| | 10 | 34 |
| | 1 | 5 |
| Example 28 | 100 | 96 |
| | 10 | 76 |
| | 1 | 25 |
| Example 9 | 100 | 94 |
| | 10 | 64 |
| | 1 | 17 |

TABLE 1-continued
| Example Number, Structure | PTP1 Inhib Conc (uM) | % Inhib |
|---|---|---|
| Example 38 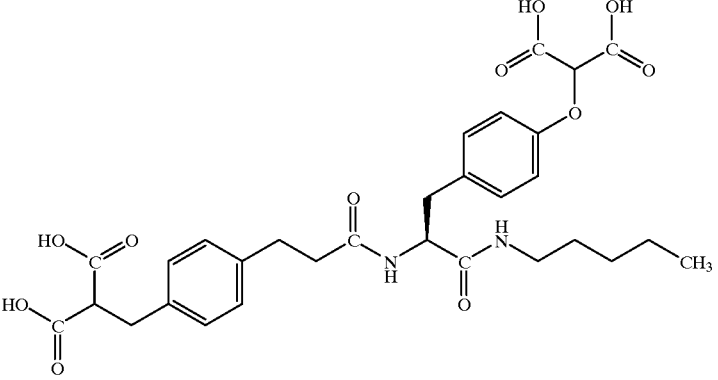 | 100<br>10<br>1 | 79<br>29<br>5 |
| Example 10 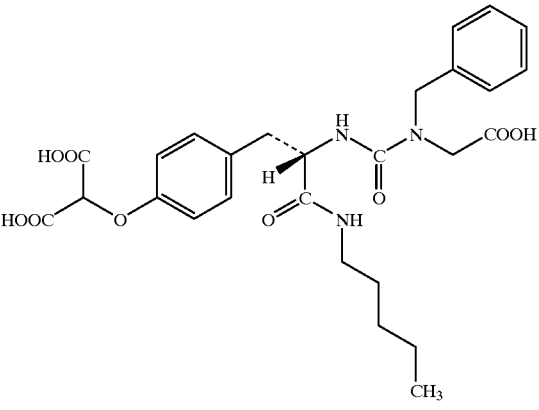 | 10<br>100<br>1 | 25<br>75<br>3 |
| Example 36 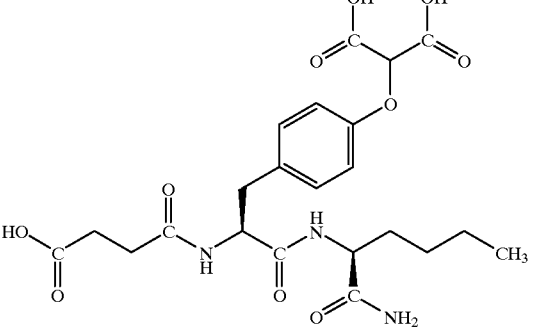 | 100<br>10<br>1 | 93<br>63<br>16 |

TABLE 1-continued

| Example Number, Structure | PTP1 Inhib Conc (uM) | % Inhib |
|---|---|---|
| Example 48 | 100<br>10<br>1 | 57<br>13<br>1 |
| Example 52 | 100<br>10<br>1 | 90<br>51<br>10 |
| Example 37 | 10<br>100<br>1 | 57<br>91<br>14 |
| Example 40 | 100<br>10<br>1 | 33<br>6<br>3 |

TABLE 1-continued

| Example Number, Structure | PTP1 Inhib | |
|---|---|---|
| | Conc (uM) | % Inhib |
| Example 49 | 100 | 43 |
| | 10 | 7 |
| | 1 | 1 |
| Example 51 | 100 | 51 |
| | 10 | 11 |
| | 1 | 0 |
| Example 53 | 100 | 94 |
| | 10 | 62 |
| | 1 | 16 |
| Example 54 | 100 | 98 |
| | 10 | 87 |
| | 1 | 42 |

TABLE 1-continued

| Example Number, Structure | PTP1 Inhib Conc (uM) | % Inhib |
|---|---|---|
| Example 50 | 100 | 56 |
| | 10 | 14 |
| | 1 | 3 |
| Example 11 | 100 | 90 |
| | 10 | 35 |
| | 1 | 5 |
| Example 58 | 100 | 93 |
| | 10 | 63 |
| | 1 | 17 |

TABLE 2
| Example No. | PTP1B Inhib | | PTP1 Inhib | |
|---|---|---|---|---|
| | PTP1B. Conc (uM) | PTP1B. % Inhib | PTP1N. Conc (uM) | PTP1N. % Inhib |
| EXAMPLE 59 | | | 100 | 98 |
| | | | 10 | 80 |
| | | | 1 | 30 |
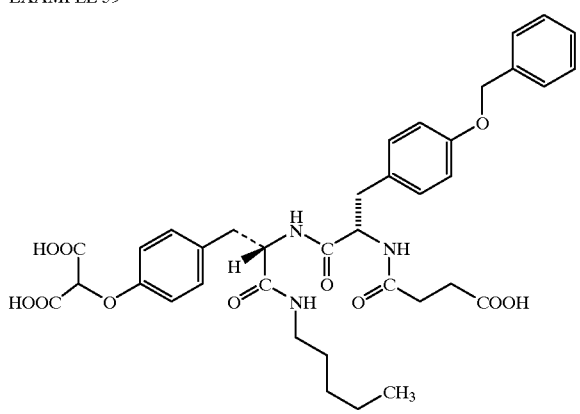
| | | | | |
|---|---|---|---|---|
| EXAMPLE 65 | 100 | 90 | 100 | 91 |
| | 10 | 42 | 10 | 44 |
| | 1 | 9 | 1 | 10 |
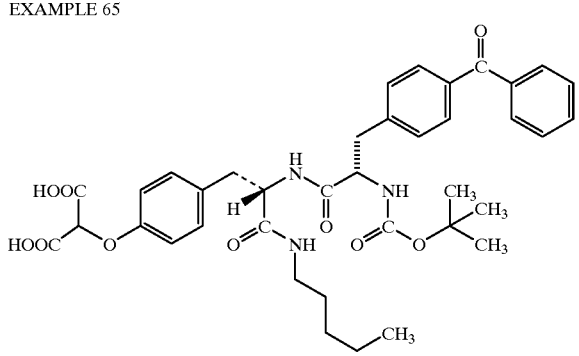
| | | | | |
|---|---|---|---|---|
| EXAMPLE 60 | | | 100 | 54 |
| | | | 10 | 13 |
| | | | 1 | 4 |
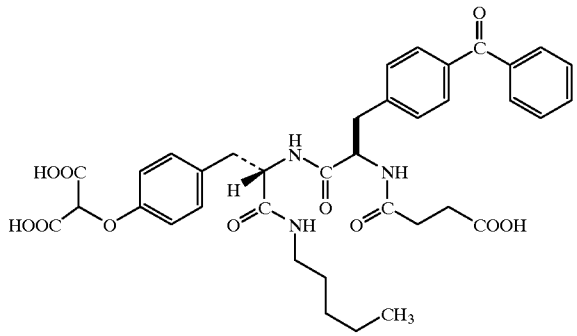
| | | | | |
|---|---|---|---|---|
| EXAMPLE 98 | | | 100 | 60 |
| | | | 10 | 13 |
| | | | 1 | 1 |
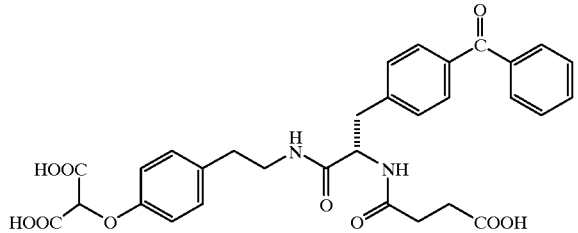

TABLE 2-continued
| Example No. | PTP1B Inhib | | PTP1 Inhib | |
| --- | --- | --- | --- | --- |
| | PTP1B. Conc (uM) | PTP1B. % Inhib | PTP1N. Conc (uM) | PTP1N. % Inhib |
| EXAMPLE 72 | | | 100 | 89 |
| | | | 10 | 47 |
| | | | 1 | 9 |
| EXAMPLE 61 | | | 100 | 98 |
| | | | 10 | 70 |
| | | | 1 | 11 |
| EXAMPLE 66 | | | 100 | 85 |
| | | | 10 | 12 |
| | | | 1 | 3 |
| EXAMPLE 62 | | | 10 | 83 |
| | | | 1 | 37 |
| | | | 100 | 97 |
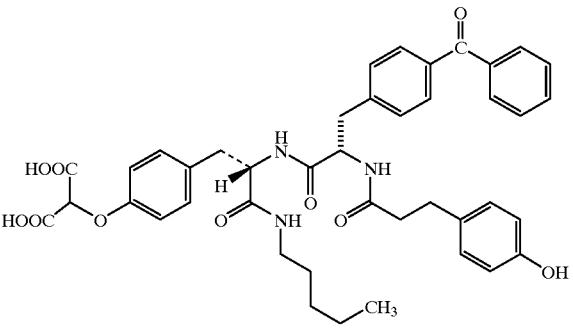
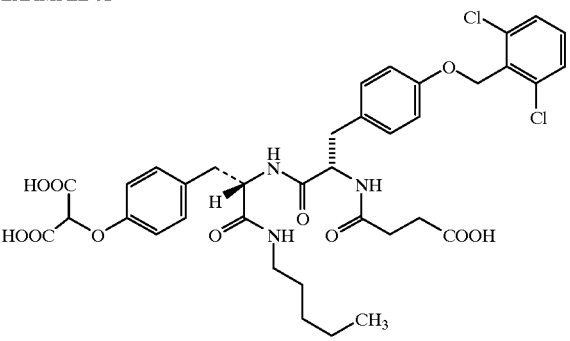
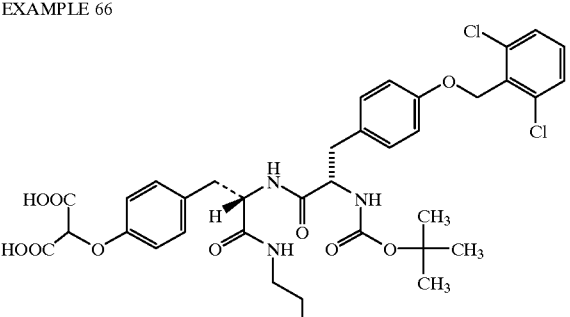
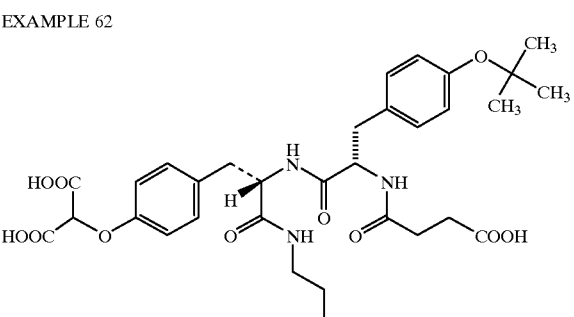

TABLE 2-continued
| Example No. | PTP1B Inhib | | PTP1 Inhib | |
| --- | --- | --- | --- | --- |
| | PTP1B. Conc (uM) | PTP1B. % Inhib | PTP1N. Conc (uM) | PTP1N. % Inhib |
| EXAMPLE 67 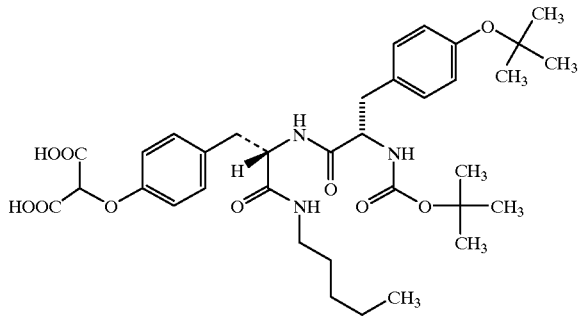 | | | 100<br>10<br>1 | 89<br>36<br>5 |
| EXAMPLE 63 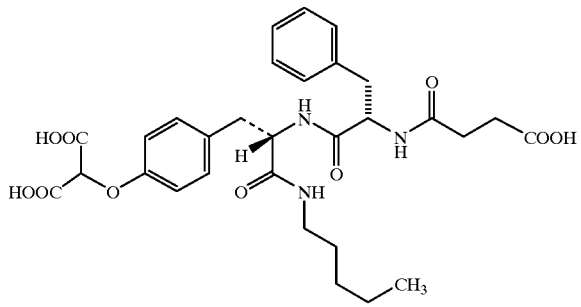 | 100<br>10<br>1 | 99<br>87<br>45 | 100<br>10<br>1 | 97<br>84<br>37 |
| EXAMPLE 68 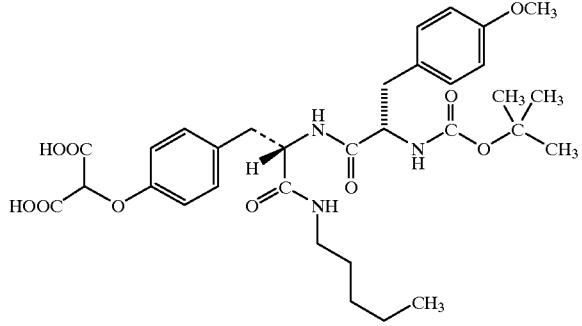 | | | 100<br>10<br>1 | 90<br>36<br>8 |
| EXAMPLE 69 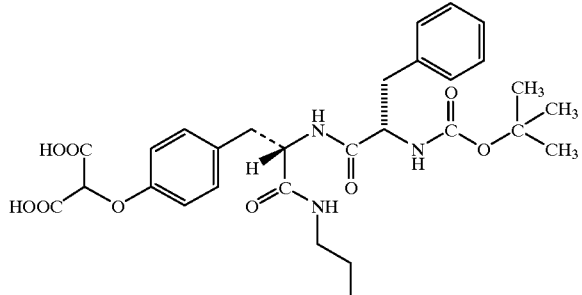 | 100<br>10<br>1 | 91<br>48<br>7 | 100<br>10<br>1 | 88<br>42<br>9 |

TABLE 2-continued

| Example No. | PTP1B Inhib | | PTP1 Inhib | |
| --- | --- | --- | --- | --- |
| | PTP1B. Conc (uM) | PTP1B. % Inhib | PTP1N. Conc (uM) | PTP1N. % Inhib |
| EXAMPLE 64 | | | 100 | 98 |
| | | | 10 | 83 |
| | | | 1 | 32 |
| EXAMPLE 70 | 100 | 83 | 100 | 76 |
| | 10 | 36 | 10 | 22 |
| | 1 | 7 | 1 | 0 |
| EXAMPLE 116 | | | 100 | 93 |
| | | | 10 | 57 |
| | | | 1 | 8 |
| EXAMPLE 71 | | | 100 | 32 |
| | | | 10 | 0 |
| | | | 1 | 0 |

TABLE 2-continued

| Example No. | PTP1B Inhib | | PTP1 Inhib | |
|---|---|---|---|---|
| | PTP1B. Conc (uM) | PTP1B. % Inhib | PTP1N. Conc (uM) | PTP1N. % Inhib |
| EXAMPLE 117 | 100 | 97 | 100 | 93 |
| | 10 | 74 | 10 | 55 |
| | 1 | 21 | 1 | 8 |
| EXAMPLE 118 | | | 100 | 92 |
| | | | 10 | 51 |
| | | | 1 | 4 |
| EXAMPLE 131 | | | 100 | 93 |
| | | | 10 | 56 |
| | | | 1 | 12 |
| EXAMPLE 119 | 100 | 97 | 100 | 96 |
| | 10 | 63 | 10 | 55 |
| | 1 | 14 | 1 | 8 |
| EXAMPLE 139 | | | 100 | 34 |
| | | | 10 | 6 |
| | | | 1 | 3 |

TABLE 2-continued
| Example No. | PTP1B Inhib | | PTP1 Inhib | |
|---|---|---|---|---|
| | PTP1B. Conc (uM) | PTP1B. % Inhib | PTP1N. Conc (uM) | PTP1N. % Inhib |
| EXAMPLE 140 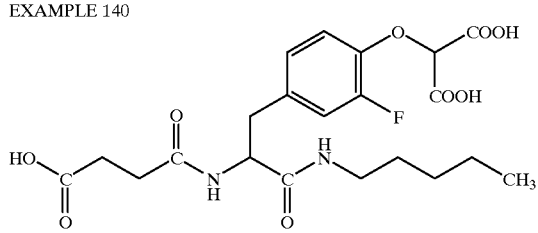 | | | 100<br>10<br>1 | 78<br>29<br>4 |
| EXAMPLE 99 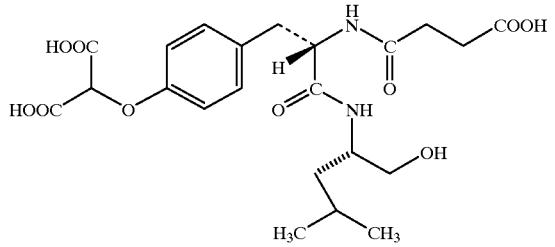 | | | 100<br>10<br>1 | 57<br>15<br>3 |
| EXAMPLE 73 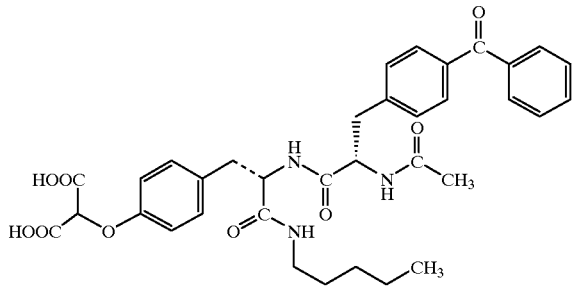 | | | 100<br>10<br>1 | 87<br>42<br>9 |
| EXAMPLE 120 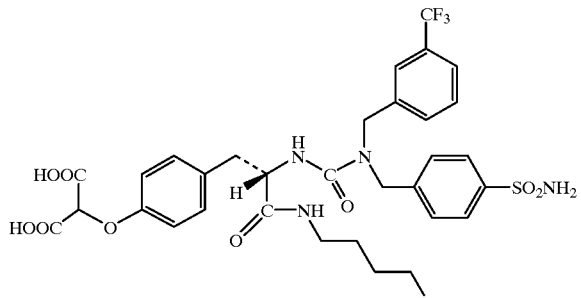 | 100<br>10<br>1 | 90<br>45<br>6 | | |

TABLE 2-continued

| Example No. | PTP1B Inhib | | PTP1 Inhib | |
| --- | --- | --- | --- | --- |
| | PTP1B. Conc (uM) | PTP1B. % Inhib | PTP1N. Conc (uM) | PTP1N. % Inhib |
| EXAMPLE 81 | 100 | 97 | 100 | 97 |
| | 10 | 78 | 10 | 84 |
| | 1 | 30 | 1 | 40 |
| | 100 | 89 | | |
| | 10 | 54 | | |
| | 1 | 15 | | |
| | 100 | 87 | | |
| | 10 | 43 | | |
| | 1 | 8 | | |
| EXAMPLE 121 | 100 | 58 | | |
| | 10 | 9 | | |
| | 1 | 3 | | |
| EXAMPLE 122 | 100 | 42 | | |
| | 10 | 8 | | |
| | 1 | 5 | | |
| EXAMPLE 123 | 100 | 95 | | |
| | 10 | 65 | | |
| | 1 | 18 | | |
| | 100 | 93 | | |
| | 10 | 59 | | |
| | 1 | 14 | | |

TABLE 2-continued

| Example No. | PTP1B Inhib PTP1B. Conc (uM) | PTP1B. % Inhib | PTP1 Inhib PTP1N. Conc (uM) | PTP1N. % Inhib |
|---|---|---|---|---|
| EXAMPLE 124 | 100 | 95 | | |
| | 10 | 68 | | |
| | 1 | 19 | | |
| | 100 | 92 | | |
| | 10 | 63 | | |
| | 1 | 19 | | |
| EXAMPLE 125 | 100 | 94 | | |
| | 10 | 63 | | |
| | 1 | 17 | | |
| EXAMPLE 100 | 100 | 44 | | |
| | 10 | 8 | | |
| | 1 | 2 | | |
| EXAMPLE 101 | 100 | 75 | | |
| | 10 | 14 | | |
| | 1 | 2 | | |
| | | | 10 | 16 |
| | | | 100 | 83 |
| | | | 1 | 3 |

TABLE 2-continued

| Example No. | PTP1B Inhib | | PTP1 Inhib | |
| --- | --- | --- | --- | --- |
| | PTP1B. Conc (uM) | PTP1B. % Inhib | PTP1N. Conc (uM) | PTP1N. % Inhib |
| EXAMPLE 74 | 100<br>10<br>1 | 86<br>40<br>9 | | |
| EXAMPLE 102 | 100<br>10<br>1<br>100<br>10<br>1 | 93<br>29<br>1<br>90<br>29<br>3 | | |
| EXAMPLE 103 | 100<br>10<br>1 | 86<br>33<br>3 | | |

TABLE 2-continued
| Example No. | PTP1B Inhib | | PTP1 Inhib | |
| --- | --- | --- | --- | --- |
| | PTP1B. Conc (uM) | PTP1B. % Inhib | PTP1N. Conc (uM) | PTP1N. % Inhib |
| EXAMPLE 104 | 100<br>10<br>1 | 79<br>28<br>6 | | |
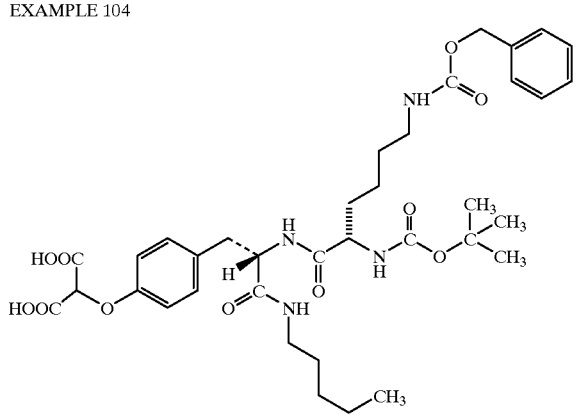
| EXAMPLE 126 | 100<br>10<br>1 | 87<br>45<br>11 | | |
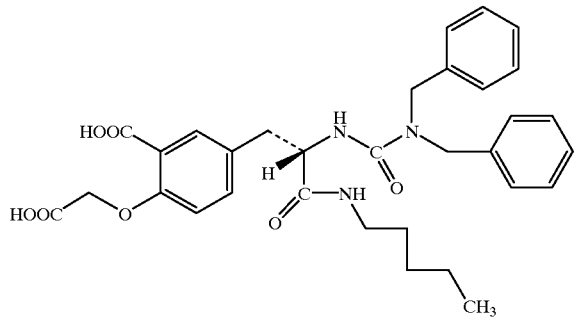
| EXAMPLE 105 | 100<br>10<br>1<br>100<br>10<br>1 | 74<br>25<br>5<br>82<br>30<br>5 | | |
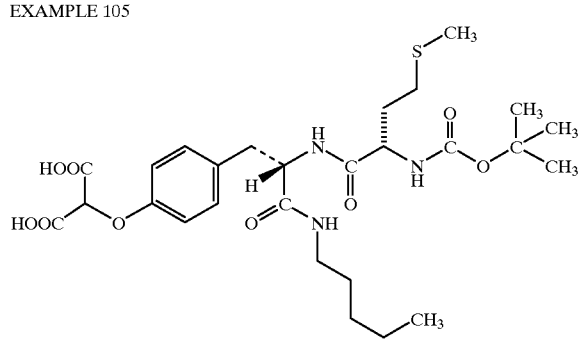
| EXAMPLE 106 | 100<br>10<br>1 | 67<br>21<br>7 | | |
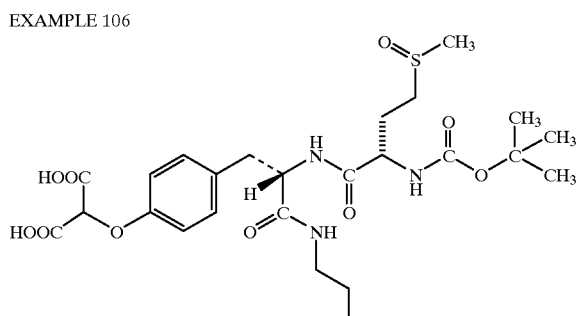

TABLE 2-continued

| Example No. | PTP1B Inhib | | PTP1 Inhib | |
| --- | --- | --- | --- | --- |
| | PTP1B. Conc (uM) | PTP1B. % Inhib | PTP1N. Conc (uM) | PTP1N. % Inhib |
| EXAMPLE 107 | 100 | 80 | | |
| | 10 | 25 | | |
| | 1 | 5 | | |
| EXAMPLE 97 | 100 | 60 | | |
| | 10 | 15 | | |
| | 1 | 4 | | |
| EXAMPLE 108 | 100 | 76 | | |
| | 10 | 24 | | |
| | 1 | 4 | | |

TABLE 2-continued
| Example No. | PTP1B Inhib | | PTP1 Inhib | |
|---|---|---|---|---|
| | PTP1B. Conc (uM) | PTP1B. % Inhib | PTP1N. Conc (uM) | PTP1N. % Inhib |
| EXAMPLE 109 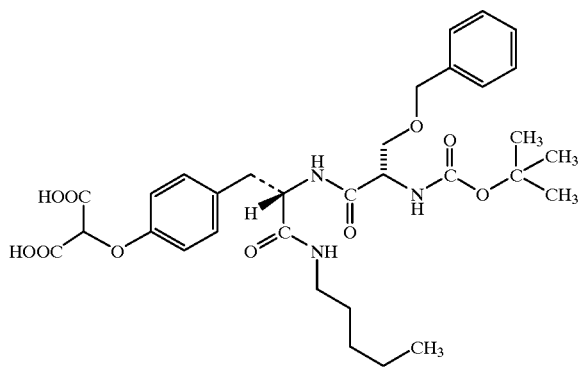 | 100<br>10<br>1 | 71<br>19<br>3 | | |
| EXAMPLE 110 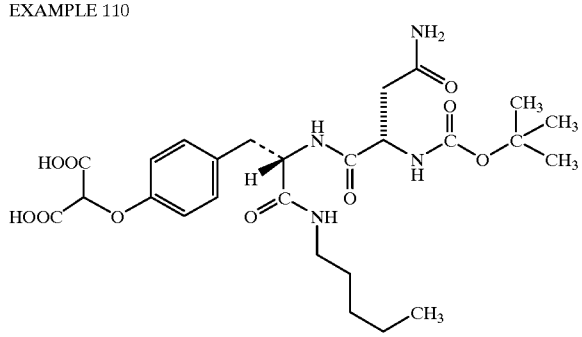 | 100<br>10<br>1 | 85<br>40<br>9 | | |
| EXAMPLE 111 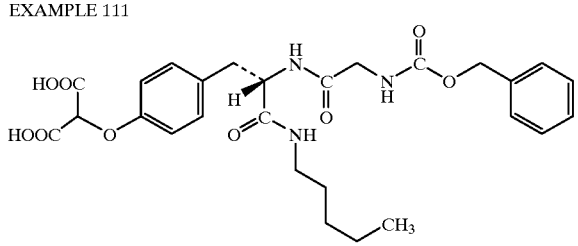 | 100<br>10<br>1 | 66<br>19<br>6 | | |
| EXAMPLE 112 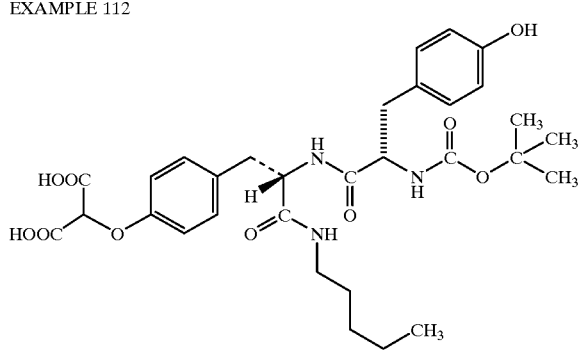 | 100<br>10<br>1 | 90<br>50<br>10 | | |

TABLE 2-continued
| Example No. | PTP1B Inhib | | PTP1 Inhib | |
|---|---|---|---|---|
| | PTP1B. Conc (uM) | PTP1B. % Inhib | PTP1N. Conc (uM) | PTP1N. % Inhib |
| EXAMPLE 113 | 100 | 58 | | |
| | 10 | 7 | | |
| | 1 | 2 | | |
| | 100 | 77 | | |
| | 10 | 17 | | |
| | 1 | 2 | | |
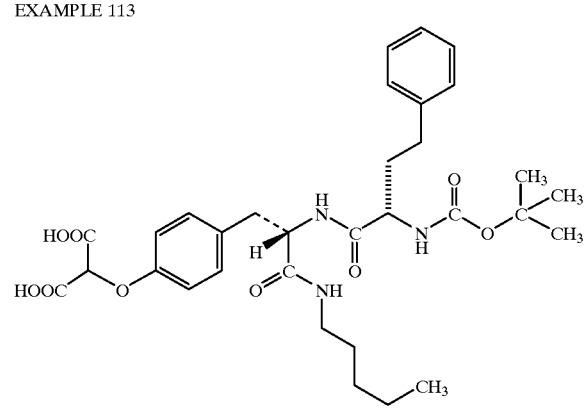
| EXAMPLE 82 | 100 | 98 | | |
|---|---|---|---|---|
| | 10 | 93 | | |
| | 1 | 64 | | |
| | 100 | 98 | | |
| | 10 | 92 | | |
| | 1 | 66 | | |
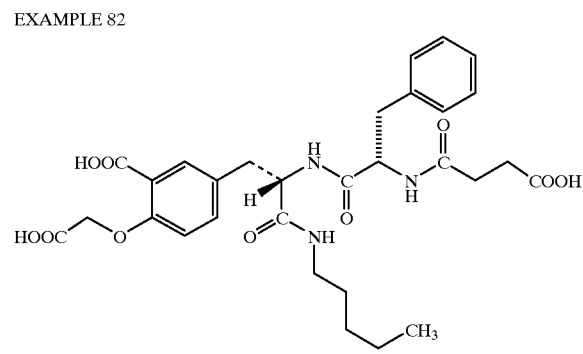
| EXAMPLE 75 | 100 | 86 | | |
|---|---|---|---|---|
| | 10 | 40 | | |
| | 1 | 9 | | |
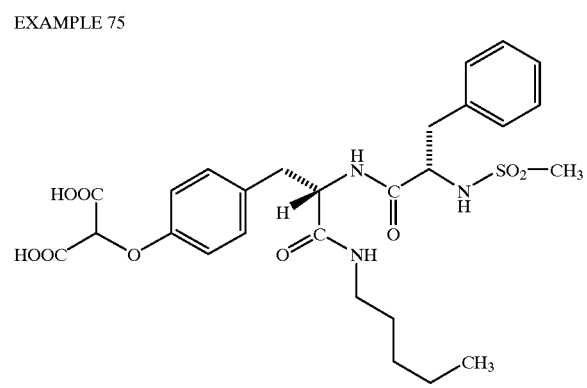
| EXAMPLE 76 | 100 | 92 | | |
|---|---|---|---|---|
| | 10 | 54 | | |
| | 1 | 12 | | |
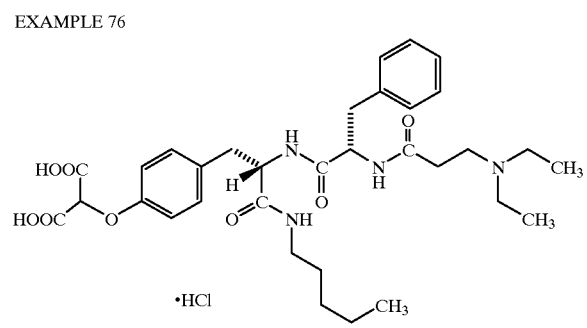

TABLE 2-continued
| Example No. | PTP1B Inhib | | PTP1 Inhib | |
| --- | --- | --- | --- | --- |
| | PTP1B. Conc (uM) | PTP1B. % Inhib | PTP1N. Conc (uM) | PTP1N. % Inhib |
| EXAMPLE 77 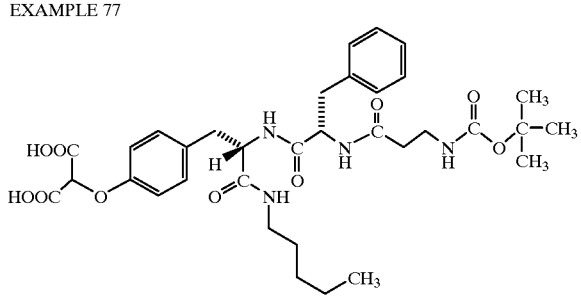 | 100<br>10<br>1 | 93<br>62<br>14 | | |
| EXAMPLE 114 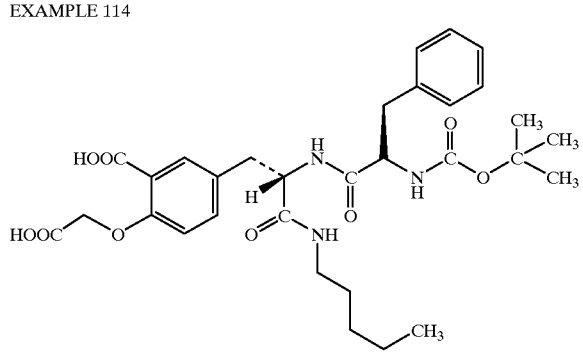 | 100<br>10<br>1 | 69<br>19<br>2 | | |
| EXAMPLE 115 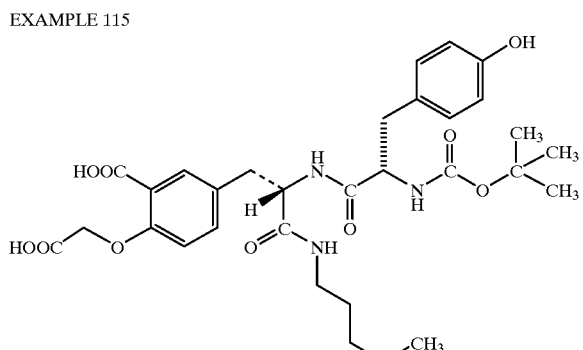 | 100<br>10<br>1<br>100<br>10<br>1 | 97<br>81<br>32<br>96<br>78<br>28 | | |
| EXAMPLE 128 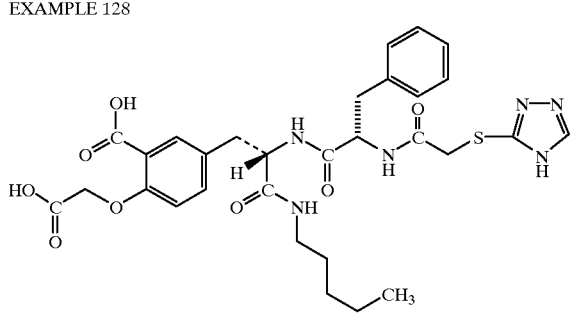 | 100<br>10<br>1 | 96<br>82<br>36 | | |

TABLE 2-continued
| Example No. | PTP1B Inhib | | PTP1 Inhib | |
|---|---|---|---|---|
| | PTP1B. Conc (uM) | PTP1B. % Inhib | PTP1N. Conc (uM) | PTP1N. % Inhib |
| EXAMPLE 129 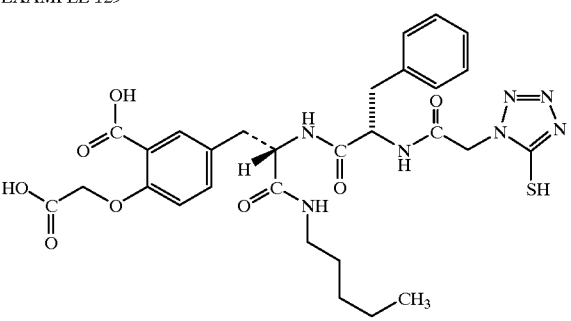 | 100<br>10<br>1 | 98<br>91<br>57 | | |
| EXAMPLE 130 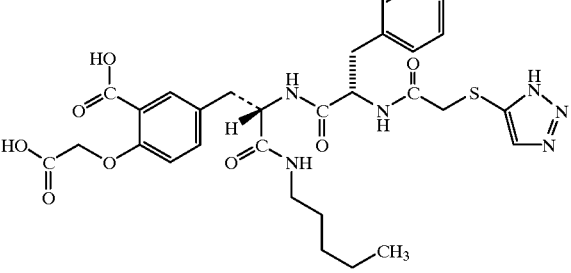 | 100<br>10<br>1 | 98<br>88<br>49 | | |
| EXAMPLE 132 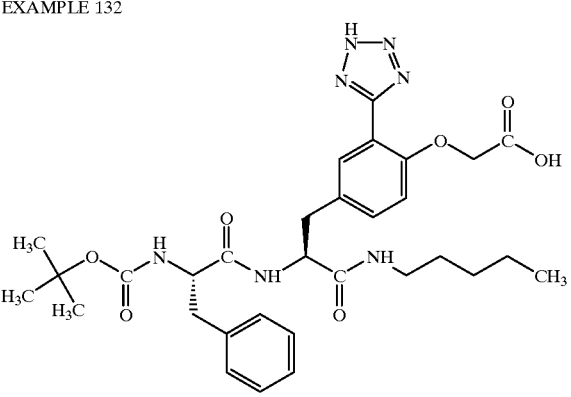 | 100<br>10<br>1<br>100<br>10<br>1 | 87<br>39<br>8<br>87<br>33<br>0 | 100<br>10<br>1 | 97<br>77<br>27 |
| EXAMPLE 133 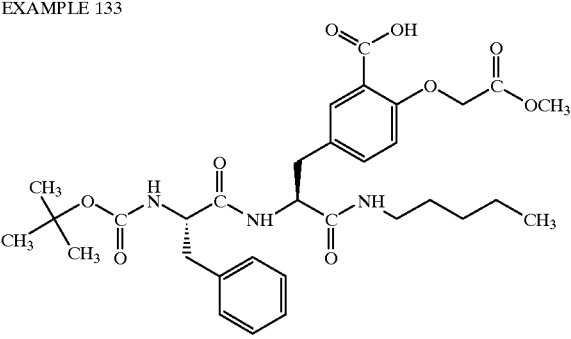 | 100<br>10<br>1 | 25<br>5<br>3 | | |

TABLE 2-continued
| Example No. | PTP1B Inhib | | PTP1 Inhib | |
| --- | --- | --- | --- | --- |
| | PTP1B. Conc (uM) | PTP1B. % Inhib | PTP1N. Conc (uM) | PTP1N. % Inhib |
| EXAMPLE 141 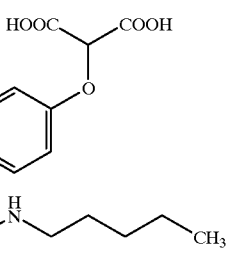 | 100<br>10<br>1 | 48<br>15<br>9 | | |
| EXAMPLE 78 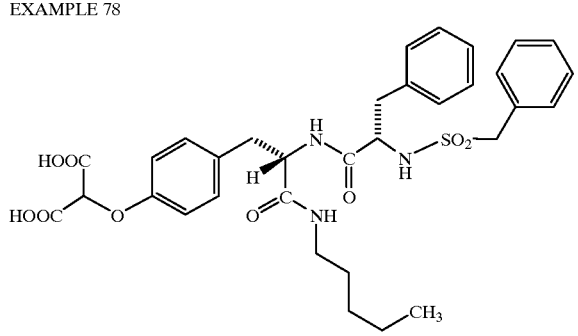 | 100<br>10<br>1 | 62<br>16<br>4 | | |
| EXAMPLE 83 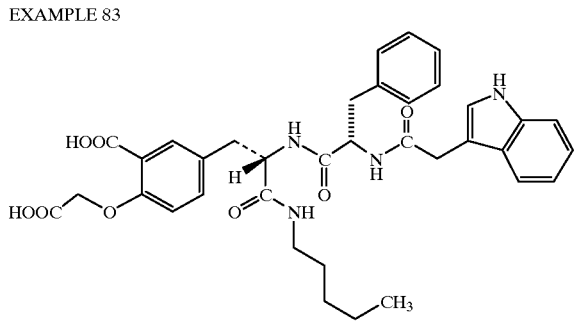 | 100<br>10<br>1 | 98<br>88<br>47 | | |
| EXAMPLE 84 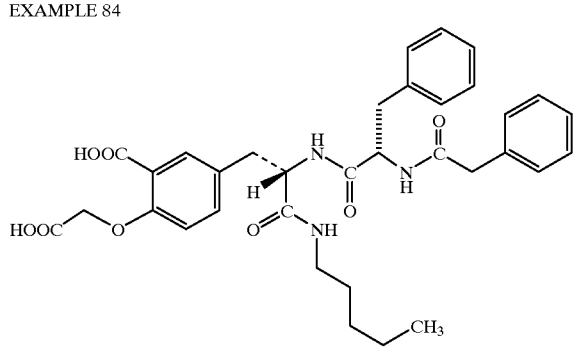 | 100<br>10<br>1 | 98<br>87<br>45 | | |

TABLE 2-continued
| Example No. | PTP1B Inhib | | PTP1 Inhib | |
| --- | --- | --- | --- | --- |
| | PTP1B. Conc (uM) | PTP1B. % Inhib | PTP1N. Conc (uM) | PTP1N. % Inhib |
| EXAMPLE 85 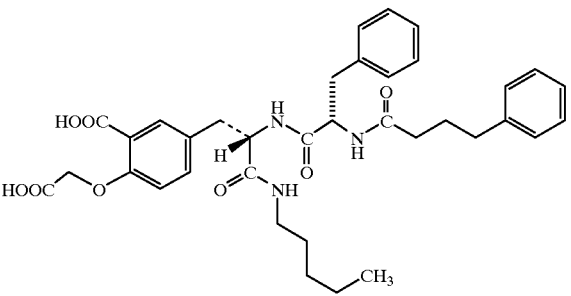 | 100<br>10<br>1 | 96<br>70<br>19 | | |
| EXAMPLE 86 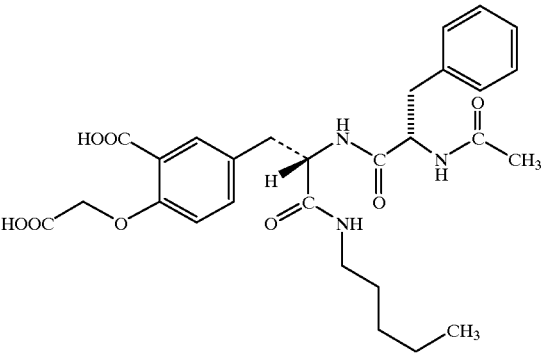 | 100<br>10<br>1 | 96<br>77<br>28 | | |
| EXAMPLE 87 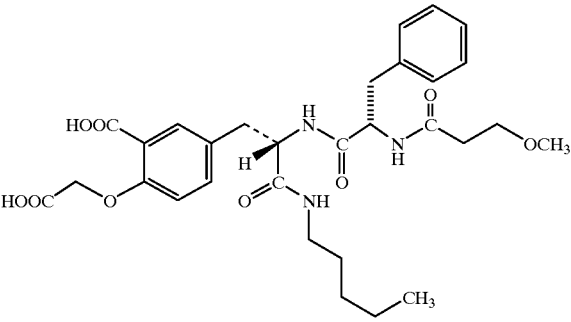 | 100<br>10<br>1 | 97<br>83<br>37 | | |
| EXAMPLE 137 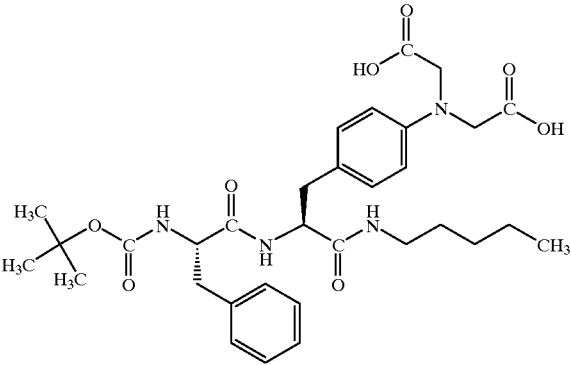 | 100<br>10<br>1 | 29<br>6<br>3 | | |

TABLE 2-continued
| Example No. | PTP1B Inhib | | PTP1 Inhib | |
| --- | --- | --- | --- | --- |
| | PTP1B. Conc (uM) | PTP1B. % Inhib | PTP1N. Conc (uM) | PTP1N. % Inhib |
| EXAMPLE 79 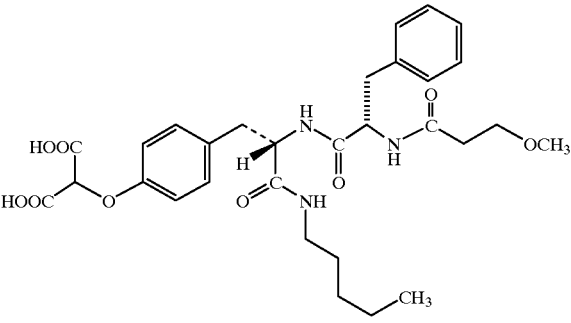 | 100<br>10<br>1 | 94<br>65<br>19 | | |
| EXAMPLE 134 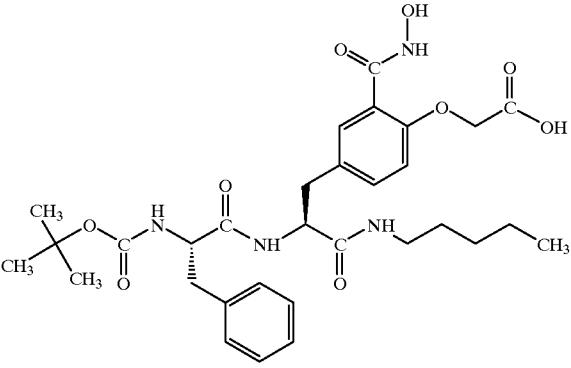 | 100<br>10<br>1 | 54<br>13<br>5 | | |
| EXAMPLE 88 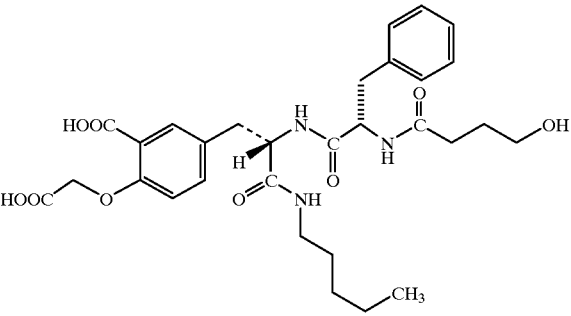 | 100<br>10<br>1 | 96<br>78<br>23 | | |
| EXAMPLE 89 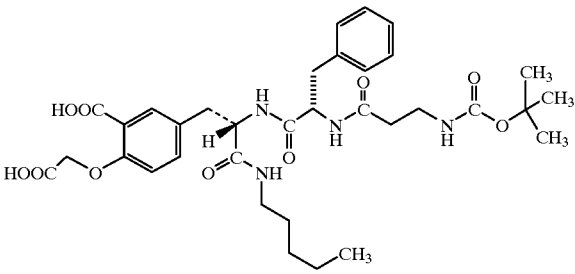 | 100<br>10<br>1 | 96<br>75<br>19 | | |

TABLE 2-continued
| Example No. | PTP1B Inhib | | PTP1 Inhib | |
|---|---|---|---|---|
| | PTP1B. Conc (uM) | PTP1B. % Inhib | PTP1N. Conc (uM) | PTP1N. % Inhib |
| EXAMPLE 90 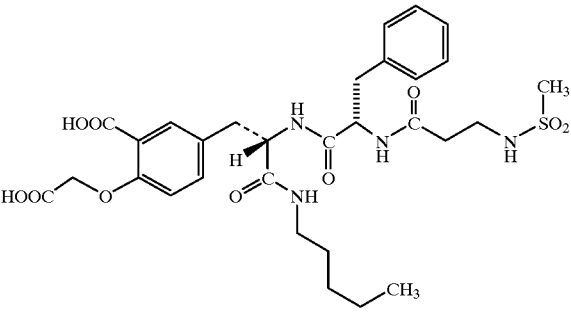 | 100<br>10<br>1 | 95<br>73<br>15 | | |
| EXAMPLE 127 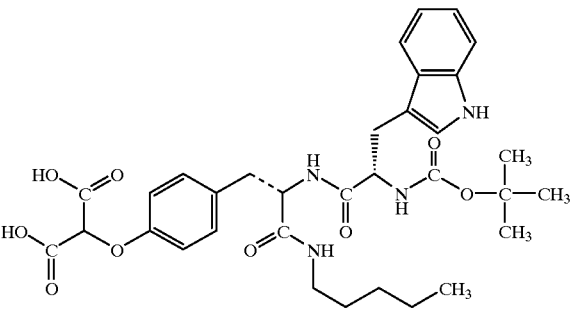 | 100<br>10<br>1 | 89<br>44<br>10 | | |
| EXAMPLE 135 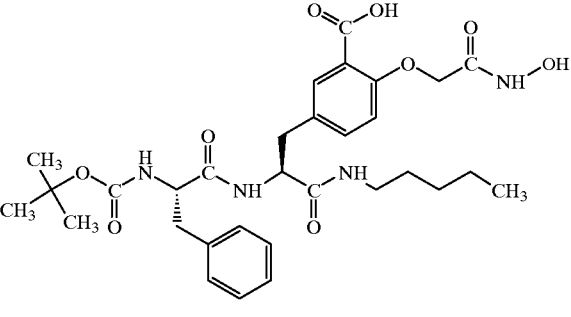 | 100<br>10<br>1 | 30<br>8<br>6 | | |
| EXAMPLE 91 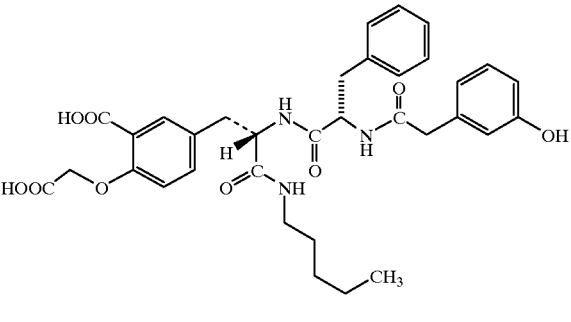 | 100<br>10<br>1 | 98<br>86<br>43 | | |

TABLE 2-continued
| Example No. | PTP1B Inhib | | PTP1 Inhib | |
| --- | --- | --- | --- | --- |
| | PTP1B. Conc (uM) | PTP1B. % Inhib | PTP1N. Conc (uM) | PTP1N. % Inhib |
| EXAMPLE 92 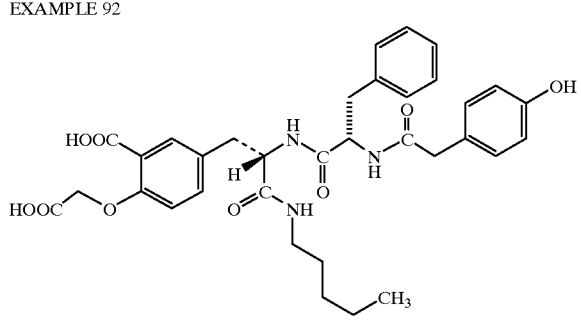 | 100<br>10<br>1 | 98<br>88<br>46 | | |
| EXAMPLE 93 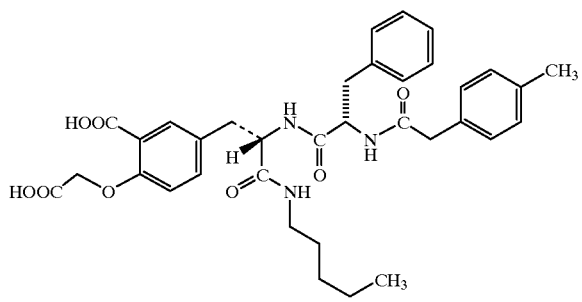 | 100<br>10<br>1 | 98<br>85<br>39 | | |
| EXAMPLE 94 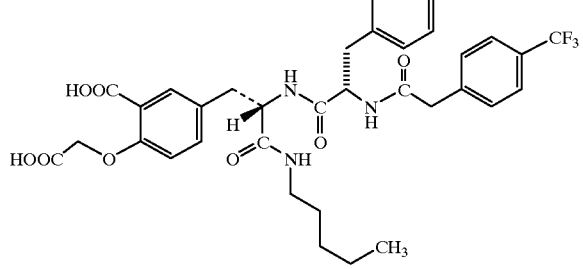 | 100<br>10<br>1 | 98<br>85<br>39 | | |
| EXAMPLE 95 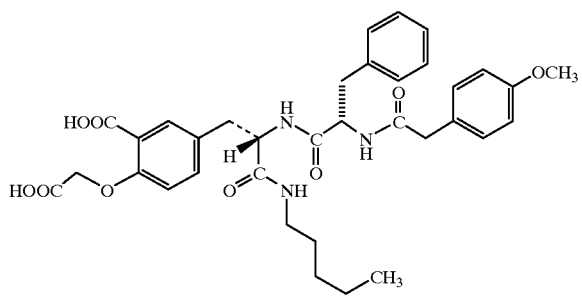 | 100<br>10<br>1 | 97<br>87<br>46 | | |

TABLE 2-continued
| Example No. | PTP1B Inhib | | PTP1 Inhib | |
| --- | --- | --- | --- | --- |
| | PTP1B. Conc (uM) | PTP1B. % Inhib | PTP1N. Conc (uM) | PTP1N. % Inhib |
| EXAMPLE 142 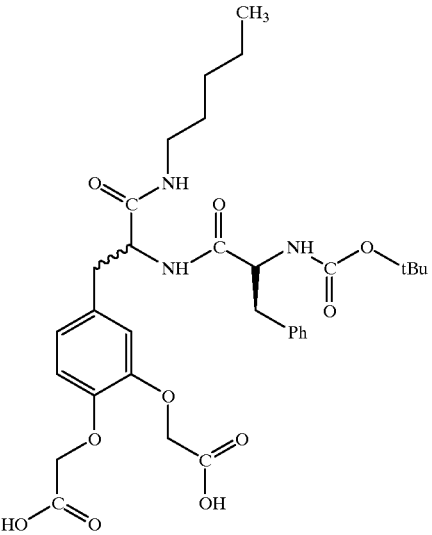 | 100<br>10<br>1 | 25<br>5<br>1 | | |
| EXAMPLE 80 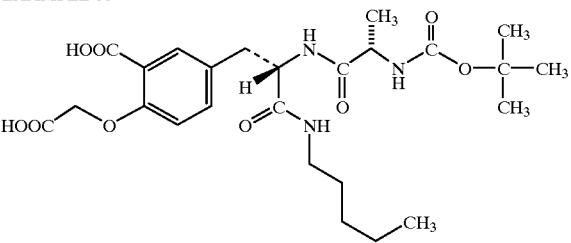 | 100<br>10<br>1 | 86<br>43<br>8 | | |
| EXAMPLE 96 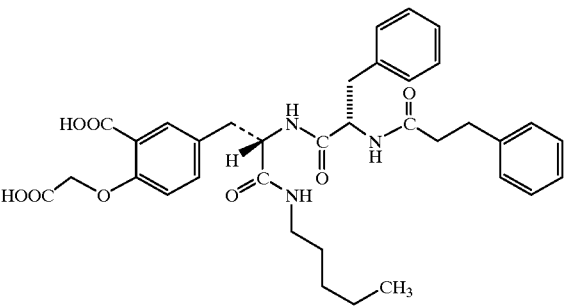 | 100<br>10<br>1 | 95<br>74<br>22 | | |

TABLE 2-continued

| Example No. | PTP1B Inhib | | PTP1 Inhib | |
|---|---|---|---|---|
| | PTP1B. Conc (uM) | PTP1B. % Inhib | PTP1N. Conc (uM) | PTP1N. % Inhib |
| EXAMPLE 143 | 100 | 94 | | |
| | 10 | 71 | | |
| | 1 | 24 | | |
| EXAMPLE 144 | 100 | 95 | | |
| | 10 | 76 | | |
| | 1 | 34 | | |
| EXAMPLE 145 | 100 | 98 | | |
| | 10 | 93 | | |
| | 1 | 64 | | |
| EXAMPLE 138 | 100 | 80 | | |
| | 10 | 31 | | |
| | 1 | 5 | | |

TABLE 2-continued

| Example No. | | PTP1B Inhib | | PTP1 Inhib | |
|---|---|---|---|---|---|
| | | PTP1B. Conc (uM) | PTP1B. % Inhib | PTP1N. Conc (uM) | PTP1N. % Inhib |
| EXAMPLE 136 | | | | 100 | 70 |
| | | | | 10 | 14 |
| | | | | 1 | 1 |

TABLE 3

| Example Number | Concentration ($\mu$M) | % Inhibition | Ki ($\mu$M) |
|---|---|---|---|
| 158 | 100 | 97 | 0.87 |
| | 10 | 85 | |
| | 1 | 43 | |
| 157-12 | 100 | 95 | |
| | 10 | 76 | |
| | 1 | 27 | |
| 157-14 | 100 | 94 | |
| | 10 | 67 | |
| | 1 | 20 | |
| 157-16 | 100 | 97 | |
| | 10 | 83 | |
| | 1 | 38 | |
| 157-21 | 100 | 95 | |
| | 10 | 73 | |
| | 1 | 24 | |
| 153 | 100 | | 30 |
| | 10 | | |
| | 1 | | |
| 146 | | | 20 |
| 147 | | | 46 |
| 157-28 | | | 0.4 |
| 157-2 | 100 | 98 | |
| | 10 | 93 | |
| | 1 | 64 | |
| 157-3 | 100 | | |
| | 10 | 94 | 72 |
| | 1 | 22 | |
| 157-1 | 100 | | |
| | 10 | 97 | 84 |
| | 1 | 39 | |
| 148 | 100 | | |
| | 10 | 80 | 31 |
| | 1 | 5 | |
| 154-2 | 100 | | |
| | 10 | 95 | 72 |
| | 1 | 23 | |
| 154-8 | 100 | | |
| | 10 | 97 | 81 |
| | 1 | 30 | |
| 154-9 | 100 | | |
| | 10 | 97 | 85 |
| | 1 | 37 | |
| 154-11 | 100 | | |
| | 10 | 95 | 73 |
| | 1 | 22 | |
| 154-15 | 100 | | |
| | 10 | 97 | 31 |
| | 1 | 80 | |
| 154-19 | 100 | | |
| | 10 | 98 | 55 |
| | 1 | 40 | |
| 154-20 | 100 | | |
| | 10 | 98 | 79 |
| | 1 | 27 | |
| 154-26 | 100 | | |
| | 10 | 97 | 78 |
| | 1 | 30 | |
| 154-34 | 100 | | |
| | 10 | 96 | 77 |
| | 1 | 26 | |
| 156-1 | 100 | | |
| | 10 | 95 | 69 |
| | 1 | 18 | |
| 156-7 | 100 | | |
| | 10 | 95 | |
| | 1 | 69 | 18 |
| 156-16 | 100 | | |
| | 10 | 95 | |
| | 1 | 72 | 20 |

The Ki values were calculated from IC50-values obtained from a dose-response curve pre using the inhibition assay described above.

What is claimed is:

1. Compounds of formula I wherein $G^1$ is
 a) —$R^2$;
wherein $G^2$ is
 c) $CH_2OH$;
wherein $R^1$ is
 a) —$OSO_3H$,
 b) —$OCH(CO_2R^5)_2$,
 c) —$OCH_2(CO_2R^5)$,
 d) —$OCH(CO_2R^5)CH_2CO_2R^5$,
 e) —$OC(CO_2R^5)=CHCO_2R^5$,
 f) —$CH_2CH(CO_2R^5)_2$, g) —CH=C(CO$_2$R$^5$)$_2$,
h) —OCH$_2$CONHOH,
i) —N(CH$_2$CO$_2$R$^5$)$_2$, or
j) —OCHF(CO$_2$R$^5$);
wherein R$^2$ is
d) —CH(R$^7$)NHXR$^6$, or
e)

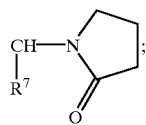

wherein R$^5$ is
a) —H,
b) —C$_1$–C$_{10}$ alkyl, or
c) —C$_1$–C$_5$ alkyl-phenyl;
wherein R$^6$ is
a) C$_1$–C$_{10}$ alkyl,
b) C$_0$–C$_6$ alkyl-G$^3$,
c) C$_1$–C$_6$ alkyl CONH$_2$,
d) C$_1$–C$_6$ alkyl NHCO$_2$R$^5$,
e) C$_1$–C$_6$ alkyl-OR$^5$,
f) C$_1$–C$_6$ alkyl-NHSO$_2$Me,
g) C$_1$–C$_6$ alkyl-O—G$^3$,
h) C$_1$–C$_6$ alkyl-S—G$^3$, or
i) —C$_1$–C$_6$ alkyl-CO$_2$R$^5$;
wherein R$^7$ is
a) —H,
b) —C$_1$–C$_6$ alkyl-G$^3$,
c) —C$_1$–C$_6$ alkyl-CO$_2$R$^5$,
d) C$_1$–C$_6$ alkyl CONH$_2$,
e) C$_1$–C$_6$ alkyl NHCO$_2$R$^5$,
f) C$_1$–C$_{10}$ alkyl,
g) C$_1$–C$_{10}$ cycloalkyl,
h) —C$_1$–C$_6$ alkyl-SR , or
i) —C$_1$–C$_6$ alkyl-S(=O)R$^5$;
wherein G$^3$ is
a) phenyl substituted by zero (0) to three (3) R$^9$,
b) naphthyl substituted by zero (0) to three (3) R$^9$, or
c) het$_1$ substituted by zero (0) to three (3) R$^9$;
wherein het$_1$ is a 5- or 6-membered saturated or unsaturated ring containing from one (1) to four (4) heteroatoms selected from the group consisting of nitrogen, oxygen and sulfur; and including any bicyclic group in which any of the above heterocyclic rings is fused to a benzene ring, C$_3$–C$_8$ cycloalkyl, or another heterocycle; and optionally, the nitrogen and sulfur heteroatoms may be in oxidized form;
wherein R$^9$ may be any of the following:
a) C$_1$–C$_8$ alkyl substituted by zero (0) to three (3) halo,
b) C$_2$–C$_8$ alkenyl,
c) OH,
d) O—C$_1$–C$_5$ alkyl,
e) O—C$_0$–C$_5$ alkyl-phenyl,
e) —(CH$_2$)$_n$—O—C$_1$–C$_5$ alkyl substituted by zero (0) to three (3) hydroxy,
f) —(CH$_2$)$_n$—O—C$_2$–C$_7$ alkenyl substituted by zero (0) to three (3) hydroxy,
g) halo,
h) NH$_2$,
i) amino-C$_1$–C$_5$ alkyl,
j) mono- or di-C$_1$–C$_5$ alkylamino,
k) —C(O)—C$_1$–C$_5$ alkyl,
l) —CHO,
m) —C(O)—C$_0$–C$_5$ alkyl-phenyl,
n) —COOR$^5$,
o) —CON(R$^5$)$_2$,
p) —C$_3$–C$_7$ cycloalkyl,
q) —NO$_2$,
r) —CN,
s) —SO$_3$H,
t) —SO$_2$N(R$_5$)$_2$,
u) —O[(CH$_2$)$_2$—O]$_n$—CH$_3$,
v) —[CH$_2$—O]$_n$—C$_1$–C$_3$ alkyl,
w) —NR$^5$(CO)—NR$^5$,
x) —CF$_3$,
y) —NR$^5$(CO)C$_1$–C$_5$ alkyl,
z) —N(R$^5$)—SO$_2$—R$^5$,
a1) —O—C(O)—R$^5$,
b1) —S(O)—R$^5$,
c1) —SR$^5$, or
d1) —SO$_2$—R$^5$;
wherein R$^{10}$ is
a) —H,
b) CO$_2$R$^5$,
c) CONHOH,
d) 5-tetrazolyl,
e) F, or
f) OCH$_2$CO$_2$R$^5$;
wherein R$^{11}$ is
a) H;
wherein X is —CO— or —SO$_2$— or —CO$_2$—;
wherein n is zero, one, two or three;
or a pharmaceutically acceptable salt thereof;
provided that when R$^{10}$ is H, R$^1$ is other than —OCH$_2$(CO$_2$R$^5$).

2. Compounds of the formula VI:

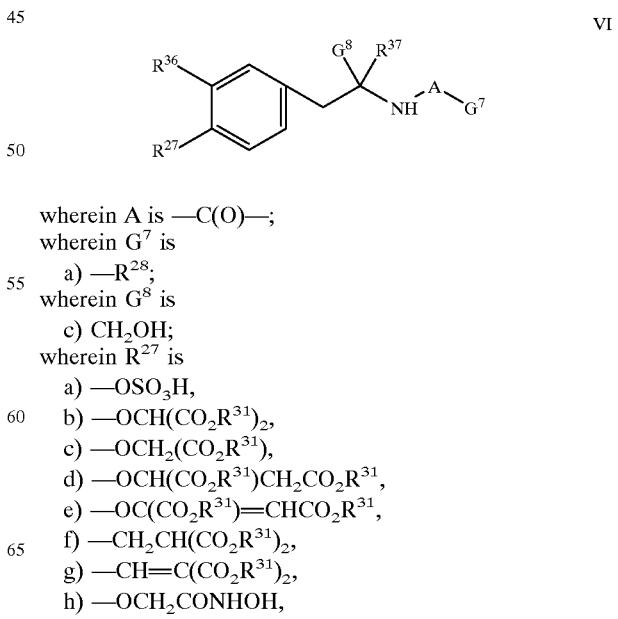

VI wherein A is —C(O)—;
wherein G$^7$ is
a) —R$^{28}$;
wherein G$^8$ is
c) CH$_2$OH;
wherein R$^{27}$ is
a) —OSO$_3$H,
b) —OCH(CO$_2$R$^{31}$)$_2$,
c) —OCH$_2$(CO$_2$R$^{31}$),
d) —OCH(CO$_2$R$^{31}$)CH$_2$CO$_2$R$^{31}$,
e) —OC(CO$_2$R$^{31}$)=CHCO$_2$R$^{31}$,
f) —CH$_2$CH(CO$_2$R$^{31}$)$_2$,
g) —CH=C(CO$_2$R$^{31}$)$_2$,
h) —OCH$_2$CONHOH, i) —N(CH$_2$CO$_2$R$^{31}$)$_2$, or
j) —OCHF(CO$_2$R$^{31}$);
wherein R$^{28}$ is
e) —CH(R$^{33}$)NHXR$^{32}$, or
f)

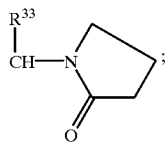

wherein R$^{31}$ is
a) —H,
b) —C$_1$–C$_{10}$ alkyl, or
c) —C$_1$–C$_5$ alkyl-phenyl;
wherein R$^{32}$ is
a) —C$_1$–C$_{10}$ alkyl,
b) —C$_0$–C$_6$ alkyl-G$^9$,
c) —C$_1$–C$_6$ alkyl CONH$_2$,
d) —C$_1$–C$_6$ alkyl NHCO$_2$R$^{31}$,
e) —C$_1$–C$_6$ alkyl-OR$^{31}$,
f) —C$_1$–C$_6$ alkyl-NHSO$_2$Me,
g) —C$_1$–C$_6$ alkyl-O—G$^9$,
h) —C$_1$–C$_6$ alkyl-S—G$^9$, or
i) —C$_1$–C$_6$ alkyl-CO$_2$R$^{31}$;
wherein R$^{33}$ is
a) —H,
b) —C$_1$–C$_6$ alkyl-G$^9$,
c) —C$_1$–C$_6$ alkyl-CO$_2$R$^{31}$,
d) —C$_1$–C$_6$ alkyl CONH$_2$,
e) —C$_1$–C$_6$ alkyl NHCO$_2$R$^{31}$,
f) —C$_1$–C$_{10}$ alkyl,
g) —C$_1$–C$_{10}$ cycloalkyl,
h) —C$_1$–C$_6$ alkyl-SR$^{31}$, or
i) —C$_1$–C$_6$ alkyl-S(=O)R$^{31}$;
wherein R$^{34}$ is
a) C$_0$–C$_6$ alkyl-G$^9$,
b) CH(R$^{33}$)CO$_2$R$^{31}$,
c) CH(R$^{33}$)CH$_2$CO$_2$R$^{31}$, or
d) CH(R$^{33}$)CONHCH$_2$CO$_2$R$^{31}$;
wherein G$^9$ is
a) phenyl substituted by zero (0) to four (4) R$^{35}$,
b) naphthyl substituted by zero (0) to three (3) R$^{35}$, or
c) het$_1$ substituted by zero (0) to three (3) R$^{35}$;
wherein het$_1$ is a 5- or 6-membered saturated or unsaturated ring containing from one (1) to four (4) heteroatoms selected from the group consisting of nitrogen, oxygen and sulfur; and including any bicyclic group in which any of the above heterocyclic rings is fused to a benzene ring, C$_3$–C$_8$ cycloalkyl, or another heterocycle; and optionally, the nitrogen and sulfur heteroatoms may be in oxidized form;
wherein R$^{35}$ may be any of the following:
a) C$_1$–C$_8$ alkyl substituted by zero (0) to three (3) halo,
b) C$_2$–C$_8$ alkenyl,
c) OH,
d) O—C$_1$–C$_5$ alkyl,
e) O—C$_0$–C$_5$ alkyl-phenyl,
f) —(CH$_2$)$_n$—O—C$_1$–C$_5$ alkyl substituted by zero (0) to three (3) hydroxy, g) —(CH$_2$)$_n$—O—C$_2$–C$_7$ alkenyl substituted by zero (0) to three (3) hydroxy,
h) halo,
i) NH$_2$,
j) amino-C$_1$–C$_5$ alkyl,
k) mono- or di-C$_1$–C$_5$ alkylamino,
l) —C(O)—C$_1$–C$_5$ alkyl,
m) —CHO,
n) —C(O)—C$_0$–C$_5$ alkyl-phenyl,
o) —COOR$^{31}$,
p) —CON(R$^{31}$)$_2$,
q) —C$_3$–C$_7$ cycloalkyl,
r) —NO$_2$,
s) —CN,
t) —SO$_3$H,
u) —SO$_2$N(R$^{31}$)$_2$,
v) —O[(CH$_2$)$_2$—O]$_n$—CH$_3$,
w) —[CH$_2$—O]$_n$—C$_1$–C$_3$ alkyl,
x) —NR$^{31}$(CO)—NR$^3$,
y) —CF$_3$,
z) —NR$^{31}$(CO)C$_1$–C$_5$ alkyl,
a1) —N(R$^{31}$)—SO$_2$—R$^{31}$,
b1) —O—C(O)—R$^{31}$,
c1) —S(O)—R$^{31}$,
d1) —SR$^{31}$,
e1) —SO$_2$—R$^{31}$,
f1) phenyl, or
g1) oxo;
wherein R$^{36}$ is
a) —H,
b) —CO$_2$R$^{31}$,
c) —CONHOH,
d) het$_2$ substituted by zero to three R$^{35}$, where in het$_2$ is a 5- or 6-membered saturated or unsaturated ring containing from one (1) to four (4) heteroatoms selected from the group consisting of nitrogen, oxygen and sulfur,
e) F,
f) OCH$_2$CO$_2$R$^{31}$, or
g)

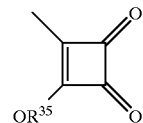

wherein R$^{37}$ is
a) H;
wherein X is —CO— or —SO$_2$— or —CO$_2$—;
wherein n is zero, one, two or three;
or a pharmaceutically acceptable salt thereof;
provided that when R$^{36}$ is H, R$^{27}$ is other than —OCH$_2$(CO$_2$R$^{31}$).

3. The compound of claim 1 selected from the group consisting of:

5-[(2S)-2-({(2S)-2-[(tert-butoxycarbonyl)amino]-3-phenylpropanoyl}amino)-3-hydroxypropyl]-2-(carboxymethoxy)benzoic acid or a pharmaceutically acceptable salt thereof.

4. A pharmaceutical composition, comprising the compounds of claim 1 and a pharmaceutically acceptable carrier.

5. A pharmaceutical composition, comprising the compounds of claim 2 and a pharmaceutically acceptable carrier.

6. A method for treating a patient suffering from non-insulin dependent diabetes mellitus by administering an effective amount of a compound of claim 1.

7. A method for treating a patient suffering from non-insulin dependent diabetes mellitus by administering an effective amount of a compound of claim 2.

8. The method for treating a patient suffering from non-insulin dependent diabetes mellitus according to claim 6, wherein said patient is a human.

9. The method for treating a patient suffering from non-insulin dependent diabetes mellitus according to claim 7, wherein said patient is a human.

10. The compound of claim 1, wherein $G^1$ is —$R^1$;

$G^2$ is $CH_2OH$;

$R^1$ is —$CH_2(CO_2R^5)_2$;

$R^2$ is

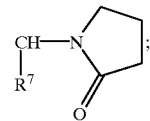

$R^5$ is —H;

$R^7$ is —$C_1$–$C_6$ alkyl-$G^3$;

$G^3$ is phenyl substituted by 0 to 3 $R^9$; and $R^{10}$ is 5-tetrazolyl.

* * * * *